United States Patent [19]
Johnson et al.

[11] Patent Number: 6,005,916
[45] Date of Patent: Dec. 21, 1999

[54] APPARATUS AND METHOD FOR IMAGING WITH WAVEFIELDS USING INVERSE SCATTERING TECHNIQUES

[75] Inventors: Steven A. Johnson; David T. Borup; James W. Wiskin, all of Salt Lake City, Utah; Frank Natterer; F. Wübeling, both of Muenster, Germany; Yongzhi Zhang, Madison, Wis.; Scott Charles Olsen, Salt Lake City, Utah

[73] Assignee: Techniscan, Inc., Salt Lake City, Utah

[21] Appl. No.: 08/972,101

[22] Filed: Nov. 17, 1997

Related U.S. Application Data

[63] Continuation of application No. 08/706,205, Aug. 29, 1996, which is a continuation-in-part of application No. 08/486,971, Jun. 22, 1995, abandoned, which is a continuation-in-part of application No. 07/961,768, Oct. 14, 1992, Pat. No. 5,588,032.

[51] Int. Cl.$^6$ .................................................. G01N 23/201
[52] U.S. Cl. ............................... 378/87; 378/98; 378/99; 600/425; 600/437
[58] Field of Search ................................... 378/8, 86, 87, 378/90, 98, 901; 600/410, 425, 437, 476

[56] References Cited

U.S. PATENT DOCUMENTS

| | | | |
|---|---|---|---|
| 4,622,222 | 11/1986 | Johnson | 73/602 |
| 4,727,550 | 2/1988 | Chang et al. | 372/2 |
| 4,798,209 | 1/1989 | Klingenbeck et al. | 128/653 |
| 5,227,797 | 7/1993 | Murphy | 342/22 |
| 5,588,032 | 12/1996 | Johnson et al. | 378/8 |
| 5,667,893 | 9/1997 | de Hoop et al. | 367/50 |

OTHER PUBLICATIONS

Berggren, M.J., Johnson, S.A., Kim, W.W., Borup, D.T., Eidens, R.S., and Zhou, Y., (1987)"Acoustic Inverse Scattering Images from Simulated HIgher Contrast Objects and from Laboratory Test Objects," *Acoustical Imaging 16*, Chicago, Ill., Jun.

Berggren, M.J., Johnson, S.A., Carruth, B.L., Kim, W.W., Stenger, F., and Kuhn, P.L., (1986) "Performance of Fast Inverse Scattering Solutions for the Exact Helmholtz Equation Using Multiple Frequencies and Limited Views," *Acoustical Imaging 15*, Halifax, Nova Scotia, Jul.

Bolemy, J.C., and Pichot, C., (Apr. 1991) "Some Applications of Diffraction Tomography to Electromagnetics—The Particular Case of Microwaves," in *Inverse Problems in Scattering and Imaging*, edited by M. Bertero and E.R. Pike, Adam Higler (Publisher), New York, 1992. Presented at the Proceedings of a Nato Advanced Research Workshop, Cape Cod, Apr., 1991.

Borup, D.T., and Gandhi, O.P., (1984) Fast–Fourier–transform method for the calculation of SAR distributions in finely discretized models of biological bodies, *IEEE Trans. Microwave Theory Tech., MIT–32*, 355–360.

Borup, D.T., and Gandhi, O.P., (1985) "Calculation of High–Resolution SAR Distribution in Biological Bodies Using the FFT Algorithm and the Conjugate Gradient Method," *IEEE Trans. Microwave Theory Tech., MIT–33*, 417–419.

Borup, D.T., (1989) *Fast–Fourier–Transform Based Interation Methods for Solving the Electric Field Integral Equation for Anatomically Detailed Man Models*, Ph.D. Dissertation, University of Utah, Salt Lake City, Utah.

Borupt, D.T., Johnson, S.A., Kim, W.W., and Berggren, M.J., (1992) "Nonperturbative Difraction Tomography via Gauss–Newton iteration applied to the Scattering Integral Equation," *Ultrasonic Imaging 14*, pp. 69–85, Jan.

Broquetas, A., Romeu, J., Rius, J.M., Elis–Fuste, A.R., Cardama, A. and Jofre, L., (1991) "Cylindrical Geometry: A Further Step in Active Microwave Tomograph," *IEEE Trans. Microwave Theory Tech.*, vol. 39, No. 5, pp. 836–844, May.

Candy, J.V. and Pichot, C., (1991) "Active Microwave Imaging: A Model Based Approach," *IEEE Trans. Antennas Propagat*, vol. 39, No. 3, pp. 285–290, Mar.

Cavicchi, T.J., Johnson, S.A., and O'Brien, Jr., W.D., (1988) Application of the Sinc Basis Moment Method to the Reconstruction of Infinite Circular Cylinders, *IEEE Trans. Ultrasonics, Ferroelectr., Freq. Control, UFFC–35*, 22–23.

Chew, W.C. and Wang, Y.M., (Jan. 1990) "Reconstruction of Two–Dimensional Permittivity Distribution Using the Distorted Born Iterative Method," *IEEE Microwave Theory Tech.*, pp. 218–225.

Chew, W.C. and Wang, Y.M., (May, 1990) "A Fast Algorithm for Solution of a Scattering Problem Using a Recursive Aggregate Tau Matrix Method," *Microwave and Opt. Tech Let*, vol. 3, No. 5, pp. 164–169, May.

Datta, A.N. and Bandyopadhyay, B., (1986) "Nonlinear Extension to a Moment Method Iterative Reconstruction Algorithm for Microwave Tomography," *Proceed. IEEE*, vol. 74, No. 4, pp. 604–606, Apr.

Kim, W.W., Borup, D.T., Johnson, S.A., Berggren, M.J., and Zhou, Y. (1987) "Accelerated Inverse Scattering Algorithms for Higher Contrast Objects," in *1987 IEEE Ultrasonics Symposium*, 903–906, (Ieee Cat. No. 87ch2492–7.

Johnson, S.A., Zhou, Y., Tracy, M.K., Berggren, M.J., and Stenger, F.F. (1984) "Inverse Scattering Solutions by a Sinc Basis, Multiple Source, Moment Method—Part III: Fast Algorithms," *Ultrasonic Imaging 6*, pp. 103–116.

Johnson, S.A., Zhou, Y., Tracy, M.L., Berggren, M.J., and Stenger, F. (1984) "Inverse Scattering Solutions by a Sinc Basis, Multiple Source, Moment Method—Part I: Theory," *Ultrasonic Imaging 5*, 361–375.

Johnson, S.A., Zhou, Y., Berggren, M.J., and Tracy, M.L. (1983) "Acoustical Inverse Scattering Solutions by Moment Methods and Backprojection," in *Conference on Inverse Scattering: Theory and Application*, SIAM, Philadelphia.

Norton, S.J., (1988) "Iterative Seismic Inversion," *Geophysical Journal*, No. 94, pp. 457–468.

Robinson, B.S., and Greenleaf, J.F. (1990) "An Experimental Study of Diffraction Tomography under the Born Approximation," *Acostical Imaging 18*, No. 18, Jun.

Sarkar, T.K., Arvas, E., and Rao, S.M. (1986) "Application of FFT and the Conjugate Gradient Method for the Solution of Electromagnetic Radiation from Electrically Large and Small Conducting Bodies," *IEEE Trans. Antennas Propagat.*, vol. AP–34, pp. 635–640, May.

Tracy, M.L., and Johnson, S.A. (1983) "Inverse Scattering Solutions by a Sinc Basis, Multiple Source, Moment Method—Part II: Numerical Evaluations," *Ultrasonic Imaging 5*, 376–392.

Wombel, R.J., and Fiddy, M.A., (1988) "Inverse Scattering within the Distorted–Wave Born Approximation," *Inverse Problems 4*, (1988).

Borup, D.T., S.A. Johnson, J.W. Wiskin, and M.J. Berggren, "An Integral Equation Method for Nonlinear Imaging of Acoustic and Elastic Parameters," Poster session at the SEG Research Workshop on Recording and Processing of Vector Wave Field Data held at Snowbird, Utah, Aug. 13–17, 1989.

Zhou, Y., S.A. Johson, M.J. Berggren, B. Carruth, and W.W. Kim, "Constrained Reconstruction of Object Acoustic Parameters from Noisy Ultrasound Scattering Data," *Proc. of the IEEE 1987 Ultrasonics Symposium pp. 897–901*.

Kim, W.W., S.A. Johnson, M.J. Berggren, F. Stenger, and C.H. Wilcox, "Analysis of Inverse Scattering Solutions from Single Frequency, Combined Transmission and Reflection Data for the Helmholtz and Riccati Exact Wave Equations," *Acoustical Imaging 15*, pp. 359–369, Plenum Press (1987).

Ladas, Kostas T, and A.J. Devaney, "Iterative Methods in Geophysical Diffraction Tomography," Inverse Problems 8, (1992).

Kennett, B.L.N., and N.J. Kerry, "Seismic Waves in a Stratified Half Space," *Geophys. J.R. astr. Soc. 57, 557*, 1979.

Muller, G., "The Reflectivity Method: a Tutorial," *J.Geophys* 58: 153, 1985.

Wiskin, J.W., "Geometric and Integral Equation Methods for Scattering in Layered Media," Ph.D. dissertation, Dept. Math. University of Utah, publ. Oct. 15, 1991.

Aymi–Bellegarda, E.J. and Habashy, T.M., "Forward Ultrasonic Scattering of Multidimensional Solid or Fluid Inclusions Buried in Multilayered Elastic Structures.", IEEE Trans. Ultras., Ferro., and Freq. Cont., vol. 39, No. 1, Jan. 1992.

Aymi–Bellegarda, E.J. and Habashy T.M., "Ultrasonic Inverse Scattering of Multidimensional Objects Buried in Multilayered Elastic Background Structures.", IEEE Trans. Ultras., Ferro., and Freq. Cont., vol. 39, No. 1, Jan. 1992.

Pan, G.S., R.A. Phinney, and R.I. Odom, :Full–waveform inversion of plane–wave sismograms in stratified acoustic media: Theory and feasibility, Geophysics, vl.53, 1, (1988).

Williamson, P.R. Tomographic Inversion in Reflection Seismology, *Geophys. J. Int. 100*, 1990.

Wilcox, C.H., "Ultrasound Imaging at the AIM Laboratory, University of Utah," Lecture at IMACS International Symposium of Computational Acoustics, Harvard University, Jun., 1991.

Mora, Peter, "Nonlinear Two–Dimensional Elastic Inversion of Multioffset Seismic Data," *Geophysics*, vol. 52, 9, Sep. 1987.

Crase, E. Pica, A.M. Noble, J. McDonald, and A. Tarantola, "Robust Elastic Nonlinear Waveform Inversion: Application to Real Data," *Geophysics*, 55, 5 (May 1990).

Franssens, G.R., "Calculation of the Elasto–dynamic Green's Function in Layered Media by Means of a Modified Propagator Matrix Method.", *Geophys. J.R. asrttr. Soc. 75, 1983*.

Wannamaketer, P.E., G.W. Hohmann, and W.A. SnaFilipo, "Electromagnetic Modeling of Three–dimensional bodies in Layered Earth Using Integral Equations.".

Cohen, J.K. and F.G. Hagin, "Velocity Inversion using a Stratified Reference," *Geophysics, 50, 11*, 1985.

*Primary Examiner*—David Vernon Bruce
*Attorney, Agent, or Firm*—Workman, Nydegger & Seeley

[57] ABSTRACT

An apparatus and method for rapid real time imaging with wavefield energy using a C.P.U. programmed to process data derived from wavefield energy that has been transmitted and scattered by an object so as to reconstruct a wavefield image of the object. Electronic signals are propagated and are transduced into wavefield energy waves which in turn are propagated toward the object. Detectors detect the wavefield energy waves scattered by the object. The detected wavefield energy waves are then electronically processed and input into a high-speed digital computer which may comprise a C.P.U. and/or a C.P.U. in combination with an array or parallel processor. Data is also prepared and input to the computer representing the incident field and the computer then reconstructs a high-quality image of the object having high spacial resolution and including actual properties of the object. The media in which the object is embedded may be fluid or solid, homogeneous, or layered (such as stratigraphic layering, or ocean velocity layers, or layering of composites in nondestructive imaging applications), or may consist of porous material (either sedimentary deposits or composites in nondestructive testing).

193 Claims, 83 Drawing Sheets

Microfiche Appendix Included (17 Microfiche, 379 Pages)

Hermitian Conjugate of the second
Lippman-Schwinger operator
$(I - G^*Y^*)f_{\omega\phi} = f_{\omega\phi}^{inc}$
Input $G^*$ is the complex conjugate
of the Fourier Transform of
$G$, $\bar{\gamma}$, or $\gamma^*$ is the complex
conjugate of $\gamma$ Form the pointwise product of the complex conjugate of the scattering potential estimate, with the input to this subroutine $\gamma \cdot f_{\omega\phi}$ store in vector $y(i,j)$ — 1242

Take the Fast Fourier Transform — 1244

Pointwise multiply by $G_\omega^*$ - the conjugate of the Fast Fourier Transform of the Green's function at frequency omega — 1246

Take the Inverse Fast Fourier Transform of the product — 1248

Form the difference $f_{\omega\phi}(i,j) - y(i,j)$
$f_{\omega\phi}(i,j) - y(i,j)$ — 1252

FIG. 15

METHOD FOR SOLVING FOR THE OBJECT FUNCTION $\gamma$ BY USE OF SQUARE INVERSION IN THE SCATTERED FIELD DOMAIN.

METHOD FOR SOLVING FOR THE OBJECT FUNCTION $\gamma$ BY USE OF SQUARE INVERSION IN THE OBJECT FUNCTION DOMAIN.

APPARATUS AND METHOD FOR IMAGING WITH WAVEFIELDS USING INVERSE SCATTERING TECHNIQUES

This patent application is a continuation of U.S. patent application Ser. No. 08/706,205 filed on Aug. 29, 1996, which is a continuation-in-part of U.S. patent application Ser. No. 08/486,971 filed on Jun. 22, 1995 now abandoned, which is a continuation-in-part of U.S. patent application Ser. No. 07/961,768 filed on Oct. 14, 1992 now U.S. Pat. No. 5,588,032, all of which are incorporated herein by reference.

BACKGROUND

A portion of the disclosure of this patent application contains material to which a claim of copyright protection is made. The copyright owner(s) has/have no objection to the facsimile reproduction by any one of the patent document or the patent disclosure as it appears in the Patent and Trademark Office patent file or records, but reserves all other rights in the copyrighted work. Appendices A-L, L1, M1, M1, M2, and M3, referred to herein, may be found in the microfiche appendices attached hereto. The microfiche appendices is comprised of one microfiche sheet for each of the Appendices A-L, L1, M1, M1, M2 and M3, for a total of seventeen (17) sheets.

1. Field of the Invention

This invention related to an apparatus and method for imaging in either homogeneous, or layered, or porous media. The media may be fluid or solid, the imaging energy may be electromagnetic, elastic (seismic-like energy) or acoustic (sound/ultrasound energy). Furthermore, the ambient media (in which the object to be imaged is embedded) may have layering (such as stratigraphic layering, or ocean velocity layers, or layering of composites in nondestructive imaging applications) or consist or porous material (either sedimentary deposits or composites in nondestructive testing).

2. The Prior Art

It has long been known that elastic, electromagnetic or acoustic waves in homogeneous and layered environments in the frequency range of a fraction of a cycle per second up to hundreds of millions of cycles per second and higher can be propagated through many solids and liquids. Elastic waves are waves that propagate through solids, and have components of particle motion both parallel (longitudinal, or pressure, wave) and perpendicular (shear wave) to the direction of propagation of the wave energy itself. In contrast to this, acoustic waves are those waves that generate particle motion that is exclusively parallel to the propagation of wave energy. Electromagnetic waves have components of variation of field strength solely in the direction perpendicular to the direction of propagation. All of these types of waves may be used to image the acoustic longitudinal wavespeed and absorption, the electromagnetic wavespeed and absorption, the shear wavespeed, and the density of the material through which the wave energy has travelled.

It is also known that scattering is produced not only by spatial fluctuations in acoustic impedance, which is the product of mass density times wavespeed, but also by independent fluctuations in electromagnetic permeability, permittivity and conductivity, elastic compressibility, shear modulus, density, and absorption. These lead to variations in phase speed (which is the speed of propagation of fronts of constant phase) and in impedance (for the electromagnetic case, the ratio of the electric to the magnetic field strength). The net property of an object which describes the phenomenon of scattering in a given modality, is called the "scattering potential".

Other imaging methods have been applied to one or the other modality, or restricted to acoustic or elastic media, the method described in this patent is applicable to any type of wave motion, whether electromagnetic, elastic (including shear wave effects) or acoustic (scalar approximation valid in liquid and gases). Furthermore, the ambient media may have some forms of structure (layering) or microstructure (porosity) relevant to the medical, geophysical, or nondestructive imaging applications envisioned for this technology. In the prior art the presence of this layering or porosity has greatly diminished the effectiveness of the imaging program. The method of this patent minimizes the obscuring effect of such structures in the ambient media. In addition, we have made several changes to the previous U.S. Pat. No. 4,662,222 that significantly extend the applicability and speed of our algorithm. These changes are described, in part, below:

As discussed in U.S. Pat. No. 4,662,222, by one of the present authors, these principles can be used to image scattering bodies within a given medium. Some definitions will clarify the procedures and methods used:

The direct or forward scattering problem is concerned with a determination of the scattered energy or fields when the elastic or electromagnetic properties of the scattering potential are known.

The inverse scattering problem, by contrast, consists in the use of scattered electromagnetic, elastic, or acoustic waves to determine the internal material properties of objects embedded in a known (ambient) medium. An incident wave field is imposed upon the ambient medium and the scatterer. The scattered field is measured at detectors placed a finite distance from the scattering objects. The material parameters of the scatterer are then reconstructed from the information contained in the incident and scattered fields. In other words, as defined herein, acoustic or electromagnetic imaging using inverse scattering techniques is intended to mean electronic or optical reconstruction and display of the size shape, and unique distribution of material elastic or electromagnetic and viscous properties of an object scanned with acoustic, electromagnetic or acoustic energy, i.e., reconstruction of that scattering potential which, for a given incident field and for a given wave equation, would replicate a given measurement of the scattered field for any source location.

The description of prior art summarized in U.S. Pat. No. 4,662,222 (referred to as "the previous Patent") is also relevant here. It is sufficient to say here, that the use of the conjugate gradient algorithms discussed in the previous patent brought the attainment of inverse scattering into a practical reality. Previous to that U.S. Pat. No. (4,662,222), only linear approximations to the full inverse scattering problem were amenable to solution, even with the aid of modern high speed digital computers. The resolution achievable with the inverse scattering methods described in the previous patent was far superior to any ultrasound imaging in medicine previous to that time,

SUMMARY AND OBJECTS OF THE INVENTION

Inversion methods applied to the modalities discussed here have been independently pursued in linear approximation (so called diffraction) tomography in previous state of the art, this method and the apparatus discussed herein provide much greater resolution in real time, and since the technique is equally applicable to the various (elastic—including shear waves—electromagnetic, and acoustic compressional) modalities, they can be synergistically combined to image material parameters of geophysical, commercial and/or military significance. ("Elastic" media support shear wave motion perpendicular to the wave propagation direction, "acoustic" waves are considered purely longitudinal or compressional by convention, in this patent). This is accomplished by incorporating information resulting from acoustic imaging, into the electromagnetic imaging process, and vice versa.

There will be several types of algorithms discussed herein:

(1) sinc basis, rectangular coordinate, convolutional algorithms (2) cylindrical and rectangular coordinate recursion (3) Parabolic (Spectral and Finite difference) marching methods (4) Refraction corrected reflectivity and brightness functional gradient method adaptive focus.

(5) Necessary calibration algorithms which must be employed in the cases (1), (2), and (3) above in order to achieve the optimal resolution and quantitative accuracy.

These methods all reflect the common theme in this patent for generating images from wave field energy applied to an unknown scattering object, which is then measured at some finite distance away from said scattering object. The ultimate aim is the production of accurate reconstructions of distributions of parameters which characterize the scattering object. These parameters may be "reflectivity" in the case of the more primitive, but faster algorithms (such as (4) above), or they may be speed of sound, attenuation, compressibility, electromagnetic dielectric constants, conductivity, or Lame' parameters in the case of the more advanced and time intensive algorithms (1–3). Furthermore, the reconstructions may or may not be quantitatively accurate depending upon the computational complexity of a given algorithm, and the amount of computational effort expended to obtain the reconstruction image.

We have included the calibration as a separate part of the patent to emphasize this often overlooked step. Calibration is less important in method (4), but for the inverse scattering algorithms (1), (2), and (3) it greatly enhances the inversion capability.

These issues will be dealt with in more detail in the discussion of each individual algorithm, below.

Although the first (1) technique is emphasized we will give examples of the other methods to show that they are equally applicable to the imaging problem in a variety of environments. A discussion of many of the features of the first approach can be found in [Wiskin, 1991, Ph. D. dissertation, Univ. of Utah, Salt Lake City] and [Borup et al., Ultrasound Imaging, January, 1992], both being herein incorporated by reference.

Although similar techniques have appeared in the scientific literature as theory only or in algorithms that, due to lack of efficiency, cannot handle problems of practical size, these methods are substantially different from other algorithms that cannot be used in a practical imaging device such as Diffraction Tomography, Colton and Monk's method. Although some of the methods introduced by Borup, Johnson, Wiskin, and co-workers were available earlier, other factors had to come together before the present apparatus and method become applicable to concrete problems in medical imaging, geophysical imaging, and nondestructive imaging (NDI) in layered and porous media.

The previous state of the art includes the existence of algorithms that superficially resemble the method described here. The implementation of these algorithms is generally restricted to simple problems of small size and contrast, they are too small in fact to be realistic or practical.

This observation is supported by the fact that although there has been a pressing need for high resolution imaging technology for several decades in the medical, NDI and geophysical fields, there has never been, until now, a successful implementation capable of solving practical problems. In particular (1) this method has been incorporated into a device soon capable of imaging human breast tissue, with the purpose of determining position and size of any tumor present, and aid the determination of its benign/malignant character non-invasively.

(2) Furthermore, this process and method is being built into a system capable of imaging objects in marine sedimentary deposits to aid in determining whether they are implanted ordnance, or harmless objects.

(3) This process is being incorporated into a system which uses electromagnetic and acoustic (compressional)/elastic (including shear) wave energy to image potentially hazardous (to the environment) waste.

The implementation of this process into

A. breast scanners, medical imaging

B. buried mine (ordnance) detection scanners

C. nondestructive evaluation imagers (both electromagnetic and elastic modes)

D. ground penetrating radar

E. Inverse scattering optical microscopes would be impossible without the improvements in speed of convergence and imagable contrast.

The improvements of this patent over previous state of the art (U.S. Pat. No. 4,662,222 for example) apparatus and methods, are enumerated below:

1. This algorithm is capable of imaging larger and higher contrast objects than the previous state of the art. (U.S. Pat. No. 4,662,222) This is partly due to the greatly increased speed discussed below, but independently, also through the use of the scattering potential ($\gamma$) as the sole independent variable.

In the previous Patent both y and the internal fields, $f$, are considered to be independent variables of equal importance, in the nonlinear minimization problem related to inverse scattering. (see example 1 below, for details).

We have consciously emphasized the Frechet (or functional) derivative (see glossary) in a particular manner. In particular we define a functional $F \equiv \|R\|^2$ where the residual R is defined as the difference between two values at the detectors: these two values being (1) the scattered field value at the detectors predicted by the forward problem on the basis of a postulated scattering potential distribution and (2) the measured value of the scattered field, i.e. $R = f^{calc} - f^{meas}$.

The essence of the method (apart from the appropriate techniques to substantially reduce the computational cost of the algorithm) is the iterative construction of $\gamma^{(n)}$, for n=1,2, . . . , such that $\gamma^{(n)} \approx \gamma^{true}$, until finally $\nabla F \approx 0$. Given a guess $\gamma^{(n)}$, we must calculate the derivative of F with respect to $\gamma$, in order to calculate the next guess, $\gamma^{(n+1)}$. The actual calculation of this derivative is detailed below. We have interpreted this functional we wish to minimize as depending on the scattering potential alone. This is distinct from prior art, as represented in U.S. Pat. No. 4,662,222 in that previously we considered the functional as dependent upon both the internal fields and the scattering potential. Symbolically, if we call the functional that is minimized F, we can write: F≡F(γ,f) to indicate the dependence upon γ, the scattering potential (see glossary), and f, the total field inside of the object. In this patent, we consider the internal fields f as intermediate variables dependent upon γ, i.e. f=f (γ) so that the functional F=F(γ,f(γ))≡F(γ).

This employment of one variable instead of two involves much more than merely neglecting (or holding constant) one of the variables. Rather, as indicated above, the effect of changing variable γ, has a nontrivial effect upon the other variables $f_{\omega\phi}(\gamma)$, the field due to the incident wave from position φ and at frequency ω, for each possible φ and ω. The net result is a functional that is highly nonlinear in the remaining variable γ, and therefore much more difficult to solve numerically. This explains in part the reason this approach had not been applied previous to our implementation.

2. This patent improves the previous state of the art by increasing the rate of convergence to real-time convergence—see below—of the forward problem. ("real-time" is defined as the performance which allows for practical, clinical implementation of breast scanners, or of geophysical imaging apparatus, or of Non-Destructive Imaging of composite material. The data is collected and processed on-site, not sent off-site to be processed).

3. We have significantly increased the domain of applicability of the inverse scattering algorithm by the construction and utilization of suitable Green's functions (e.g. the layered Green's function). The layered Green's function takes the place of the free space Green's function in the presence of multiple layering in the environment surrounding the space to be imaged. See FIG. 1 for a typical scenario in which the layered Green's function is applicable. This so-called "layered Green's function" plays a similar role in our advanced algorithm that the "free space" Green's function played in the previous patent. This layered Green's function allows the quantitative imaging of objects located within an arbitrary distribution of layers of constant speed. In particular, attempts to image an object located beneath an inhomogeneous layer using present state of the art algorithms (including U.S. Pat. No. 4,662,222) would require an impractically large computational grid to model the presence of these layers. In contrast to this the present imaging technology incorporates the presence of these layers within the Green's function, obviating the need to encompass them within the computation grid.

This generalization of the free space Green's function to this new type of environment was certainly known to be possible in theory. The true difficulty lay in the ability to construct the inverse scattering algorithm and Green's function in such a way that "convolution" is preserved, since it is the convolutional character that allows the use of the Fast Fourier Transform (FFT), which in turn makes the imaging process practical for the medical/geophysical/ Nondestructive Evaluation (NDE) scanners mentioned above. (Actually it is convolution/correlation which is preserved, however, the correlation is accomplished by turning it into a convolution via a mathematical transformation.) It is this convolution property that enables us to perform the inversion with such unusual speed. There are several non-trivial changes to the flowcharts that must be made in order to accommodate the effects of the layering, these changes are shown below in the accompanying flowcharts.

Previous state of the art imaging processes have utilized this "convolutional" structure to some greater or lesser degree, but never in an algorithm capable of implementation in an actual imaging device. The reasons for this include the fact that the numerical implementation of this algorithm is still computationally intensive, as will be shown below. Furthermore, this convolutional structure is incorporated into not only-the free space Green's function, but also into the layered Green's , the acoustic Biot Green's function, the elastic (including shear wave motion) Green's function, and into all combinations of these Green's functions. Furthermore the direct application of this convolutional structure to the inverse scattering algorithm is used in conjunction with several implementations unique to our approach, such as the use of biconjugate gradients, and BiConjugate Gradients Stabilized [BiSTAB].

The layered Green's function can be constructed for the electromagnetic waves as well as for the elastic case discussed in [Wiskin, 1991]. However, the use of the Green's function in the prior art is restricted to the "forward problem". This forward problem is computationally much easier than the inverse (imaging) problem. The prior art is restricted to the implementation of the forward problem, it does not address the inverse problem without drastic (linear) approximations.

4. An important feature of our algorithms is the use of state of the art iterative methods for the overall nonlinear system and the linear systems that arise during its solution. Three different nonlinear iterations are used: the Gauss-Newton (GN) iteration, the Fletcher-Reeves (FR) nonlinear conjugate gradient iteration, and a modification of the Fletcher-Reeves algorithm—the Ribiere-Polak (RP) iteration. All three nonlinear iterations are described in [Fletcher, R. D., 1980, *Practical Methods of Optimization, Vol. I, Unconstrained Optimization*, John Wiley and Sons, New York] herein incorporated by reference.

The GN iteration is the fastest in CPU time per step but is not guaranteed to be globally convergent unless CPU time intensive exact line searches are used. Empirically we find that the GN method sometimes fails or requires more steps in the presence of high contrast in the scattering parameters. The more CPU intensive FR and RP iterations have been found to succeed for many of these high contrast/large size problems. The optimum strategy is often to use a combination: start with FR or RP when far from the solution and then switch to the faster GN iteration as the solution is neared. All three methods require utilization of the Jacobian of the scattering equations.

Perhaps the most significant advance contained in this patent application, over the method in our previous patent, is that a method is included whereby the Jacobian can be implemented entirely with shift invariant operations (FFT computable), thus avoiding explicit storage and time consuming direct matrix calculations. This is opposed to other techniques which require explicit storage of the Jacobian (requiring a very large amount of memory) and which implement its effect on a given vector by a direct matrix product (requiring enormous CPU time).

During the computation of a nonlinear step with the above methods, linear systems are encountered. The use of the minimum residual conjugate gradient (MRCG) method and the biconjugate gradient (BCG) (and the more recent stabilized BCG or "BiSTAB") method, for the efficient solution of these linear systems are among the other ideas that must be present in order to create a workable and practical method of imaging in real time. Biconjugate gradients (or BiSTAB) is used to solve the forward problems. These problems are amenable to the BCG method because they have the same number of unknowns as they have equations to solve (they are "square" systems). The use of BCG results in approximately the square root of the number of iterations required by traditional conjugate gradients (CG) used in our previous patent. This BCG implementation of the forward problem also plays a critical role in the shift invariant operator implementation of the Jacobian.

The MRCG algorithm is utilized in our approach to solve the overdetermined (non-square) Jacobian equation that is encountered when computing a GN linearization. This obviates the need for a computationally intensive matrix inversion and avoids the introduction of a "regularizing" parameter since the MRCG algorithm is self-regularizing. This also results in a substantial savings in time. The FR and RP iterations are themselves nonlinear versions of the MRCG algorithm.

5. The examples given in this patent all assume that the different frequencies, $\omega$, and source positions, $\phi$, are all computed in serial fashion. It is important to note, however, that another important link in the real time implementation of our algorithm, is the fact that the different frequencies and different views are independent computations (in both the forward problem and Jacobian calculations), and therefore can be computed in parallel. The implementation of this parallelization is explained in detail below. The omission of any one of these important links renders the algorithm intolerably slow for the practical medical/geophysical/NDE scanners listed above.

6. We make a Born-like approximation within the Jacobian. This is NOT the standard Born approximation common in optics and acoustical imaging (diffraction imaging). This approximation has a much greater radius of convergence than the standard Born approximation. [Borup, 1992]. Its purpose is to give a much faster way of computing the Jacobian in the presence of high contrast objects than would be possible if the exact Jacobian (see glossary for definition of terms) were used in the Gauss-Newton algorithm (or FR and RP algorithms).

7. Another important improvement over our previous patent is the addition of boundary value projection operators. In our previous patent, receivers were constrained to lie within the range of the FFT implemented convolution. Our new algorithms include operators based on Green's theorem that allow the scattering at the border of the convolution range to be extrapolated to receivers at any position external to the border. This approach also allows for receivers with complicated shapes (non-point receivers) to be used. Furthermore, empirical measurements of the radiation patterns of the receiver elements (and their mutual coupling and cross talk) can be built into these projection operators. This advance is critical in applying our algorithms to data collected with real devices.

8. A further improvement is the inclusion of Electromagnetic modalities within the inverse scattering scheme. By electromagnetic imaging we include zero-frequency electromagnetic waves, i.e. that which is commonly called "current imaging". We have incorporated the electromagnetic inverse scattering scheme derived here into a process to image position and extent of hazardous waste underground. The algorithm as discussed in the previous patent was restricted to acoustic data. This is no longer the case. We have also incorporated the electromagnetic imaging technology into an optical microscope device that will enable the imaging of biologically important material/cells, and a microwave imaging device The manifold applications of our scheme, which utilizes electromagnetic radiation (including the zero frequency or DC component) imaging include, but are not restricted to:

Electromagnetic Medical Imaging

Electromagnetic Geophysical Imaging

Electromagnetic Nondestructive imaging/evaluation method

9. A further improvement of this patent is the incorporation of elastic (vector) as well as acoustic (scalar) waves. Previous state of the art as embodied in the previous patent was restricted to imaging acoustic parameters (i.e. parameters associated with the scalar wave equation). The resulting algorithm was applicable primarily to the Breast Scanner device and to the acoustic approximation in geophysics. In the improvements listed here both types of waves (elastic—which includes two shear modes and one compressional mode) can be utilized to obtain the characteristics of the scattering potential. We will incorporate this technology into our Hazardous Waste Scanner, our mine detection scanner, our Cross Borehole and Reflection Tomography device, and into non-destructive imaging for quality control, i.e. imaging in any medium which supports shear wave energy transport.

The previous technology was restricted to the acoustic or scalar approximation to the full vector equations of motion, and therefore restricted the resulting applications of the imaging algorithm.

10. The present invention also retains, and improves upon the capability of the previous invention regarding the "incomplete view problem." That is, it provides an apparatus and method for obtaining quantitative images of high-spatial resolution of multiple elastic and viscous material properties in geometries where the source or receiver locations do not completely circumscribe the object or where the solid angles defined by the source or receivers with respect to the body are small. This applies to not only the acoustic case, but also to the elastic and electromagnetic scenarios. The presence of layering is now incorporated into the Green's function so that it actually helps to increase the resolution in the incomplete view problem.

11. Furthermore, all the advantages over state of the art discussed in the previous patent remain in the present one, and with the additional improvements enumerated above. The speed up of the imaging process, even though it covers several orders of magnitude, does not result from any degradation in image quality, just as discussed in the previous patent. Virtually all the quantitative tissue characterization capabilities of the previous algorithm are retained in the present case, with its substantial improvement over the B-scanners presently in use for medical diagnostic imaging.

12. We also add to our previous set of algorithms, a whole new class based on recursive operations. As stated above, our methods obtain much of their speed by relying on the exploitation of the Cartesian convolution structure of the scattering equations. We have recently found that when expressed in cylindrical coordinates, the scattering equations become separably symmetric in the radial coordinate while retaining convolutional form in the angular coordinate. A general 1-D operator requires order $N^2$ arithmetic operations. One dimensional convolutions can be implemented by FFT in order $N\log_2(N)$ arithmetic operations while separably symmetric kernels can be implemented recursively with order N arithmetic. Thus, cylindrical coordinates offer considerable improvement in speed. An even greater savings can be realized by going a step further by radially recurring multiple view scattering operators. This allows the calculation of the solution of the forward problems for all views (source positions) in order $N^3\log_2(N)$ arithmetic as compared to order Nbcg $N^3\log_2(N)$ arithmetic for the 2-D FFT, BCG approach ($N_{bcg}$ is the number of BCG iterations required for adequate convergence). The new approach to forward problems scattering also has the advantage that it is non-iterative—it requires a fixed amount of computation. This is particularly fortuitous since there are cases where the BCG iteration fails to converge. A detailing of this approach is given below.

13. Concepts learned during the development of our cylindrical coordinate recursionL algorithm have recently evolved into a new approach based on another scattering matrix recursion in rectangular coordinates. This new approach can be shown to require only order $N^3$ operations for computing all views of a 2-D scattering problem. While we have not completed the realization of this method into an imaging algorithm, we have tested the component recursion and have verified its accuracy. A description of the scheme is given below.

To give some idea of the type of speed-up to be expected by the judicious use of Gauss-Newton-FFT-BCG and cylindrical recursion techniques, consider the Techniscan internal report which shows that using the FFT-BCG method (the least efficient of our methods) requires approximately 0.71 sec. of CPU time (assuming 200 mflops) to solve a forward problem for a 100 by 100 sized array. Since approximately 100 views are required for the calculation of the inverse problem, 71 seconds are required to complete one forward problem, with all views and one frequency—such as would be required in the case of a transmission mode problem. The same computation carried out using standard LU decomposition requires approximately 49 minutes.

It is also reasonable, based upon computational complexity, to suppose that 2 forward problems take approximately the same amount of time as does a single Gauss-Newton correction in the inversion algorithm. Finally a typical problem may require approximately 6 or 7 Gauss-Newton corrections before it is converged. Therefore, the total time to convergence for the FFT-BCG method is approximately 213·6=1278, or about 20 minutes. This is to be compared with the LU decomposition procedure, where it is found that 486 minutes, or about 8 hours are required for the convergence. Finally, the cylindrical recursion method for solving the forward problem, by virtue of its ability to solve all views simultaneously converges in approximately 200 to 500 seconds (this depends upon the particular implementation), i.e approximately 3½ to 8 minutes.

It is very important to note that these calculations do not make any use of the parallelizability of our methods and hardware. The implementation of the simple-minded parallelization discussed in this patent results in an immediate speedup of 10 to 100 times, allowing us to do much larger problems in minutes versus the 8 hours required by the conventional approaches. This is very rough, however, the simple calculation above supports our claim that our methods far surpass present technology in wave-field imaging. The 100 by 100 problem is large enough to be practical for applications in medical technology, geophysical imaging, non-destructive testing, and environmental imaging that require a high degree of resolution in real time. For those situations that require the application of multiple frequencies (such as multiparameter imaging, and such as for reflection mode imaging) a smaller edge dimension is called for, however, the resolution achievable with our technology is much greater than present state of the art.

The ramifications of this technology translate into saved lives, and increased quality of life for many individuals. One example is breast cancer among women. This terrible disease is now expected to affect approximately 1 women in 8 within the United States. The early detection of cancerous tumours is critical to a satisfactory prognosis. The ability of our techniques to independently, accurately, and relatively quickly image material parameters of breast tissue will allow the development of a data base which contains the density, compressibility and absorption characteristics of malignant and benign tumors in various age and ethnic groups of women. The implications for early detection, and the obviation of painful biopsies renders this technology an important tool in the alleviation of suffering.

Furthermore, the development of a fast reliable technology to image position and degree of diffusion of buried hazardous waste is of critical importance to the preservation of a clean environment. Present seismic/acoustic or electromagnetic methods must make drastic simplifying assumptions which destroy resolving capabilities in order to guarantee real-time convergence. The examples contained in this patent demonstrate clearly the superiority of our imaging methods over state of the art seismic time of flight, and diffraction tomographic technology. At the same time, the simple calculation carried out above vindicates our claim to real-time for practical applications.

The optical microscopic inversion apparatus may appear to have less immediate benefits for society, but in fact its importance in biomedical research, bespeaks of manifold reasons for its dispersion also, as soon as possible.

The novel incorporation of the layered structure, while preserving the speed of the free space case, and the ability to resolve independent material parameters, and invert full 3-D vector electromagnetic wave equations are extremely noteworthy characteristics of this technology, meriting patent protection, in our view.

The purpose of the present patent, is to create images of objects which, reside in environments which were hitherto not amenable to inverse scattering. These scenarios include those that have a priori known layering, or microstructure. Furthermore, the apparatus and method described are applicable to elastic and electromagnetic layered media in addition to scalar (acoustic, or TM mode electromagnetic) media. The present patent application specifically addresses itself to areas of imaging technology (such as geophysical imaging) which were heretofore not amenable to the inverse scattering algorithm for the following very important reason: Geophysical scenarios involve, in general, relatively high contrast stratigraphic layers that are results of sedimentation of other geophysical processes. These layers have the effect of essentially "masking" the material properties (wave speed, compressibility, density and absorption) that must be imaged by the inverse scattering algorithm. The recent development of our layered Green's function, has enabled us to account for the perturbing effects of these layers in an exact manner, thereby, allowing us to, in essence, "see through" these masking layers to the important geophysical objects, scattering potential, buried therein, in real-time, and with on-site processing.

This invention will be incorporated into several devices which are designed to 1. image breast tissue, identify and locate possibly malignant tumor growth,
2. image position and spatial distribution and extent of hazardous waste buried in underground depositories. This is necessary preliminary to digging to recover and move such hazardous (or radioactive) waste, or to determine of said waste poses a threat to the water table or other aspects of the environment
3. locate schools of fish and estimate their size. This will be used to estimate fish populations and distributions
4. locate and identify undersea ordnance, distinguishing such from harmless buried objects 5. give indication of prevalence and spatial distribution of archaeological artefacts preliminary to digging.

6. Advanced Imaging Optical Microscope

The apparatus and method of the present invention provide high-quality images with high-spatial resolution of an object, including the actual internal viscous and elastic properties of the object, derived from acoustic energy propagated through the object. This is accomplished by means of sending and receiving acoustic or elastic or electromagnetic energy waves. The apparatus and method include the means for sending and receiving these waves and for the subsequent reconstruction of the image using state-of-the-art electronics to optimize the system's speed and resolution capabilities. The improvements to resolution quality of the reconstructed image is achieved using high-speed computer-aided data analysis based upon new inverse scattering techniques.

The primary object of the present invention is to provide an improved apparatus and method for acoustic, elastic, and electromagnetic property imaging.

Another primary object of the present invention is to provide the apparatus and method for reconstructing images of the actual internal material properties of an object using inverse scattering techniques, and thereby without degrading image quality through the drastic linearization approximations, such as geometrical or ray acoustic approximations or perturbation theories that include the Born or Rytov approximations.

A further purpose of this patent, is to show that the inverse scattering problem can now be solved in real-time, by the use of the improvements in the algorithm which are discussed below. The attainment of bona fide real-time, in fact is demonstrably possible with the added implementation of parallel processing, and optical computing devices. This yields a method for the real-time early detection of cancer in human tissue, Another object of the present invention is to provide substantially improved spatial resolution of an image in real time.

Exactly as in the previously patent, and for the same reasons, the full spectrum of effects due to the wave equation formulation of inverse scattering are accounted for these effects have a deleterious effect on the image quality when other methods (approximations) are used. These effects include diffraction, refraction, multiple scattering, etc. This patent continues to solve the Helmholtz wave equation exactly thereby providing the additional superior resolution, but by using the mathematical and computational aids listed above, it does this at a much faster speed than has been heretofore possible.

Still another important objective that is retained is the quantitative nature of the reconstruction, just as in the previous patent. That is, the numerical value of the actual velocity profile is constructed. This is different from the state of the art methods of inversion, where only quantitative contrasts are inverted for. The quantitative value must be known to accurately determine non-invasively the likelihood of malignancy, or failure due to mechanical imperfection in NDI.

Also, the restricted view problem has been addressed in both this and the U.S. Pat. No. 4,662,222. The solution provided by the inverse scattering procedure and method herein described is demonstrably superior to any other existing practical method of reconstruction. Mathematical proofs exist in the literature for similar results, but these have never been translated into a working, usable, imaging technology, with apparatus.

This increase is accomplished through the use of convolution and recursion exploitation coupled with the use of state of the art iterative algorithms.

We have, furthermore, extended the inverse scattering method and apparatus to image objects using electromagnetic wave energy for geophysical inverse scattering. A fundamental advance in this area is the optical imaging microscope discussed in the next section.

THE ADVANCED IMAGING OPTICAL MICROSCOPE

The optical microscope is still the main microscope for used in cytology, pathology and many areas of biology and geology. This dominance has not been changed in spite of the higher spatial resolving power of the electron microscope. There are several reason for this dominance including: (1) the lower cost of optical microscopes; (2) the ability to study live cells; (3) the ability to use stains; (4) better penetration through thin sections; (5) less complicated sample preparation.

The very presence of optical, electron and other forms of microscopy illustrates a set of principles:

1. for solving a problem no one single technology has all of the advantages
2. a more expensive technology of a certain type (e.g. electron microscopy) will always have enough advantages (e.g. better spatial resolution) over less expensive technology of another type (e.g. optical microscopy) to capture a market segment
3. the amount of use (market size) of a technology is directly proportional to its advantages and is inversely proportional to its cost.

These principles suggest that if the spatial resolution of an optical microscope could be doubled and if the capability to make quantitative images of dielectric constant (refractive index) and of absorption (e.g. dye concentrations) was also added, then its demand would be large and inversely proportional to price.

We believe that, for the lowest price class of instruments, the increase in capability of the inverse scattering microscope will be greater than the increase in its price . Even the higher priced and more sophisticated instruments will have a market segment. Thus, there will be a demand for the proposed instruments.

Based on the rapid growth of the use of confocal microscopes and given the superior performance of the inverse scattering microscope in terms of spatial resolution, contrast resolution and quantitative 3-D imaging of material properties, it also follows there will be a demand for the proposed instruments.

The advantages of the inverse scattering tomographic optical microscope can be listed:

1. double spatial resolution over present microscopes
2. equal or greater contrast resolution than confocal microscopes
3. the unique ability to make 3-D tomographic images (or multiple 2-D slices) of the refractive index and absorption coefficient of the sample.
4. the unique ability to make 3-D tomographic images (or multiple 2-D slices) of the quantitative concentration of dyes or stains within cells.
5. the ability to expand the technique to ultraviolet or soft x-ray wavelengths for their improvement in spatial resolution.

History of Problem

The common optical microscope took on most of its present perfected form due to the work of Ernst Karl Abbe in the latter half of the 19th century. He derived the first complete theoretical foundations for design all optical instruments and developed the general rules for optimizing their performance. All modern compound microscopes are basically his designs supplemented with the added benefits of more modern compound lenses and materials of construction (that further reduce lens aberrations and reduce scatter by the use of anti-reflection coatings). For such histories, see [Principles of Optics, *The New Encyclopaedia Britannica*, 15-th Edition, Vol. 25, pp 202–216, (1988), M. Born and E. Wolf, *Principals of Optics*, 4th Edition, Pergamon Press, Oxford, (1970)] which are herein incorporated by reference.

The confocal microscope system is a new and revolutionary new development because it increases the contrast sensitivity (or contrast resolution) and makes possible the visualization of structures within cells that have been invisible heretofore. It adds to the standard compound microscope the new elements of: (1) focal point scanning and (2) electronic image detection. Focal point scanning is achieved by a special condenser lens that focuses a transmitted light beam to a point in the focal plane of the main microscope objective lens (thus forming a confocal lens pair). Reflection versions have been developed. In either version, this point of light is then scanned in a raster (or the specimen is moved in a raster). In some versions a scanned laser beam is used. The use of a single illumination point minimizes the scattering of light from other parts of the specimen. This scattered light would normally mask or hide the subtle changes in transmission or reflection from cell structures. The use of electronic image detection (such as by a charge coupled solid state camera) provides the added advantages of being more sensitive than the human eye to small changes in brightness and allows the scanned image to be integrated. The integrated image is scanned electronically, digitized, enhanced and displayed on a television monitor or photographed.

In spite of their greater contrast resolution, confocai microscopes, like all other compound microscopes, have three basic limitations: (1) spatial resolution is still limited to about one wave length of light; (2) the images made are not truly three-dimensional; and (3) the images are not truly quantitative in intrinsic properties. Spatial resolution is given by the formula (Rayleigh limit) $\Delta x \geq 1.22 \lambda/(n \sin \phi)$, where n is the index of refraction of the media between the objective lens and the specimen, and where $\phi$ is the half angle of the cone defined by the objective lens and the region in the specimen under study. In air, using $\phi=60$ degrees, a good objective lens would give $\Delta x \geq 1.22 \lambda/[(1.0) (0.866)] = 1.41 \lambda$. Even an oil immersion systems, where $n \approx 1.5$ and $\phi$ is limited to about 60 degrees, gives $\alpha x \geq 1.22 \lambda/[(1.5) (0.866)] = 0.94 \lambda$.

Solution to optical microscope improvement by inverse scattering

We have developed a high resolution, quantitative tomographic imaging method called inverse scattering tomography [Borup, 1992 and Wiskin, 1991]. This algorithm and the corresponding software inverts the electromagnetic wave equation to produce three-dimensional (3-D) images of dielectric constant and conductivity of bodies. This inverse scattering algorithm provides images of speed of light $c(x)$ and optical absorption $\alpha(x)$ which is proportional to conductivity. The theory for finding the these parameters has been described in the previous discussion on electromagnetic imaging. The speed of light $c(x)$ and the optical absorption $\alpha(x)$ are related to the permittivity and conductivity by the respective equations $c(x)=(\epsilon_0/\epsilon(X))^{1/2}$, and $\alpha(x)=(\omega/c)2^{1/2}[(1+\omega^{-2} \sigma^2(x)\epsilon^{-2}(x))^{1/2}-1]^{1/2}$. For $\sigma(x)<\omega\epsilon(x)$, the expression for $\alpha(x)$ simplifies to $\alpha(x)=\sigma(x)/(2c(x)\epsilon(x))$.

We have tested this method using microwaves in the laboratory and have found that we can produce images of light $c(x)$ and the optical absorption $\alpha(x)$. All inverse scattering methods are applicable to any system that can provide both amplitude and phase data. When both the amplitude and phase of the scattered field are known, then images with ½ wave length spatial resolution can be computed. The projected importance of such new imaging capabilities to the fields of medicine, biology and material science is truly enormous.

Before leaving this section, it is important to point out that the laser based interferometric approach, described here, is not restricted to visible light. Indeed, present state of the art techniques in x-ray optics such as x-ray laser sources, x-ray mirrors and lenses, etc., suggest the potential for an x-ray inverse scattering microscope.

These and other objectives of the present invention will become more fully apparent from the following description and appended claims taken in conjunction with the accompanying drawings and flowcharts.

DETAILED DESCRIPTION OF INVENTION

The following explanation of notation is given to facilitate obtaining an understanding of the invention. Unless otherwise noted, the notation will essentially be the same as U.S. Pat. No. 4,662,222. The scattering potential $\gamma$ changes from point to point within an object or body as well as changing with frequency of the incident field. Thus $\gamma_{\omega j} \equiv \gamma_\omega(x_j)$, $x_j \in R^3$ or $R^3$ used to signify the scattering potential at pixel j or point j, for the incident field at frequency $\omega$. $\gamma_\omega$ can be considered to be the vector composed of all values of j, i.e. for all pixels: $\gamma_\omega \equiv (\gamma_{\omega 1}\ \gamma_{\omega 2}\ \cdots\ \gamma_{\omega N})^T$, where T indicates "transpose". For our purposes of exposition and simplicity, we will hence forth consider the case where $\gamma$ is independent of frequency, although this is not necessary. This convention also is essentially the same as that employed in the U.S. Pat. No. 4,662,222.

NOTATION

VECTOR FIELD NOTATION

The following notation will be used throughout the patent to denote a vector field describing elastic waves, or electromagnetic waves:

$$\mathbf{f}(\mathbf{r}) \equiv \begin{pmatrix} f_x(x, y, z) \\ f_y(x, y, z) \\ f_z(x, y, z) \end{pmatrix} \equiv (f_x\ f_y\ f_z)^T$$

(T—denotes "transpose") is used to represent the total field.

$$\mathbf{f}^i(\mathbf{r}) \equiv \begin{pmatrix} f^i_x(x, y, z) \\ f^i_y(x, y, z) \\ f^i_z(x, y, z) \end{pmatrix} \equiv (f^i_x\ f^i_y\ f^i_z)^T$$

(T—denotes "transpose") is used to denote the incident field. The incident field is the field that would be present if there was no object present to image. In the case of layering in the ambient medium, it is the field that results from the unblemished, piecewise constant layering.

The scattered field is the difference between the total field and the incident field, it represents that part of the total field that is due to the presence of the inhomogeneity, i.e. the "mine" for the undersea ordnance locater, the hazardous waste cannister for the hazardous waste locator, the school of fish for the echo-fish locator/counter, and the malignant tumor for the breast scanner: $\mathbf{f}^s(r) \equiv \mathbf{f}(r) - \mathbf{f}^i(r)$ $$\mathbf{f}^s(\mathbf{r}) \equiv \begin{pmatrix} f_x^s(x,y,z) \\ f_y^s(x,y,z) \\ f_z^s(x,y,z) \end{pmatrix} \equiv (f_x^s \ f_y^s \ f_z^s)^T$$

T—denotes "transpose"

$f_{\omega\phi}^{inc}(r)$ denotes the scalar incident field coming from direction (source position) $\phi$ at frequency $\omega$. The r could represent either a 3 dimensional, or a 2 dimensional vector of position.

SCALAR FIELD NOTATION

A scalar field is indicated by a nonbold $f(r)$, $r \in R^3$.

EXAMPLE 1

ACOUSTIC SCATTERING—SCALAR MODEL EQUATIONS

This first example is designed to give the basic structure of the algorithm and to point out why it is so fast in this particular implementation compared to present state of the art. The background medium is assumed to be homogeneous medium (no layering). This example will highlight the exploitation of convolutional form via the FFT, the use of the Frechet derivative in the Gauss-Newton and FR-RP algorithms, the use of the biconjugate gradient algorithm (BCG) for the forward problems, the independence of the different view, and frequency, forward problems. It will also set up some examples which will elucidate the patent terminology. The field can be represented by a scalar quantity $f$. The object is assumed to have finite extent The speed of sound within the object is $c=c(x)$. The speed of sound in the background medium is the constant $c_o$. The mass density is assumed to be constant. The attenuation is modelled as the imaginary part of the wavespeed. These are simplifying assumptions, which we make so as to focus on the important aspects of the imaging algorithm. By no means is the imaging algorithm restricted to the scalar case, either in theory, or, more importantly, in practical implementation.

We consider the two dimensional case first of all (equivalently the object and incident fields are assumed to be constant in one direction). Given an acoustic scatterer with constant mass density and constant cross-section in z, illuminated by a time harmonic incident field, $f_{\omega\phi}^{inc}$, with $e^{i\omega t}$ time dependence and source position (incident angle), $\phi$, the total field satisfies the following integral equation.

$$f_{\omega\phi}^{inc}(\bar{\rho}) = f_{\omega\phi}(\bar{\rho}) - \int\int \gamma(\bar{\rho'}) f_{\omega\phi}(\bar{\rho'}) g_\omega(|\bar{\rho} - \bar{\rho'}|) dx' dy' \quad (1)$$

where $$\gamma = \frac{c_0^2}{c^2} - 1,$$

$\bar{\rho}=(x,y)$ and where $f \equiv f_{\omega\phi}$ is the field internal to the object at frequency $\omega$ and resulting from the incident field from source position $\phi,$: $f_{\omega\phi}^{inc}$. The 2-D Helmholtz Green's function is given by:

$$g_\omega(|\bar{\rho} - \bar{\rho'}|) = \frac{k_\omega^2}{4i} H_0^{(2)}(k_\omega |\bar{\rho} - \bar{\rho'}|), k_\omega = \frac{\omega}{c_0}.$$

where $H_o^{(2)}$ is the Hankel function of the second kind, and zeroth order.

Now it is required to compare the field measured at the detectors, with the field as predicted by a given guess, $\gamma^{(n)}$, for $\gamma$. To accomplish this, first define the scattered field at the detectors as the total field minus the incident field.

$$f_{\omega\phi}^{sc}(\bar{\rho}) = f_{\omega\phi}(\bar{\rho}) - f_{\omega\phi}^{inc}(\bar{\rho})$$

This represents the field due entirely to the scattering potential. Using this relation to rewrite (1), gives $$f_{\omega\phi}^{sc}(\bar{\rho}) = \int\int \gamma(\bar{\rho'}) f_{\omega\phi}(\bar{\rho'}) g_\omega(|\bar{\rho} - \bar{\rho'}|) dx' dy' \quad (2)$$

These two equations, (1) and (2) are the basis of the imaging algorithm. They must be discretized, then exported to the computer in order to solve practical imaging problems. The purpose of the apparatus and method herein described, is to solve the discretized form of these equations without making any linearizing assumptions (such as used in conventional diffraction tomography), and in real time, with presently available computers.

Discretization of the Acoustic Free-Space Lippmann Schwinger Integral Equation and Green's Function—2D Free Space Case Let us for a moment drop the frequency and source position subscripts. The scalar field "$\gamma f$" is given by $$\gamma f \begin{pmatrix} x' \\ y' \end{pmatrix} \equiv \gamma \begin{pmatrix} x' \\ y' \end{pmatrix} f \begin{pmatrix} x' \\ y' \end{pmatrix}$$

Discretization of the integral equation is achieved by first decomposing this function into a linear combination of certain (displaced) basis functions $$\gamma f \begin{pmatrix} x' \\ y' \end{pmatrix} \approx \sum_{n'=1}^{N_x} \sum_{m'=1}^{N_y} a_{n'm'} S\begin{pmatrix} x' - n'\delta \\ y' - m'\delta \end{pmatrix} \quad (3)$$

where it has been assumed that the scatterer $\gamma$ lies within the support $[0,N_x\delta] \times [0,N_y\delta]$—a rectangular subregion.

The basis functions S can be arbitrary except that we should have cardinality at the grid nodes:

$$S\begin{pmatrix} 0 \\ 0 \end{pmatrix} = 1$$

whereas for all other choices of n', m', $$S\begin{pmatrix} n'\delta \\ m'\delta \end{pmatrix} = 0, n', m' \neq 0$$

FIG. 2 shows an example of such a function, the 2-D "hat" function. Our algorithm uses the "sinc" function has its basic building block—the Whittaker sinc function which is defined as:

$$\text{sinc}(x) = \frac{\sin(\pi x)}{\pi x}$$

The two dimensional basis functions are defined by the tensor product:

$$S\begin{pmatrix} x' - n'\delta \\ y' - m'\delta \end{pmatrix} = \text{sinc}((x' - n'\delta)/\delta) \cdot \text{sinc}((y' - m'\delta)/\delta) \quad (4)$$

If the equality in equation (3) is presumed to hold at the grid points x=nδ, y=mδ: the coefficients $\alpha_{nm}$ can be determined to be precisely the value of the field γf:

$$\gamma f\begin{pmatrix} x' \\ y' \end{pmatrix} \equiv \sum_{n'=1}^{N_x} \sum_{m'=1}^{N_y} \gamma\begin{pmatrix} n'\delta \\ m'\delta \end{pmatrix} f\begin{pmatrix} n'\delta \\ m'\delta \end{pmatrix} S\begin{pmatrix} x' - n'\delta \\ y' - m'\delta \end{pmatrix} \quad (5)$$

Now this expression for the product γf can be substituted into (1):

$$f^i\begin{pmatrix} x \\ y \end{pmatrix} = f\begin{pmatrix} x \\ y \end{pmatrix} - \frac{k_\omega^2}{4i} \sum_{n'} \sum_{m'} \gamma_{n'm'} f_{n'm'} \int H_0^{(2)}(k_\omega|\bar{\rho} - \bar{\rho}'|) S\begin{pmatrix} x' - n'\delta \\ y' - m'\delta \end{pmatrix} d^2\rho' \quad (6)$$

In particular this equation holds at $$\begin{pmatrix} x \\ y \end{pmatrix} = \begin{pmatrix} n\delta \\ m\delta \end{pmatrix}$$

for which we get:

$$f_{nm}^i = f_{nm} - \sum_{n'=1}^{N_x} \sum_{m'=1}^{N_y} \gamma_{n'm'} f_{n'm'} g_{n-n',m-m'}, \quad \begin{array}{l} n = 1, \ldots, N_x \\ m = 1, \ldots, N_y \end{array} \quad (7)$$

where the 2-D discrete Green's function is defined as:

$$g(n - n', m - m') \equiv \quad (8)$$

$$\frac{k^2}{4i} \int H_0^{(2)}\left(k\left|\begin{pmatrix} n\delta - x' \\ m\delta - y' \end{pmatrix}\right|\right) S\begin{pmatrix} x' - n'\delta \\ y' - m'\delta \end{pmatrix} d^2\rho'$$

Although it is not clear that the dependence of g on m and n is as so stated, in is indeed the case, since we have by the substitution of the transformation x'→x'+nδ y'→y'+mδ into this last equation shows explicitly that the discretized Green's function "g", does in fact depend only on the differences n—n', and m—m". Thus the discrete equation (7) has inherited the convolutional form of the continuous equation (1). It is this fact which allows the use of the 2-D FFT to compute the summation in (8) in only order $N_x N_y \log_2(N_x N_y)$ arithmetic operations and is therefore critical to the real-time speed of the algorithm.

EXPRESSION OF THE DISCRETIZED LIPPMANN-SCHWINGER EQUATION IN COMPACT NOTATION

The discretized Lippmann-Schwinger equation can be rewritten using a compact operator notation. We write (7) as:

$$f_{\omega\phi}{}^i = (I - G_\omega[\gamma])f_{\omega\phi} \quad (9)$$

where $G_\omega$ represents 2-D discrete convolution with the discrete, 2-D Green's function for frequency ω and [γ] denotes the operator consisting of pointwise multiplication by the 2-D array γ. I denotes the identity operator.

In exactly the same manner, and with the same definitions, we can write the scattered field equation (2) as:

$$f_{\omega\phi}{}^{sc} = G_\omega[\gamma]f_{\omega\phi} \quad (10)$$

for the scattered field inside of the object, and finally $$f_{\omega\phi}{}^{meas} = T(f_{\omega\phi}{}^{sc}) = T(G_\omega[\gamma]f_{\omega\phi}) \quad (11)$$

for the measured value of the scattered field at the detectors. The T operator is used to indicate the "truncation" of the calculated scattered field, calculated on the entire convolution range (a rectangle of samples $[1,N_x] \times [1,N_y]$ covering γ), onto the detectors which lie outside the support of γ. (see FIG. 1.). In other words T is simply the operation of "picking" out of the rectangular range of the convolution, those points which coincide with receiver locations.

EXTENSION OF THE METHOD TO REMOTE RECEIVERS WITH ARBITRARY CHARACTERISTICS

In the event that the receivers do not lie within the range of the convolution and/or they are not simple point receivers, we need to modify the measurement equations (11). It is well known that, given source distributions within an enclosed boundary, the scattered field everywhere external to the boundary can be computed from the values of the field on the boundary by an application of Green's theorem with a suitably chosen Green's function, i.e.:

$$f^s(\bar{p}) = \oint_B f^s(\bar{p}')P(\bar{p}, \bar{p}')dl', \bar{p} \text{ outside boundary } B \quad (12)$$

where P is the Green's function, the integral is about the boundary, and dl' is the differential arclength (in the 3-D case, the integral is on an enclosing surface). Equation (12) allows for the construction of a matrix operator which maps the boundary values of the rectangular support of the convolution ($2N_x + 2N_y - 4$ values in the discrete case) to values of the scattered field external to the rectangle. Furthermore, this "propagator matrix" can be generalized to incorporate more complex receiver geometries. For example, suppose that the receiver can be modeled as an integration of the scattered field over some support function, i.e.;

$$v_n \equiv \text{signal from receiver } n = \int\int f^s(\bar{p})S_n(\bar{p})ds \quad (13)$$

where $S_n$ is the support of receiver n. Then from (12):

$$v_n = \oint_B f^s(\bar{p}')\left\{\int\int S_n(\bar{p})P(\bar{p},\bar{p}')ds\right\}dl', \bar{p} \text{ outside boundary } B \quad (14)$$

$$= \oint_B f^s(\bar{p}')P'(n,\bar{p}')dl', P'(n,\bar{p}') = \int\int S_n(\bar{p})P(\bar{p},\bar{p}')ds$$

Discretizing the integral gives the matrix equation:

$$v_n = \sum_{l=1}^{N_b} P'_{nl}f_l^s, n = 1, \ldots, N_d \quad (15)$$

where $N_b=2N_x+2N_y-4$ is the number of boundary (border) pixels and $N_d$ is the number of receivers. Equation (15) defines the matrix that we shall henceforth refer to as P or the "propagator matrix" for a given distribution of external receivers. The equation:

$$v_{\omega\phi}^{meas}=P_\omega(G_\omega[\gamma]f_{\omega\phi}) \quad (16)$$

includes (11) as a special case for which the receivers are point receivers inside the convolution support. Note that P is a function of frequency, but is not a function of source position. $v_{\omega\phi}^{meas}$ is a vector of dimension $N_d$.

The added flexibility of this propagator matrix formulation is particularly advantageous when interfacing our algorithms with real laboratory or field data. Often times the precise radiation patterns of the transducers used will not be known a priori. In this event, the transducers must be characterized by measurements. The results of these measurements can be easily incorporated into the construction of the propagator matrix P allowing the empirically determined transducer model to be accurately incorporated into the inversion.

Equations (9) and (16) then provide in compact notation the equations which we wish to solve for the unknown scattering potential, $\gamma$. First we consider the forward problem, i.e. the determination of the field $f_{\omega\phi}$ for a known object function $\gamma$ and known incident field, $f_{\omega\phi}^i$. Then we establish how this forward problem is then incorporated into the solution of the inverse problem, i.e., the determination of $\gamma$ when the incident fields, and the received signals from a set of receivers are known. Note that the internal field to the object is also—along with the object function $\gamma$, an unknown in the inverse problem.

Since (9) is linear in $f_{\omega\phi}$ it can be solved by direct inversion of the linear system:

$$f=(I-G[\gamma])^{-1}f^i \quad (17)$$

In discrete form, this is just a matrix equation (after linearly ordering the 2-D supports of the domain and range into vectors). Since the dimension of the range and domain of the linear system is $N_xN_y$, the dimension of the linear system is the same giving a total of $(N_xN_y)^2$ elements. The arithmetic required to solve the system by standard direct means is thus order $(N_xN_y)^3$. In other words, a doubling of the edge dimension of the problem space will increase the CPU time required by a factor $2^6=64$ times! The arithmetic work required will quickly become intolerable as the size of the problem increases. It is precisely this large growth rate which has convinced many researchers not to pursue inverse scattering approaches based on integral equations. One could, of course, go to an iterative method. A single iteration of an iterative linear system solver, such as bi-conjugate gradients requires order $(N_xN_y)^2$ operations (essentially a matrix-vector product). It can be shown that the growth rate in the number of required iterations for sufficient convergence for the BCG algorithm is order N for this equation. Thus, the overall computational complexity is order $N^5$—only one order of N has been saved over direct inversion. Since inverse problems in 2-D generally require order N views, the iteration must be done N times and we are back to order $N^6$ computation for BCG.

The key to overcoming this objection is the convolutional form of (7). If this is exploited by use of the FFT algorithm, the computation needed to perform a matrix-vector product is only order $N_xN_y \log_2(N_xN_y)$. This allows the BCG algorithm to be applied to a single view with order $N^3 \log_2(N)$ operations and to all views with order $N^4 \log_2(N)$ operations. Due to the slow growth rate of $\log_2(N)$, this is essentially a reduction of two orders of N over nonconvolutional methods. Also, this convolutional approach avoids the necessity of storing the order $N^4$ computer words needed to contain the linear system in full matrix form. Only order $N^2$ words are needed due to the shift invariance of the discrete Green's kernel in (7). It is these two savings, more than any other advance that we have made, that allows us to perform inverse scattering in reasonable time for meaningfully sized problems. The use of BCG over the original CG algorithm also represents a major advance since it converges in essentially the square root of the number of iterations needed by CG. This combination of FFT and CG algorithm was originally developed in [Borup, 1989, Ph. D. dissertation, Univ. of Utah, Salt Lake City], herein incorporated by reference.

THE IMAGING OR INVERSE PROBLEM

In order to solve the imaging problem, we need a set of equations relating the unknown scattering potential, $\gamma$, and total fields, $f_{\omega\phi}$, with measurements of the scattered field on a set of external detectors. These detector equations are given in (16). Equation (16), and the internal field equations (9) are the equations which are solved simultaneously to determine $\gamma$ and the $f_{\omega\phi}$. There are $N_xN_y$ unknowns corresponding to the $\gamma$ values at each of the grid points, and $N_xN_y \times \Omega \times \Phi$, unknowns corresponding to the unknown fields, $\Omega$ is the number of frequencies, and $\Phi$ is the number of source positions (angles). We have improved upon the state of the art by considering the internal field equations to define $f_{\omega\phi}$. for a given $\gamma$. Thus the total number of unknowns is reduced to $N_xN_y$.

The total number of measurement equations is $N_d \times \Omega \times \Phi$ where $N_d$ is the number of detectors. In the general case, where, the sources and detectors do not completely surround the object, the problem of determining $\gamma$ is "ill-posed", in a precise mathematical sense, therefore, in order to guarantee a solution, the number of equations $N_d \times \Omega \times \Phi > N_xN_y$, is chosen to be larger than the number of pixel values for over determination. Then the system is solved in the least squares sense. More specifically the solution of (9,16) for $\gamma$ and the set of fields, $f_{\omega\phi}$, in the least squares sense is obtained by minimizing the real valued, nonlinear functional:

$$\min_\gamma \sum_{\omega,\phi} \|r_{\omega\phi}\|^2 \equiv \min_\gamma \sum_{\omega,\phi} \|v_{\omega\phi}^{meas} - P_\omega G_\omega[f_{\omega\phi}]\gamma\|^2 \quad (18)$$

subject to the satisfaction of the total field equations, (9), as constraints. The vector $r_{\omega\phi}$ of dimension $N_d$ is referred to as the "residual" for frequency, $\omega$, and angle, $\phi$.

The methods used to solve the nonlinear optimization problem in our inverse scattering algorithms are, thus far, all "gradient methods" in that second derivative information is not used (as it is in the full Newton and quasi-Newton methods). The principal computation involves the calculation of the gradient vector of (18). A straight forward calculation gives the gradient formula: $\nabla f(x)=-J^H(x)r(x)$ where the superscript H denotes the Hermitian transpose (complex conjugate transpose of the matrix) and J is the Jacobian of the nonlinear system:

$$J(x) = \begin{bmatrix} \frac{\partial}{\partial x_1}a_1 & \cdots & \frac{\partial}{\partial x_N}a_1 \\ \vdots & \ddots & \vdots \\ \frac{\partial}{\partial x_1}a_M & \cdots & \frac{\partial}{\partial x_N}a_M \end{bmatrix}. \tag{19}$$

The simplest gradient algorithm is the Gauss-Newton (GN) iteration. The GN iteration for finding a solution to $\nabla f=0$ is given by:

$$x^{(n)} = y - a(x^{(n)}) \tag{20.1}$$

$$\delta x^{(n)} = (J_n^H J_n)^{-1} J_n^H r^{(n)}, \tag{20.2}$$

$$x^{(n+1)} = x^{(n)} + \delta x^{(n)}. \tag{20.3}$$

where a is the vector of nonlinear equations. This iteration is well defined assuming that the columns of $J_n$ remain linearly independent. Since (20.2) is equivalent to the quadratic minimization problem:

$$\min_{\delta \mathbf{x}^{(n)}} \| J_n \delta \mathbf{x}^{(n)} - \mathbf{r}^{(n)} \|_M^2 \tag{21}$$

it can be solved by the minimum residual conjugate gradient method (MRCG). This approach also ensures that small singular values in $J_n$ will not amplify noise if care is taken not to overconverge the iteration.

In the previous U.S. Pat. No. 4,662,222 the fields $f_{\omega\phi}$ were considered to be independent variables. In this present patent these fields are considered to be dependent variables, with dependence upon $\gamma$ given implicitly by $$f_{\omega\phi}^{(n)} = (I - G_\omega[\gamma^{(n)}])^{-1} f_{\omega\phi}^{inc}.$$

In order to find the Jacobian expression we must then differentiate the residual vector defined in (18) with respect to $\gamma$. The details of this calculation are given in [Borup, 1992.]. The result is:

$$J_{\omega\phi} = \frac{\delta r_{\omega\phi}}{\delta \gamma} = P_\omega (I - [\gamma] G_\omega)^{-1} [f_{\omega\phi}] \tag{22}$$

The final Gauss-Newton algorithm for minimizing (18) subject to equality constraints (9) is:

GN 1.  Select an initial guess, $\gamma^{(0)}$.

GN 2  Set $n = 0$

GN 3  Solve the forward problems using (biconjugate gradients)

$$\text{BCG:} \quad f_{\omega\phi}^{(n)} = (I - G_\omega[\gamma^{(n)}])^{-1} f_{\omega\phi}^{inc}, \quad \begin{array}{l} \omega = 1, \ldots, \Omega \\ \phi = 1, \ldots, \Phi. \end{array}$$

GN 4  Compute the detector residuals:

$$r_{\omega\phi}^{(n)} = v_{\omega\phi}^{meas} - P_\omega G_\omega [f_{\omega\phi}^{(n)}] \gamma^{(n)}, \quad \begin{array}{l} \omega = 1, \ldots, \Omega \\ \phi = 1, \ldots, \Phi. \end{array}$$

GN 5  If $\sum_{\omega\phi} \| r_{\omega\phi}^{(n)} \|^2 < \varepsilon$, stop.

GN 6  Use MRCG to find the least squares solution to the quadratic minimization problem $$\min_{\delta\gamma^{(n)}} \sum_{\omega\phi} \| r_{\omega\phi}^{(n)} + P_\omega G_\omega (I - [\gamma^{(n)}] G_\omega)^{-1} [f_{\omega\phi}^{(n)}] \delta\gamma^{(n)} \|^2$$

for $\delta\gamma^{(n)}$.

GN 7  Update $\gamma$: $\gamma^{(n+1)} = \gamma^{(n)} + \delta\gamma^{(n)}$.

GN 8  Set $n = n + 1$, go to GN 3

The crux of the GN iteration is GN 6 where the overdetermined quadratic minimization problem is solved for the scattering potential correction. This correction is approximated by applying a set of M iterations of the MRCG algorithm. The details of GN 6 are:

GN.6.1  Initialize the zeroth iterate of MRCG: $\delta\gamma^0 = 0$

GN.6.2  Initialize the MRCG residuals equal to the GN outer loop residuals: $r_{\omega\phi}^0 = r_{\omega\phi}^{(n)}$ Note that iterates pertaining to the MRCG iteration are indexed without the ( ) in order to distinguish them from outer GN loop iterates.

GN.6.3  Compute the gradient of the MRCG quadratic functional:

$$g^0 = \sum_{\omega\phi} [f_{\omega\phi}^{*(n)}] (I - G_\omega^* [\gamma^{*(n)}])^{-1} G_\omega^* P_\omega^H r_{\omega\phi}^0$$

GN.6.4  Set the initial search direction equal to minus the gradient: $p^0 = -g^0$ GN.6.5  Set $m = 0$ GN.6.6  Compute $$t_{\omega\phi}^m = P_\omega G_\omega (I - [\gamma^{(n)}] G_\omega)^{-1} [f_{\omega\phi}^{(n)}] p^m, \quad \begin{array}{l} \omega = 1, \ldots, \Omega \\ \phi = 1, \ldots, \Phi. \end{array}$$

GN.6.7  Compute the quadratic step length:

$$a^m = \sum_{\omega\phi} \| t_{\omega\phi}^m \|^2 / \| g^m \|^2$$

GN.6.8  Update the solution of the quadratic minimization:

$$\delta\gamma^{m+1} = \delta\gamma^m + a^m p^m$$

GN.6.9  Update the MRCG residuals:

$$r_{\omega\phi}^{m+1} = r_{\omega\phi}^m + a^m t_{\omega\phi}^m$$

GN.6.10  Compute the gradient of the MRCG quadratic functional:

$$g^{m+1} = \sum_{\omega\phi} [f_{\omega\phi}^{*(n)}] (I - G_\omega^* [\gamma^{*(n)}])^{-1} G_\omega^* P_\omega^H r_{\omega\phi}^{m+1}$$

GN.6.11  Compute:

$$\beta^m = \| g^{m+1} \|^2 / \| g^m \|^2$$

-continued

GN.6.12 Update the MRCG search direction:

$$p^{m+1} = -g^{m+1} + \beta^m p^m$$

GN.6.13 If $m = M$, go to GN.6.15

GN.6.14 $m = m + 1$, go to GN.6.8

GN.6.15 Equate the solution of the quadratic minimization problem with the last iterate MRCG:

$$\delta\gamma^{(n)} = \delta\gamma^M$$

6.16 Return to the GN algorithm at GN 7.

A problem with the algorithm above is the presence of the inverse of the transposed total field equation $(I-[\gamma^{(n)}]G_\omega)^{-1}$ in the computation of the Jacobian and its adjoint in 6.3 and 6.10 Since we do not invert (or even store) these large linear systems, the occurrence of these inverse operators must be dealt with. This problem can however be overcome by computing the action of this operator on a given vector, as needed during the MRCG iteration, by a few iterations of BCG. When performed in this way, the shift invariance of the Green's function is exploited in a maximal way. No large matrices need to be inverted or stored. This is because the Jacobian implementation now consists exclusively of shift invariant kernels (diagonal kernels such as pointwise multiplication by $\gamma$ or $f$ and the shift invariant kernel composed of convolution with the Green's function) Such shift invariant kernels can be implemented efficiently with the FFT as previously described.

An even greater increase in numerical efficiency can be obtained in cases for which the approximation:

$$(I-[\gamma^{(n)}]G_\omega)^{-1} \approx (I+[\gamma^{(n)}]G_\omega) \quad (23)$$

(which is similar to the Born approximation of the forward problem) can be used in the Jacobian. This has been found to be the case for many acoustic scattering problems for biological tissue, and for EM problems for which the contrast in dielectric contrast is small.

The other two gradient algorithms that are used to solve the inverse scattering equations are the Fletcher-Reeves and Ribiere-Polak algorithms. For the inverse scattering equations, they are given by the iteration:

RP 1. Select an initial guess, $\gamma^{(0)}$.

RP 2 Solve the forward problems using (biconjugate gradients) BCG:

$$f_{\omega\phi}^{inc} = (I - G_\omega[\gamma^{(0)}])f_{\omega\phi}^{(0)}, \quad \begin{array}{l}\omega = 1, \ldots, \Omega \\ \phi = 1, \ldots, \Phi.\end{array}$$

for the internal fields, $f_{\omega\phi}^{(0)}$.

RP 3 Compute the detector residuals:

$$r_{\omega\phi}^{(0)} = P_\omega G_\omega[f_{\omega\phi}^{(0)}]\gamma^{(0)} - v_{\omega\phi}^{meas}, \quad \begin{array}{l}\omega = 1, \ldots, \Omega \\ \phi = 1, \ldots, \Phi.\end{array}$$

RP 4 Compute the gradient:

$$r_{\omega\phi}^{(0)} = P_\omega G_\omega[f_{\omega\phi}^{(0)}]\gamma^{(0)} - v_{\omega\phi}^{meas}, \quad \begin{array}{l}\omega = 1, \ldots, \Omega \\ \phi = 1, \ldots, \Phi.\end{array}$$

RP 5 Compute the search direction:

-continued $$p^{(0)} = -g^{(0)}$$

RP 6 $n = 0$

RP 7 Compute the Jacobian operating on the search direction:

$$t_{\omega\phi}^{(0)} = P_\omega G_\omega(I - [\gamma^{(0)}]G_\omega)^{-1}[f_{\omega\phi}^{(0)}]p^{(0)}, \quad \begin{array}{l}\omega = 1, \ldots, \Omega \\ \phi = 1, \ldots, \Phi.\end{array}$$

RP 8 Compute the step length (quadratic approximation):

$$\alpha_n = -Re \sum_{\omega\phi} (r_{\omega\phi}^{(n)}, t_{\omega\phi}^{(n)}) / \sum_{\omega\phi} \|t_{\omega\phi}^{(n)}\|^2$$

RP 9 Update the solution:

$$\gamma^{(n+1)} = \gamma^{(n)} + \alpha_n p^{(n)}$$

RP 10 Solve the forward problems using (biconjugate gradients) BCG:

$$f_{\omega\phi}^{inc} = (I - G_\omega[\gamma^{(n+1)}])f_{\omega\phi}^{(n+1)}, \quad \begin{array}{l}\omega = 1, \ldots, \Omega \\ \phi = 1, \ldots, \Phi.\end{array}$$

RP 11 Compute the detector residuals:

$$r_{\omega\phi}^{(n+1)} = P_\omega G_\omega[f_{\omega\phi}^{(n+1)}]\gamma^{(n+1)} - v_{\omega\phi}^{meas}, \quad \begin{array}{l}\omega = 1, \ldots, \Omega \\ \phi = 1, \ldots, \Phi.\end{array}$$

RP 12 If $\sum_{\omega\phi} \|r_{\omega\phi}^{(n)}\|^2 < \varepsilon$, stop.

RP 13 Compute the gradient:

$$g^{(n+1)} = \sum_{\omega\phi} [f_{\omega\phi}^{*(n+1)}](I - G_\omega^*[\gamma^{*(n+1)}])^{-1} G_\omega^* P_\omega^H r_{\omega\phi}^{(n+1)}$$

RP 14 Compute:

$$\beta_n = \begin{cases} \|g^{(n+1)}\|^2 / \|g^{(n)}\|^2, & \text{Fletcher-Reeves} \\ (g^{(n+1)}, g^{(n+1)} - g^{(n)}) / \|g^{(n)}\|^2, & \text{Ribere-Pollack} \end{cases}$$

RP 15 Update the search direction:

$$p^{(n+1)} = -g^{(n+1)} + \beta_n p^{(n)}$$

RP 16 $n = n + 1$, go to RP 7

The distinction between FR and RP lies in the calculation of $\beta$ in RP 14. It is generally believed that the RP calculation is more rapidly convergent. Our experience indicates that this is true and so we generally use the RP iteration rather than FR.

Comparison of the linear MRCG iteration and the nonlinear RP iteration reveals that they are very similar. In fact, RP is precisely a nonlinear version of MRCG. Note that the only difference between them lies in the fact that the RP residuals, computed in steps RP.10 and RP.11 involve recomputation of the forward problems while the MRCG residuals are simply recurred in 6.9 (additional, trivial, differences exist in the computation of the $\alpha$'s and $\beta$'s). In other words, the RP iteration updates the actual nonlinear system at each iteration, while the MRCG simply iterates on the quadratic functional (GN linearization). The overall GN-MRCG algorithm contains two loops—the outer linearization loop, and the inner MRCG loop, while the RP algorithm contains only one loop. Sine the RP algorithm updates the forward solutions at each step, it tends to converge faster than GN with respect to total iteration count (number of GN outer iterations times the number, M, of inner loop MRCG iterates). The GN method is, however, generally faster since an MRCG step is faster than an RP step due to the need for forward recomputation in the RP step. The overall codes for the GN-MRCG algorithm and the RP algorithm are so similar that a GN-MRCG code can be converted to an RP code with about 10 lines of modification.

Before leaving this example it is important to note that the examples given in this patent all assume that the different frequencies, ω, and views, φ, are all computed in serial fashion. It is important to note however, that another important link in the real time implementation of our algorithm, is the fact that the different frequencies and different views are independent in both the forward problem and Jacobian calculations, and therefore can be computed independently and in parallel. This should be clear by examining, for example, the computations in GN.3 and GN.6.3. The forward problem calculations, GN.3 are completely independent and in the gradient calculation, GN.6.3, the computations are independent in frequency and view up to the point at which these contributions are summed to give the gradient. The GN and RP algorithms could thus be executed on a multinode machine in parallel with node intercommunication required only 2 to 3 times per step in order to collect sums over frequency and view number and to distribute frequency/view independent variables, such as scattering potential iterates, gradient iterates, etc., to the nodes.

EXAMPLE 2

IMAGE RECONSTRUCTION IN LAYERED AMBIENT MEDIA USING OPTIMIZATION OF A BILINEAR OR QUADRATIC OBJECTIVE FUNCTION CONTAINING ALL DETECTOR MEASUREMENT EQUATIONS, AND WITH INTERNAL FIELDS REPRESENTED AS A FUNCTION OF THE SCATTERING POTENTIAL

The examples in the previous U.S. Pat. No. 4,662,222 were characterized by the consideration of both the internal fields, and the object function γ to be independent variables of equal importance. The example given above, however, has the distinguishing characteristic that the object function γ is considered to be the sole independent variable, and the internal field resulting from the incident field and γ interaction is considered to be a function of this γγ. We may write $$\mathbf{f}^{sc}_{\omega\phi} \equiv \mathbf{f}^{sc}_{\theta\omega}(\gamma) \ \forall \ \begin{array}{l} \theta = 1, \ldots, \Theta \\ \omega = 1, \ldots, \Omega \end{array} \quad (24)$$

for the scattered field.

The difference between this example, and the previous one is that the background medium, in which the object is assumed to be buried, is assumed to be homogeneous in the previous case, whereas it is here assumed that the background is layered. The residual is defined in the same way as the previous example, with $d_{\theta\omega}$ used to represent the $N_d$-length vector of measured scattered field at the detector positions. That is, the residual vectors for all ω, θ are defined in the following way.

$$\mathbf{r}_{\theta\omega} \equiv \mathbf{f}^{sc}_{\theta\omega}(\gamma) - \mathbf{d}_{\theta\omega} = \mathbf{0} \ \forall \ \begin{array}{l} \theta = 1, \ldots, \Theta \\ \omega = 1, \ldots, \Omega \end{array} \quad (25)$$

The functional F(γ), dependent upon γ is defined in the same way as example 1:

$$F(\gamma) \equiv \sum_{\theta\omega} \|\mathbf{r}_{\theta\omega}\|_2^2 \quad (26)$$

This is the functional, dependent upon the object function γ in a highly nonlinear manner, which must be minimized in order to determine the γ values at each gridpoint in the object space.

It is again necessary to compute the Jacobian:

$$\left(\frac{\partial \mathbf{f}^{sc}_{\theta\omega}}{\partial \gamma}\right) = \mathbf{T} \circ ((\mathbf{I} - \mathbf{G}_\omega \cdot [\gamma])^{-1}(\mathbf{G}_\omega \cdot [\mathbf{f}_{\theta\omega}])) \ \forall \ \begin{array}{l} \theta = 1, \ldots, \Theta \\ \omega = 1, \ldots, \Omega \end{array} \quad (27)$$

where θ again refers to the multiple views and the ω to the multiple frequencies available to us. That is, we again assume that the noise level in the system is zero. We apply the Gauss Newton algorithm to the associated least squares problem and get the same result. This leads to the overdetermined system described above (the notation is identical to the previous example, the difference lies in the actual form of the layered Green's function).

$$[\mathbf{T} \circ ([\mathbf{I} - \mathbf{G}_k \cdot [\gamma]]^{-1} \mathbf{G}_k) \otimes \mathbf{I}_{\Theta \times \Theta}] \begin{bmatrix} [f_{1k}] \\ \vdots \\ [f_{\Theta k}] \end{bmatrix} \delta\gamma^{(n)} = - \begin{bmatrix} [r^{(n)}_{1k}] \\ \vdots \\ [r^{(n)}_{\Theta k}] \end{bmatrix} \forall k: \quad (28)$$

which must be solved for the γ-update δγ. The left hand side of the above formula is given by (29)

$$\mathbf{T} \circ ([\mathbf{I} - \mathbf{G}_k \cdot [\gamma]]^{-1} \mathbf{G}_k) \otimes \mathbf{I}_{\Theta \times \Theta} \equiv$$

$$\left\{ \begin{bmatrix} T\mathbf{G}_k(I - [\gamma^{(n)}]\mathbf{G}_k)^{-1} & 0.. & & 0 \\ 0 & \ddots & & \cdot \\ \cdot & & \ddots & \cdot \\ \cdot & & \ddots & 0 \\ 0 & & ..0 & T\mathbf{G}_k(I - [\gamma^{(n)}]\mathbf{G}_k)^{-1} \end{bmatrix} \right\}$$

Again, we can use the complex analytic version of the Hestenes overdetermined conjugate gradient algorithm, adapted for least squares problems to iteratively solve this system. This is equivalent to finding the minimum norm solution.

The formula for the Jacobian in the layered medium situation in the presence of multiple frequencies, is, $$\left(\frac{\partial \mathbf{f}^{sc}_{\theta\omega}}{\partial \gamma}\right) = \mathbf{T} \circ ((\mathbf{I} - \mathbf{G}_\omega \cdot [\gamma])^{-1}(\mathbf{G}_\omega \cdot [\mathbf{f}_{\theta\omega}])) \ \forall \ \begin{array}{l} \theta = 1, \ldots, \Theta \\ \omega = 1, \ldots, \Omega \end{array} \quad (30)$$

where $G_\omega$ is the Layered Green's function for the frequency ω. Therefore, in effect, to determine the γ-update, δγ, we merely solve the multiple view problem for each particular frequency, that is, we solve the overdetermined system:

$$[\mathbf{T} \circ ([\mathbf{I} - \mathbf{G}_k \cdot [\gamma]]^{-1} \mathbf{G}_k) \otimes \mathbf{I}_{\Theta \times \Theta}] \begin{bmatrix} [f_{1k}] \\ \vdots \\ [f_{\Theta k}] \end{bmatrix} \delta\gamma^{(n)} = - \begin{bmatrix} [r^{(n)}_{1k}] \\ \vdots \\ [r^{(n)}_{\Theta k}] \end{bmatrix} \quad (31)$$

-continued $$\forall k = 1, \ldots, \Omega$$

which in component form is:

$$[T \circ ([I - G_k \cdot [\gamma]]^{-1} G_k)][f_{jk}] \delta \gamma^{(n)} = -[r_{jk}^{(n)}] \; \forall \; \begin{aligned} k &= 1, \ldots, \Omega \\ j &= 1, \ldots, \Theta \end{aligned} \quad (32)$$

See also the computer code in this patent for the complete description of this procedure.

For multiple view and multiple frequency inversion then, the inversion scheme in layered media reads:

STEP 1. Choose an initial guess for the scattering potential, $$\gamma^{(0)}.$$

STEP 2. Set $n = 0$

STEP 3. solve the forward problems $$(I - G[\gamma])f_{\theta\omega} = f_{\theta\omega}^{inc}, \; \forall \; \begin{aligned} \theta &= 1, \ldots, \Theta \\ \omega &= 1, \ldots, \Omega, \end{aligned}$$

using biconjugate gradients, and use the result to compute the $\phi$- forward maps $$\phi_{\theta\omega}(\gamma^{(n)}) \text{ and } r_{\theta\omega}^{(n)} \equiv \phi_{\theta\omega}(\gamma^{(n)}) - d_{\theta\omega} = 0 \; \forall \; \begin{aligned} \theta &= 1, \ldots, \Theta \\ \omega &= 1, \ldots, \Omega. \end{aligned}$$

STEP 4. Determine the $L_2$ norm of the total residual vector:

$$tr^{(n)} \equiv \begin{bmatrix} \begin{bmatrix} r_{11}^{(n)} \\ \vdots \\ r_{\Theta 1}^{(n)} \end{bmatrix} \\ \ddots \\ \begin{bmatrix} r_{1\Omega}^{(n)} \\ \vdots \\ r_{\Theta\Omega}^{(n)} \end{bmatrix} \end{bmatrix}$$

STEP 5. If $\|tr^{(n)}\|^2 \equiv \sum_{\omega=1}^{\Omega} \sum_{\theta=1}^{\Theta} \|r_{\theta\omega}^{(n)}\|^2 < \varepsilon$ then stop.

STEP 6. Solve the $N_d \Theta \Omega$ by $N$ overdetermined system:

$$T \circ \begin{bmatrix} ([I - G_1 \cdot [g]]^{-1} G_1) \otimes I_{\Theta \times \Theta} & \cdots & 0 \\ \vdots & \ddots & \vdots \\ 0 & \cdots & ([I - G_\Omega \cdot [g]]^{-1} G_\Omega) \otimes I_{\Theta \times \Theta} \end{bmatrix} \begin{bmatrix} \begin{bmatrix} f_{11} \\ \vdots \\ f_{\Theta 1} \end{bmatrix} \\ \ddots \\ \begin{bmatrix} f_{1\Omega} \\ \vdots \\ f_{\Theta\Omega} \end{bmatrix} \end{bmatrix} \delta g^{(n)} = - \begin{bmatrix} \begin{bmatrix} r_{11}^{(n)} \\ \vdots \\ r_{\Theta 1}^{(n)} \end{bmatrix} \\ \ddots \\ \begin{bmatrix} r_{1\Omega}^{(n)} \\ \vdots \\ r_{\Theta\Omega}^{(n)} \end{bmatrix} \end{bmatrix}$$

in the least squares sense for $\delta \gamma^{(n)}$, using the conjugate gradient algorithm adapted for least squares problems.

STEP 7. Update $\gamma$ via the formula $$\gamma^{(n+1)} = \gamma^{(n)} + \delta \gamma^{(n)}$$

STEP 8. Set $n = n + 1$, go to begin

The actual values of the angles of incidence $\theta$ are chosen to diminish as much as possible the ill conditioning of the problem. Equally spaced values $0 \leq \theta \leq 2\pi$ are ideal, but experimental constraints may prohibit such values, in which case the multiple frequencies are critical.

For biological contrasts ($\gamma < 0.15$ say) the following approximation, which is essentially identical to the assumption in the previous example, is valid:

$$[I - G_\omega[\gamma]]^{-1} \approx [I + G_\omega[\gamma]] \quad (33)$$

This is the same Born-like approximation restricted to the Jacobian calculation only, that is assumed in example 1. This approximation has a much larger radius of convergence than the standard born approximation, but substantially reduces the computational complexity of the problem.

HOW TO IMPLEMENT THE CONVOLUTION AND CORRELATION IN LAYERED MEDIUM IMAGING

All of the above calculations have been carried out without using the fact that the operation of matrix multiplication with G is in fact the sum of a convolution and a correlation, which is transformed into a pair of convolutions. Symbolically $G^L = G_R + G_V$, where $G_R$ is the correlation and $G_V$ is a convolution operator. The actual numerical implementation of the above formulas, therefore, is somewhat different than would naively appear. The implementation of the correlation with convolution is a little more challenging than the convolution in the homogeneous case, in that a change of variables must be used to convert the correlation to a convolution before the Fast Fourier Transform (FFT)s can be applied. A "reflection" operator must be applied to $\gamma$ before the convolution is applied, this operator is denoted by Z, and is defined by:

$$(Zf)(x,y,z) \equiv f(x,y,h-z) \quad (34)$$

The use of this operator is incorporated into the action of the Lippmann-Schwinger equation on the field $f$. That is, the equation for the internal fields, which in example 1 read: $(I-G\gamma)f = f^{inc}$, Now becomes $(I - G_V\gamma - G_R Z\gamma)f = f^{inc}$.

This change has non-trivial ramifications for the construction of the algorithms discussed above. The FFT implementation of this is given below. To prevent the notation from getting out of hand we use [ ] to indicate that a diagonal matrix is constructed out of an n vector, so that $[\gamma^{(n)}]f_\Phi^{(n)}$ denotes pointwise multiplication of the vectors $\gamma$ and $f$. Also F is used to denote the Fourier transform, and * is used to indicate "convolution". In this notation, the Lippmann-Schwinger equation becomes, in the symbolic form adopted above, $$(I - G_V\gamma - G_R Z\gamma)f = (f - G_V *([\gamma]f) - G_R * Z([\gamma]f)) = \quad (35)$$
$$(f - \mathcal{F}^{-1}\{(\mathcal{F}(G_V) \cdot \mathcal{F}([\gamma]f)) - (\mathcal{F}(G_R) \cdot \mathcal{F}\{Z([\gamma]f)\})\})$$

Substantial savings is achieved through the observation that the Fourier Transforms of $G_V$ and $G_R$ need only be done once, then stored, and finally, that the reflection operator, Z, will commute with Fourier transformation in the x and y (horizontal) directions, since it only involves reflection in the z (vertical) direction.

There are changes also, for example in the computation of $f$. The biconjugate gradient algorithm requires the use of the adjoint in the solution of the above equation. This adjoint differs from the homogeneous ambient medium case with the introduction of the correlation operator. Also, there are substantial changes in the implementation of the overdetermined conjugate gradient algorithm used to solve (in the least squares sense) the overdetermined system of equations. In this section, as before, we incorporate the $k_{sc}^2$ factor into the $G_V$ and $G_R$ terms. Of course, rather than carry out the inversion of a matrix, we use biconjugate gradients and Fast Fourier Transforms (FFT's), which require the Lippmann Schwinger operator, which we denote by LS, and its adjoint, which are defined by the following formulas:

$$(LS)f \equiv (I - F^{-1}[(\tilde{G}_V F) + (\tilde{G}_R \cdot F \cdot Z)])([\gamma]f) \quad (36)$$

where $\tilde{G}_V \equiv F(G_V)$ and $\tilde{G}_R \equiv F(G_R)$ are the Fourier Transforms of $G_V$ and $G_R$, and need only be calculated once, then stored. The unitarity of F is used below to determine the adjoint $(LS)^H$.

$$(LS)^H \equiv \left(\left(I - \mathcal{F}^{-1}\left[\left(\tilde{G}_V \cdot \mathcal{F}\right) + \left(\tilde{G}_R \cdot \mathcal{F} \circ Z\right)\right]\right)[\gamma]\right)^H \quad (37)$$
$$= [\bar{\gamma}]\left(I - \left[\left(\mathcal{F}^{-1}\tilde{G}_V^H\right) + \left(Z^H \mathcal{F}^{-1}\tilde{G}_R^H\right)\right](\mathcal{F}^{-1})^H\right)$$
$$= [\bar{\gamma}]\left(I - \left[\left(\mathcal{F}^{-1}\overline{\tilde{G}_V}\right) + \left(Z\mathcal{F}^{-1}\overline{\tilde{G}_R}\right)\right]\mathcal{F}\right)$$

where we have used the unitarity of Fourier Transformation F: $FH = F^{-1}$, and the fact that point wise multiplication is used, and the fact that $Z^H = Z$. For practical problems it is best to obtain a reasonable first guess using low frequency data, then to build on this using the higher frequency information.

THE ACTUAL CONSTRUCTION OF THE LAYERED GREENS FUNCTION

Up to this point, we have assumed the existence of the layered Green's function, but have not shown explicitly how to construct it. This is an essential step. For simplicity we deal with the scalar case, although the inclusion of shear wave phenomena is conceptually no more difficult than this case. The details are given in [Wiskin, 1991]. The general idea is based upon standard ideas in the literature concerning reflection coefficients in layered media. See for example [Muller, G., 1985, *Journal of Geophysics*, vol. 58] which is herein incorporated by reference. The novelty is the combination of the reflection coefficients into a bona fide Green's function, and the utilization of this in a forward problem, then more importantly, in the inverse problem solution. The procedure involves decomposing the point response in free space into a continuum of plane waves. These plane waves are multiply reflected in the various layers, accounting for all reverberations via the proper plane wave reflection/transmission coefficients. The resulting plane waves are then re-summed (via a Weyl-Sommerfeld type integral) into the proper point response, which in essence, is the desired Green's function in the layered medium. The final result is:

$$G_V(x - x'; |\Delta z - \Delta z'|) = \quad (38)$$
$$\int_{-\infty}^{\infty} e^{i\omega u(x-x')} C(u) \left[e^{-i\omega b_{sc}|\Delta z - \Delta z'|} + R^+ R^- e^{i\omega b_{sc}|\Delta z - \Delta z'|}\right] du,$$

and $$G_R(x - x'; \Delta z + \Delta z') = \quad (39)$$
$$\int_{-\infty}^{\infty} e^{i\omega u(x-x')} C(u) \left[R^+ e^{-i\omega b_{sc}(\Delta z + \Delta z')}\right] \left[R^- e^{-i\omega b_{sc}(\Delta z + \Delta z')}\right] du,$$

where $$C(u) = (I - R^+ R^-)^{-1} \frac{i\omega u}{b_{sc}}.$$

$R^-$ and $R^+$ are the recursively defined reflectivity coefficients described in Muller's paper, u is the horizontal slowness, $$u \equiv \frac{\sin\theta}{c}.$$

Recall that Snell's law guarantees that u will remain constant as a given incident plane wave passes through several layers.

ω is the frequency $b_{sc}$ is the vertical slowness for the particular layer hosting the scattering potential This Green's function for imaging inhomogeneities residing within Ambient Layered Media must be quantized by convolving with the sinc (really Jinc) basis functions described below. This is done analytically in [Wiskin, 1991], and the result is given below.

DISCRETIZATION OF LAYERED MEDIUM LIPPMANN-SCHWINGER EQUATION

Unfortunately the basis functions that were used in the free space case (example 1) cannot be used to give the discretization in the layered medium case because of the arbitrary distribution of the layers above and below the layer which contains the scattering potential. The sinc functions may continue to be used in the horizontal direction, but the vertical direction requires the use of a basis function with compact support (i.e. should be nonzero only over a finite region). The sampled (i.e. discrete) Green's operator in the layered case is defined by $$G^L(j,k,m) = G^L(j\delta, k\delta, m\delta) \quad (40)$$

where the three dimensional basis functions are of the form:

$$B(x) = B(x,y,z) = S_{(j,\delta)}(x) S_{(k,\delta)}(y) \Lambda_m(z), \quad (41)$$

(I is the set of integers) and where:

$$\mathbf{x} = \begin{pmatrix} x \\ y \\ z \end{pmatrix} \in \mathcal{R}^3$$

$$\mathbf{x}_{jkm} \equiv \begin{pmatrix} j\delta \\ k\delta \\ m\delta \end{pmatrix} \quad j,k,m \in \mathbf{I}$$

The basis functions in the horizontal (x-y) plane $S_{(j,\delta)}$ are based upon the Whittaker sinc function:

$$\text{sinc}(x) = \frac{\sin(\pi x)}{\pi x}$$

The basis functions in the vertical (z) direction, on the other hand, are given by $$\Lambda_m(z) = \Lambda(z - m\delta),$$

where $\Lambda(z)$ is the "tent" function:

$$\Lambda(z) = \begin{cases} \frac{1}{\delta}(z + \delta) & z \in [-\delta, 0] \\ -\frac{1}{\delta}(z - \delta) & z \in [0, \delta] \end{cases}$$

The form of the discretized Lippmann Schwinger equation is $$f^{inc}\begin{pmatrix} n\delta \\ m\delta \\ l\delta \end{pmatrix} \equiv f^{inc}_{nml} = f\begin{pmatrix} n\delta \\ m\delta \\ l\delta \end{pmatrix} - k_{sc}^2 \sum_{n',m',l'} G^V_{\pi/\delta}\begin{pmatrix} n-n' \\ m-m' \\ l-l' \end{pmatrix} \gamma^L f\begin{pmatrix} n'\delta \\ m'\delta \\ l'\delta \end{pmatrix} - \quad (42)$$

$$k_{sc}^2 \sum_{n',m',l'} \hat{G}^R_{\pi/\delta}\begin{pmatrix} n-n' \\ m-m' \\ l-l' \end{pmatrix} \gamma^L f\begin{pmatrix} n'\delta \\ m'\delta \\ l'\delta \end{pmatrix},$$

with the vectors $G_{\pi/\delta}^R$ and $G_{\pi/\delta}^V$ are the result of first convolving the Green's function with the basis functions, and then sampling at the gridpoints. The superscript R refers to the correlation part, whereas the superscript V refers to the convolution part of the Green's function. Both are computed via Fast Fourier Transforms, and are very fast. In the free space case the correlation part is zero. That is, we make the definition for L=V or R-(ie. convolution or correlation):

$$G^L_{\pi/\delta}(n,m,l) \equiv \int\int\int_{R^3} S(x') S(y') \Lambda(z') G^L\begin{pmatrix} n\delta - x' \\ m\delta - y' \\ l\delta - z' \end{pmatrix} dx' dy' dz', \quad (43)$$

substitution into equation (17) yields the form (42).

In matrix notation, this equation gives:

$$f = (I - k_{sc}^2 G_V^* \gamma_L - k_{sc}^2 \hat{G}_R^* Z \gamma_L)^{-1} f^{inc} \quad (44)$$

where now * represents discrete convolution in 3D. Now that we have constructed the Integral equations in discrete form, we must derive the closed form expression for the layered Green's operators. The construction of the closed form expression of the sampled and convolved acoustic layered Green's function $G^L_{\pi/\delta}$, from the layered Green's function given in equations (38 and 39) above is given by performing the integration in (43) analytically. This process is carried out in [Wiskin, 1991]. The final result is, for the convolutional part, $$G_v(m, n) = \begin{cases} A \int_{u=0}^{u_\delta} J_0 C(u) \frac{2}{i\omega b_{sc}} \left\{ R^- R^+ \left\{ -1 + \frac{(e^{i\omega b_{sc}\delta} - 1)}{i\omega b_{sc}\delta} \right\} + \left\{ 1 - e^{-i\omega b_{sc}\delta} \frac{(e^{i\omega b_{sc}\delta} - 1)}{i\omega b_{sc}\delta} \right\} \right\} du & n = 0 \\ A \int_{u=0}^{u_\delta} J_0 C(u) \frac{1}{\omega^2 b_{sc}^2 \delta} \{2 - e^{i\omega b_{sc}\delta} - e^{-i\omega b_{sc}\delta}\} \{e^{-i\omega b_{sc}|n\delta|} + R^- R^+ e^{i\omega b_{sc}|n\delta|}\} du & |n| \geq 1 \end{cases} \quad (45)$$

$\forall m \in [0, M-1], \forall n \in [-N+1, N-1]$
and $$G_r(m, n) = A \int_{u=0}^{u_\delta} J_0 C(u) \frac{\{2 - e^{i\omega b_m \delta} - e^{-i\omega b_m \delta}\}}{\omega^2 b_{sc}^2 \delta} \{R^+(e^{-i\omega b_{sc}(h+2d)} e^{-i\omega b_{sc} n\delta}) + R^-(e^{i\omega b_{sc}(h+2d)} e^{i\omega b_{sc} n\delta})\} du \quad (46)$$

$\forall m \in [0, M-1], \forall n \in [-N+1, N-1]$

In the above formulas $J_0 \equiv J_0(u\omega|m|\delta)$ is the zero$^{th}$ order Bessel Function, and the upper limit $u_\delta$ is defined as:

$$u_\delta = 1/c_\delta = k_\delta \frac{1}{\omega} = \frac{\pi/\delta}{\omega}$$

for wavenumber $k_\delta = \pi/\delta$. Also, $C(u) \equiv (1-R^-R^+)^{-1} S^c$ where $$S^c = \frac{i\omega u}{b_{sc}},$$

with $b_{sc}$ defined as the vertical slowness in the layer containing the scattering point. When this layer is assumed to have acoustic wave velocity $\beta_{sc}$, it is given explicitly by:

$$b_{sc} = \sqrt{\frac{1}{\beta_{sc}^2} - u^2}.$$

These expressions give the discretized 3D Acoustic layered Green's function, which is used in the layered media discretized Lippmann-Schwinger equation to obtain the solution field within the inhomogeneity. It is also used in the detector equations (9), which correspond to the detector equations (11).

This patent differs from the previous art in the important aspect of including the correlation part of the green's function. This correlation part is zero for the free space case. This correlational part is directly applicable as it occurs above to the fish echo-locator/counter, and to the mine detection device in the acoustic approximation. (There are specific scenarios, where the acoustic approximation will be adequate, even though shear waves are clearly supported to some degree in all sediments). The inclusion of shear waves into the layered media imaging algorithm (the technical title of the algorithm at the heart of the hazardous waste detection device, the fish echo-locator, and the buried mine identifier) is accomplished in Example 6 below. Actually a generalized Lippmann-Schwinger equation is proposed. This general equation is a vector counterpart to the acoustic Layered Green's function, and must be discretized before it can be implemented. The process of discretization is virtually identical to the method revealed above. Furthermore, the BCG method for solving the forward problem, the use of the sinc basis functions, and the use of the Fast Fourier Transform (FFT) are all carried out identically as they in the acoustic (scalar) case.

EXAMPLE 3

IMAGING WITH ELECTROMAGNETIC WAVE ENERGY

The use of electromagnetic energy does not greatly affect the basic idea behind the imaging algorithm, as this example will demonstrate. Furthermore, we will see that it is possible to combine the layered Green's function with the electromagnetic free space Green's function to image materials within layered dielectrics. In fact this process of combining the layered Green's function with Green's functions derived for other structures and/or modalities than the free space acoustic case can be extended almost indefinitely. Another example is given below, where the combination of the Acoustic Biot Green's function with the layered Green's function is carried out. Further extensions that are not detailed here, are: (1) Combining Elastic (including shear wave energy) Wave equations with the layered Green's function, (3) Combining the Elastic Biot equations with the layered Green's function, (4) Combining the elastic and electromagnetic wave equations to model transducers. For simplicity, we consider a homogeneous, isotropic, non-magnetic background material. The time dependence will be $e^{i\omega t}$, the magnetic properties of free space are summarized in $\hat{z}_o \equiv i\omega\mu_o$, and the electric properties are summarized in $\hat{y}_o \equiv i\omega\epsilon_o$. Within the object being imaged the magnetic properties are $\hat{z} \equiv \hat{z}_o \equiv i\omega\mu_o$ (the equivalence with the free space value is the nonmagnetic media assumption). The electric properties of the object being imaged are summarized in $\hat{y} \equiv \sigma + \hat{y}_o \equiv \sigma + i\omega\epsilon_r\epsilon_o$, which is the complex admittivity of the object. The larger $\sigma$ is, the less able the medium is able to support electromagnetic wave transport. These properties are combined in $$k_o^2 \equiv -\hat{y}_o \hat{z}_o = \omega^2 \mu_o \epsilon_o \equiv \frac{\omega^2}{c_o^2} \quad (47)$$

which is a measure of the number of wave cycles present per unit distance for a given frequency $\omega$, when the wave speed of propagation is $c_o$. The object's electrical properties (recall it is assumed non-magnetic for simplicity) are summarized in the "object function", $\gamma$. (the normalized difference from the surrounding medium):

$$\gamma(\mathbf{r}) \equiv \frac{\hat{y} - \hat{y}_o}{\hat{y}_o} = \frac{\sigma + i\omega\epsilon_r\epsilon_o}{i\omega\epsilon_o} - 1 = -i\frac{\sigma}{\omega\epsilon_o} + \epsilon_r - 1 \quad (48)$$

The total electric field equations are:

$$\mathbf{E}^i(\mathbf{r}) = \mathbf{E}(\mathbf{r}) - (k_o^2 + \nabla\nabla \cdot) \int \gamma(\mathbf{r}') \mathbf{E}(\mathbf{r}') \frac{e^{-ik_o|\mathbf{r}-\mathbf{r}'|}}{4\pi|\mathbf{r}-\mathbf{r}'|} d^3\mathbf{r}' \quad (49)$$

where $\mathbf{E}^i(\mathbf{r})$ is the 3-D incident field, $\mathbf{E}(\mathbf{r})$ is the 3-D total field.

The construction of the sinc basis discretization and the GN and RP algorithms for this 3-D EM case is essentially equivalent to the 2-D scalar acoustic case described above. See [Borup, 1989] for the details of the discretization and solution of the forward problem by FFT-BCG. The vector—tensor nature of the fields—Green's function is the only new feature and this is easily dealt with.

For simplicity, we now look at the situation where there is no z dependence in either the object function, i.e. $\gamma(x,y,z)=\gamma(x,y)$, neither in the incident field. The vector $\rho=(x,y)$ is used for the position vector in $(x,y)$-space.

$$E^i(\rho) = E(\rho) - (k_o^2 + \nabla\nabla \cdot) \int \gamma(\rho')E(\rho')\frac{1}{4i}H_0^{(2)}(k_o|\rho-\rho'|)d^2\rho' \quad (50)$$

in matrix form the equation (50) looks like:

$$\mathbf{E}^i(\rho) = E(\rho) - \begin{bmatrix} k_o^2 + \frac{\partial^2}{\partial x^2} & \frac{\partial^2}{\partial x \partial y} \\ \frac{\partial^2}{\partial y \partial x} & k_o^2 + \frac{\partial^2}{\partial y^2} \\ & & k_o^2 \end{bmatrix} \int \gamma(\rho')E(\rho')\frac{1}{4i}H_0^{(2)}(k_o|\rho-\rho'|)d^2\rho' \quad (51)$$

From this form of the equation, it is clear that the electric field in the z-direction is uncoupled with the electric field in the x-y plane. Thus, in this situation the field consists of two parts. The so-called transverse electric (TE) mode, in which the electric field is transverse to the z direction, and the transverse magnetic (TM) mode, in which the electric field has a nonzero component only in the z direction. The TM mode is governed by the scalar equation:

$$E_z^i(\rho) = E_z(\rho) - \frac{k_o^2}{4i}\int \gamma(\rho')E_z(\rho')H_0^{(2)}(k_o|\rho-\rho'|)d^2\rho' \quad (52)$$

where $\mathbf{E}^i(\rho) \equiv \begin{pmatrix} E_x^i \\ E_y^i \\ E_z^i \end{pmatrix}$ and $\mathbf{E}(\rho) \equiv \begin{pmatrix} E_x \\ E_y \\ E_z \end{pmatrix}(x,y)$ which is identical to the 2-D acoustic equation discussed previously. Thus, the 2-D TM electromagnetic imaging algorithm is identical to the 2-D acoustic case discussed in detail above.

The TE mode is given by the following equation:

$$\begin{pmatrix} \mathbf{E}_x^i(\rho) \\ \mathbf{E}_y^i(\rho) \end{pmatrix} = \begin{pmatrix} \mathbf{E}_x(\rho) \\ \mathbf{E}_y(\rho) \end{pmatrix} - \quad (53)$$

$$\frac{1}{4i}\begin{bmatrix} k_o^2 + \frac{\partial^2}{\partial x^2} & \frac{\partial^2}{\partial x \partial y} \\ \frac{\partial^2}{\partial y \partial x} & k_o^2 + \frac{\partial^2}{\partial y^2} \end{bmatrix}\int \gamma(\rho')\begin{pmatrix} \mathbf{E}_x(\rho') \\ \mathbf{E}_y(\rho') \end{pmatrix}H_0^{(2)}(k_o|\rho-\rho'|)d^2\rho'$$

The field is a two component vector and the Green's function is a 2×2 tensor Green': function:

$$\mathbf{G} = \begin{bmatrix} g_{xx} & g_{xy} \\ g_{xy} & g_{yy} \end{bmatrix} \quad (54)$$

-continued $$= \frac{1}{4i}\begin{bmatrix} k_o^2 + \frac{\partial^2}{\partial x^2} & \frac{\partial^2}{\partial x \partial y} \\ \frac{\partial^2}{\partial y \partial x} & k_o^2 + \frac{\partial^2}{\partial y^2} \end{bmatrix} H_0^{(2)}(k_o|\rho-\rho'|)$$

In compact notation:

$$E^i = (I - G\Gamma)E$$

where:

$$\mathbf{E}^i = \begin{bmatrix} E_x^i \\ E_y^i \end{bmatrix}, \mathbf{E} = \begin{bmatrix} E_x \\ E_y \end{bmatrix}, \mathbf{I} = \begin{bmatrix} I & 0 \\ 0 & I \end{bmatrix} \quad (55)$$

and $$\Gamma = \begin{bmatrix} \gamma & 0 \\ 0 & \gamma \end{bmatrix}$$

This equation also has a convolution form and can thus be solved by the FFT-BCG algorithm as described in [Borup, 1989] The construction of the GN-MRCG and RP imaging algorithms for this case is identical to the 2-D acoustic case described above with the exception that the fields are two component vectors and the Green's operator is a 2×2 component Green's function with convolutional components.

Finally, note that the presence of layering parallel to the z direction can also be incorporated into these 2-D algorithms in essentially the same manner as above. Special care must be taken, of course, to insure that the proper reflection coefficient is in fact, used. The reflection coefficient for the TM case is different from the TE case.

THE ELECTROMAGNETC IMAGING ALGORITHM

The electromagnetic imaging algorithm is virtually the same as the imaging algorithm for the scalar acoustic mode shown in the previous example, and therefore, will not be shown here. The Microwave Nondestructive Imager is one particular application of this imaging technology, another example is the advanced imaging optical microscope.

EXAMPLE 4

ADVANCED IMAGING MICROSCOPE

The microscope imaging algorithm requires the complex scattered wave amplitude or phasor of the light (not the intensity, which is a scalar) at one or more distinct pure frequencies (as supplied by a laser). Since optical detectors are phase insensitive, the phase must be obtained from an interference pattern. These interference patterns can be made using a Mach-Zehnder interferometer. From a set of such interference patterns taken from different directions (by rotating the body for example), the information to compute the 3-D distribution of electromagnetic properties can be extracted. A prototype microscope system is shown in FIG. G01 and discussed in the Detailed Description Of The Drawings. There are two interferometer paths A and B where A is the path containing the microscope objective lenses and sample and B is the reference path containing a beam expander to simulate the effect of the objective lenses in path A. These paths are made to be nearly identical. If the paths are equal in length and if the beam expander duplicates the objective lenses, then the light from these two paths has equal amplitude and phase. The resulting interference pattern will be uniformly bright. When any path is disturbed and interference pattern will result. In particular if path A is disturbed by placing a sample between the objective lenses, an interference pattern containing information of the object will result. When path B has an additional phase shift of 90 degrees inserted, then the interference pattern will change by shifted (a spatial displacement) corresponding to 90 degrees.

The problem of extracting the actual complex field on a detector (such as a CCD array face) from intensity measurements can be solved by analysis of the interference patterns produced by the interferometer. It is possible to generate eight different measurements by: (1) use of shutters in path A and path B of the interferometer; (2) inserting or removing the sample from path A; and (3) using 0 or 90 degree phase shifts in path B. It is seen that all eight measurements are necessary.

The procedure to extract amplitude and phase from the interference patterns can be seen after defining variables to describe the eight measurements. Let:

$$f_o^{(det)}{}_{\phi\omega A} = A_{o\phi\omega x} e^{i\omega t + i\alpha(\phi,\omega,x)}$$

be the incident field on the detector from path A (with no energy in path B) when no sample is in place, $A_{o\phi\omega x} = |A_{o\phi\omega x}|$, $$f_o^{(det)}{}_{\phi\omega xB} = B_{1\phi\omega x} e^{i\omega t + i\beta(\phi,\omega,x)}$$

be the incident field on the detector from reference path $B_1$ when no additional phase shift is introduced in path B (with no energy in path A), $B_{1\phi\omega x} = |B_{1\phi\omega x}|$, $$f_1^{(det)}{}_{\phi\omega xB} = B_{2\phi\omega x} e^{i\omega t + i\beta(\phi,\omega,x) + i\pi/2}$$

be the incident field on the detector from reference path B when π/2 additional phase shift is introduced in path B (with no energy in path A), $B_{2\phi\omega x} = |B_{2\phi\omega x}|$, $$f_o^{(det)}{}_{\phi\omega xC} = C_{o1\phi\omega x} e^{i\omega t + i\theta(\phi,\omega,x)}$$

be the field on the detector when both path A and path $B_1$ are combined when no sample is in place, $C_{o1\phi\omega x} = |C_{o1\phi\omega x}|$, $$f_o^{(det)}{}_{\phi\omega xC} = C_{o2\phi\omega x} e^{i\omega t + i\theta(\phi,\omega,x) + i\pi/2}$$

be the field on the detector when both path A and path $B_2$ are combined when no sample is in place, $C_{o2\phi\omega x} = |C_{o2\phi\omega x}|$, $$f^{(det)}{}_{\phi\omega xA} = A_{\phi\omega x} e^{i\omega t + i\psi(\phi,\omega,x)}$$

be the field on the detector from path A (with no energy in path B) when a sample is present, $A_{\phi\omega x} = |A_{\phi\omega x}|$,
$$f^{(det)}{}_{\phi\omega xC} = C_{1\phi\omega x} e^{i\omega t + i o_1(\phi,\omega,x)}$$

be the field on the detector when both path A and path $B_1$ are combined when the sample is in place, $C_{1\phi\omega x} = |C_{1\phi\omega x}|$, $$f^{(det)}{}_{\phi\omega xC} = C_{2\phi\omega x} e^{i\omega t + i o_2(\phi,\omega, x)}$$

be the field on the detector when both path A and path $B_2$ are combined when the sample is in place, $C_{2\phi\omega x} = |C_{2\phi\omega x}|$, φ be the rotation angle of the sample holder
ω be the frequency of the light
x be the 2-D address of a pixel on the detector.

Now consider the one pixel for one rotation angle and at one frequency of light so that we may suppress these indices temporarily. The measurement made by the CCD camera is not of the field but rather of the square of the modulus of the field (i.e., the intensity). Thus, eight intensity fields can be measured on the detector:

$$M_1^2 = A_{o\phi\omega x}^2 \quad M_2^2 = B_{1\phi\omega x}^2$$
$$M_3^2 = B_{2\phi\omega x}^2 \quad M_4^2 = C_{o1\phi\omega x}^2$$
$$M_5^2 = C_{o2\phi\omega x}^2 \quad M_6^2 = A_{\phi\omega x}^2$$
$$M_7^2 = C_{1\phi\omega x}^2 \quad M_8^2 = C_{2\phi\omega x}^2$$

Because of the nature of an interferometer, the eight measurements are not independent. In particular, $M_4^2$ is dependent on $M_1^2$ and $M_2^2$. $M_5^2$ is dependent on $M_1^2$ and $M_3^2$. $M_7^2$ is dependent on $M_1^2$, $M_2^2$, $M_4^2$ and $M_6^2$. $M_8^2$ is dependent on $M_1^2$, $M_3^2$, $M_5^2$ and $M_6^2$. Also, $M_3^2 = KM_2^2$ (where, K=1 for a perfect phase shifter). Thus, $$B_2^2 = KB_1^2$$

There are four ways to add the two beams on specifying sample in or sample out and specifying 0-degree phase shift or 90-degree phase shift. For sample out:

$$M_4^2 = C_{o1\phi\omega x}^2 = |A_o e^{i\omega t + i\alpha(\phi,\omega,x)} + B_1 e^{i\omega t + i\beta(\phi,\omega,x)}|^2$$
$$= A_o^2 + B_1^2 + 2A_o B_1 \cos(\beta - \alpha),$$

$$M_5^2 = C_{o2\phi\omega x}^2 = |A_o e^{i\omega t + i\alpha(\phi,\omega,x)} + B_2 e^{i\omega t + i\beta(\phi,\omega,x) + i\pi/2}|^2$$
$$= A_o^2 + B_2^2 + 2A_o B_2 \cos(\beta - \alpha + \pi/2)$$
$$= A_o^2 + B_2^2 - 2A_o B_2 \sin(\beta - \alpha)$$

$(\beta-\alpha) = -\arctan \{M_3[M_4^2 - M_1^2 - M_2^2]/M_2[M_5^2 - M_1^2 - M_3^2]\}$
For sample in:.

$$M_7^2 = C_{1\phi\omega x}^2 = |A_{\phi\omega x} e^{i\omega t + i\psi(\phi,\omega,x)} + B_{1\phi\omega x} e^{i\omega t + i\beta(\phi,\omega,x)}|^2$$
$$= A^2 + B_1^2 + 2AB_1 \cos(\beta - \psi),$$

$$M_8^2 = C_{2\phi\omega x}^2 = |A_{\phi\omega x} e^{i\omega t + i\psi(\phi,\omega x)} + B_{2\phi\omega x} e^{i\omega t + i\beta(\phi,\omega,x)}|^2$$
$$= A^2 + B_2^2 + 2AB_2 \cos(\beta - \psi + \pi/2)$$
$$= A^2 + B_2^2 - 2AB_2 \sin(\beta - \psi).$$

$(\beta-\psi) = -\arctan \{M_3[M_7^2 - M_6^2]/M_2[M_8^2 - M_6^2 - M_3^2]\}$
$(\beta-\alpha) - (\beta-\psi) = (\psi-\alpha)$ = phase shift introduced by sample
The scattering equations are $$f(x) - f^{(inc)}(x) = C(x-y) * ([\gamma(y)]_D f(y)),$$

$$f^{(sc-det)}(z) = f^{(det)}(z) - f^{(inc)}(z) = D(z-x) * ([f(x)]_D \gamma(x)).$$

Here, the symbol * means convolution and the symbol $[\cdot]_D$ means the vector $[\cdot]$ is replaced by a diagonal matrix. When written in terms of the phase shift introduced by the sample these equations become:

$$(f(x)/f^{(inc)}(x)) - 1 = C(x-y) * ([\gamma(y)]_D (f(y)/f^{(inc)}(x)))$$

$$f^{(sc-det)}(z)/f^{(inc)}(z) = (f^{(det)}(z)/f^{(inc)}(z)) - 1 = D(z-x) * ([f(x)/f^{(inc)}(z)]_D \gamma(x))$$

If the incident field is known then then these equations can be solved. If the incident field is not known explicitly, but is known to be a plane wave incident normal to the detector, then the phase and amplitude is constant and can be divided out of both pairs of equations. It is the latter case that is compatible with the data collected by the interferometer. If the incident field is not a plane wave then, the amplitude and phase everywhere must be estimated, but the constant (reference) phase and amplitude will still cancel. The incident field can be estimated by inserting known objects into the microscope and solving for the incident field from measured interference patterns or from inverse scattering images.

The basic microscope has been described in its basic and ideal form. A practical microscope will incorporate this basic form but will also include other principles to make it easier to use or easier to manufacture. One such principle is immunity to image degradation due to environmental factors such as temperature changes and vibrations. Both temperature changes and vibration can cause anomalous differential phase shifts between the probing beam and reference beam in the interferometer. There effects are minimized by both passive and active methods. Passive methods isolate the microscope from vibrations as much as possible by adding mass and viscous damping (e.g. an air supported optical table). Active methods add phase shifts in one leg (e.g. the reference leg) to cancel the vibration or temperature induced phase shifts. One such method we propose is to add one or more additional beams to actively stabilize the interferometer. This approach will minimize the degree of passive stabilization that is required and enhance the value of minimal passive stabilization.

Stabilization will be done by adjusting the mirrors and beam splitters to maintain parallelness and equal optical path length. A minimum of three stabilizing beams per mirror is necessary to accomplish this end optimally (since three points determine a plane uniquely including all translation). These beams may be placed on the edge of the mirrors and beam splitters at near maximum mutual separation. The phase difference between the main probing and main reference beam occupying the center of each mirror and beam splitter, will remain nearly constant if the phase difference of the two component beams for each stabilizing beam is held constant. Note that one component beam propagates clockwise in the interferometer, while the other propagates counterclockwise. Stabilization can be accomplished by use of a feed back loop that senses the phase shift between the two component beams for each stabilizing beam, and then adjusts the optical elements (a mirror in our case) to hold each phase difference constant. This adjustment of the optical elements may be done by use of piezoelectric or magnet drivers.

We now describe how use of the several stabilizing beams operates to stabilize the interferometer and the microscope. Since the stabilization of a single beam is known to those working with optical interferometers, the description given here will be brief. The description is easily seen by a simple mathematical analysis of the interaction of the two components of the stabilizing beam. The electric field of the light at a point in space may be represented $E = E_o \exp(i2\pi ft)$, where $E_o$ contains the spatial dependence and $\exp(i2\pi ft)$ contains the temporal component, where f is the frequency of oscillation and t is time. For the remainder of this discussion we assume $\exp(i2\pi ft)$ time dependence at a single frequency f and this factor will be omitted. Let the electric field of the output of the interferometer for one component beam be A and let the electric field output of the second component be $B \exp(i\theta)$. Then the combined output is $[A + B \exp(i\theta)]$. The light intensity of the combined output that is detected is $|A + B\exp(i\theta)|^2 = A^2 + B^2 + 2AB \cos\theta$.

The feedback conditions can be easily derived from the above equation. The feedback signal can be derived by: (1) synchronous detection of the summed beams when one of the beams, say beam B, is modulated; or (2) by use of the differences in intensity of the transmitted and reflected beam exiting the final beam splitter. We now describe the operation of the first method of synchronous detection.

Let $\theta = (\theta_o + \epsilon \sin(\omega t))$ represent phase modulation of phase $\theta$ around equilibrium phase $\theta_o$ by amount $\epsilon$ at frequency $\omega$. The frequency $\omega$ is typically 100 Hz to 1000 Hz. Suppose that phase difference of zero degrees between beam A and beam B is required. Setting $\theta_o = \delta$ and noting that both $\epsilon$ and $\delta$ are small we see that $\cos\theta = \cos(\delta + \epsilon \sin(\omega t))$. By use of the trigonometric identity for the cosine of the sum of two angles we get $\cos\theta = \cos\delta \cos(\epsilon \sin(\omega t)) - \sin\delta \sin(\epsilon \sin(\omega t))$. On expanding this expression to second order in $\delta$ we obtain $\cos\theta = (1 - \delta^2/2) - (\frac{1}{2})\epsilon^2(1-\delta^2)\sin^2(\omega t) - \delta\epsilon \sin(\omega t)$. We wish to force $\delta$ to zero for optimal phase lock. There are two ways to accomplish this end: (1) by maximizing the modulus of the signal component $\epsilon^2(1-\delta^2)\sin^2(\omega t)$; or (2) by minimizing the modulus of the signal component $\delta\epsilon \sin(\omega t)$. The former method is accomplished by mixing (multiplying) $|A + B \cos\theta|^2$ by $\sin^2(\omega t)$, low pass filtering and then maximizing the signal by feedback changes to $\delta$.

To lock the phase difference to $\pi/2$ a modification of the above procedure may be used. Set $\theta = \pi/2 + \delta + \epsilon \sin(\omega t)$. Then $\cos\theta = \cos(\pi/2 + \delta + \epsilon \sin(\omega t)) = -\sin(\delta + \epsilon \sin(\omega t)) = -\sin\delta \cos(\epsilon \sin(\omega t)) + \cos\delta \sin(\epsilon \sin(\omega t))$. On expanding this expression to second order in $\delta$ we obtain $\cos\theta = (1 - \delta^2/2)\epsilon \sin(\omega t) - \delta(1 - (\frac{1}{2})\epsilon^2 \sin^2(\omega t))$. Again, we wish to force $\delta$ to zero for optimal phase lock. There are again two ways to accomplish this end: (1) by maximizing the modulus of the signal component $(1 - \delta^2/2)\epsilon \sin(\omega t)$; or (2) by minimizing the modulus of the signal component $\delta(1 - (\frac{1}{2})\epsilon^2 \sin^2(\omega t))$. The former method is accomplished by mixing $|A + B \cos\theta|^2$ with $\sin(\omega t)$, low pass filtering and maximizing the result by changing to $\delta$ through feedback. The latter method is accomplished by mixing $|A + B \cos\theta|^2$ with $\sin^2(\omega t)$, low pass filterings and minimizing the resulting signal by feedback to change $\delta$.

We now describe a second or non-hetrodyning method of phase locking beam A and B to a constant phase difference. The net intensity of the respective transmitted and reflected beams from a beam splitter have different dependency of the phase difference from the that combines two beams. Let the two beams coincident on the beamsplitter be A and B $\cos\theta$. Then the two exit beams from the beam splitter have respective intensities $|A + B \cos\theta|^2$ and $|A - B \cos\theta|^2$. This follows from a difference in phase of 180 degrees in the reflected beam depending on whether the incident medium has a higher or lower dielectric constant than the medium beyond the reflecting surface. The difference of the signals from detectors that detect transmitted and reflected beams is given by $|A + B \cos\theta|^2 - |A - B \cos\theta|^2 = 4AB \cos\theta$. If the desired phase angle is $\pi/2$ and the error is $\delta$ then 4AB $\cos\theta = -4AB \sin\delta \approx -4AB\delta$. Thus, the error signal $\delta$ can be used in a feedback loop to drive the difference in the two optical paths to $\pi/2$. This technique can be refined by dividing by the product of A and B. Since A is proportional to B dividing by $A^2$ will be equivalent. The value of A is proportion to the sampled laser power that is used to generate beam A and beam B $\cos\theta$.

EXAMPLE 5

EXTENSION TO BIOT THEORY (ACOUSTIC APPROXIMATION)

In the article [Boutin, 1987, *Geophys. J. R. astr. Soc., vol. 90*], herein incorporated by reference, a greens function for the determination of a point response to a scattering point located in an isotropic, homogeneous, porous medium that supports elastic waves is developed. The implementation of this Greens' function into an imaging algorithm has never been carried out before. In this section, we have adapted their approach to derive an acoustic approximation to the fully elastic Biot theory that enables us to present a simplified practical tool for the imaging of porosity-like parameters in a geophysical context. The implementation of the full elastic Biot imaging algorithm using the Green's function of [Boutin, 1987] in place of the one derived in [Wiskin, 1992] is no different from the discretization employed here. The use of the sinc basis functions, the FFT's, the biconjugate gradients, and so on, is identical.

We have developed a model that incorporates the parameters of fluid content, porosity, permeability, etc, but instead of the 3+1 degrees of freedom of the two phase elastic model, has only 1+1, corresponding to the two independent variables, $P_s$, and $P_l$, the pressure field within the solid (modelled as a liquid in this approximation) and truly liquid phase respectively. As with the previous example. The use of the Biot theory Green's function can be combined profitably with layering, to image material in a layered background.

Define (see [Boutin, 1987]., for more complete discussion of the parameters):

$\omega$ as the frequency of the interrogating wave $\rho_l$ as the density of the liquid phase $\rho_s$ as the density of the solid phase n as a saturation parameter $K(\omega)$ as the generalized, explicitly frequency-dependent Darcy coefficient introduced via homogenization theory.

$\alpha_o$, $\theta$, $\rho$ are parameter's defined in the following way:

$$\rho = (1-n)\rho_s + \rho_1[n + \rho_1 \omega^2 K(\omega)/i\omega]\theta = K(\omega)/i\omega$$

$$\alpha_o = \alpha + \rho_1 \omega^2 K(\omega)/i\omega = \alpha + \rho_1 \omega^2 \theta$$

The "acoustic two phase Green's function" is the Green's function obtained by solving the above system with a distributional right hand side, where $\delta(x)$ is the Dirac delta distribution. That is we seek the solution to the following matrix operator equation: $BG_{Biot} + I_{2\times 2}\delta(x) = 0$, where $G_{Biot}$: $R^{2,3} \to R^2$ is a function on $R^3$ or $R^2$ and $I_{2\times 2}$ is the two dimensional identity matrix. B is given by:

$$B = \begin{bmatrix} \theta\nabla^2 - \beta & -\alpha_0 \\ -\alpha_0\nabla^2 & \lambda\nabla^2 + \omega^2\rho \end{bmatrix}$$

This author obtained $$G_{Biot} = \frac{1}{4\pi\theta\lambda} \frac{\alpha_0}{(\delta_2^2 - \delta_1^2)} \left\{ (w \cdot d)\begin{bmatrix} \lambda & 0 \\ \alpha_0 & \theta \end{bmatrix} + (w \cdot v)\begin{bmatrix} \overline{\rho}\omega^2 & \alpha_0 \\ 0 & -\overline{\beta} \end{bmatrix} \right\}$$

where $w: R^3 \to R^2$ is the 2D vector defined by:

$$w \equiv \begin{pmatrix} \dfrac{e^{-i\delta_1|x|}}{|x|} \\ \dfrac{e^{-i\delta_2|x|}}{|x|} \end{pmatrix}$$

and $x \in R^3$ for the acoustic two-phase 3D model, and where d and v are 2 component vectors (representing the two phases) given by $$d = \begin{pmatrix} -\delta_1^2 \\ \delta_2^2 \end{pmatrix}, v = \begin{pmatrix} 1 \\ -1 \end{pmatrix}$$

A very similar analysis gives an equation and corresponding Green's Operator for the acoustic two-phase 2D (two spatial independent variables) case, in which $w: R^2 \to R^2$ and $x \in R^2$. The operator is very similar except that the w vector contains Hankel functions of the zeroth order:

$$w = \begin{pmatrix} \dfrac{i}{4}H_0^{(2)}(\delta_1|x|) \\ \dfrac{i}{4}H_0^{(2)}(\delta_2|x|) \end{pmatrix}$$

Notice the existence of the two wavenumbers $\delta_1$ and $\delta_2$ in this acoustic approximation to Biot theory guarantee the existence of a fast and slow compressional wave—a distinguishing characteristic of the classical elastic Biot theory.

More importantly this algorithm provides us with a computationally feasible means of inverting for phenomenological parameters derived from the classical elastic two phase Biot Theory.

Finally, it is important to point out that convolving the above functions with the sinc basis function analytically is done in exactly the same manner with $G_{Biot} = G_{2\times 2}$ above as it was done above because x only occurs in the form of the scalar acoustic Green's operator. This is why it is possible to create very efficient algorithms based upon the sinc-Galerkin method and FFT's as described in [Borup, 1992], using the Green's Operator described above.

It is now possible to obtain an algorithm for the inversion of the 2D Biot porous medium by analogy with the algorithm based upon the Lippmann-Schwinger equation used earlier. This new algorithm is based upon a "two phase" Lippmann-Schwinger type equation derived in a future publication.

$$r_0(x) = r(x) - \begin{bmatrix} -\overline{b}_1 & 0 \\ 0 & \overline{b}_2 \end{bmatrix} \int\int\int G_{2\times 2}(x-\xi)D'(\xi)r(\xi)d^3\xi$$

where $$D'(x) = \begin{bmatrix} \gamma_1 & 0 \\ 0 & \gamma_2 \end{bmatrix}$$

and the object functions $\gamma_i$ are given by $$\gamma_j(x) \equiv (-1)^j \left( \frac{b_j(x)}{\overline{b}_j} - 1 \right) \quad j = 1, 2$$

This equation is discretized in the same manner as above, and the convolution character is preserved. With the explicit form of the discretized Biot Lippmann-Schwinger Integral Equation the imaging problem is solved by applying the analogous conjugate gradient iterative solution method to the Gauss-Newton Equations in a manner exactly analogous to the discussion above (see future publication for details).

Finally, as mentioned above, it is certainly possible to construct, using the above principles, a layered Green's function for the Biot theory in exact analogy with the construction for the acoustic layered Green's Operator. This operator will be a matrix operator (as is the acoustic two phase Green's Operator constructed above), and will consist of a convolutional and correlational part (as does the acoustic single phase Green's Operator constructed earlier). Because of these convolutional and correlational parts, the FFT methods discussed above are directly applicable, making the algorithm feasible from a numerical standpoint.

EXAMPLE 6

NON-PERTURBATIVE INVERSION OF ELASTIC INHOMOGENEOUS STRUCTURES BURIED WITHIN A LAYERED HALF SPACE

In elastic media (by convention in this patent, media that supports shear wave activity) the relevant parameters are $\gamma$, $\mu$, (Lame' parameters), $\rho$ (density) and absorption. The inversion for these elastic parameters (i.e. the first and second Lame' parameters, $\lambda$ and $\mu$, follows virtually the same prescription as was outlined above for the acoustic scalar case. In a manner similar to the Electromagnetic Inversion problem discussed above, it is possible to break up the arbitrary 3 dimensional vector u(x,y,z), representing the displacement into components that propagate independently. The exact description of this procedure is given in [Wiskin, 1991], and [Muller, 1985]. This example will not deal with this decomposition since the idea behind this is more easily seen by looking at the electromagnetic example given earlier.

The idea here is to incorporate the above solution to the layered inversion problem directly into the Green's operator. As before, in the electromagnetic and the acoustic case, this Green's function is used in the integral equation formulation of the inversion problem of imaging an inhomogeneous body extending over an arbitrary number of layers.

The following is the general elastic partial differential equation which governs the displacement vector field u in the general case where $\lambda$ and $\mu$ both depend upon $x \in R^3$. When $\lambda$ and $\mu$ are independent of x, we have the homogeneous elastic case.

$$-\omega^2 \rho(x) u^i(x) - \frac{\partial}{\partial x^i}\left[\lambda(x)\frac{\partial}{\partial x^k}u^k(x)\right] + \frac{\partial}{\partial x^i}\left[\mu(x)\left\{\frac{\partial}{\partial x^i}u^k(x) + \frac{\partial}{\partial x^k}u^i(x)\right\}\right] = f^i(x)$$

$f^i(x)$ represents the applied body force, and $\mu(x)$ and $\lambda(x)$ are the Lame' parameters, their dependence upon $x \in R^3$ is the result of both the inhomogeneity to be imaged and the ambient layered medium. In particular $u_i(\vec{y})$ $\vec{y} \in R^3$ is the $i^{th}$ component (i=1,2,3) of the displacement field at point $\vec{y} \in R^3$ $u_i^0(\vec{y})$ is the $i^{th}$ component of the incident field.

$\rho_1(\vec{x})+\rho_0(z)=\rho(\vec{x})$ is the total density variation, it consists of the 3-D variation in $\rho_1$ and the vertical 1-D variation in $\rho_o$.

$\lambda_1(\vec{x})+\lambda_0(z)=\lambda(\vec{x})$ is the total variation in $\lambda$, the first Lame' parameter, $\lambda_1$ has 3-D variation, and $\lambda_o$ has 1-D vertical variation.

$\mu_1(\vec{x})+\mu_0(z)=\mu(\vec{x})$ is the total variation in the second Lame' parameter $\mu$. The $\mu_1$ has variation in 3-D, the $\mu_2$ has variation in 1-D (vertical).

$\rho(\vec{x})$=density=$\rho_1(\vec{x})+\rho_0(z)$, where $\rho_0(\vec{x})$ represents the layered medium without the object, and $\rho_1(\vec{x})$ represents the object to be imaged.

$\lambda_0(z)$ and $\mu_0(z)$ are the z-dependent Lame' parameters representing the layered medium $\lambda_1(\vec{x})$ and $\mu_1(\vec{x})$ are the Lame' parameters representing the object to be imaged The above differential equation is converted to the following elastic "Generalized Lippmann-Schwinger equation"

$$u_i(\vec{y}) = u_i^0(\vec{y}) - \int\int\int_{Vol} \{G_{im}^{(LAY)}(\vec{y},\vec{x})\} u_m(\vec{x}) d\vec{x}, \; i = 1, 2, 3$$

by means of the kernel $G_{im}^{(LAY)}(\vec{y},\vec{x})$, which is constructed below. Where the volume integral is performed over the finite volume that contains the image space (and the object being imaged, for example, an ore body, submarine mine, oil reservoir, etc). This is the basic integral equation which forms the theoretical foundation for the Layered Green's Operator approach to Inverse Scattering in a layered medium.

This kernel is a 3 by 3 matrix of functions which is constructed by a series of steps:

STEP 1:

Beginning with the acoustic (scalar or compressional) Green's function given by $$G(k_o|\mathbf{r}-\mathbf{r}'|) = \frac{e^{-ik_o|\mathbf{r}-\mathbf{r}'|}}{4\pi|\mathbf{r}-\mathbf{r}'|}$$

STEP 2:

The free space elastic Green's matrix is a 3 by 3 matrix of functions, built up from the free space Green's function. It's component functions are given as $$G_{im}(k_T;k_L|\mathbf{r}-\mathbf{r}'|) = \mu G(k_T|\mathbf{r}-\mathbf{r}'|)\delta_{im} + \frac{\mu}{k_T^2}\frac{\partial^2}{\partial x^i \partial x^m}[G(k_T|\mathbf{r}-\mathbf{r}'|) - G(k_L|\mathbf{r}-\mathbf{r}'|)]$$

STEP 3:

Next the layered Green's function, $G_{im}^L(\vec{y},\vec{x})$, for a layered elastic medium is defined. It is defined in terms of $G_{im}$, the components i,m=1, . . . , 3, of the elastic Green's function in homogeneous elastic media given above. The components of the layered Green's matrix are integrals over Bessel functions and reflection coefficients in essentially the same manner as the acoustic layered Green's function consisted of integrals over wavenumber, of the acoustic reflection coefficients. This dyadic is patterned after [Muller, 1985], in the manner discussed in [Wiskin, 1992].

STEP 4:

Finally the layered Green's kernel $G_{im}^{(LAY)}$, is constructed $\vec{x} \in R^3$ $$G_{im}^{(LAY)}(\vec{y},\vec{x}) = -\omega^2 G_{im}^L(\vec{y},\vec{x})\rho_1(\vec{x}) - \frac{\partial}{\partial x^m}\left\{\left(\frac{\partial}{\partial x^j}G_{ij}^L(\vec{y},\vec{x})\right)\lambda_1(\vec{x})\right\} +$$

-continued $$\frac{\partial}{\partial x^j}\left\{\left(\frac{\partial}{\partial x^m}G_{ij}^L(\vec{y},\vec{x}) + \frac{\partial}{\partial x^j}G_{im}^L(\vec{y},\vec{x})\right)\mu_1(\vec{x})\right\}$$

where $G_{im}^L(\vec{y},\vec{x})$ is the layered Green's function for the elastic layered medium. The progressive constructions can be represented in the following way, beginning with the acoustic free space Green's function:

$$G(k_o|r-r'|) = \frac{e^{-ik_o|r-r'|}}{4\pi|r-r'|} \Rightarrow\Rightarrow \boxed{G_{im}(\vec{y},\vec{x})} \Rightarrow\Rightarrow \boxed{G_{im}^L(\vec{y},\vec{x})} \Rightarrow\Rightarrow \boxed{G_{im}^{(LAY)}(\vec{y},\vec{x})}$$

Alternatively, in words:

| Acoustic free space Green's function | elastic free space Greens function | elastic layered Green's function | kernel for elastic layered Lippmann-Schwinger equation |
|---|---|---|---|

Using the last "kernel" in this series in the generalized elastic layered Lippmann-Schwinger Equation gives the vector displacement.

$$u_i(\vec{y}) = u_i^0(\vec{y}) - \int\int\int_{Vol}\{G_{im}^{(LAY)}(\vec{y},\vec{x})\}u_m(\vec{x})d\vec{x}$$

which is then discretized, using the sinc basis in exactly the same way as for the previous examples, and, the FFT, and biconjugate gradient, and conjugate gradient algorithms are then applied to this vector equation, in the same way as done above. Thus the elastic modality (including shear waves) is accounted for.

The construction of the layered Green's function in the full elastic case (with shear wave energy included is slightly more complicated than the purely scalar case. For this reason, we look at the construction in more detail, see also [Wiskin, 1993]

For discretization of the resulting equations see the electromagnetic case discussed in example 3.

The Construction of the Continuous Form of the Layered Green's Operator $G^L$-3D and with full elastic mode conversion Case Now we proceed with the construction of the continuous variable form of the Layered Green's operator. The closed form expression for the discretized form of the bandlimited approximation to this continuous variable Green's operator is constructed in a manner exactly analogous to the vector electromagnetic case discussed in example 3.

By analogy with the acoustic (scalar) situation, the construction of the layered Green's operator can be viewed as a series of steps beginning with the 3D free space Green's operator.

Step a) Decompose a unit strength point source into a plane wave representation (Weyl-Sommerfeld Integral). For the elastodynamic (vector) case we must consider the the three perpendicular directions of particle motion, which we take to be the horizontal direction, the direction of propagation, and the direction perpendicular to the previous two. Muller has given the representation for a point source in elastic media in [Muller, 1985]

Step b) Propagate and reflect the plane waves through the upper and lower layers to determine the total field at the response position. The total field will consist of two parts: $u^{up}(r)$, the upward propagating particle velocity, and $u^d(r)$, the downward propagating particle velocity at position r. This propagation and reflection is carried out analytically by means of the reflection coefficients, which in the elastic case, are the matrices $R^-$ and $R^+$ ($R^-$ and $R^+$ are 2×2 matrices), and the scalars, $r^-$, and $r^+$. The matrices correspond to the P-SV (compressional and shear vertical polarized waves) for the case of horizontal stratification. (x is the horizontal, and z is the vertical coordinate, z is positive downward). The scalar coefficients correspond to the SH (horizontally polarized) shear waves, which propagate without mode conversion to the other types for the case of horizontally layered media.

$R^-$ and $r^-$, represent the wave field reflected from the layers below the source position, and $R^+$ and $r^+$ represent the cumulative reflection coefficient from the layers above the source position, for the matrix and scalar cases respectively.

These total reflection coefficients are formed recursively from the standard reflection coefficients found in the literature (e.g. Muller [1985], and Aki and Richards, Quantitative Seismology, Freeman and Co., 1980, herein included as a reference].

FIGS. 1-C and 27 should be kept in mind throughout the following discussion.

As in the scalar case, in order to have a single reference position $R^+$ and $R^-$ are both given with respect to the top of layer that contains the scattering point, which is denoted by "sc". That is, $R^+$ represents the reflection coefficient for an upgoing wave at the interface between layer sc and sc-1. FIG. 27 displays the relevant geometry.

In our case the expressions $S^u$ and $S^d, S^d$ and $S^u$, and are those derived from the Sommerfeld integral representation of a point source of unit strength, given in Muller. [see also Aki and Richards, 1980]. For example:

$S^d = e^{i\omega b_{sc}(z'-z_{sc})} = e^{i\omega b_{sc}\Delta z'}$ $S^u = e^{-i\omega b_{sc}(z'-z_{sc})} = e^{-i\omega b_{sc}\Delta z'}$ for the scalar case.

As shown in detail, by Muller, the total contribution of the upward travelling wave is given by $$S^u + R^-R^+S^u + R^-R^+R^-R + S^u + R^-R^+R^-R^+S^u +$$
$$\ldots = [1 + R^-R^+ + R^-R^+R^-R^+ + R^-R^+R^-R^+R^-R^+ + \ldots]S^u =$$
$$[1 - R^-R^+]^{-1}S^u$$

for the transverse shear wave (SH or horizontal shear wave), and $$S^u + R^-R^+S^u + R^-R^+R^-R + S^u + R^-R^+R^-R^+S^u +$$

-continued $$\ldots = [1 + R^-R^+ + R^-R^+R^-R^+ + R^-R^+R^-R^+R^-R^+ + \ldots]S^u = [1 - R^-R^+]^{-1}S^u$$

for the P-SV matrix case. Note that some care must be exercised in the convergence of the matrix series, however, for practical situations we can omit this detail.

Step c) The process of forming the total field at the response point must be broken up into two cases:

Case 1: the response point is above the scatter point, that is $\Delta z - \Delta z' < 0$ ($\Delta z$ is the distance from the interface above the scattering layer, to the response point, the z axis is positive downward), and Case 2, where the response point is below the scattering point $\Delta z - \Delta z' < 0$.

Furthermore each case consists of an upward travelling, and a travelling wave:

Upward travelling wavefield:

First, in case 1:

$[1-R^-R^+]^{-1}S^u$ and $[1-R^-R^+]^{-1}S^u$ represent the contribution to $u^{up}$ from the upward travelling part of the source. A similar expression can be formed for the contribution from the downward travelling part of the source, it is $[1-R^-R^+]^{-1}R^-S^d$, and $[1-R^-R^+]^{-1}R^-S^d$ Thus, the total upward component of the wave field at the response point is formed from:

$$\mathbf{u}^{up} \equiv \begin{pmatrix} (\mathbf{I} - \mathbf{R}^-\mathbf{R}^+)^{-1}(\mathbf{S}^u + \mathbf{R}^-\mathbf{S}^d) \\ (I - r^-r^+)^{-1}(S^u + r^-S^d) \end{pmatrix}$$

Case 2: the response point is below the scatter point, that is $\Delta z - \Delta z' > 0$ The result here is similar, the change occurring in the coefficient of the $S^u$, and $S^u$.

$$\mathbf{u}^{up} \equiv \begin{pmatrix} (\mathbf{I} - \mathbf{R}^-\mathbf{R}^+)^{-1}(\mathbf{R}^-\mathbf{R}^+\mathbf{S}^u + \mathbf{R}^-\mathbf{S}^d) \\ (I - r^-r^+)^{-1}(S^u + r^-S^d) \end{pmatrix}$$

Downward Component of Wavefield

Case 1: A similar expression gives the downward component of the total wave field at the response point r, for case 1:

$$\mathbf{u}^{down} \equiv \mathbf{u}^d \equiv \begin{pmatrix} (\mathbf{I} - \mathbf{R}^+\mathbf{R}^-)^{-1}\mathbf{R}^+\mathbf{R}^-\mathbf{S}^d \\ (I - r^+r^-)^{-1}r^+r^-S^d \end{pmatrix} + \begin{pmatrix} (\mathbf{I} - \mathbf{R}^+\mathbf{R}^-)^{-1}\mathbf{R}^+\mathbf{S}^u \\ (I - r^+r^-)^{-1}r^+S^u \end{pmatrix}$$

or $$\mathbf{u}^{down} \equiv \mathbf{u}^d \equiv \begin{pmatrix} (\mathbf{I} - \mathbf{R}^+\mathbf{R}^-)^{-1}(\mathbf{R}^+\mathbf{R}^-\mathbf{S}^d + \mathbf{R}^+\mathbf{S}^u) \\ (I - r^+r^-)^{-1}(r^+r^-S^d + r^+S^u) \end{pmatrix}$$

Case 2: For case 2, the result is similar, here the response point resides below the scatter point, that is $\Delta z - \Delta z' > 0$ $$\mathbf{u}^{down} \equiv \mathbf{u}^d \equiv \begin{pmatrix} (\mathbf{I} - \mathbf{R}^+\mathbf{R}^-)^{-1}(\mathbf{S}^d + \mathbf{R}^+\mathbf{S}^u) \\ (I - r^+r^-)^{-1}(r^+r^-S^d + r^+S^u) \end{pmatrix}$$

Step d) The final step in the process is the recombination of the plane waves to obtain the total wavefield (upgoing and downgoing waves) at the response position:

For the scalar case 1 $\Delta z - \Delta z' < 0$, and:

$G^L(x-x', y-y', z|z') = f^u + f^d$, with $$u^{up} = \int J_0(u\omega/r - r'|)[1 - R^-R^+]^{-1}[S^u + R^-S^d]\exp^{i\omega b_{sc}(z-z_{sc})}du$$

$$u^d = \int J_0(u\omega/r - r'|)[1 - R^-R^+]^{-1}[R^+S^u + R^+R^-S^d]\exp^{-i\omega b_{sc}(z-z_{sc})}du,$$

so that $$G^L(x-x', y-y', z|z') =$$
$$\int J_0(u\omega/r - r'|)[1 - R^-R^+]^{-1}[S^u + R^-S^d]\{e^{i\omega b_{sc}(z-z_{sc})} + R^+ e^{i\omega b_{sc}(z-z_{sc})}\}du,$$

While for case 2, $\Delta z - \Delta z' > 0$, similar algebra gives:

$$G^L(x-x', y-y', z|z') =$$
$$\int J_0(u\omega/r - r'|)[1 - R^-R^+]^{-1}[R^+S^u + S^d][e^{-i\omega b_{sc}(z-z_{sc})} + R^- e^{-i\omega b_{sc}(z-z_{sc})}]du.$$

For case 1 this can be rewritten as:

$$G^L(r-r', z|z') =$$
$$A\int_{u=0}^\infty C(u: \mathbf{r}-\mathbf{r}')\{S^u e^{i\omega b_{sc}\Delta z} + R^-S^d e^{i\omega b_{sc}\Delta z} + R^+S^u e^{-i\omega b_{sc}\Delta z} + R^+R^-S^d e^{-i\omega b_{sc}\Delta z}\}du$$

where the coefficient function C(u:r−r') is given by:

$$C(u: \mathbf{r}-\mathbf{r}') = J_0(u\omega|\mathbf{r}-\mathbf{r}'|)(1 - R^-R^+)^{-1}\frac{i\omega u}{b_{sc}}.$$

For case 2, $G^L$ can be written as:

$$G^L(r-r', z|z') =$$
$$A\int_{u=0}^\infty C(u: \mathbf{r}-\mathbf{r}')\{R^+R^-S^u e^{i\omega b_{sc}\Delta z} + R^-S^d e^{i\omega b_{sc}\Delta z} + R^+S^u e^{-i\omega b_{sc}\Delta z} + S^d e^{-i\omega b_{sc}\Delta z}\}du$$

Finally, using the definitions for $S^u$ and $S^d$ and recognizing that products such as $S^d e^{i\omega b_{sc}\Delta z}$ can be rewritten as $S^d e^{i\omega b_{sc}\Delta z} = e^{i\omega b_{sc}\Delta z'} e^{i\omega b_{sc}\Delta z} = e^{i\omega b_{sc}(\Delta z+\Delta z')}$ the operator $G^L$ turns out (after rearrangement of the above equations) to be the sum of a convolution and a correlation kernel:

$G^L(r-r',z|z') = G_R(r-r',z+z') + G_V(r-r',z-z')$.

Case I has $(\Delta z - \Delta z') \leq 0$, where $\Delta z = z - Z_{sc}$ and $\Delta z' = z' - z_{sc}$ with $z_{sc}$ being the z co-ordinate of the top part of the layer that contains the scatterer. In fact $G_R$ and $G_V$ turn out to be given by the following formulae (they appear to differ from the integrals above because of the rearrangement that leads to the decomposition into convolutional and correlational parts):

$$G_R(\mathbf{r}-\mathbf{r}', \Delta z | \Delta z') =$$
$$A \int_{u=0}^{\infty} J_0(u\omega|\mathbf{r}-\mathbf{r}'|)C(u)\{R^+ e^{-i\omega b_{sc}(\Delta z+\Delta z')} + R^- e^{i\omega b_{sc}(\Delta z+\Delta z')}\}du$$

$$G_V(\mathbf{r}-\mathbf{r}', \Delta z | \Delta z') =$$
$$A \int_{u=0}^{\infty} J_0(u\omega|\mathbf{r}-\mathbf{r}'|)C(u)\{R^+ R^- e^{-i\omega b_{sc}(\Delta z+\Delta z')} + e^{i\omega b_{sc}(\Delta z+\Delta z')}\}du,$$

where, now:

$$C(u) = (1 - R^+ R^-)^{-1} \frac{i\omega u}{b_{sc}},$$

$R^-$ and $R^+$ are the recursively defined reflectivity coefficients described in Muller's paper,
u is the horizontal slowness, $$u \equiv \frac{\sin\theta}{c}.$$

Recall that Snell's law guarantees that u will remain constant as a given incident plane wave passes through several layers.
- $\omega$ is the frequency
- $b_{sc}$ is the vertical slowness for the particular layer hosting the scattering potential Case II consists of the case where $(\Delta z - \Delta z') \geq 0$. The $G_R$ and $G_V$ are now given by the following:

$$G_V(\mathbf{r}-\mathbf{r}', z | z') =$$
$$A \int_{u=0}^{\infty} J_0(u\omega|\mathbf{r}-\mathbf{r}'|)C(u)\{R^+ R^- e^{i\omega b_{sc}(\Delta z+\Delta z')} + e^{-i\omega b_{sc}(\Delta z+\Delta z')}\}du,$$

and $$G_R(\mathbf{r}-\mathbf{r}', z | z') =$$
$$A \int_{u=0}^{\infty} J_0(u\omega|\mathbf{r}-\mathbf{r}'|)C(u)\{R^- e^{i\omega b_{sc}(\Delta z+\Delta z')} + R^+ e^{-i\omega b_{sc}(\Delta z+\Delta z')}\}du.$$

These expressions can be combined into one equation by the judicious use of absolute values. The correlational part of the Green's operator can be transformed into a convolution by a suitable change of variables. The resulting Green's function for imaging inhomogeneities residing within Ambient Layered Media must be quantized by convolving with the sinc (really Jinc) basis functions described below. This is done analytically and the result is given below.

The same process is carried out as detailed above, in order to determine the P-SV total wavefield (the 2 by 2 matrix case), and is not repeated.

The matrix case is handled in exactly the same manner, with allowance for the differing algebra associated with matrices, the preservation of the convolution is preserved for the same reason as shown above in the scalar situation.

On avoiding convergence problems due to the presence of derivatives in the elastic Green's function (i.e. with shear wave motion)

One difficulty with this formulation is the presence of four derivatives acting upon the acoustic free space Green's function in the construction of the dyadic $G^{(LAY)}$. This problem we have overcome (see related code in Appendix E) by the following method:

Given an inhomogeneous distribution of isotropic density $\rho$ and Lamé parameters $\lambda$ and $\mu$, imbedded in a homogeneous medium with density $\rho_0$ and Lamé parameters $\lambda_0$ and $\mu_0$, the total infinitesimal displacement vector u satisfies the partial differential equation $$\omega^2 \rho u_i + (\lambda u_{j,j})_{,i} + [\mu(u_{i,j}+u_{j,i})]_{,j} = 0 \qquad (1)$$

while the incident displacement field $u^i$ satisfies $$\omega^2 \rho u_i^i + (\lambda_0 u_{j,j}^i)_{,i} + [\mu_0(u_{i,j}^i+u_{j,i}^i)]_{,j} = 0 \qquad (2)$$

where $\rho_0$, $\lambda_0$, and $\mu_0$ are the homogeneous parameters of the imbedding medium. Subtracting (2) from (1) and rearranging results in $$u_i^s + \left(\frac{1}{k_p^2} - \frac{2}{k_s^2}\right)(u_{j,j}^s)_{,i} + \frac{1}{k_s^2}[(u_{i,j}^s + u_{j,i}^s)]_{,j} = -f_i \qquad (3)$$

for the scattered displacement field $u^s = u - u^i$. The inhomogeneous term f is given by $$f_i = \left(\frac{\rho}{\rho_0} - 1\right)u_i - \qquad (4)$$
$$\left(\frac{1}{k_p^2} - \frac{2}{k_s^2}\right)\left\{\left(\frac{\lambda}{\lambda_0} - 1\right)u_{j,j}\right\}_{,i} + \frac{1}{k_s^2}\left\{\left(\frac{\mu}{\mu_0} - 1\right)(u_{i,j}+u_{j,i})\right\}_{,j}$$

where the respective shear-wave and compression-wave velocities $c_s$ and $c_p$ and corresponding wave numbers ks and kp are given by $$c_s^2 = \frac{\mu_0}{\rho_0}; k_s^2 = \frac{\omega^2}{c_s^2}; c_p^2 = \frac{\lambda_0 + 2\mu_0}{\rho_0}; k_p^2 = \frac{\omega^2}{c_p^2} \qquad (5)$$

for the imbedding medium. Introducing the scattering potentials $$\gamma_\rho = \frac{\rho}{\rho_0} - 1; \gamma_\lambda = \left(\frac{1}{k_p^2} - \frac{2}{k_s^2}\right)\left(\frac{\lambda}{\lambda_0} - 1\right); \gamma_\mu = \frac{1}{k_s^2}\left(\frac{\mu}{\mu_0} - 1\right) \qquad (6)$$

gives $$f_i = \gamma_\rho u_i + \{\gamma_\lambda u_{j,j}\}_{,i} + \{\gamma_\mu(u_{i,j}+u_{j,i})\}_{,j} \qquad (7)$$

Solution of (3) by the introduction of the free-space Green's function results in $$u_i^s = G_{ij} * f_j = \int_v f_j(\mathbf{r}')G_{ij}(F-\mathbf{r}')dv' \qquad (8)$$

where * denotes 3-D convolution, v is the support of the inhomogeneity, and the Green's function is given by [Aki and Richards, Quantitative Seismology, Freeman and Co., 1980, herein included as a reference]:

$$G_{ij}(\mathbf{r}-\mathbf{r}') = k_s^2 g(k_s|\mathbf{r}-\mathbf{r}'|)\delta_{ij} + \frac{\partial^2}{\partial x_i \partial x_j}\{g(k_s|\mathbf{r}-\mathbf{r}'|) - g(k_p|\mathbf{r}-\mathbf{r}'|)\} \qquad (9)$$

where g(kR) is the scalar Helmholtz Green's function $$g(kR) = \frac{e^{ikR}}{4\pi R}. \quad (10)$$

where $e^{i\omega t}$ time dependence has been assumed. Inserting (7) into (8) and integrating by parts yields the following integral wave equation:

$$u_i^s = G_{ij}*\{\gamma_\rho u_j\} + G_{ij,j}*\{\gamma_\lambda u_{k,k}\} + G_{ij,k}*\{\gamma_\mu(u_{j,k}+u_{k,j})\}. \quad (11)$$

For now, consider the case where $\gamma_\mu = 0$ and note that:

$$G_{ij,j} = k_s^2 \frac{\partial}{\partial x_i} g(k_s R) + \frac{\partial}{\partial x_i}(\nabla^2 g(k_s R) - \nabla^2 g(k_p \mathbf{R})). \quad (12)$$

using $$(\nabla^2 + k^2)g(kR) = -\delta(|r-r'|) \quad (13)$$

reduces (12) to:

$$G_{ij,j} = k_p^2 \frac{\partial}{\partial x_i} g(k_p \mathbf{R}), \quad (14)$$

which will henceforth be denoted $C_i$. We have now arrived at the integral equation:

$$\begin{bmatrix} u_x^i \\ u_y^i \\ u_z^i \end{bmatrix} = \begin{bmatrix} u_x \\ u_y \\ u_z \end{bmatrix} - \begin{bmatrix} G_{xx} & G_{xy} & G_{xz} & C_x \\ G_{yx} & G_{yy} & G_{yz} & C_y \\ G_{zx} & G_{zy} & G_{zz} & C_z \end{bmatrix} * \begin{bmatrix} \gamma_\rho & 0 & 0 & 0 \\ 0 & \gamma_\rho & 0 & 0 \\ 0 & 0 & \gamma_\rho & 0 \\ 0 & 0 & 0 & \gamma_\lambda \end{bmatrix} \begin{bmatrix} u_x \\ u_y \\ u_z \\ \nabla \cdot \mathbf{u} \end{bmatrix} \quad (15)$$

since $u_{k,k} = \nabla \cdot \mathbf{u}$.

The integral equation (15) can be solved by application of the 3-D FFT to compute the indicated convolutions, coupled with the biconjugate gradient iteration, or similar conjugate gradient method. [Jacobs, 1981]. One problem with (15) is, however, the need to compute $\nabla \cdot \mathbf{u}$ at each iteration. Various options for this include taking finite differences or the differentiation of the basis functions (sinc functions) by FFT. Our experience with the acoustic integral equation in the presence of density inhomogeneity indicates that it is best to avoid numerical differentiation. Instead, the system is augmented as:

$$\begin{bmatrix} u_x^i \\ u_y^i \\ u_z^i \\ \nabla \cdot \mathbf{u}^i \end{bmatrix} = \begin{bmatrix} u_x \\ u_y \\ u_z \\ \nabla \cdot \mathbf{u} \end{bmatrix} - \begin{bmatrix} G_{xx} & G_{xy} & G_{xz} & C_x \\ G_{yx} & G_{yy} & G_{yz} & C_y \\ G_{zx} & G_{zy} & G_{zz} & C_z \\ C_x & C_y & C_z & D \end{bmatrix} * \quad (16)$$

$$\begin{bmatrix} \gamma_\rho & 0 & 0 & 0 \\ 0 & \gamma_\rho & 0 & 0 \\ 0 & 0 & \gamma_\rho & 0 \\ 0 & 0 & 0 & \gamma_\lambda \end{bmatrix} \begin{bmatrix} u_x \\ u_y \\ u_z \\ \nabla \cdot \mathbf{u} \end{bmatrix}$$

where $$D = C_{x,x} + C_{y,y} + C_{z,z} = k_p^2 \nabla^2 g(k_p R) = -k_p^2 \{k_p^2 g(k_p R) + \delta(R)\}. \quad (17)$$

Iterative solution of (16) for the four unknown fields $u_x$, $u_y$, $u_z$, and $\nabla \cdot \mathbf{u}$ now involves no numerical differentiation of u, since all derivative operators have now been applied analytically to the Green's function. The incident component $\nabla \cdot \mathbf{u}^i$ is assumed known. Equation (16) can be written symbolically as $$U^i = (I - \mathbb{G}[\gamma]_{diag})U \quad (18)$$

where $U^i$ and U are the augmented 4-vectors in Eq. (16), $[\gamma]_{diag}$ is the diagonal operator composed of $\gamma_\rho$ and $\gamma_\lambda$, and $\mathbb{G}$ is the 4×4 dyadic Green's function in Eq. (16). Inclusion of $\gamma_\mu$ Scattering to Give the General Elastic-wave Integral Equations.

We now give a method for solving integral equations in the general case for the inhomogeneous material properties $\rho$, $\lambda$, and $\mu$.

Because the inclusion of the more complicated term in $\gamma_\mu$ causes the matrix notation used above to require breaking the equations into parts on several lines, we elect for efficiency of space to use the more compact tensor notation. This should cause no difficulty because the translation is clear on comparing the special case of $\gamma_\mu = 0$ in the general tensor equations which follow with the previous matrix notation for this same case.

First we give again (see Eq (11)) the integral equations (which in practice have been discretized by sinc basis functions) for inhomogeneous $\rho$, $\lambda$, and $\mu$. Here * means convolution (the integration operation):

$$u_i^s = G_{ij}*[\gamma_\rho u_j] + G_{ij,j}*[\gamma_\lambda u_{k,k}] + G_{ij,k}*[\gamma_\mu(u_{j,k}+u_{k,j})] \quad (19)$$

We note that the displacement field $u_j$ and its derivatives also $u_{j,k}$ appear. We choose not to compute derivatives of the fields numerically and avoid the associated numerical instability. Instead, we augment the above equation with additional equations to compute the derivatives in a more stable way by solving for them directly. Thus, solving for $(u_{i,l}+u_{l,i})$ directly is more efficient and replaces computation of nine fields with only six. Forming the six unique symmetric-derivative pairs, we obtain an integral equation for these pairs.

$$u_{i,1}^s + u_{1,i}^s = (G_{ij,1}+G_{1j,i})*[\gamma_\rho u_j] + (G_{ij,k1}+G_{1j,ki})*[\gamma_\mu(u_{jk}+u_{kj})] + (G_{ijj1} + G_{1jii})*[\gamma_\lambda u_{k,k}] \quad (20)$$

Note that $$G_{ij,jl} = k_p^2 \frac{\partial^2}{\partial x_i \partial x_j} g(k_p \mathbf{R}) \quad (21)$$

We now augment the system Eq. (19) for the three components of $u_i^s$ with the system Eq. (20) which has six pairs of unique component derivatives.

These nine equations can also be placed in a matrix form similar to that of the augmented system given in Eq (16). The augmented system of nine components could be solved for $\gamma_\rho$, $\gamma_\lambda$, and $\gamma_\mu$, assuming knowledge of the fields $u^i$ and derivatives $u^i_{,k}$. Since the fields and derivatives are also unknown, we must solve for them simultaneously with $\gamma_\rho$, $\gamma_\lambda$, and $\gamma_\mu$. This is done by adding these constraint equations. These nine equations are composed of the three equations for $u_i$ $$u_i^i = u_i - G_{ij}*(\gamma_\rho u_j) - G_{ij,j}*[\gamma_\lambda u_{k,k}] - G_{ij,k}*[\gamma_\mu(u_{j,k}+u_{k,j})] \quad (22)$$

and the six equations for $U_{j,k}+u_{k,j}$ $$(u_{i,l}^j + u_{l,i}^j) = (u_{i,l} - u_{l,i}) - (G_{ij,l} + G_{lj,i}) * [\gamma_\rho u_j] - \qquad (23)$$
$$(G_{ij,kl} + G_{lj,ki}) * [\gamma_\mu(u_{jk} + u_{kj})] -$$
$$(G_{ij,jl} + G_{lj,ji}) * [\gamma_\lambda u_{k,k}]$$

These 9 equations can also be placed in a matrix form similar to that of the augmented system given in Eq (16).

Solving these twelve equations (Eq. (19, 22, 23)) for $(\gamma_\rho, \gamma_\lambda, \gamma_\mu)$, the fields, and their derivatives is accomplished using the Frechet derivative methods described next. As in Eq. (16) for the $\mu=\mu_0$ case, Eq. (23) can be written symbolically as $$\mathbf{U}^i = (\mathbf{I} - \mathbf{G}[\gamma]_{diag})\mathbf{U} \qquad (24)$$

where the operators $\mathbb{G}$ and $[\gamma]_{diag}$ are now 9×9, and the vectors U and $\mathbf{U}^i$ consist of the three components of u and its six symmetric derivative sum-pairs.

EXAMPLE 7

CYLINDRICAL COORDINATE METHODS FOR NUMERICAL SOLUTION OF THE SIE

The above examples all use the FFT-BCG algorithm for imaging. This method is one of three methods discussed in this patent. The other two methods are (1) The cylindrical coordinate recursion method (Cylindrical Recursion)
(2) Rectangular recursion of scattering matrix method (Rectangular Recursion for short reference)

We now discuss the cylindrical recursion method:

7.1 CYLINDRICAL COORDINATE SIE FORMULATION AND DISCRETIZATION

We begin with the acoustic scattering integral equation (SIE) for the constant density case:

$$f^i(\rho) = f(\rho) - \frac{k_0^2}{4i} \int\int \gamma(\rho')f(\rho')H_0^{(2)}(k_0|\rho-\rho'|)d^2\rho. \qquad (1.1)$$

Let each field be expanded in a Fourier series in the angular variable:

$$f(\rho) = \sum_n f_n(\rho)e^{in\phi}.$$

Then using Graf's addition theorem:

$$H_0^{(2)}(k_0|\rho-\rho'|) = \begin{cases} \sum_n H_n^{(2)}(k_0\rho)J_n(k_0\rho')e^{in(\phi-\phi')} & \rho > \rho' \\ \sum_n H_n^{(2)}(k_0\rho')J_n(k_0\rho)e^{in(\phi-\phi')} & \rho < \rho' \end{cases} \qquad (1.2)$$

results in the cylindrical coordinate form of (1.1):

$$f_n^i(\rho) = f_n(\rho) - \frac{\pi k_0^2}{2i}\int_0^a \left\{\sum_m \gamma_{n-m}(\rho')f_m(\rho')\right\}B_m(k_0\rho)C_m(k_0\rho')\rho' d\rho' \qquad (1.3)$$

where the kernel is separably symmetric:

$$B_m(k_0\rho)C_m(k_0\rho') = \begin{cases} H_n^{(2)}(k_0\rho)J_n(k_0\rho') & \rho > \rho' \\ H_n^{(2)}(k_0\rho')J_n(k_0\rho) & \rho < \rho' \end{cases} \qquad (1.4)$$

Henceforth assume that $k_0=1$. Discretizing the radial integral by trapezoidal rule using an increment of $\Delta$ results in:

$$f_{l,n}^i = f_{nl,n} - \left\{h_{l,n}\sum_{l'=1}^l (\gamma f)_{l',n} j_{l',n} + j_{l',n}\sum_{l'=l+1}^L (\gamma f)_{l',n} h_{l',n}\right\} \qquad (1.5)$$

where $$f_{l,n} = f_n(l\Delta),\ h_{l,n} = \Delta\sqrt{\frac{\pi}{2i}}H_n^{(2)}(l\Delta),\ j_{l,n} = \Delta\sqrt{\frac{\pi}{2i}}J_n(l\Delta) \qquad (1.6)$$

and $$(\gamma f)_{l',n} = l'\sum_m \gamma_{l',n-m}f_{l',m} \qquad (1.7)$$

Notice that the extra l' resulting from the ρ' in the integral in (1.3) has been placed in the definition of $(\gamma f)_{l',n}$. Equation (1.5) is the final discrete linear system for the solution of the scattering integral equation in cylindrical coordinates. It can be rewritten as:

$$\mathbf{f}_l^i = \mathbf{f}_l - \left\{[\mathbf{h}_l]\sum_{l'=1}^l [\mathbf{j}_{l'}][\gamma_{l'}^*]\mathbf{f}_{l'} + [\mathbf{j}_l]\sum_{l'=l+1}^L [\mathbf{h}_{l'}][\gamma_{l'}^*]\mathbf{f}_{l'}\right\} \qquad (1.8)$$

where the vector components are the Fourier coefficients:

$$\mathbf{f}_l = \begin{bmatrix} f_{l,-N} \\ \vdots \\ f_{l,N} \end{bmatrix}, \text{ or, equivalently, } \{\mathbf{f}_l\}_n = f_{l,n},\ n = -N, \ldots, N \qquad (1.9)$$

where N is the range of the truncated Fourier series (The vectors are length 2N+1). The notation [x] denotes a diagonal matrix formed from the vector elements:

$$[x] = \begin{bmatrix} x_{-N} & 0 & \cdots & 0 \\ 0 & \ddots & & \vdots \\ \vdots & & \ddots & \\ 0 & & & x_N \end{bmatrix} \qquad (1.10)$$

and the notation $[\gamma_{l'}^*]$ denotes a convolution (including the l' factor):

$$\{[\gamma_{l'}^*]\mathbf{f}_{l'}\}_n = l' \sum_{m=-N}^{N} \gamma_{l',n-m} f_{l',m}, \quad n = -N, \ldots, N. \quad (1.11)$$

Writing (1.8) out in full gives the matrix equation:

$$\begin{bmatrix} \mathbf{f}_1^i \\ \vdots \\ \mathbf{f}_L^i \end{bmatrix} = A \begin{bmatrix} \mathbf{f}_1 \\ \vdots \\ \mathbf{f}_L \end{bmatrix} \quad (1.12)$$

where $$A = \begin{bmatrix} I & 0 & \cdots & \cdots & 0 \\ 0 & \ddots & & & \vdots \\ \vdots & & \ddots & & \vdots \\ \vdots & & & \ddots & 0 \\ 0 & \cdots & \cdots & 0 & I \end{bmatrix} - \quad (1.13)$$

$$\begin{bmatrix} [\mathbf{j}_1][\mathbf{h}_1] & [\mathbf{j}_1][\mathbf{h}_2] & \cdots & [\mathbf{j}_1][\mathbf{h}_L] \\ [\mathbf{h}_2][\mathbf{j}_1] & & & \vdots \\ \vdots & & & \vdots \\ [\mathbf{h}_L][\mathbf{j}_1] & [\mathbf{h}_L][\mathbf{j}_2] & \cdots & [\mathbf{j}_L][\mathbf{h}_L] \end{bmatrix} \cdot \begin{bmatrix} [\gamma_1] & 0 & \cdots & 0 \\ 0 & & & \vdots \\ \vdots & & & 0 \\ 0 & \cdots & 0 & [\gamma_L] \end{bmatrix}$$

Notice that the kernel is composed of a L×L block matrix with 2N+1×2N+1 diagonal matrix components and that the L×L block matrix is symmetric-separable, i.e.:

$$L_{nm} = \begin{cases} [\mathbf{j}_n][\mathbf{h}_m], & n \leq m \\ [\mathbf{h}_n][\mathbf{j}_m], & n > m \end{cases} \quad (1.14)$$

where $L_{nm}$ is one of the L×L component matrices.
For reference in the next section, we make the definitions:

$$\mathbf{s}_l \equiv \sum_{l'=l}^{L} [\mathbf{h}_{l'}][\gamma_{l'}^*]\mathbf{f}_{l'} \quad (1.15)$$

$$\mathbf{p}_l \equiv \sum_{l'=1}^{l-1} [\mathbf{h}_{l'}][\gamma_{l'}^*]\mathbf{f}_{l'} \quad (1.16)$$

7.2 RECURSIVE SOLUTION OF THE CYLINDRICAL COORDINATE SIE

The recursion for the 2-D cylindrical equation is:
Initialize:

$$P_L = 0 \quad (2.1)$$

$$\{s_L\}_n = f_{L,n}^s / h_{L,n}$$

For l=L, . . . ,1

$$s_{l-1} = s_l - [j_l][\gamma_l^*]\{[h_l]s_l + [j_l]p_l\}$$

$$p_{l-1} = p_l + [h_l][\gamma_l^*]\{[h_l]s_l + [j_l]p_l\}$$

Next l.

Thus far, we have assumed that the number of angular coefficients is the same for each radius l. In fact, the number of angular coefficients should decrease as l decreases. We find that for $\Delta = \lambda/4$, an accurate interpolation is achieved with $N_l = 2l-1$, $n = -N_l, \ldots, N_l$ Fourier coefficients. To introduce this modification, we must slightly redefine the operators as:

$$\{[\mathbf{j}_l]\mathbf{x}\}_n = \begin{cases} j_{l,n} x_n, & |n| \leq N_l \\ 0, & |n| > N_l \end{cases} \quad (2.2)$$

$$\{[\gamma_l^*]\mathbf{x}\}_n = \begin{cases} l \sum_{m=-N_l}^{N_l} \gamma_{l,n-m} x_m, & |n| \leq N_l \\ 0, & |n| > N_l \end{cases} \quad (2.3)$$

where the vector operated on is always length N where N is now the maximum number of Fourier coefficients, $N = N_L$. The total field at each layer, l, is given by:

$$f_{l,n} = \begin{cases} h_{l,n} s_{l,n} + j_{l,n} p_{l,n} + f_{l,n}^i, & |n| \leq N_l \\ 0, & |n| > N_l \end{cases} \quad (2.4)$$

In order to eliminate the need to know the starting values, $S_L$, we note that at each iteration, $s_l$ and $p_l$ are linear functions of $S_L$:

$$s_l = A_l s_L + b_l, \quad p_l = C_l s_L + d_l \quad (2.5)$$

where the matrices $A_l$, $C_l$ (dimension 2N+1×2N+1) and the vectors $b_l$, $d_l$ (dimension 2N+1) have the initial values:

$$A_L = I, \quad C_L = 0, \quad b_L = 0, \quad d_L = 0 \quad (2.6)$$

Using (2.5) and (2.6) in (1.1) and equating common terms leads a matrix and a vector recursion:
Initialize:

$$A_L = I, C_L = 0 \quad \mathbf{b}_L = \mathbf{0}, \mathbf{d}_L = \mathbf{0} \quad (2.7)$$

For $l = L, \ldots, 1$ $$A_{l-1} = A_l - [\mathbf{j}_l][\gamma_l^*]\{[\mathbf{h}_l]A_l + [\mathbf{j}_l]C_l\}$$

$$\mathbf{b}_{l-1} = \mathbf{b}_l - [\mathbf{j}_l][\gamma_l^*]\{[\mathbf{h}_l]\mathbf{b}_l + [\mathbf{j}_l]\mathbf{d}_l + \mathbf{f}_l^i\}$$

$$C_{l-1} = C_l + [\mathbf{h}_l][\gamma_l^*]\{[\mathbf{h}_l]A_l + [\mathbf{j}_l]C_l\}$$

$$\mathbf{d}_{l-1} = \mathbf{d}_l + [\mathbf{h}_l][\gamma_l^*]\{[\mathbf{h}_l]\mathbf{b}_l + [\mathbf{j}_l]\mathbf{d}_l + \mathbf{f}_l^i\}$$

Then using the fact that $s_L = 0$ leads to the solution:

$$A_0 s_L + b_0 = 0, \quad s_L = -A_0^{-1} b_0, \quad f_{L,n}^s = s_{L,n}/h_{L,n} \quad (2.8)$$

for the scattered field at the outer boundary. Iteration (1.1) with (1.4) can then be used to evaluate the total field internal to the object.

Notice that the LHS matrix recursion in (2.7) is independent of the incident field. Once it is used to compute $A_0$, the RHS vector recursion can be done for any number of incident fields. Concurrent solution for any number of incident fields can be obtained by replacing the RHS vector recursion with the matrix recursion:

$$B_L = 0, D_L = 0 \quad (2.9)$$

$$B_{l-1} = B_l - [\mathbf{j}_l][\gamma_l^*]\{[\mathbf{h}_l]B_l + [\mathbf{j}_l]D_l + F_l^i\}$$

$$D_{l-1} = D_l + [\mathbf{h}_l][\gamma_l^*]\{[\mathbf{h}_l]B_l + [\mathbf{j}_l]D_l + F_l^i\}$$

where the matrices $B_l$, $D_l$ are 2N+1×$N_v$ where $N_v$ is the number of views and the matrix of incident fields, $F_l^i$ is given by:

$$F_l^i = \begin{bmatrix} f_{l,-N}^{i,1} & \cdots & f_{l,-N}^{i,N_v} \\ \vdots & & \vdots \\ f_{l,N}^{i,1} & \cdots & f_{l,N}^{i,N_v} \end{bmatrix} \quad (2.10)$$

where the superscript after i is the view number (note that although the incident matrix is written as $2N+1 \times N_v$, the entries are zero for the row index $N_i < |n| \leq N$). A more compact recursion can be obtained by concatenating the two recursions to give:

$$G_L = [A_L, B_L] = [I, 0], \quad H_L = [C_L, D_L] = [0, 0] \quad (2.11)$$

For l=L, ..., 1

$$G_{l-1} = G_l - [j_l][\gamma_l^*]\{[h_l]A_l + [j_l]C_l + [0, F_l^i]\}$$

$$H_{l-1} = H_l + [h_l][\gamma_l^*]\{[h_l]A_l + [j_l]C_l + [0, F_l^i]\}$$

where the matrices $G_l$, $H_l$ are $2N+1 \times 2N+1+N_v$ and in the notation [A,B] the first matrix is $2N+1 \times 2N+1$ and the second is $2N+1 \times N_v$. Then $G_0 = [A_0, B_0]$ and the solution for all views is given by:

$$F_L^s = \begin{bmatrix} f_{L,-N}^{s,1} & \cdots & f_{L,-N}^{s,N_v} \\ \vdots & & \vdots \\ f_{L,N}^{s,1} & \cdots & f_{L,N}^{s,N_v} \end{bmatrix} = [h_L]A_0^{-1}B_0 \quad (2.12)$$

A slightly modified recursion can be shown to yield the scattering matrix of the object. Recall that the total field is given by:

$$f_l = [h_l]s_l + [j_l]p_l + f_l^i \quad (2.13)$$

Any externally generated incident field can be expanded in a bessel series which implies that there exists a sequence, $g_{-N}^i, \ldots, g_N^i$ such that:

$$f^i(\rho, \phi) = \Delta \sqrt{\frac{\pi}{2i}} \sum_n g_n^i J_n(\rho) e^{in\phi} \quad (2.14)$$

(recall that we are assuming that $k_0 = 1$) which means that $$f_l^i = [j_l]g^i \quad (2.15)$$

Redefining $p_l \rightarrow p_l + g^i$ then gives $f_l = [h_l]s_l + [j_l]p_l$ and leads easily to the iteration:

$$G_L = [I, 0], \quad H_L = [0, I] \quad (2.16)$$

For l=L, ..., 1

$$G_{l-1} = G_l - [j_l][\gamma_l^*]\{[h_l]A_l + [j_l]C_l\}$$

$$H_{l-1} = H_l + [h_l][\gamma_l^*]\{[h_l]A_l + [j_l]C_l\}$$

where the matrices are now $2N+1 \times 2(2N+1)$. The last iterate $G_0 = [A_0, B_0]$ yields the scattering matrix:

$$S(\gamma) = A_0^{-1} B_0 \quad (2.17)$$

for the body y which relates the incident field coefficients to the scattering coefficients:

$$\mathbf{g}^s = S\mathbf{g}^i, \text{ where } f^s(\rho, \phi) = \Delta \sqrt{\frac{\pi}{2i}} \sum_n g_n^s H_0^{(2)}(\rho) e^{in\phi} \quad (2.18)$$

for all incident field coefficient vectors, $\mathbf{g}^i$. Notice that in the previous notation:

$$g_n^i = f_{L,n}^i/j_{L,n}, \quad g_n^s = f_{L,n}^s/h_{L,n} \quad (2.19)$$

7.3 COMPUTATIONAL FORMULAS FOR THE JACOBIAN AND ITS ADJOINT

In order to apply the Gauss-Newton iteration to the solution of the imaging problem we must first derive recursive formulas for the application of the Jacobian and its adjoint. The Jacobian of the scattering coefficient vector, $S_L$, operating on a perturbation in $\gamma$ is given by:

$$J\delta\gamma = \sum_{l'=1}^{L} \sum_{n'=-N_{l'}}^{N_{l'}} \delta\gamma_{l',n'} \frac{\partial}{\partial \gamma_{l',n'}} s_L \quad (3.1)$$

From (2.8) we get:

$$s_L' = -A_0^{-1}(b_0' + A_0' s_L) \quad (3.2)$$

where the prime denotes differentiation followed by summation over the elements of $\delta\gamma$.

$$s_L' = J\delta\gamma = \sum_{l'=1}^{L} \sum_{n'=-N_{l'}}^{N_{l'}} \delta\gamma_{l',n'} \frac{\partial}{\partial \gamma_{l',n'}} s_L \quad (3.3a)$$

$$b_0' = \sum_{l'=1}^{L} \sum_{n'=-N_{l'}}^{N_{l'}} \delta\gamma_{l',n'} \frac{\partial}{\partial \gamma_{l',n'}} b_0 \quad (3.3b)$$

$$A_0' = \sum_{l'=1}^{L} \sum_{n'=-N_{l'}}^{N_{l'}} \delta\gamma_{l',n'} \frac{\partial}{\partial \gamma_{l',n'}} A_0 \quad (3.3c)$$

Equation (3.2) provides the formula for computing $J\delta\gamma$ is recursive formulas for $A_0'$ and $b'$ can be found. Define the notation:

$$A_l' = \sum_{l'=l+1}^{L} \sum_{n'=-N_{l'}}^{N_{l'}} \delta\gamma_{l',n'} \frac{\partial}{\partial \gamma_{l',n'}} A_l \quad (3.4a)$$

$$C_l' = \sum_{l'=l+1}^{L} \sum_{n'=-N_{l'}}^{N_{l'}} \delta\gamma_{l',n'} \frac{\partial}{\partial \gamma_{l',n'}} C_l \quad (3.4b)$$

(note the lower limit of the l' summation). Then using the LHS recursion in (2.7), it is simple to show that:

$$A_{l-1}' = A_l' - [j_l]\{[\gamma_l^*]\{[h_l]A_l' + [j_l]C_l'\} + [\delta\gamma_l^*]\{[h_l]A_l + [j_l]C_l\}\} \quad (3.5a)$$

$$C_{l-1}' = C_l' + [h_l]\{[\gamma_l^*]\{[h_l]A_l' + [j_l]C_l'\} + [\delta\gamma_l^*]\{[h_l]A_l + [j_l]C_l\}\} \quad (3.5b)$$

A further reduction in computational requirements can be achieved by noting from (3.2) that we do not need $A_0'$ but rather $A_0' S_L$ where $S_L$ is the matrix whose columns are the $S_L$'s for each view. The matrix $A_0$ is $2N+1 \times 2N+1$ while the matrix $A_0' S_L$ is $2N+1 \times N_v$. Thus define:

$$A'^s_l \equiv A'_l S_L, \; C'^s_l \equiv C'_l S_L, \; A^s_l \equiv A_l S_L, \; C^s_l \equiv C_l S_L \quad (3.6)$$

Then we get the recursion:

$$A^s_L = A_L S_L = I S_L = S_L, \; C^s_L = 0, \; A'^s_L = 0, \; C'^s_L = 0 \quad (3.7a)$$

For l=L, ... ,1

$$A'^s_{l-1} = A'^s_l - [j_l]\{[\gamma_l^*]\{[h_l]A'^s_l + [j_l]C'^s_l\} + [\delta\gamma_l^*]\{[h_l]A^s_l + [j_l]C^s_l\}\} \quad (3.7b)$$

$$C'^s_{l-1} = C'^s_l + [h_l]\{[\gamma_l^*]\{[h_l]A'^s_l + [j_l]C'^s_l\} + [\delta\gamma_l^*]\{[h_l]A^s_l + [j_l]C^s_l\}\} \quad (3.7c)$$

$$A^s_{l-1} = A^s_l - [j_l][\gamma_l^*]\{[h_l]A^s_l + [j_l]C^s_l\} \quad (3.7d)$$

$$C^s_{l-1} = C^s_l + [h_l][\gamma_l^*]\{[h_l]A^s_l + [j_l]C^s_l\} \quad (3.7e)$$

Similarly, for the b's and d's we get the recursion:

$$B_L = 0, \; D_L = 0, \; B'_L = 0, \; D'_L = 0 \quad (3.8a)$$

For l=L, ... ,1

$$B'_{l-1} = B'_l - [j_l]\{[\gamma_l^*]\{[h_l]B'_l + [j_l]D'_l\} + [\delta\gamma_l^*]\{[h_l]B_l + [j_l]D_l + F^i_l\}\} \quad (3.8b)$$

$$D'_{l-1} = D'_l + [h_l]\{[\gamma_l^*]\{[h_l]B'_l + [j_l]D'_l\}[\delta\gamma_l^*]\{[h_l]B_l + [j_l]D_l + F^i_l\}\} \quad (3.8c)$$

$$B_{l-1} = B_l - [j_l][\gamma_l^*]\{[h_l]B_l + [j_l]D_l + F^i_l\} \quad (3.8d)$$

$$D_{l-1} = D_l + [h_l][\gamma_l^*]\{[h_l]B_l + [j_l]D_l + F^i_l\} \quad (3.8e)$$

where the matrices are all $2N+1 \times N_v$. The final Jacobian is then:

$$S'_L = -A_0^{-1}(B'_0 + A'^s_0) \quad (3.9)$$

where the columns of $S'_L$ are the vectors $J_n \delta\gamma$ for each view, n=1, ... ,$N_v$.

We can of course concatenate these two recursions to give:

$$G_L = [S_L, 0], \; H_L = [0, 0], \; G'^s_L = [0, 0], \; H'_L = [0, 0] \quad (3.10a)$$

For l=L, ... ,1

$$G'_{l-1} = G'_l - [j_l]\{[\gamma_l^*]\{[h_l]G'_l + [j_l]H'_l\} + [\delta\gamma_l^*]\{[h_l]G_l + [j_l]H_l + [0, F^i_l]\}\} \quad (3.10b)$$

$$H'_{l-1} = H'_l + [h_l]\{[\gamma_l^*]\{[h_l]G'_l + [j_l]H'_l\} + [\delta\gamma_l^*]\{[h_l]G_l + [j_l]H_l + [0, F^i_l]\}\} \quad (3.10c)$$

$$G_{l-1} = G_l - [j_l][\gamma_l^*]\{[h_l]G_l + [j_l]H_l + [0, F^i_l]\} \quad (3.10d)$$

$$H_{l-1} = H_l + [h_l][\gamma_l^*]\{[h_l]G_l + [j_l]H_l + [0, F^i_l]\} \quad (3.10e)$$

where, at the last iterate, $G'_0 = [A'^s_0, B'_0]$. The matrices (G's and H's) in this recursion are all $2N+1 \times 2N_v$. This is the form of the Jacobian recursion used in the imaging programs.

EXAMPLE 8

RECTANGULAR SCATTERING MATRIX RECURSION

This section describes a new recursive algorithm the used scattering matrices for rectangular subregions. The idea for this approach is an extension and generalization of the cylindrical coordinate recursion method discussed in the previous section. The computational complexity is even further reduced over CCR. The CCR algorithm derives from the addition theorem for the Green's function expressed in cylindrical coordinates. The new approach generalizes this by using Green's theorem to construct propagation operators (a kind of addition theorem analogue) for arbitrarily shaped, closed regions. In the following, it is applied to the special case of rectangular subregions, although any disjoint set of subregions could be used.

Consider two rectangular subregions A and B of $R^2$ as shown in FIG. 16. Although the regions are drawn as disjoint, assume that they touch at the center of the figure. Let C denote the external boundary of the union of A and B. Define the scattering operator, $S_A$, of region A as the operator that gives the outward moving scattered field on the boundary A, given the inward moving field, due to external sources, evaluated on the boundary A. Similarly, define the scattering matrix for boundary B. The goal is to find the scattering matrix for boundary C, given $S_A$ and $S_B$—the scattering matrices for A and B.

Let the incident field due to sources external to boundary C, evaluated on boundary A be denoted $f_A^i$ and similarly define $f_B^i$. For the total problem (A and B both containing scatterers) there exists a net, inward moving field at boundary A. Denote this field $f_A^{in}$ and similarly define $f_B^{in}$. The total field leaving boundary A is then $f_A^{out} = S_A f_A^{in}$. Knowledge of the radiated field on a closed boundary due to internal sources allows the field external to the boundary to be computed at any point. Let the operator that maps $f_A^{out}$ onto the boundary B be denoted $T_{BA}$ (rectangular translation operator from A to B). Similarly denote the operator mapping $f_B^{out}$ to boundary A be denoted $T_{AB}$.

The total, inward moving field at boundary A has two parts—that due to the incident field external to C and that due to sources internal to boundary B. From the forgoing definitions, it should be obvious that the inward moving fields satisfy:

$$f_A^{in} = f_A^i + T_{AB} S_B f_B^{in} \quad (1a)$$

$$f_B^{in} = f_B^i + T_{BA} S_A f_A^{in} \quad (1b)$$

Solving for the total inward moving fields gives:

$$\begin{bmatrix} \mathbf{f}_A^{in} \\ \mathbf{f}_B^{in} \end{bmatrix} = \begin{bmatrix} I & -T_{AB} S_B \\ -T_{BA} S_A & I \end{bmatrix}^{-1} \begin{bmatrix} \mathbf{f}_A^i \\ \mathbf{f}_B^i \end{bmatrix} \quad (2)$$

The total scattered field at boundary A has two components—one from inside A and one from inside B. It should be obvious that the total scattered fields at boundaries, A and B are given by:

$$f_A^s = S_A f_A^{in} + T_{AB} S_B f_B^{in} \quad (3a)$$

$$f_B^s = T_{BA} S_A f_A^{in} + S_B f_B^{in} \quad (3b)$$

or $$\begin{bmatrix} \mathbf{f}_A^s \\ \mathbf{f}_B^s \end{bmatrix} = \begin{bmatrix} S_A & T_{AB} S_B \\ T_{BA} S_A & S_B \end{bmatrix} \begin{bmatrix} \mathbf{f}_A^{in} \\ \mathbf{f}_B^{in} \end{bmatrix} \quad (4)$$

Combining (2) and (4) gives:

$$\begin{bmatrix} \mathbf{f}_A^s \\ \mathbf{f}_B^s \end{bmatrix} = \begin{bmatrix} S_A & T_{AB} S_B \\ T_{BA} S_A & S_B \end{bmatrix} \begin{bmatrix} I & -T_{AB} S_B \\ -T_{BA} S_A & I \end{bmatrix}^{-1} \begin{bmatrix} \mathbf{f}_A^i \\ \mathbf{f}_B^i \end{bmatrix} \quad (5)$$

Assuming that the scattering operators are invertible, then we have the equivalent form:

$$\begin{bmatrix} \mathbf{f}_A^s \\ \mathbf{f}_B^s \end{bmatrix} = \begin{bmatrix} I & T_{AB} \\ T_{BA} & I \end{bmatrix} \begin{bmatrix} S_A^{-1} & -T_{AB} \\ -T_{BA} & S_B^{-1} \end{bmatrix}^{-1} \begin{bmatrix} \mathbf{f}_A^i \\ \mathbf{f}_B^i \end{bmatrix} \qquad (6)$$

The scattered field on the boundary C can be obtained from $\mathbf{f}_A^s$ and $\mathbf{f}_B^s$ by simple truncation (and possible re-ordering depending on how the boundaries are parameterized). Let the operator that does this be denoted:

$$\mathbf{f}_C^s = \begin{bmatrix} C_A & C_B \end{bmatrix} \begin{bmatrix} \mathbf{f}_A^s \\ \mathbf{f}_B^s \end{bmatrix} \qquad (7)$$

Let the incident field on boundary C due to external sources be denoted $\mathbf{f}_C^i$. There exist operators $D_A$ and $D_B$ that operate on $\mathbf{f}_C^i$ to give $\mathbf{f}_A^i$ and $\mathbf{f}_B^i$ (similar to the external translation operators $T_{AB}$ and $T_{BA}$). Thus:

$$\mathbf{f}_C^s = \begin{bmatrix} C_A & C_B \end{bmatrix} \begin{bmatrix} I & T_{AB} \\ T_{BA} & I \end{bmatrix} \begin{bmatrix} S_A^{-1} & -T_{AB} \\ -T_{BA} & S_B^{-1} \end{bmatrix}^{-1} \begin{bmatrix} D_A \\ D_B \end{bmatrix} \mathbf{f}_C^i \qquad (8)$$

from which we see that the scattering matrix for boundary C is given by:

$$S_C = \begin{bmatrix} C_A & C_B \end{bmatrix} \begin{bmatrix} I & T_{AB} \\ T_{BA} & I \end{bmatrix} \begin{bmatrix} S_A^{-1} & -T_{AB} \\ -T_{BA} & S_B^{-1} \end{bmatrix}^{-1} \begin{bmatrix} D_A \\ D_B \end{bmatrix} \qquad (9)$$

Equation (9) then gives the core computation for our rectangular scattering matrix recursion algorithm. Technical details concerning the existence and discrete construction of the translation and other needed operators has been omitted in this write-up. We have, however written working first-cut programs that perform (9).

AN O(N³) ALGORITHM FOR COMPUTING ALL SCATTERING VIEWS BASED ON RECTANGULAR SCATTERING MATRIX RECURSION

Consider a region containing scattering material covered by an N×N array of rectangular sub regions as shown in FIG. GO2.

Again, although drawn as disjoint, assume that the subregions touch. Assume that the scattering matrix for each subregion is known (for example, if each subregion is only $\lambda/2$ on edge, the calculation of S is trivial given the material enclosed). Now coalesce 2×2 sets of these scattering matrices into larger scattering matrices (this coalesce of 4 subregions into one is similar to the algorithm defined above for coalescing two subregions). There are N/2×N/2 such 2×2 blocks to coalesce. When done, we have scattering matrices for the set of larger subregions shown in FIG. GO4.

This process is continued until, at the final stage, the scattering matrix for the total region is computed. Note that the physical parameters of the scattering media (speed of sound, absorption, etc.) are used only in the first stage (computation of the N×N array of scattering matrices).

Assuming that N is a power of two, the algorithm will terminate after $\log_2(N)$ such stages with the scattering matrix for the whole region. A careful accounting of the computation required reveals that the total computation is $O(N^3)$. The end resulting scattering matrix then allows fast calculation of the scattered field anywhere external to the total region for any incident field (angle of view).

Although derived assuming that N is a power of 2, the algorithm can be generalized by including 3×3 (or any other sized) coalescing at a stage, allowing thereby algorithms for any N (preferably N should have only small, say 2,3,5, prime factors). Also, there is no reason that the starting array of subregions cannot be N×M (by using more general nxm coalescing at some stages).

In addition, the existence of layering can be included. If layering occurs above and below the total region so that the total inhomogeneity resides in a single layer, then the algorithm proceeds as before. Once the total region scattering matrix has been obtained, its interaction with the external layering can be computed. If inhomogeneous layer boundaries lie along horizontal borders between row of subscatterers, then the translation matrices can be modified when coalescing across such boundaries, properly including the layer effects. This is an advantage over our present layered Green's function algorithms which require that the inhomogeneity lie entirely within a single layer (This can be fixed in our present algorithms but at the expense of increased computation).

The $O(N^3)$ computation of this approach is superior to the $O(N^4 \log_2(N))$ computation of our original FFT-BCG approach and our present recursion based on cylindrical coordinates which is $O(N^3 \log_2(N))$.

EXAMPLE 9

MODELING SYSTEM TRANSFER FUNCTION INCLUDING DRIVING VOLTAGE, TRANSMITTING TRANSDUCERS RECEIVING TRANSDUCERS, PREAMPLIFIERS, ANALOG TO DIGITAL CONVERTER ETC

Let the transfer function of the transmitting waveform generator, power amplifier, transmitting multiplexer, transmitting transducer, ocean/sediment, receiving transducers, preamplifiers, differential amplifier, differential waveform generator, and analog to digital converter be, respectively, $T_{TWG}$, $T_{PA}$, $T_{TM}$, $T_{TT}$, $T_{O/S}$, $T_{RT}$, $T_{RM}$, $T_{DA}$, $T_{DWG}$, and $T_{DAC}$. These separate transfer function can be identified with the system hardware in the Figure below. Then the total transfer function is:

$$T_{total} = T_{DAC}(T_{DA1}T_{RM}T_{RT}T_{O/S}T_{TT}T_{TM}T_{PA}T_{TWG} - T_{DA2}T_{DWG})$$

Note that the term $T_{DA2} T_{DWG}$ is subtracted in order to remove direct path energy and to remove reverberations in the transducers and the platform; this subtraction effectively increases the analog to digital converter dynamic range. The signal in the differential waveform generator is programmed to produce a net zero signal output from the analog to digital converter for the case of no sediment present.

Recall that the equation for the scattered field $f^{(sc)}$ (from the sediment) at a transducer (not the output voltage) at a given temporal frequency is given in terms of the transducer-to-sediment Green's function D, the sediment's acoustic properties $\gamma$ and the internal field in the sediment f by $$f^{(sc)} = D\gamma f.$$

The field (at a given temporal frequency) within the sediment itself f is given in terms of the incident field $f^{(inc)}$, the sediment's acoustic properties $\gamma$, and the sediment-to-sediment Green's function C by $$f^{(inc)} = (I - C\gamma)f.$$

On combining these two equations we eliminate the internal field and find the scattered field in terms of the incident field and the sediment properties $$f^{(sc)} = D\gamma(I - C\gamma)^{-1} f^{(inc)}.$$

These equations involving C and D are true for both the free space Green's function ["Nonperturbative Diffraction Tomography Via Gauss-Newton Iteration Applied to the Scattering Integral Equation, Borup, D. T. et al., Ultrasonic Imaging] and our newly developed layered Green's functions Johnson, S. A., D. T. Borup, M J. Berggren, Wiskin, J. W., and R. S. Eidens, 1992, "Modelling of inverse scattering and other tomographic algorithms in conjunction with wide bandwidth acoustic transducer arrays for towed or autonomous sub-bottom imaging systems," *Proc. of Mastering the Oceans through Technology* (*Oceans* 92), 1992, pp 294–299.]. We now combine the scattering equations with the transfer functions. First, identify $f^{(sc)}$ with $T_{O/S}$ $T_{TT}$ $T_{TM}$ $T_{PA}$ $T_{TWG}$ and $f^{(inc)}$ with $T_{TT}$ $T_{TM}$ $T_{PA}$ $T_{TWG}$. Next we note that measuring $f^{(inc)}$ is a direct way of finding the product $T_{TT}$ $T_{TM}$ $T_{PA}$ $T_{TWG}$. We also note that $T_{total}$ can be written as $$T_{total}(\gamma, T_{TWG}) = T_{DAC}(T_{DA1} T_{RM} T_{RT} D\gamma(I-C\gamma)^{-1} T_{TT} T_{TM} T_{PA} T_{TWG} - T_{DA2} T_{DWG}).$$

Then $T_{total}(\gamma, T_{TWG})$ is a nonlinear operator that transforms $(\gamma, T_{TWG})$ into recorded signals $T_{total\text{-}measured}$. Thus, for a given set of $T_{total\text{-}measured}$ measurements and for a given $T_{TWG}$, we may in principal find $\gamma$ by a nonlinear inverse operator $$\gamma = T_{total}^{-1}(T_{total\text{-}measured}(\gamma, T_{TWG})).$$

Since the exact form of $T_{total}^{-1}$ is not known, we find $\gamma$ by a Gauss-Newton iteration method. This requires that the Jacobian of $T_{total}(\gamma, T_{TWG})$ be computed. The Jacobian is readily computed in closed form [Borup, 1992] and is given by $$J(\gamma) = -\partial T_{total}(\gamma^{(n)}, T_{TWG})/\partial \gamma.$$

Then the Gauss-Newton iteration for computing $\gamma$ is given by: (1) set n=1, estimate a value for $\gamma^{(n)}$; (2) compute $J(\gamma^{(n)})$; (3) solve $J^T(\gamma^{(n)}) J(\gamma^{(n)}) \delta\gamma^{(n)} = -J^T(\gamma^{(n)}) (\gamma^{(n)})[T_{total\text{-}measured} - T_{total}(\gamma^{(n)}, T_{TWG})]$ for $\delta\gamma^{(n)}$; (4) update $\gamma^{(n)}$ by the formula $\gamma^{(n+1)} = \gamma^{(n)} + \delta\gamma^{(n)}$; (5) if $[T_{total\text{-}measured} - T_{total}(\gamma^{(n)}, T_{TWG})] < \epsilon$ then set $\gamma = \gamma^{(n+1)}$ and quite, else go to step 2.

The extra dynamic range provided by the differential waveform generator/analog to digital converter circuit raises questions as to the optimal setup procedure (e.g. how many bits to span the noise present with no signal). We have modeled the signal to noise ratio that can be achieved by a beamformer which delays and sums multiple channel signals, each channel being such a circuit. We find as a rule of thumb, that the lowest order one or two bits should span either the noise or the signal, depending which ever is smaller (i.e., for signal to noise ratios greater than unity the noise should be spanned, but for signal to noise ratios less than unity the signal should be spanned). Upon using commercial 16 or 18 bit analog to digital converters this method may well extend their range to 20 bits or more.

2. MODEL ELECTRICAL CROSSTALK, ACOUSTIC CROSSTALK

Electrical cross talk can be removed by use of knowledge of the cross coupling matrix M. Let $V_n^{(true)}$ be true electrical signal at transducer n and let $V_m^{(meas)}$ be the measured signal at transducer m. Then $V_n^{(meas)} = M_{nm} V_n^{(true)}$. We observe for small cross talk that matrix M has the form $M = D_2(I+\epsilon)D_1$, where I is the identity matrix, $D_1$ and $D_2$ are diagonal matrices and $\epsilon$ is the differential cross talk matrix whose elements are small in value. We seek $V_n^{(true)} = M^{-1} V_n^{(meas)}$. By the binomial theorem $(I+\epsilon)^{-1} \approx (I-\epsilon)$. Thus, $M^{-1} \approx D_1^{-1}(I-\epsilon)D_2^{-1}$. Once $D_1$, $D_2$, and M are measured the problem of removing cross talk is quite inexpensive numerically (even if $\epsilon$ is not small the exact inverse $M^{-1}$ can be computed once and stored). If the matrix M turns out to be noninvertible (as can be the case for large magnitude coupling) then we can alternatively concatenate M onto the inverse scattering equation to give:

$$v_{\omega\phi}^{(meas)} = M_\omega P_\omega G_\omega [f_{\omega\phi}]\gamma$$

to which the inverse scattering algorithm can be directly applied.

We believe that cross talk can be removed by good fabrication techniques including careful shielding. Nevertheless, the above numerical method can be used if necessary.

Acoustic cross talk can be removed by several methods: (1) acoustic baffling of each transducers; (2) calibration of individual (isolated) transducers, computing the acoustic coupling in the array from wave equations methods, then inverting the model by a cross talk matrix as above; (3) direct measurement of the coupling in a finished array to find the cross talk matrix and then inverting as shown above. A more difficult type of cross talk to remove is the direct mechanical coupling between transducers. This problem will be attacked by using vibration damping techniques in mounting each transducer on the frame. We believe that such damping methods will eliminate direct mechanical coupling. As a backup we note that modeling of the coupled system are theoretically possible and has been successfully accomplished by the university's AIM Lab for circular mounting geometries (by derivation of a new "total system Green's function" for the imaging system that that includes cross coupling between elements).

EXAMPLE 10

INCLUSION OF TRANSDUCER COUPLING

In the event that significant coupling exists between the object to be imaged and the transducers (and/or coupling between transducers is not negligible), a computationally efficient means of incorporating this coupling into the inverse scattering algorithm is needed. Equivalently, the transducers must be included as part of the scattering problem This section details a computational algorithm for achieving this incorporation.

Consider an object to be imaged, $\gamma$, illuminated by a transmitter, T, with the scattering received by a receiver, R, as shown in FIG. 24 Let C denote a closed surface separating $\gamma$ from the transceivers.

Let S be the scattering matrix of $\gamma$ which, given the incident field generated from sources outside of C, gives the outward moving scattered field evaluated on C. This operator can be computed by solving a sufficient number of forward scattering problems for the object $\gamma$.

Let $P_R$ denote the operator that computes the field impinging on R due to sources inside of C from the scattered field evaluated on C. This is a simple propagation operator computable by an angular spectrum technique.

Let $P_T$ denote the operator that computes the field impinging on T due to sources inside of C from the scattered field evaluated on C. This is a simple propagation operator computable by an angular spectrum technique.

Let $A_{RT}$ denote the operator that computes the field impinging on R due to scattering from T (it operates on the net total field incident on T). This operator is computed by a moment method analysis of the transmitter structure.

Let $A_{TR}$ denote the operator that computes the field impinging on T due to scattering from R (it operates on the net total field incident on R). This operator is computed by a moment method analysis of the receiver structure.

Let $B_T$ denote the operator that computes the field on C due to scattering from T (it operates on the net total field incident on T). This operator can be computed by a moment method analysis of the transmitter structure.

Let $B_R$ denote the operator that computes the field on C due to scattering from R (it operates on the net total field incident on R). This operator can be computed by a moment method analysis of the receiver structure.

Assume that the transmitter T also produces a field, $f^i$, due to eternally applied excitation (electrical). Denote by $f_C^i$ the values of this field on C. Denote by $f_R^i$ the values of this field on the receiver surface. We assume that these field values are known (i.e., we know the free-space radiation characteristics of the transmitter).

Given these definitions, the total field incident from outside of C evaluated on C is given by:

$$f_C^{tot} = f_C^i + B_T f_T^{tot} + B_R f_R^{tot} \qquad 1$$

where the superscript tot indicates the field incident on the particular element due to all other sources. For T and R we have:

$$f_T^{tot} = P_T S f_C^{tot} + A_{TR} f_R^{tot} \qquad 2$$

$$f_R^{tot} = f_R^i + P_T S f_C^{tot} + A_{RT} f_T^{tot} \qquad 3$$

Note that the formula for $f_T^{tot}$ has no superscript i term since the incident field emanates from its interior. Solving 1–3 for the tot fields gives:

$$\begin{bmatrix} f_C^{tot} \\ f_T^{tot} \\ f_R^{tot} \end{bmatrix} = \begin{bmatrix} I & -B_T & -B_R \\ P_T S & I & -A_{TR} \\ P_R S & -A_{RT} & I \end{bmatrix}^{-1} \begin{bmatrix} f_C^i \\ 0 \\ f_R^i \end{bmatrix} = \begin{bmatrix} f_C^{tot} \\ f_T^{tot} \\ f_R^{tot} \end{bmatrix} \qquad 4$$

The size of this matrix operator is $O(N \times N)$ and so computation of its inverse does not require much CPU time (mere seconds). In order to compute the signal received by the receiver transducer, we take $f_R^{tot}$ computed in 4 and compute the surface currents (EM case) or surface velocities (acoustic case) from which the signal from the receiver can be computed.

This procedure for analyzing a scatterer in the presence of coupling between the T/R pair includes all orders of multiple interaction allowing transducers with complex geometries to be incorporated into our inverse scattering algorithms.

EXAMPLE 11

FREQUENCY DEPENDENT SCATTERING PARAMETERS

Throughout the previous sections it has been assumed that $\gamma$ is independent of frequency. Suppose now that $\gamma$ is a function of frequency. In the event that only a single frequency is needed (transmission mode with encircling transducers and only one complex parameter to be imaged) this is not a problem—the algorithm will simply image the 2 or 3-D distribution of $\gamma$ evaluated at that frequency.

However, in reflection mode or when imaging multiple parameters, multiple frequencies are needed. This increases the number of unknowns to $\Omega * N_x * N_y$ if we naively seek a separate image at each frequency. Since multiple frequencies were already needed to complete the data for a frequency independent unknown, we have no way of correspondingly increasing the number of equations by a factor of $\Omega$. Instead, consider approximating the frequency variation with a set of parameters at each pixel:

$$\gamma_{nm}(\omega) \approx \gamma_{nm}^{(0)} \psi^{(0)}(\omega) + \gamma_{nm}^{(1)} \psi^{(1)}(\omega) + \ldots + \gamma_{nm}^{(q-1)} \psi^{(q-1)}$$

where the basis functions $\psi$ are selected based on the physics of the frequency dependence (we may, for example, simply use the monomial basis: $\psi^{(n)}(\omega) \equiv \omega^n$ or, perhaps a rational function basis might be chosen since simple relaxation dispersion is a rational function). The formula for the GN update for this case is:

$$P_\omega G_\omega ((I - [\gamma_\omega G_\omega])^{-1} [f_{\omega \phi}] M_{\omega,j} \delta \gamma^{(j)} = -r_{\omega \phi}$$

where summation over j is assumed and the matrix M is given by:

$$M = \begin{bmatrix} \psi^{(1)}(\omega_1) & \psi^{(2)}(\omega_1) & \ldots & \psi^{(q-1)}(\omega_1) \\ \psi^{(1)}(\omega_2) & \psi^{(2)}(\omega_2) & \ldots & \psi^{(q-1)}(\omega_2) \\ \psi^{(1)}(\omega_\Omega) & \psi^{(2)}(\omega_\Omega) & \ldots & \psi^{(q-1)}(\omega_\Omega) \end{bmatrix}$$

Solution for the $q \times N_x \times N_y$ unknowns, assuming that q is sufficiently smaller than $\Omega$ can then carried out via the GN-MRCG or RP algorithms. We have already verified the success of this approach using quadratic polynomial models of the frequency variation (q=3, $\psi^{(n)}(\omega) \equiv \omega^n$).

EXAMPLE 12—PARABOLIC MARCHING METHODS

Having seen in the previous pages how the full nonlinear inversion yields substantial increases in resolution and utility of image, we are now prepared to discuss the advanced marching technique employed in both the forward problem and the Jacobian calculations (as well as the closely related Hermitian conjugate of the Jacobian calculation).

Scientific Background and Detailed Description to Advanced Parabolic Marching Method The parabolic equation method is a very efficient method for modelling acoustic wave propagation through low contrast acoustic materials (such as breast tissue). The original or classical method requires for its applicability that energy propagate within approximately ±20° from the incident field direction. Later versions allow propagation at angles up to ±90° from the incident field direction. Further modifications provide accurate backscattering information, and thus are applicable to the higher contrasts encountered in nondestructive imaging, EM and seismic applications. [M. D. Collins, A two-way parabolic equation for acoustic backscattering in the ocean, Journ. Acoustical Society of America, 1992, 91, 1357–1368, F. Natterer and F. Wübbeling, "A Finite Difference Method for the Inverse Scattering Problem at Fixed Frequency,"Lecture Notes in Physics, 1993, vol. 422:157–166, herein included as reference]. The source/receiver geometry we use in this device, and the relatively low contrast of breast tissue, allow us to utilize this efficient approximation. The resulting speed up relative to the Gauss Newton, conjugate gradient method [Borup et al., 1992] described in the previous patent, is dependent upon the contrast but is estimated to be 100–400 times. Furthermore the coarse grain parallelization employed in the integral equation method is equally applicable to the parabolic algorithm. The basic structure of the parabolic inversion algorithm is also essentially unchanged. The main difference is in the use of the Parabolic equation approximation, and more exactly, the "split step Fourier Method" [R. H. Hardin and F. D. Tappert "Applications of the split-step fourier method to the solution of nonlinear and variable coefficient wave equations," SIAM Rev. 15, 423 (1973). and M. D. Collins, "A Split-step Pade' solution for the parabolic equation method," J. Acoust. Soc. Am. 93, 1736–1742 (1993), herein included as reference] in the construction of both the Jacobian of the residual function, and the solution to the forward problems for each view. The source/receiver geometry requirements and the relatively low contrast of breast tissue, allow us to utilize this efficient approximation, for breast cancer scanner applications, for example. In particular because we may elect to use only transmission data in the breast problem, we are able to use this "parabolic approximation" in a straight-forward, simple manner [see Hardin and Tappert].

To derive and elucidate the parabolic equation method, we begin with the 2-D Helmholtz wave equation governing wave propagation in inhomogeneous media:

$$\left\{ \frac{\partial^2}{\partial x^2} + \left(k^2(x, y) + \frac{\partial^2}{\partial y^2}\right)\right\} f(x, y) = 0 \qquad 1$$

Now Fourier transforming y to $\lambda$ results in:

$$\left[\frac{\partial^2}{\partial x^2} + \left(\frac{1}{2\pi}\hat{k}^2(\lambda)^* - \lambda^2\right)\right]\tilde{f}(x, \lambda) = 0 \qquad 2$$

where:

$$\hat{k}^2(\lambda) \equiv \hat{k}^2(x, \lambda) \equiv \int_{-\infty}^{\infty} k^2(x, y)e^{-i\lambda y} dy \qquad 3$$

and the * notation denotes convolution:

$$f(\lambda) * g(\lambda) = \int_{-\infty}^{\infty} f(\lambda - \lambda') g(\lambda') d\lambda' \qquad 4$$

Eqn (2) can be factored in the sense of pseudo-differential operators [M. E. Taylor, "Pseudo-differential Operators," Princeton University Press, Princeton, 1981, herein included as reference]

$$\left(\frac{\partial}{\partial x} + i\sqrt{\frac{1}{2\pi}\hat{k}^2(\lambda)^* - \lambda^2}\right)\left(\frac{\partial}{\partial x} - i\sqrt{\frac{1}{2\pi}\hat{k}^2(\lambda)^* - \lambda^2}\right)\tilde{f}(x, \lambda) = 0 \qquad 5$$

An intuitive feel for the manner in which the Parabolic equation arises can be seen by looking at particularly simple case: when k is a constant, then we have, upon Fourier Transforming (1):

$$\left(\frac{\partial}{\partial x} + i\sqrt{k^2 - \lambda^2}\right)\left(\frac{\partial}{\partial x} - i\sqrt{k^2 - \lambda^2}\right)\tilde{f}(x, \lambda) = 0 \qquad 6$$

where the square root is now simply the square root of a scalar. From 6, it is clear that in this special case, two solutions exist:

$$\left(\frac{\partial}{\partial x} + i\sqrt{k^2 - \lambda^2}\right)\tilde{f}(x, \lambda) = 0, \tilde{f}(x, \lambda) = g(\lambda)e^{-ix\sqrt{k^2 - \lambda^2}} \qquad 7$$

for an arbitrary function g, which represents a rightmoving wave for $e^{i\omega t}$ time dependence and:

$$\left(\frac{\partial}{\partial x} - i\sqrt{k^2 - \lambda^2}\right)\tilde{f}(x, \lambda) = 0, \tilde{f}(x, \lambda) = g(\lambda)e^{ix\sqrt{k^2 - \lambda^2}} \qquad 8$$

representing a wave which "moves" to the left. Suppose that we know that the field is due to sources entirely on the LHS of the x-y plane. Then, for x>0 we must have:

$$\tilde{f}(x, \lambda) = g(\lambda)e^{-ix\sqrt{k^2 - \lambda^2}} \qquad 9$$

Note that knowledge of f on the line x=0 (boundary condition) completes the solution since:

$$\tilde{f}(0,\lambda) = g(\lambda) \qquad 10$$

and so, on inverse Fourier Transforming:

$$f(x, \lambda) = \frac{1}{2\pi}\int_{-\infty}^{\infty} \tilde{f}(0, \lambda)e^{-ix\sqrt{k^2-\lambda^2}} e^{i\lambda y} d\lambda, x > 0 \qquad 11$$

In fact, for any $x_0 > 0$:

$$f(x, y) = \frac{1}{2\pi}\int_{-\infty}^{\infty} \tilde{f}(x_0, \lambda)e^{-i(x-x_0)\sqrt{k^2-\lambda^2}} e^{i\lambda y} d\lambda, x > x_0 > 0 \qquad 12$$

The idea behind the parabolic equation method is to try to factor a general inhomogeneous (i.e. k=k(x,y)) problem into forward and backward moving (in x) factors and then solve only the forward (+x) moving part (assuming that the field source is to the left (on the x-axis) of the scatterer).

Let $x_n = n\Delta$, n=0, . . . then 12 is:

$$f_{n+1}(y) = \frac{1}{2\pi}\int_{-\infty}^{\infty} \tilde{f}_n(\lambda)e^{-i\Delta\sqrt{k^2-\lambda^2}} e^{i\lambda y} d\lambda \qquad 13$$

Since 13 is local to $x=(n+\frac{1}{2})\Delta$ we consider the discretization/approximation:

$$f_{n+1}(y) = \frac{1}{2\pi}\int_{-\infty}^{\infty} \tilde{f}_n(\lambda)e^{-i\Delta\sqrt{k^2(x_{n+1/2},y)-\lambda^2}} e^{i\lambda y} d\lambda \qquad 14$$

for propagating forward through k that is inhomogeneous in x and y ie. k=k(x,y), and $f_n(y)=f(x_n, y)$. Computationally (14) would be an inverse Fourier transform except for the y-dependence of k. Defining $$k_n^2 = k^2(x_{n+\frac{1}{2}})$$

gives $$f_{n+1}(y) = \frac{1}{2\pi}\int_{-\infty}^{\infty} \tilde{f}_n(\lambda) e^{-i\Delta\sqrt{k^2(x_{n+1/2},y)-\lambda^2}} e^{i\lambda y} d\lambda$$

Advanced Parabolic Marching Method

Now we desire to take the y—dependence out from under the square root in order that it may then be factored out from under the integral, which will result in the integral being an inverse Fourier Transform, and yield a substantial increase in efficiency. This goal can be achieved approximately in the following manner:

$$e^{-i\Delta k_{n,m}\sqrt{1-(\lambda/k_{n,m})^2}} \approx e^{i\Delta(k_{n,m}-k_n)} e^{-i\Delta k_n \sqrt{1-(\lambda/k_n)^2}}$$

so that, defining $k_{n,m} \equiv k(x_{n+½}, y_m)$, and $y_m = m\Delta$, then yields:

$$f_{n+1}(y_m) \approx \frac{1}{2\pi}\int_{-\infty}^{\infty} \tilde{f}_n(\lambda) e^{-i\Delta(k_{n,m}-k_n)} e^{-i\Delta k_n\sqrt{1-(\lambda/k_n)^2}} e^{i\lambda y_m} d\lambda \quad 15$$

or $$f_{n+1}(y_m) \approx \frac{e^{-i\Delta(k_{n,m}-k_n)}}{2\pi}\int_{-\infty}^{\infty} \tilde{f}_n(\lambda) e^{-i\Delta k_n\sqrt{1-(\lambda/k_n)^2}} e^{i\lambda y_m} d\lambda$$

We have thus approximately maintained the y variation in k, while simultaneously giving a Fourier Transform formulation for the field $f_{n+1}$.

$$f_{n+1}(y) \approx \frac{e^{-i\Delta(k_{n,m}-k_n)}}{2\pi}\int_{-\infty}^{\infty} \tilde{f}_n(\lambda) e^{-i\Delta k_n\sqrt{1-(\lambda/k_n)^2}} e^{i\lambda y} d\lambda$$

and in fact using the notation:

$$\hat{f}(y) \equiv \frac{1}{2\pi}\int_{-\infty}^{\infty} f(\lambda) e^{-i\lambda y} d\lambda$$

to indicate the Inverse Fourier Transform, gives:

$$f_{n+1}(y) = \widehat{\tilde{f}_n(\lambda) P_n}$$

where $P_n$ is the range dependent propagator defined as:

$$P_n(y) \equiv e^{-i\Delta\sqrt{k^2(x_{n+1/2})-\lambda^2}}$$

This is one basic equation for the parabolic split step method. Various alternative forms can be used in similar algorithms. A common form for the parabolic equation is derived by using the binomial approximation:

$$\sqrt{1-(\lambda/k_n)^2} \approx \frac{1}{2}\left(\frac{\lambda}{k_n}\right)^2$$

in the above integral. This yields a "standard" form of the split-step parabolic equation method:

$$f_{n+1}(y_m) = \frac{e^{-i\Delta k_{n,m}}}{2\pi}\int_{-\infty}^{\infty} \tilde{f}_n(\lambda) e^{i\Delta\frac{\lambda^2}{2k_0}} e^{i\lambda y_m} d\lambda \quad 16$$

Numerical experiments have indicated the superiority of 15 over 16. In Fourier notation, 16 is:

$$f_{n+1}(y_m) = e^{-i\Delta k_{n,m}} F^{-1}\left\{e^{i\Delta\frac{\lambda^2}{2k_0}} F\{f_n\}(\lambda)\right\}(y_m) \quad 17$$

This is the usual form of the split-step PE method. Our more general equation is (in Fourier notation):

$$f_{n+1}(y_m) = e^{-i\Delta(k_{n,m}-k_n)} F^{-1}\left\{e^{-i\Delta k_n\sqrt{1-(\lambda/k_n)^2}} F\{f_n\}(\lambda)\right\}(y_m)$$

An interesting interpretation of the split step method is evident from this: The algorithm step consists of an exact propagation a distance of $\Delta$ in $k_0$ (which includes diffraction) followed by a phase shift correction, i.e, multiplication by $$e^{-i\Delta(k_{n,m}-k_0)} \quad 18$$

which corrects the phase of a plane wave travelling forward.

Relation to the Generalized Born Approximation

The above split step Fourier method can be seen to be a generalization of the "Generalized Born" method as developed at TechniScan scientific research division in the following manner. Suppose that we assume that the field variation in y is very slow, i.e., $$F\{f_n\}(\lambda) \approx 0 \text{ for } \lambda \neq 0$$

so that we may replace $$e^{-i\Delta k_n\sqrt{1-(\lambda/k_n)^2}} \approx e^{-i\Delta k_n}$$

in the above integral which $$\frac{1}{2\pi}\int_{-\infty}^{\infty} \tilde{f}_n(\lambda) e^{-i\Delta\sqrt{k^2-\lambda^2}} e^{i\lambda y} d\lambda \approx f_n(y) e^{-ik_0\Delta} \quad 19$$

Then 28 is:

$$f_{n+1}(y_m) = e^{-i\Delta k_{n,m}} f_n(y_m), f_{n+1}(y_m) = e^{-i\Delta \sum_{n=0}^{n} k_{n,m}} \quad 20$$

(since $f_0(y) = 1$)

which is:

$$f(x, y) = e^{-i\int_0^x k(x',y)dx'} \quad 21$$

This is the generalized Born approximation to the field. Thus, the PE formula 17 reduces to the GB formula if straight line propagation and no diffraction are assumed.

The PE method should be significantly superior to GB, particularly if the PE total field is rescattered:

$$f^s(\rho) = k_0^2 \int\int \gamma(\rho') f^{PE}(\rho') \frac{H_0^{(2)}(k_0|\rho-\rho'|)}{4i} ds' \quad (22)$$

where $f^{PE}$ is computed from 17 by the split step algorithm. This will also improve the calculation of side and backscatter. The PE formulation has no backscatter (or large angle scattering) in it. Equation 33 is a way to put it back in, in a manner that gives a good approximation for weak scattering.

It is important to note that the above formulation of the parabolic equation inversion method does not require the storage of any fields (unlike the integral equation method of the previous patent). Of course, this method (as in the previous method) does not require the storage of a large Jacobian, or its adjoint.

Inverse Problem and Construction of Jacobian

The construction of the inversion algorithm requires the formula for the Jacobian:

$$\frac{\partial}{\partial k_{i,j}} f_{n+1}(y_m) =$$

$$e^{-i\Delta(k_{n,m}-k_o)}(-i\Delta\delta_{[n,m]}^{[i,j]})F^{-1}\left\{e^{-i\Delta k_o\sqrt{1-(\lambda/k_o)^2}} F\{f_n\}(\lambda)\right\}(y_m) +$$

$$e^{-i\Delta(k_{n,m}-k_o)^2}F^{-1}\left\{e^{-i\Delta k_o\sqrt{1-(\lambda/k_o)^2}} F\left\{\frac{\partial}{\partial k_{i,j}}f_n\right\}(\lambda)\right\}(y_m)$$

More exactly, we use the conjugate gradient algorithms in our inversion, and consequently require only the action of the Jacobian defined above on the perturbation $\delta k_{i,j}$, i.e. the total variation of f with respect to k:

$$\delta f_{n+1}(y_m) \equiv \sum_{i,j} \frac{\partial f_{n+1}}{k_{i,j}}(y_m)\delta k_{i,j}$$

The recursion formula for the action of the Jacobian on the perturbation in k is given by $$\delta f_{n+1}(y_m) = e^{-i\Delta(k_{n,m}-k_o)}(-i\Delta\delta k_{n,m})F^{-1}\left\{e^{-i\Delta k_o\sqrt{1-(\lambda/k_o)^2}} F\{f_n\}(\lambda)\right\}(y_m) +$$

$$e^{-i\Delta(k_{n,m}-k_o)}F^{-1}\left\{e^{-i\Delta k_o\sqrt{1-(\lambda/k_o)^2}} F\{\delta f_n\}(\lambda)\right\}(y_m)$$

It is advisable to rewrite the recursion expression for the field values $f_{n+1}(y_m)$ as:

$$f_{n+1}(y_m) = t_{n,m}\int_{-\infty}^{\infty}\tilde{f}_n(\lambda)e^{-i\Delta\sqrt{k_0^2-\lambda^2}}e^{i\lambda y_m}d\lambda$$

Where either $$t_{n,m} \equiv \frac{2}{1+\sqrt{\gamma_{n,m}+1}}e^{-i\Delta(k_{n,m}-k_o)}$$

or $$t_{n,m} \equiv \frac{2}{1+\sqrt{\frac{\gamma_{n-1,m}+1}{\gamma_{n,m}+1}}}e^{-i\Delta(k_{n,m}-k_n)}$$

is the "transmission coefficient+phase mask" characterizing the medium, depending upon The form used depends upon whether the model used as the background medium includes a priori known layering or not. In this case the equation for the Jacobian itself reads:

$$\frac{\partial}{\partial t_{i,j}}f_{n+1}(y_m) = \delta_{[n,m]}^{[i,j]}F^{-1}\left\{e^{-i\Delta\sqrt{k_0^2-\lambda^2}} F\{f_n\}(\lambda)\right\}(y_m) +$$

$$t_{n,m}F^{-1}\left\{e^{-i\Delta\sqrt{k_o^2-\lambda^2}} F\left\{\frac{\partial f_n}{\partial t_{i,j}}\right\}(\lambda)\right\}(y_m)$$

and the total variation in terms of $\delta t$ is:

$$\delta f_{n+1}(y_m) \equiv \sum_{i,j} \frac{\partial f_{n+1}}{\partial t_{i,j}}(y_m)\delta t_{i,j}$$

The recursion formula for $\delta f$ is therefore:

$$\delta f_{n+1}(y_m) = \delta t_{n,m}F^{-1}\left\{e^{-i\Delta\sqrt{k_o^2-\lambda^2}} F\{f_n\}(\lambda)\right\}(y_m) +$$

$$t_{n,m}F^{-1}\left\{e^{-i\Delta\sqrt{k_o^2-\lambda^2}} F\{\delta f_n\}(\lambda)\right\}(y_m)$$

The Formula for the Hermitian Conjugate of the Jacobian

The recursion for the total variation in the data $\delta f_N$ can be written as:

$$\delta f_N = \delta t_N \hat{x} v_N + W_N \delta f_{N-1}$$

where $\hat{x}$ denotes the Hadamard product, which is defined in the following manner $$t \otimes v \equiv \begin{bmatrix} t_1 \\ \vdots \\ t_{N-1} \\ t_N \end{bmatrix} \otimes \begin{bmatrix} v_1 \\ \vdots \\ v_{N-1} \\ v_N \end{bmatrix} \equiv \begin{bmatrix} t_1 v_1 \\ \vdots \\ t_{N-1} v_{N-1} \\ t_N v_N \end{bmatrix}$$

Also, the matrix $W_j$ is defined as:

$$W_j = [t_j]A_j$$

where $[t_j]$ represents the diagonal matrix:

$$[t_j] \equiv \begin{bmatrix} t_{j,1} & 0 & 0 & 0 \\ 0 & t_{j,2} & 0 & 0 \\ 0 & 0 & \ddots & 0 \\ 0 & 0 & 0 & t_{j,M} \end{bmatrix}$$

whose diagonal terms consist of the elements of the vector $t_j$, and $A_j$ is the matrix defined as (where juxtaposition always indicates matrix multiplication:

$$A_j = F^{-1}P_jF$$

Also the vector $v_j$ is defined as $$v_j \equiv A_j f_{j-1}$$

i.e.

$$v_j = F^{-1} P_j F f_{j-1}$$

Note that with the definitions:

$$A \equiv \begin{bmatrix} \mathbf{a}_1 \\ \vdots \\ \mathbf{a}_M \end{bmatrix} \quad t \equiv \begin{bmatrix} t_1 & 0 & 0 & 0 \\ 0 & t_2 & 0 & 0 \\ 0 & 0 & \ddots & 0 \\ 0 & 0 & 0 & t_M \end{bmatrix}$$

for the M×M matrices A, and [t], it follows that the matrix product is given by:

$$[t]A \equiv \begin{bmatrix} t_1 \mathbf{a}_1 \\ \vdots \\ t_M \mathbf{a}_M \end{bmatrix}$$

That is, the $i^{th}$ row of [t]A, is $t_i$ multiplied by the $i^{th}$ row of A.

With these notational assumptions, the recursion for the total variation becomes:

$$\delta f_N = [v_N]\delta t_N + W_N[v_{N-1}]\delta t_{N-1} +$$
$$W_N W_{N-1}[v_{N-2}]\delta t_{N-2} + \ldots + (W_N W_{N-1} \ldots W_1)[v_o]\delta t_o$$

The total variation can be written as a matrix product to facilitate the formation of the adjoint (Hermitian conjugate):

$$[\delta f_N] = ([v_N] \; W_N[v_{N-1}] \; \cdots \; (W_N W_{N-1} \ldots W_1)[v_o]) \begin{bmatrix} [\delta t_N] \\ [\delta t_{N-1}] \\ [\delta t_{N-2}] \\ \vdots \\ [\delta t_0] \end{bmatrix}$$

Defining the matrix M as:

$$M \equiv ([v_N] W_N[v_{N-1}] \ldots (W_N W_{N-1} \ldots W_1)[v_o])$$

one can form the Hermitian conjugate, which is (using the symmetry of the diagonal matrices $[v_k]$):

$$M^H = \begin{bmatrix} \overline{[v_N]} \\ \overline{[v_{N-1}]} W_N^H \\ \overline{[v_{N-2}]} W_{N-1}^H W_N^H \\ \vdots \\ \overline{[v_o]}(W_1^H \cdots W_{N-1}^H W_N^H) \end{bmatrix}$$

The equation for the action of the Hermitian of the Jacobian acting on $\delta f_N$ is then:

$$\begin{bmatrix} [\delta t_N] \\ [\delta t_{N-1}] \\ [\delta t_{N-2}] \\ \vdots \\ [\delta t_0] \end{bmatrix} = \begin{bmatrix} \overline{[v_N]} \\ \overline{[v_{N-1}]} W_N^H \\ \overline{[v_{N-2}]} W_{N-1}^H W_N^H \\ \vdots \\ \overline{[v_o]}(W_1^H \cdots W_{N-1}^H W_N^H) \end{bmatrix} [\delta f_N]$$

For computational purposes it is advantageous to write this equation as follows:

$$\begin{bmatrix} [\delta t_N] \\ [\delta t_{N-1}] \\ [\delta t_{N-2}] \\ \vdots \\ [\delta t_0] \end{bmatrix} = \overline{M^H [\delta f_N]} = M^T \overline{[\delta f_N]}$$

Thus the matrix required is actually $M^T$:

$$M^T = \begin{bmatrix} [v_N] \\ [v_{N-1}] W_N^T \\ [v_{N-2}] W_{N-1}^T W_N^T \\ \vdots \\ [v_o](W_1^T \cdots W_{N-1}^T W_N^T) \end{bmatrix}$$

The expression for $W^T$ is (as always F will denote Fourier Transform.):

$$(W_j)^T = A_j^T[t_j] = FP_j F^{-1}[t_j]$$

where use has been made of the fact that since the propagator P is a diagonal operator:

$$P_j = P_j^T$$

The $v_j = F^{-1} P_j F f_{j-1}$ are computed and stored as the forward fields are computed within the "subroutine jach" which computes the action of the Hermitian conjugate of the jacobian on (the complex conjugate of) the residual vector.

The updates for one view, then, are constructed in sequence using the formulae:

$$[\delta t_N] = [v_N]\overline{[\delta f_N]}$$
$$[\delta t_{N-1}] = [v_{N-1}]W_N^T \overline{[\delta f_N]} = [v_{N-1}]FP_N F^{-1}[t_j]\overline{[\delta f_N]}$$

etc.

See FIGS. 39 and forward for the flowchart, and the microfiche documentation for the source code.

SCIENTIFIC BACKGROUND FOR THE GENERALIZED BORN APPROXIMATION:

The exact scattering 2D integral equation is given by:

$$f^{scat}(\rho) = k_0^2 \int\int \gamma(\rho')f(\rho') \frac{H_0^{(2)}(k_0|\rho - \rho'|)}{4i} ds' \qquad 1$$

where f is the exact total field. The generalized Born approximation is obtained by approximating f in (1) with a straight-line phase integrated field approximation. For a plane wave traveling in the +x direction, this approximation is:

$$f(x', y') \approx e^{-ik_0 x'} e^{-i\omega \int_{-\infty}^{x'} (1/c(x'', y') - 1/c_0) dx''} \qquad (2)$$

which has the proper phase (time delay) assuming straight-line propagation. For a point source incident field, the approximation is:

$$f(x', y') \approx \frac{H_0^{(2)}\left(\omega \int_{\rho_{tran}}^{\rho'} (dl/c(l))\right)}{4i} \qquad (3)$$

where $\rho_{tran}$ is the position of the point source. For a point receiver at $\rho_{rec}$, equation 1 using equation 3 gives:

$$f^{scat}(\rho_{rec}) = \qquad (4)$$

$$k_0^2 \int\int \gamma(\rho') \frac{H_0^{(2)}\left(\omega \int_{\rho_{tran}}^{\rho'} (dl/c(l))\right)}{4i} \frac{H_0^{(2)}(k_0|\rho_{rec}-\rho'|)}{4i} ds'$$

Where the path of integration from $\rho_{tran}$ to $\rho'$ is a straight line.

Tranfromation to the time domain

Using the asymptotic approximation:

$$H_0^{(2)}(x) \xrightarrow[x\to\infty]{} \sqrt{\frac{2i}{\pi x}} e^{-ix} \qquad (5)$$

gives the approximation:

$$f^{scat}(\rho_{rec}, \rho_{tran}, \omega) = \qquad (6)$$

$$-\frac{i\omega}{8\pi c_0} \int\int \gamma(\rho') \frac{\left(e^{-i\omega \int_C (dl/c(l))}\right)\left(e^{-i\omega|\rho_{rec}-\rho'|/c_0}\right)}{\sqrt{|\rho_{tran}-\rho'||\rho_{rec}-\rho'|}} ds'$$

where the path integral is given by:

$$\int_C (dl/c(l)) \equiv \int_{\rho_{tran}}^{\rho'} (dl/c(l))$$

Transforming to the time domain gives:

$$f^{scat}(\rho_{rec}, \rho_{tran}, t) = \qquad (7)$$

$$-\frac{1}{8\pi c_0} \frac{\partial}{\partial t} \int\int \gamma(\rho') \frac{\delta\left(t - \int_{\rho_{tran}}^{\rho'} (dl/c(l)) - |\rho_{rec}-\rho'|/c_0\right)}{\sqrt{|\rho_{tran}-\rho'||\rho_{rec}-\rho'|}} ds'$$

In reflection mode ($\rho_{rec}$ on the same side of the body as $\rho_{tran}$), there is a problem with equation 7 in that the scattering from point $\rho'$ arrives at the receiver at the wrong time. The transmitter pulse arrives at $\rho'$ at the properly delayed time, $$\int_{\rho_{tran}}^{\rho'} (dl/c(l)),$$

but then the response travels back to the receiver as if the body were absent (time back to receiver=$|\rho_{rec}-\rho'|/c_0$). Thus, equ. 7 is acausal. To correct this, in reflection mode, we time delay the receiver path as well:

$$f^{scat}(\rho_{rec}, \rho_{tran}, t) = \qquad (8)$$

$$-\frac{1}{8\pi c_0} \frac{\partial}{\partial t} \int\int \gamma(\rho') \frac{\delta\left(t - \int_{\rho_{tran}}^{\rho'} (dl/c(l)) - \int_{\rho'}^{\rho_{rec}} (dl/c(l))\right)}{\sqrt{|\rho_{tran}-\rho'||\rho_{rec}-\rho'|}} ds'$$

Equation 8 has been found to be quite accurate in reflection mode. In transmission mode, we retain 7 because in transmission, the scattered field is, in fact, acausal (in the sense that part of the scattered field arrives as if no body were present).

In reality, transducers have a limited bandwidth. Let s(t) be the system response of the transducers. Then equation 8 becomes:

$$f^{scat}(\rho_{rec}, \rho_{tran}, t) = \qquad (9)$$

$$-\frac{1}{8\pi c_0} s'(t) * \int\int \gamma(\rho') \frac{\delta\left(t - \int_{\rho_{tran}}^{\rho'} (dl/c(l)) - \int_{\rho'}^{\rho_{rec}} (dl/c(l))\right)}{\sqrt{|\rho_{tran}-\rho'||\rho_{rec}-\rho'|}} ds'$$

where the * denotes convolution in time. Equation 9 provides a very powerful algorithm for time-domain, reflection-mode scattering calculation. It's main advantage over, say, the parabolic algorithm, is that it is in the time domain. Reflection mode scattering using the parabolic method requires that each frequency be computed separately, while equ. 9 gives the full time waveform with one computation.

The addition of attenuation into equ. 9 is trivial:

$$f^{scat}(\rho_{rec}, \rho_{tran}, t) = -\frac{1}{8\pi c_0} s'(t) *$$

$$\int\int \gamma(\rho') \frac{e^{-\int_{\rho_{tran}}^{\rho'} \alpha(l) dl} e^{-\int_{\rho'}^{\rho_{rec}} \alpha(l) dl} \delta\left(t - \int_{\rho_{tran}}^{\rho'} (dl/c(l)) - \int_{\rho'}^{\rho_{rec}} (dl/c(l))\right)}{\sqrt{|\rho_{tran}-\rho'||\rho_{rec}-\rho'|}} ds'($$

where $\alpha$ is the inhomogeneous attenuation.

Imaging algorithms can be derived from 9–10 by using these equations as the nonlinear operator (in $\gamma$) for predicting the scattering data and applying our standard Fletcher-Reeves or Ribere-Polack approach.

BASIS FOR FAST COMPUTATIONAL ALGORITHM BASED WARPING OF METRIC IN IMAGE SPACE

The 1-D Generalized Born formula in the frequency domain is:

$$f^s(\omega,-d) = \frac{\omega e^{-i\omega d/c_0}}{2ic_0} \int_0^a \gamma(x) e^{-i\omega\left\{\frac{2}{c_0}\int_0^x S_r(x')dx' + d/c_0\right\}} dx \quad 1$$

(assuming $f^i(\omega,x) = e^{-i\omega(x+d)/c_0}$) where:
$S_r(x)$=relative slowness=$\sqrt{\gamma(x)+1}$
Inverse Fourier transformation of 1 to time gives::

$$-2c_0 F^{-1}\left\{\frac{f^s(\omega,-d)}{i\omega}\right\}(t) = \int_0^a \gamma(x)\delta\left(t - \frac{2}{c_0}\int_0^x S_r(x')dx' - 2d/c_0\right)dx \quad 2$$

or:

$$-2c_0 \int_0^t f^s(t'+2d/c_0,-d)dt' = \int_0^a \gamma(x)\delta\left(t - \frac{2}{c_0}\int_0^x S_r(x')dx'\right)dx \quad 4$$

Change of variables:

$$z = \int_0^{x(z)} S_r(x')dx', \quad dx = \frac{dz}{S_r(x(z))} \quad 5$$

to get:

$$-2c_0 \int_0^t f^s(t'+2d/c_0,-d)dt' = \int_0^{z(a)} \frac{\gamma(x(z))}{S_r(x(z'))} \delta\left(t - \frac{2}{c_0}z'\right)dz' \quad 6$$

which gives:

$$-4 \int_0^{2z/c_0} f^s(t'+2d/c_0,-d)dt' = \frac{\gamma(x(z))}{S_r(x(z))} \quad 7$$

where x(z) is defined in 5 which is also:

$$x(z) = \int_0^z \frac{dz}{S_r(x(z))} \quad 8$$

which provides a recursive formula for x(z) for the discretized case. For example, trapazoidal integration of 8 gives:

$$x_n - \frac{\Delta}{2}\frac{1}{S_r(x_n)} = \frac{\Delta}{2}\left\{\frac{1}{S_r(0)} + 2\sum_{l=1}^{n-1}\frac{1}{S_r(x_l)}\right\}, \quad 9$$

$$x_n = x(z_n), \quad z_n = \Delta n$$

which is easy to solve for $x_n$ if, for example, $S_r$ is piecewise constant.

This simple one dimensional example illustrates the technique for changing the metric to obtain a fast algorithm. The 2D case is exactly similar, with the direction of the incident plane wave being rotated to correspond to the x-axis in the above algorithm.

SCIENTIFIC BACKGROUND FOR PROPAGATION-BACKPROPAGATION METHOD AND PROPAGATION-CG GENERALIZATION

This section is by nature technical. The pseudo-code and flowcharts which follow would be unwieldly and large unless this section presented the technical terms and definitions, with some motivation.

As with the previous patent, this patent is concerned with solving the Helmholtz Equation (also referred to as the "reduced wave equation" exactly (ie. without any type of linearization or perturbation assumption) in order to reconstruct certain parameters in an object. The unknown object is illuminated with some type of wave energy (whether acoustic, or electromagnetic). The wave equation that is solved is of the form:

$$\nabla^2 f + k_o^2(1-\gamma)f = 0$$

where $k_o$ is the wavenumber in free space. Note that Natterer uses the notation $\nabla^2 \equiv \Delta$ for the Laplacian, therefore in the following, this notation will be used. The $\gamma$ is the object function:

$$\hat{\gamma}(\mathbf{r}) \equiv 1 - \frac{c_o^2}{c^2(\mathbf{r})} = -\left(\frac{c_o^2}{c^2(\mathbf{r})} - 1\right) = -\gamma(\mathbf{r})$$

Where $\hat{\gamma}$ is the object function definition employed by Natterer. It is the negative of the standard definition of $\gamma$ as defined and used in this patent. Furthermore, in the papers included as reference, written by Natterer, and Natterer and Wubbeling, the notation $f$ is used to represent $\hat{\gamma}$.

For purposes of this discussion we will define $v_\theta$ in the following manner: $f \equiv e^{ik_o\theta \cdot r}(1+v_\theta)$, where $\theta$ is a unit vector in $R^2$. In other words $f \equiv e^{ik_o\theta \cdot r} + e^{ik_o\theta \cdot r}v_\theta$, so that $e^{ik_o\theta \cdot r}$ is the incident plane wave and $v_\theta$ is $e^{-ik_o\theta \cdot r}f^{sc}$, where $f^{sc}$ is the scattered field.

NOTE: The definition of $\hat{\gamma}(r)$ here is designed to correspond to the object function used in "A Propagation-Backpropagation Method for Ultrasound Tomography", Frank Natterer. This definition is the negative of the standard $\gamma$ used in this patent., and previous patents,.

When the definition for the field $f$ is substituted into the Helmholtz equation, the result is the equation that $v_\theta$ must solve:

$$\Delta v_j + 2ik_o\theta_j \cdot \nabla v_j - k_o^2(1+v_j)\hat{\gamma} = 0$$

The geometry of FIG. 34 will be referred to several times in this patent. This figure shows the incident field direction $\theta_j$, the boundary in the backscattered direction, $\Gamma_j^-$, the boundary in the sidescattered direction, $\Gamma_j$, as well as in the forward scattered direction $\Gamma_j^+$ The ultimate goal is to determine the distribution of appropriate scattering coefficients, $\gamma$, or $\hat{\gamma}$, given the measured fields $g_{\theta_j} \equiv g_j$ on $\partial Q_j = \Gamma_j^+ \cup \Gamma_j \cup_j^-$, for j=1, . . . ,$N_{view}$, where $N_{view}$ is the number of views. $\partial Q_j$ is the boundary of $Q_j$. This goal will be achieved by applying the Paige-Saunders Least Squares conjugate gradient algorithm to the functional which is the difference between the measured field on $\Gamma_j^+$, and the calculated scattered field on $\Gamma_j^+$. The scattered field on $\Gamma_j^-$, and on the sides $\Gamma_j$ is also incorporated into the algorithm, since these values are used as boundary values in the numerical solution of the partial differential equations enumerated below.

As is well known, we are required to calculate the "derivative of $v_j$ with respect to $\gamma$" in order to utilize the method of conjugate gradients. This derivative will be denoted by $$\frac{\partial v_j}{\partial \gamma},$$

and is also referred to as the Frechet Derivative. It is the functional analysis equivalent of the Jacobian in the calculus of several variables. This "Frechet derivative" is a linear operator which acts upon object functions, δγ, and delivers up a calculated total field on Q: ie.

$$\frac{\partial v_j}{\partial \gamma} \delta \gamma$$

is a total calculated field. Now, in accordance with the papers by F. Natterer and F. Wubbeling included herein as references, we will also introduce the notation $R_j(\gamma) = v_j|_{\Gamma_j^+}$. That is, $R_j(\gamma) = v_j$ restricted to $\Gamma_j^+$, the forward scattering part of the boundary of Q. By definition, the derivative $$\frac{\partial R_j(\gamma^r)}{\partial \gamma}$$

is the restriction of $$\frac{\partial v_j}{\partial \gamma}$$

to the forward scattered direction:

$$\left( \frac{\partial R_j(\gamma^r)}{\partial \gamma} \equiv \frac{\partial v_j}{\partial \gamma} \right)\bigg|_{\Gamma_j^+}.$$

We will calculate these operators explicitly below. To be exact, the conjugate gradient algorithm we employ requires the calculation of $$\frac{\partial v_j}{\partial \gamma}$$

acting on δγ, for specific, known δγ, ie the calculation of the function $$\frac{\partial v_j}{\partial \gamma} \delta \gamma.$$

To make the equations easier to read, this function will be notated as $\omega_j$, that is:

$$\omega_j \equiv \frac{\partial v_j}{\partial \gamma} \delta \gamma$$

is a function representing a total field on region Q.

First, consider the forward problem in the direction j, which we have denoted (as in F. Natterer's papers) by $R_j$: given some object function γ, which describes the distribution of parameters within the image grid Q, determine the solution $v_j$, to the following boundary value problem.

$$\Delta v_j + 2ik_o \theta_j \cdot \nabla v_j - k_o^2 (1+v_j)\hat{\gamma} = 0 \text{ for } j=1, \ldots N_{view}$$

subject to the conditions (from measured values $g_j$:

$$v_j = g_j \text{ on } \Gamma_j \cup \Gamma_j^- \text{ and } \frac{\partial v_j}{\partial \nu} = \frac{\partial g_j}{\partial \nu} \text{ on } \Gamma_j^-$$

Then $R_j(\gamma) = v_j$ restricted to $\Gamma_j^+$ ie. $R_j(\gamma) \equiv v_j|_{\Gamma_j^+}$. Where $v_j$ is the solution to the above boundary value problem.

NOTE: The solution of this boundary value problem requires the knowledge of the total field on the sides and backscatter direction, and the normal derivative of the total field on the backscatter direction boundary $\Gamma_j^-$, by virtue of the finite difference marching method employed to solve the partial differential equation. Thus, from a physical point of view the aperture is 360°. The side scattered and backscattered fields are both included in the solution.

The system that we require to solve for γ is a nonlinear system, of the form:

$$R_j(\gamma) = g_j|_{\Gamma_j^+} \quad (1)$$

Recall that $g_j$ is the measured data in the direction $\theta_j$. Because it is a nonlinear system, it must be solved iteratively by means of the Newton-Raphson method. To this end, given a guess $\gamma^r$, as an approximation to the solution of (1) consider $R_j(\gamma^r + \delta \gamma^r)$. One can write:

$$R_j(\gamma^r + \delta \gamma^r) \approx R_j(\gamma^r) + \left[ \frac{\partial R_j}{\partial \gamma} \right] \delta \gamma^r$$

where $$\left[ \frac{\partial R_j}{\partial \gamma} \right]$$

is the "Jacobian" map which linearly approximates $R_j$ at $\gamma^r$. Note that this is a linear map:

$$\left[ \frac{\partial R_j}{\partial \gamma} \right] : \begin{pmatrix} \text{OBJECT} \\ \text{FUNCTIONS} \end{pmatrix} \Rightarrow \begin{pmatrix} \text{MEASURED} \\ \text{FIELDS} \end{pmatrix}.$$

We can use this fact to obtain an explicit representation of the function $$\left[ \frac{\partial R_j}{\partial \gamma} \right] \delta \gamma$$

Let $(v_j + \delta v_j)$ be the total field resulting from applying the incident field in direction j to the object function $(\gamma^r + \delta \gamma^r)$ That is, $\Delta(v_j + \delta v_j) + 2ik_o \theta_j \cdot \nabla(v_j + \delta v_j) - k_o^2(1+(v_j + \delta v_j))(\hat{\gamma}^r + \delta \hat{\gamma}^r) = 0$.

Restricting $(v_j + \delta v_j)$ to the forward scattering border gives the symbolic equation:

$$R_j(\gamma^r + \delta \gamma^r) = (v_j + \delta v_j)|_{\Gamma_j^+}$$

Using the fact that $$\Delta(v_j) + 2ik_o \theta_j \cdot \nabla(v_j) - k_o^2(1+v_j)(\hat{\gamma}^r) = 0$$

gives $$\Delta(\delta v_j) + 2ik_o \theta_j \cdot \nabla(\delta v_j) - k_o^2(\delta v_j)(\hat{\gamma}^r) = k_o^2[(1+v_j)\delta \hat{\gamma}^r + \delta \hat{\gamma}^r \delta v_j]$$

The last term on the right hand side contains the quadratic terms in δγ and so will be ignored, since we are interested in the linear variation of $v_j$ with $\gamma$. Therefore, using the definition $$\omega_j \equiv \frac{\partial v_j}{\partial \gamma} \delta\gamma,$$

which is the part of $\delta v_j$ which is linear in $\delta\gamma$., it follows that $\omega_j$ is the solution to the following initial value problem with known, nonzero right hand side.

$$\Delta(\omega_j)+2ik_o\theta_j\cdot\nabla(\omega_j)-k_o^2\omega_j\hat{\gamma}'=k_o^2(1+v_j)\delta\hat{\gamma}'$$

with the boundary values:

$$\omega_j = 0 \text{ on } \Gamma_j \cup \Gamma_j^-, \text{ and initial value } \frac{\partial \omega_j}{\partial \nu} = 0 \text{ on } \Gamma_j^-$$

The boundary values follow from the following considerations: Since $\omega_j$ is the linear part of the total variation of $v_j$ it follows that $v_j + \delta v_j \equiv v_j + \omega_j +$ higher order terms . . .

It follows that, at the boundaries: $v_j + \delta v_j = g_j$, but $v_j = g_j$ at the boundaries, by definition of $v_j$, therefore $\delta v_j = 0$ at the boundaries, as stated.

For purposes of the Paige-Saunders method, or for direct application as backpropagation, it is important to determine a similar explicit reprentation for the Hermitian adjoint or Hermitian transpose of the "Jacobian map"

$$\left[\frac{\partial R_j}{\partial \gamma}\right]:$$

Again, it is the action of the Hermitian transpose on a given function which is actually used by the conjugate gradient type algorithms.

$$\left[\frac{\partial v_j}{\partial \gamma}\right]^H : \begin{pmatrix} \text{TOTAL} \\ \text{FIELDS} \end{pmatrix} \Rightarrow \begin{pmatrix} \text{OBJECT} \\ \text{FUNCTIONS} \end{pmatrix}$$

Using the definition of $R_j$ as the restriction of the total field to $\Gamma_j^+$, it follows that the Hermitian conjugate of $$\left[\frac{\partial R_j}{\partial \gamma}\right]$$

is a linear map:

$$\left[\frac{\partial R_j}{\partial \gamma}\right]^H : \begin{pmatrix} \text{MEASURED} \\ \text{FIELDS ON } \Gamma_j^+ \end{pmatrix} \Rightarrow \begin{pmatrix} \text{OBJECT} \\ \text{FUNCTIONS} \end{pmatrix}$$

The calculation of the action of $$\left[\frac{\partial R_j}{\partial \gamma}\right]^H$$

on a given measured field on $\Gamma_j^+$ is a somewhat tedious process carried out in Natterer "A Propagation-Backpropagation Method for Ultrasound Tomography" [included in this patent as reference]. The final result is: Given $g_j$, a function on $\Gamma_j^+$, the action of $$\left[\frac{\partial R_j}{\partial \gamma}\right]^H \text{ on } g_j, \text{ is}$$

$$\left[\frac{\partial R_j}{\partial \gamma}\right]^H_j (g_j) \equiv k_o^2(1+\overline{v}_j)z$$

where $z$ is the solution to the initial boundary value problem:

$$\Delta z + 2ik_o\theta_j\cdot\nabla z - k_o^2\overline{\gamma}z = 0$$

(where $\overline{\gamma}(r)$ denotes the complex conjugate of $\hat{\gamma}$) with boundary values:

$$z = 0 \text{ on } \Gamma_j \cup \Gamma_j^+, \text{ and initial value } \frac{\partial z}{\partial \nu} = g_j \text{ on } \Gamma_j^+$$

NOTE that $g_j$ is used only on the forward scattering border $\Gamma_j^+$, which is as it should be since this is the only place that the function $g_j$ is defined. Note that the $g_j$ is "back-propagated" back across the region Q, in order to obtain the function $z$, which is then used to obtain the function $$\left[\frac{\partial R_j}{\partial \gamma}\right]^H g_j,$$

which is defined on all of Q.

NEWTON-RAPHSON METHOD APPLIED TO INVERSION

Now consider the system:

$$g_j = R_j(\gamma^r + \delta\gamma^r) \approx R_j(\gamma^r) + \left[\frac{\partial R_j}{\partial \gamma}\right]\delta\gamma^r$$

Rewriting this gives the following linear system which must be solved in order to obtain $\delta\gamma$.

$$\left[\frac{\partial R_j}{\partial \gamma}\right](\delta\gamma^r) = g_j - R_j(\gamma^r)$$

The vastly underdetermined form of this system leads one to define the function $d$ such that the following equation holds:

$$\delta\gamma^r \equiv \left[\frac{\partial R_j}{\partial \gamma}\right]^H d$$

Then the corresponding system for $d$ is:

$$\left[\left[\frac{\partial R_j}{\partial \gamma}\right]\left[\frac{\partial R_j}{\partial \gamma}\right]^H\right]d = g_j - R_j(\gamma^r)$$

and the expression for $\delta\gamma^r$ is given by:

$$\delta\gamma^r \equiv \left[\frac{\partial R_j}{\partial \gamma}\right]^H d = \left[\frac{\partial R_j}{\partial \gamma}\right]^H \left[\left[\frac{\partial R_j}{\partial \gamma}\right]\left[\frac{\partial R_j}{\partial \gamma}\right]^H\right]^{-1}(g_j - R_j(\gamma^r))$$

Now, the efficient method for the determination of $\delta\gamma^r$, will involve some form of approximation:

$$C_j \approx \left[\left[\frac{\partial R_j}{\partial \gamma}\right]\left[\frac{\partial R_j}{\partial \gamma}\right]^H\right]^{-1}$$

For example $C_j$=Identity has been shown to work well (This is the approach taken by Natterer in "A Propagation-Backpropagation Method for Ultrasound Tomography". Other choices include $C_j$=some diagonal matrix. One could also use Paige-Saunders Least Squares Conjugate Gradient method to find the minimum norm solution to:

$$\left[\frac{\partial R_j}{\partial \gamma}\right]\delta\gamma^r = g_j - R_j(\gamma^r)$$

In any case, once the update $\delta\gamma^r$ has been found. It is added to the previous guess with some multiplicative factor $\mu \leq 1$ to obtain the new estimate for the $\gamma$.

$$\gamma^{r+1} = \gamma^r + \mu(\delta\gamma^r)$$

This process is repeated for $j=1, \ldots N_{view}$. This approach differs significantly from the approach described earlier in that a vastly underdetermined problem is solved for each direction, as opposed to solving an overdetermined problem for the update $\delta\gamma$.

Note that the forward problem can be updated after 1, 2, or any finite number of directions have been carried out. The tradeoffs are that it is much more difficult to calculate the forward problem each time for each direction. However, the speed up in the convergence may make it worth the computational effort.

SCIENTIFIC BACKGROUND AND DETAILED DESCRIPTION FOR BRIGHTNESS FUNCTIONAL APPROACH TO PHASE ABERRATION CORRECTION WITH CONJUGATE GRADIENT METHODS

The scientific background to the phase aberration correction based upon the brightness functional is simply that the $L_2$ norm (functional) of the B-scan image intensity is maximized when the phase shifts (time delays) are such that the image is maximally focused [L. Nock and G. E. Trahey, "Phase aberration correction in medical ultrasound using speckle brightness as a quality factor," Journ. Acoustical Society of America, 1989, 85, 1819–1833, herein included as reference].

FIG. 45 shows the geometry of a linear B-scan acoustic transducer array illuminating an anatomical region through an aberrating layer of fat. We develop the algorithm here for the linear array for simplicity. Modification for convex, sector scanning arrays etc. is trivial. A region of interest (ROI), selected by the user, is also shown. The image in the ROI is formed by M beams produced by the beamformer hardware. The transducer elements that contribute to the formation of the M beams in the ROI are denoted $e_{m1}$ to $e_{m2}$.

The goal of the algorithm is to focus the image in the ROI by finding a set of time delays applied to the signals from each transducer element $e_{m1}$ to $e_{m2}$ such that the brightness functional in the ROI (square of the L2 norm of the image intensity, B(t), over the ROI) is maximized:

$$B(\mathbf{t}) \equiv \sum_{(n,m) \in ROI} I_{n,m}^2, \; \underset{\mathbf{t}}{\text{maximize}}\{B(\mathbf{t})\}$$

where $I_{n,m}$ is the image intensity at pixel (n,m) and the vector $\mathbf{t}$, $t_m$: $m=m_1, \ldots, m_2$ is the vector of transducer element time delays. Our algorithm applies gradient based optimization methods (steepest descent, Fletcher- Reeves conjugate gradients, Ribere Polak conjugate gradients, etc.) to solve the maximization problem.

Clinical B-scanners operate by breaking the image up in range into a number of focal zones. The receiver beamformer then focuses the transmitter and receiver at a focal range equal to the center of the focal zone. Thus, each beam (laterally scanned) has one delay set (one delay for ech element contributing to the beam) over the focal zone range. If the ROI is contained entirely within one focal zone (as in FIG. 45), then the delay perturbations for focusing need to be added to only one beamformer delay set per beam. In the case that the ROI overlaps two of more focal zones, the time delay perturbations must be added to the beam delay sets for each focal zone.

The only hardware needed to implement this phase aberration correction algorithm is a B-scanner with a computer iterface, allowing the image to be read from the B-scanner into the computer memory and allowing the beamformer hardware delays in the B-scanner to be reset from the computer.

Nearly all ultrasound clinical scanners use and display the envelope of the RF beam signals as the image intensity. This is done by low pass filtering the modulus of the analytic RF signal or, in some low cost systems, by low pass filtering the rectificated video. The enveloping process is often followed by further processing that includes time variable bandwidth filtering to supress noise and by logarithmic compression to extend dynamic range. We emphasise that the proper use of the brightness phase aberration correction algorithm must de- emphasize the amount of, or eliminate entirely, logarithmic compression, else logarithmic emphasized excess brightness in the side lobes of the point response function will destroy the attempt to focus the image by maximizing the strength of the central lobe of the point responce function of the image.

The following steps outline the algorithm for brightness based phase- aberration correction.

Choose $\delta t$=the time perturbation to be added to a selected element delay for derivative calculation.

Choose line search time increment, $\delta\tau$, and number of line search steps, $N_s$.

1. Load the beamformer with precalculated delays based on 1540 m/s tissue average speed.
2. Aquire the initial image from the b-scanner.
3. Select the ROI (region of interest) comprising one or more receiver and transmit and one or more beam locations and focal ranges.
   This selection determines a sub set of transducer elements that are used in the image formation of this ROI, $e_{m1}, \ldots, e_{m2}$ where m1 is the first element and $m_2$ is the last. eg. $m_1, m_2 \in [1, \ldots, N_{tran}]$ for an $N_{tran}$ element array.
   Set itertype='SD', 'FR', 'RP' or 'RPP' for steepest descents, Fletcher-Reeves, Ribere-Polack, or Ribere-Polak with the Powel modification.
   Set $h_m=0$, $m=m_1, \ldots, m_2$, set $p_m=0$, $m=m_1, \ldots, m_2$.
   Set r0=1.
   Set $t_m=0$, $m=m_1, \ldots, m_2$ the element time delay perturbation vector.
4. For l=1, . . .

5. Compute $b_0$=sum of squares of the image intensity on the ROI.
   If l=0, $b_{intial}=b_0$.
6. For m=$m_1$, . . . ,$m_2$
   6.a. Calculate a new delay set with δt added to all delays for which element $e_m$ is the transducer element used.
   6.b Load the new delay set into the beamformer.
   6.c Acquire the new image from the B-scanner.
   6.d Compute $b_m$=sum of squares of the image intensity on the ROl.
   6.e $g_m=(b_m-b_0)/δt$.
   6.f Next m.
7. If (itertype='SD') set $p_m=g_m$, m=$m_1$, . . . ,$m_2$, go to 13.
8. Compute $$r_1 = \sum_{m=m_1}^{m_2} g_m^2.$$

9. If(itertype='FR') $\beta=r_1/r_0$.
10. If(itertype='RP')

$$\beta = \sum_{m=m_1}^{m_2} g_m(g_m - h_m)/r_0.$$

11. If (itertype='RPP') then, If β<0, β→0.
12. Update the search direction and save the gradient in vector h:
   $p_m \to g_m+\beta p_m$, m=$m_1$, . . . ,$m_2$
   $h_m \to g_m$, m=$m_1$, . . . ,$m_2$
   $r_0 \to r_1$
13. Compute $$M = \max_{m=m_1,\dots,m_2} |p_m|.$$

14. Line search by Trial and Error. For n=1, . . . , $N_s$:
   14.a $f_m=t_m+nδσp_m/M$, m=$m_1$, . . . ,$m_2$.
   (Note that this formula ensures that the maximum time perturbation is $N_s \cdot δτ$.
   14.b Compute the new beamformer delay set with element time delay perturbation vector f.
   14.c Aquire the new B-scan image and compute the brightness $b_n$ over the ROI.
   14.d Next n.
15. Determine n for which $b_n$ is maximum, then set: $t_m \to t_m+ nδτp_m/M$, m=$m_1$, . . . ,$m_2$.
   Steps 14 thru 15 can easily be replaced by a gradient, or quadratic, or Fibonacci search, or other line search for efficiency,. The above trial and error method is included for concreteness only)
16. Load new delays into beamformer with vector t of element time delay perturbations added.
17. Display B-scan image.
18. Check convergence criteria such as the percent change in brightness functional is less than some small and arbitrary number such as 5%. Do another gradient convergence step? If yes, increase l by 1, (go to 5).

Clearly computing the gradient by perturbation of each time delay in sequence is one of many ways and is straightforward. It is possible to use a basis set for the gradient based upon the singular value decomposition of the Hessian of the Brightness functional (which is closely related to the Jacobian of the Brightness vector—ie the vector whose modulus squared is the Brightness functional)

The number of significant singular vectors will generally be somewhat less than $m_2-m_1$, so that using the singular vectors as a basis for finding the gradient will in general be much more efficient.

SCIENTIFIC BACKGROUND FOR IMAGING WITH DIFFUSION EQUATION MODELS

Electric Conductivity Imaging by Frequency Domain, Nonlinear Inversion (the method we use for wave equation inversion, now modified for the Diffusion Equation)

We start with the receiver and media diffusion equations, modified to eliminate the Electric field E, internal to the image grid, which then becomes a non-linear expression for the conductivity (or its reciprocal, resistivity) in terms of the incident field and the measured field at a fixed frequency ω. Define the residual field R (note the frequency, source and receiver indices of R are suppressed, but under stood to be active) by the standard formula:

$$R=E_m-E_b+D[\backslash\gamma\backslash]([I-C[\backslash\gamma\backslash]]^{-1}E_b=0 \quad (1)$$

Here, $E_m(r)$ is the measured electric field, $E_s=E_m-E_b$ is the measured scattered electric field, and $E_b(r)$ is the incident field or response in the (homogeneous) background medium.

NOTE THAT THESE DEFINITIONS ARE ISOMORPHIC TO THE WAVE EQUATION DEFINITIONS GIVEN IN THE PREVIOUS EXAMPLES, ONLY THE GREEN'S FUNCTIONS HAVE CHANGED, BUT THESE ARE READILY AVAILABLE FROM ["Morse and Feschback, Methods of Theoretical Physics, Vols.1, and 2, McGraw-Hill.", herein included as reference]

This provides the correct value for the measured field Electric field $E_m$ when substituting the correct value for γ and $E_b$, and on setting R=0. We solve for γ by finding the γ that minimizes R by minimizing the objective functional $$F(\gamma)=(\tfrac{1}{2})\|E-Eb-D[\backslash\gamma\backslash]([I-C[\backslash\gamma\backslash]]^{-1}Eb\|^2=(\tfrac{1}{2})\|R\|^2$$

In general, we can define the norm of the residual vector R to be general enough to weight each frequency component of F(γ) to increase the convergence rate in some cases:

$$F(\gamma)=(\tfrac{1}{2})\|R\|^2=\Sigma_{frequency\ \omega}\Sigma_{sources\ s}\Sigma_{receivers\ m}|W_\omega R_{\omega sm}|^2$$

Define the Jacobian of the residual R with respect to γ by $$(\partial/\partial\gamma)R=-D(I-[\backslash\gamma\backslash]C)^{-1}[\backslash E\backslash]]$$

Then the Gauss-Newton algorithm for finding the γ that minimizes F(γ) is isomorphic to the earlier wave equation case, and is given by:

(a) Select an initial guess $\gamma^{(n)}$. Set n=0.
(b) Solve the forward problem for $E^{(n)}$ by us of the biconjugate gradient (BCG) or stabilized biconjugate gradient (BiSTAB) algorithms.
$E^{(n)}=([I-C[\backslash\gamma^{(n)}\backslash]]^{-1}E_b$
(c) compute the receiver residuals
$R^{(n)}=E_m-E_b+D[\backslash\gamma^{(n)}\backslash]([I-C[\backslash\gamma^{(n)}\backslash]]^{-1}E_b$ (d) For some small number ε the size of the noise to signal ratio,
if $\|R^{(n)}\|/\|E_m\|<\epsilon$, then stop. Else
(e) Minimize $\|(\partial/\partial\gamma)R^{(n)}\delta\gamma^{(n)}+R^{(n)}\|^2$ for $\delta\gamma^{(n)}$ by using the conjugate gradient algorithm.

(f) Update $\gamma$ by $\gamma^{(n+1)}=\gamma^{(n)}+\delta\gamma^{(n)}$ (g) Set n=n+1, go to (b).

We note that for many problems that the Jacobian can be approximated by the first two terms of the Neumann series $$(\partial/\partial\gamma)R=-D(I+[\backslash\gamma\backslash]C)[\backslash E\backslash]]$$

This is like a Born approximation to the Jacobian, but it is not the Born approximation to the scattering equations. We find that this Jacobian has a larger radius of convergence than the Born approximation itself.

This method tends to be self regularizing if the iterations are halted when the changes in $\|R^{(n)}\|/\|E_m\|$ become small relative their early changes. Other regularization methods may also be used such as the "squaring" method described below:

SCIENTIFIC BACKGROUND ON SQUARING AN OVERDETERMINED SYSTEM TO APPLY BICGSTAB:

The basic algorithm for reconstruction of $\gamma$ is reviewed below: We start with the receiver and media propagation equations, modified to eliminate E, which then becomes a non linear expression for the object function in terms of the incident field and the measured field at a fixed frequency $\omega$. Define the residual field R (note the frequency, source and receiver indices of R are suppressed) by $$R=(E_m-E_b)-D[\backslash\gamma\backslash]([I-C[\backslash\gamma\backslash]]^{-1}E_b=0$$

Here, $E_m(r)$ is the measured field, $E_s=E_m-E_b$ is the measured scattered field, and $E_b(r)$ is the incident field or response in the (homogeneous) background medium. $[\backslash\gamma\backslash]$ is the diagonal matrix formed from the vector $\gamma$.

This provides the correct value for the measured field $E_m$ when substituting the correct value for $\gamma$ and $E_b$, and on setting R=0. We solve for $\gamma$ by finding the $\gamma$ that minimizes R by minimizing the objective functional $$F(\gamma)=(\frac{1}{2})\|E-E_b-D[\backslash\gamma\backslash]([I-C[\backslash\gamma\backslash]]^{-1}E_b\|^2=(\frac{1}{2})\|R\|^2$$

In general, we can define the norm of R to be general enough to weight each frequency component of $F(\gamma)$ to increase the convergence rate in some cases:

$$F(\gamma)=(\frac{1}{2})\|R\|^2=\Sigma_{frequency\ \omega}\Sigma_{sources\ s}\Sigma_{receivers\ m}|W_\omega R_{\omega sm}|^2$$

Define the Jacobian of the residual R with respect to $\gamma$ by $$(\partial/\partial\gamma)R=-D(I-[\backslash\gamma\backslash]C)^{-1}[\backslash E\backslash]]$$

Then The Gauss-Newton algorithm for finding the $\gamma$ that minimizes $F(\gamma)$ is given by:

(a) Select an initial guess $\gamma^{(n)}$. Set n=0.

(b) Solve the forward problem for $E^{(n)}$ by us of the biconjugate gradient (BCG) or stabilized biconjugate gradient (BiSTAB) algorithms.
$E^{(n)}=([I-C[\backslash\gamma^{(n)}]]^{-1}E_b$ (c) compute the receiver residuals
$R^{(n)}=E_m-E_b+D[\backslash\gamma^{(n)}\backslash]([I-C[\backslash\gamma^{(n)}\backslash]]^{-1}E_b$ (d) For some small number the size of the noise to signal ratio, if $\|R^{(n)}\|/\|E_m\|<\epsilon$, then stop. Else (e) Minimize $\|(\partial/\partial\gamma)R^{(n)}\delta\gamma^{(n)}+R^{(n)}\|^2$ for $\delta\gamma^{(n)}$ by using the conjugate gradient algorithm.

(f) Update $\gamma$ by $\gamma^{(n+1)}=\gamma^{(n)}+\delta\gamma^{(n)}$ (g) Set n=n+1, go to (b).

We note that for many problems that the Jacobian can be approximated by the first two terms of the Neumann series $$(\partial/\partial\gamma)R=-D)I+[\backslash\gamma\backslash]C)[\backslash E\backslash]]$$

This is like a Born approximation to the Jacobian, but it is not the Born approximation to the scattering equations. We have found that this algorithm with approximate Jacobian has a larger radius of convergence than the Born approximation per se.

This method tends to be self regularizing if the iterations are halted when the changes in $\|R^{(n)}\|/\|E_m\|$ become small relative to their early changes. Other regularization methods may also be used such as Singular Value Decomposition based methods. The difficulty with this algorithm is that it is based upon using some form of general conjugate gradients to solve an overdetermined system. The way to avoid this bottleneck is to create a square system from the overdetermined system and use BiCGStab on the square system. This can be done in several ways when the system is linear.

Investigation of a new inversion method based on finding square Jacobian.

It is known that solving the rectangular, over determined, linear system Ax=b can be accomplished by multiplying both sides of the equation by the adjoint A $\mathbb{G}$, thereby giving the square system (A $\mathbb{G}$A)x=(A $\mathbb{G}$b). This system is call the normal system and the corresponding equations the normal equations. The solution is the lest squares solution to the original over determined system. However, the new system has singular values that are the square of the singular values if the original system (i.e., A $\mathbb{G}$A is ill conditioned). This means the conjugate gradient (CG), one the most efficient of all methods, converges slowly in solving the normal equations. Although CG methods for solving the over determined system directly exist, they essential form products (A $\mathbb{G}$,A) implicitly. Thus, the speed advantages of CG are compromised. The system Ax=b in our example represents the system $(\partial/\partial\gamma)R^{(n)}\delta\gamma^{(n)}+R^{(n)}=0$, i.e. equation 4.2; 18(e), where $(\partial/\partial\gamma)R^{(n)}$ is the Jacobian $J^{(n)}$.

We note $J^{(n)}\mathbb{G}J^{(n)}$ is square but ill conditioned. In our example Ax=b, let x=By and let AB be square. Then on substitution, ABy=b. Now, y can be solved by BiCG and then x is found by a simple multiplication by B. Further, suppose that B can be chosen so that y≈b, then AB≈I., where I is the square identity matrix. In this case, solving ABy=b is very well conditioned and BiCG should converge in only a few iterations. We next generalize A and B to be nonlinear operators (not matrices). Then the Jacobian of the operator AB is square. We also may choose B to be an improved generalized Born approximation, the Born approximation, or backpropagation. These methods are discussed in the detailed description section below in conjunction with FIGS. 37 and 38.

General Discussion of Conditioning

Suppose that the goal is to find $\min_t \|At-r\|_2$, where A is m by n matrix (m<n), t is an n-dimensional vector, and r is m-dimensional "residual" vector. By making a change of variables Bs=t, to s, where B is n by m., the system to be solved is now $$ABs=r$$

and AB is a square system. Therefore the BiConjugate gradient method or BiCGsquared algorithm can be applied to this system. BiCG squared has much better convergence behaviour than standard conjugate gradient methods for non-square systems. Consequently the convergence to a solution ŝ will generally be much quicker, whereupon î=Bŝ computes the answer to the original problem. Due to the position of the conditioning matrix B, after the original coefficient matrix A, this procedure is sometimes referred to as 'postconditioning'

Two special cases:

1. $B=A^T$, in which case s is the minimum norm solution to an underdetermined problem 2. $A(\gamma) = \bigoplus_{\omega\phi} G^{sc}_\omega (I - G_\omega \gamma)^{-1} f^{inc}_{\omega\phi}$, where $\bigoplus_{\omega\phi}$ indicates the direct sum in the sense of vector spaces over all frequencies, ie concatenation.

In fact, for operators $A_1$, which act on vectors $v_j$: $A_j v_j$, the operator $$\left[\bigoplus_j A_j\right] \equiv \begin{bmatrix} A_1 & 0 & 0 & 0 \\ 0 & A_2 & 0 & 0 \\ 0 & 0 & \ddots & 0 \\ 0 & 0 & 0 & A_N \end{bmatrix}$$

acts on the total vector $$\left[\bigoplus_j v_j\right] \text{ to yield: } \left[\bigoplus_j A_j\right]\left[\bigoplus_j v_j\right],$$

where $$\left[\bigoplus_j A_j\right]\left[\bigoplus_j v_j\right] \equiv \begin{bmatrix} A_1 & 0 & 0 & 0 \\ 0 & A_2 & 0 & 0 \\ 0 & 0 & \ddots & 0 \\ 0 & 0 & 0 & A_N \end{bmatrix}\begin{bmatrix} v_1 \\ v_2 \\ \vdots \\ v_N \end{bmatrix} = \begin{bmatrix} A_1 v_1 \\ A_2 v_2 \\ \vdots \\ A_N v_N \end{bmatrix}$$

Of course, this is a nonlinear operator, and the corresponding Jacobian is $$\frac{\partial AB}{g} \equiv \frac{\partial A(\gamma)}{\partial \gamma}\frac{\partial B}{\partial g} = \left(\begin{array}{c}\text{by}\\\text{linearity}\end{array}\right) = \frac{\partial A(\gamma)}{\partial \gamma}B \quad (1)$$

This Jacobian is evaluated at some iterated guess, and is an object that is used in the BiCG minimization routine. B in this case is the Born or Rytov reconstruction.

The general procedure for the solution of the Jacobian equation:

$$\frac{\partial A(\gamma)}{\partial \gamma} B \delta g^{sc} = -r^{(n)}.$$

then involves the application of said Jacobian (1), and its conjugate transpose:

$$B^H \frac{\partial A(\gamma)^H}{\partial \gamma} r^{(n)}$$

In the above formula $g^{sc}$ is the scattered field to which the Born reconstruction procedure is applied to yield $\gamma$, $$\gamma = B g^{sc}$$

where the standard Born approximation is utilized:

$$g^{sc}(x) = \int_\Omega G(x,x')\gamma(x')f^{inc}(x')dx'$$

which upon discretization reads:

$$g^{sc} = G[f^{inc}]\gamma$$

where the standard notation for the matrix whose diagonal elements are the components of the vector $f^{inc}$ has been used:

$$[f^{inc}] \equiv \begin{bmatrix} f^{inc}_1 & & & \\ & f^{inc}_2 & & \\ & & \ddots & \\ & & & f^{inc}_N \end{bmatrix}$$

Consequently the operator B can be written explicitly:

$$B = [1/f^{inc}]G^{-1}$$

although it is important to realize that the actual inversion is never carried out: rather, the standard Born reconstruction based upon the Fourier Diffraction Theorem is used, for computational efficiency.

Scientific Background for Calibration Techniques

The idea behind the use of nonlinear optimization for calibration is to collect scattering data from several known phantoms. A computational model of the scattering process, functionally dependent on the unknown calibration parameters, is then varied with respect to these parameters until a match with the data is obtained. If the objects are sufficiently well known and sufficient in number and location, then the resulting match should provide an accurate estimate of the unknown calibration parameters.

Generic Gauss-Newton Minimization Algorithm for Calibration:

Suppose that a dataset, $f_{\theta\phi\gamma}{}^s, f_{\theta\phi}{}^i$, of scattered and incident fields is measured for several view angles q, receiver positions $f$, and known test phantoms, g. A typical phantom used in practice is an agar cylinder. Note that the incident measurements $f_{\theta\phi}{}^i$ are not dependent on the test object.

Assume further that a computational model for the scattering problem exists which predicts the measured data, given such calibration parameters as position, radius, and speed of sound in the agar cylinder, and position and orientation of the receiver array. This might be a general forward solver such as an integral equation solution or an FDTD algorithm. A simpler, less computationally involved method, in the event that the test phantoms are cylinders or collections of cylinders, is the use of the Bessel series analytic solution. Let this computational solution be denoted:

$$\phi_{\theta\phi\gamma}{}^s(C), \phi_{\theta\phi}{}^i(C)$$

for the M scattering parameters in the vector C $$C \equiv \begin{pmatrix} c_1 \\ c_2 \\ \vdots \\ c_M \end{pmatrix}$$

The optimization approach is to minimize the $L_2$ norm of the mismatch between theoretically predicted and experimentally measured fields by adjusting the values of the scattering parameters in vector C:

$$\min_{\varepsilon} F \equiv \min_{\varepsilon} \left[ |\varphi^s_{\theta\phi\gamma}(\mathbf{c}) - f^s_{\theta\phi\gamma}|^2 + |\varphi^i_{\theta\phi}(\mathbf{c}) - f^i_{\theta\phi}|^2 \right]$$

It is also possible and desirable to enforce bounds on the scattering parameters:

$$L_j \leq c_j \leq U_j, j=1, \ldots, M.$$

Minimization of the functional is computed by first explicitly deriving the elements of the Jacobian for the scattering equations:

$$\frac{\partial f^s_{\theta\phi\gamma}(\mathbf{c})}{\partial c_m} \quad \frac{\partial f^i_{\theta\phi}(\mathbf{c})}{\partial c_m}$$

The Gauss-Newton method for the minimization of the functional $$F \equiv \left[ |\varphi^s_{\theta\phi\gamma}(\mathbf{c}) - f^s_{\theta\phi\gamma}|^2 + |\varphi^i_{\theta\phi}(\mathbf{c}) - f^i_{\theta\phi}|^2 \right]$$

is the following

STEP 1: Choose an initial guess for the parameter vector, $C_o$ and put n=0.

STEP 2: Form the residual vectors $$\mathbf{r}^s_n = \boldsymbol{\phi}^s_n - \mathbf{f}^s_n, \mathbf{r}^i_n = \boldsymbol{\phi}^i_n - \mathbf{f}^i_n$$

where the vectors used in the definition of $r_j$ are given by:

$$\boldsymbol{\phi}^s_n \equiv \begin{pmatrix} \vdots \\ \varphi^s_{\theta\phi\gamma}(\mathbf{c}_n) \\ \vdots \end{pmatrix} \quad \mathbf{f}^s_n \equiv \begin{pmatrix} \vdots \\ f^s_{\theta\phi\gamma}(\mathbf{c}_n) \\ \vdots \end{pmatrix}$$

STEP 3: Form the Jacobian matrices:

$$\begin{bmatrix} \frac{\partial \phi^s_{\theta\phi\gamma}(\mathbf{c}_n)}{\partial c_m} \\ \frac{\partial \phi^i_{\theta\phi}(\mathbf{c}_n)}{\partial c_m} \end{bmatrix} \equiv \begin{bmatrix} \frac{\partial \boldsymbol{\phi}^s_n(\mathbf{c}_n)}{\partial c_m} \\ \frac{\partial \boldsymbol{\phi}^i_n(\mathbf{c}_n)}{\partial c_m} \end{bmatrix} \equiv \begin{bmatrix} J\phi^s_n(\mathbf{c}_n) \\ J\phi^i_n(\mathbf{c}_n) \end{bmatrix}$$

and solve the system:

$$\begin{bmatrix} J\phi^s_n(\mathbf{c}) \\ J\phi^i_n(\mathbf{c}) \end{bmatrix} \delta \mathbf{C}_n = - \begin{bmatrix} \mathbf{r}^s_n \\ \mathbf{r}^i_n \end{bmatrix}$$

STEP 4: Update the parameter values:

$$C_{n+1} = C_n + \delta C_n$$

and update n: n←n+1, and go to STEP 1 if a convergence criterion has not been met.

Modification of this algorithm to incorporate equality constraints can be achieved by the method of Lagrange multipliers.

Inequality constraints can be included by the use of slack variables, Sequential Quadratic Programming, Projected Gradient, Augmented Lagrangian or Generalized Reduced Gradient methods. Of course Penalty function methods can also be employed in theory, but straightforward application of this procedure is generally ill-posed in the numerical sense. Enforcement of these constraints tends to be very important for the present problem. For instance, receiver positions might be constrained to movements less than the assumed precision in their physical measurement (these physical measurments determine the starting values, $c_0$).

Modifications

Perhaps the most essential modification to the basic Gauss-Newton algorithm above, for the present problem, is the incorporation of rescaling and truncation operators. An example of rescaling would be the case where one of the unknowns is an angle, a, (linear array angle offset). In order to give this unknown angle the same weight as an unknown distance, we solve for $\delta\alpha' = r\delta\alpha$ where r is a relevent distance which may be a function of receiver position. A need for truncation is illustrated by the fact that multiple test phantoms are needed to fully test the receiver transducer pattern. For a given phantom, only a certain range of receiver pattern parameters are tested. Also, the sensitivity of each receiver position to a given pattern parameter can be estimated geometrically. This information can be incorporated into the Jacobian with a combination of rescaling (emphasising some receiver values and deemphasising others) and truncation operators (removal of data not affected by a given parameter). Rescaling and truncation improve the conditioning of the Jacobian and avoid the emphasis of noise in data not relevent to a given parameter.

Description of Calibration Procedure for Acoustic Imaging

This example gives a specific example of how the calibration procedure is employed for a particularly simple system as employed at TechniScan Inc. This example can easily be applied to electromagnetic waves with the appropriate changes in the notation.

In order to obtain a well calibrated inverse scattering image, the acoustic pressure field due to the transmitter and the sensitivity field of the receiver (equal to the pressure field produced by the receiver acting as a transmitter) must be known. Presently available transducers (PZT and PVDF) suffer from piezoelectric parameter variations, preventing the construction of a transducer with a field pattern prescribed to within better than 10%. Thus, transducer field measurements are needed to calibrate the transducer fields prior to (or concurrent with) optimization for the target acoustic parameters.

The inverse scattering algorithm also requires accurate measurement of geometrical parameters such as the physical location of the transmitter and receiver transducers relative to the region to be imaged. As a concrete example, suppose that multiple view data for the imaging of an object is obtained by a single receiver mechanically scanned to form a linear receiver array, a fixed transmitter location, and a rotated object holder: See FIG. 46 for a picture of the relevant geometry.

In FIG. 46, the object to be imaged is assumed to be fixed in the primed coordinates. The unprimed coordinates are defined by segment l connecting the transmitter center to the rotation axis of the object. $d_t$ is the unknown length of segment l, $b_t$ is the unknown transmitter misalignment angle, $q_m$, m=1, . . . ,M is the rotation angle of the object, $d_r$ is the unknown distance from the rotation center to the receiver scan line (in the direction of segment l), a is the unknown misalignment angle of the receiver scan line with respect to the normal to l, $b_r$ is the unknown misalignment angle of the receiver with respect to the scan line, D is the known receiver scan increment, $y_n$, n=−N, . . . ,N is the distance from the intersection of segment l with the receiver scan line to the nth receiver position which is known if $y_0=y_s$ and D are known. We assume that the rotation increment, dq, is known. The exact placement of the object to be imaged in the primed coordinate system is not needed since its absolute shift and rotation will be imaged. The 6 geometrical unknowns are thus: $d_t$, $d_r$, $b_t$, $b_r$, a, $y_s$. In this 2D example, the third dimension (normal to the plane of FIG. 1) is ignored. In a real experiment, displacements and angle offsets in this dimension are also unknown. However, a basic assumption of our present approach is that, even if fields with 3D variation are produced by the transmtter and receiver, if the object is 2D (no variatin in the third dimension) then there exist 2D transducers which will produce the same eikonal (total field measurement divided by the incident field measurement) data.

Calibration by Optimization

In order to determine the transducer fields and geometry of the experiment, optimization techniques are used. Consider the case where the transducers fields are known and we whish to calibrate for the geometry. Assume that a calibration phantom consisting of a saline filled plastic circular cylinder is placed in the sample holder. Assume that the thickness of the plastic is known but the exact speed of sound in the saline is unknown. Assume also that the cylinder is centered precisely on the rotation axis so that only one view is needed (if this is not so, one could rotate the object holder and include x,y displacements of the cylinder axis with respect to the rotation axis as unknowns). Adding the unknown scattering potentials of the saline and plasitic to the list of unknowns gives the 8 values $d_t$, $d_r$, $b_t$, $b_r$, a, $y_s$, $g_s$, $g_p$ to be .determined. As a further simplification, let us take the transducers to be line sources which are perfectly colinear with the cylinder axis. For these omnidirectional transducers, there are no $b_t$, $b_r$, unknowns.

As a simulation example, data was generated by analytic cylinder solution for the following parameter values:

frequency=312.5 KHz
$C_0$=1485 m/s (speed of sound in water)
Outer diameter of plastic cylinder=1"
Thickness of plastic=0.73 mm
Number of receiver positions=128
Receiver sample interval, D=1.195 mm ($y_n$=(n−64.5)D+$y_s$)
$g_s$=−0.12
$g_p$=−0.5
$d_r$=5 cm
a=3 degrees
$y_s$=3 mm
$d_t$=15.cm The data used to optimize for the parameters is the log of the eikonal: $data_n = \ln(f_n/f_n^i) = \ln(|f_n/f_n^i|) + i\,\text{Phase}(f_n/f_n^i)$ The optimization functional is then:

$$F(\gamma_s, \gamma_p, \alpha, y_s, d_r, d_t) = \sum_n |\ln(f_n/f_n^i)(\gamma_s, \gamma_p, \alpha, y_s, d_r, d_t) - data_n|^2$$

The starting guess for the optimization is:
$g_s$=−0.1
$g_p$=−0.4
$d_r$=4.5 cm
a=0.0 degrees
$y_s$0.0 mm
$d_t$=15.5.cm Computing the data for these two parrameter sets gives the comparison shown in FIGS. 50 and 51.

Solution after 3 Ribere-Polack steps applied to the minimization of the functional gives the solution:

$$\text{Normalized residual} \equiv \sqrt{\frac{F(\text{final solution})}{\sum_n |data_n|^2}} = 0.1016598$$

$$\text{Normalized gradient} \equiv \sqrt{\frac{\nabla F(\text{final solution})}{\nabla F(\text{starting guess})}} = 0.2283959$$

| | |
|---|---|
| $g_s$ = −.116789, | 2.68% error |
| $g_p$ = −0.59277, | 18.6% error |
| $d_r$ = 4.756 cm | 4.9% error |
| a = 2.29916 degrees | 23.4% error |
| $y_s$ = 2.18673 mm | 27.1% error |
| $d_t$ = 15.0 cm | 0% error |

For 5 R–P steps:

Normalized residual = 5.11123E−02
Normalized gradient = 0.122296

| | |
|---|---|
| $g_s$ = −0.117978, | 1.75% error |
| $g_p$ = −0.57, | 14.0% error |
| $d_r$ = 4.87 cm | 2.6% error |
| a = 3.08706 degrees | 2.9% error |
| $y_s$ = 2.92 mm | 2.7% error |
| $d_t$ = 15.0 cm | 0% error |

For 9 R–P steps:

Normalized residual = 1.01880E−02
Normalized gradient = 1.22823E−02

| | |
|---|---|
| $g_s$ = −0.118573, | 1.17% error |
| $g_p$ = −0.518917, | 3.78% error |
| $d_r$ = 5.0 cm | 0% error |
| a = 3.08706 degrees | 2.9% error |
| $y_s$ = 2.96672 mm | 1.1% error |
| $d_t$ = 15.0 cm | 0% error |

Overview of Calibration Steps for Acoustic 2D Geometry

First incident field, scattered field, the total field corresponding to the FIG. 46 are read into memory.

STEP 1:

Creation of receiver model. For this purpose a procedure is carried out whereby the receiver is rotated in its center position with transmitter at some fixed position. The receiver is rotated at equi-angular intervals from −p/2 to p/2. For the 2D model the receiver is modelled as 51 weighted line receivers separated by some fixed distance drec, which is fixed, as shown in FIGS. 47 and 48.

STEP 2

Next a transmitter model is constructed which consists of an infinitely long, infinite impedance cylinder with a source function on its surface. The transmitter model equivalent source surface is discretized by an np=31 pt. spline function, interpolated to n>np points for the computation of the incident field.

The np node values on the surface of the non-physical infinite impedance cylinder are the unknowns which are optimized to give a best fit in the least squares sense of the incident field as measured on the receiver array, as shown in FIG. 47.

STEP 3

The next step is the use of the incident field generated by this impedance cylinder model, and exact Bessel solution models for scattering from a cylinder to create a scattered field, which is matched with the measured scattered field, using the receiver model calculated above. The setup is as shown in FIG. 49.

SUMMARY

We have discussed several algorithms for imaging:
(1) FFT-BCG Methods
(2) Cylindrical and Rectangular Recursion
(3) Parabolic marching methods (based on filtered finite differences or filtered spectral methods
(4) Brightness functional phase aberration correction We have given examples of how this technology is used in various scenarios. We have shown how various modalities of wave propagation are amenable to the imaging algorithm. Any propagating substance or energy that can be successfully modelled with the wave equation is suitable. We have also included examples of simulated and actual data, thereby establishing the concept as workable.

BRIEF DESCRIPTION OF THE DRAWINGS

FIG. 4A illustrates, with the use of an array processor, the scanning of an object using multiple frequencies, the frequency of an oscillator being changed several times at each illustrated transmitter position, so that sequential multiple frequencies may be transmitted by changing the frequency of the oscillator.

FIG. 4C shows n transducer elements in a circular array closely spaced to form a continuous array surrounding a body for use in the present inventive method of electronically multiplexing the array elements to eliminate the need for mechanical rotation.

FIG. 4D illustrates the transducers arranged in a linear fashion for pure electronic multiplexing of a linear transducer array according to the present invention.

FIG. 4E is an electrical schematic diagram showing how the elements in FIGS. 4C and 4D may be switched to act as either a transmitter or receiver by use of an active switch.

FIG. 4F shows how a passive network of diodes and resistors may be used to allow a single element to act as either a transmitter or a receiver, or in both capacities by the use of diode networks to isolate the transmitter from the receiver circuits according to the present invention.

FIG. 5A shows multiple frequency signals transmitted by selecting and generating a type of waveform which inherently includes multiple frequencies, and using a parallel processor, so as to produce repetitive narrow bandwidth signals or a wide bandwidth signal, which differs from the system shown in FIG. 4A in that the amplified analog signals output by a preamplifier are digitized by a high-speed analog-to-digital converter rather than being input to a phase detector.

FIG. 5B shows a waveform generator having five basic components.

FIG. 11A01, 11A02 show the generic solution to the forward problem (or any square system)using a biconjugate gradient algorithm according to the present invention.

FIGS. 11B01, 11B02 show the generic solution to the forward problem using the stabilized conjugate gradient algorithm, according to the present invention

FIG. 15 illustrates the application of Hermitian conjugate of the second Lippmann Schwinger Operators

Reference is now made to the figures wherein like parts are designated with like numerals throughout.

DETAILED DESCRIPTION OF DRAWINGS

The apparatus and method of the present invention holds promise for many useful applications in various fields, including seismic surveying, nondestructive testing, sonar, radar, ground penetrating radar, optical microscopes, x-ray microscopes, and medical ultrasound imaging, to name just a few. For purposes of illustrating the utility of the present invention, the detailed description which follows will emphasize the apparatus and method of the invention in the context of a system for use in performing ultrasound imaging of human organs, such as the breast. However, it will be appreciated that the present invention as claimed herein may employ other forms of energy such as microwaves, light or elastic waves and furthermore may be used in other fields and is not intended to be limited solely to medical acoustic imaging.

1. The Scanner and Transducer Configuration

Figure 1:
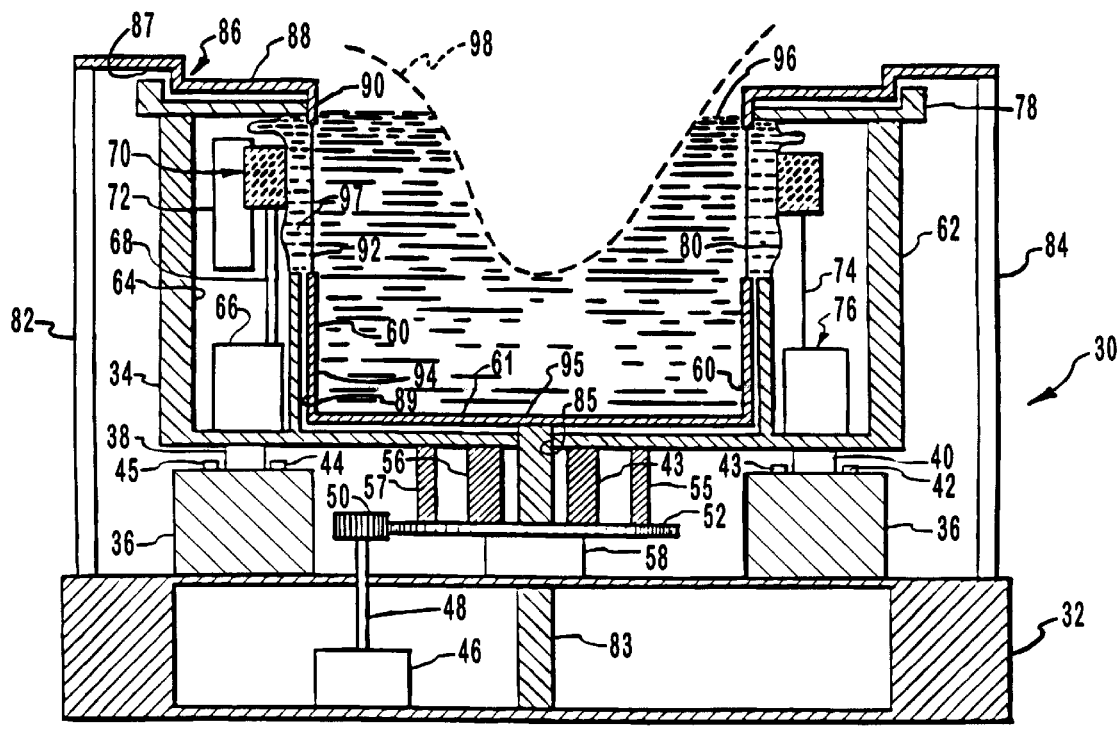
FIG. 1 is a side-elevational view shown partially in cross section which schematically illustrates an acoustic scanner which may be used with the apparatus and method of the present invention.

Reference is first made to FIG. 1 which generally illustrates one type of scanner which may be used to implement the apparatus and method of the present invention for purposes of medical ultrasound imaging of a human breast or other organs. As shown in FIG. 1, the scanning apparatus generally designated at 30 includes fixed base 32. Wheels 38 and 40 are attached to the underside of a movable carriage base 34. Small shoulders 42–45 formed on the upper surface of cylindrical pedestal 36 define a track along which the wheels 38 and 40 are guided.

A stepping motor 46 mounted within the fixed base 32 is joined by a shaft 48 to a small pinion gear 50. Pinion gear 50 engages a large drive gear 52. Pillars 54–57 are rigidly joined at one end to the top of drive gear 52 and at the opposite end to the underside of movable carriage base 34. Bearing block 58 supports drive gear 52 and movable carriage base 34.

Stepping motor 46 may be operated to turn the drive gear 52 which in turn will cause the movable carriage base 34 to rotate on top of the cylindrical pillar 36 within the tracks defined by shoulders 42–45. As hereinafter more fully described, rotation of the movable carriage base 34 may be employed to insure that an object is fully scanned from every possible angle.

With continued reference to FIG. 1, it will be seen that movable carriage base 34 has an inner cylindrical wall 60 and an outer cylindrical wall 62. The outer wall 62 and inner cylindrical wall 60 of movable carriage base 34 define a generally cylindrical chamber 64. Vertical drive motor 66 is mounted within chamber 64 and is connected by a shaft 68 to a circular ring of transducer arrays generally designated at 70. Vertical drive motor 66 permits the circular ring of transducer arrays 70 to be vertically adjusted. Slide bracket 72 is mounted within the chamber 64 and serves to guide in a sliding manner, the ring of transducer arrays 70 when it is vertically adjusted.

The ring of transducer arrays 70 is electrically connected through line 74 to components of an electronic system which may be housed in part within the chamber 64, as schematically indicated at 76. As hereinafter more fully described, the electronic system is used to control transmission and reception of acoustic signals so as to enable reconstruction therefrom of an image of the object being scanned.

Circular bracket 78 is attached to the top of the outer wall 62 of movable carriage base 34. A flexible, transparent window 80 extends between circular bracket 78 and the inner cylindrical wall 60 so as to enclose the transducer arrays 70 and stepping motor 66 within the chamber 64. The length of flexible window 80 is greater than the distance between bracket 78 and inner cylindrical wall 60. Window 80 thus serves as a flexible yet water-tight seal which permits vertical motion of the transducer arrays 70 for purposes of vertical focusing. Acoustically transparent window 80 may be made of any suitable material, such as plastic or rubber.

A stationary water tank generally designated 86 is adapted to fit within the movable carriage base 34. Water tank 86 consists of a fixed top plate 88 rigidly attached to vertical support bars 82 and 84. Support bars 82 and 84 are mounted on the fixed base 32. The length of support bars 82 and 84 is chosen such that the fixed top plate 88 of water tank 86 will be slightly suspended above the bracket 78 of movable carriage 34. Thus, a space 87 is provided between bracket 78 and fixed top plate 88. Additionally, a space 89 will be provided between side 94 and bottom 95 of water tank 86 and cylindrical wall 60 and bottom 61 of movable carriage 34. A third support bar 83 extends through a central hole (not shown) provided in block 58 and drive gear 52. Support bar 83 also extends through a watertight opening 85 provided in the bottom 61 of movable carriage 34. Support bar 83 thus helps to support water tank 86 in spaced relation from movable carriage 34. Since water tank 86 is suspended in spaced relation from movable carriage base 34, water tank 86 will remain stationary as movable carriage 34 is rotated. As hereinafter more fully described, rotation of the carriage 34 permits the transducer arrays 70 to scan the object 98 from every possible position around the object 98.

Fixed top plate 88 has a short downwardly extending lip 90 which extends over the end of circular bracket 78. A rubber-covered window 92 extends between the lip 90 and side 94 of the water tank. Window 92 encloses within space 89, water 97, or some other suitable acoustic medium so as to acoustically couple the transducer array 70 to the water 96 contained in tank 86. The rubber-covered window 92 also permits acoustic energy signals to be transmitted therethrough by the transducer arrays 70 and insures that the patient will be protected in the event window 92 should be broken.

The scanning apparatus generally described above may be employed to scan various parts of the human anatomy as, for example, a patient's breast, as schematically illustrated at 98.

The scanning apparatus generally described above may be used for nonmedical applications and may employ acoustic or electromagnetic energy wavefields. For example, the same scheme may be used with acoustic transducers for scanning nonbiological specimens such as plastic parts. As further example, the same scheme may be used with microwave wavefields. In this latter case, the use of a coupling medium such as water 96 and water 97 is optional. Indeed, at frequencies over one $GH_z$, the microwave absorption of water limits the size of the apparatus to a few centimeters. However, the use of air permits the use of electromagnetic energy over the spectrum from DC to far ultraviolet and soft x-rays. For microwave imaging, the ring of acoustic transducer arrays 70 is replaced with a corresponding ring of microwave transducer (i.e. antennas).

INVERSE SCATTERING SCATTERING SCENARIOS

FIG. 1-A shows a typical imaging scenario, such as might be encountered in the geophysical applications. Half space 1300 represents air, with a speed of sound equal to about 344 meters/sec. The image space 1312 is divided up into "pixels" (1320), which cover the region to be imaged. The object to be imaged, 1310, is located within this pixel grid. The term "pixel". is usually associated with two dimensions, however, we apply the same discretization procedure in 3-D (voxels), and higher dimensions (or lower) are certainly possible. For the sake of brevity and clarity, we refer throughout this patent to "pixels", even though their n-dimensional counterpart is meant.

The layers 1302, 1304, 1306, and 1316 are arbitrary both in vertical dimension, as well as speed of sound associated with them. The sources 1314, and receivers 1298, are in both boreholes 1308.

FIG. 1-B shows a typical scenario such as might be encountered in nondestructive evaluation, or in geophysical imaging. The source positions 1314 are located along the top of the image space at the interface of half space 1340 (sea-water), and layer 1342. Layer 1344 is basement sediment, and the image space 1312 is divided up into pixels, 1320. The detectors, 1348 are also located at the sea-water interface. Notice that the sources and receivers in this case, and the previous case, are juxtaposed to the image space 1312, which contains 1350, the object to be imaged.

FIG. 1-C shows the reflection scenario, as in FIG. 1-B, with the twist that the sources and receivers (1314 and 1308 respectively) are located at some finite distance from the image space. This remote source/receiver geometry is also implementable with the cross-borehole geometry of FIG. 1A. The layers 1302, and target to be imaged 1310 are as before in FIG. 1A. The pixels 1320 are as before. The speeds of sound are such as to be appropriate to the geophysical case.

Figure 2:
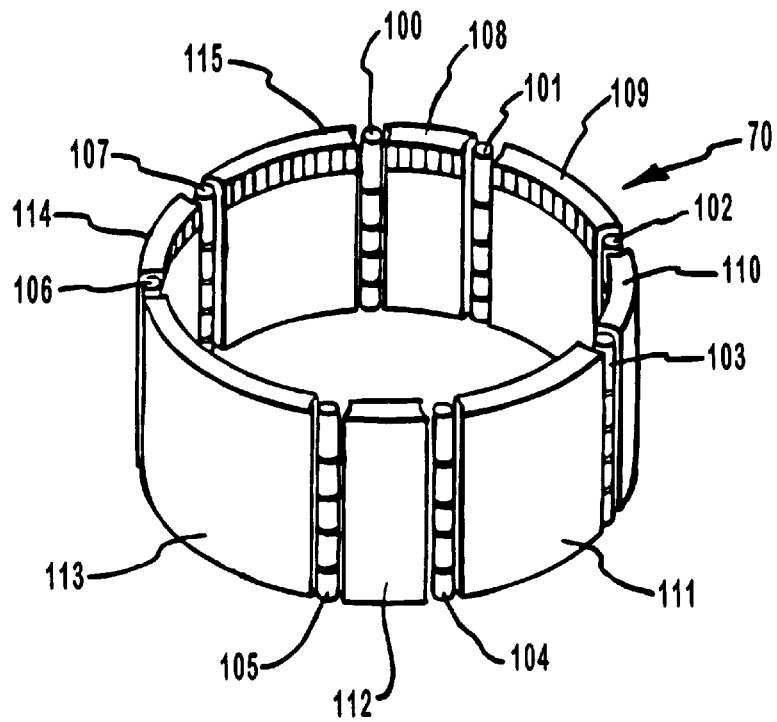
FIG. 2 is a perspective view illustrating one type of configuration which may be used for the transducer arrays employed in the scanner of FIG. 1.
Figure 3:
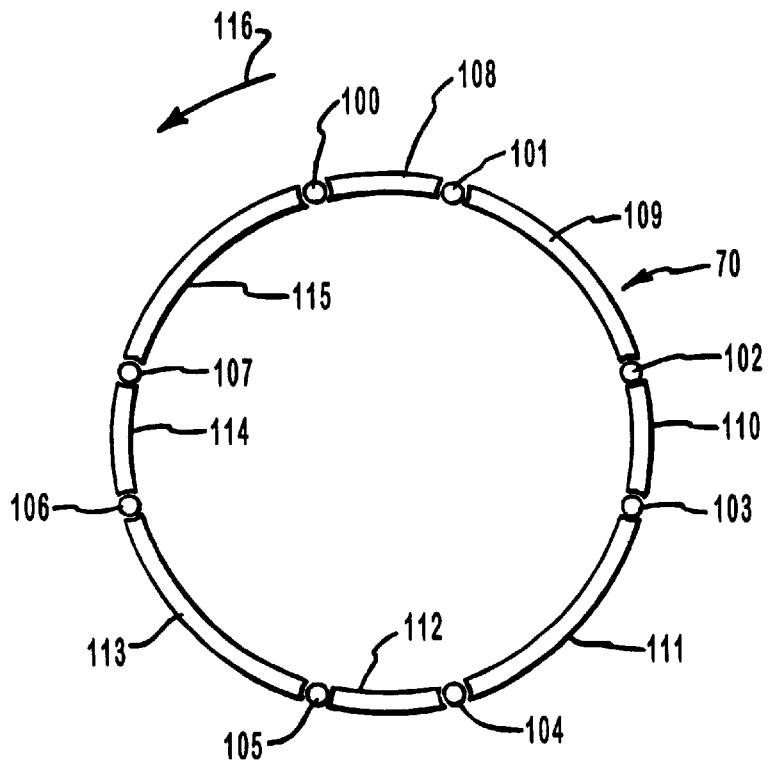
FIG. 3 is a top view of the transducer arrays shown in FIG. 2.

Reference is next made to FIGS. 2-3. FIG. 2 generally illustrates one suitable type of transducer configuration for the transducer arrays of FIG. 1. As shown in FIG. 2, the transducer configuration consists of eight transmitter arrays 100–107 and eight corresponding receiver arrays 108–115. The transmitter array 100–107 are thin, cylindrically-shaped transducer arrays which provide point-source or line-source segment transmission of acoustic energy. The receiver arrays 108–115 are arc-wise shaped arrays which are interposed between each pair of transmitter arrays 100–107. For purposes hereinafter more fully described, every other receiver array (e.g., receiver arrays 108, 110, 112 and 114) has a shortened arc-wise length.

Each of the transducer arrays 100–115 may be any of several well-known types of transducers. For example, transducers 100–115 may be piezoelectric transducers which produce ultrasound energy signals directly from high-frequency voltages applied to the transducer. Alternatively, the transducer arrays 100–115 may be magnetostrictive transducers having a magnetic coil (not shown) which receives the electrical oscillations and converts them into magnetic oscillations which are then applied to the magnetostrictive material to produce ultrasound energy signals.

With continued reference to FIG. 1, it will be seen that the transducer arrays 100–115 are arranged so as to form a cylindrical ring of arrays which encircles the object 98. By encircling the object with the transducer arrays 100–115, the arrays 110–115 may be quickly commutated by either mechanical methods, electronic methods or by a combination of both methods so as to completely scan the object in a much shorter time. In the illustrated embodiment, commutation is achieved by both mechanical rotation by stepping motor 46 and by electronic triggering of transmitter arrays 100–117 in sequence, as described more fully below.

Commutation of the transmitter arrays 100–107 permits acoustic energy to be transmitted from every possible position about the object, thus insuring that the data received (i.e. scattered acoustic energy) is complete. Commutation of the receiver arrays 108–115 insures that all spaces between receiver arrays 108–115 (known as "sound holes") will be covered, thus providing for accurate collection of all acoustic energy that is transmitted through or scattered by the object 98. However, commutation of the receiver arrays 108–115 is not necessary where transmitter arrays 100–107 are also used to receive acoustic signals. The circular configuration of transducer arrays 100–115 permits certain parts of the body to be scanned which would otherwise be inaccessible because of bones or other obstructions of the tissue.

The method for commuting the arrays 100–115 is best understood by reference to FIG. 3. First, each of the transmitter arrays 100–107 is sequentially triggered so as to transmit acoustic energy. Immediately after each transmitter array 100–107 is triggered, arrays 108–115 receive acoustic energy signals that have been either transmitted through or scattered by the object being scanned. Once this procedure has been followed for each of the transmitter arrays 100–107, the ring of arrays 70 is then mechanically rotated counterclockwise through a small angle, as schematically represented by arrow 116. The mechanical rotation is achieved by the stepping motor 46 (see FIG. 1) which rotates the movable carriage base 34, as described above.

After rotation of the arrays 100–115 to a second position, each of the transmitter arrays 100–107 is again sequentially triggered and data are again collected through receiver arrays 108–115. This procedure is repeated until acoustic energy has been transmitted at each possible point about the object.

Where the arrays 100–107 are used only for transmitting acoustic energy, a second series of rotations must then be effected to cover the sound holes between each pair of receiver arrays 108–115. For example, by rotating transmitter array 101 to the position occupied by the transmitter array 100, receiver arrays 109, 111, 113 and 115 will, because of their longer arcuate (arcwise measured) length, cover the spaces previously occupied by transmitter arrays 101, 103, 105 and 107. This procedure is repeated until all sound holes have been covered.

It should be noted that for a fixed circumference by decreasing the length of each array and increasing the number of arrays, electronic commutation may be used to reduce the angle through which the ring of transducer arrays must be rotated to achieve complete collection of both echo and transmission data.

It should also be noted that, in principal, no mechanical rotation of the array of detectors is necessary if every element is small enough and can be made to act as either a receiver or transmitter. Such an arrangement is more expensive than the technique illustrated in FIGS. 1, 2, and 3.

The transducer array 70 generally describes an implementation for an acoustic scanner and, in particular, of a breast scanner. In this case, the transducer elements generate and detect acoustic energy wavefields. However, it can be seen that the acoustic transducers can be replaced with microwave transducers (antennas). The functions of interleaving, rotation, commutation are identical, for either microwave or acoustic transducers.

2. The Electronic System

Figure 4A:
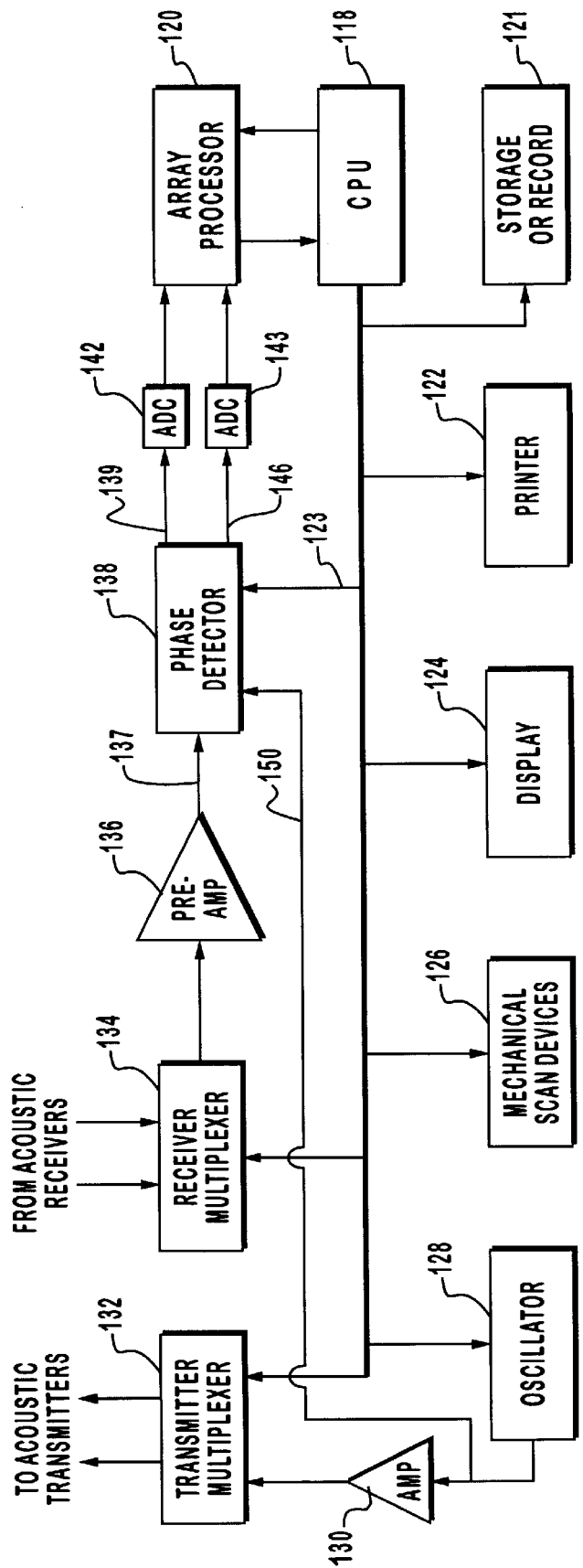
FIGS. 4A-4B are schematic diagrams illustrating one embodiment of an electronic system that may be used to implement the apparatus and method of the present invention, generally illustrate the invention in both the acoustic and electromagnetic wavefield case.
Figure 4B:
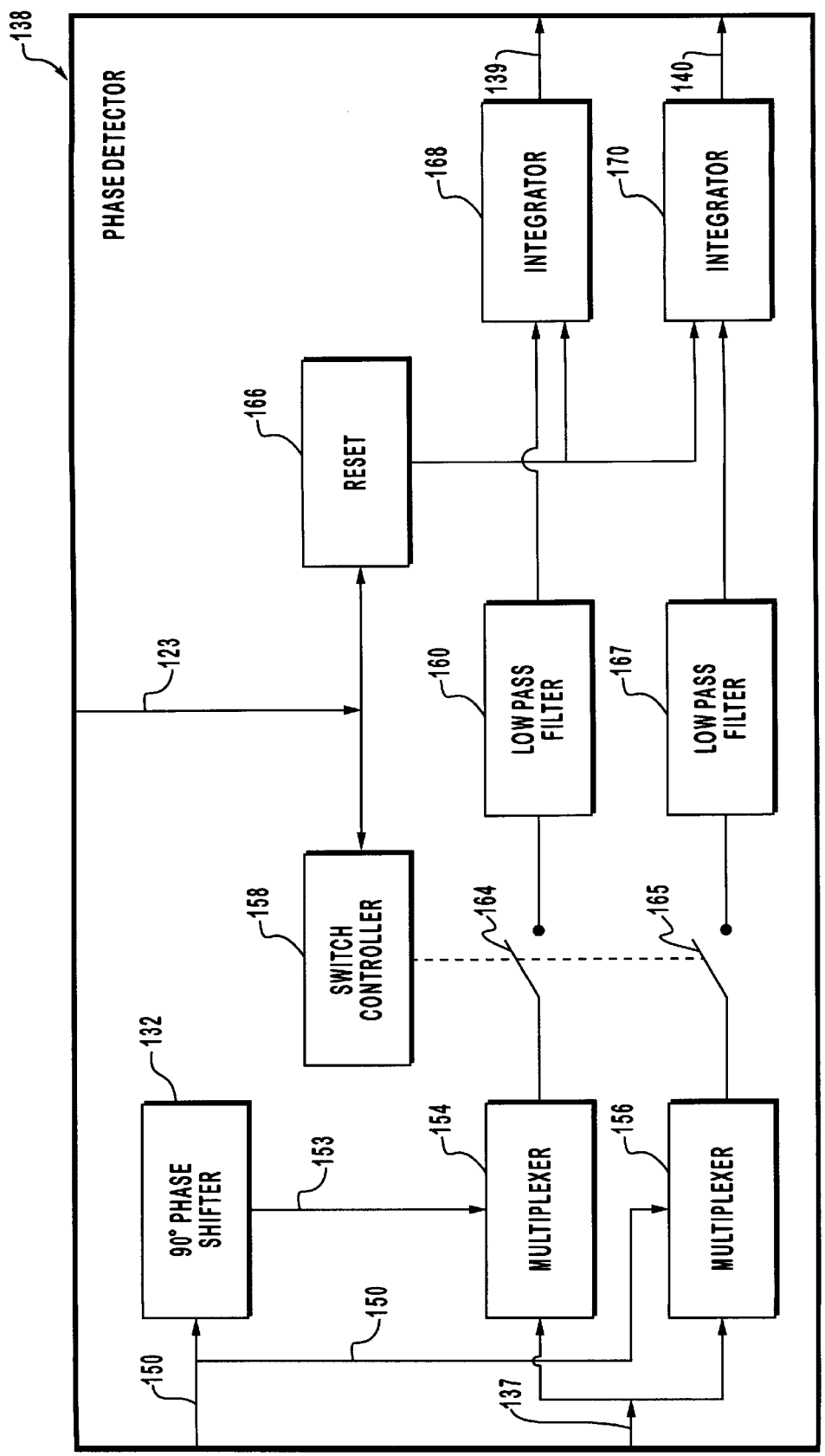

Reference is next made to FIGS. 4A-4B which schematically illustrate an electronic system which may be used to implement the apparatus and method of the present invention. It is clear from present practices in acoustics and radar technology that in both disciplines quadrature detection and analog to digital conversion are well known and widely used. Therefore, FIGS. 4A-4B generally illustrate the invention in both the acoustic and electromagnetic wavefield case. For clarity and simplicity, the electronic system is described in the context of acoustic wavefields. Following this acoustic description additional discussion on the applicability of FIGS. 4A-4B to microwave energy wavefields is made.

As hereinafter more fully described, the electronic system generates the acoustic energy that is propagated through and scattered by the object 98. The electronic system thereafter detects and processes the acoustic energy signals that are scattered by and transmitted through the object 98, and then communicates the processed signals to a computer (CPU) which interprets the signals and outputs the result in the form of a visual display or printed output.

In the transmission mode, CPU 118 causes an oscillator 128 to output a waveform which is amplified by a power amplifier 130 before being sent through multiplexer 132 to one of the transmitters. CPU 118 controls the multiplexer 132 so as to sequence each transmitter array 100–107 used to generate the acoustic energy propagated through the acoustic medium and object. If desired, after it is amplified, the waveform can also be input to an impedance matching transformer (not shown) and to a series of RC or RLC networks connected in parallel across the transmitter arrays 100–107 as illustrated and described in U.S. Pat. No. 4,222,274 (hereinafter the Johnson '274 patent), which is incorporated herein by reference. The impedance matching transformer may be used to achieve maximum power transfer while the RC or RLD networks may be used to distribute power across each transmitter array 100–107 in a way that deceases the side lobes in the transmitted signal.

Each of the acoustic receivers 108–115 (FIG. 2) are connected through a multiplexer 134 which is also controlled by CPU 118. In the receive mode, the detected signals may also be input through a delay line (not shown) to an analog adder and time variable gain circuit (not shown) to vertically focus the signals and to compensate for signal attenuation, as shown and described in the Johnson '274 patent. CPU 118 causes multiplexer 134 to sequence in turn each of the acoustic receivers 108–115 so as to gather transmitted or scattered acoustic energy around the entire circumference of the object. From receiver multiplexer 134, detected acoustic energy signals are amplified by a preamplifier 136 which may be used to logarithmically amplify the detected signal to reduce storage space required for each signal after it is digitized. The amplified signal is then processed by a phase detector 138.

The operation and components of phase detector 138 are best illustrated in FIG. 4B. As there shown, phase detector 138 receives the amplified signal as schematically represented by line 137 on which the signal is input to multipliers 154 and 156. The signal generated by oscillator 128 is input as shown at line 150 to one of the multipliers 156, and the signal from oscillator 128 is also shifted 90 degrees by the phase shifter 152 and then input as shown at line 153 to the other multiplier 154. Thus, each signal detected at the acoustic receivers is multiplied at multiplier 154 by a signal which is 90 degrees out of phase with the signal which is used to multiply the detected signal at the other multiplier 156. During the receive mode, the switch controller 158 and reset 166 are controlled as shown at line 123 by CPU 118 so that controller 158 closes each switch 164 and 165 after integrators 168 and 170 are reset. The resulting signals from multipliers 154 and 156 are then filtered by low-pass filters 160 and 162 and integrated by integrators 168 and 170. The integrated signals are then output, as shown at lines 139 and 140 to the analog to digital converters (ADCs) 142 and 143 (see FIG. 4A). The two signals which are output by phase detector 138 electronically represent the real and imaginary mathematical components of the acoustic signals which are detected at the acoustic receivers 108–115.

Once the received signals have been digitized, they are input and stored in the memory of an array processor 120. Alternately, a parallel processor or other special purpose high-speed computational device may be used for even higher computational speed. As hereinafter more fully described, CPU 118 in combination with the array processor 120 are programmed to then reconstruct the acoustic image using inverse scattering techniques, several alternatives of which are described more fully in Examples 1–3 of section 3 below. Once the acoustic image is reconstructed, it may be output either visually at a display 124 or in printed form at printer 122, or stored on a disc or other storage medium 123. Mechanical scan devices represented at 126 correspond to the motors 46 and 66 (FIG. 1) for controlling commutation and vertical positioning at the transmitter and receiver arrays 100–107 and 108–115, and are controlled by CPU 118. Other configurations of transducers can be scanned by mechanical means through use of mechanical scanning device 126.

The electronic circuits of FIGS. 4A-4B are effective over the frequency ranges of fractions of $H_z$ to hundreds of $GH_z$. The transmitter multiplexer 132 can drive signals to either acoustic or electromagnetic energy transmitting transducers. Likewise, receiving multiplexer 134 can receive signals from either acoustic or electromagnetic energy transducers. The operation of the circuit in FIG. 4A is independent of the source of the received signal at receiver multiplexer 134 or the destination of signal from transmitter multiplexer 132. The operation of the phase detector of FIG. 4B is independent of the type of wavefield used.

Figure 4C:
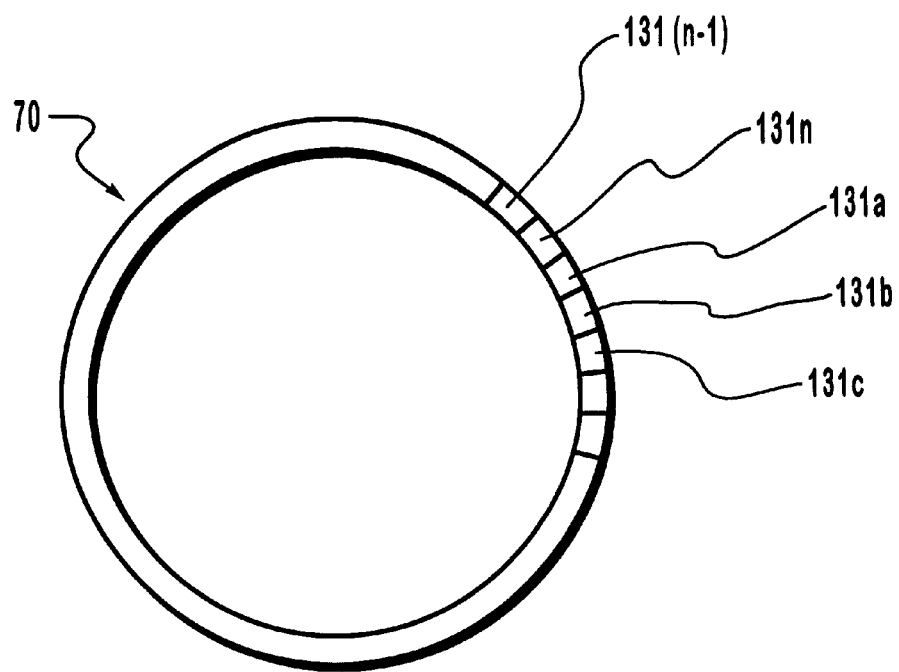
FIGS. 4C-4F schematically illustrate how electronic multiplexing may be used to eliminate the need for mechanical rotation, thus further enhancing system performance.
Figure 4D:
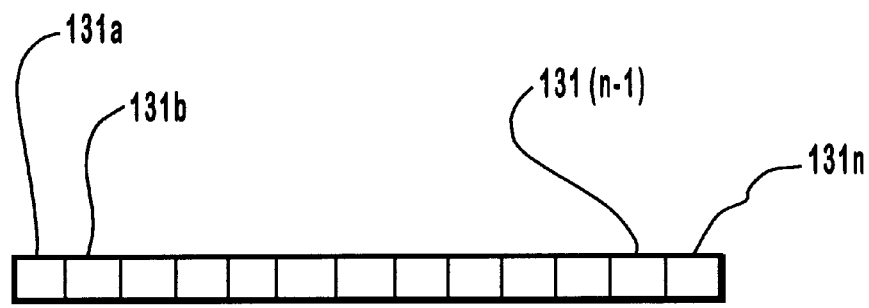

Reference is next made to FIGS. 4C–4F which schematically illustrate how electronic multiplexing may be used to eliminate the need for mechanical rotation, thus further enhancing system performance. In the following description, the term transducer applies equally well to both acoustic and electromagnetic energy types. In particular, FIG. 4C shows n transducer elements 131a through 131n of a circular array closely spaced to form a continuous array surrounding the body. The array is shown as a one-dimensional structure, but clearly could be a two-dimensional structure as in FIG. 2. FIG. 4D illustrates the n elements 131a through 131n arranged in a linear fashion. It is also clear that a planar or checkerboard two-dimensional array of element could be used.

Figure 4E:
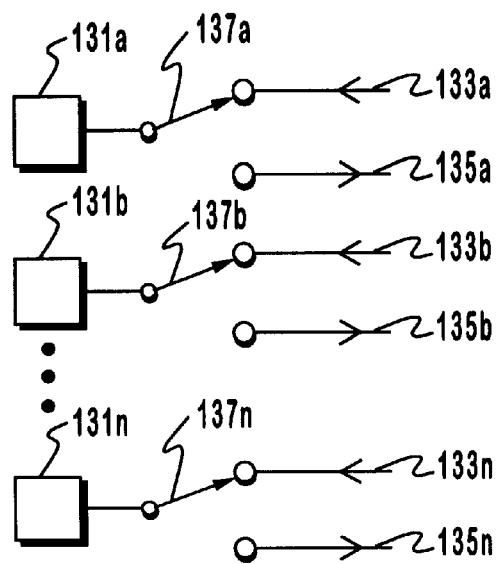
Figure 4F:
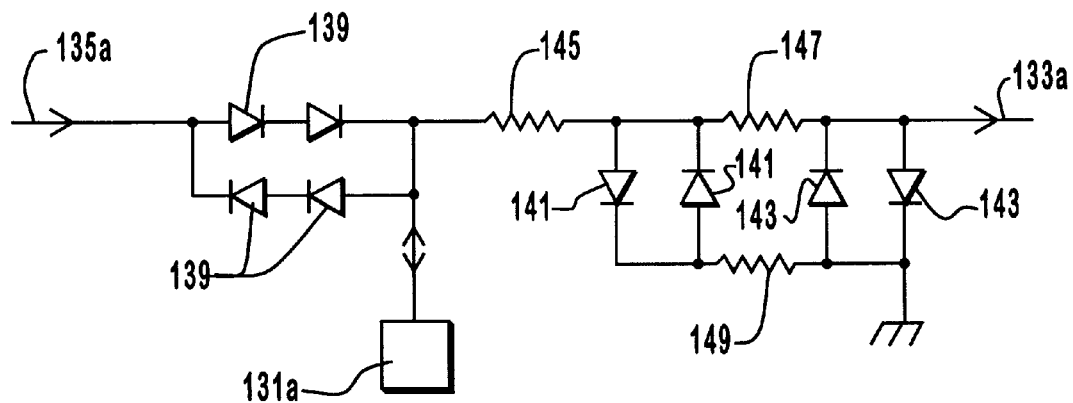
Figure 4G:
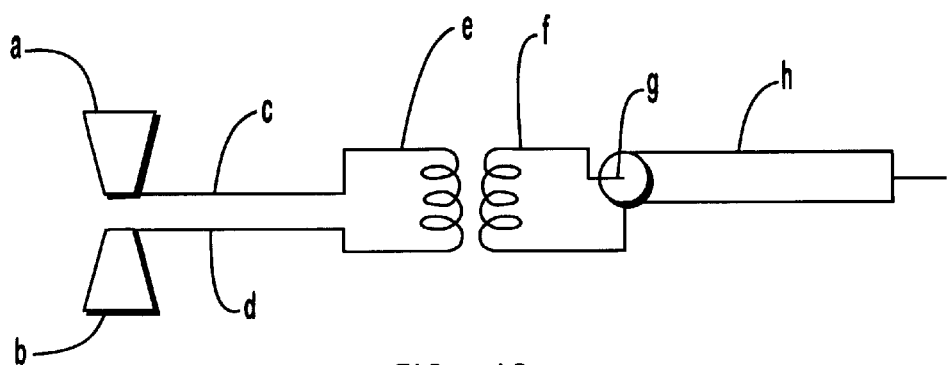
FIG. 4G is an electrical schematic illustration of a Bow-Tie Antennae used with the apparatus and method of the present invention.
Figure 4H:
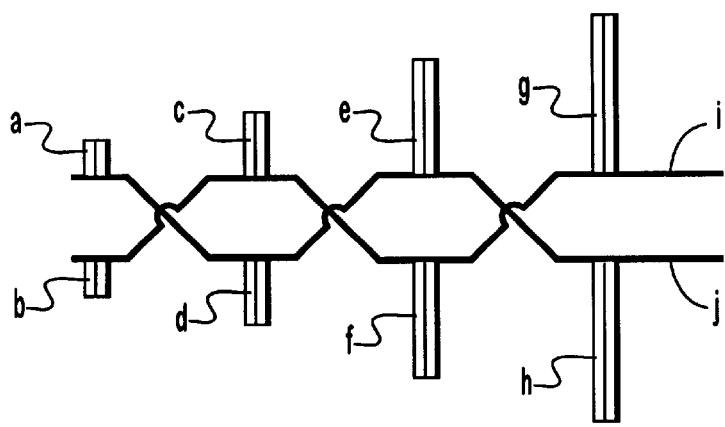
FIG. 4H is an electrical schematic illustration of a Log-Periodic Antennae used with the apparatus and method of the present invention.
Figure 4I:
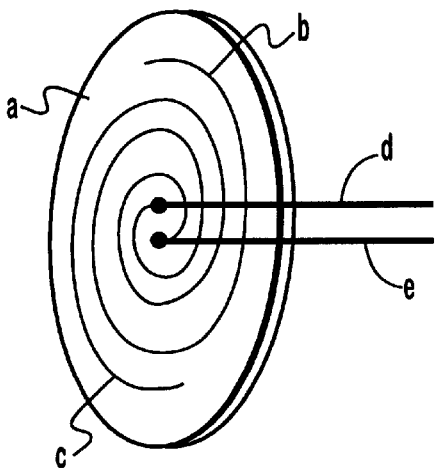
FIG. 4I is an electrical schematic illustration of a Spiral Antennae used with the apparatus and method of the present invention.

Such one-dimensional and two-dimensional arrays of receivers and transmitters have a direct application to advanced medical imaging instruments where motion of the array is undesirable or in seismic exploration in which such movements are difficult. FIG. 4E illustrates how each element 131a through 131n may be switched to either a transmitter circuit or a receiver circuit. Here, for example, element 131a is switched by switch 137a to either a receiver circuit 133a or a transmitter circuit 135a. FIG. 4F shows how a passive network of diodes and resistors may be used to allow a single element to act as either a transmitter or a receiver, or in both capacities. For example, in the transmit mode, diodes 139 are driven into conduction by transmit signal on line 135a. With two silicon diodes in series in each parallel leg, the voltage drop is a few volts. Thus, for an applied transmit signal of 20 volt or more, only a small percentage of signal power is lost across diodes 139. Diodes 139 are arranged in a series parallel network so that either polarity of signal is passed to transducer element 131a with negligible loss. In the transmit mode, resistors 145, 147, and 149 and diodes 141 and 143 prevent excessive and harmful voltage from appearing at output 133a that leads to the preamplifier multiplexer, or analog-to-digital circuits that follow. In operation, resistor 145, diode 141, and resistor 149 act as a voltage divider for the large transmit voltage present at the transducer element 131a. Diodes 141 are arranged with opposing polarity to provide a path for any polarity of signal above their turn on voltage of about 0.7 to 1.0 volts. The values of resistors 145 and 149 are typically so that the impedance of resistor 145 is greater than or equal to that of the internal impedance of transducer element 131a. Resistor 149 is chosen to be some fraction of resistor 145, such as one-fifth. Resistor (resistor 147) typically is chosen to be about equal to the resistance of resistor 149. Thus,during transmission, the voltage appearing at output 133a is only the conduction voltage drop across diodes 143.

In the receiving mode, signals received at transducer element 131a are typically less than one diode voltage drop (about 0.7 volt) and thus are isolated from transmitter 135a, since point 135a is a ground and diodes 139 are not conducting. Diodes 141 and 143 are not conducting and therefore output 133a is not shunted. Thus, the preamplifier following 133a would only see an impedance of resistor 145 plus resistor 147 plus that of the transducer element 131a. In practice, resistor 145 plus resistor 147 can be made about equal to or less than the impedance of transducer element 131a to minimize signal loss. It is clear that the principles illustrated in FIGS. 4C–4F may also be applied in the case of wide bandwidth signal transmission as described further below in connection with FIGS. 5A-5B.

FIG. 4F describing the use of diode networks to isolate the transmitter from the receiver circuits is commonly used in ultrasound scanners and sonar systems. Similar circuits are used in some radar systems. At radar frequencies other methods of isolation such as gas diodes, directional couplers, active diode switches, etc. are also used.

Figure 5A:
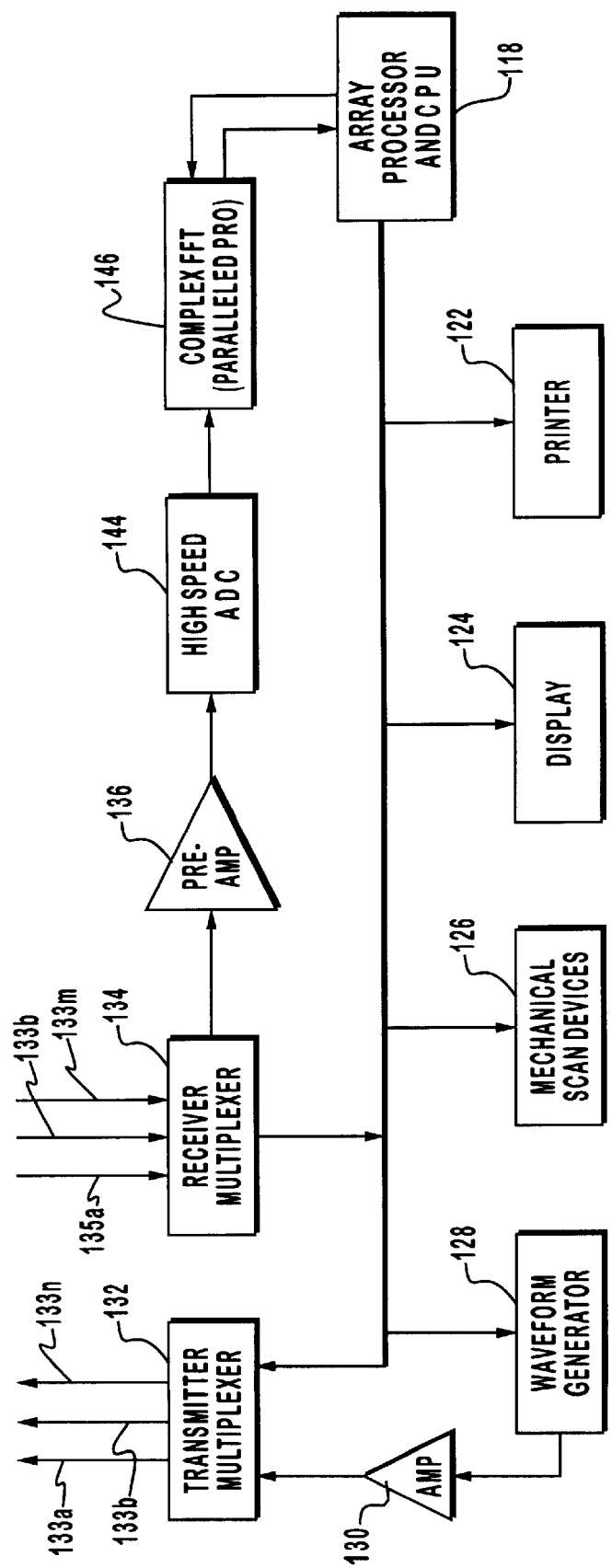
FIGS. 5A and 5B schematically illustrate another electronic system which can be used to implement the apparatus and method of the present invention.
Figure 5B:
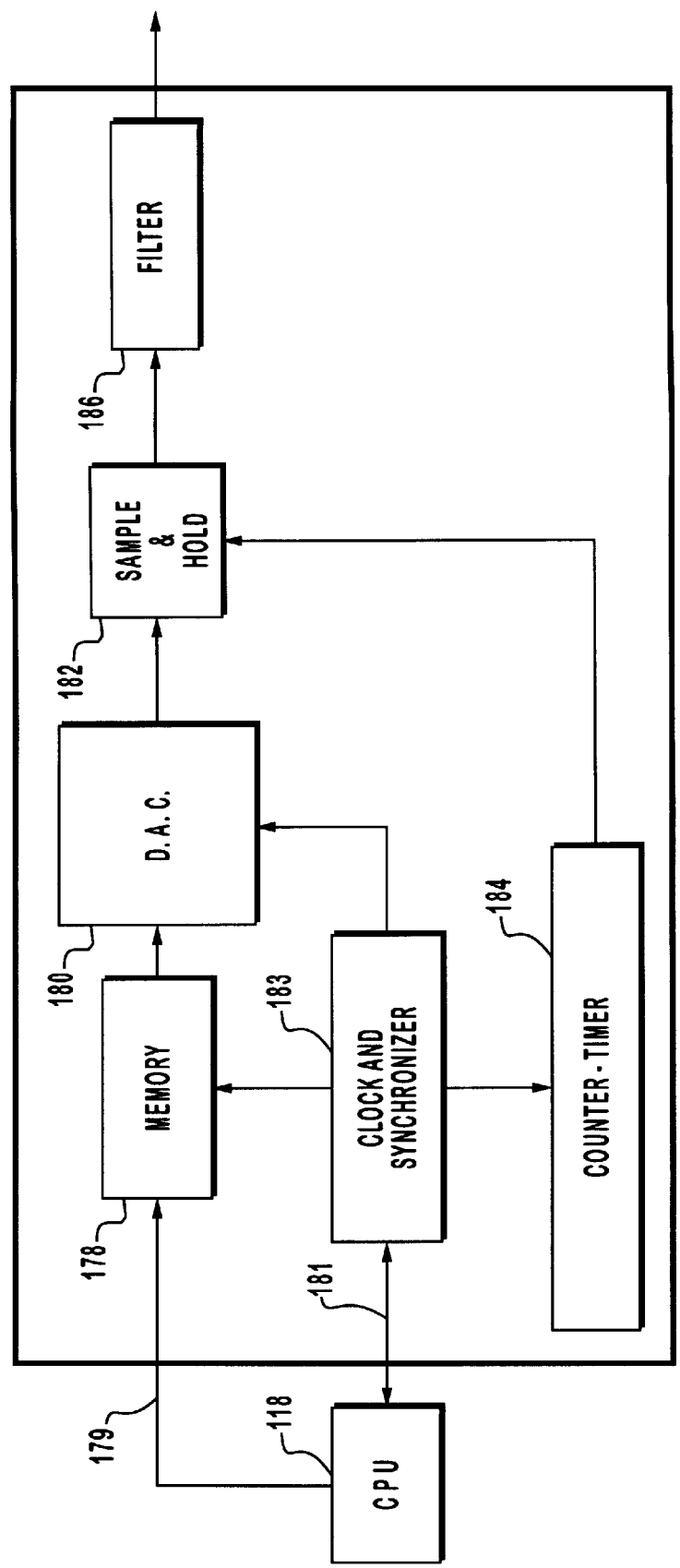

FIGS. 5A and 5B schematically illustrate another electronic system which can be used to implement the apparatus and method of the present invention. In the description that follows, the circuit is specifically designed for driving acoustic transmitting transducers and for digitizing signals from acoustic transducers, but the same circuit also applies to electromagnetic transducers (antennae) as well. In FIG. 5A, oscillator 128 has been replaced by waveform generator 129 that can produce repetitive narrow bandwidth signals or a wide bandwidth signal. The advantages of using a suitable wide bandwidth signal is that in one transmit-receive event, information at all frequencies of interest may be collected. Typically, it will be preferable to scan the object under consideration with signals having several different frequencies. This may be especially true in cases where it is not possible to encircle the object with a ring of transducer arrays, as in the case of seismic imaging. Moreover, by using multiple frequencies, it will typically be possible to obtain more data for use in reconstructing the image. The lowest frequency used for the signal must be such that the wavelength of the signal is not significantly larger than the object to be imaged. The highest frequency must be such that the acoustic signal may be propagated through the object without being absorbed to such an extent as to render detection of the scattered signal impossible or impractical. Thus, depending upon the absorption properties and size of the object which is to be scanned, use of multiple frequencies within the range indicated will typically enhance the ability to more accurately reconstruct the image of the object.

The use of multiple frequencies or signals containing many frequencies also has the advantage of obtaining data that may be used to accurately reconstruct frequency dependent material properties.

In the electronic system of FIG. 4A, in order to scan the object using multiple frequencies, the frequency of oscillator 128 must be change several times at each transmitter position. This increases the time involved in transmitting and detecting the scattered acoustic energy from which the image is reconstructed. In the electronic system of FIG. 5, a special waveform is used which inherently includes multiple frequencies within it. The type of waveform generated by waveform generator 129 may be the well-known Tanaka-Einuma kernel or the Ramachandran and Lakshiminaraynan kernel, as illustrated and described in the Johnson '274 patent. Swept frequency signals such as the well-known frequency modulated chirp or other types of waveforms could also be used to provide acceptable results.

As shown in FIG. 5B, the waveform generator 129 basically comprises five elements. An electronic memory device 178 is connected to the CPU 118 through read-and-write lines 179 and 181. CPU 118 determines the numerical value for a series of discrete points on the selected waveform. These numerical values are stored in binary form in memory device 178. Each of the discrete values stored in the memory device 178 is then sent to a digital to analog converter (DAC) 180. DAC 180 then transforms each of these digital values into a corresponding analog pulse which is then input to a sample and hold circuit 182. Sample and hold circuits, such as that schematically illustrated at 182, are well-known in the art and operate to hold each analog signal for a predetermined period of time. Counter-timer 184 is used to control the amount of time that each signal is held by the sample and hold circuit 182. Clock and synchronizer 183 is triggered by computer 118 and advances the memory address in memory 178, synchronizes the DAC 180, and controls the sample and hold 182.

With each clock pulse from counter-timer 184, the sample and hold circuit 182 retrieves one of the analog signals from DAC 180 and then holds the value of that signal for the duration of the clock pulse. Sample and hold circuit 182 thus outputs the approximate shape of the desired waveform which is then input to a low pass filter circuit 186 which is used to smooth the shape of the waveform before amplification and transmission through multiplexer 132 to one of the transmitters.

The electronic system of FIG. 5A also differs from the system shown in FIG. 4A in that the amplified analog signals output by the preamplifier 136 are digitized by a high-speed analog-to-digital converter 144 rather than being input to a phase detector. The digitized signals are then transformed by a complex fast Fourier transform (hereinafter "FFT") operation provided by a parallel processor 146 prior to being input and stored in the memory of the CPU 118. As described further in section 3 below, CPU 118 then reconstructs the image using a novel inverse scattering technique. Use of array processor 120 with CPU 118 in FIG. 4A and parallel processor 146 with CPU 118 in FIG. 5A is arbitrary and in principle either array processor 120 or parallel processor 146 or special purpose hard wired computational hardware could also be used in either FIG. 4A or 5A to accomplish the image reconstruction, as described further in section 3.

Optical Microscope

Figure 6A:
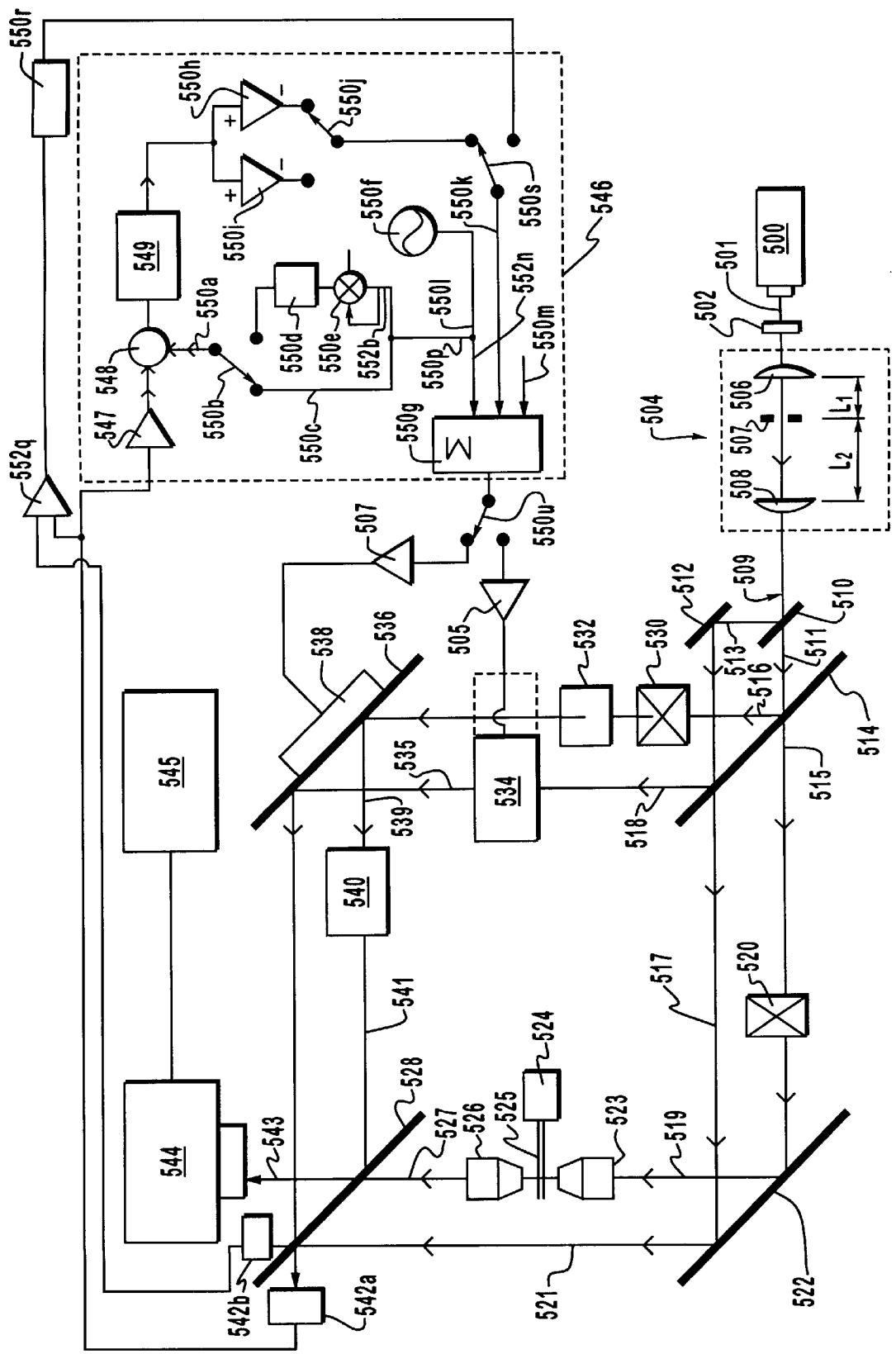
FIG. 6A is a system block diagram of an optical microscope used with the apparatus and method of the present invention.

The operation of the inverse scattering microscope can be seen in block diagram form in FIG. 6A. This figure explains the operation of a specially modified Mach Zehnder interferometer based detection system. This detection system produces the information from which phase and modulus information is produced that is needed by an inverse scattering algorithm. A monochromatic, coherent light source such as laser 500 produces an approximately parallel beam of light 501 that passes through polarizer 502 and passes into beam expander and spatial filter 504. Such beam expanders are well known and a representative form is shown wherein the input beam enters a positive lens 506 with focal length $L_1$. A pin hole is placed at a distance of $L_1$ from lens 506 to remove unwanted spatial frequency spectral components. Light from pin hole 508 is reconverted into output parallel beam 509 by lens 508 with focal length $L_2$. The pinhole 508 is placed at a distance $L_2$ from lens 508. Output of beam expander 504 is beam 509 which passes to beam splitter 510 and split into two beams: beam 511 and beam 513. Beam 511 is the precursor of the main beams 515 and 516. Beam 513 is the precursor of stabilizing beams 517 and 518.

The operation of main beams 515 and 516 is now described. Beam 515 is the precursor of a beam that will pass through the interferometer in a clockwise direction and will pass through and scatter from the sample and will act as a probing beam. Main beam 516 is the precursor of a beam that will not pass through the sample, but will act as a reference beam as it traverses the interferometer in a counterclockwise direction. The probing beam and the reference beam will be combined to produce various interference patterns from which phase and modulus information can be obtained. Beam 515 passes through shutter 520 and then is reflected by mirror 522 to become beam 519. Beam 519 passes through objective lens 523 into sample holder 525. The light that is scattered by the sample and the sample holder is collected by objective lens 526 and passed as beam 527 to beam splitter 528. Companion main beam 516 passes from beam splitter 514 through shutter 530 to phase shifter 532. Phase shifter 532 can be set to introduce either a 0 degree phase shift or a 90 degree phase shift. Beam 533 is the output of phase shifter 532.

The purpose of objective lens 526 is to collect as large an angle of scattered light as possible. Objective lens 523 serves several purposes including: (1) that of focusing a small spot of light onto the sample holder of higher intensity than normally would be present in beam 519 in order to improve the signal to noise ratio; and (2) that of restricting the illumination to a narrow, focal spot region with desirable, plane-wave-like phase fronts with lateral amplitude anodizing.

Light beam 531 from shutter 530 passes through transmission-type phase shifter 532 where its phase is shifted either 0 degrees or 90 degrees. Beam 533 exits transmission-type phase shifter 532 and passes to mirror 536. At mirror 536 beam 533 is reflected to become light beam 539. Mirror 536 is driven by optional mirror driver 538 in small amplitude, periodic motion at frequency ω and in a direction perpendicular to the mirror face in its resting position. As mirror 538 vibrates it introduces a small periodic phase shift modulation to beam 537, but this phase shift is negligible. The purpose of either transmission-type phase shifter 534 or reflection phase shifter 538 is to impart a small periodic phase shift, typically from 1 degree to 10 degrees at frequency ω into beam 518 in order to stabilize the main beams 527 and 541 as combined to form beam 543. Either of these phase modulation methods is workable either separately or in combination. Usually, for cost reasons, only one of these phase modulation methods will be implemented in hardware.

Beam 539 emerges from mirror 538 and passes through beam transformer 540 and thence to beam splitter 528. Beam transformer 540 serves the purpose of adjusting the phase fronts and lateral amplitude of beam 541 to match those of beam 527 at the mirror 528 and at camera 544. While such matching may not be strictly necessary it does provide a more simple interference pattern that is mostly a function of the inserted object and not a function of the interferometer itself. Beam transformer 540 could be constructed in a number of ways, but one obvious way would be to replicate objective lens pair 523 and 526, however with the following modifications: (1) the sample holder and object is omitted; or (2) the sample holder is present but no object is present.

Beams 541 and 527 are combined by beam splitter 528, now acting as a beam combiner, and produce an interference pattern on the sensitive one-dimensional or two-dimensional solid state array of detector cells in camera 544. The intensity pattern on the array of detector cells is then converted into an electrical signal that is sent to the digitizer and computer 545 where this signal is digitized and stored in memory. Computer 545 controls the angular position of sample holder 525 by means of rotation device 524. Rotation device 524 also serves the function, under direction of computer 545, of inserting or removing the object from the beam. Rotation device 524 may be a stepping motor or a worm gear driven rotation stage as is common in optical technology. Computer 545 also controls the transmission of shutters 520 and 530, controls the phase of phase shifter 532, and controls the digitizing of camera 544. Computer 545 performs the important role of creating different diffraction patterns by changing the combinations of: (1) sample in or sample out; (2) main beam A only or main beam B only or their sum; or (3) phase sifter in main beam set at 0 degrees or at 90 degrees. From these different diffraction patterns, as described by the eight measurements and equations in the summary of invention section, computer 545 can compute the scattered detected field from the object. By including various test objects of know properties the incident field present at object 526 can be calculated. The set of scattered fields calculated for each of the various respective adjusted angular position of the object holder 525 is used as the detected scattered fields in the inverse scattering algorithms. Likewise, the incident field in and around the sample holder is taken as the incident fields in the inverse scattering algorithms.

Returning to FIG. 6A, note that a second set of beams defined as stabilizing beams is shown and these beams also are caused to interfere by the same mirrors and beam splitters as is traversed by the main beams. The function and justification for using these stabilizing beams is described in the summary of invention section. Note beam 513 is reflected by mirror 512 into beam splitter 514 to become beams 517 and 518. Beam 517 is reflected by mirror 522 to become beam 521 which then passes to beam splitter 528 where it is reflected into detector 542a and transmitted into detector 542b. Beam 518 passes through phase modulator 534 to mirror 536 where it is reflected and becomes beam 537. A fraction of beam 537 then passed through beam splitter 528 to detector 542a where it interferes with reflected version of beam 521. A fraction of beam 537 is also reflected into detector 542b where it combined with a fraction of beam 521. Detector 542a typically would be a semiconductor pn diode or pin diode. The output of detectors 542a and 542b passes to locking amplifier system 546 which adjusts the mean phase shift imposed by mirror 536.

Locking amplifier system 546 functions in the following manner. The signal from detector 542a passes into locking amplifier system to amplifier 547. Output of amplifier is the input of multiplier 548. Multiplier has a second input 550a. The product of the output of amplifier 547 and input 550a passes through low pass filter 549 thence both to non inverting amplifier 550h and to inverting amplifier 550i. Switch 550j selects either the output of noninverting amplifier 550h or that of inverting amplifier 550i. The output of switch 550j passes to switch 550s and thence to summing amplifier 550g. Input 550a to multiplier 548 originates in oscillator 550f at frequency ω. The output of oscillator 550f is shown as signal 550l and is split into two parts: one part, signal 552n, is an input to summing amplifier 550g; the other part, signal 550p, is in turn split into two signals 550c and signal 552q. Signal 550c is one input to switch 550b. Signal 552q is imposed on both inputs of multiplier 550e. The effect of multiplying a signal by itself is to produce sum and difference signal. The difference signal is at zero frequency while the sum frequency is at double the input frequency. The output of multiplier 550e passed through high pass filter 550d to switch 550b. High pass filter 550d rejects the zero frequency signal but passes the doubled frequency. An offset constant voltage 550m is also an input of the summing amplifier 550g. Summing amplifier 550g sums signals 550m, 550k and 552n. The output of summing amplifier 550g is then sent to a phase modulator which may be mirror driver 538 or phase modulator 534. If output of summing amplifier 550g is sent to mirror driver 538 then this signal is first amplified by amplifier 507. If output of summing amplifier 550g is sent to phase modulator 534 then this signal is first amplified by amplifier 505.

The phase locking circuits can function in several modes. In a first mode, heterodyning techniques are used. In the summary of the invention section four different heterodyning methods are described. The hetrodyning mode is now described. One of two heterodyne methods to lock the two component beams at the same phase is now described. The output of amplifier 547 is multiplied by signal of frequency ω at multiplier 548 and the resulting signal is low pass filtered in low pass filter 549. The output is then passed through inverting amplifier 550i or noninverting amplifier 550h and thence through switches 550j and 550s to summing amplifier 550g and thence to phase modular 534 or phase modulator 538. The feedback loop adjusts the phase shifters 534 or 538 to minimize the signal component at ω present in the signal output of amplifier 547.

One of two heterodyne methods to lock the two component beams in quadrature (i.e. 90 degree phase difference) is now described. The output of amplifier 547 is multiplied by signal of frequency 2ω from high pass filter 550d. The signal from high pass filter 550d passes through switch 550b to multiplier 548 and thence to low pass filter 549. From low pass filter 549 the signal passes through either inverting amplifier 550i or noninverting amplifier 550h to switch 550j and thence to switch 550s and thence to input 550k to summing amplifier 550g. Output from summing amplifier 550g then drives either phase modulator 534 or mirror driven 538 to maximize the signal component at 2ω present in the signal output of amplifier 547.

The phase locking circuit can operate in a second mode where no heterodyning techniques are used. In this mode, output signal from detector 542a and output signal from detector 542b are passed to differential amplifier 552q, whose output is proportional to the difference in voltage between these two input signals. The output of differential amplifier is low pass filtered by low passs filter 550r to remove high frequency noise and passed to switch 550s and thence to summing amplifier 550g. The output of summing amplifier is then sent to either mirror driver 538, or phase modular 534. The advantage of this method is a reduction in parts, since no heterodyning circuits are required. Also significant is the elimination of phase modulators. Only the mirror driver for zero frequency baseband stabilization adjustments is necessary. A possible disadvantage may be an insensitivity to systematic errors.

Figure 6B:
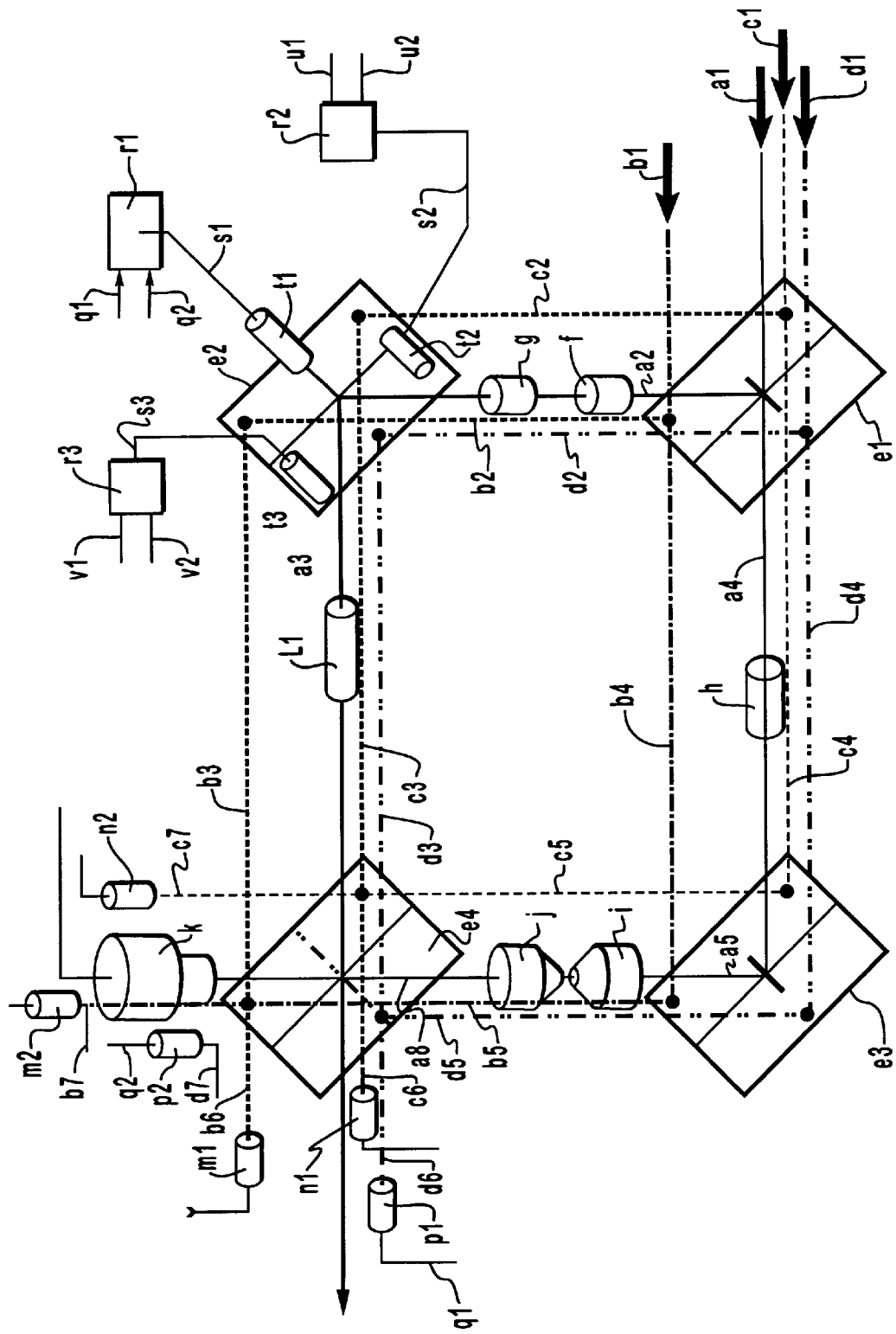
FIG. 6B is a perspective view which schematically illustrates an interferometer used with the apparatus and method of the present invention.

Referring to FIG. 6B, a perspective drawing of the interferometer section of the optical microscope of FIG. 6A is shown. This drawing is useful for visualizing the spatial relationships between the main imaging beam (located in the center of the mirrors and beam splitters) and the stabilizing beams (located at the edges of the mirrors and beam splitters). The main beam passes through the sample and objective lenses. The stabilizing beam passes around and misses the objective lenses and sample. The main beam is collected by solid state camera k, but stabilizing beams are collected by photodetectors m1, m2, n1, n2, p1 and p2. The normals to mirrors e2 and e3 and the normals to beam splitters e1 and e4 are mutually parallel. Main beam a1 enters the interferometer and is split by beam splitter e1 into beams a2 and a4. Beam a2 passes through shutter f and through phase shifter g to mirror e2. From mirror e2 the reflected version of beam a3 passes through wave front transformer $L_1$ to mirror e4 where it combines with beam a8 and passes to the solid state camera k. Main beam a4 passes through shutter h to mirror e3 where it is reflected and becomes beam a5. Beam a5 passes through objective lens i and lens j and becomes beam a8. The sample is placed between objective lens i and objective lens j as shown in FIG. 6A.

The paths of the stabilization beams are now described. The stabilization beams are comprised of three parallel beams. These beams enter mirror e1, as respective beams b1, c1, and d1. They leave in the clockwise direction as respective beams b4, c4, and d4 and reach mirror e3. They leave mirror e3 as respective beams b5, c5, and d5 and reach beam splitter e4. Beams b1, c1, and d1 also incident at beam splitter e1 produce respective counterclockwise directed beams b2, c2 and d2 which leave beam splitter e1 and are reflected from mirror e2 to become respective beams b3, c3, d3. Beams b3, c3 and d3 reach beam splitter e4 where they combine with respective beams b5, c5 and d5. This combination then exits beam splitter e4 as respective pairs b6, c6 and d6 to the right, and as respective pairs b7, c7, and d7 to the top. Beams b6, c6, and d6 are detected by respective detectors m1, n1 and p1. Beams b7, c7 and d7 are detected by detectors m2, n2, and p2, respectively. Outputs of m1 and m2 are combined to form a first feedback signal for mirror and beam splitter alignment. Outputs of n1 and n2 are combined to form a second feedback signal for mirror and beam splitter alignment. Outputs of p1 and p2 are combined to form a third feedback signal for mirror and beam splitter alignment. The stabilization scheme show in FIG. 6B is the nonheterodyne method described in the brief summary and object of the invention section. Clearly, the heterodyne methods may also be used.

The function of the feedback signals is now described. The signal outputs of detectors p1 and p2 are respectively q1 and q2 and these pass into differential amplifier r1. The output of differential amplifier V1 passes to linear actuator t1, that moves mirror e2. A solid frame is not shown on which linear actuators t1, t2 and t3 are mounted as well as components e1, e3, e4, i, j, m1, n1, p1, m2, n2, p2, and h. Differential actuator provides motion parallel to normal of mirror e2. Detectors m1 and m2 produce respective signals U1 and U2 that pass to differential amplifier r2 and thence becomes signal S2 that drives linear actuator t2 at mirror e2. Detectors n1 and n2 produce respective signals v1 and v2 that pass to differential amplifier r3 and thence as signal s3 to linear activator t3 on mirror e2. Once mirrors e2 and e3 and beam splitters e1 and e4 are aligned, the stabilizing feedback loops just described will maintain alignment.

SOFTWARE DESCRIPTIONS

Figure 8:
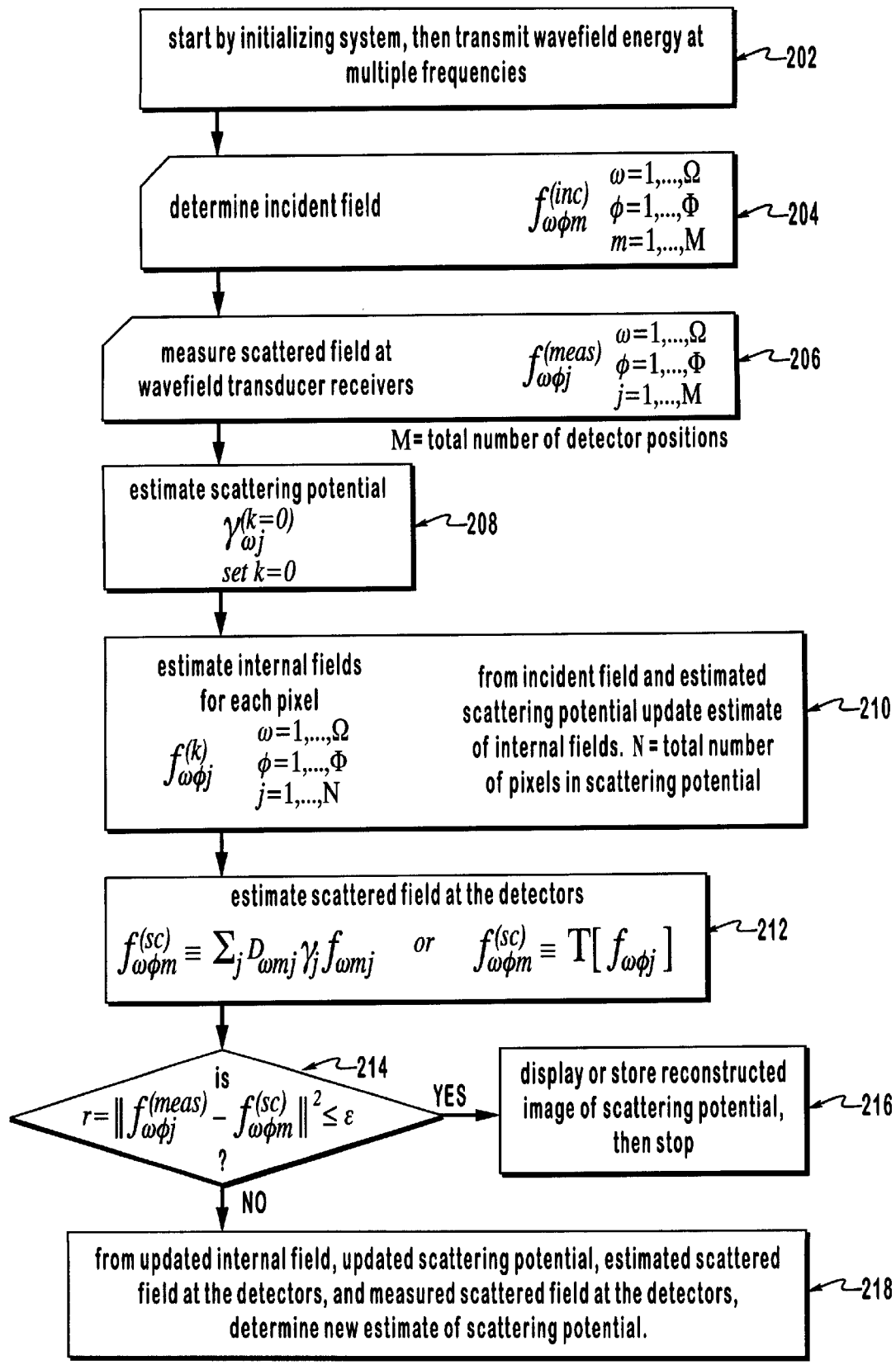
FIG. 8 illustrates a generic imaging algorithm, according to the present invention.

Having described some examples in the previous section which illustrate mathematical and physical models which may be used to model scattered wavefield energy and to process data so as to reconstruct an image of material parameters using inverse scattering theory, reference is next made to FIG. 8.

Figure 1A:
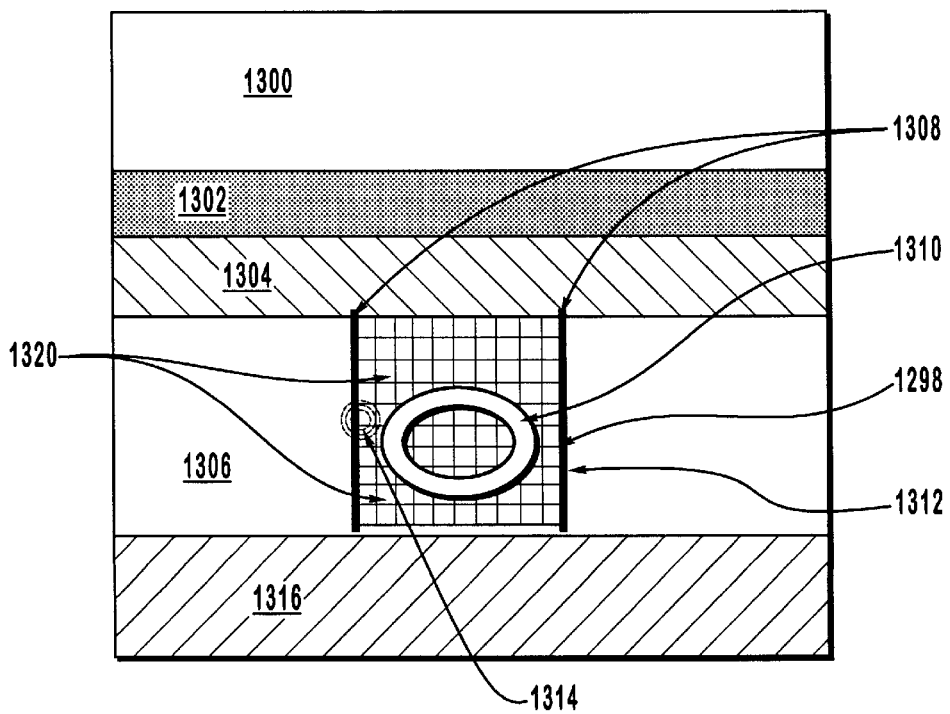
FIG. 1A is a two dimensional view of a cross-borehole geometry imaging method, according to the present invention, using inverse scattering.

This figure schematically illustrates a flow diagram for programming the CPU No. 118 or combination of CPU 118 and array processor 120 or parallel processor 146 in order to enable CPU 118 or said combination to control the electronic system of FIGS. 4 and 5 and the apparatus of FIGS. 1, 2, and 3 in accordance with one presently preferred method of the invention. It should also be understood that special purpose computational hardware should be constructed to incorporate the flow diagrams including FIGS. 8–26 and also explicitly encoded in Appendices A-J. These flow diagrams of FIGS. 8–26 are merely illustrative of one presently preferred method for programming CPU 118 using the scalar Helmholtz wave equation or vector wave equation or similar wave equation for modeling scattered wavefield energy as described in Example 1 in the Summary of the Invention section. Any suitable computer language which is compatible with the type of CPU 118 that is used in the electronic system can be used to implement the program illustrated in the diagrams and flowcharts. As shown in FIG. 8, the CPU 118 is programmed so that it will first cause the transmitter multiplexer 132 to sequence in turn each transducer or antenna so that each transmitter or antenna will in turn propagate a signal at a selected frequency. In the case of FIG. 4A, for each transmitter position sequential multiple frequencies may be transmitted by changing the frequency of the oscillator 128. On the other hand, in the system of FIG. 5A multiple frequency signals are transmitted by selecting and generating a type of waveform which inherently includes multiple frequencies. As schematically illustrated in Step 202, for each transmitter from which a signal is sent CPU 118 next causes a receiver multiplexer 134 to sequence each receiver array 108–115 so as to detect the scattered wavefield energy at each position around the ring of transducers 70. The source receiver geometry represented by Step 202 is not restricted to the ring of transducers 70. One alternative source receiver geometry is depicted in FIG. 1A. This figure depicts inverse scattering in a cross-borehole geometry relevant to geophysical imaging. This FIG. 1A shows four layers representing sedimentation sandwiched between two half spaces which represent, respectively, the ocean and the basement sediment. The image space is depicted and an object to be imaged, 1310 is shown. The sources and receivers are located down two boreholes which exist on either side of the image space. The receiver arrays 1308 detect scattered wavefield energy for each frequency that is transmitted. As described previously, the electronic system then amplifies the detected signals and processes the signals in order to develop the electronic analog of the real and imaginary components of each signal and in order to digitize each detected signal.

Once the scattered wavefield energy has been detected, processed, and digitized, CPU 118 next determines the incident field $f_{\omega\phi}^{inc}$, as indicated at step 204. The incident field is determined from the wavefield energy [i.e., frequency and amplitude components of the transmitted waveform] and transducer geometry from which the incident field is transmitted. The process of determining this incident field may involve direct measurement of the incident field or calculation of the incident field using the appropriate Green's function whether it be Biot, elastic, electromagnetic, scalar, vector, free space or some combination or permutation of these. The incident field is determined at each pixel in the imaged space for each source position $\phi=1,\ldots,\Phi$ and for each frequency $\omega$, which varies from 1 to $\Omega$. In step 206, the scattered wavefield is measured, recorded and stored at the wavefield transducer receivers for each $\omega$, varying from 1 to $\Omega$ each source position 1–$\Phi$, and each pixel element at each wavefield transducer receiver position. As described in step 208, the initial estimate for the scattering potential is input directly into CPU 118 or estimated within CPU 118 from data input to it from some outside source. The initial estimate for the scattering potential can be set at either 0 or at an average value which is derived from the average material parameters estimated a priori for the object. When applicable, a lower resolution image of $\gamma$, such as produced by a more approximate method such as the time of flight method described in U.S. Pat. No. 4,105,018 (Johnson) may also be used to advantage (in the acoustic case) to help minimize the number of iterations. Similar approximations for other forms of wavefield energy may be used to advantage to help minimize the number of iterations.

Figure 7:
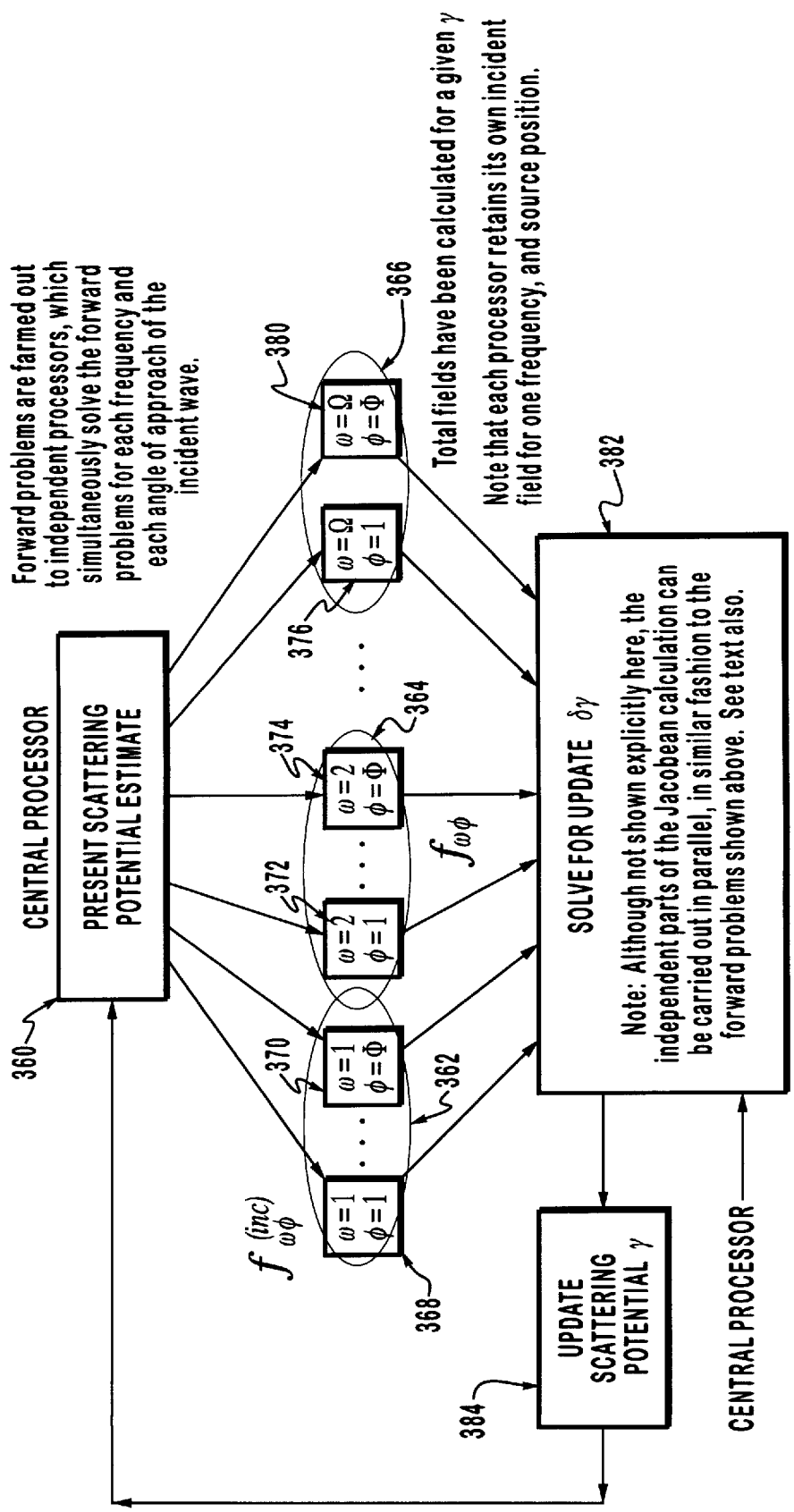
FIG. 7 shows parallelization of the forward problem according to the present invention.

CPU 118 next determines in step 210 an estimate of the internal fields for each pixel in the image space and for each frequency $\omega$, and each source position $\Omega$. This estimate is derived from the incident field and the estimated scattering potential. This step corresponds to step 222 in FIG. 9A as well as to step 210 in FIG. 8. FIG. 7 is also relevant here. As is indicated in step 360 of FIG. 7, the present scattering potential estimate is used simultaneously in several independent processors so that the forward problems are farmed out to these independent processors which simultaneously solve the forward problems for each frequency and for each source position of the incident wavefield. These independent processors are labeled 368–380 in FIG. 7. It may be that there are not enough parallel processors available to farm out each incident field for each frequency and source position. However, effort should be made to delegate and solve as many forward problems independently and in parallel as possible. Ovals 362, 364 and 366 indicate that the forward problems for all possible source positions and a given fixed frequency can be calculated in one processor and simultaneously a second frequency forward problem can be calculated simultaneously in a second parallel independent processor. There is great flexibility in this approach and this example is not meant to be restrictive; for example, it is not difficult to see that the multiple frequency and source position parts of the Jacobian calculation can also be done in parallel in the same manner.

The total fields are then stored in central processor 382 of FIG. 7. For a given and fixed frequency $\omega$, and fixed source position $\phi$, the forward problem consists of using equation 1 or 17 of the Summary of Invention section to determine the total field $f_{\omega\phi}$ given the scattering potential $\gamma$ and the incident field $f^{inc}_{\omega\phi}$ and the appropriate Green's function. This Green's function could be the scalar Green's function which is essentially the Hankel function of the second kind of zero order, or it could be the elastic Green's functions which is derived from the scalar Helmholtz Green's function, or it could be the Biot Green's function, or it could be the electromagnetic vector or scalar Green's function as well as a layered Green's function derived from one of the preceding green's function in the manner described in the Summary of the Invention section. The process whereby this is done is elucidated in FIGS. 11A01, 11A02.

Figure 1B:
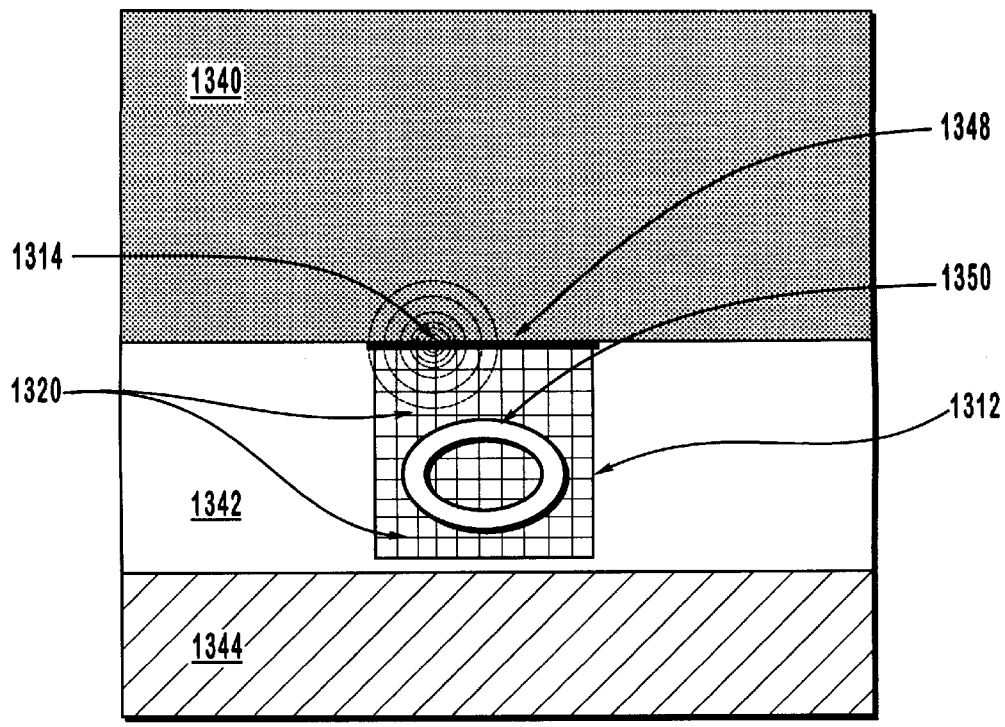
FIG. 1B is a two dimensional view of a reflection geometry imaging method, according to the present invention, using inverse scattering with both a wave energy source means and wave energy detection means juxtaposed to the image field.

Before applying this algorithm, it is required to discretize equation 1 or 17 of the Summary of Invention section so that it may be input into the CPU. This process is described in detail in the Summary of the Invention. The subroutine that solves the forward problem is given explicitly in Appendix B for the two-dimensional case and in Appendix F for the three-dimensional forward problem solution. Our algorithm uses the Whittaker sinc function which is defined on page 18, equation E of the Summary of the Invention. We use the sinc function because of its optimal approximating qualities. However, the infinite support of the sinc function precludes its use in certain situations. More specifically in the presence of layering, one-dimensional "hat" functions are required. This is outlined in detail after eqn (41) in the Summary of the Invention. The number of frequencies that are used in the inverse scattering problem is a function of the source receiver geometry, among other things. FIG. 1B shows the reflection-only source-receiver geometry prevalent in geophysics. In this scenario it is imperative to use multiple frequencies which distinguishes this case from FIG. 1A where, because the source receiver geometry allows transmission mode imaging only a small number of frequencies may be used. An example of such code using transmission mode imaging is given in Appendix H.

Figure 10:
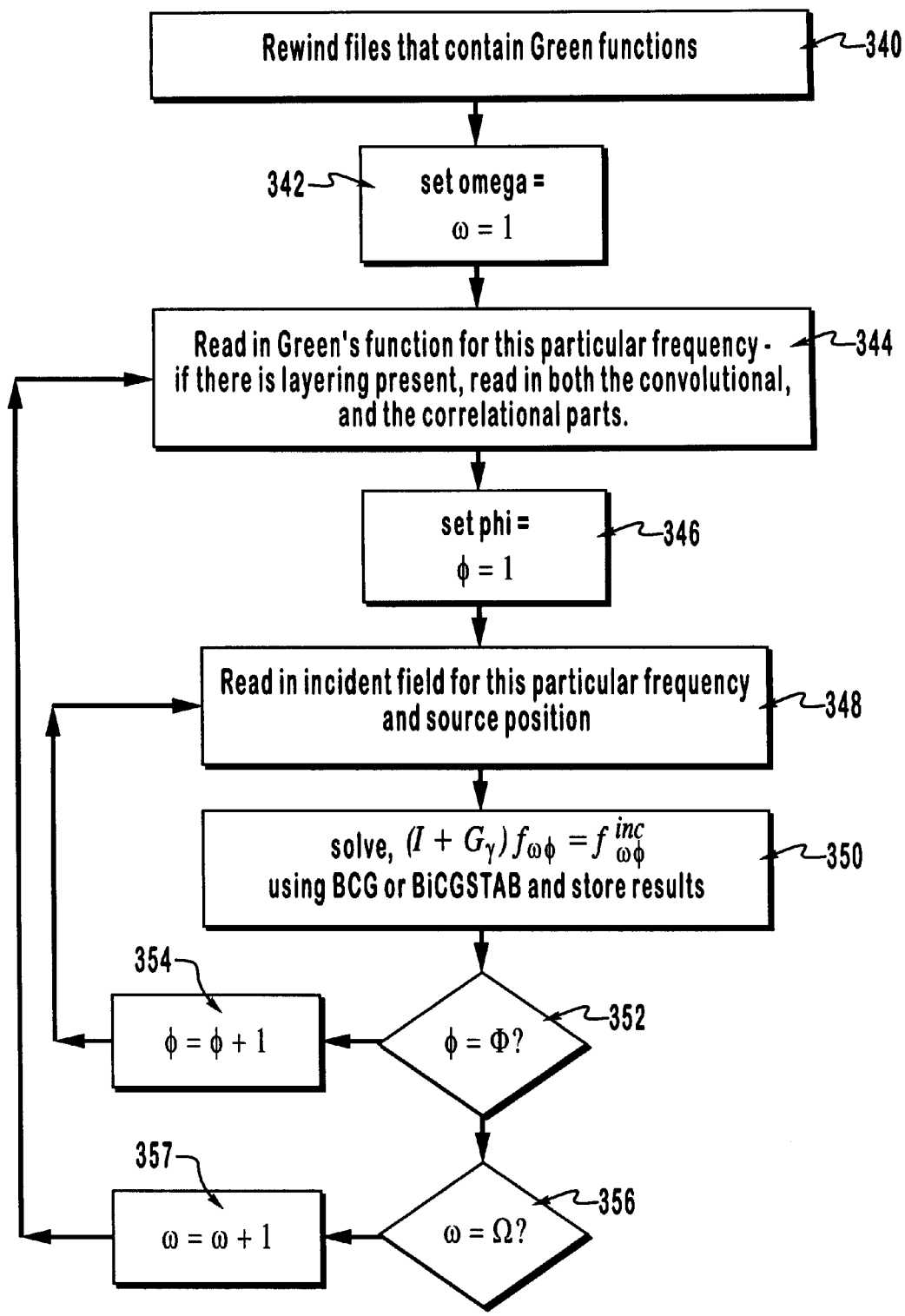
FIG. 10 shows the generic solution to the forward problem according to the present invention.
Figures 1, 11A:
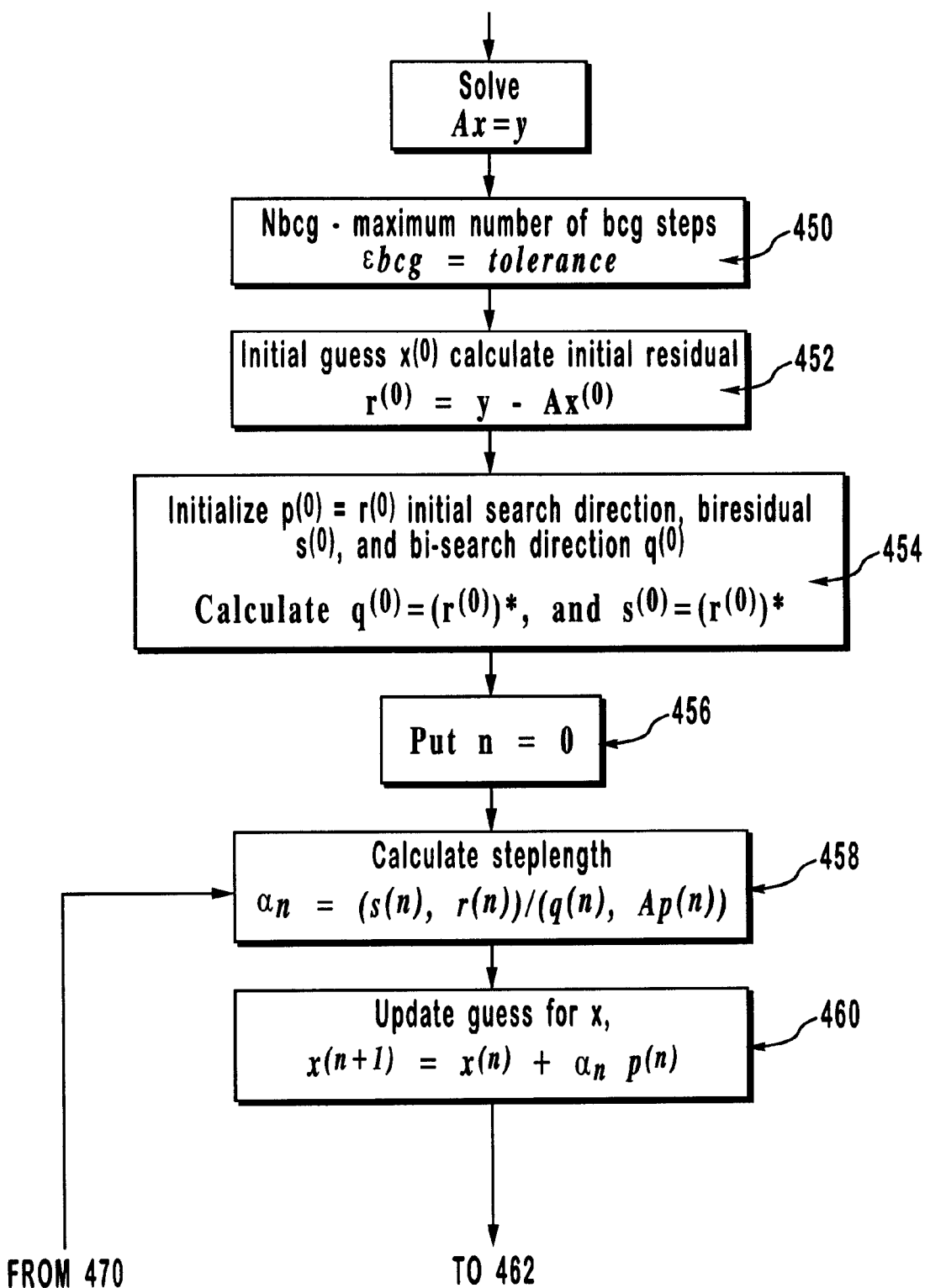
Figures 2, 11A:
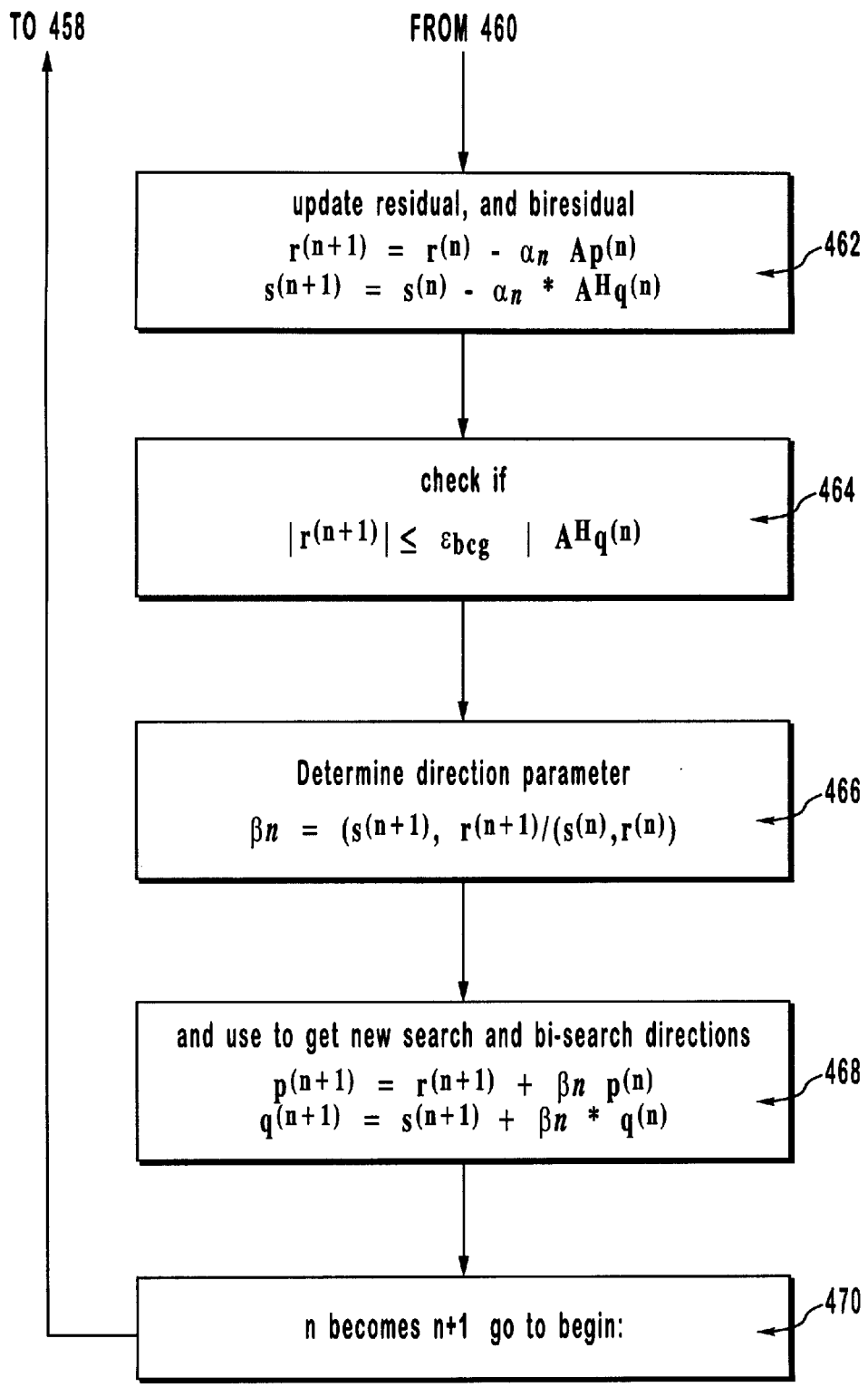

All forward problems for all possible frequencies, and all possible source positions are solved with one call of the subroutine in Appendix B for the two-dimensional case, and Appendix F for the three-dimensional case, whichever is relevant. FIG. 10 gives in detail the procedure for solving for the internal fields at all possible source positions and all possible frequencies. From step 222 in FIG. 9A we enter step 340 on FIG. 10. In step 340 of FIG. 10, all of the files that contain all of the Green's functions for all possible frequencies and the files that contain the incident fields for all possible frequencies and all possible source positions are rewound. In step 342 of FIG. 10, $\omega$ is set equal to 1, i.e., we indicate that we are about to calculate the forward problem for the first frequency. In step 344 of FIG. 10, the Green's function for this particular frequency is read into memory. In step 346 of FIG. 10, the source position index $\phi$, is set equal to 1 indicating that we are solving the forward problem for the first source position. In step 348, the incident field for this particular $\phi$, i.e., source position, and this particular $\omega$, i.e., frequency, is read into memory. In step 350, the forward problem for this particular frequency and this particular source position is solved using either biconjugate gradients or BiSTAB. This process is detailed in FIG. 11A01/02 for the biconjugate gradient or BCG algorithm and FIGS. 11B01/11B02 for the BiSTAB or biconjugate gradient stabilized algorithm. In FIG. 11A01, in step 450 which follows step 350 in FIG. 10, the predetermined maximum number of biconjugate steps and tolerance are read into memory, and the forward problem, which in discrete form reads $(I-G_\omega)f=f^{inc}$, is solved. For purposes of generality, we consider the BCG or biconjugate gradient algorithm applied to the system $Ax=y$. A is a matrix which is square, x and y is a vector of suitable dimension. Step 452 consists of reading in an initial guess $X^0$ and calculating an initial residual which is calculated by applying A to the initial guess $X^0$ and subtracting from the right-hand side Y. In step 454, the initial search direction $P^0$, bi-search direction Q, bi-residual S are calculated and stored. In step 456, we put N equal to 0. In step 458, we calculate the step length $\alpha_n$ by taking the inner product of the two vectors s and r, the bi-residual and residual respectively, and dividing by a quantity which is the inner product of two vectors. These two vectors are 1) q, the bi-search direction, and 2) the result of the application of the operator A to the present search direction P. In step 460 of FIG. 11A01, the guess for x is updated as per the equation that is shown there. In Step 462, the residual R is updated as per the formula given, and the bi-residual S is updated as per the formula given. (H indicates Hermitian conjugate.) In particular, the bi-residual is given by the previous bi-residual $S^n$ minus a quantity which is given as $\alpha^*_n$, which is the complex conjugate of $\alpha_n$, multiplied by a vector, which is the result of the operation of the Hermitian conjugate of the operator A, applied to the vector q, the bi-search direction. This is carried out by a call to FIG. 13, which we discuss below. In step 464, check to see if the stop condition has been satisfied, i.e., is the present updated residual less than or equal to $\epsilon$ (which is given a priori) multiplied by the initial residual in absolute value. Step 466 consists of the determination of $\beta$, the direction parameter, which is given as the ratio of two numbers. The first number in this ratio is the inner product of the new updated bi-residual with the updated residual and the denominator is the inner product of the previous residual with the previous bi-residual, which has already been calculated in box 458. In step 468, use the calculated $\beta$ to update and get a new bi-search direction, and a new search direction given by the formulas shown. In step 470, N is incremented by 1 and control is taken back to step 458. In step 458, a new step length is calculated, etc. This loop is repeated until the condition in step 464 is satisfied, at which time control is returned to step 350 in FIG. 10. The forward problem for this particular frequency and this particular source position has now been solved and the result, i.e. the internal field, is now stored.

Figures 1, 11B:
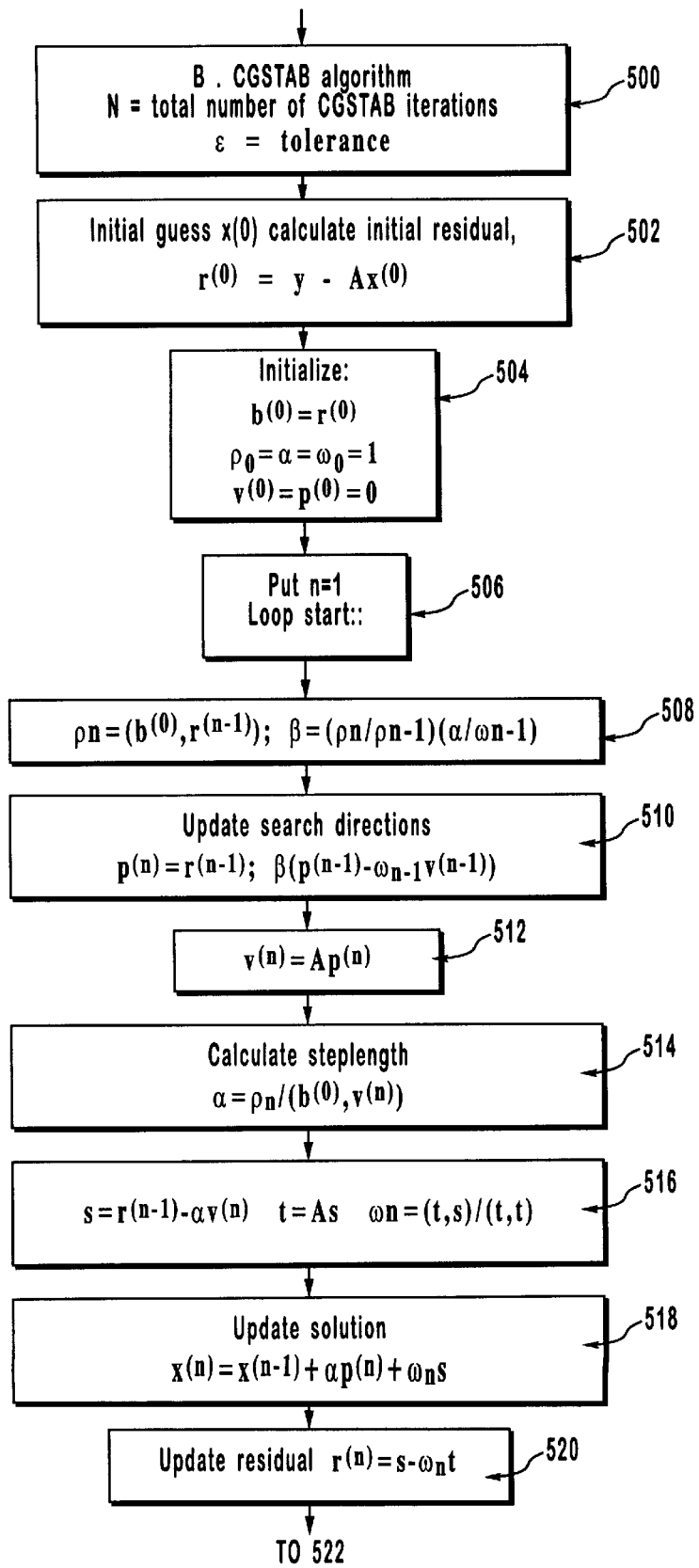
Figures 2, 11B:
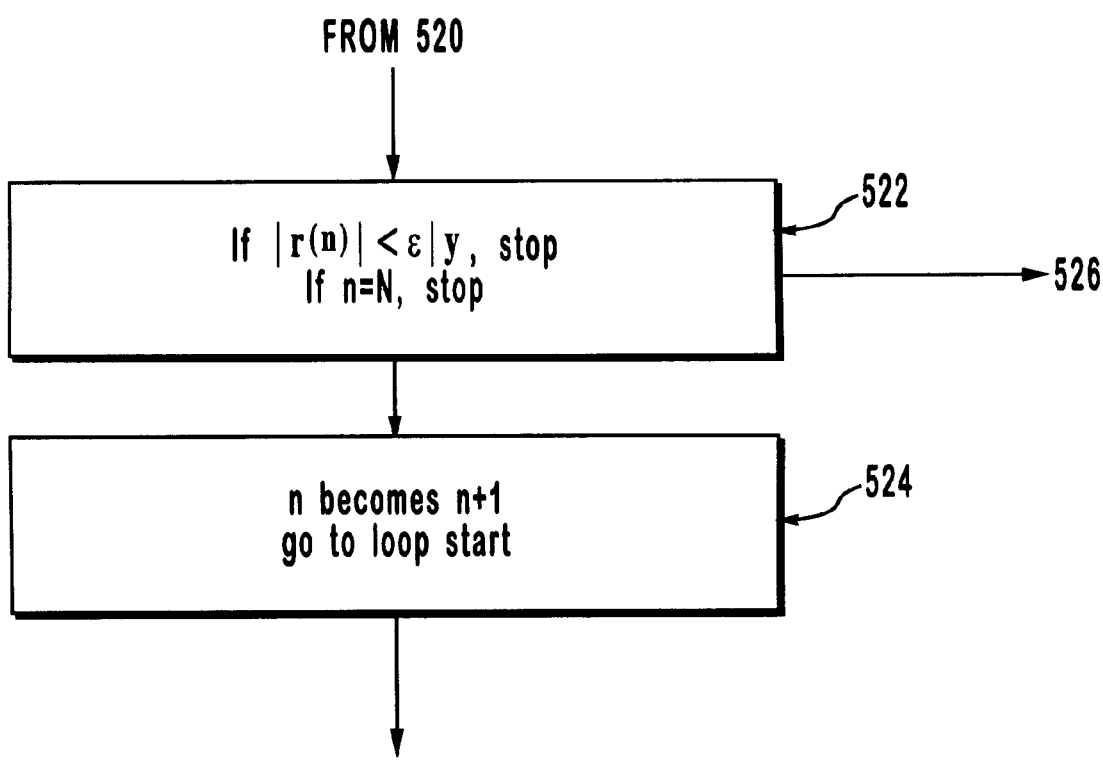
Figure 11C:
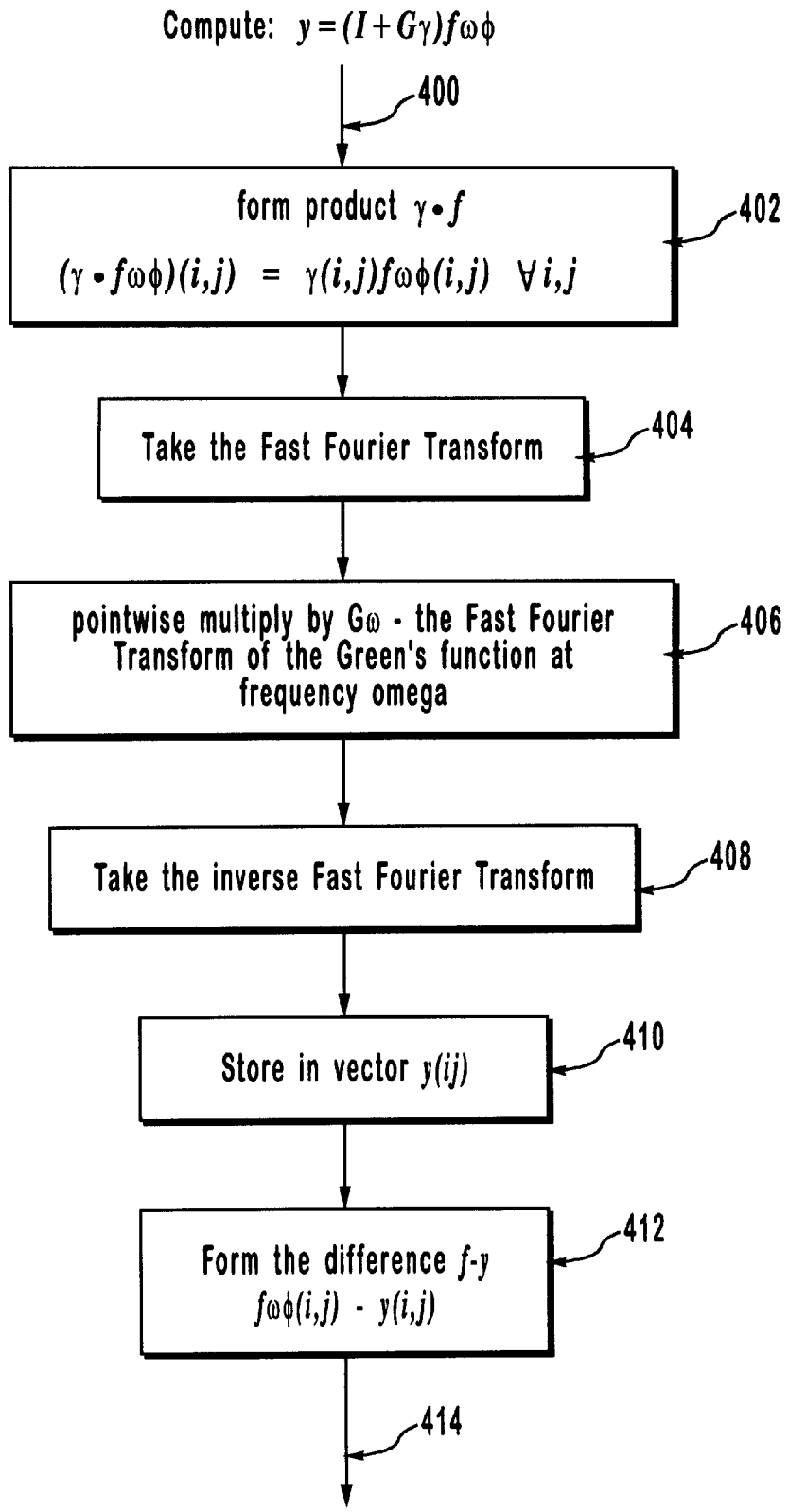
FIG. 11C illustrates the application of the Lippmann-Schwinger Operator to the internal field estimate according to the present invention.
Figure 13:
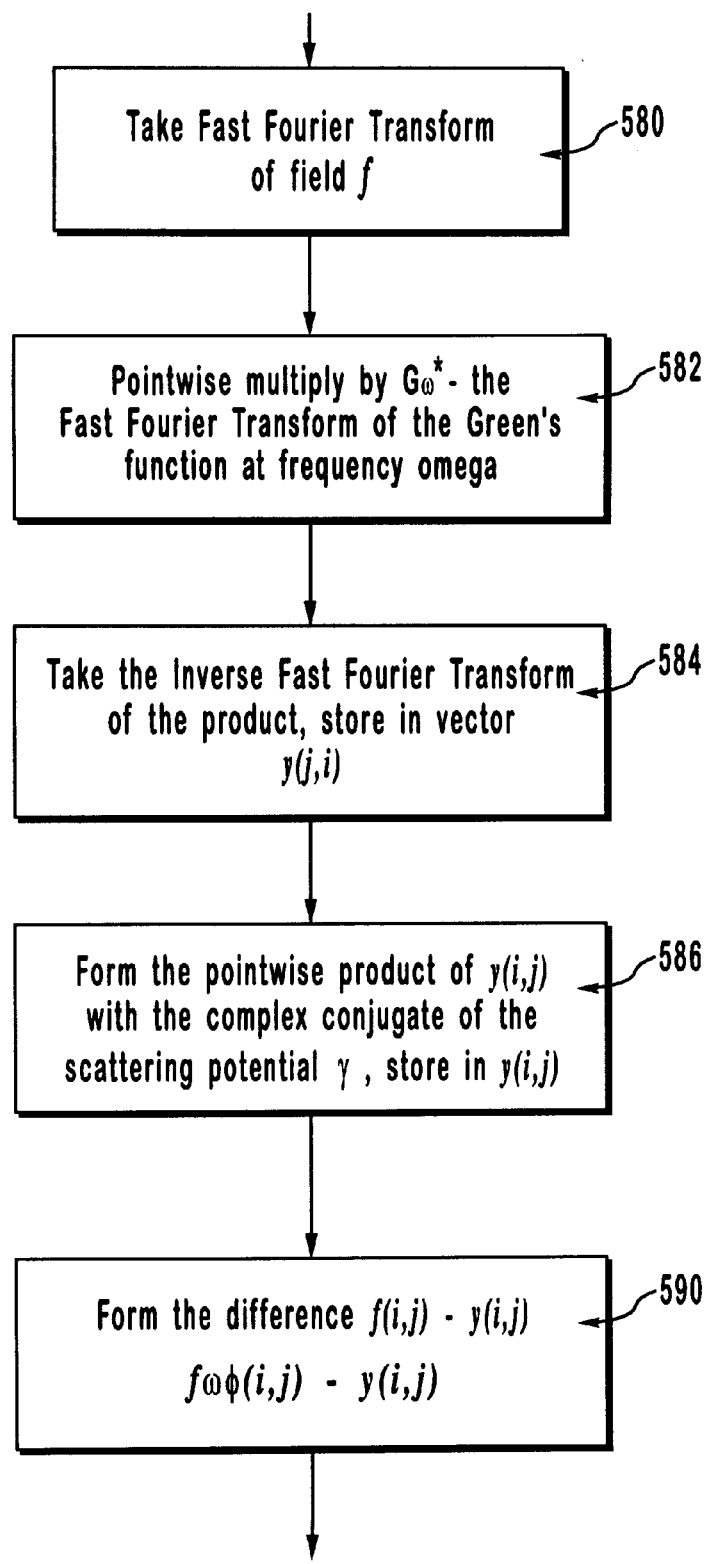
FIG. 13 illustrates the application of the Hermitian conjugate of the Lippmann-Schwinger operator.

In step 352, back in FIG. 10, it is determined if $\phi$ is equal to $\Phi$, i.e. have we computed all the forward problems for this particular frequency for all possible source positions. If not, then $\phi$ is incremented by 1 in step 354 and control is returned to step 348 of FIG. 10. If so, we have calculated the forward problem for all possible source positions $\phi$ and control is transferred to step 356 where it is determined if $\omega$ is equal to $\Omega$, i.e. have we calculated the forward problem for all possible frequencies $\omega$?" If not, $\omega$ is incremented by 1 in box 357 and control is returned to step 344. If so, we have completed the computation of the internal fields for all possible source positions and all possible frequencies and have stored the results, i.e. we have finished the subroutine in Appendix B and Appendix F for the two-dimensional or three-dimensional problem, respectively. Control is now transferred to the main program which is in Appendix A for the two-dimensional case, and in Appendix E for the three-dimensional case. This corresponds to step 224 in FIG. 9A. This also corresponds to step 212 of FIG. 8. FIGS. 9A, 9B, 9C, 9D together comprise an expanded version of the inverse scattering algorithm in its entirety, which is given in compressed form by FIG. 8. Before proceeding further to describe in detail step 212 of FIG. 8, i.e. also FIG. 226 of FIG. 9A, we mention that the BCG algorithm just described may be replaced by the BiSTAB (biconjugate gradient stabilized algorithm) of FIGS. 11B01/11B02. Furthermore, in the calculation of both the BiSTAB algorithm or the biconjugate gradient algorithm, the implementation of the operation of the operator A acting on the vector x is carried out in a very specific manner which is described in FIG. 11C. Furthermore, in FIG. 13, the hermitian conjugate of the operator A, denoted $A^H$, is applied to vectors in its domain. Specifically, in step 400 of FIG. 11C, we come in from any step in FIG. 11B01/11B02 or 11A01/11A02, respectively, the conjugate gradient stabilized algorithm or the bi-conjugate gradient algorithm which requires the calculation of the operation of the operator A acting on the vector "x". In step 402, the pointwise product of the scattering potential γ and the present estimate of the internal field at frequency ω and source position φ is formed and stored. Step 404, the Fast Fourier Transform (FFT) of this pointwise product is taken. In step 406, the result of the Fast Fourier Transform (FFT) taken in step 404 is pointwise multiplied by $G_ω$ which is the Fast Fourier Transform (FFT) of the Green's function at frequency ω, which has been stored and retrieved. In step 408, the inverse Fast Fourier Transform (FFT) is taken the pointwise multiplication that was formed in the previous step. In step 410 this result is stored in vector y. In step 412 the difference, taken pointwise, of the $f_{ωφ}$, the present value for the internal field at frequency ω, and source position φ, and the constructed vector y is taken. Step 414 returns control to either the BCG or the BiSTAB algorithm, whichever has been called by step 350 of 10. The application of the operator which is described in FIG. 11C is carried out multiple times for a given call of the biconjugate gradient or the BiSTAB algorithm, it is imperative, therefore, that this step be acomputed extremely quickly. This explains the presence of the fast Fourier transforms to compute the convolutions that are required. This operator, (I–Gγ) symbolically written, we refer to as the Lippmann-Schwinger operator. FIG. 13 calculates the adjoint or hermitian conjugate of the given Lippman-Schwinger operator and applies this to a given vector. Step 580 of FIG. 13 takes control from the appropriate step in the biconjugate gradient algorithm. It is important to note that *the BiSTAB algorithm does not require the computation of the adjoint of the Lippmann-Schwinger operator*. Therefore, FIG. 13 is relevant only to FIGS. 11A01/11A02, i.e. the biconjugate gradient algorithm. In step 580 of FIG. 13 the Fast Fourier Transform (FFT) of the field f to which the adjoint of the Lippmann-Schwinger operator is being applied, is taken. In step 582 of FIG. 13, the Fast Fourier Transform (FFT) computed above is pointwise multiplied by $G^*_ω$, the complex conjugate of the Fast Fourier Transform (FFT) of the Green's function at frequency ω. In step 584, the inverse Fast Fourier Transform (FFT) of this pointwise product is taken and stored in vector y. In step 586, the pointwise product of the complex conjugate of γ, the present estimate of the scattering potential is taken with the vector y. The result is stored in vector y. In step 590, the difference is formed between the original field to which the adjoint of the Lippmann-Schwinger operator is being applied, and the vector y just calculated. Now (I–Gγ)

$^H f_{ωφ}$ has been calculated and control is now returned to box 462 of FIG. 11A01/11A02, the biconjugate gradient algorithm, where use is made of the newly created vector, $A^H q$. Next the stop condition is checked at step 464.

Figure 9A:
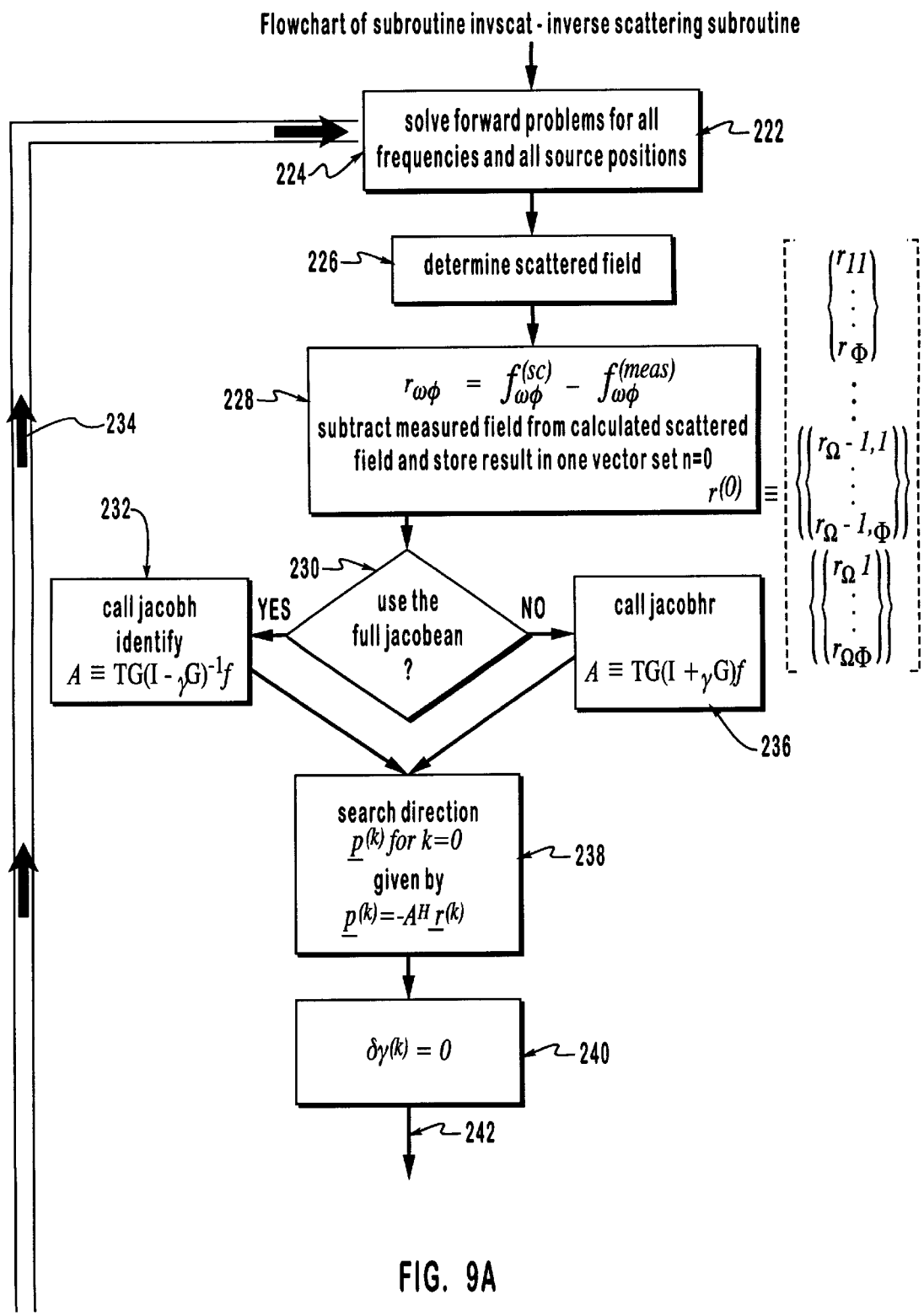
FIGS. 9A through 9D detail an expanded imaging algorithm with respect to that shown in FIG. 8 which schematically illustrates a flow diagram for programming a computer or combination of computer and array processor or parallel processor to enable the computer or combination mentioned to control the electronic system of FIGS. 4 or 5 and the apparatus of FIGS. 1-3 so as to rapidly develop a reconstruction of the image of an object from scattered acoustic energy using inventive scattering techniques, in accordance with one presently preferred method of the invention.
Figure 9B:
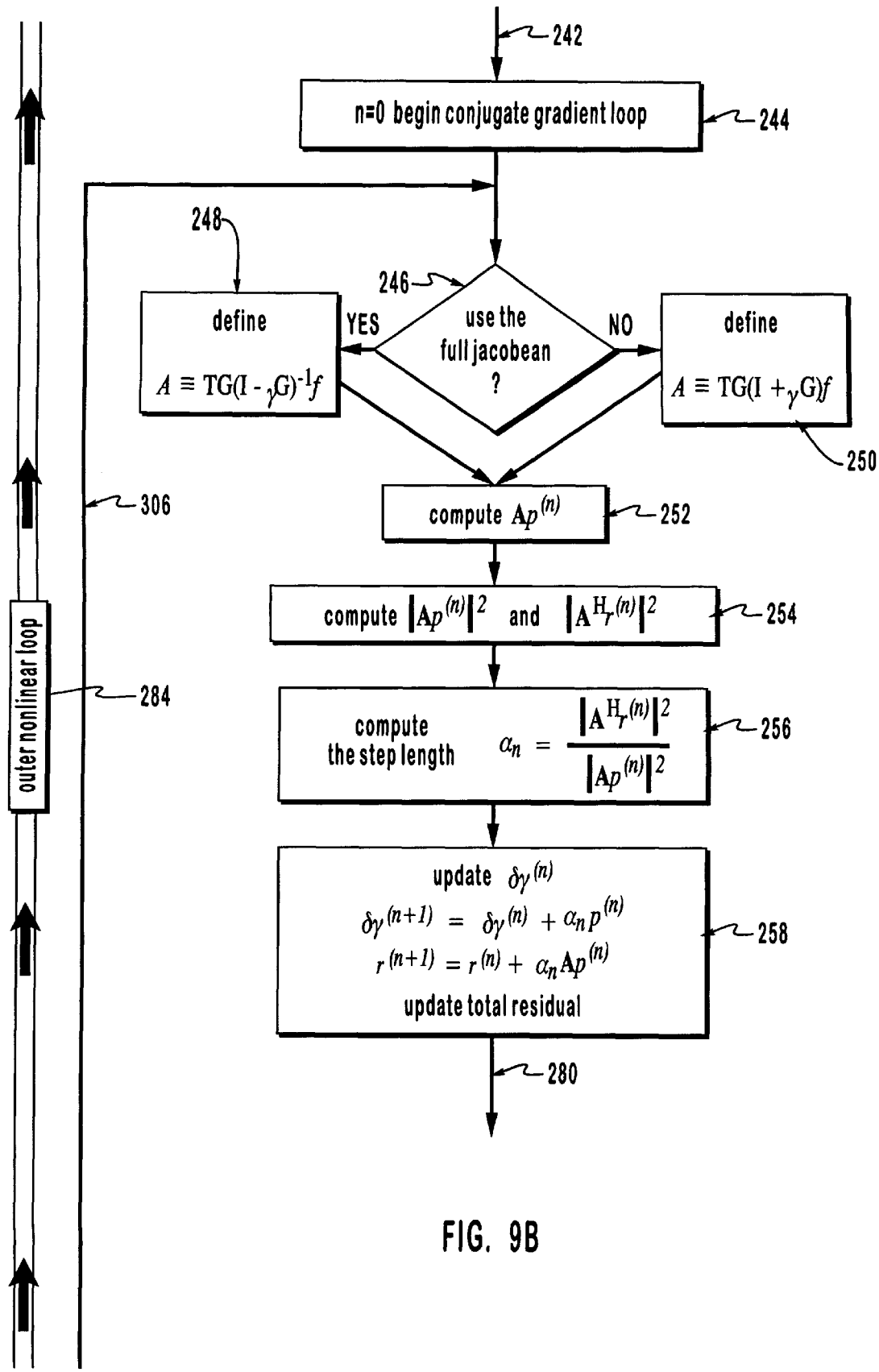
Figure 9C:
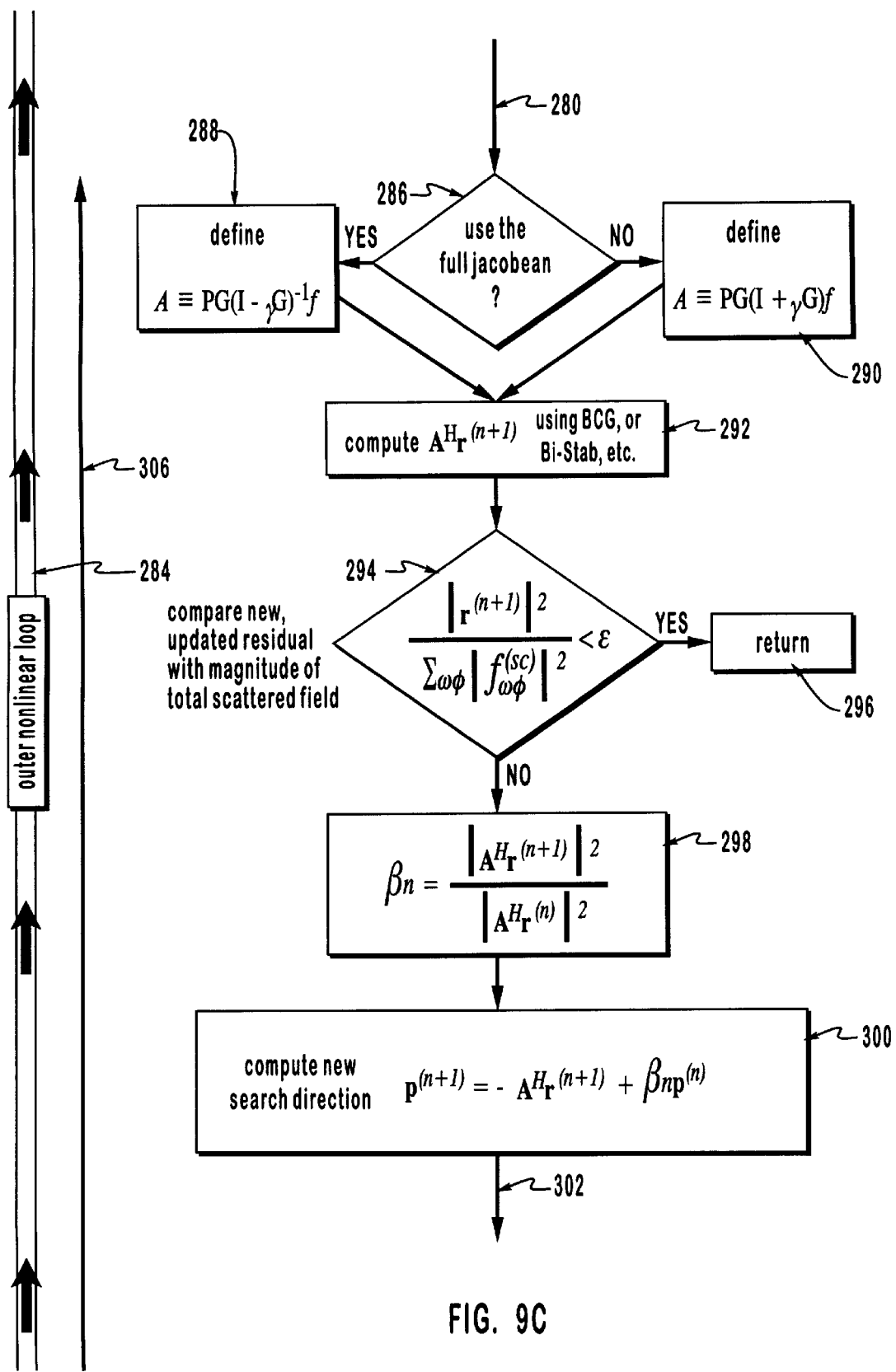
Figure 9D:
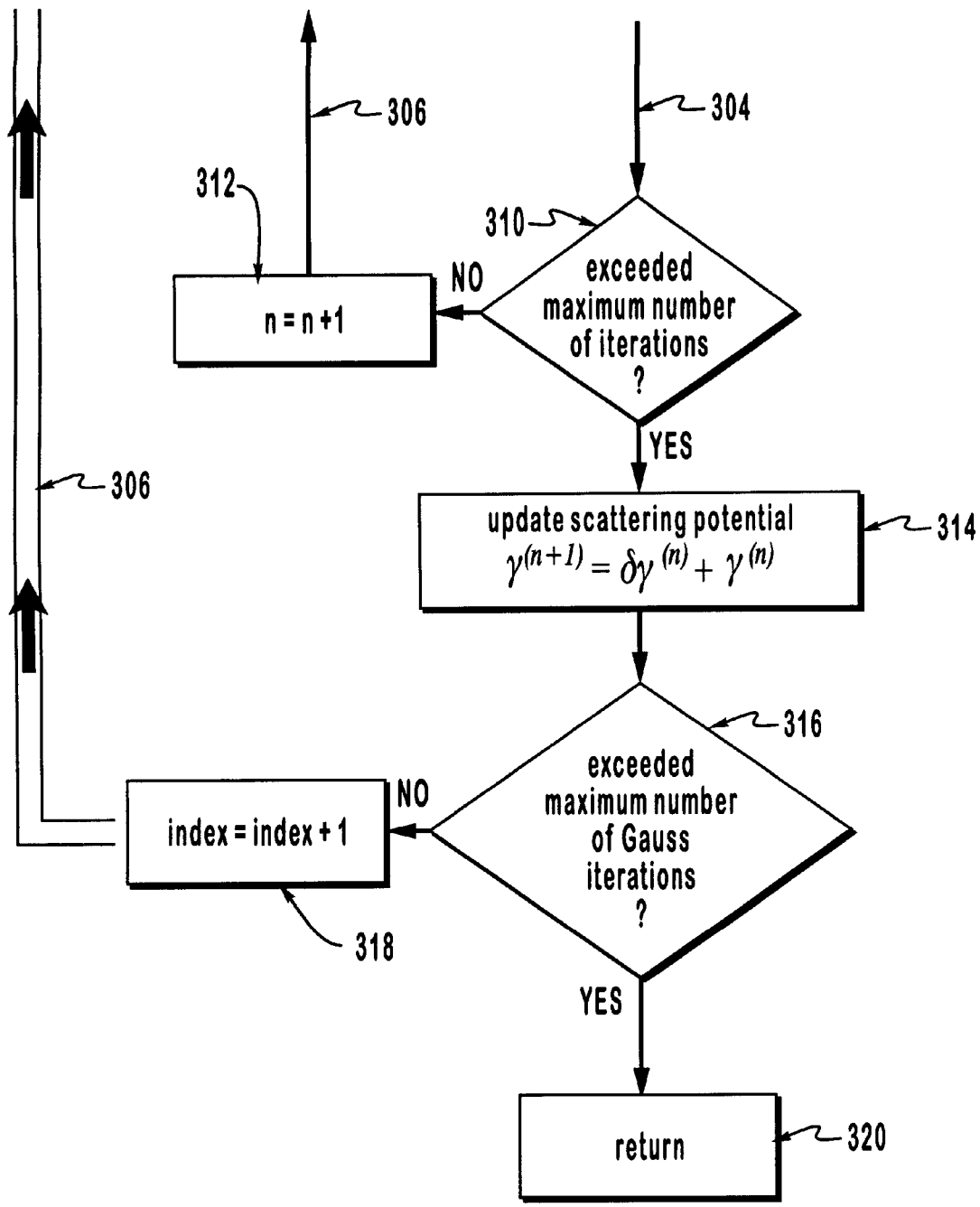

We now return to step 224 of FIG. 9A, i.e. step 212 of FIG. 8 where we determine the scattered field at the detector locations for all possible source positions, i.e. incident fields and also all possible frequencies ω. This process is carried out in FIG. 26, to which we now turn.

Figure 21:
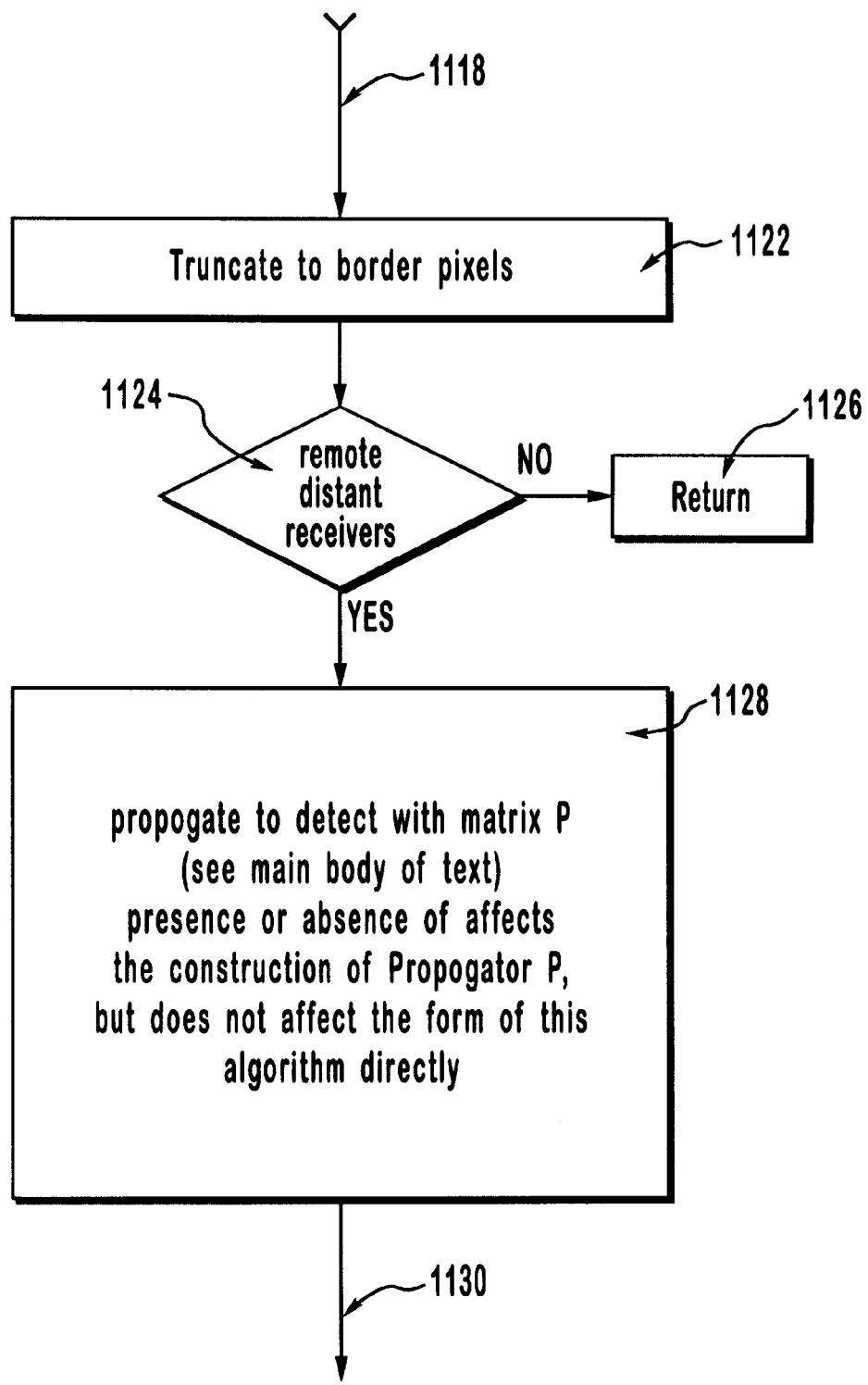
FIG. 21 illustrates the propagation or transportation of fields from image space to detector position.
Figure 26:
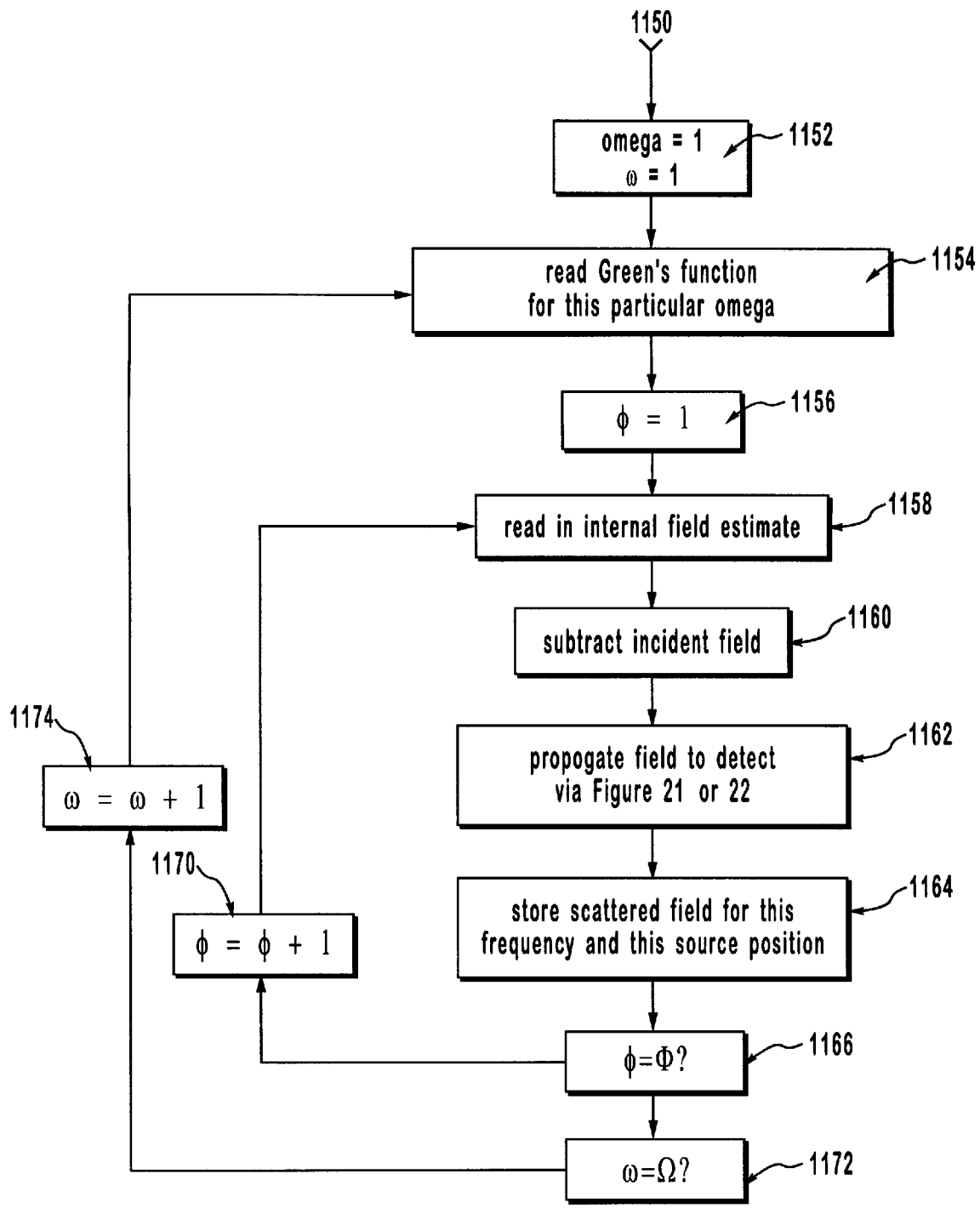
FIG. 26 illustrates the scattering subroutine, according to the present invention.
Figure 27:
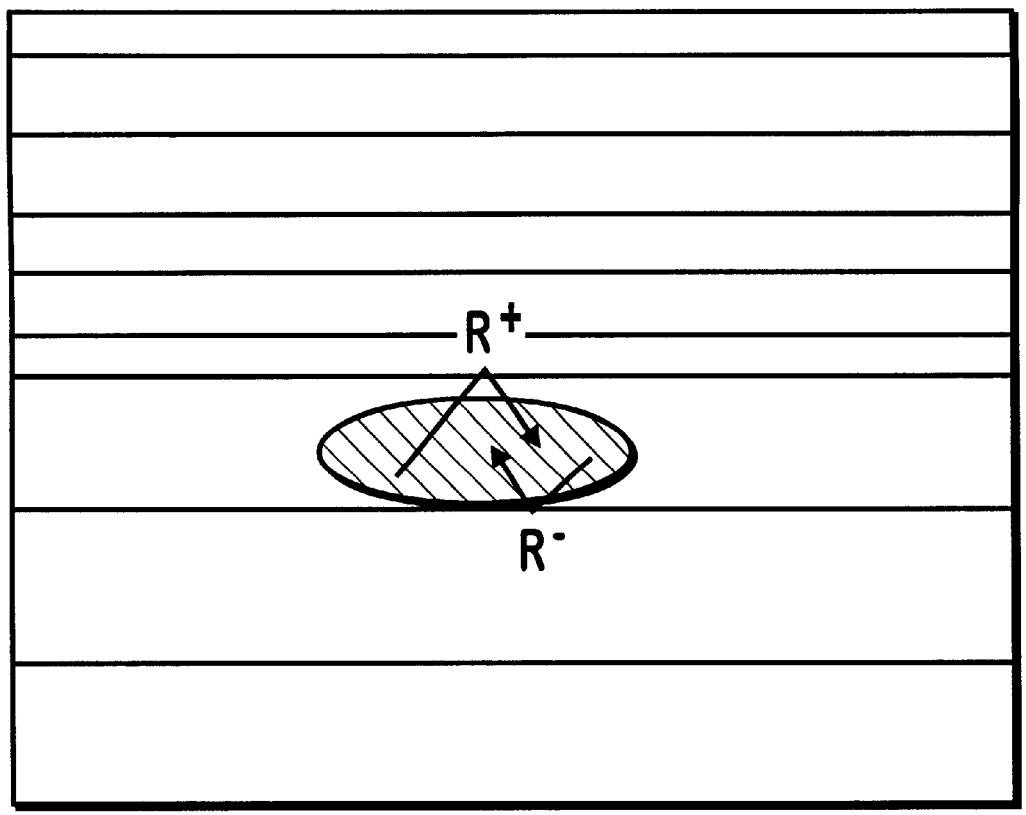
FIG. 27 is schematic showing the Reflection coefficients relevant to the layered medium Green's function approach.

Step 1150 of FIG. 26 transfers control to step 1152 of FIG. 26 where ω is set equal to 1. Control is then transferred to step 1154 where the Green's function for this particular ω is read into memory. Control is then transferred to step 1156 where φ is set equal to 1. Control is then transferred to step 1158 where the internal estimate for this source and this frequency is read into memory. Control is then transferred to step 1160 where the incident field is subtracted from estimated total internal field. In step 1162 the truncation or propagation operator shown FIG. 21 is performed. When the truncation or propagation has been performed, control is transferred back to FIG. 26 and in step 1164 the calculated scattered field is stored. In step 1166 it is determined if φ is equal to Φ, if it is not, then φ is incremented by one, in step 1170, and control is returned to step 1158 of FIG. 26. If φ is equal to Φ, then control is transferred to step 1172 where it is determined if ω is equal to Ω. If it is not, ω is incremented by one in step 1174, and control is returned to step 1154 of FIG. 26. If ω is equal to Ω, then control is returned to step 226 of FIG. 9A, the inverse scattering subroutine.

Now consider FIG. 21, which was called by FIG. 26 above.

Figure 1C:
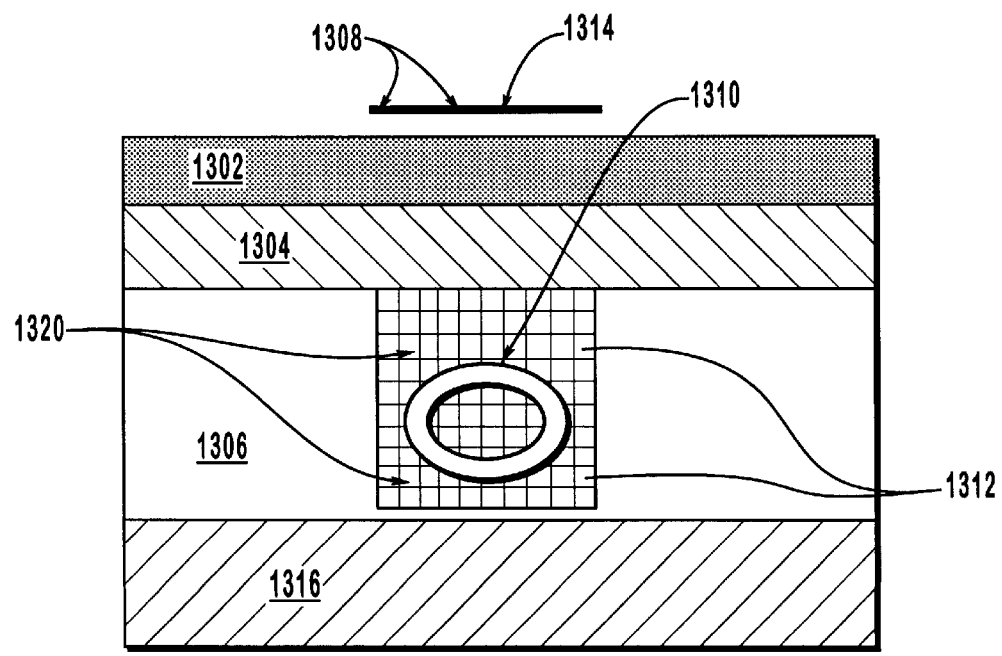
FIG. 1C is a two dimensional view of a reflection geometry imaging method, according to the present invention, using inverse scattering with a remote wave energy source means and remote wave energy detection means.

Step 1118 of FIG. 21 transfers control to step 1122 where the input is truncated to the border pixels. Control is passed to step 1124 which determines if the receivers are distant from the image space as in FIG. 1C or whether the receivers are juxtaposed to the image space as in FIGS. 1A or 1B. If the detectors are in fact juxtaposed to the image space, then control is transferred to step 1126 and from there to the calling subroutine. If the detectors are not juxtaposed to the image space, the fields are propagated to the detector positions. The details of this propagation are given in the "EXTENSION OF THE METHOD TO REMOTE RECEIVERS WITH ARBITRARY CHARACTERISTICS" section of this patent. Actually, there are several methods which could be used to accomplish this. For example, an application of Green's theorem is one possibility. The beauty and utility of the method shown in the "Extension of the method to remote receivers with arbitrary characteristics" section however, is that the normal derivatives of the Green's function, or the fields themselves, do not need to be known or estimated.

The input to FIG. 21 is a vector of length $N_x N_y$. FIG. 21 represents the subroutine that is called by the Jacobian calculation or following immediately after the calculation of the internal fields. The input in the first case of the Jacobian calculation consists of box 720 of FIG. 20B. The input in the second case is the scattered field calculated for a particular frequency ω and a particular source position φ. The purpose of FIG. 21 is to propagate the input (scattered field in the image space) to the detector positions. In step 1124 it is determined whether the receivers are distant. If the detector positions are located at some distance from the image space, the subroutine passes control from step 1124 to step 1128.

In step 1128, the matrix P, constructed earlier is used to propagate the field to remote detectors. In step 1130 of 21, control is returned to the program which called the subroutine. The matrix P will change when correlation is present; the fundamental form of the propagation algorithm remains unchanged, however.

These scattered fields are stored in vector $d^{\omega\phi}$. Control is then transferred to step 228 in FIG. 9A which subtracts the measured scattered field from the calculated scattered field and stores the result in one vector $r_{\omega\phi}$ which is the residual vector for frequency $\omega$ and source position $\phi$. This step is repeated until all possible frequencies and all possible source positions have been accounted for, whereupon the residual vectors $r_{\omega\phi}$ for all possible $\omega$'s and $\phi$'s are stored in one large residual vector shown in FIG. 9A as step 228. We now apply the Hermitian conjugate of the Jacobian to the residual vector r just calculated in order to establish the search direction $P^n$ where n=0, i.e. the initial search direction. The search direction is given explicitly by the negative of the action of the hermitian conjugate of the Jacobian acting upon the residual vector r, in step 238.

There are in effect at least two possibilities regarding the use of the Jacobian. First, the full Jacobian could be used or, secondly, an approximation to the Jacobian could be used. The determinator of which path to follow is the programmer, who bases his decision on the magnitude of the $\gamma$ which is to be solved in the full inverse scattering problem. If the $\gamma$ is large, the exact Jacobian must be used. On the other hand, if the $\gamma$ is reasonably small, although still larger than required for the Born or Rytov approximation, the approximation to the full exact Jacobian which is shown on FIG. 9A, step 236 may be used. The application of the exact or approximate Jacobian will be discussed later.

Now we step through FIGS. 9A to 9D to get an overall view of how the algorithm works.

Step 238 computes the initial search direction $P^{(0)}$ Step 240 of FIG. 9A zeros the initial guess for $\delta\gamma$, which is the Gauss-Newton (or Ribiere-Polak, or other) update to $\gamma$, the scattering potential. $\gamma$ can be initially set=0. A large portion of the rest of FIG. 9A, 9B, 9C, 9D is concerned with the calculation of $\delta\gamma$. This is used in FIG. 8 also, of course.

Step 212 of FIG. 8 has estimated the scattered field at the detector positions. Step 214 of FIG. 8 now determines if the residual (which is given by the magnitude squared of the difference between the measured scattered field and the calculated scattered field, for each possible source position and each possible frequency) is less than some predetermined $\epsilon$ tolerance. If the condition is satisfied then control is transferred to Step 216 where the reconstructed image of the scattering potential is either displayed or stored. If the condition is not met, then from the updated internal field calculated in Step 210 of FIG. 8 and also from the most recent estimate of the scattering potential and also from the estimated scattered field at the detectors calculated in Step 212 of FIG. 8 and also from the measured scattered field at the detectors, a new estimate of the scattering potential $\gamma$ is calculated in a manner to be made explicit below. This updated scattering potential estimate is derived in Step 218, and is now used in Step 210 of FIG. 8 to calculate a new update of the estimate of the internal fields, for each possible frequency $\omega$ and each possible source position $\phi$. Then in Step 212 of FIG. 8 a new estimated scattered field at the detectors is calculated by means of Green's theorem as shown in FIG. 26. This new estimate of the scattered field is then used in Step 214 as before, to estimate the magnitude of the residual vector between the measured scattered field and the calculated scattered field to determine if this quantity is less than $\epsilon$, the predetermined tolerance. As before if this tolerance is exceeded the loop just described, is repeated until such time as either the tolerance is satisfied or the maximum number of iterations of this loop has been exceeded. This maximum number is predetermined by the operator.

We have just concluded a general description of the overall inverse scattering algorithm leaving out many important details. We now look at each of the steps in more detail. First, we explain how the $\delta\gamma^{(0)}$ shown in Step 240 of FIG. 9A is related to Step 218 of FIG. 8. $\delta\gamma^{(0)}$ in FIG. 8 is the first estimate of $\delta\gamma$ in Step 314, which is the vector which is solved for, in Steps 244 through to Step 314 in FIGS. 9B through 9D. This $\delta\gamma$ is the correction term to the scattering potential which is applied to the present estimated scattering potential $\gamma^{(n)}$ in Step 314 of FIG. 9D in order to get the updated scattering potential $\gamma^{(n+1)}$. Once this new updated scattering potential has been determined, transfer to Step 316 of FIG. 9D where it is determined if the maximum number of Gauss-Newton corrections have been exceeded. Each pass through Steps 244 through 314, to calculate $\delta\gamma$ is one Gauss-Newton step. These Gauss-Newton steps are repeated until one of two things occurs. Either the maximum number of Gauss-Newton corrections is exceeded, or the tolerance condition of Step 294 is satisfied. It is important to reiterate that which was noted earlier, namely, that the description of the Gauss-Newton algorithm here, does not preclude the use of a suitable Ribiere-Polak, or Fletcher-Reeves non-linear algorithm, or other non-linear system solver. The changes in detail do not change the overall character of the minimization algorithm.

The appendix A contains the main program for imaging in two dimensions, which represents the code associated with the FIGS. 9A through 9D. More specifically Appendix A deals with the two-dimensional situation whereas Appendix E deals with the three-dimensional imaging situation.

It is important to note that the code in Appendices A, B, C, F, and G, deal with the most general case. This means that they can account for layering as is discussed in the Summary of the Invention Example 2. This means that the Lippman-Schwinger operator described earlier incorporates a convolution and correlation part. If it is known a priori that there is negligible layering in the geophysical or non-destructive testing or other scenario envisioned then it is appropriate to use the code given in Appendix H and Appendix I which deals with the case of no correlation part in the Green's function. The great simplification of the code that results from this omission and specialization is reflected in the fact that the code in Appendix H contains both the main imaging program and the forward problem solution. Furthermore, this code also computes the two-dimensional free space Green's function from scratch. This is in contradistinction to the codes in Appendix A or B or C where in the two-dimensional case in the presence of layering, three separate programs are used to solve the inverse scattering problem, the forward problem and the construction of the layered Green's function. The construction of this layered Green's function which is discussed in Example 2 for the acoustic scalar case, requires substantial amount of time for its computation. However, it is important to note that once the Green's function has been constructed for a given layered scenario, in a geophysical context, for example, it is not necessary to recalculate this Green's function iteratively. Rather the Green's function once it has been determined by methods discussed in the literature, see for example, [Johnson et al. 1992, or Wiskinet al, 1993], is used in the code in Appendix A and Appendix B to complete the imaging problem. To display the versatility of this inverse imaging code note that the code in Appendix H deals with the transmission mode imaging problem with the particular modality being electromagnetic wave propagation in particular in the microwave frequency range. Note also that Appendix H incorporates within it the situation where the detectors are at some finite distance away from the image space, i.e. they are not juxtaposed to the image space. The implication being that Green's theorem or some type of "scattering matrix" is required to propagate the field from the border pixels of the image space to the detector positions at some finite distance away from the image space. Such a scattering matrix is constructed earlier.

It is also important to note that all of the Appendices, with the exclusion of Appendix D, deal with the rectangular iterative method. Appendix D in distinction deals with the two-dimensional cylindrical recursion method for solving the forward problems in less time than the rectangular recursion method for Gauss-Newton iteration. It is also important to recognize that the construction of the layered Green's function as shown in Summary of the Invention, Example 2 shows explicitly how the convolution and correlation are preserved even though the distribution of the layers above and below the layer containing the image space are arbitrarily distributed. The preservation of convolution and correlation is a critical element of the ability to image objects in a layered or Biot environment (Biot referring to the Biot theory of wave propagation in porous media) in real time. The reflection coefficients which are used in the construction of the layered Green's function in the acoustic, elastic and the electromagnetic case are well known in the literature. See, for example [Muller, 1985] or Aki and Richards, 1980. The incorporation of this Green's function for layered media in the acoustic, elastic and electromagnetic case for the express purpose of imaging objects buried within such a layered medium is novel. The ability to image in real time is critical to practical application of this technology in the medical, geophysical, non-destructive and testing microscopic environments.

We now elucidate the steps shown in FIG. 9A. We have already discussed in detail, steps up to 240, Step 242 of FIG. 9A begins the conjugate gradient loop. Step 244 of FIG. 9A sets n equal to 0.

Figure 20A:
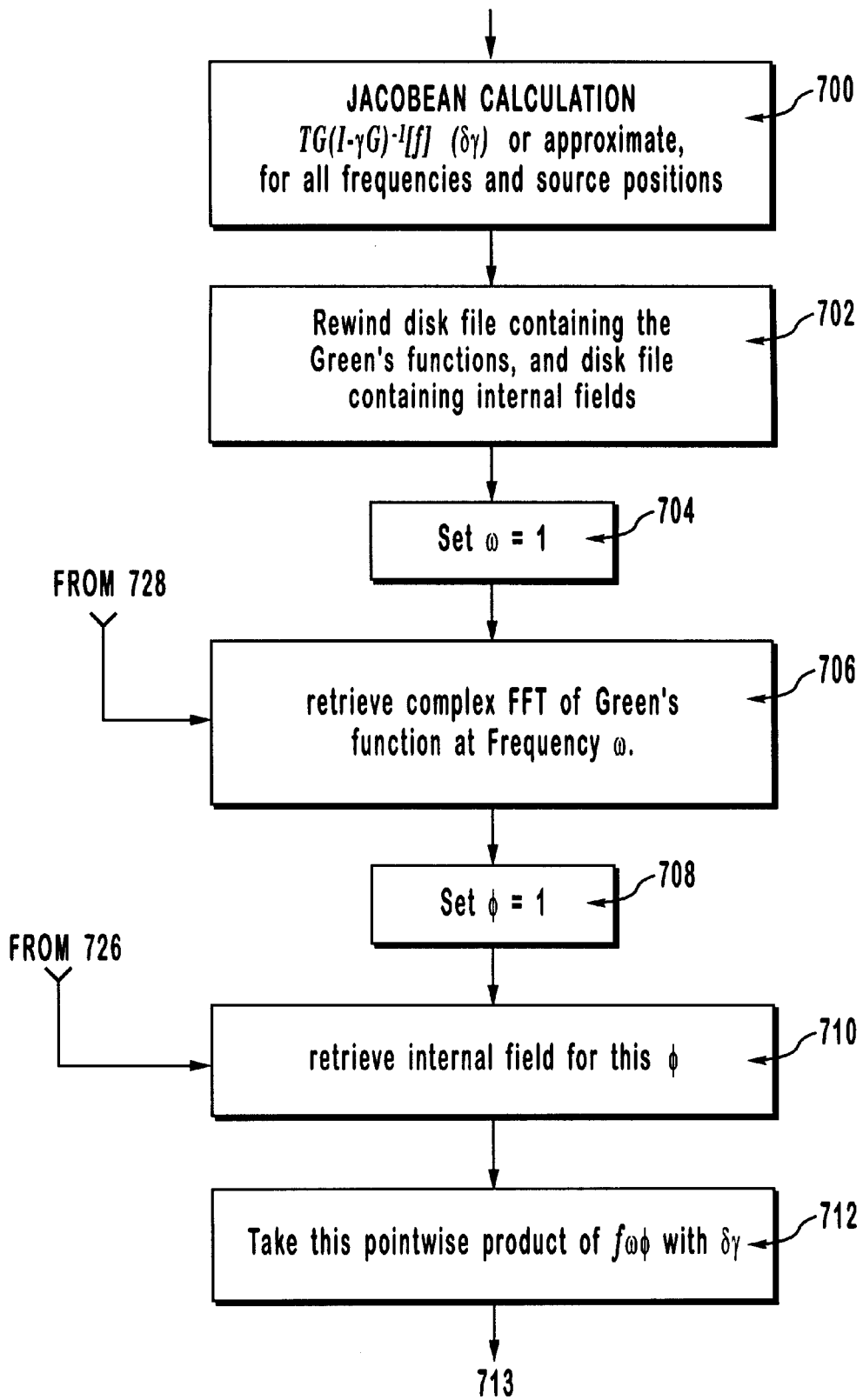
FIGS. 20A/20B/20C illustrate application of the Jacobian Matrix in the generic case (free space—or no layering), according to the present invention.
Figure 20B:
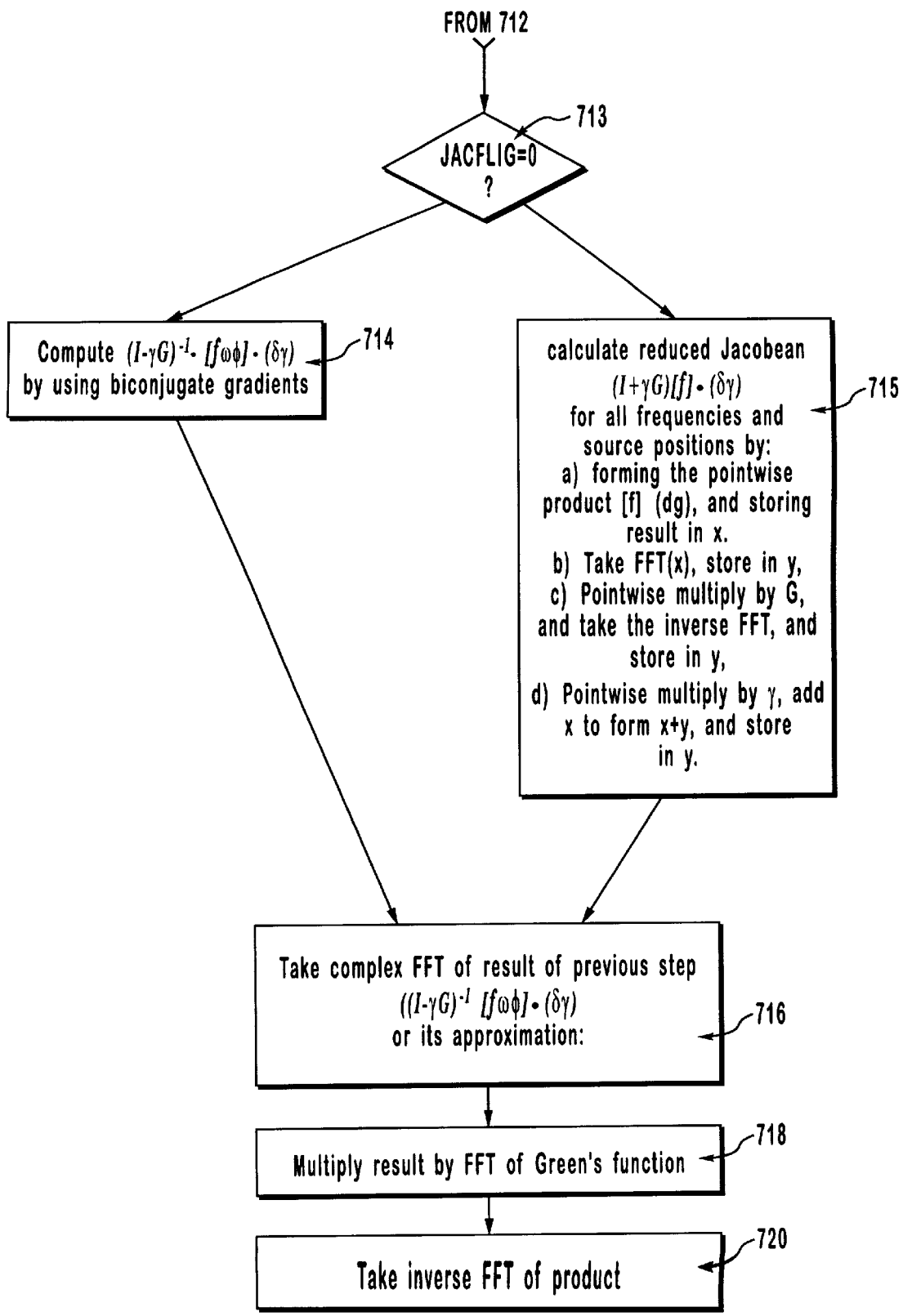
Figure 20C:
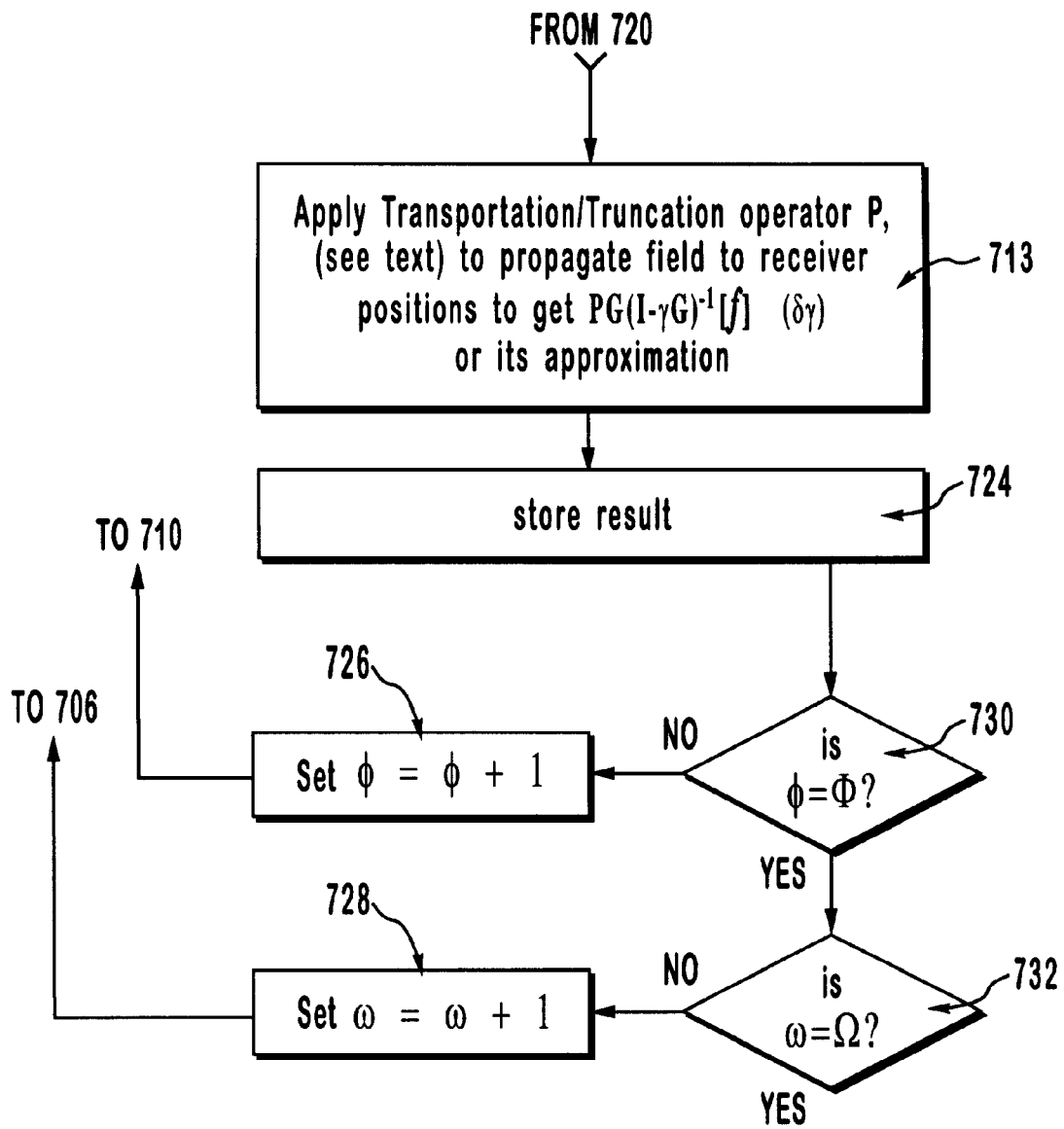

This n is the counter that keeps track of the number of conjugate, gradient steps that have been performed in the pursuit of δγ, the update to the scattering potential estimate. Step 246 of FIG. 9A again determines if the full Jacobian will be used. As in previous step 230 of FIG. 9A the answer depends on the magnitude of γ. In the case that the γ is large, the approximation given in Step 250 is not appropriate. Furthermore the actual implementation of the algorithm depends on whether there is correlation present. They are sufficiently different to warrant separate flow charts. FIGS. 20A/B/C deal with the free space case. Considering this case first, JACFLAG is set to one and Step 252 is computed via FIG. 20A/B/C. Step 700 of FIG. 20A transfers the algorithm control to Step 702 where the disk file containing the Green's functions and the disk file containing the internal fields for all possible ω and all possible φ source positions are rewound. Control is then transferred to Step 704 where ω, the index for the frequency, is set equal to 1. In Step 706 thereafter, the complex Fast Fourier Transform (FFT) of the Green's function; at this particular frequency, is retrieved. In Step 708, φ, the counter corresponding to the source positions, is set equal to 1. The Step 710 in FIG. 20A/B/C retrieves the internal field for this particular source position φ, the Step 712 takes the point-wise product of this internal field which was retrieved in Step 710, with the δγ which is the input to FIG. 20A/B/C and is also the same δγ which is being sought after in the main program in FIG. 9A through 9D. In Step 252 of FIG. 9B which is where we have come from in FIG. 20A/B/C, the Jacobian is applied to p, which is the search direction for δγ. That is p is the input to FIG. 20A/B/C, i.e. δγ in this call of FIG. 20A/B/C is p of Step 252 in FIG. 9B. In Step 714 of FIG. 20A/B/C either the inverse of a certain operator or the first order binomial approximation of the inverse, is applied to the point-wise product produced in Step 712. This operator, (I−γG), is similar to, but not the same, as the Lippmann-Schwinger operator which is represented as (I−Gγ). Note, the determinator of which operator $(I-G\gamma)^{-1}$ or $(I+G\gamma)$ is applied is the JACFLAG variable defined in FIG. 9B. JACFLAG=1 corresponds to application of $(I-G\gamma)^{-1}$.

It is important to note that the inverse of this operator, $(I-\gamma G)^{-1}$, is never explicitly calculated in Step 714. The actual computation of the inverse of this operator, which in discrete form is represented as a matrix would be computationally very expensive. Therefore, the inverse action of the operator $(I-\gamma G)^{-1}$ acting on the point-wise product calculated in Step 712 is calculated by using bi-conjugate gradients or BiCGStab as indicated in Step 714 of FIG. 20A/B/C. This bi-conjugate gradient algorithm is the same bi-conjugate algorithm shown in FIG. 11A01/11A02 and was used to calculate the application of the Lippman-Schwinger operator [I−Gγ] on a vector f. However, it is important to note that the operator represented by the matrix A in Step 450 of FIG. 11A01 is not the Lippman-Schwinger operator, rather it is the above (I−γG) operator in this case. As before, the BiCGStab or Biconjugate gradient stabilized algorithm may be used in place of the bi-conjugate gradient algorithm. This BiCGStab or conjugate gradient stabilized algorithm is shown in FIG. 11B01/11B02. The application of the algorithm shown in FIG. 11C for the actual application of the operator A in BiCGStab, FIG. 11B01/11B02, or BCG, FIG. 11A01/11A02, will of course, differ, in that the point-wise multiplication by γ will be performed after the convolution with the Green's function G appropriate to this frequency ω, in this case. However, the changes that must be made to FIG. 11C are clear in this case. Namely, the point-wise product shown in Step 402 is taken after the computation of the inverse Fast Fourier Transform (FFT) in Step 408 instead of before. A similar comment applies to FIG. 13 where the Hermitian conjugate of I−γG is computed. In this case the Hermitian conjugate of the operator I−γG requires that the point-wise product of the conjugate of γ which is carried out in Step 586 of FIG. 13 be calculated before the Fast Fourier Transform (FFT) is taken in Step 580 of FIG. 13. Step 254 of FIG. 9B now calculates the magnitude of the vector computed in Step 252 namely, the application of the vector A to the search direction p. Step 254 of FIG. 9B also computes the magnitude of the vector which is the result of the application of the Hermitian conjugate of the vector A to the residual vector r. Again, A is either the exact Jacobian or the approximation to the Jacobian shown in Step 250. The Step 256 computes the square of the ratio of the two magnitudes computed in Step 254, this ratio is denoted by α. Step 258 of FIG. 9B now updates δγ which is the Gauss-Newton correction sought after in the loop from Step 244 to 314 of FIGS. 9B through 9D. The update is given explicitly in Step 258 of FIG. 9B. Also at the same time the residual is updated via the formula shown explicitly in Step 258 of FIG. 9B. Step 260 transfers control to the Step 286 in FIG. 9C which determines if the full, exact Jacobian will be used or the approximation shown explicitly in Step 290. Depending upon which A is defined i.e. either the exact Jacobian or the approximation, JACFLAG is set to 1 or 0 and Step 292 is carried out. It is the application of the Hermitian conjugate of the matrix A which is defined in either Step 290 or 288, depending upon whether the exact Jacobian is used. The Hermitian conjugate of A is applied to the updated residual vector r. Step 294 calculates the ratio of two numbers. The first number is the magnitude of the updated residual calculated in Step 292, the second number is the magnitude of the scattered field for all possible ω's, i.e. source positions, and φ's i.e. frequencies, and compares this ratio to ε the pre-determined tolerance. If the tolerance is larger than this calculated number, control is transferred to Step 296 which effectively stores the image of the scattering potential and/or displays this image. If the tolerance is not satisfied, control is transferred to Step 298 where β is calculated as shown explicitly in Step 298.

Step 300 calculates the new search direction which is given by the explicit formula shown. Note that the Hermitian conjugate applied to the residual vector r has already been calculated in previous Step 298. Now transfer to Step 304 of FIG. 9D and it is determined in Step 310 if the maximum number of iterations allowed for the conjugate gradient solution have been exceeded. If no, then n, the counter for the conjugate gradient steps is incremented by one, and control is transferred to Step 246 of FIG. 9B. If, however, the maximum number of conjugate gradient iterations has been in fact exceeded, control is transferred to Step 314 of FIG. 9D. This is the step that has been discussed previously in which the scattering potential is updated by the δγ vector which has been computed by the conjugate gradient iterations. Control is then transferred to Step 316 of FIG. 9D where it is determined if the maximum number of Gauss-Newton corrections, specifically the δγ's, have been calculated. If the maximum number of Gauss-Newton (see earlier note regarding Gauss Newton vs Ribiere Polak) steps has been exceeded then the control is transferred to Step 320 where the present scattering potential estimate is stored and/or displayed. If the maximum number of Gauss-Newton corrections has not been exceeded then the index parameter that counts the number of Gauss-Newton corrections that have been computed, is incremented by 1 and control is transferred to Step 308 which transfers to Step 284 (arrow) of FIG. 9C which transfers control to Step 244 (arrow) of FIG. 9B which transfers control to Step 236 (arrow) of FIG. 9A which transfers control to Step 222 of FIG. 9A. Again as before, in Step 222 the forward problems for all possible it's and all possible φ's are calculated. More specifically control is transferred to Step 340 of FIG. 10. This Figure has been discussed in detail above.

The loop just described and displayed in FIG. 9A through 9D is now reiterated as many times as necessary to satisfy the tolerance condition shown in Step 294 of 9C or until the maximum of Gauss-Newton iteration steps has been performed.

It is appropriate to study in detail the application of the Lippman-Schwinger operator and the Jacobian in the situation where layering is present. It is important to note that the discussion heretofore, has emphasized the special situation where layering is not present so that the free space or similar Green's function not involving any correlation calculation, has been used. This specialization is appropriate for pedagogical reasons, however, the importance of the layered Green's function makes it necessary to discuss in detail the application of the Lippman-Schwinger operator in this case. Before doing this however, we look at FIG. 25A/B/C where the Hermitian conjugate of the Jacobian calculation is considered in the free space case. Just as in the calculation of the Jacobian itself (or its approximation) the variable JACFLAG determines whether BCG (or variant thereof) is applied or whether the binomial approximation shown is used.

In Step 600 the full Hermitian conjugate of the Jacobian calculation is undertaken with the disk files containing the Green's functions and the disk files containing the internal fields for each ω and each φ being rewound. In Step 604 ω is set equal to 1, i.e. the first frequency is considered. In Step 606 the complex Fast Fourier Transform (FFT) of the Green's function at this particular frequency ω is retrieved from disk where it has been stored previously. In Step 608 φ is set equal to 1 indicating we are dealing with the first source position. Step 610 retrieves the internal field f$_{\omega\phi}$, for this source position φ at frequency ω. Step 612 propagates the scattered field from the detector positions to the border pixels of the image space. Also in Step 612 the field values at the non-border pixels of the image space are equated to 0. In Step 614 the Fast Fourier Transform (FFT) of the field resulting from Step 612 is computed and stored in vector x. In Step 616 the complex conjugate of the Fast Fourier Transform (FFT) of the Green's function G is point-wise multiplied by x, the vector computed in Step 614. As before the actual computation of this inverse operator is computationally prohibitive. Therefore, the application of the inverse of I−G*γ* to the vector x is carried out by using bi-conjugate gradients or BiCGStab as discussed above. In Step 620 either the inverse of the operator I−G*γ* or the approximation (I+G*γ*) is applied to this result. The system [I−G*γ*] y=x is solved for y using BCG. See FIGS. 11A01/11A02. In Step 622 of FIG. F01 the point-wise multiplication by the complex conjugate of f$_{\omega\phi}$, the internal field for this frequency and source position, is carried out. This point-wise multiplication is the product with the result of Step 620. The Step 624 stores the result of this point-wise multiplication. Step 626 determines if φ is equal to Φ, the maximum number of source positions. If the maximum number of source positions has not yet been achieved, then the φ is incremented by 1 to indicate movement to the next source position. Transfer of control is now made to Step 610, where the internal field for this particular source position is retrieved. The loop from Step 610 to Step 626 is performed iteratively until the maximum number of source positions has been achieved. When this occurs, it is determined if ω is equal to Ω, the maximum number of frequencies, in Step 630. If the maximum number of frequencies has been achieved then control is transferred to Step 634 which transfers control back to FIG. 9A where the Hermitian conjugate of the Jacobian, or its approximation, was being applied. If, however, the maximum number of frequencies has not been achieved then transfer is made to Step 632 where the frequency index is incremented by 1 and control is transferred to Step 606 of FIG. F01 which is the retrieval of the complex Fast Fourier Transform (FFT) of the Green's function at new frequency ω. This loop is now repeated until all possible frequencies and all possible source positions have been exhausted. At this time control is transferred to the inverse scattering routine in FIG. 9A through 9D.

It is appropriate now to turn to that part of FIG. 20A/B/C which details the application of the reduced Jacobian calculation which is used by FIG. 9A through 9D, i.e. the Gauss-Newton iteration in the situation where it is permissible to use the approximation to the Jacobian in place of the exact Jacobian. This calculation is called the reduced Jacobian calculation by virtue of the fact that no inverse operator is required to be calculated in this Figure. Therefore, the total computational complexity of this part of FIG. 20A/B/C (ie.Step 715) is less than the corresponding Step 714 of FIG.

20A/B/C, in which the full exact Jacobian calculation is carried out. When the Jacobian calculation in FIG. 20A/B/C is being carried out to compute Step 252 in FIG. 9B δγ is in fact p″, the search direction for the conjugate gradient step in determining δγ, which in turn is the update to the scattering potential determined δγ this particular Gauss-Newton step. In Step 715a) the point-wise product is stored in vector x. In Step 715b) the Fast Fourier Transform (FFT) of the point-wise product is computed and in Step 715c) this Fast Fourier Transform (FFT) is taken with a point-wise product with the Fast Fourier Transform (FFT) of the Green's function for this particular frequency ω, and the inverse Fast Fourier Transform (FFT) of the point-wise product is taken to yield G convolved with the product f*δγ which result is stored in vector y. In Step 715d) the point-wise product of vector y is taken with γ and the vector x computed and stored in Step 715a) is added to it. The Fast Fourier Transform (FFT) of this sum is calculated in Step 716 of FIG. 20A/B/C and the algorithm finishes exactly as described previously. Recall that transportation takes place in the scenario where the receivers exist at some finite distance from the image space in contradistinction to the truncation operation which takes place when the receivers exist at the border pixels of the image space. The truncation or transportation operator is discussed in FIG. 21 for the general case in which correlation, i.e. layering, is present or absent.

It is very important to note that the correlation that is calculated in the case of layering is, without exception, calculated as a convolution by a change of variables. It is the presence of the convolution which allows the introduction of the Fast Fourier Transform (FFT) and allows this algorithm to be completed in real time when the Fast Fourier Transform (FFT) is used in conjunction with the other specific algorithms and devices of this apparatus.

Figure 23A:
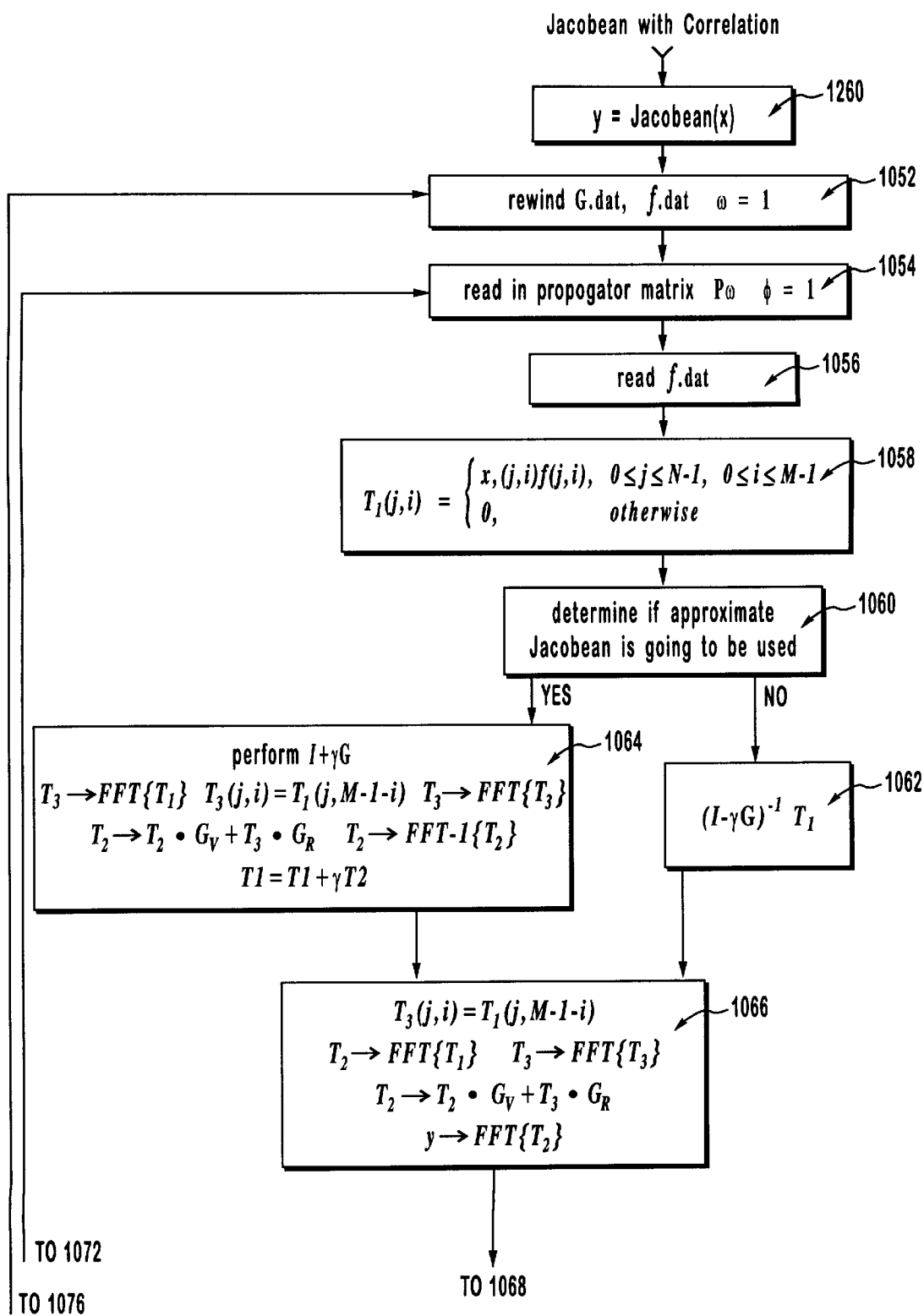
FIG. 23A/B illustrates application the Jacobian Matrix with correlations according to the present invention.
Figure 23B:
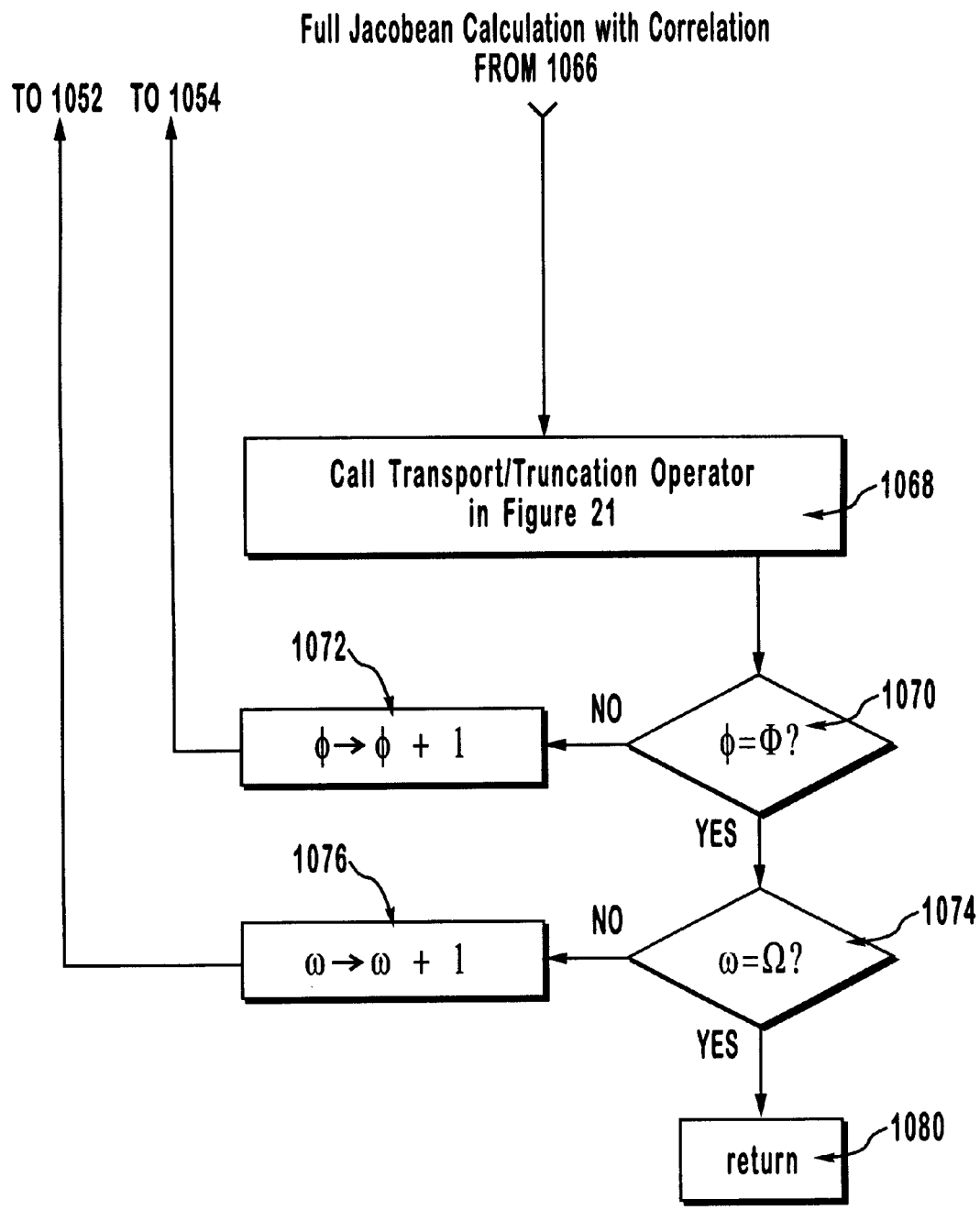
Figure 24:
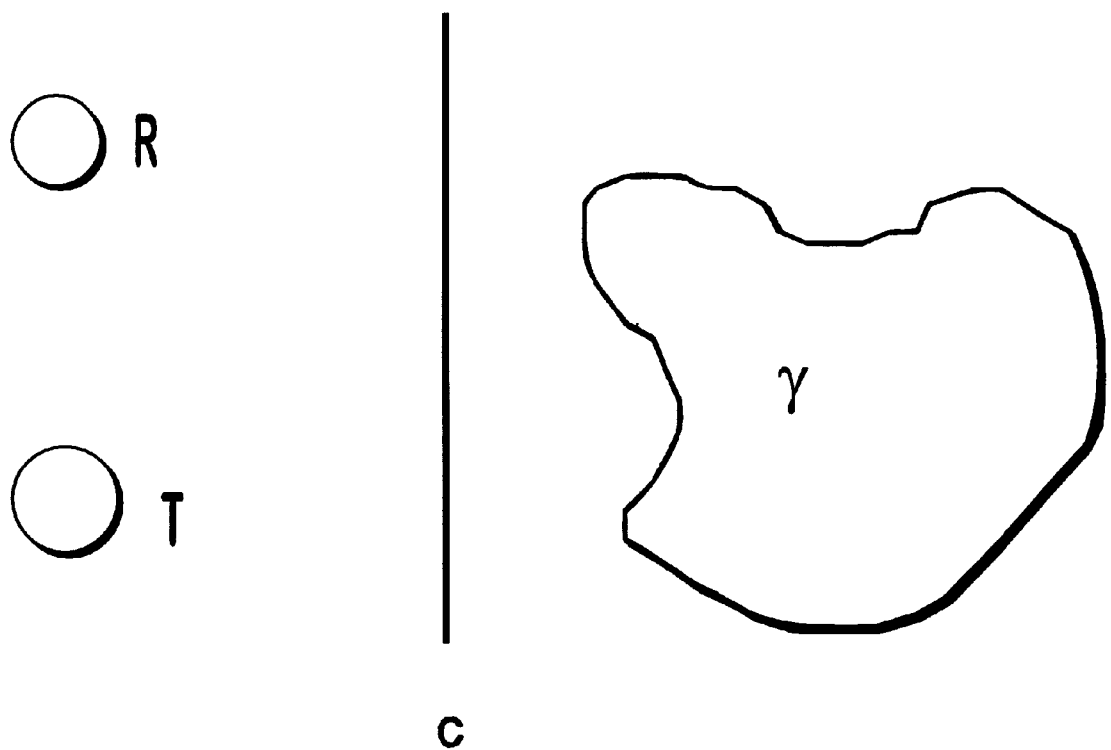
FIG. 24 shows a transducer coupling according to the present invention.
Figure 25A:
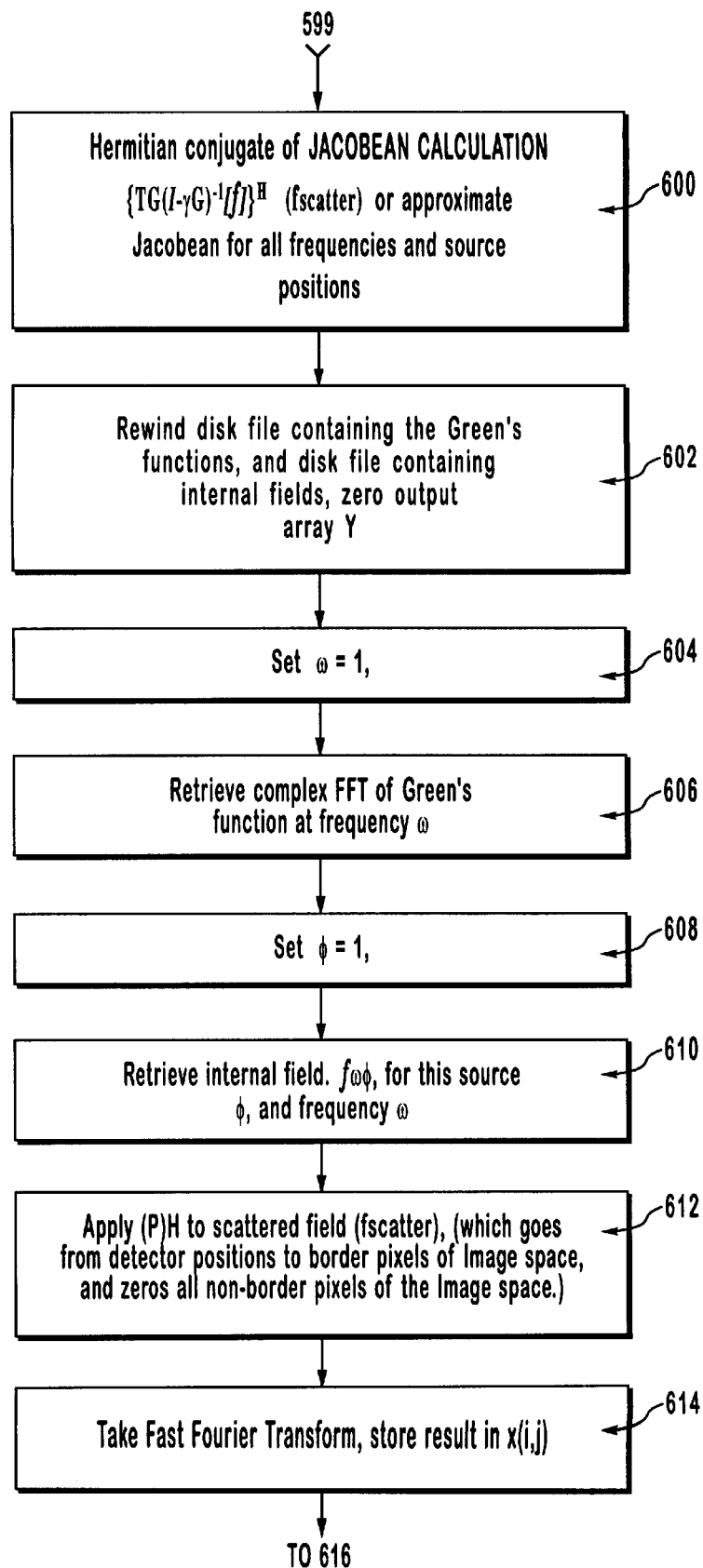
FIG. 25A/B/C illustrates application of the Hermitian Jacobian Matrix in the generic case according to the present invention.
Figure 25B:
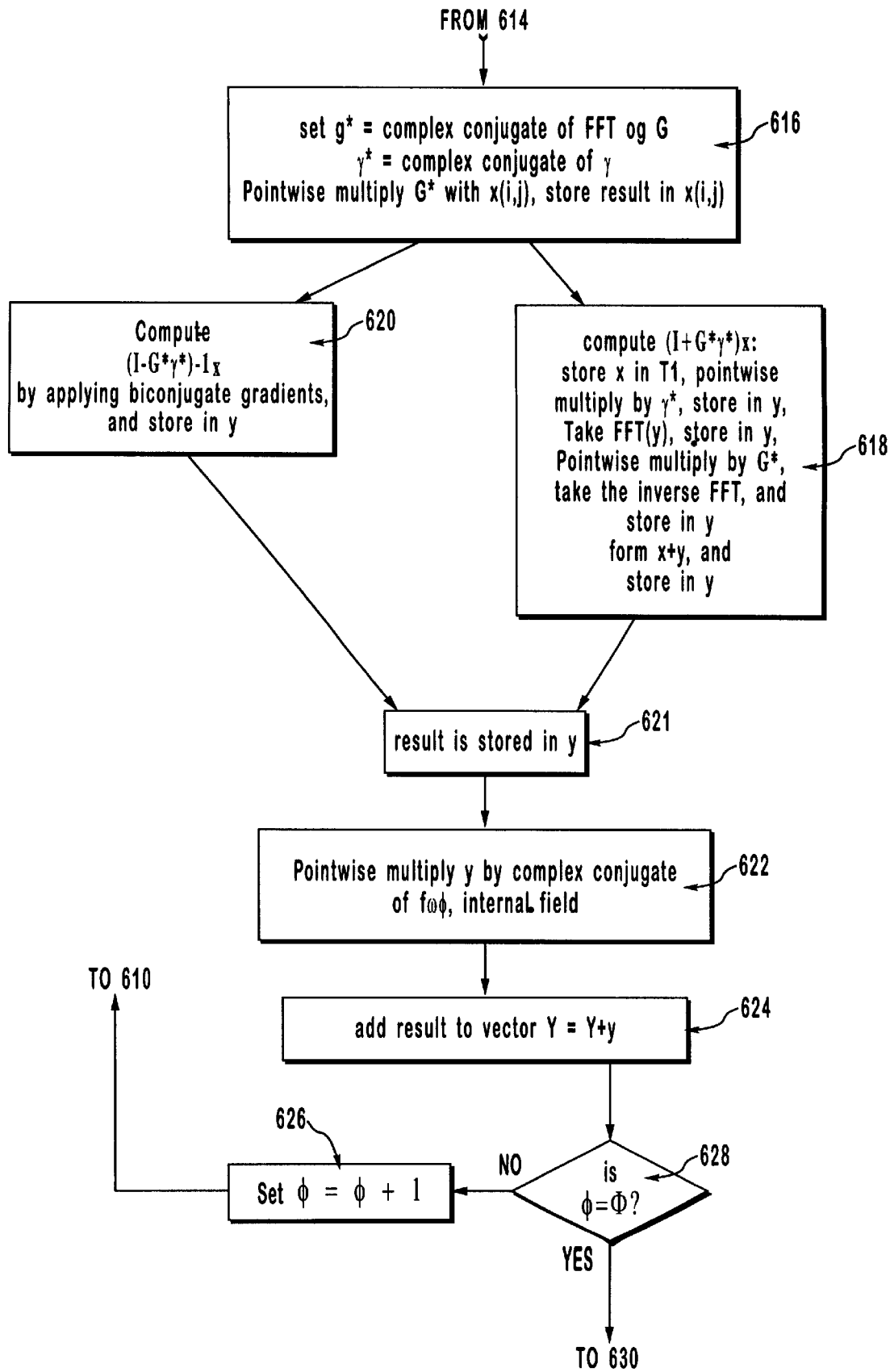
Figure 25C:
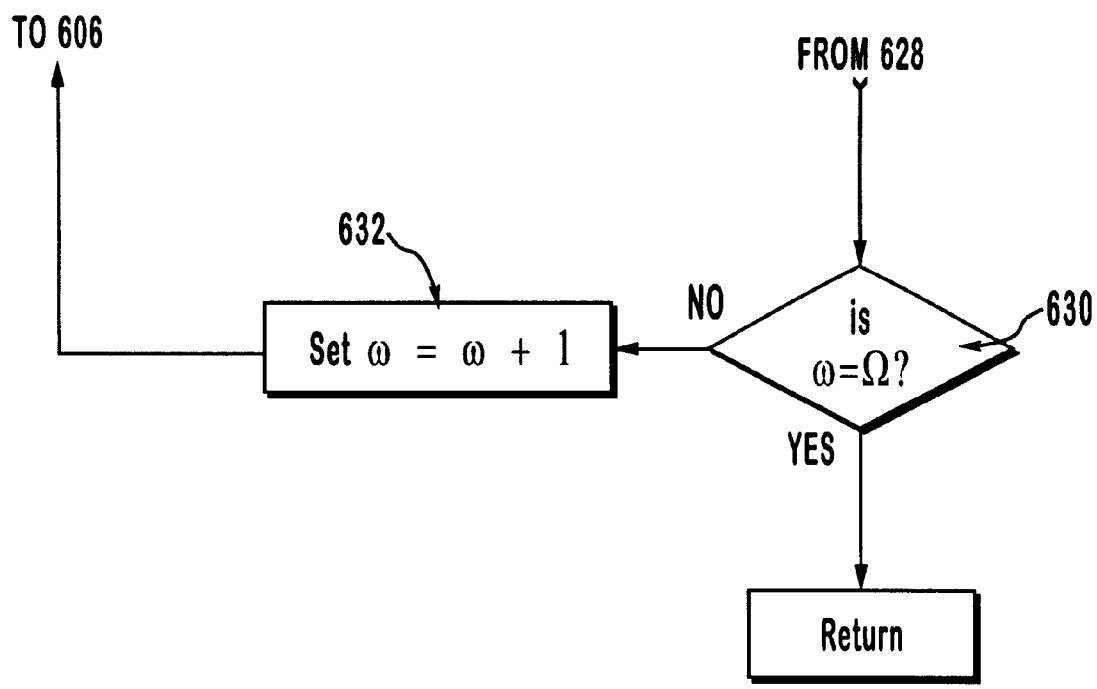

It is now appropriate to consider in detail the action of the Lippmann-Schwinger operator and the Jacobian in the case when layering is present. FIG. 23A/B displays this case.

It is also important to note regarding the Jacobian calculation with correlation, that both the reduced and the exact form have their counterpart in the Hermitian conjugate. This is discussed in FIGS. 19A/B. In Step 654, the rewinding of the disk with the Green's function and the disk with the internal fields is carried out, and ω is set equal to 1. In Step 658 the complex Fast Fourier Transform (FFT) of the Green's function at this particular frequency ω is retrieved. Step 658 also sets φ (source position) equal to 1. Step 660 retrieves the internal field for this φ. Step 662 calculates the Hermitian conjugate of the truncation operator which puts values in border positions of the image space of the appropriate field and zeros everywhere else. Step 664 point-wise multiplies the result of 662 by complex conjugate of the Fast Fourier Transform (FFT) of the Green's function. Step 668 takes the inverse Fast Fourier Transform (FFT) and stores this in vector y. Now, in Step 670 depending upon the value for JACFLAG, either the full inverse $(I-G^*\gamma^*)^{-1}$ (via BCG or BiSTAB, etc.) or $(I+G^*\gamma^*)$ is applied directly to y. The second alternative is carried out in the standard manner. That is, one takes the point-wise multiplication of the complex conjugate of γ, the scattering potential estimate at this time with the vector y. The one takes the Fast Fourier Transform (FFT) of the result and takes the point-wise multiplication of the complex conjugate of the Fast Fourier Transform (FFT) with this result. Finally one adds the vector y and stores it in vector y, (overwriting y). The Step 672 multiplies the final result point-wise, with the complex conjugate of the internal field for this particular frequency and source position, and stores the result. Step 672 transfers control to 674 where it is determined if φ is equal to Φ. If no, then φ is incremented by 1 and returned to Step 660 in Step 676. If yes, control is transferred to 680 where it is determined if ω is equal to Ω; if yes, increment ω by 1 in Step 682, and transfer control to Step 656. If no, transfer control to Step 684 where control is transferred back to the inverse scattering main algorithm, FIGS. 9A through 9D.

Figure 12:
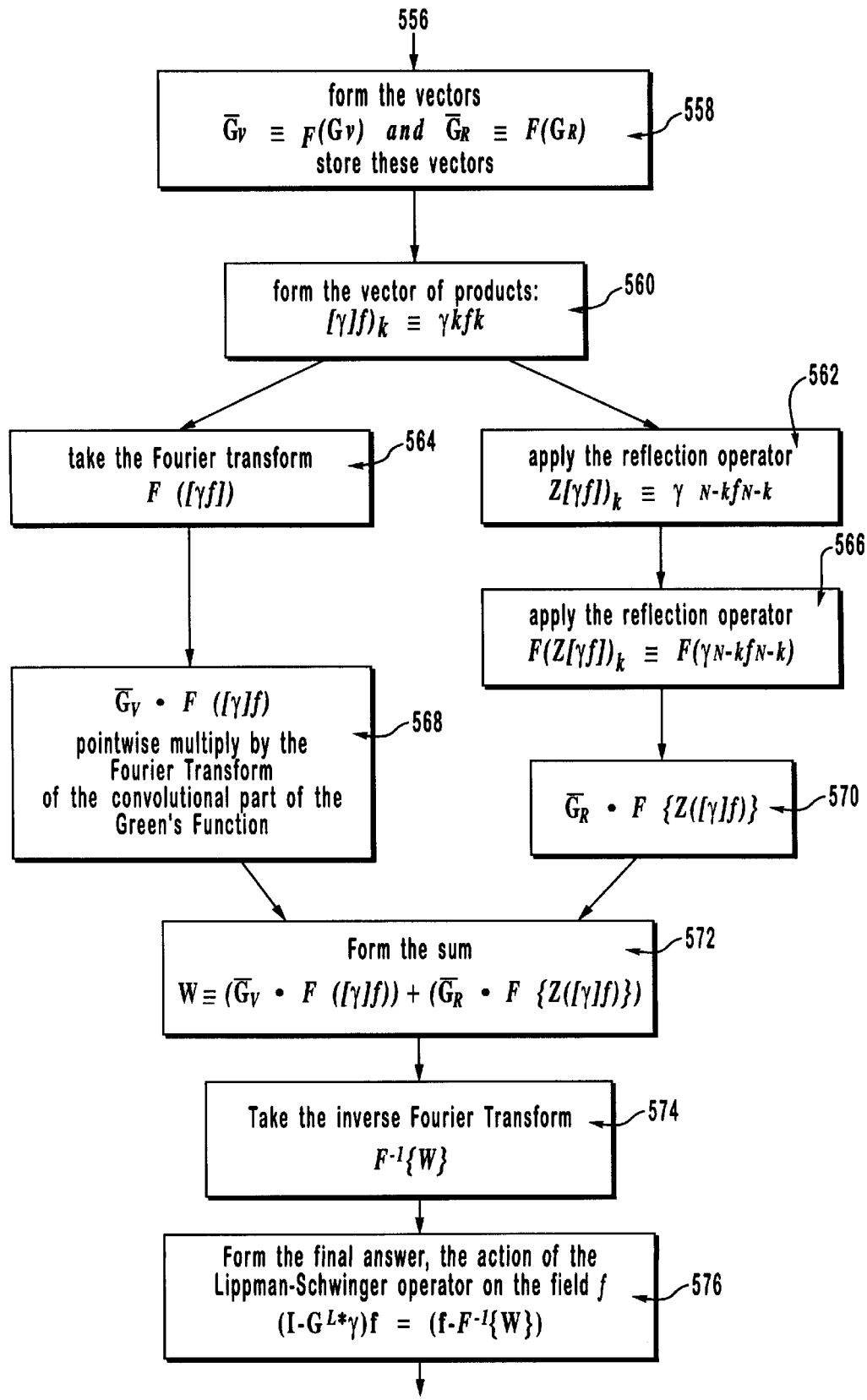
FIG. 12 illustrates the application of the Lippmann-Schwinger Operator in the presence of layering to the internal field estimate according to the present invention.

It is important to note at this point that when the operator I−Gγ is applied to the vector $T_1$, and also when the Lippmann-Schwinger operator I−Gγ is applied to any input vector in the layering scenario, FIG. 12 must be followed. Step 556 of FIG. 12 forms the vectors which store the Fast Fourier Transform (FFT) of the convolutional and the correlational parts of the layered Green's function separately. These convolutional and correlational parts are computed by appendices C and G for the two and three-dimensional cases, respectively, and are given explicitly by the formulas given on page 35 of the Summary of the Invention section.

The step 558 passes control to step 560 where the vector of pointwise products shown explicitly there, is formed. This pointwise produce of γ, the scattering potential estimate, and F, the internal field, is Fourier transformed in step 564 and in parallel simultaneously in step 562, the reflection operator is applied to this pointwise product γF computed in step 560. In step 566, following step 562, the Fourier Transform of the reflected product γF is taken. In step 570 and in step 568, there is pointwise multiplication by the correlational part and the convolutional part of the layered Green's function, respectively. The correlational part of the layered Green's function is pointwise multiplied by the Fast Fourier Transform (FFT) computed in step 566, the convolutional part of layered Green's function fast Fourier transformed is pointwise multiplied by the Fast Fourier Transform (FFT) which was computed in step 564. In step 572, the vector W, which is the difference of the results of step 568 and 570, is computed and stored. In step 574, the inverse Fast Fourier Transform (FFT) of the vector W is computed. In step 576, the final answer which is the action of the Lippmann-Schwinger operator acting upon the field f is computed for the layered medium case, i.e., the case in which correlation exists. This process of applying a Lippmann-Schwinger operator in the presence of layering established in FIG. 12 is used explicitly in the calculation of the forward problems in step 222 of FIG. 9A in the presence of layering. It is also carried out explicitly in Appendices B and P for the two and three-dimensional cases, respectively. It is also required in some of the calculations of the application of the Jacobian in the layered medium case.

Figure 14:
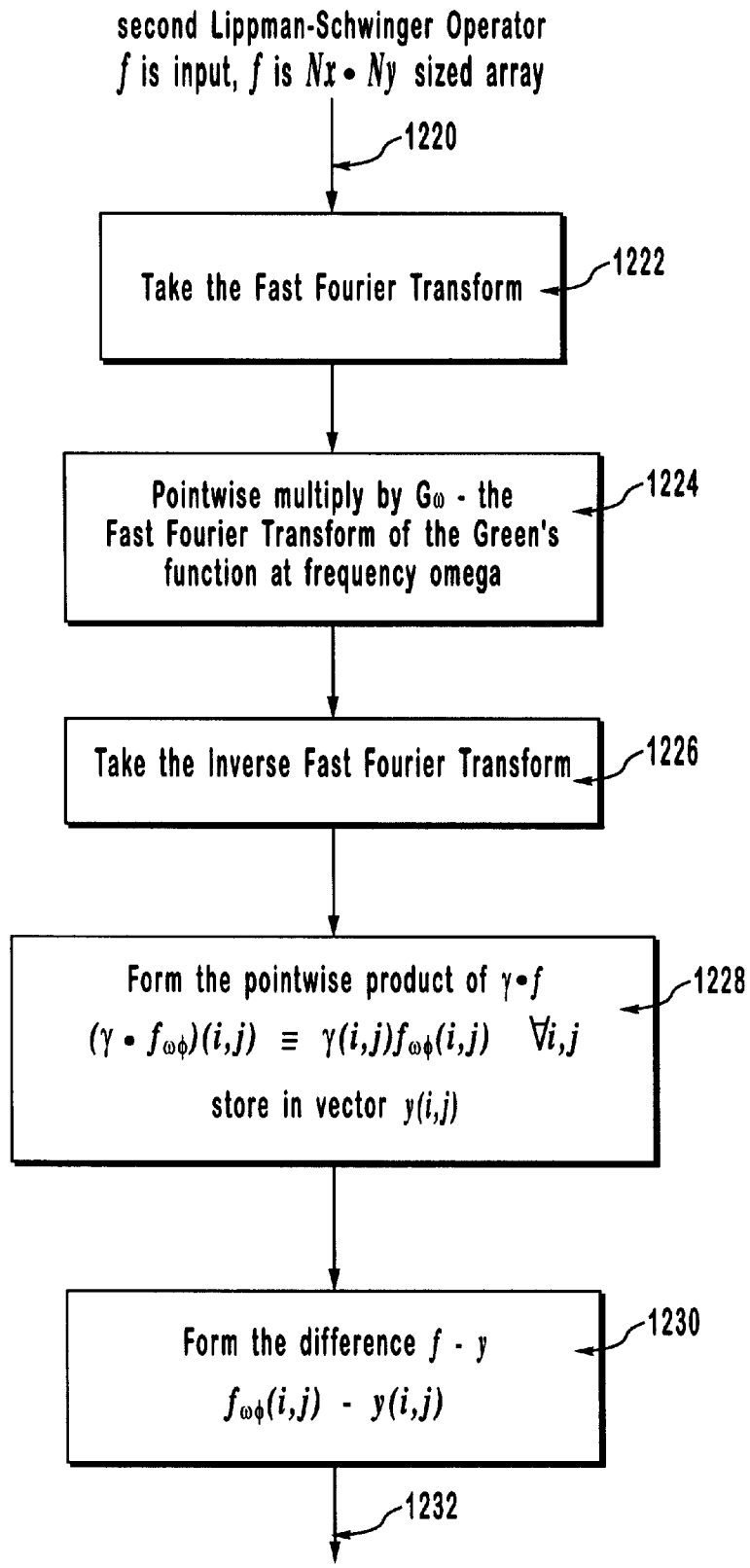
FIG. 14 illustrates the application of the second Lippmann-Schwinger operator in the generic case.
Figure 16:
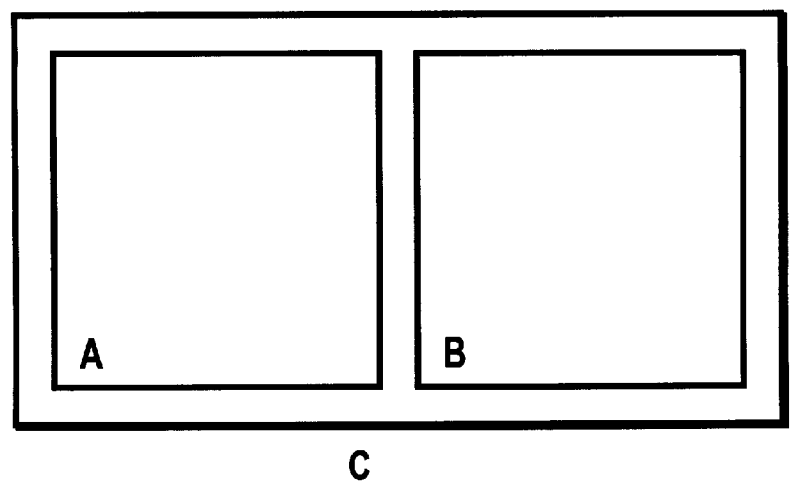
FIG. 16 illustrates a rectangular scattering matrix according to the present invention.
Figure 17:
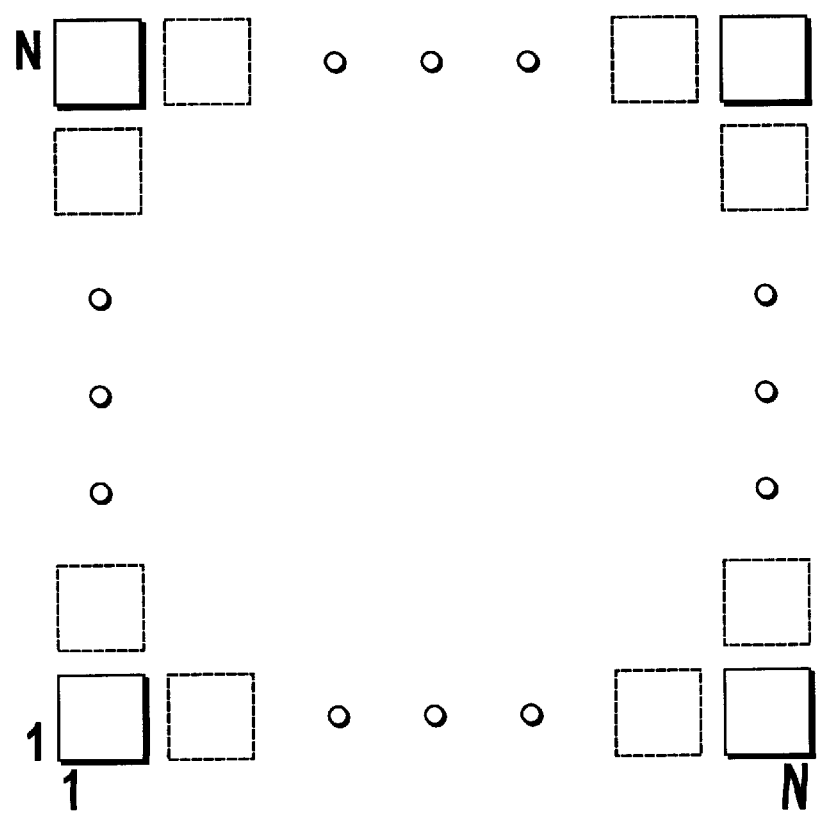
FIG. 17 illustrates a N-by-N scattering region according to the present invention.
Figure 18:
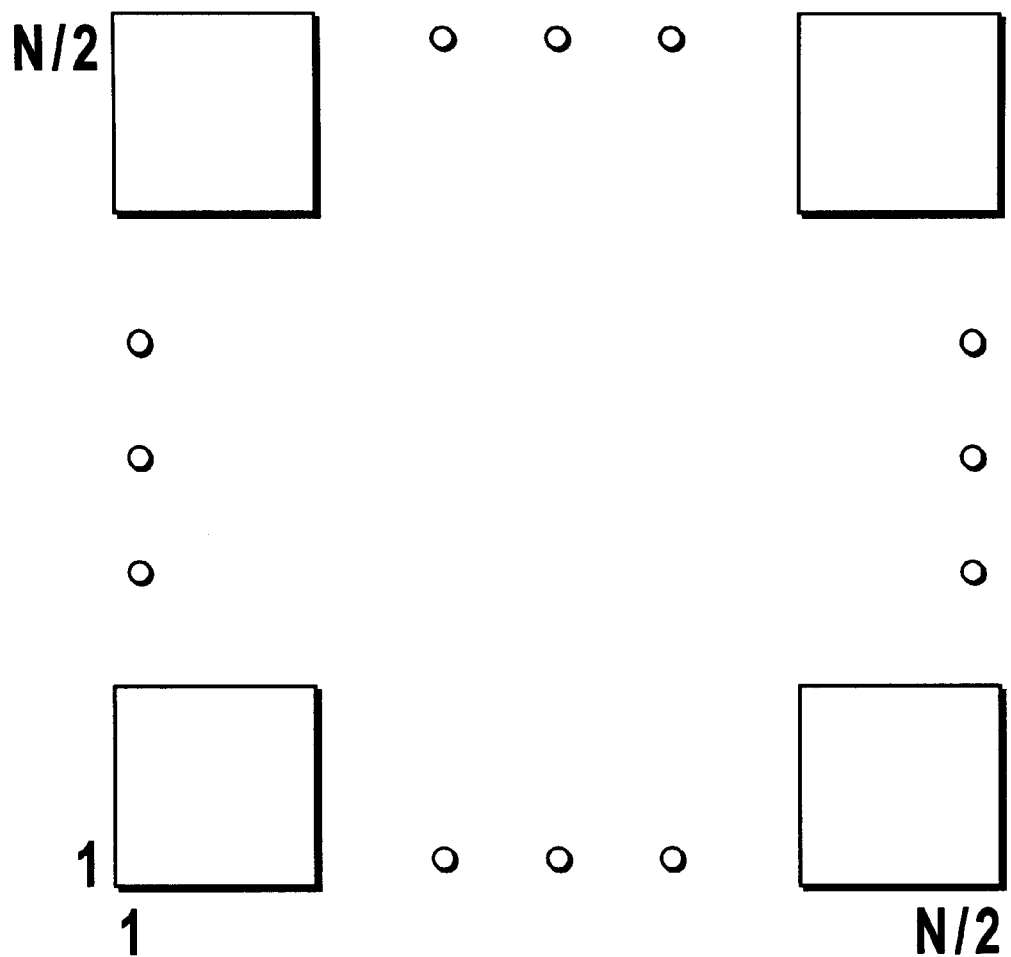
FIG. 18 illustrates a N-by-N scattering coalesced region according to the present invention.

The operator described by FIG. 14, (I−γG), is called the "Second Lippmann-Schwinger operator". This operator is in fact the transpose of the "Lippmann-Schwinger" operator so-called, i.e. (I−Gγ). Note that this is not the Hermitian adjoint of the Lippmann-Schwinger operator, precisely because no complex conjugate is taken.

The input to FIG. 14 is Fast Fourier Transformed in step 1222. The result is then pointwise multiplied by the Fast Fourier Transform (FFT) of the Green's function for this particular frequency. The result is inverse Fast Fourier Transformed and stored in vector y, in step 1226. The pointwise product γ·y is computed and stored in vector y. Finally the difference between input vector x, and y is formed in step 1230. Finally, the control is transferred back to the calling subroutine.

FIG. 15 details the application of the hermitian conjugate of the "second Lippmann-Schwinger" operator In 15 control is transferred to step 1242, where the pointwise product is formed, between the complex conjugate of the scattering potential estimate, and the input to this subroutine, x. The Fast Fourier Transform (FFT) is then applied to this product in step 1244. In step 1246 the pointwise multiplication by G*, the complex conjugate of the Fast Fourier Transform (FFT) of the Green's function at frequency ω, is effected. In step 1248, the Inverse Fast Fourier Transform (FFT) of the product is taken, and finally the result is stored in y. In step 1252, the difference is formed between the input to this subroutine, x, and the computed vector y, and the result is stored in y.

FIG. 21 delineates the propagation operator that takes fields in the image space, and propagates them to the remote receivers at some distance from the image space. This propagator is discussed elsewhere in more detail.

In FIG. 21, the input is truncated to the border pixels, in step 1122. Next it is determined if the receivers are remote, or juxtaposed to the image space. If the detectors are in fact juxtaposed to the image space, the control is returned to the calling subroutine.

If the detectors are remote, the field is propagated with the aid of the propagator matrix P (described in section EXTENSION OF THE METHOD TO REMOTE RECEIVERS WITH ARBITRARY CHARACTERISTICS), in step 1128. Control is then transferred to the calling subroutine in the situation where the detectors are remote.

Figure 22:
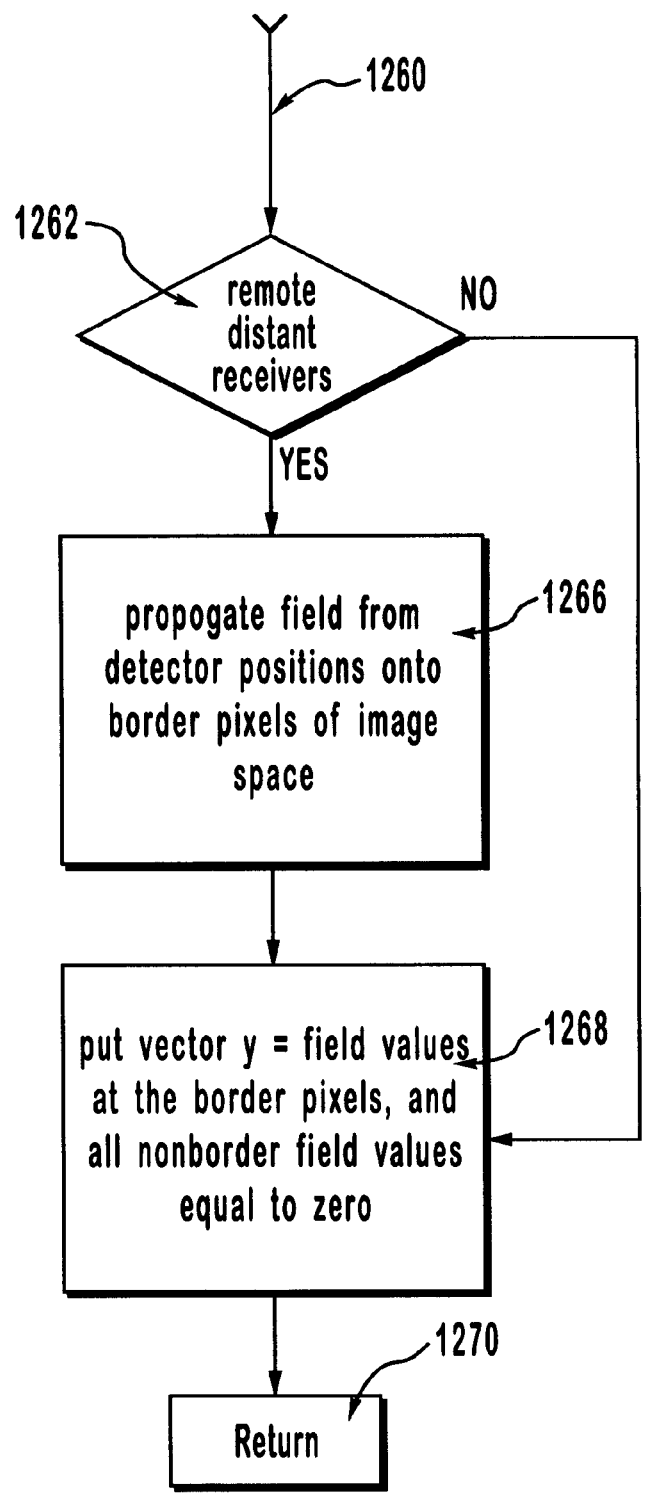
FIG. 22 the illustrates application the Hermitian conjugate of transportation of fields from image space to detector position.

FIG. 22 details the Hermitian conjugate of the propagation operator discussed in FIG. 21:

In FIG. 22, the Hermitian conjugate of the Propagation operator P, it is first determined in step 1262, whether the receivers are at some remote location. If not, then control is transferred directly to step 1268. If the detectors are in fact remote, then control is passed to step 1266, where the fields are propagated via the propagation matrix to the border pixels of the image space. In either case, control is passed then to step 1270, and on to the calling subroutine.

FIG. 23A/B determines the effect of the Jacobian on an input vector x in the presence of layering. Step 1050 transfers control to step 1052 where ω is set equal to 1. Also the files containing the Greens function for this frequency (both the correlations and the convolutional parts), and the internal field estimates, and the propagator matrix are rewound. Control is then transferred to step 1054 where the propagator matrix for this frequency is read in and also the Greens function for this particular frequency is read into memory. Also in step 1054 φ resource position index is set equal to 1. Control is then transferred to step 1056 where the file that contains the internal field estimate for this particular frequency and source position is read into memory. Control is then transferred to step 1058 where the pointwise product of the internal field estimate and the input vector x is computed. Next in step 1060 it is determined if the approximate Jacobian or the full Jacobian will be used. If the full Jacobian is to be used then control is transferred to step 1062 where biconjugate gradients or biconjugate gradients stabilized is used to solve for the action of the inverse matrix of I–γG acting on $T_1$. Recall $T_1$ is the temporary matrix which holds the pointwise product computed in step 1058. Control is then transferred to step 1066. If in step 1060 the determination is made to perform the approximate Jacobian operation then control is transferred to step 1064. In step 1064 the Fast Fourier Transform (FFT) is taken of the vector $T_1$ and it is stored in temporary vector $T_2$. Also the reflection operator is applied to the vector $T_1$ and the result is stored in vector $T_3$. Also the Fast Fourier Transform (FFT) is taken of the result of the planar reflection operator which is stored in $T_3$ and $T_2$ now contains the pointwise product of the convolutional part of the Greens function and the previous $T_2$ added to the pointwise product of $T_3$ with the correlational part of the Greens function for this particular frequency. The inverse Fast Fourier Transform (FFT) is applied to vector $T_2$ and the result is stored in vector $T_2$. Finally, the pointwise product between γ and $T_2$ is formed and the result is added to vector $T_1$ and the result is stored in vector $T_1$. Regardless of whether step 1064 or 1062 has just been completed in step 1066 the reflection operator is applied to the result of either box 1062 or 1064 and the result is Fast Fourier transformed in vector $T_3$. Also the original vector $T_1$ is Fast Fourier transformed and the result is stored in Vector $T_2$. $T_2$ is the pointwise multiplied by the convolutional part of the layered Greens function at this particular frequency and the result is added to the pointwise product of $T_3$ with the correlational part of the layered Greens function at this frequency. The result is stored in vector $T_2$. Finally a Fast Fourier Transform (FFT) is applied to the resulting vector $T_2$ control is then transferred to step 1068 where the transportation or truncation operator given in FIG. 21 is applied to the result. In step 1070 it is determined if φ is equal to Φ if in fact φ is equal to Φ control is transferred to step 1074 where it is determined if ω is equal to ω. If φ is not equal to Φ control is transferred to step 1072 where φ is incremented by 1 and control is then transferred back to step 1056. If in step 1074 ω is determined to be equal to Ω control is transferred to step 1076 where φ is incremented by 1 and control is transferred back to step 1054. If ω is equal to Ω in step 1074 control is transferred step 1080 from there control is returned to the calling subroutine.

Figure 19A:
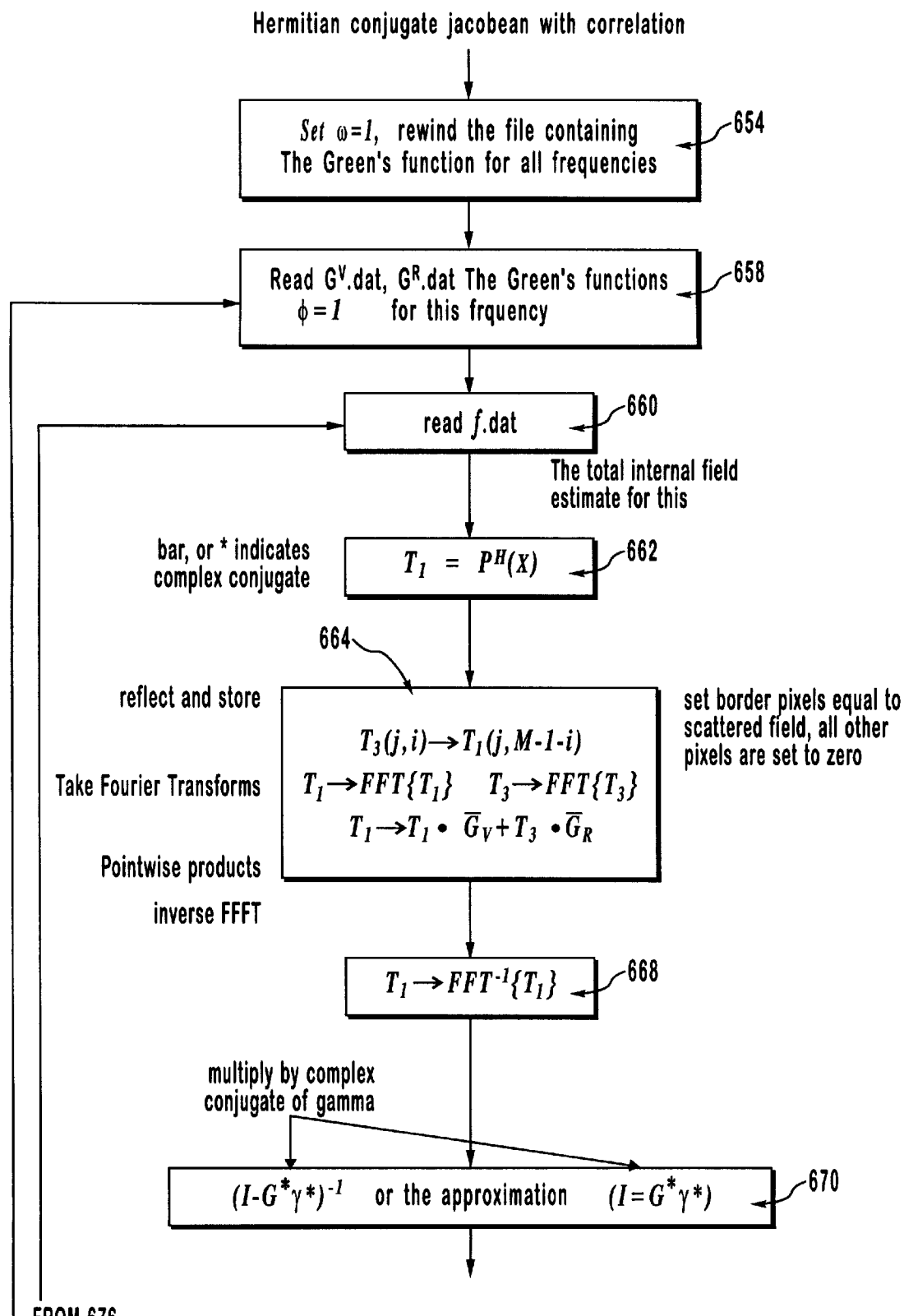
FIGS. 19A/B illustrate application of the Hermitian conjugate of the Jacobian Matrix in the presence of layering according to the present invention.
Figure 19B:
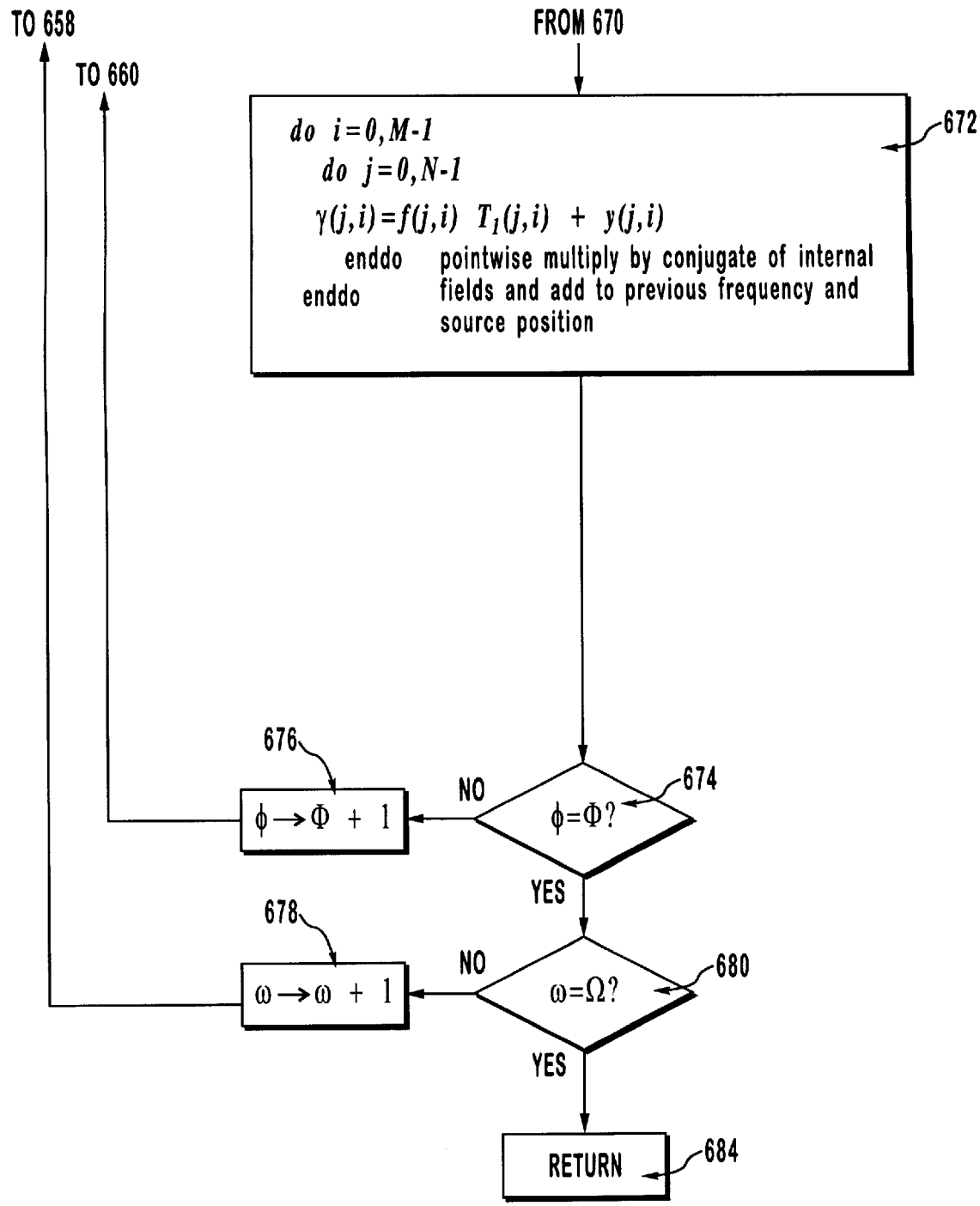

In FIG. 19A the Hermitian conjugate Jacobian with correlation present is applied to an input vector x in step 654 of FIG. 19A ω is set equal to 0 and the files containing the Greens functions for all frequencies are rewound in step 658. The Greens function both the convolutional and the correlational parts for this particular frequency are read into memory, also φ is set equal to 1. In step 660 the file containing the internal field estimate for this particular source position and frequency is read into memory in step 662 the Hermitian conjugate of the propagation operator is applied to the vector x the result is stored in vector $T_1$. In step 664 the reflection operator is applied to the vector $T_1$ and the result is stored in vector $T_3$ also Fast Fourier transforms are applied to both vector $T_1$ and vector $T_3$. Finally the pointwise product of the FFT of the complex conjugate of the convolution part of the layered Greens function is formed with T1 and the result is added to the pointwise product of $T_3$ with the FFT of the correlational part of the layered Greens function with its complex conjugate taken. The result is stored in vector $T_1$. Control is then transferred to step 668 where the inverse Fast Fourier Transform (FFT) of $T_1$ is taken and the result is stored in vector $T_1$. In step 670 either the approximation or the full action of the inverse of the second Lippmann-Schwinger operator with Hermitian conjugate taken is applied as before. If the inverse operator is applied it is approximated by the solution to a system via biconjugate gradients or biconjugate gradients stabilized. In step 670 also, the approximation I+G* γ* is applied to the vector $T_1$ resulting from step 668, and the pointwise product with Gamma* ie the complex conjugate of γ is taken. The Fast Fourier Transform (FFT) of the result is then pointwise multiplied by G* the complex conjugate of the Greens function, with care being taken to insure that the convolution and the correlational parts are performed separately as before. This result is added to $T_1$, then stored in $T_1$ and control is then transferred to step 672 where the result is pointwise multiplied by the complex conjugate of the internal field estimates and the result is added to the previous frequency and source position result. Then control is transferred to step 674 where it is determined if $\phi$ is equal to $\Phi$ if not $\phi$ is incremented by 1 and control is transferred to step 660 if it is, control is transferred to step 680 where it is determined if $\omega$ is equal to $\Omega$. If not the $\omega$ in incremented by 1 and control is transferred back to step 658. If it is, control is transferred back to the calling subroutine.

Figure 28A:
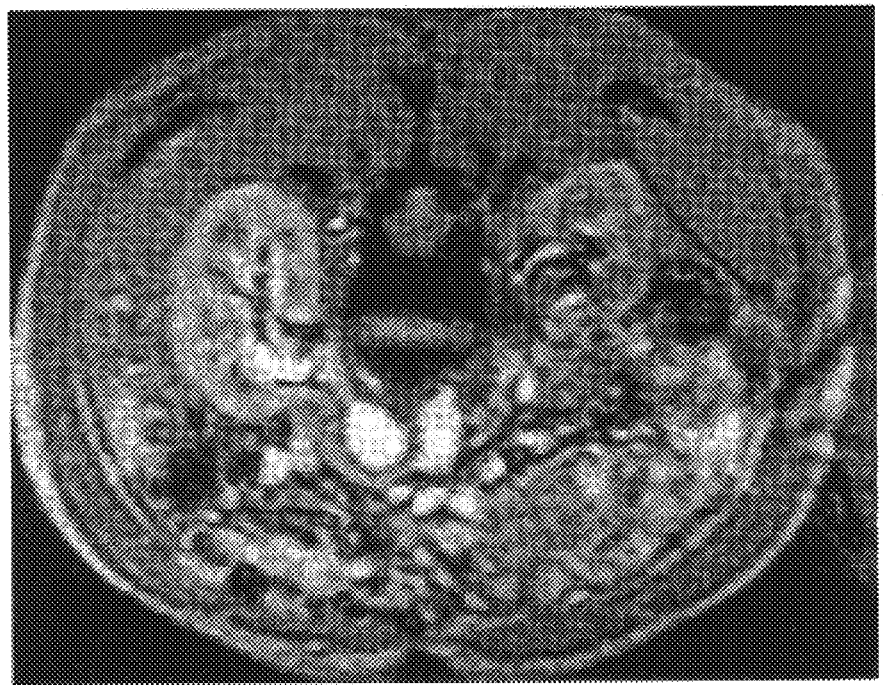
FIGS. 28A/B, 29A–29E are photographs of a television display screen showing an image that simulates a cancer and an active image obtained as the inverse scattering solution using the method and a computer simulation of the apparatus of the present invention.
Figure 28B:
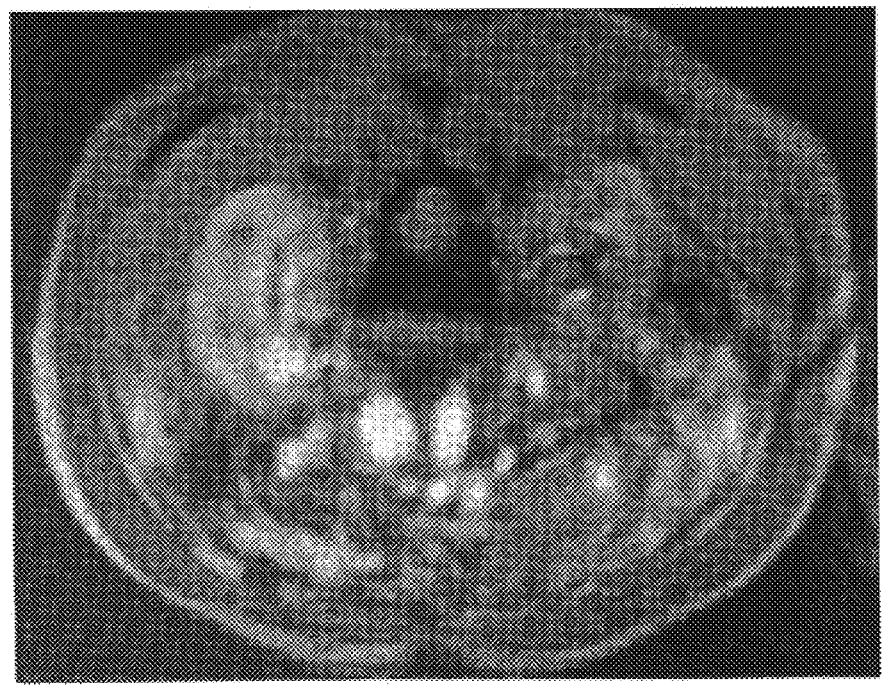

FIGS. 28A and 28B show an example of the application of inverse scattering to medical imaging through the use of computer simulation. FIGS. 28A and 28B also illustrate the powerful impact of a large inverse scattering image. FIG. 28A is a photograph of a cross section of a human through the abdomen that could appear in an anatomy atlas. The image was actually made on a magnetic resonance clinical scanner. This image is 200 by 200 pixels, each pixel being ¼ wave length square. It was used a the starting image in the process of creating synthetic scattering data. The pixel values in this image were assigned to a set of speed of sound values in a range that is typical for soft tissue. This range is typically plus or minus 5 percent of the speed of sound of water. Using this image of speed of sound the forward scattering algorithm then computed the scattered field at a set of detectors on the perimeter of the image for the case of incident plane waves for 200 source directions equally spaced in angle around 360 degrees. The detectors enclosed the cross section on all sides and numbered 4(200)×4=796. This set of synthetic scattering data was used to compute the inverse scattering image of FIG. 28B.

FIG. 28B shows the inverse scattering image computed from the synthetic data generated from the image in FIG. 28A. Note that the quantitative values in each pixel are preserved and that the spatial resolution is only slightly degraded.

Figure 29A:
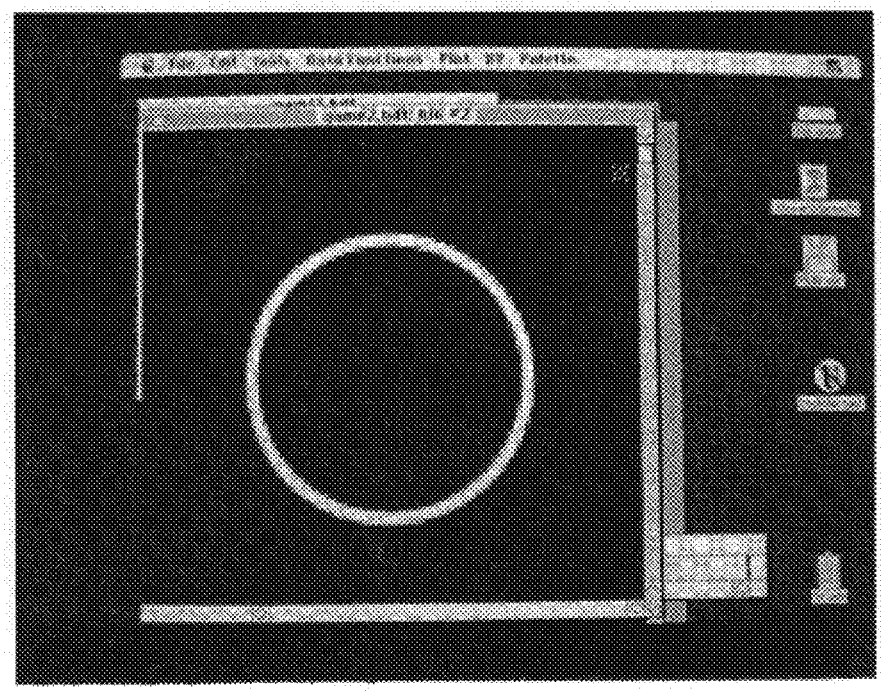
Figure 29B:
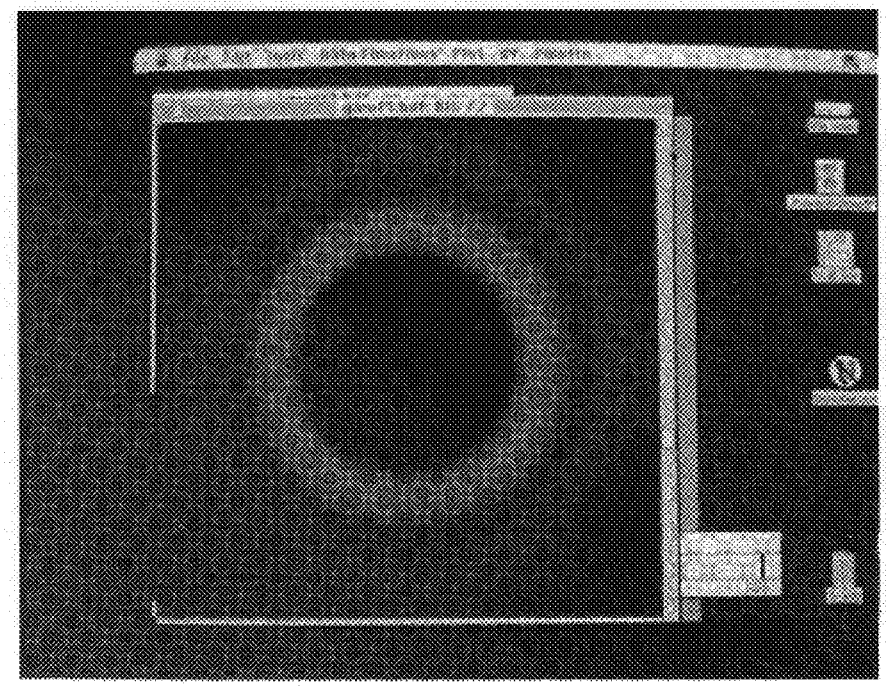

FIGS. 29A and 29B show that the quality of inverse scattering images of a test object computed from real data collected in the laboratory is excellent. The laboratory data was collected using microwave energy at 10 GHz. FIG. 29A is the image of the cross section of a test object that is a thin walled plastic pipe with an outside diameter of 6 cm and a wall thickness of 4 mm. This pipe was illuminated by microwaves at 10 GHz from a horn antenna. A second receiver horn antenna was rotated 120 degrees in both clock wise and counter clock wise directions from the forward propagation direction, about the sample to pick up the scattered field. The receiving antenna rotates around an axis that is parallel to the axis of the pipe. The transmitting antenna and the receiving antenna lie in a common plane that is perpendicular to the axis of the pipe. FIG. 29B is the inverse scattering image made from the data collected by the receiving antennas. The thickness of the pipe wall has been broadened because the true pipe wall thickness is less than one half wave length at 10 GHz. The reconstructed wall thickness is about 0.6 wave length.

Figure 29C:
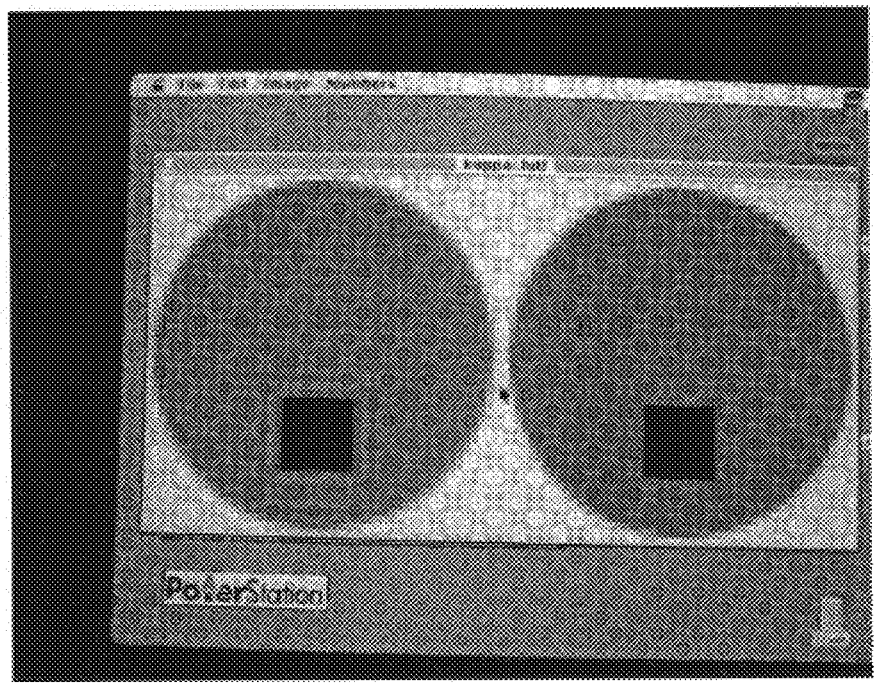
Figure 29D:
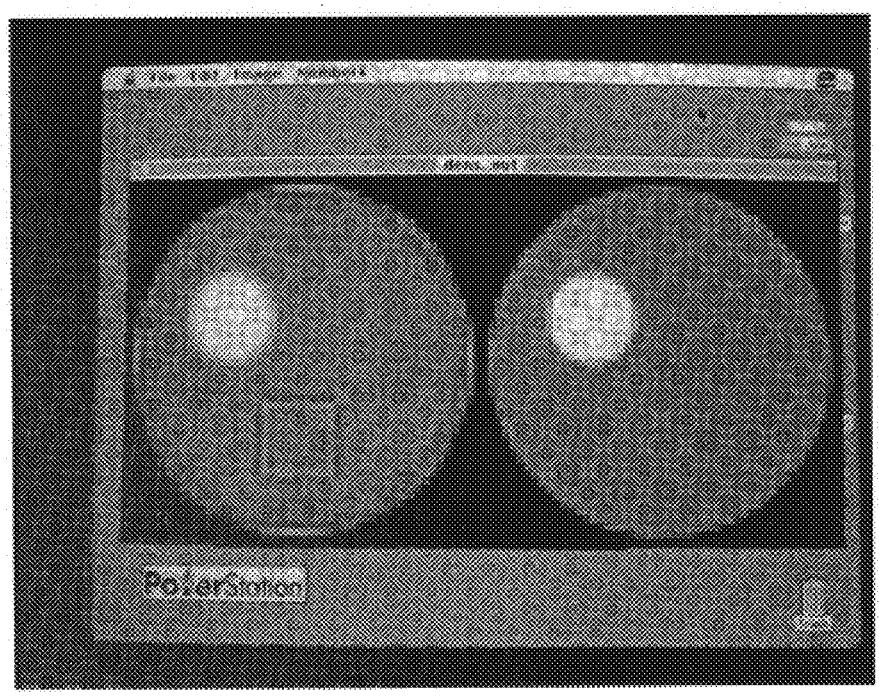
Figure 29E:
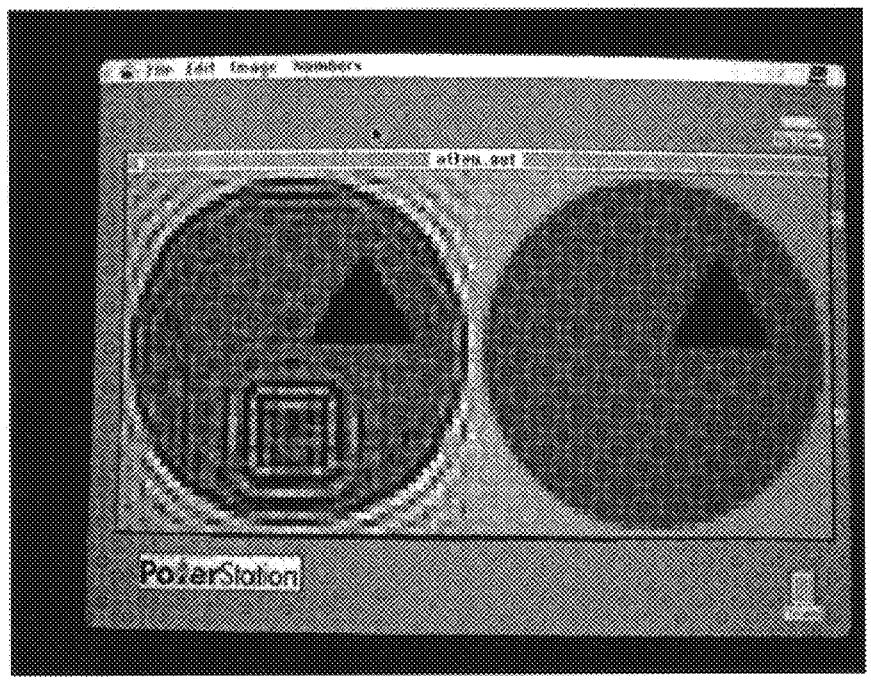

FIGS. 29C, 29D and 29E demonstrate through computer simulation that three different and independent acoustic parameters can be imaged accurately by inverse scattering. FIGS. 29C, 29D and 29E show respective images of compressibility, density and acoustic absorption. The images are 50 by 50 pixels, each pixel being ¼ wavelength square, and were reconstructed from frequencies in the range from $f_{max}$ to $f_{max}/50$. The sources were 8 plane waves equally distributed around 360 degrees. The receivers surrounded the object and were placed on the perimeter of the image space. In FIG. 29C an image of true compressibility in the test object is on the right while the reconstructed compressibility is shown on the left. The compressibility scattering potential component has a range of values spanning 0.2 for black, 0.1 for gray and 0 for white. The compressibility region is square in shape. Note that little cross coupling from density and absorption is present. FIG. 29D shows on the right an images of true density in the test object, while the reconstructed density is shown on the left. The density scattering potential component has a range of values spanning 0 for black, −0.025 for gray and −0.05 for white. The density region is circular in shape. Note that little cross coupling from absorption is present and a small amount from compressibility is present. FIG. 29E shows on the right an image of true acoustic absorption in the test object, while the reconstructed acoustic absorption is shown on the left. The attenuation scattering potential component has a range of values spanning 0 for white, 0.01 for gray and 0.02 for black. The absorption region is triangular in shape. Note that little cross coupling from density is present but a little cross coupling from compressibility is present.

Figure 30A:
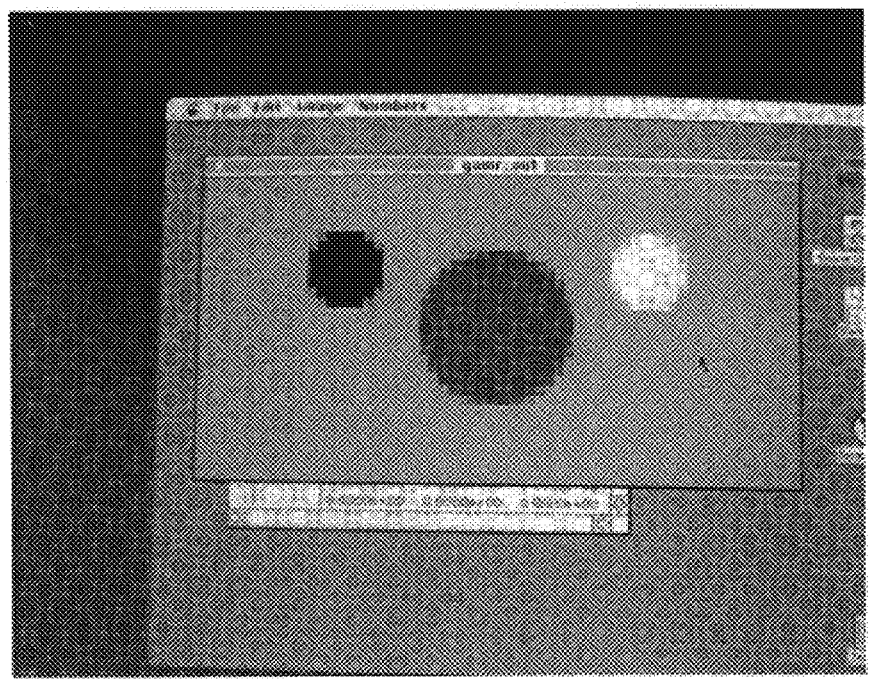
FIG. 30 A/B/C shows the application of inverse scattering to the case where sources and detectors are limited to a single line (as in the case of 2-D scattering) or a single plane (as in the case of 3-D scattering).
Figure 30B:
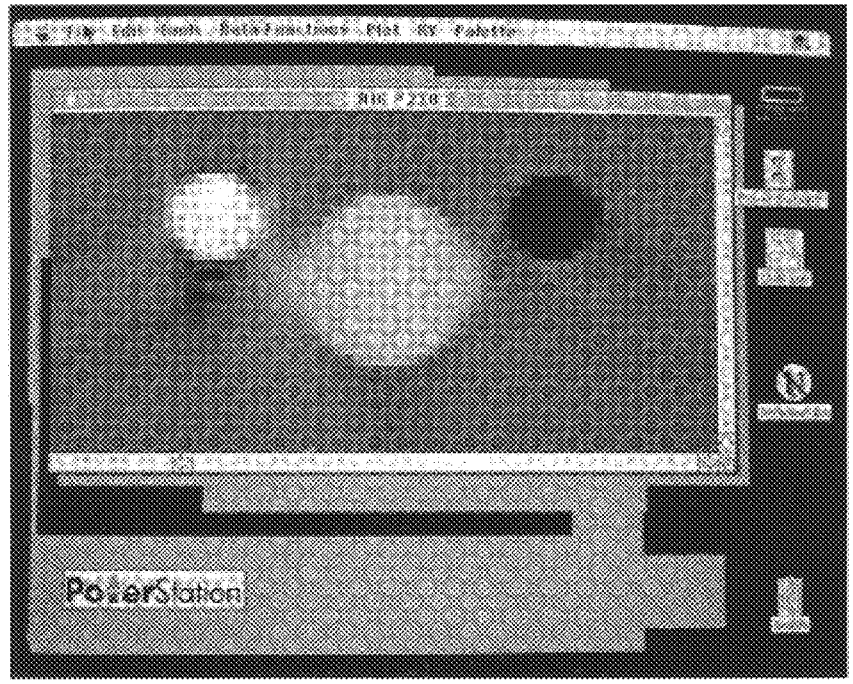
Figure 30C:
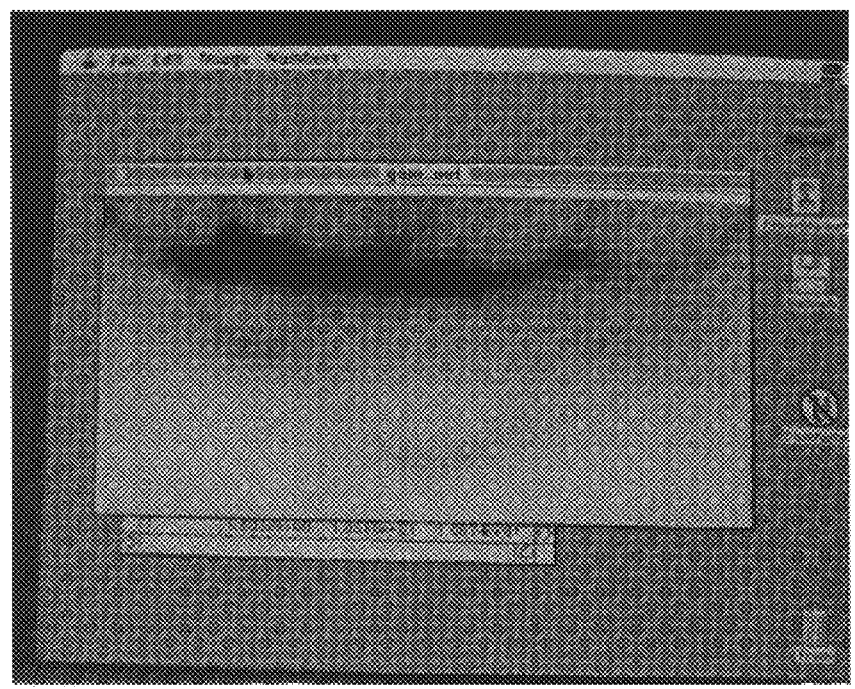
Figure 31:
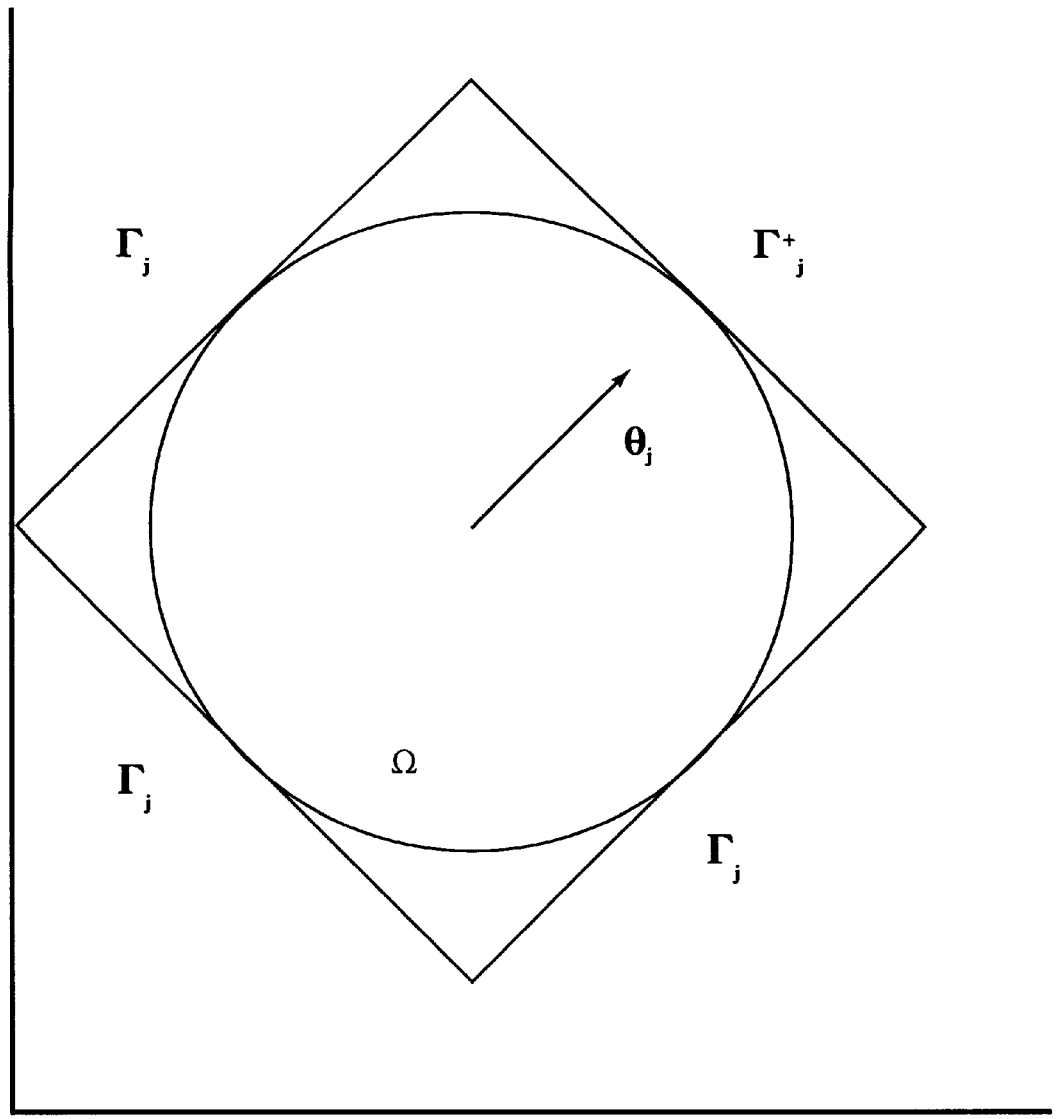
FIG. 31 shows the renumbering scheme for the grid points (case n=4) for the forward propagation method described in the paper "A finite difference method for the inverse scattering problem at fixed frequency", F. Natterer, F. Wuebbling, which is included herein as reference. It is referred to as "FIG. 1"0 in this paper.
Figure 32:
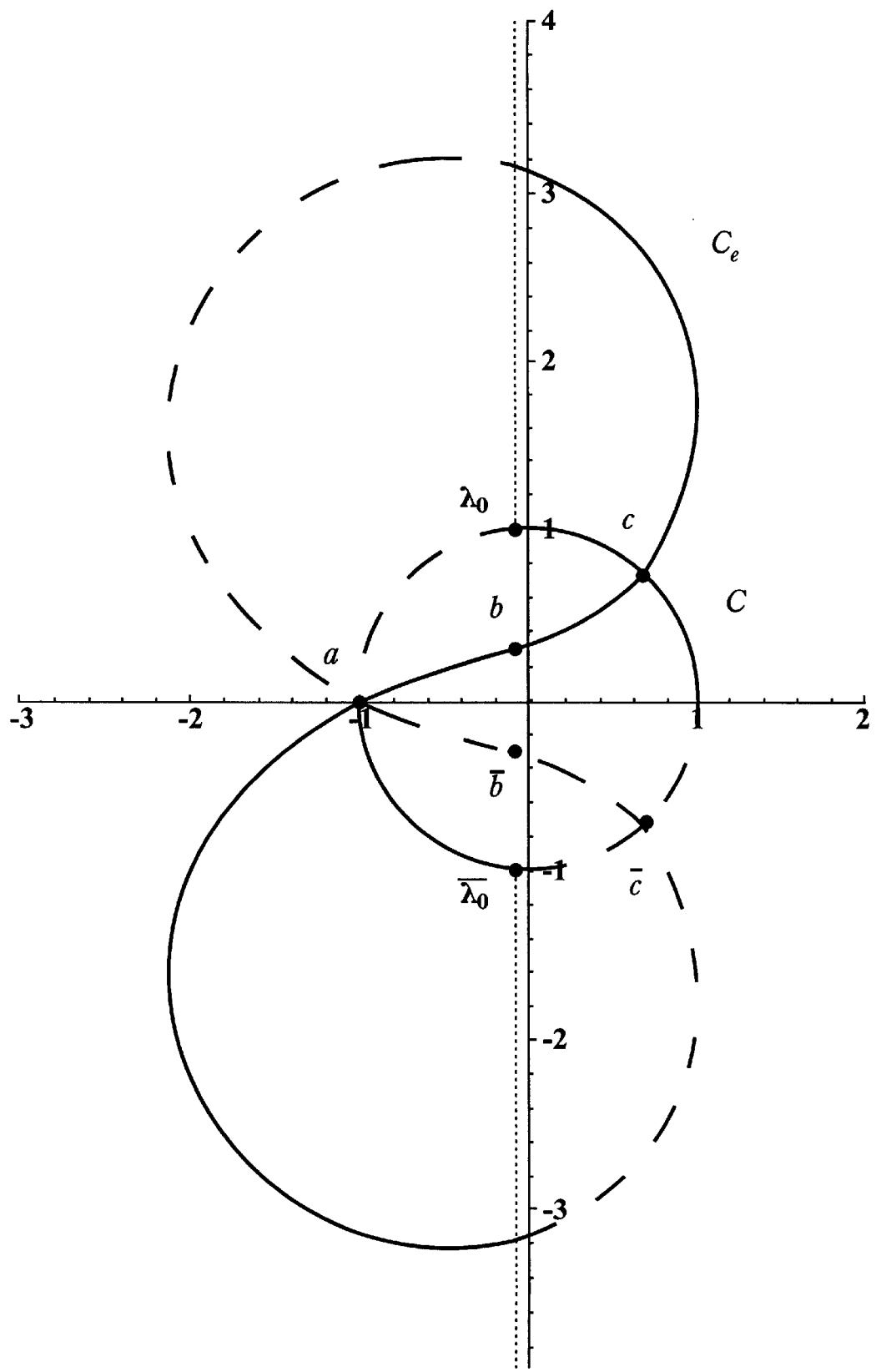
FIG. 32 shows the curve $\lambda=\lambda(\phi)$, for $0 \leq \phi < 2\pi$ for $\epsilon=\pi$ (solid line) and $\epsilon=2\pi$ (dashed line)—see the paper "A finite difference method for the inverse scattering problem at fixed frequency", F. Natterer, F. Wuebbling, which is included herein as reference, for explanation of terminology. These lines are curves of integration used in the investigation of the stability of the finite difference procedure used to solve the forward problem. This is referred to as FIG. 2 in this paper.
Figure 33:
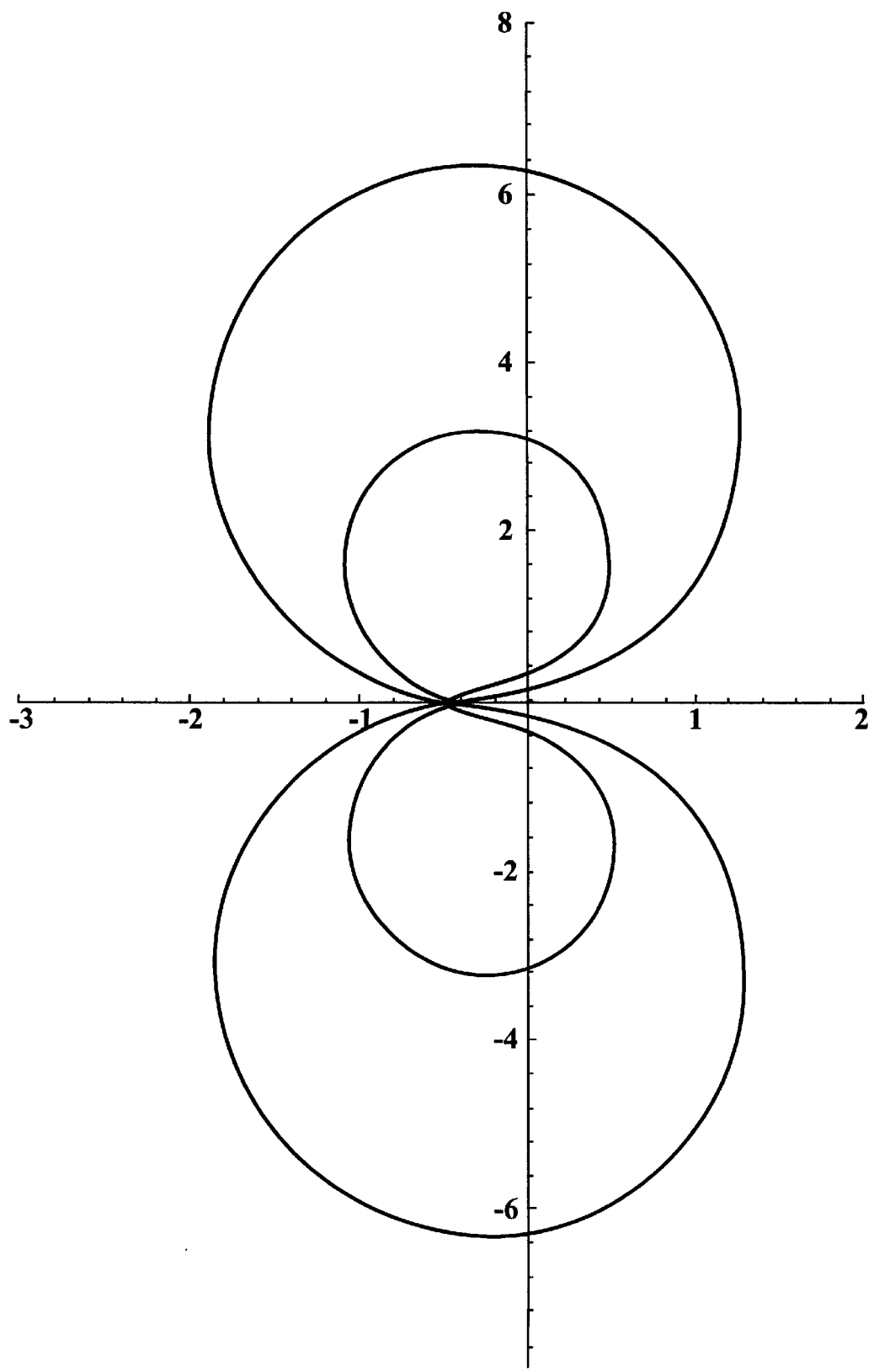
FIG. 33 is referred to as FIG. 3 in the paper "A finite difference method for the inverse scattering problem at fixed frequency", F. Natterer, F. Wuebbling, which is included herein as reference. The curves are $C_\epsilon$ (for $\epsilon=\pi$) and C on the Riemann surface $\Lambda$. The solid line is on the upper sheet of the Riemann surface and the dashed line is on the lower sheet of the Riemann surface. The dots indicate the branch cuts which join these upper and lower Riemann sheets to form the complete Riemann surface in the sense of complex variable theory.
Figure 34:
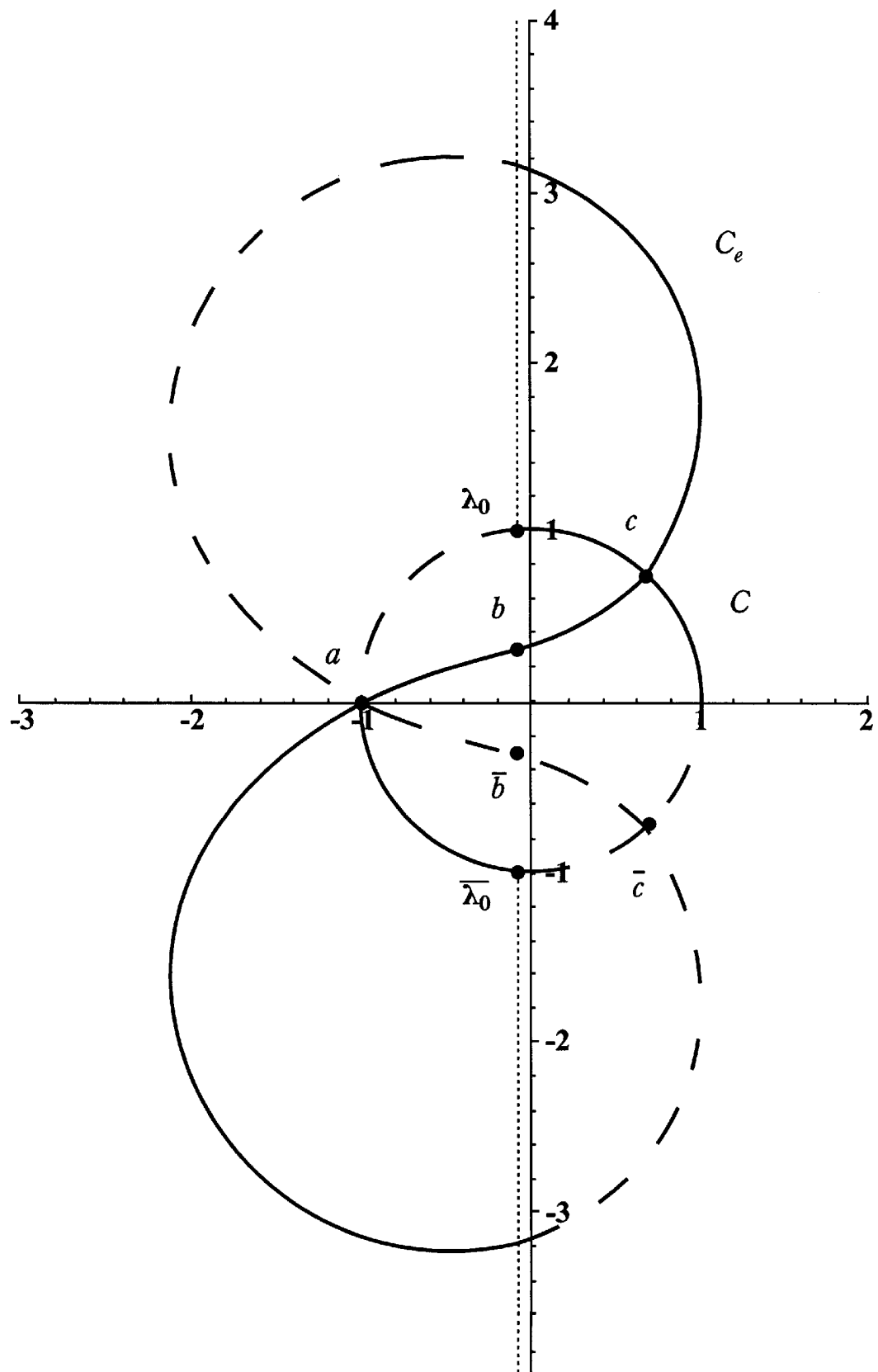
FIG. 34 shows the basic Geometry for the paper "A Propagation-Backpropagation Method for Ultrasound Tomography", Frank Natterer, which is included herein as reference. This is referred to as FIG. 1 in this paper. The square $Q_j$ is the square of sidelength $2\rho$ whose boundary is made up of $\Gamma_j$ (side-scatter directions), $\Gamma_j^-$ (Backscatter direction), and $\Gamma_j^+$ (forward scatter direction). It encompasses the region $\Omega$, which contains the support of the object function $\gamma$. $\theta_j$ is the direction of the incident wavefield propagation.
Figure 35:
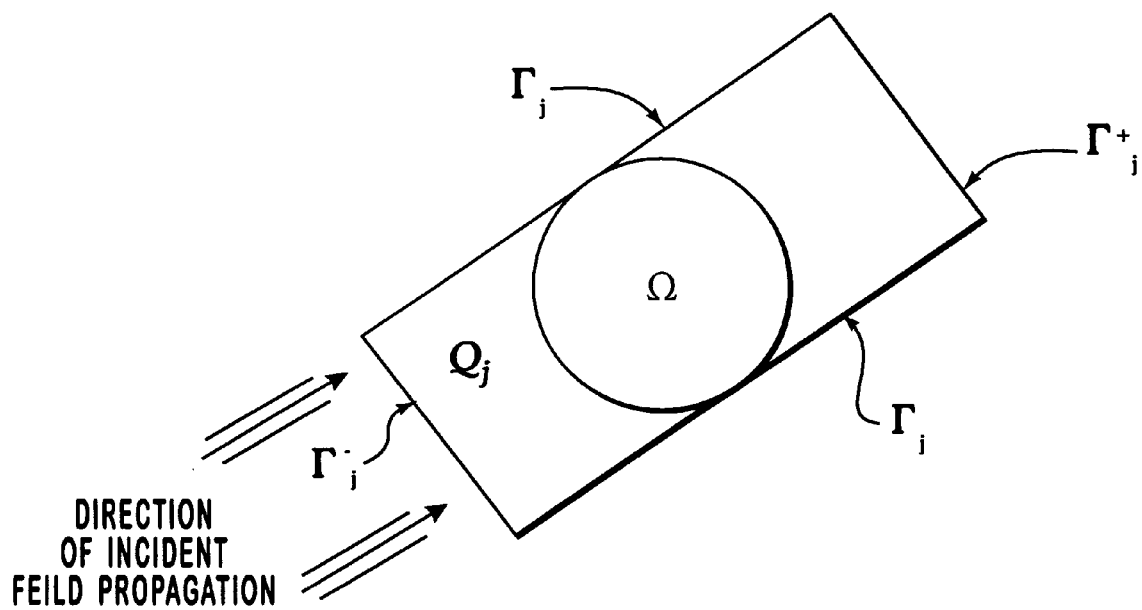
FIG. 35 shows an elongated rectangle $Q_j$ enclosing the region $\Omega$, with boundaries $\Gamma_j$ (side-scatter directions), $\Gamma_j^-$ (Backscatter direction), and $\Gamma_j^+$ (forward scatter direction). $\theta_j$ is the direction of the incident wavefield propagation.
Figure 36:
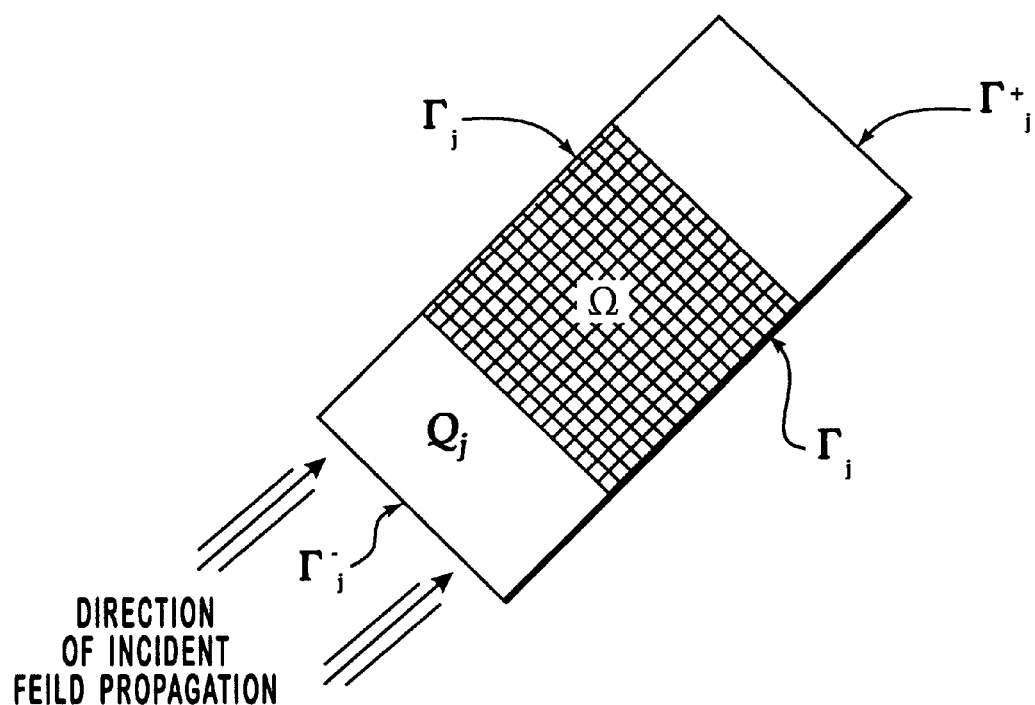
FIG. 36 shows the same rectangle with the pixelated region containing the support of the object function $\gamma$. Once again, $\theta_j$ is the direction of the incident wavefield propagation.

FIGS. 30A, 30B and 30C describe the application of inverse scattering to the case where sources and detectors are limited to a single line (as in the case of 2-D scattering) or a single plane (as in the case of 3-D scattering). FIG. 30A shows the true scattering potential values for a test object. In this example, the scattering potential variation corresponds to different dielectric constants. The background dielectric constant corresponds to earth with a dielectric constant of 18 and extends to infinity on both sides and below the image space. Air, with a dielectric constant of unity lies above and next to the top of the image. The small black circle has a dielectric constant of 21.6; the small white circle on the right has a dielectric constant of 16.2; and the larger gray circle in the center has a dielectric constant of 19.8. The pixels are ¼ wave length on a side at the highest frequency. A set of 32 frequencies uniformly distributed between the highest to 1/32 of the highest are used. The image space is 64 pixels horizontally and 32 pixels vertically. 64 detectors and 5 sources are uniformly placed across the top of the image space. The scattering potential values, relative to the background dielectric constant of 18, (scattering potential=$\epsilon$/$\epsilon$background−1) span the range of 0.1 for black to −0.1 for white. A dielectric constant of 18 therefore corresponds to a scattering potential of zero.

FIG. 30B shows the inverse scattering reconstruction generated by imaging data synthesized from the model in FIG. 30A (please note that the image in this figure was accidentally video reversed). The synthesized data was inverted using a layered Green's function. Note the excellent spatial resolution and excellent quantitative accuracy of the reconstruction.

FIG. 30C shows an image generated by using conventional radar beam forming methods. This conventional method places echoes at a given range and angle by processing the transmitted signals into transmit beams and the received signals into receiver beams. This conventional method is mathematically equivalent to seismic migration imaging. Such methods are linear, not nonlinear as is inverse scattering. As such, linear methods do not accurately model multiple scattering, reverberation from the air-soil interface, and refraction. Such images are not quantitative. Note the inferior quality of this image relative to the inverse scattering image in FIG. 30B.

Figure 39A:
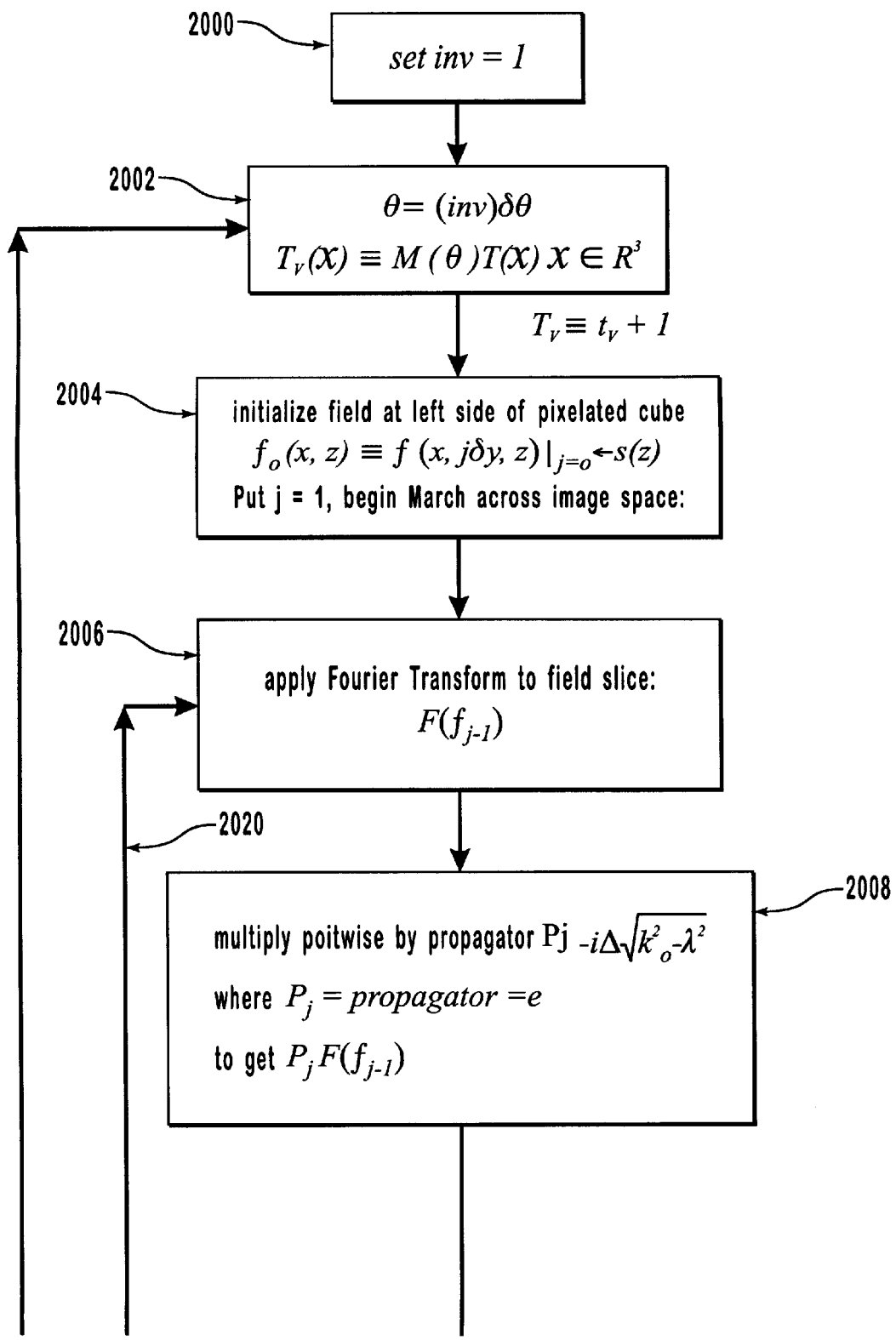
FIG. 39 A/B show the flowchart for the solution of the forward problem by means of the Parabolic FFT Marching method.
Figure 39B:
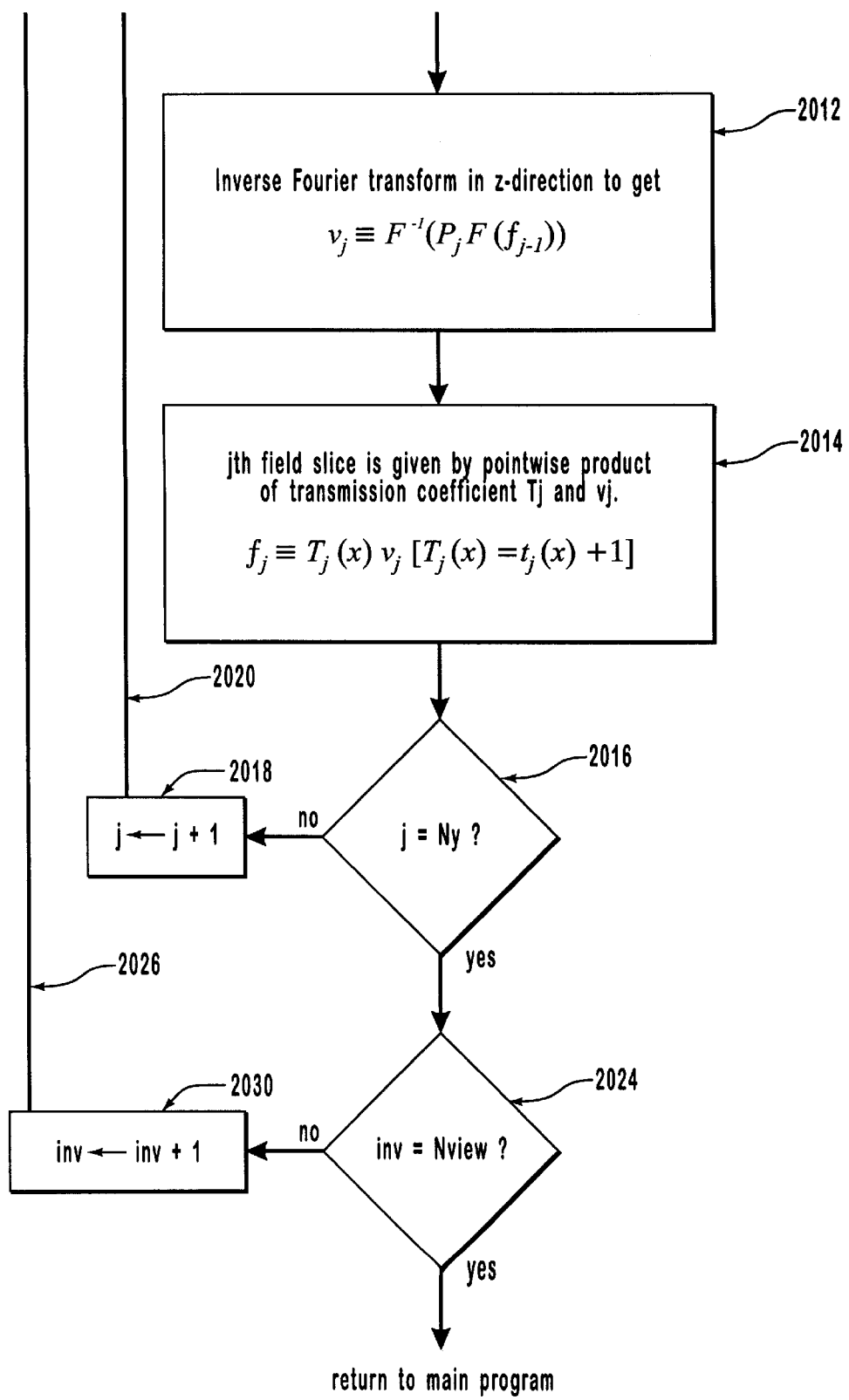

Detailed Description of FIGS. 39A, B

Subroutine "scatter" is called from main program in FIG. 39A, in order to effect the forward calculation of the fields for each view. Control is transferred to box 2000, where inv is set=1 (inv is the index of views). Next, in box 2002, is the calculation of rotation angle θ=(inv−1)δθ, and the setting up of rotation matrix M(θ), which is then applied to transmission coefficient matrix T to yield $T_v(x)=M(\theta)T(x) x \in R^3$ Next control is moved to box 2004, where the field for the first "slice" (ie. j=1) is set to predetermined values: s(i,k), and the y index, "j" is set=1, $f_o(x, z) \equiv f(x, j\delta y, z)|_{j=0} \leftarrow s(z)$.

Control is then transferred to box 2006, where the Fourier Transform is applied to field slice j−1 $F(f_{j-1})$ Control is then transferred to box 2008, where the pointwise product is taken between the propagator $P_j$, defined as $$P_j = \text{propagator} = e^{-i\Delta\sqrt{k_o^2-\lambda^2}},$$

and the result from box 2006, to get $P_j F(f_{j-1})$. Now transfer to box 2012 where we take the Inverse Fourier transform in z-direction to get $v_j=F^{-1}(P_j F(f_{j-1}))$. Then move to box 2014, where $j^{th}$ field slice is given by pointwise product of transmission coefficient $T_j$ and $v_j$. $f_{j=Tj}(x)v_j$. Then transfer control to decision box 2016, whereupon: if j is strictly less than $N_y$, then control moves to box 2018, where index j is increased by 1, and control is directed along arrow 2020 to box 2006. If j is exactly $N_j$, control is transferred to decision box 2024. Then, if inv<$N_{view}$, control is transferred to box 2030 where inv is incremented by 1 to inv+1, and control is then transferred along arrow 2026 to box 2002. When inv=$N_{view}$, control is returned to the main program.

Figure 40A:
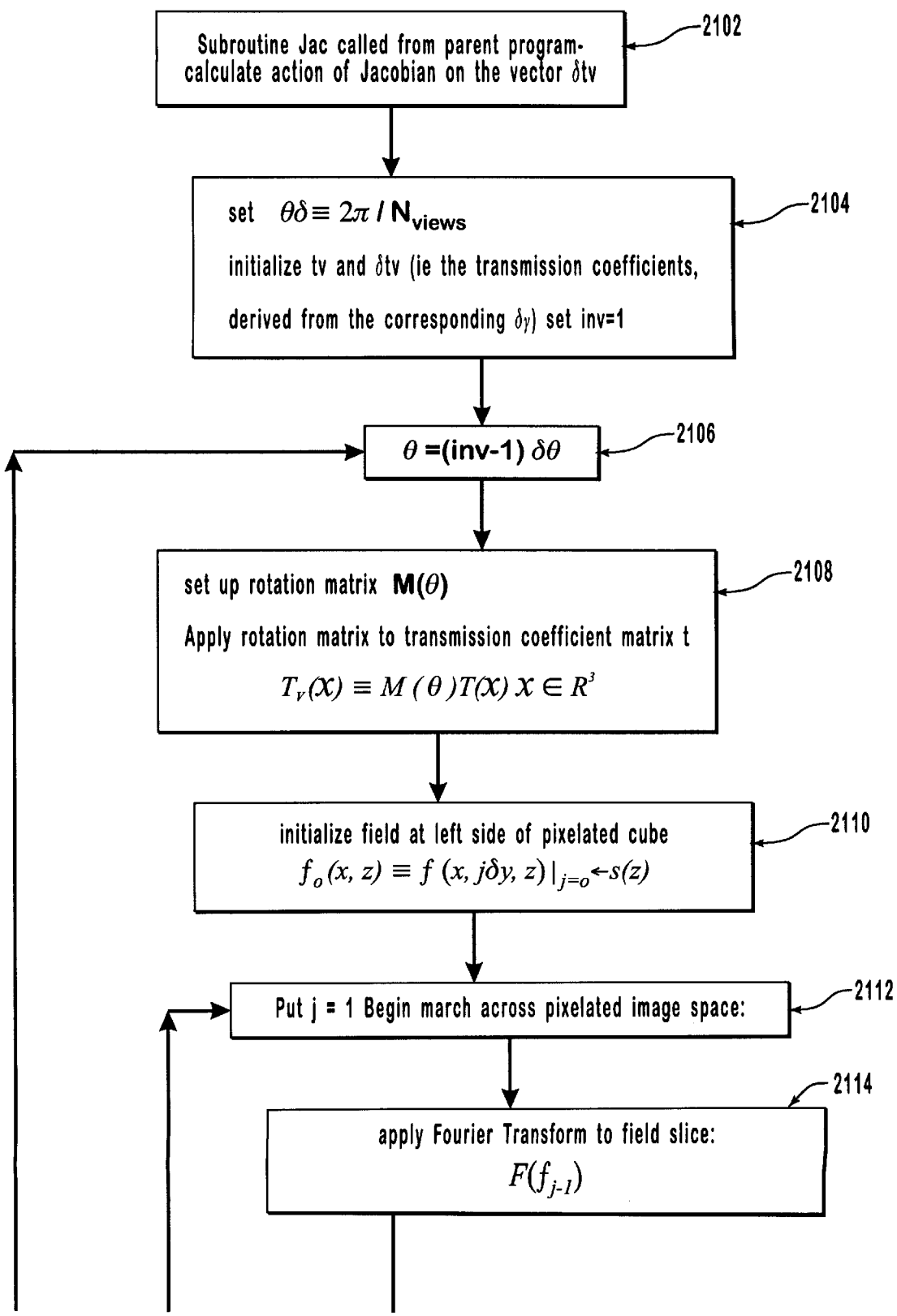
FIG. 40 A/B/C show the flowchart for the solution of the Jacobian of the forward problem for the Parabolic FFT Marching method.

Detailed Description of FIGS. 40A, B, C

Control is passed to subroutine Jac from the parent program in box 2102 It will calculate the action of the Jacobian of the forward problem on the vector δγ. Control is transferred to box 2104 where δθ is determined via the formula δθ≡2π/$N_{views}$, the spatially dependent transmission coefficient $T_v=t_v+1$ ($T_v=T_v$ (x,y,z) and the inputδt, or the corresponding δγ (object function) are also initialized, and inv is set=1, ie. the index corresponding to view number Control is then transferred to box 2106 where one sets θ=(inv−1)δθ, and thus to box 2108 which sets up rotation matrix M(θ), and applies rotation matrix to transmission coefficient matrix T: $T_v(x)=M(\theta)T(x) x \in R^3$. Control is then transferred to box 2110 which initializes field at left side of pixelated cube using the formula $f_o(x, z) \equiv f(x, j\delta y, z)|_{j=0} \leftarrow s$(z).

Figure 40B:
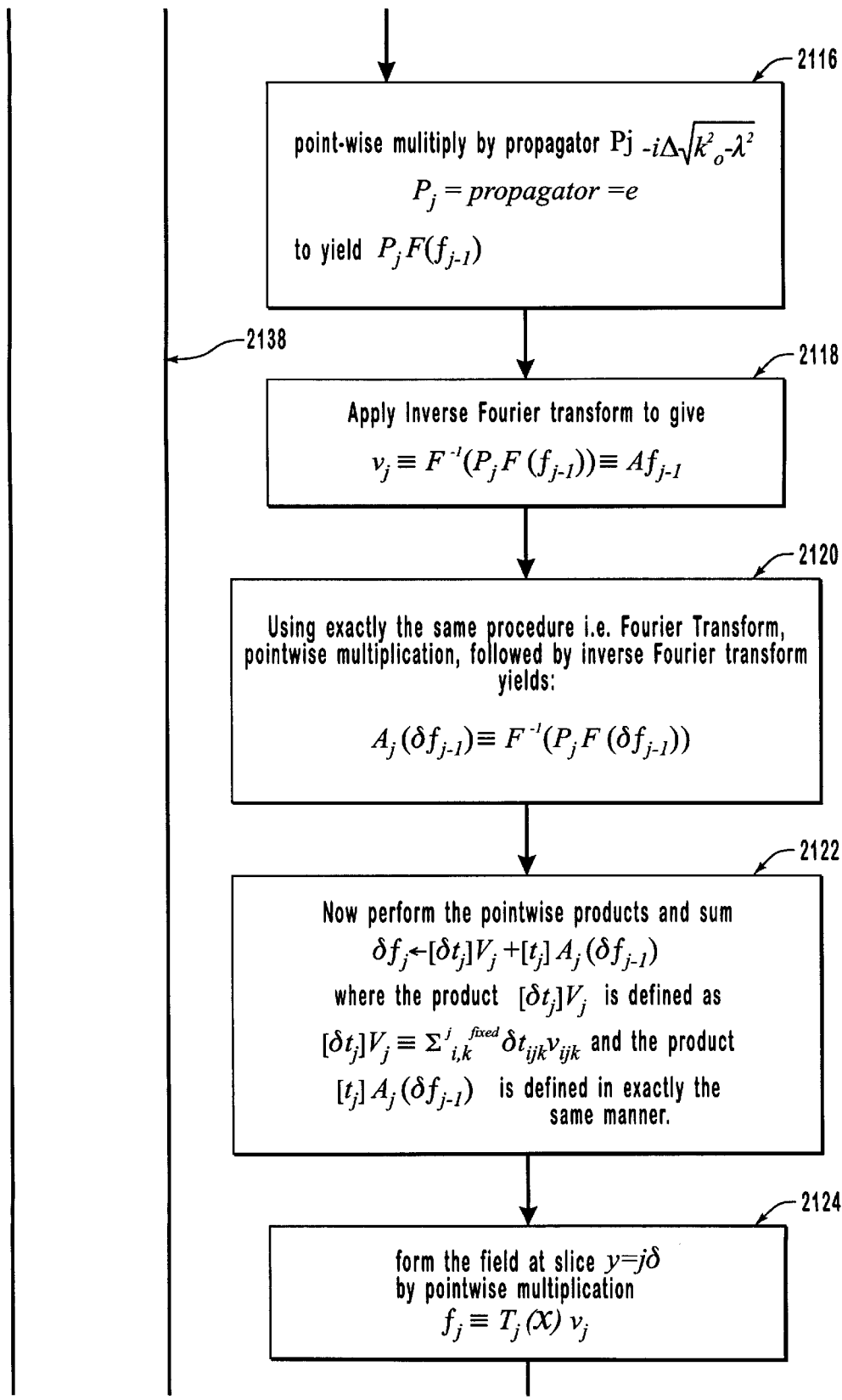

Now begin the march across the pixelated image space by transferring control to box 2112 where j (y index) is set=1. Then control moves to box 2114 where we apply Fourier Transform to field slice j−1: $F(f_{j-1})$. Then control is transferred to box 2116 of FIG. 40B where we multiply pointwise by propagator $P_j$ $$P_j = \text{propagator} = e^{-i\Delta\sqrt{k_o^2-\lambda^2}}$$

to get $P_j F(f_{j-1})$. We now move to box 2118 where the Inverse Fourier transform in z-direction is applied to get $v_j=F^{-1}(P_j F(f_{j-1}))\equiv \Lambda f_{j-1}$ (this slice $v_j$ will be used later, and so is not overwritten). Control is then transferred to box 2120, where $A_j(\delta f_{j-1})\equiv F^{-1}(P_j F(\delta f_{j-1}))$ is computed in exactly the same manner, i.e. the Fourier transform is applied to $\delta f_{j-1}$, then the propagator is pointwise multiplied, and finally the inverse Fourier Transform is taken.

Control is then transferred to box 2122, where the pointwise product between the $v_j$ (calculated above) and $\delta t_j$, $[\delta t_j]v_j$ is formed. Also the pointwise product involving$t_j$: $[t_j]A_j(\delta f_{j-1})$ is formed. The definition of the pointwise product is given explicitly by $$[\delta t_j]v_j \equiv \sum_{i,k}^{j\, fixed} \delta t_{ijk}\, v_{ijk}.$$

Finally form the sum of the resulting "vectors", $\delta f_j \leftarrow [\delta t_j]v_j+[t_j]A_j(\delta f_{j-1})$.

Control is then transferred to box 2124, where the field at slice γ=δjis formed to obviate the need to store/read the fields on disk, which is very time consuming. The field is given by the pointwise product of transmission coefficient $T_j$ and "slice" vj.: $f_j \equiv T_j(x)v_j$ Control is now transferred to decision box 2126: If j=$N_y$ (ie the right hand side of the pixelated image space has been reached) then control is transferred to decision box 2130. If, however, the answer to query j=$N_y$? is no", then control is transferred to 2128 where the "slice" index is incremented by +1, and control is transferred along arrow 2138 to box 2114 of FIG. 40A, where the Fourier transform is applied to the field slice $f_{j-1}$.

Figure 40C:
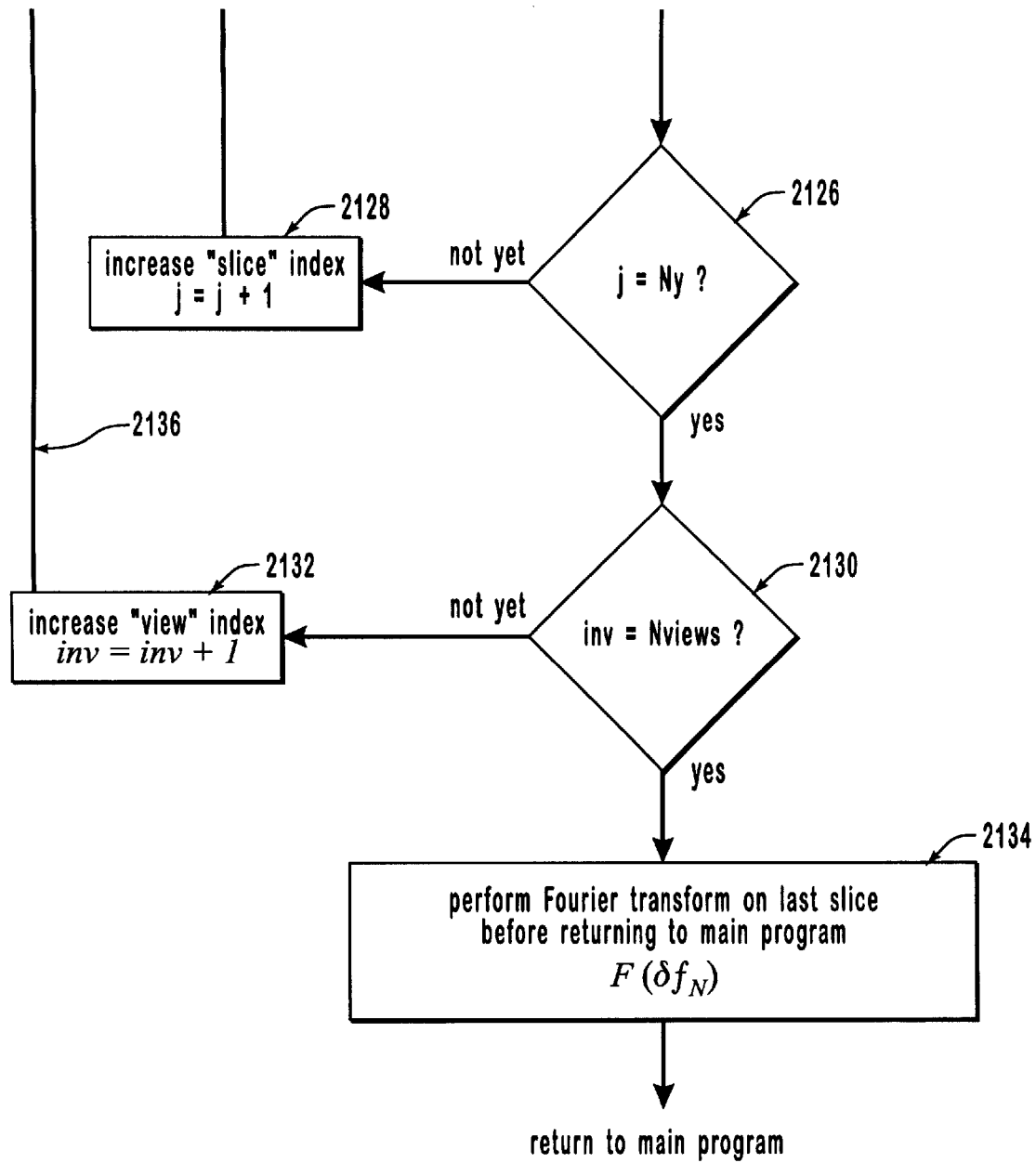
Figure 41A:
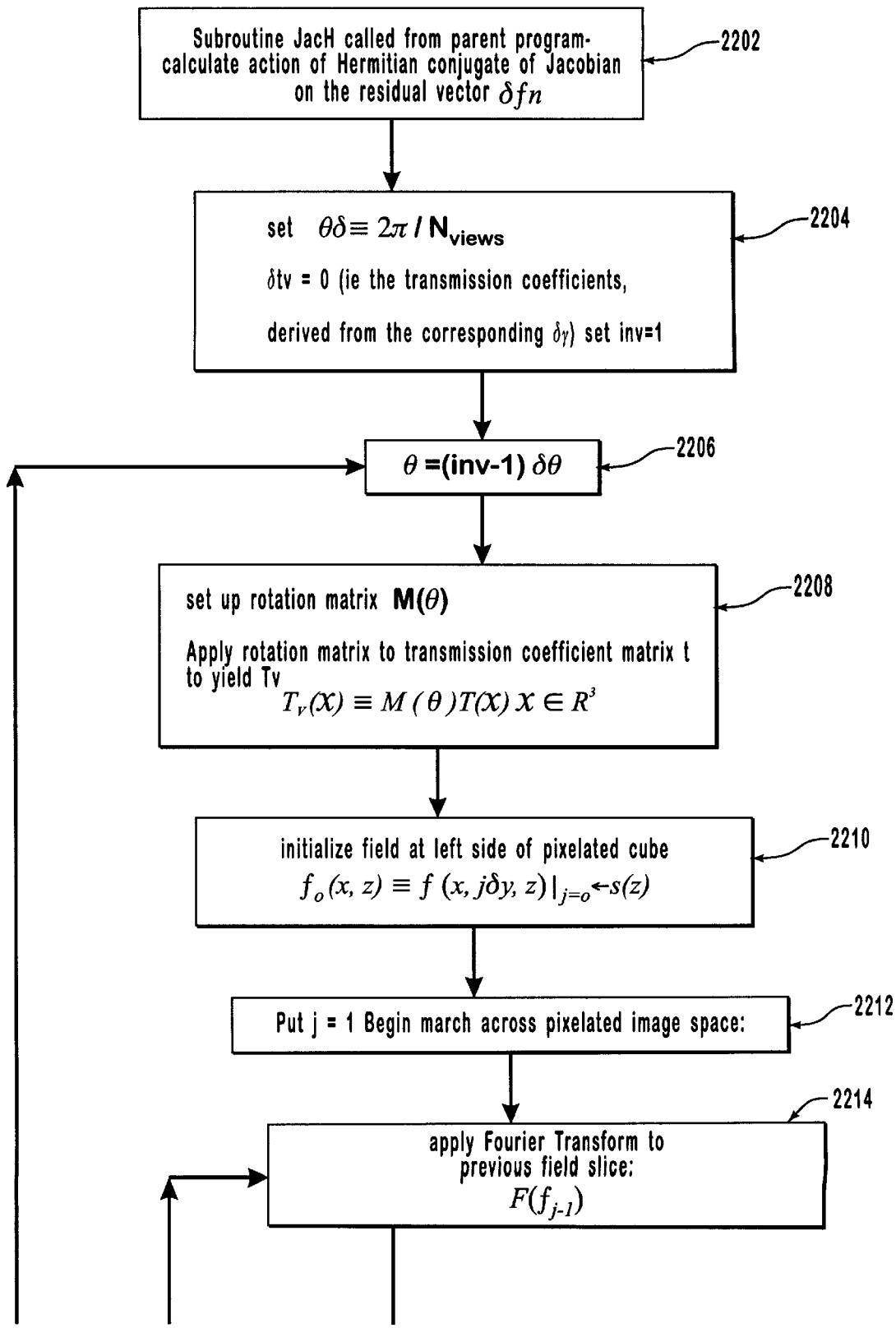
FIGS. 41 A/B/C/D show the flowchart for the action of the Hermitian conjugate of the Jacobian for the Parabolic FFT Marching method.
Figure 41B:
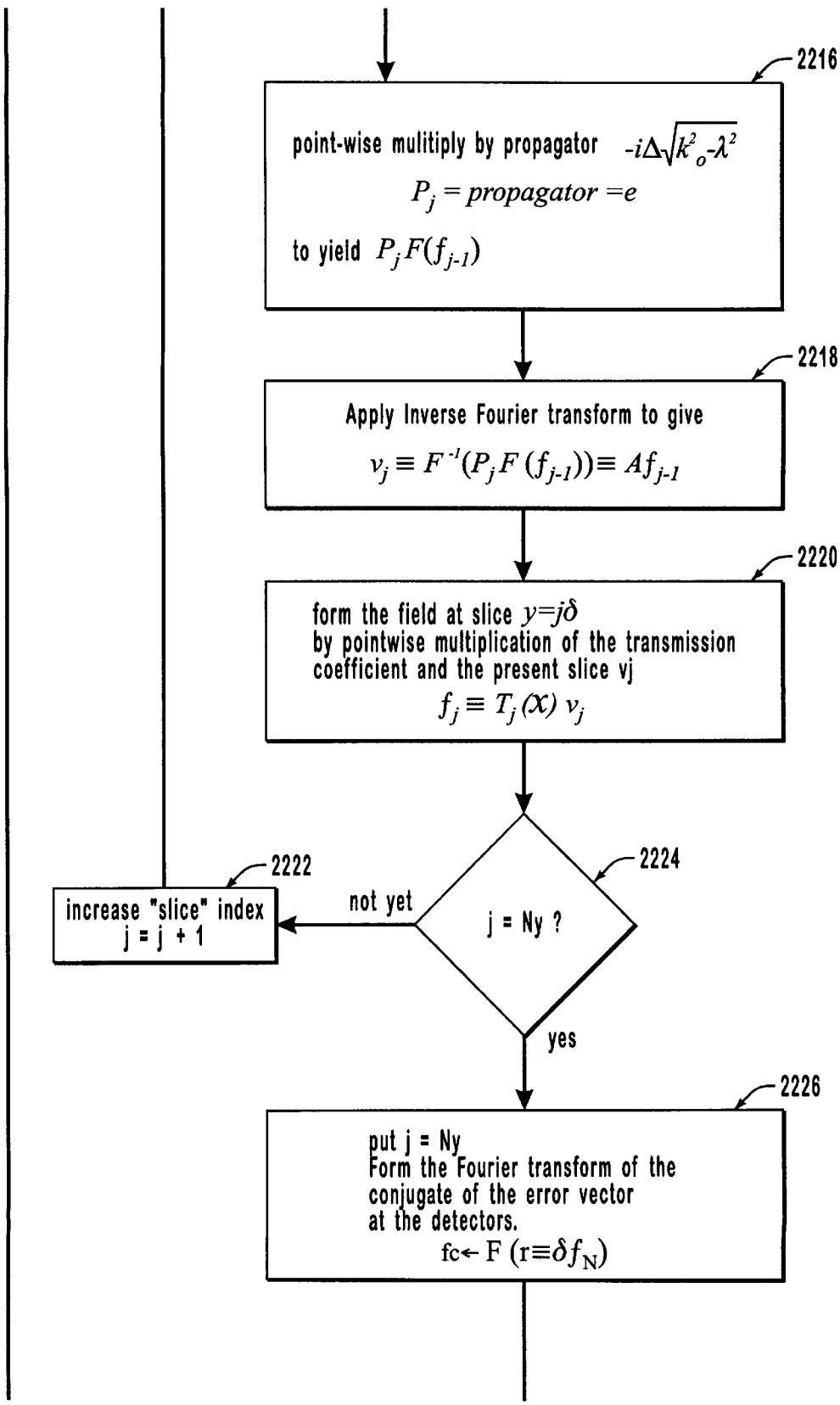
Figure 41C:
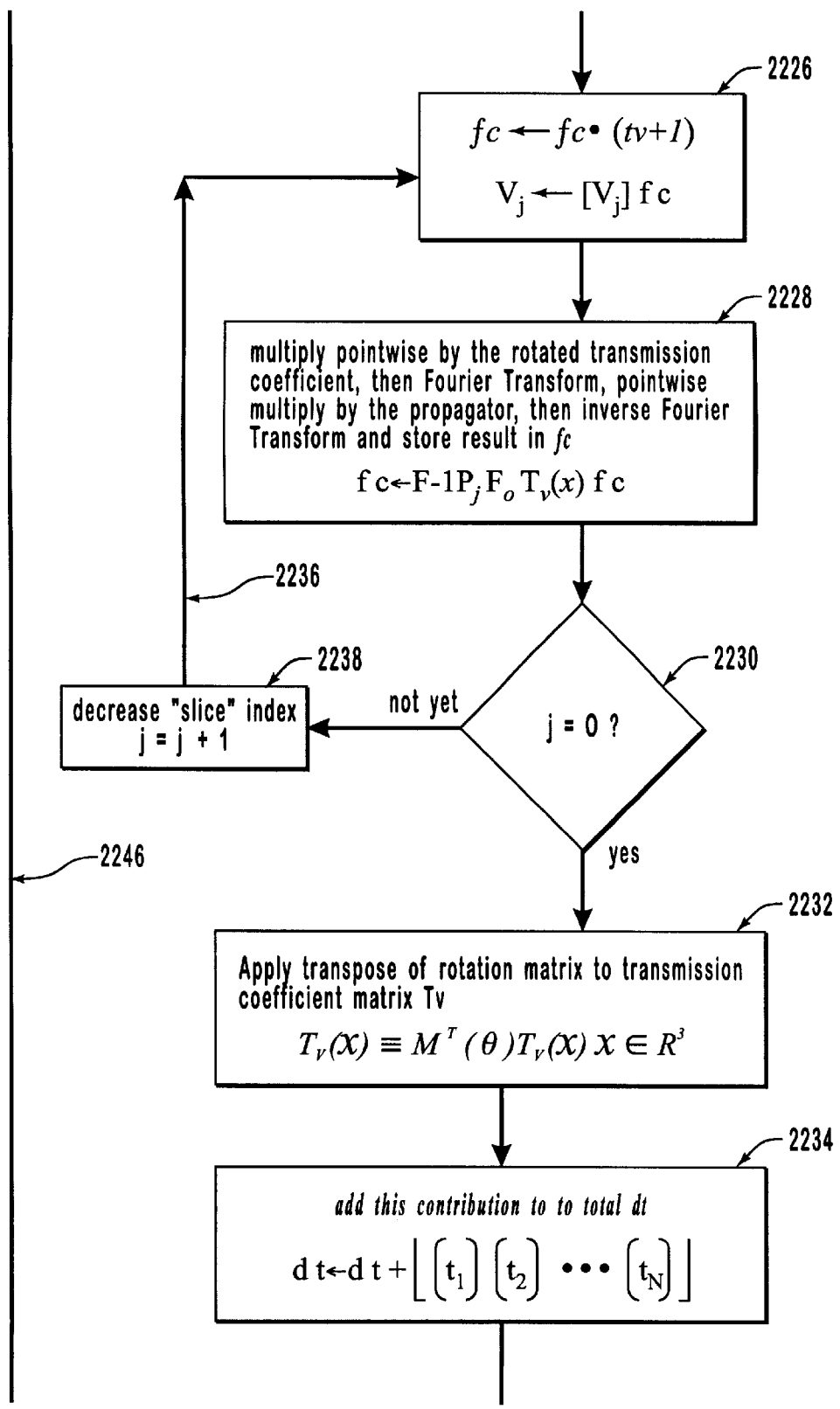
Figure 41D:
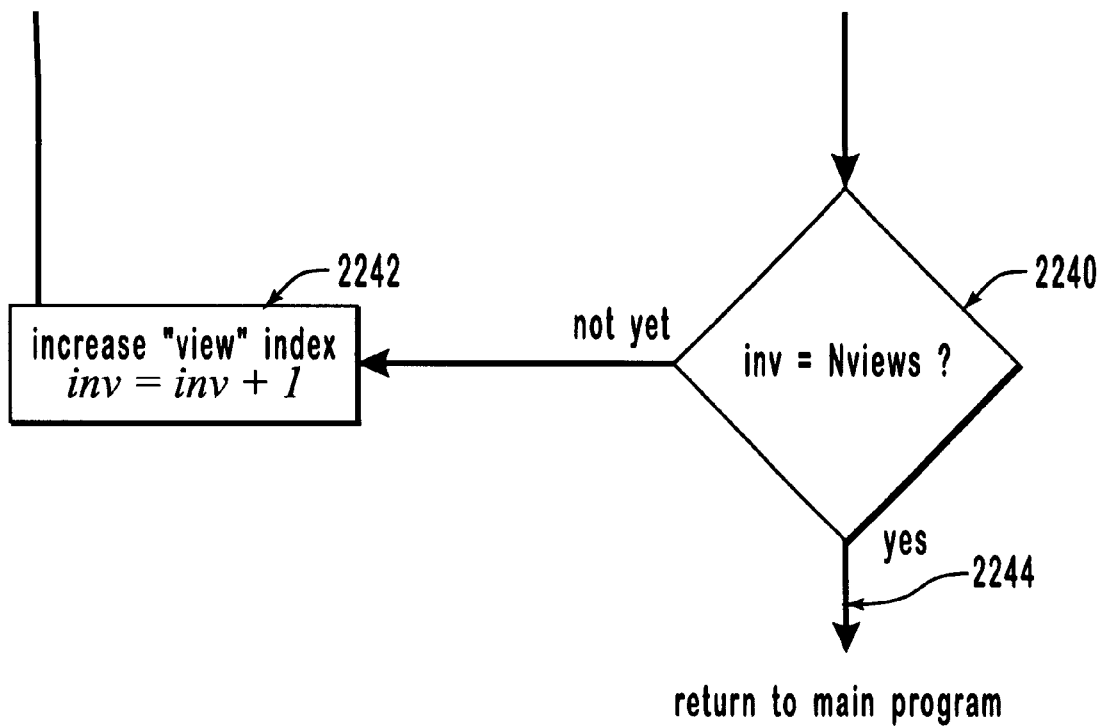

If control has been transferred to decision box 2130 of FIG. 40C, and if the index for "view", inv=$N_{view}$, then control moves to box 2134, where the Fourier Transform is applied to the error on the detectors $\delta f_N$: $fc \leftarrow F(r \equiv \delta f_N)$, The resulting $fc$ is pointwise multiplied by a scaling which in some cases, leads to more rapid convergence. This scaling is not critical to the implementation of the algorithm. The vector $fc$ (scaled or not) is the output for the subroutine.

Detailed Description of FIGS. 41 A,B,C

Subroutine JacH(r) is called from parent program—it will calculate action of Hermitian conjugate of Jacobian on the residual vector r. Control is transferred from box 2202 to box 2204 where δθ is determined: δθ≡2π/$N_{views}$, also δt is initialized=0 and inv is set=1. Control is transferred then, to box 2206 where θ is defined according to: θ=(inv−1)δθ. Control is transferred to box 2208, where the rotation matrix M(θ) is defined, and applied to transmission coefficient matrix T toyield $T_v$. $T_v(x)=M(\theta)T(x)$ $x \in R^3$. Then control is transferred to box 2210, where the field at the left side of the pixelated cube is initialized: $f_o(x, z) \equiv f(x, j\delta y, z)|_{j=0} \leftarrow s(z)$ Next control is transferred to box 2212, where j is set=1, and the march across the pixelated image space is begun.

Next control is transferred to box 2214 the Fourier transform is applied to the field slice $f_{j-1}$:$F(f_{j-1})$ and control is transferred to box 2216, where pointwise multiplication by the propagator $P_j$ is carried out, where $P_j$=propagator=$e^-$ $$P_j = \text{propagator} = e^{-i\Delta\sqrt{k_o^2-\lambda^2}}.$$

The result, $P_j F(f_{j-1})$ is then transferred to box 2218 where the inverse Fourier transform in the z (vertical) direction is applied, yielding $v_j=F^{-1}(P_j F(f_{j-1}))$. This $v_j$ will be used below, and so is saved.

From this, control moves to box 2220, where the field slice at γ=jδ (recall that field values are recomputed to obviate the time consuming storage/retrieval of these on disk) is given by pointwise product of transmission coefficient $T_j$ and $v_j$. $f_j \equiv T_j(x)v_j$. Control now goes to decision box 224, whereupon if j is strictly less than $N_y$, control is switched to box 9292, where index j is increased by 1, and control reverts to box 2214, where the Fourier transform of the next field slice is taken. When j is equal to $N_y$, control is transferred to box 2226 of FIG. 41B. This is the beginning of the backward moving loop (ie. j decreases from $N_y$ to 1). Here we form the Fourier transform of the conjugate of the error vector at the detectors, and store result in $fc$: $fc \leftarrow F$ ($r \equiv \delta f_N$).

Now use $v_j$ (calculated in loop above) and fields $fc_j$ to calculate action of Jacobian on r, the error in field at the detector (far side of image space) in the following manner:

Control then moves to box 2226 where $fc$ is redefined as $fc \cdot (t_v + 1)$ and the pointwise product between the resulting $fc$, and $v_j$ is taken, and stored in $v_j \leftarrow [v_j]fc$. Control is then transferred to box 2228 where we pointwise multiply $fc$ by rotated transmission coefficient $T_v$, Fourier Transform the result, pointwise multiply by propagator $P_j$, then inverse Fourier Transform (in z direction) the result; finally store the resulting slice in $fc$ (overwriting previous contents) $fc \leftarrow F^{-1} P_j F \circ T_v(x)fc$. Next, control is transferred to box 2230, in order to test whether j=0. If not, then control is transferred to box 2238, where the y index, "j", is decreased by one (put j←j−1), and control is transferred along arrow 2236, back to box 2226. If, however, j does=0, then the loop is done, and control moves to box 2232, where the hermitian conjugate of rotation matrix is applied to matrix of transmission coefficients tv computed in the above loop, where:

$$tv \equiv [(v_1)\ (v_2)\ \ldots\ (v_N)]$$

in order to rotate (estimate of) object back to original orientation $$[(t_1)\ (t_2)\ \ldots\ (t_N)] \equiv Rot^H(tv)$$

Then, control moves to box 2234, where we add contribution for this view to total transmission coefficient adjustment dt $$dt \leftarrow dt + [(t_1)\ (t_2)\ \ldots\ (t_N)]$$

Now control is transferred over to decision box 2240, where it is determined if index inv=$N_{views}$. If it is, then control is transferred over to box 2242, where index inv is increased by 1: inv←inv+1, and control is transferred up arrow 2242 to box 2246 to do the next view If it is determined that index inv does in fact=$N_{views}$, the control is passed along arrow 2244, to return to the calling program, with output →($\delta t$)

Figure 42A:
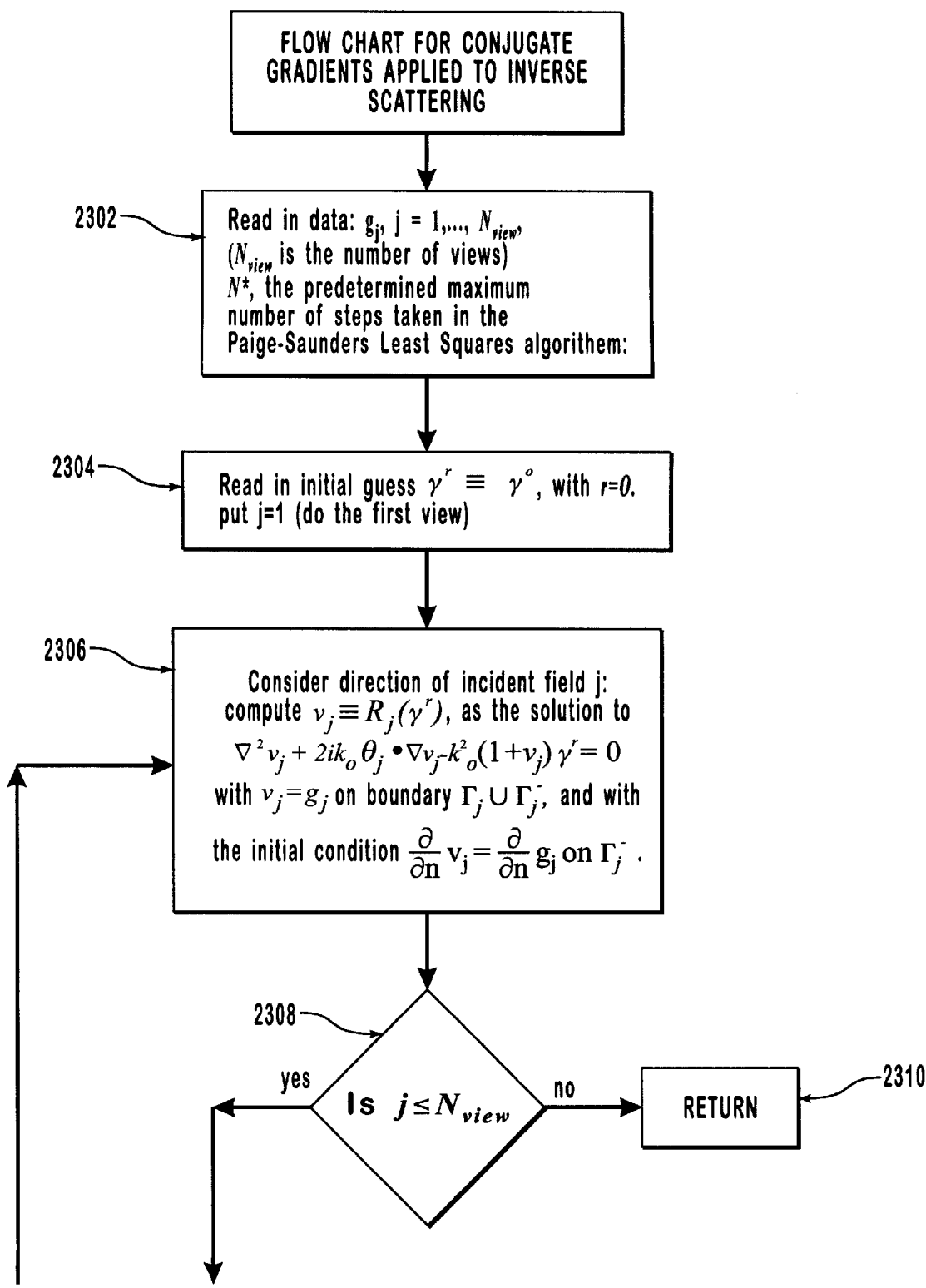
FIGS. 42 A/B/C/D show the flowchart for the application of the conjugate gradient method applied to the generalization of the Propagation-Backpropagation method of Inverse Scattering.
Figure 42B:
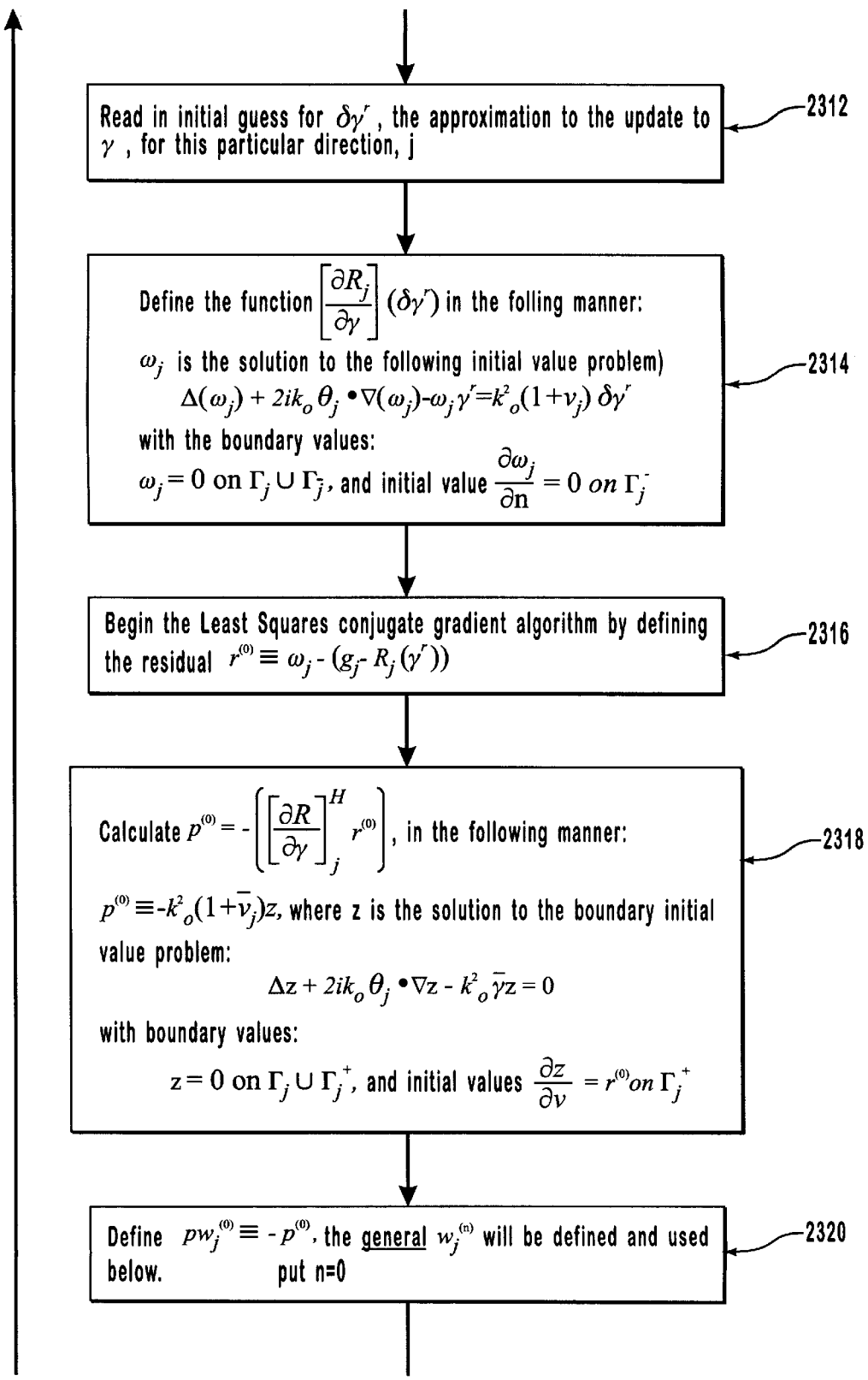
Figure 42C:
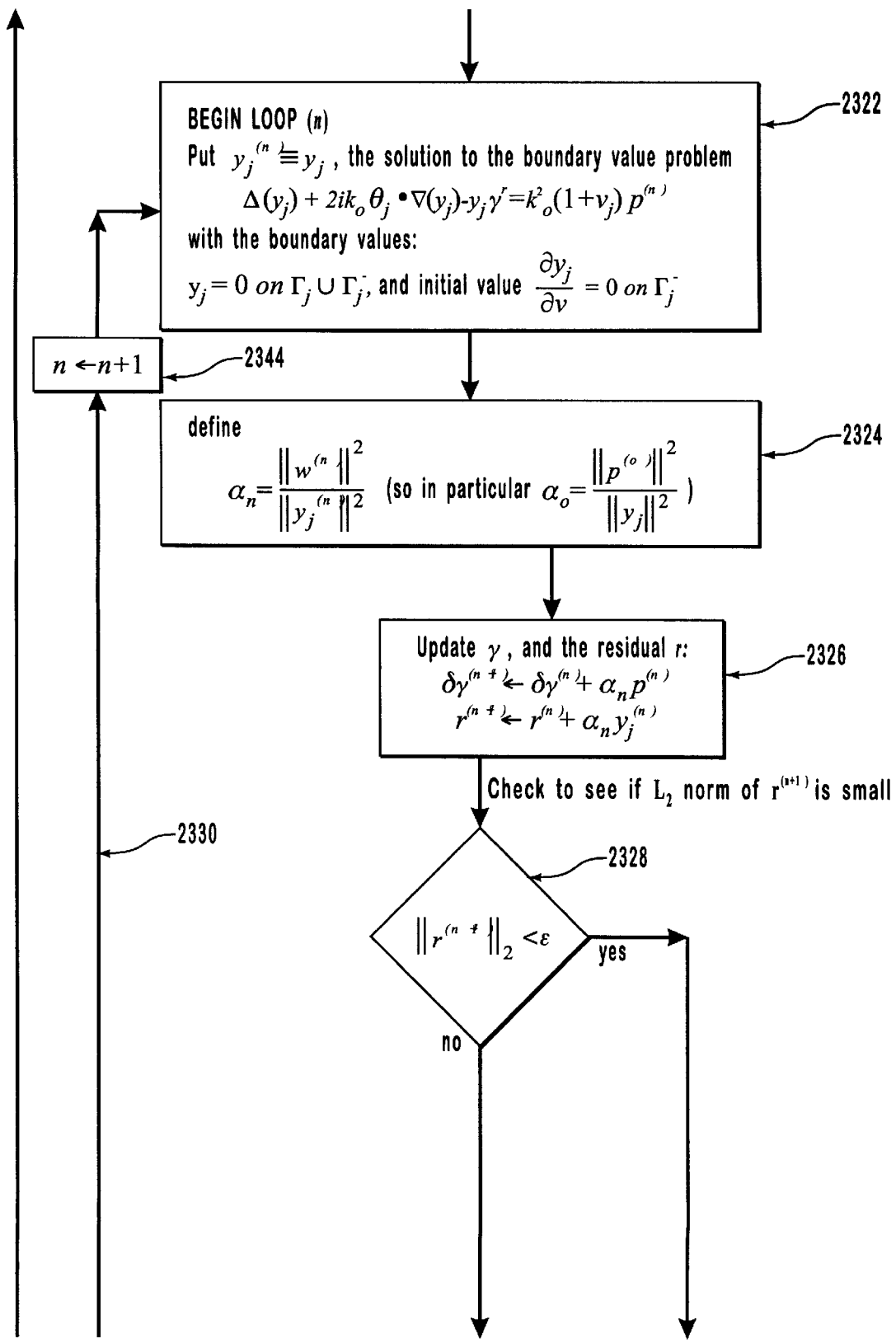
Figure 42D:
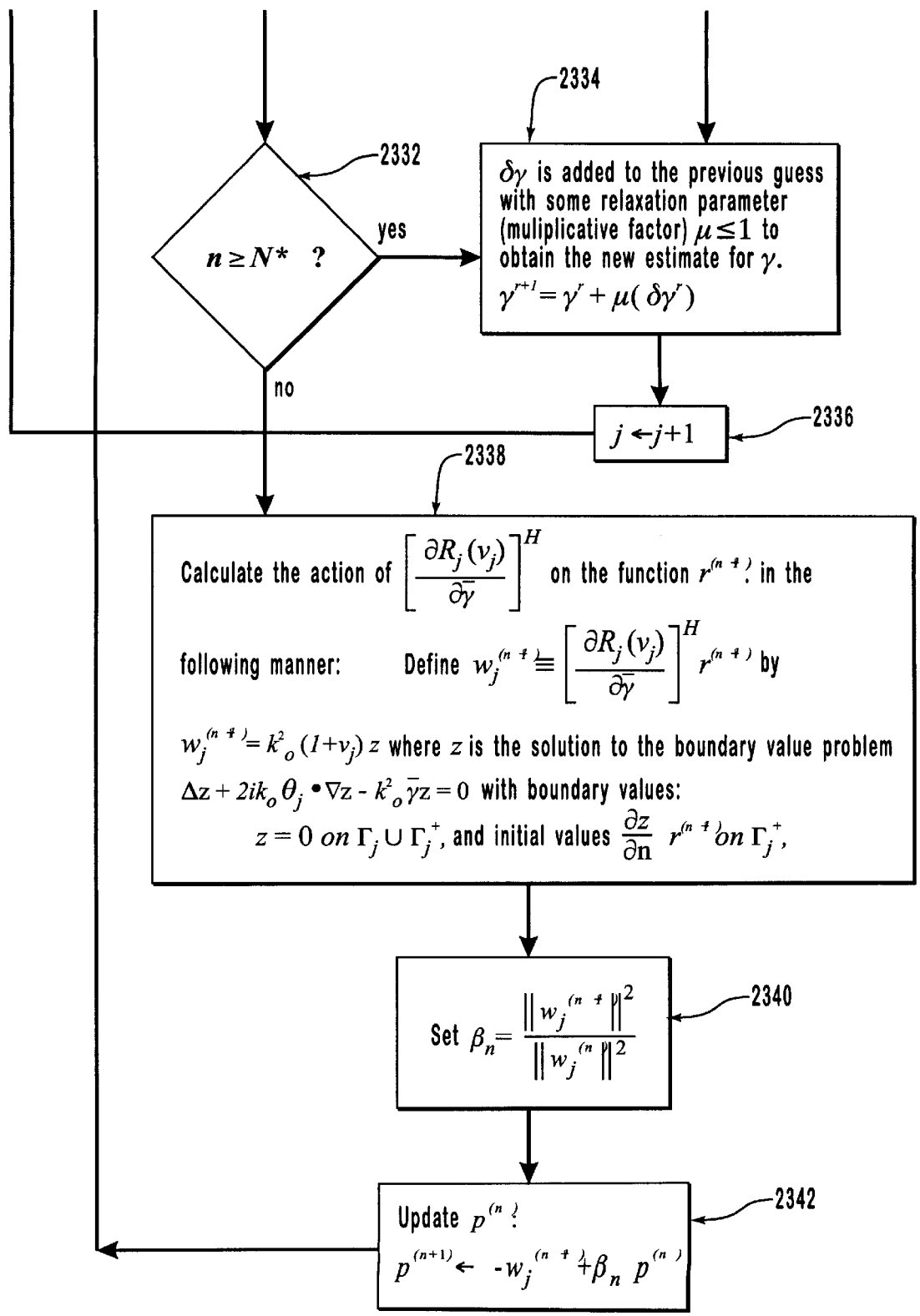

Detailed Description of FIGS. 42A/B/C/D

Control is transferred from the calling program through arrow 2300 on FIG. 42A to 2302 where the data $g_j$, for j=1, . . . ,$N_{view}$ is read in, and the predetermined maximum number of steps taken in the conjugate gradient method is read in as well. Then control is transferred to box 2304 of FIG. 42A where the initial guess for γ the object function, is read into memory. Also, in this box 2304, the index j is set=1 to indicate that the first view is being considered. Then control is transferred down to box 2306 where the the forward problem for direction j is solved, that is, the partial differential equation for $v_j$ is solved:

$$\nabla^2 v_j + 2ik_o \theta_j \cdot \nabla v_j - k_o^2(1+v_j)\gamma^r$$

with $v_j = g_j$ on boundary $\Gamma_j \cup \Gamma_j^-$, and with the initial condition $$\frac{\partial}{\partial \mathbf{n}} v_j = \frac{\partial}{\partial \mathbf{n}} g_j$$

on $\Gamma_j^-$. The notation ∂/∂n designates the interior normal derivative. The forward operator R is defined as follows: $R_j(\gamma^r) = v_j|_{\Gamma_j^+}$, that is, $R_j(\gamma) = v_j$− restricted-to-$\Gamma_j^+$, $\Gamma_j^+$ being the forward scattering part of the boundary of Q.

Now the control is transferred over to decision box 2308, where it is determined if j≤$N_{view}$. If it is not, then the algorithm continues to box 2310, where control is returned to a calling subprogram, or the final image is stored and displayed. That is, if j>$N_{view}$, then the algorithm has updated the object function γ for all incident directions, and control is transferred to back to the calling program or the image is stored/displayed.

If j≤$N_{view}$, then control is transferred over to box 2312, where an initial guess for $\delta\gamma^r$, the update to γ for this particular direction j. is read in.

Control is then transferred to box 2314 (if j≤$N_{view}$) where the solution to the initial value problem $\Delta(\omega_j) + 2ik_o\theta_j \cdot \nabla(\omega_j) - \omega_j \gamma^r = k_o^2(1+v_j)\delta\gamma^r$ with the boundary values:

$\omega_j = 0$ on $\Gamma_j \cup \Gamma_j^-$, and initial value $$\frac{\partial \omega_j}{\partial \nu} = 0$$

on $\Gamma_j^-$ is determined by the method of finite differences or the marching method described in this patent (F. Natterer and F. Wubbelling paper). The $v_j$ is the same as in box 2306. The solution to this problem, the function $\omega_j$, is the result of applying the Jacobian of $R_j$ to the current guess for the "object function correction," δγ.

Next control is transferred to box 2316 where the residual $r^{(0)} = -(g_j - R_j(\gamma^r))$ is defined. Next control is transferred to box 2318, where the boundary initial value problem:

$$\Delta z + 2ik_o\theta_j \cdot \nabla z - k_o^2 \bar{\gamma} z = 0$$

with boundary values:

$z = 0$ on $\Gamma_j \cup \Gamma_j^+$, and initial values $$\frac{\partial z}{\partial \nu} = r^{(0)}$$

on $\Gamma_j^+$ is solved. Then, the function $$p^{(0)} = -\left(\left[\frac{\partial R}{\partial \gamma}\right]_j^H r^{(0)}\right)$$

is defined as $\rho^{(0)} = -k_o^2(1+\bar{v}_j)z$, where z is the solution to the above initial value problem. Note: in the above formula: $\bar{v}_j$ is the complex conjugate of $v_j$.

Now, control is transferred to box 2320, where the definition $w_j^{(0)} = -\rho^{(0)}$ is enforced—the general $w_j^{(n)}$ will be defined and used later in this algorithm, also the loop index n is set=0. Then control is transferred to box 2322 where we define $y_j^{(n)} = y_j$, with $y_j$ the solution to the boundary value problem $$\Delta(y_j) + 2ik_o\theta_j \cdot \nabla(y_j) - y_j\gamma^r = k_o^2(1+v_j)\rho^{(n)}$$

with the boundary values:

$y_j=0$ on $\Gamma_j \cup \Gamma_j$, and initial value $$\frac{\partial y_j}{\partial v} = 0$$

on $\Gamma_j^{31}$

Then control is transferred to box 2324, where an is defined as an appropriate ratio. Then control is transferred to box 2326 where the correction to the object function $\delta\gamma$ and the residual r are updated. Control is then transferred to decision box 2328, where it is determined whether or not the magnitude of the vector of residuals is smaller than some predetermined and fixed $\epsilon$. If it is not then control is transferred to decision box 2332, where it is determined whether the index n is larger than N*. If either of these two criteria are met, then it is assumed that the subprocess that converges to $\delta\gamma_j$ is finished, and control is transferred to box 2334 where the object function $\gamma$ is updated by the formula $\gamma^{r+1}=\gamma^r+\mu(\delta\gamma^r)$. Then in box 2336 the view index j is incremented by 1, and control is then transferred back to box 2306 to read in the next initial guess $\delta\gamma$.j for the next direction.

If neither of these conditions is met then control is transferred to box 2338, where the action of the Hermitian adjoint of the Jacobian $$\left[\frac{\partial R_j}{\partial \gamma}\right]$$

on the function $r^{(n+1)}$, $$\left(\text{symbolically represented as } \left[\frac{\partial R_j}{\partial \gamma}\right]^H r^{(n+1)}\right)$$

is calculated. We use the notation $$w_j^{(n+1)} \equiv \left[\frac{\partial R_j(v_j)}{\partial \gamma}\right]^H r^{(n+1)}.$$

This $w_j^{(n+1)}$ is explicitly calculated in two stages:
(1) Calculate z as the solution to the boundary value problem $\Delta z + 2ik_o\theta_j \cdot \nabla z - k_o^2 \bar{\gamma} z$ with boundary values:

$z=0$ on $\Gamma_j \cup \Gamma_j^+$, and initial values $$\frac{\partial z}{\partial v} = r^{(n+1)}$$

on $\Gamma_j^+$,
(2) $w_j^{(n+1)} = k_o^2(1+\bar{\gamma}_j)z$

Control is then transferred to box 2340 where the constant $\beta_n$ is calculated via the formula:

$$\beta_n = \frac{\|w_j^{(n+1)}\|^2}{\|w_j^{(n)}\|^2}.$$

Contol is then transferred to box 2342 where the search direction $\rho^{(n)}$ is updated via the formula $\rho^{(n+1)} \leftarrow -w_j^{(n+1)} + \beta_n \rho^{(n)}$. Now one loop of the conjugate gradient algorithm has been completed and control is transferred up to box 2344 where the loop index n is increased by 1 and control is then transferred to box 2322 where the next solution to the given boundary value problem is calculated. Note that the $\gamma^r$, and the $v_j$ are both known. This loop is repeated until one of the criteria in box 2328 or 2332 is finally met, whereupon control is transferred to the box 2306 and the next view is dealt with.

Figure 43A:
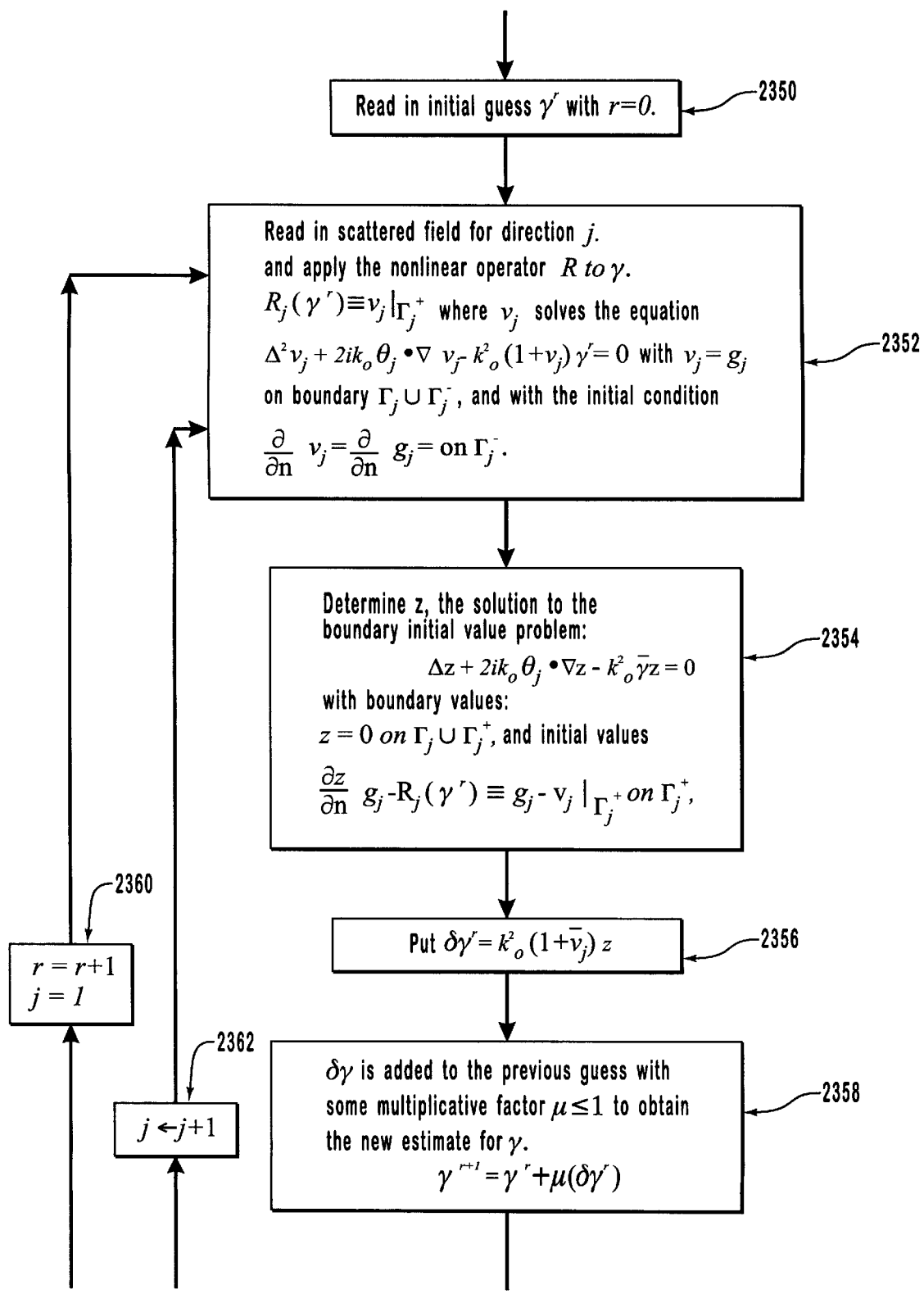
FIGS. 43 A/B is the flowchart for the original Propagation-Backpropagation Method described in the paper "A Propagation-Backpropagation Method for Ultrasound Tomography", Frank Natterer, which is included herein as reference.
Figure 43B:
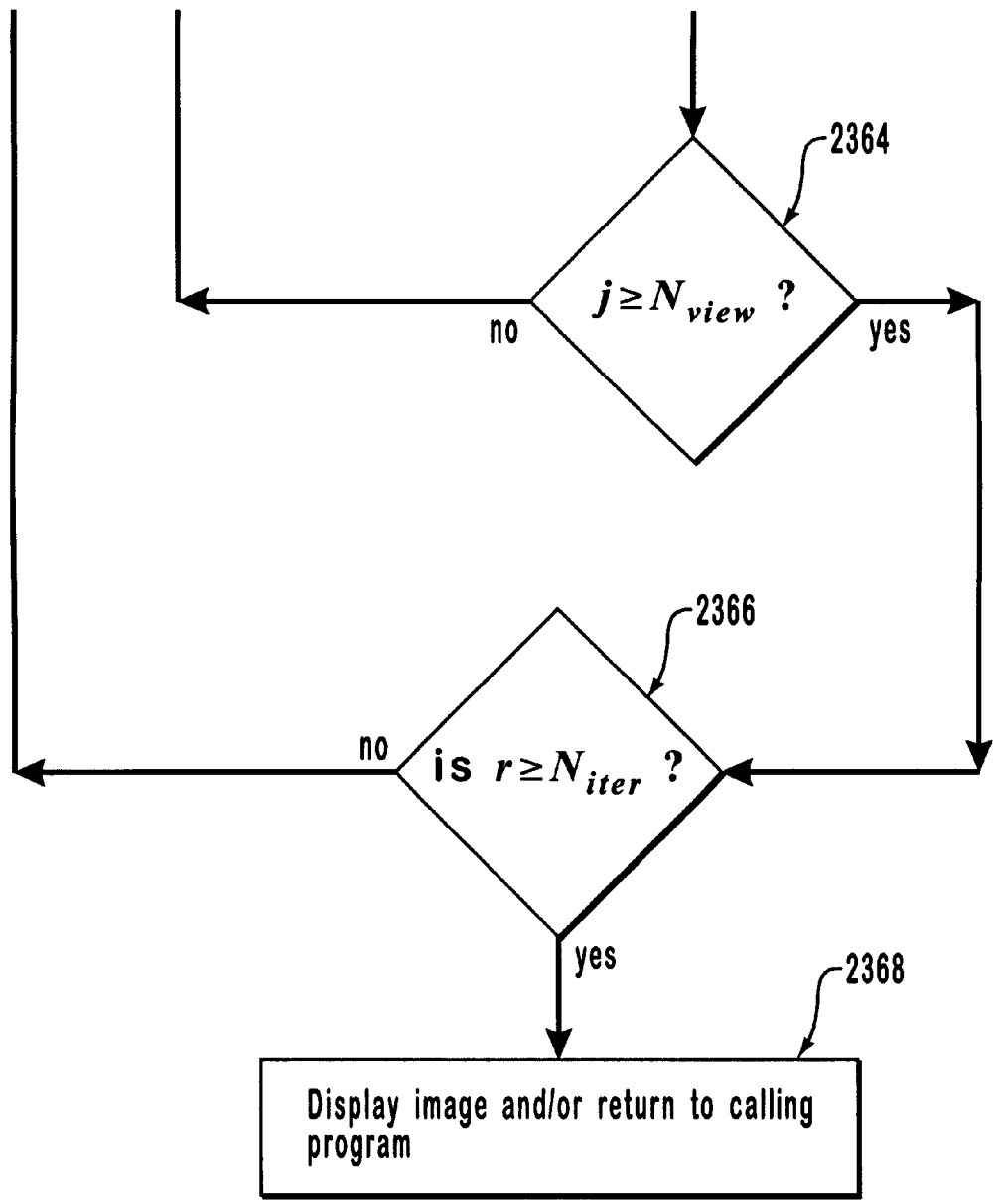

Detailed Description of Flow Chart for
Propagation-Backpropagation Method, FIGS. 43A/B

Control is transferred to box 2350 of FIG. 43A, where the initial guess or estimate for $\gamma$. From there control is transferred to box 2352 where the data (scattered or total field) is read in. Also in this box the forward problem with an object function of $\gamma^r$ is carried out for the $j^{th}$ direction.

Next control is transferred to box 2354 where the initial value and boundary value problem shown in that box, is solved. This is part of the back-propagation stage of the process. Then control is transferred over to box 2356 where the back-propagation process is completed by the definition of $\delta\gamma$ given there. Then control is transferred down to box 2358 where $\delta^r$ is updated with a multiplicative factor of $\delta\gamma$. Then control is transferred over to box 2364 where it is determined if j is greater than or equal to $N_{view}$. If so, then control is transferred over to box 2366 where it is determined if r is greater than or equal to $N_{iter}$. If r is greater than or equal to $N_{iter}$, then control is transferred down to box 2368 where control is transferred over to the calling program and/or the image of $\gamma$ is displayed. If the criterion in box 2364 is not satisfied, control is transferred to 2362 where j is increased by 1. Then control is taken back to box 2352 where the data (scattered or total field) for new direction j is taken, and the corresponding forward problem is solved for direction j. If the r counter is not greater than $N_{iter}$, control is transferred to box 2360, where j is reset to 1, since it has already been determined in box 2364 that all the views have been processed. Also the iteration counter r is increased by 1, and control is returned to box 2352, where the forward problem corresponding to the direction j=1 is performed. Note that one may wish to bypass the redoing of the forward problem after each iteration in the r variable. This would require the storing of each $v_j$ for all of the directions, furthermore, since the computation of the forward problem is very fast, it is approximately as efficient to recompute the forward problem each iteration of r, as opposed to going through several iterations before recomputing the forward solutions.

Figure 44A:
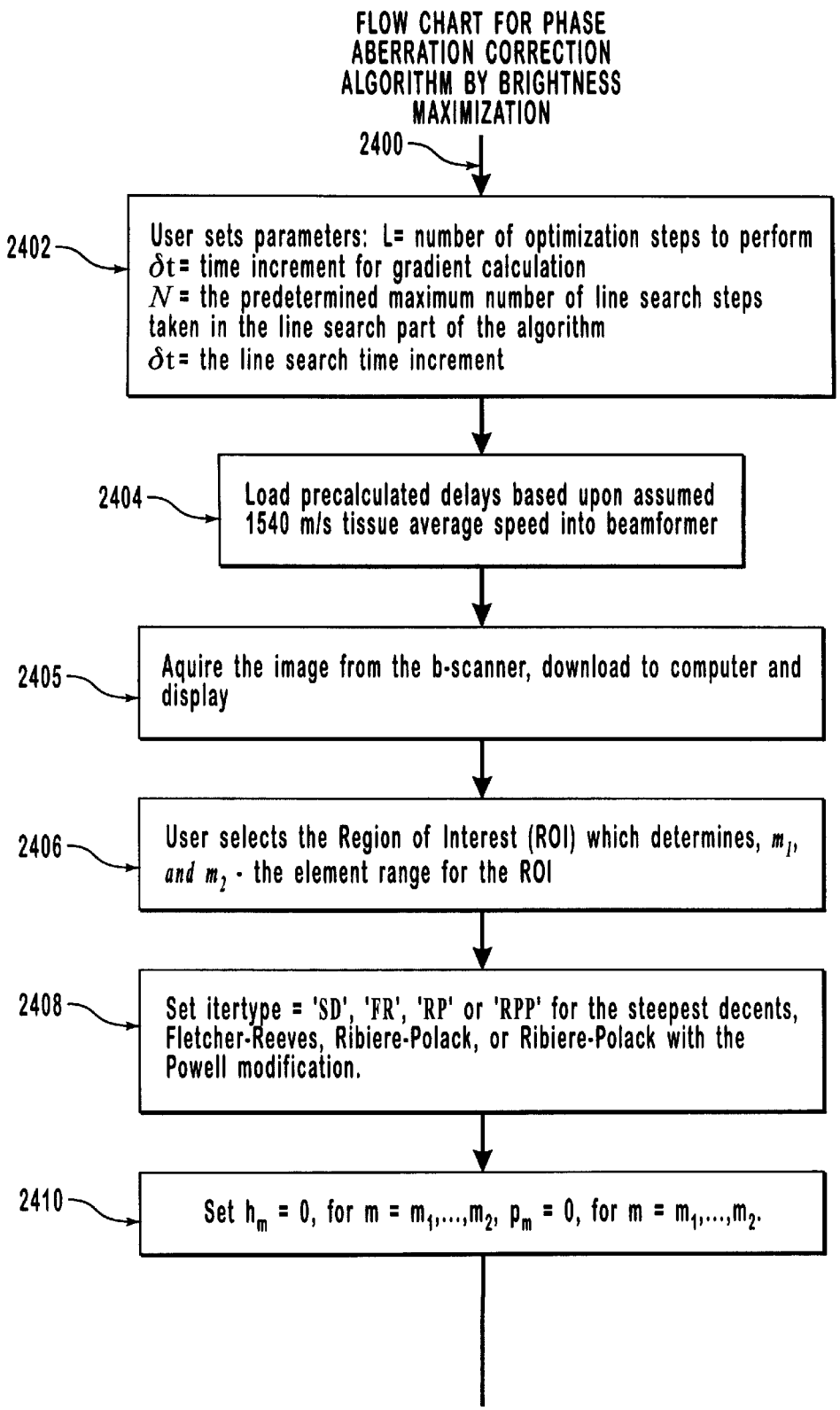
FIGS. 44 A/B/C/D/E show the flowchart for the brightness maximization based phase aberration correction algorithm.

DETAILED DESCRIPTION OF FLOW CHART FOR MAXIMIZATION OF BRIGHTNESS PHASE ABERRATION CORRECTION FIGS. 44A/B/C/D/E

First, flow is transferred down arrow 2400 from the calling program. Then in box 2402 $\delta t$, the time increment for gradient calculation, $\delta\tau$, the line search time step, $N_s$ the predetermined maximum number of line search steps, and L, the predetermined total number of CG iterations to be performed, are read in. Control is then transferred over to box 2404, where the precalcuated beamformer delays based upon an assumed speed of sound in the tissue are loaded into the beamformer hardware. Then control is transferred to box 2405, where the b-scan image is aquired. Then control is transferred to box 2406 where the Region of Interest (ROI) is selected by the user. The element range used to form the image in the ROI, $m_1$ to $m_2$, are determined for this ROI. Then control is moved to box 2408 where the type of iteration is chosen: itertype='SD' corresponds to steepest descents, itertype='FR' corresponds to Fletcher Reeves', 'RP' corresponds to Ribiere-Polak, and finally 'RPP' corresponds to Ribiere-Polak with the Powell modification. Next control is transferred to box 2410 where the vector h with components $h_m$ for $m=m_1, \ldots, m_2$ is set identically=0, similarly all of the components of the vector p, $p_m$ are set=0.

Figure 44B:
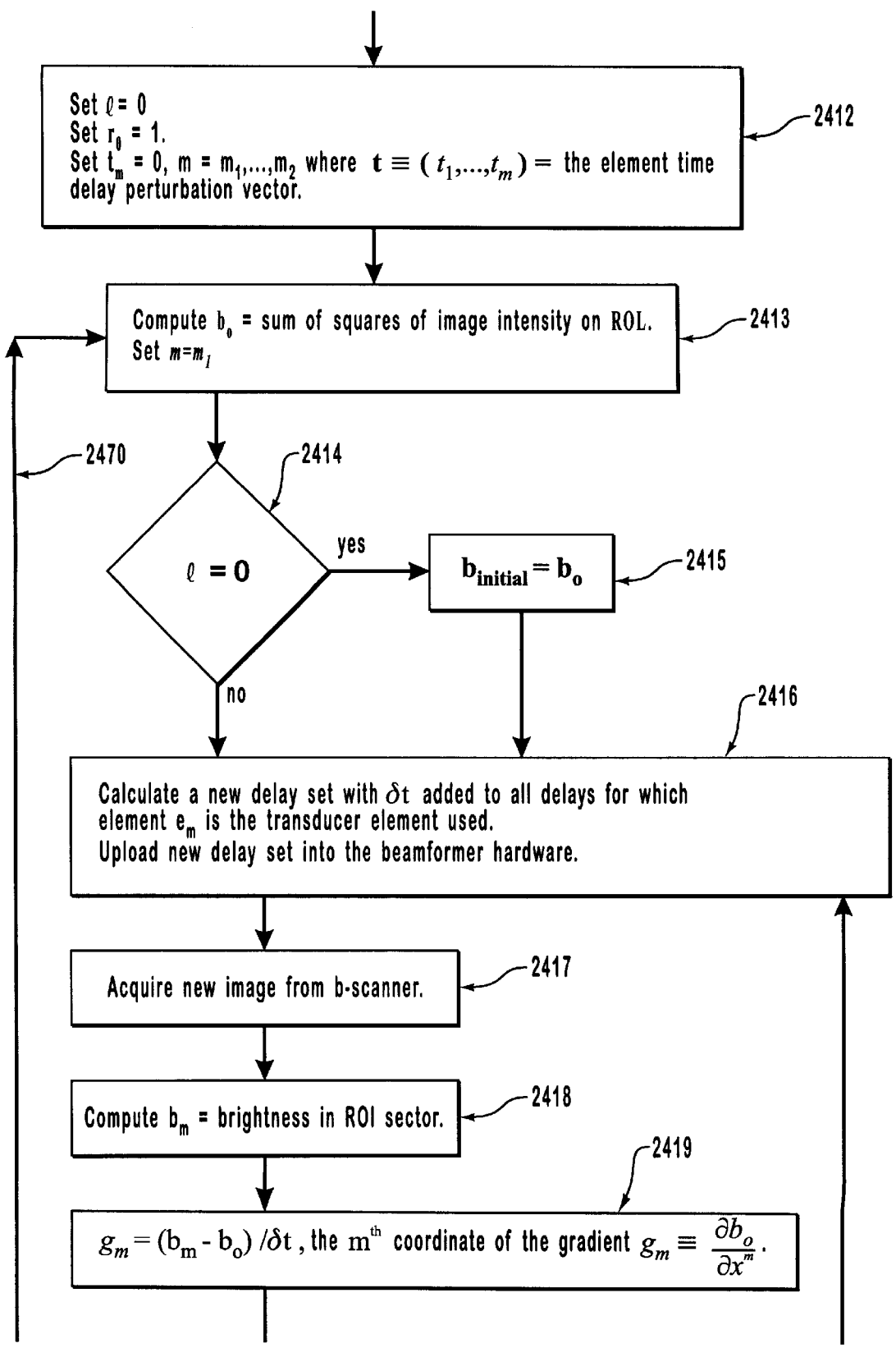
Figure 44C:
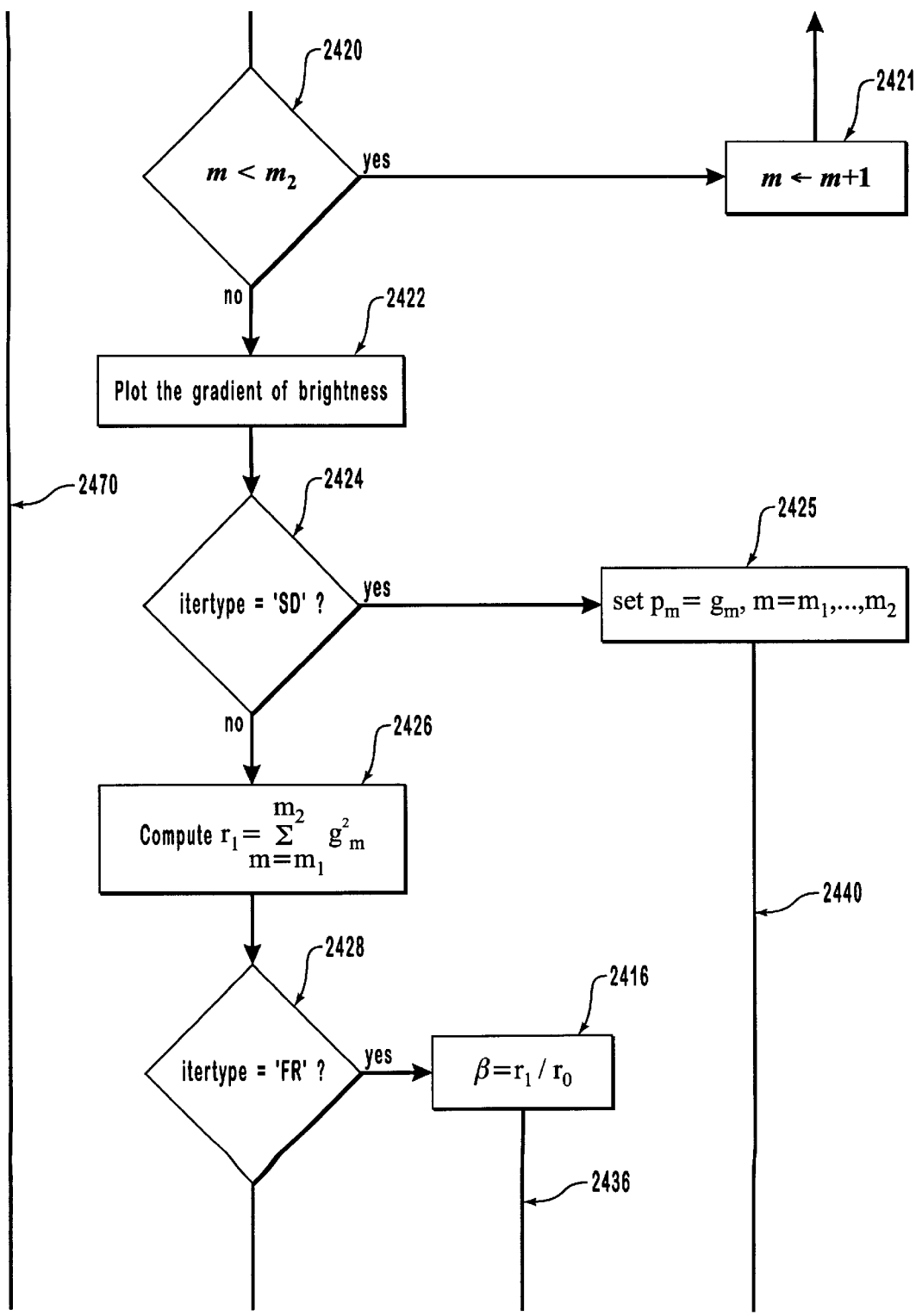
Figure 44D:
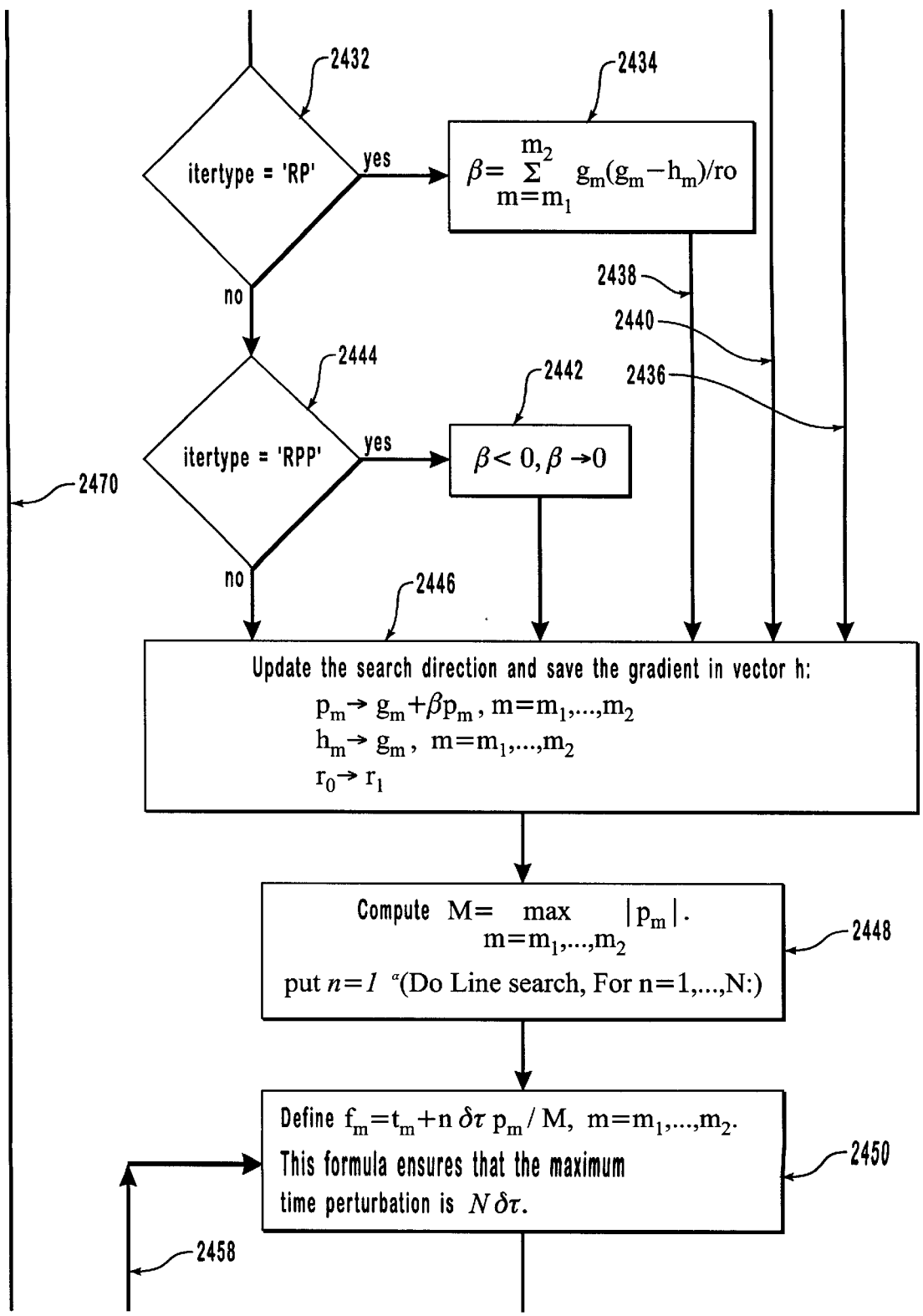
Figure 44E:
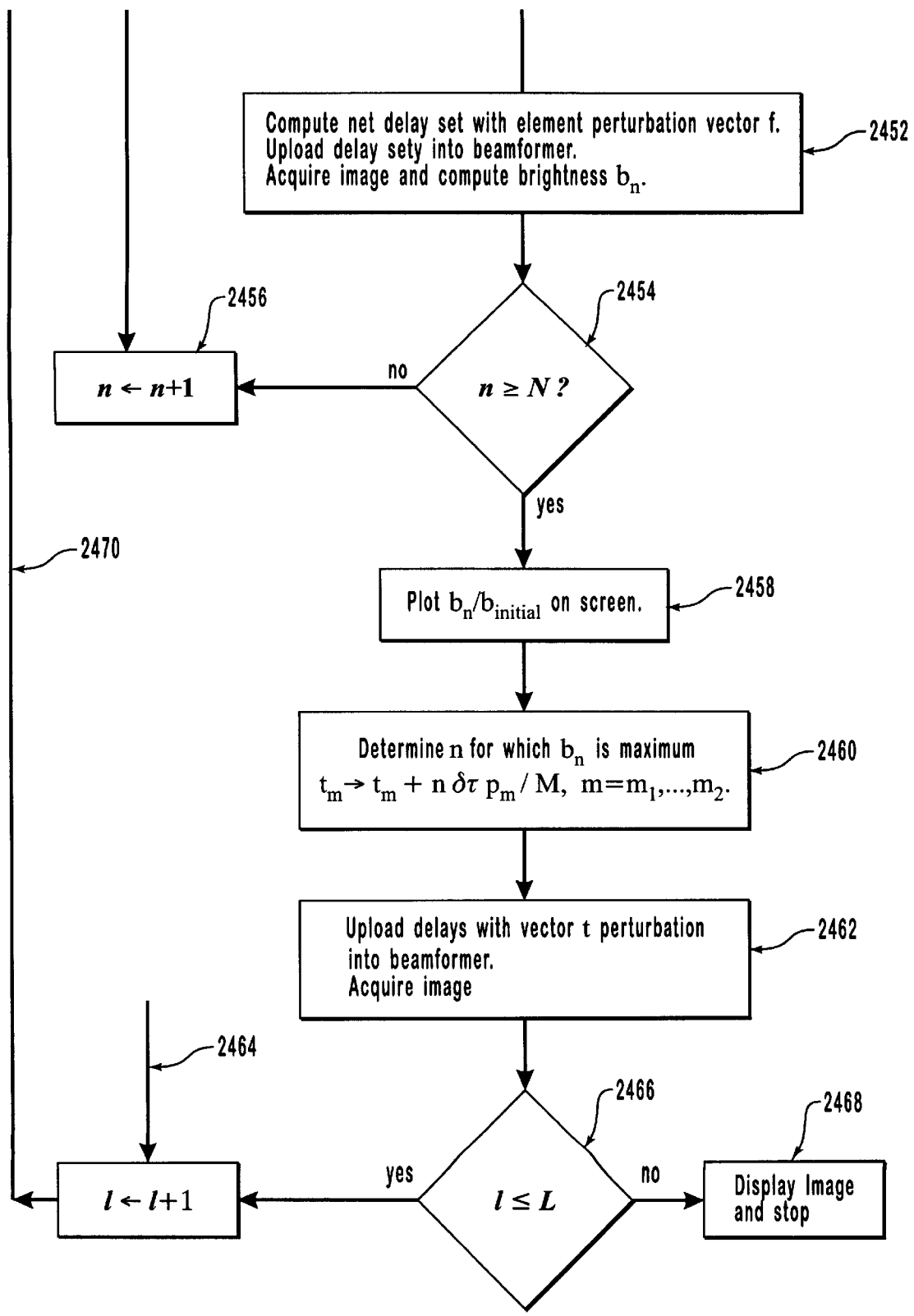

Next control is transferred to box 2412 of FIG. 44B, where the initial gradient magnitude, $r_o$, is set=1, and the vector t (with components $t_m$=the time delay perturbation for element m) is set=0. Now control is transferred to Box 2413 where the index l is set equal to zero, and the sum of squares of the image intensity in the ROI is computed and stored in $b_o$. Now control is transferred to decision box 2414 where it is determined if index l=0. If it is then control is transferred to box 2415, $b_o$ is stored in $b_{initial}$, and control is transferred down to box 2416. If l≠0, then control is transferred to box 2416 where δt (NOT δτ) is added to all beamformer delays which correspond to transducer element $e_m$. The new (perturbed) delay set is uploaded to the beamformer, and control goes to box 2417, where the new image is aqcquired form the b-scanner. Next control goes to box 2418, where the brightness in the ROI is computed and stored in $b_m$. Now control is transferred over to box 2419, where the gradient component $g_m$ is approximated by a finite difference formula. Then control is transferred to box 2420, where it is determined if $m<m_2$., if it is then control goes to box 2421, where index m is increased by 1 and control goes back to box 2416. If not, then control is transferred down to box 2422, where the gradient of brightness is plotted. Next control is transferred to decision box 2424, if itertype='SD', then the vector p is set equal to the gradient g and control is transferred directly down to box 2446 via arrow 2440. If itertype is not='SD', then transfer goes to box 2426, where the gradient magnitude $r_1$ is computed as the sum of squares of the components of the vector g, the gradient. Next control is transferred down to decision box 2428, where itertype is compared to 'FR'. If they are not equal then control goes to decision box 2432, where itertype is compared with 'RP'. If they are in fact equal, then control is transferred to box 2430, where the constant β is defined as the ratio: $r_1/r_o$. Control is then transferred to box 2446 via arrow 2438.

At decision box 2432 it is determined if itertype='RP'. It it is true then control is switched over to box 2434 where the constant β is calculated as shown. If itertype is not='RP', then control is transferred down to boxx 2444 where it is determined if itertype='RPP'. If it is, then control is transferred over to box 2442, where β is checked to make sure that it is non-negative, if not, then β is set=0 and control is transferred over to box 2446. If it is, in fact non-negative, then control is transferred over to box 2446, where the search direction p is updated as shown in box 2446. Also in box 2446 the vector g with components, $g_m$ with $m=m_1, \ldots, m_2$.is stored in vector h, and $r_o$ is redefined to be equal to $r_1$, that is, the value $r_1$ is stored in $r_o$. The control is then transferred over to box 2448, where the constant M is calculated as the maximum of the absolute values of the components of direction p. Also in this box, n the line search index is set=1. Then control is transferred down to box 2450, where the vector f with components $f_m$ is determined. Then control is transferred down to box 2452 where the net delay set with element perturbation vector f is computed and uploaded to the beamformer hardware. The corresponding image is aquired from the b-scanner and the resultant brightness in the ROL, $b_n$, is computed (as the sum of squares mentioned before). Then control is transferred to box 2454 where it is determined if n is greater than or equal to $N_s$ the predetermined number of steps in the line search. If so, then control is transferred down to box 2458 where the normalized values $b_n/b_{initial}$ are plotted. If not, then control is transferred over to box 2456, where the index n is increased by 1, and control is then transferred up to box 2450 where the perturbation vector f is recalculated with the new value of n.

Once control has been passed down to box 2458 and the normalized $b_n/b_{initial}$ for $n=1,2,\ldots N_s$, has been plotted, then control is transferred to box 2460, where the n for which $b_n$ is maximal is determined. Then control moves to box 2462, where the delays $t_m$ (the components of vector t) are uploaded into the beamformer hardware. These delays are the ones which maximize the brightness of the image in the direction of the present search direction. Next control is transferred down to decision box 2466, where it is determined if l is strictly less than L, the predetermined number of iterations in the brightness maximizing subroutine. If it is true, then control is transferred to box 2464, where the index l is increased by 1, and control is transferred up to box 2413 where the image is aquired for the given beamformer delays. Also, the index m is reset to equal $m_1$, in order that the gradient can be calculated once more.

If the predetermined number of steps have been carried out, then control is then transferred over to box 2468, where the image is aquired from the b-scanner using the time delays in t and control reverts to the calling program, or else a "stop" is executed.

Figure 37:
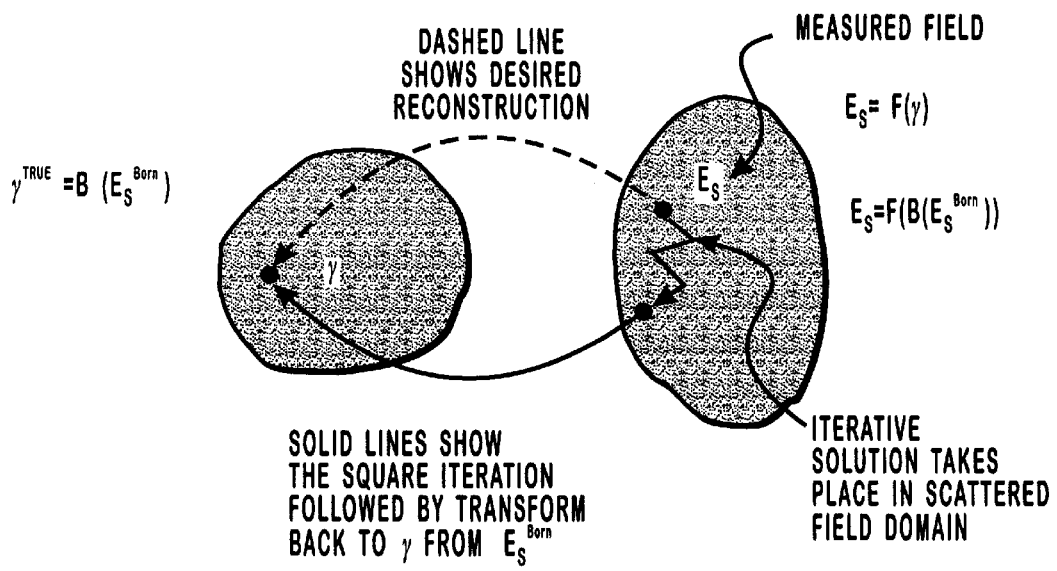
FIG. 37 shows the method for solving for the object function $\gamma$ by means of a SQUARE nonlinear map, iteratively, in the scattered field domain.

FIG. 37 shows the method for solving for the object function γ in the scattered field domain as discussed in METHOD 1 directly below. It uses an iterative procedure applied to a square non-linear operator to first determine an equivalent scattered field, and then transform to the object function solution. Since the nonlinear system is square, it is possible to use BiCGStab (BiConjugate Gradients Stabilized) in place of generic Conjugate Gradients in the solution algorithm, which is a great advantage.

Figure 38:
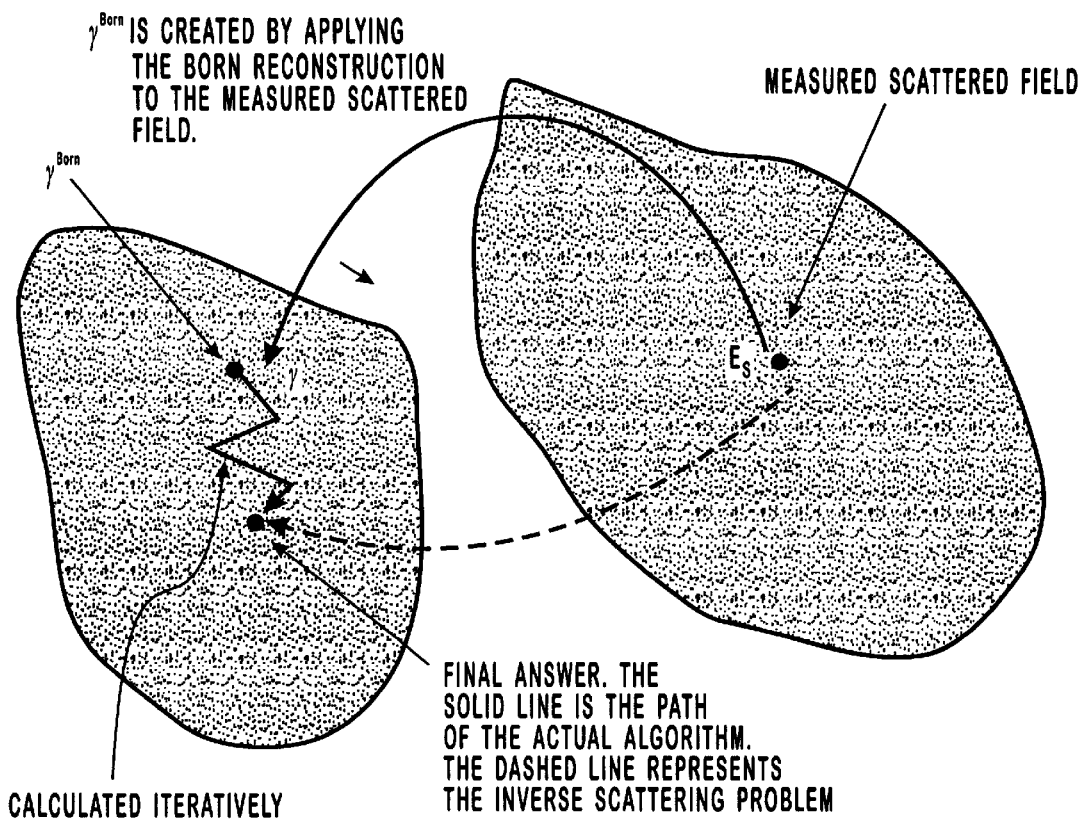
FIG. 38 shows the iterative method for solving for the object function by menas of a SQUARE nonlinear map in the object function ($\gamma$) domain.

FIG. 38 shows the method for solving for the object function γ iteratively in the object function domain. The method is discussed as METHOD 2 directly below. Again, since the system is square, it follows that BiCGStab is the proper algorithm to use.

METHOD 1: iteration in the scattered field manifold

Solving for γ by inverting $E_s=F(\gamma)$, where $F(\gamma)=D\gamma(I-C\gamma)^{-1}E_b$, requires inverting from a range to a domain that are not the same size. Define $E_s^{Born}=D\gamma E_b$. It is now possible to solve for $E_s^{Born}$ from the square system $E_s=F(B(E_s^{Born}))$. After finding $E_s^{Born}$ we find γ by the direct substitution $\gamma=B(E_s^{Born})$. This has the advantage of allowing use of square system solvers, such as biconjugate gradients (BCG) or stabilized biconjugate gradients (BiSTAB), which are faster and better conditioned than rectangular system solvers, e.g. conjugate gradients (CG). The function B can be any one-to-one mapping such as the Born approximation or backpropagation. Thus, we will also investigate and develop the potentially faster non linear, square system method described in FIG. 37.

Solving for γ by inverting $E_s=F(\gamma)$, where $F(\gamma)=D\gamma(I-C\gamma)^{-1}E_b$, requires inverting from a range to a domain that are not the same size. However, we can solve for $E_s^{Born}$ from the square system $E_s=F(B(E_s^{Born}))$. After finding $E_s^{Born}$ we find γ by the direct substitution $\gamma=B(E_s^{Born})$. This method has the advantage of allowing use of square system solvers, such as biconjugate gradients (BCG) or stabilized biconjugate gradients (BiSTAB), which are faster and better conditioned than rectangular system solvers, e.g. conjugate gradients (CG). The function B can be any one-to-one mapping such as the Born approximation or backpropagation.

METHOD 2: iteration in the object function manifold

Use the Born approximation as an example.

$$E_s = D\gamma^{Born} E_b = [DE_b]\gamma^{Born}$$

Then $$\gamma^{Born} = [DE_b]^{-1} E_s$$

Where $[DE_b]^{-1}$ represents the Born reconstruction. Multiply both sides of $$E_s = D\gamma(I-C\gamma)^{-1} E_b$$

by $[DE_b]^{-1}$, that is, apply the Born reconstruction procedure to both sides.

Now, solve square nonlinear system $$\gamma^{Born} = [DE_b]^{-1} D\gamma(I-C\gamma)^{-1} E_b,$$

for $\gamma$, in the $\gamma$ domain by means of BiCGSTAB. The Jacobian will be square. There may be less work than with Method 1.

Actually this will involve approximately the same workload as Method 1 at each iteration. This is because in Method 2, each iteration requires the application of the Born reconstruction procedure, whereas in Method 1), we are also required to calculate the Born approximation to the scattered field at each iteration, and then finish off with one application of the Born reconstruction procedure in order to get $\gamma$.

METHOD 3:' Use previous guess $\gamma^{(n-1)}$

To understand the third method and put all 3 methods into a consistent framework, consider the nonlinear operator "$\phi$", which maps "object functions" $\gamma$ to "scattered fields":

$$\phi(\gamma) = D[\gamma](I-C[\gamma])^{-1} E_b$$

In terms of this operator, the equation we wish to solve for $\gamma$, is $$\phi(\gamma) = E_m$$

where $E_m$ is the measured field (as above). The standard approach is to solve the least squares minimization problem $\min_\gamma \|E_m - \phi(\gamma)\|^2$, as discussed above. This involves the use of conjugate gradient methods. However, if we now define the "Born approximation operator", B $$B: E_m \gamma^B$$

which maps a measured field to the corresponding Born approximation, we can apply B to both sides of $\phi(\gamma) = E_m$, to yield:

$$B\phi(\gamma) = \gamma^B$$

This provides a nonlinear operator $B\phi$ acting on $M_\gamma = \{$manifold of all possible $\gamma$'s$\}$. This operator also has as its range this same $M_\gamma$. As with any nonlinear operator we will solve it iteratively. Each iteration involves the solution of the linear system of equations:

$$[Jac_{B\phi}](\delta\gamma) = -(B\phi(\gamma^{(n)}) - \gamma^B)$$

where the "Jacobian" $Jac_{B\phi} \equiv$ $$Jac_{B\phi} \equiv \frac{\partial B\phi}{\partial \gamma} = B\frac{\partial \phi}{\partial \gamma},$$

by virtue of the linearity of B.

Method 2) above, proposes the use of BiCGStab to solve the system $[Jac_{B\phi}](\delta\gamma) = -(B\phi(\gamma^{(n)}) - \gamma^B)$. Then adjust $\gamma$ via $\gamma^{(n+1)} \leftarrow \gamma^{(n)} + \delta\gamma^{(n)}$.

Similarly method 1) above defines a different operator $\phi B(E_s) = E_m$, and solves this system for $E_s$, which is then used to give $\gamma$ via: $\gamma = B(E_s)$.

The advantage of having a square operator (Domain and Range of the operator are of equal dimension) is that the BiCGStab method is used to solve the linear equation for the update $\delta\gamma$.

Within this context method 3) can be explained as follows:

Suppose we have (as before):

$$\phi(\gamma) = D[\gamma](I-C[\gamma])^{-1} E_b$$

The system (nonlinear) we are required to solve for an estimate of $\gamma$ is $$\phi(\gamma) = E_m$$

which in traditional methods involves some kind of minimization: $\min_\gamma \|E_m - \phi(\gamma)\|^2$ using rectangular CG.

In Methods 1), and 2) we made particular use of the Born reconstruction operator:

$$B: E_m \gamma^B$$

to ameliorate the difficulties associated with ill-conditioning of the rectangular system by enabling use of BiCG. Now, however, imagine that we can define some nonlinear operator:

$$\hat{\phi}: E_m \gamma \in M_\gamma$$

As yet, this operator is undefined, but a particular example might be the Born reconstruction operator. With this more general, and as yet undetermined $\hat{\phi}$ operator, $B\phi(\gamma) = \gamma^B$ becomes $\hat{\phi}\phi(\gamma) = \hat{\gamma}$. Now suppose that $\hat{\phi}$ can vary with the iteration number k: $\hat{\phi}^{(\kappa)}\phi(\gamma) = \hat{\gamma}$ This provides a nonlinear operator $\hat{\phi}\phi$ acting on $M_\gamma = \{$manifold of all possible $\gamma$'s$\}$. This operator also has as its range this same $M_\gamma$. As with any nonlinear operator we will solve it iteratively. Each iteration involves the solution of the linear system of equations:

$$[Jac_{\hat{\phi}\phi}](\delta\gamma) = -(\hat{\phi}\phi(\gamma^{(n)}) - \hat{\gamma})$$

where $\hat{\gamma} = \hat{\phi}(E_m)$. Using $\hat{\gamma}^{(n)} = \hat{\phi}^{(n)}(E_m) = \gamma^{(n-1)}$ as the definition of $\hat{\phi}^{(n)}$ means that each iteration solves (using BiCGStab) the system $[Jac_{\hat{\phi}\phi}](\delta\gamma) = -(\hat{\phi}\phi(\gamma^{(n)}) - \gamma^{(n-1)})$. Then adjust $\gamma$ via $\gamma^{(n+1)} \leftarrow \gamma^{(n)} + \delta\gamma^{(n)}$ Method 4). uses very similar ideas but instead of solving $\hat{\phi}^{(\kappa)}\phi(\gamma) = \hat{\gamma}$, it solves $\phi\hat{\phi}(E_s) = E_m$ iteratively for $E_s$, and hence $\gamma = \hat{\phi}(E_s)$. Both of these methods 3) and 4) are, in actual fact, finding fixed points of square (nonlinear) maps:

METHOD 3) SCHEMATIC

Solve:

$$\hat{\phi}\phi(\gamma) = \gamma \text{ subject to } \hat{\phi}(E_m) = \gamma$$

Determine $\hat{\phi}^j \to \hat{\phi}$ iteratively. instead of using the Born reconstruction operator.

METHOD 4) SCHEMATIC
Solve:

$\phi\hat{\phi}(E_m)=E_m$ then determine $\gamma=\hat{\phi}(E_m)$

Again $\hat{\phi}^j \to \hat{\phi}$ is determined iteratively in a similar manner to the method described for Method 3).

Figure 45:
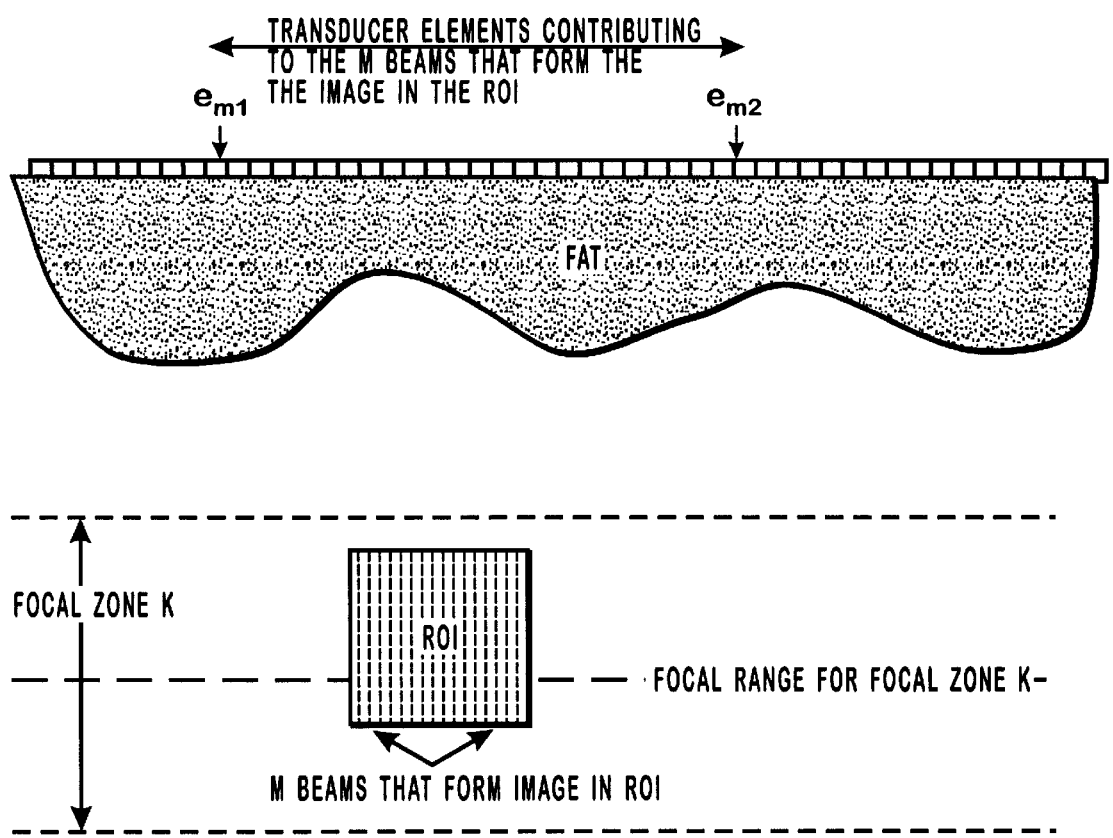
FIG. 45 shows the geometry of an acoustic transducer array illuminating an anatomical region through an aberrating layer of fat. A region of interest (ROI), selected by the user, is also shown. The transducer elements that contribute to the image in the ROI are denoted $e_{m1}$ to $e_{m2}$.
Figure 46:
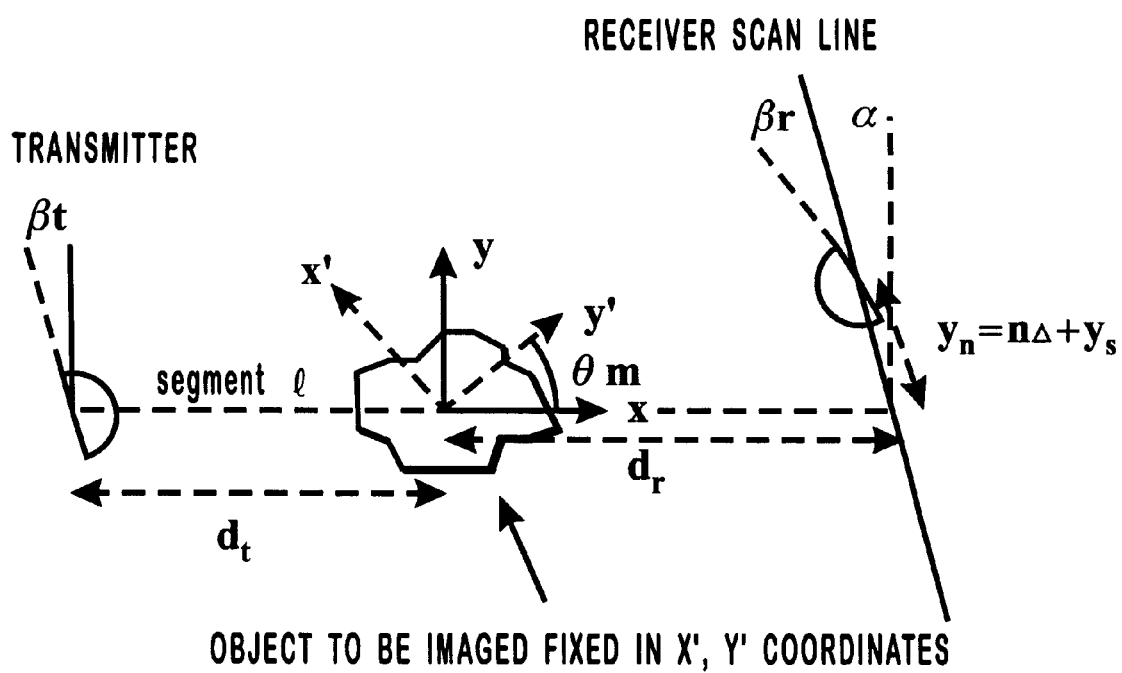
FIG. 46 shows the geometric set up for a typical calibration procedure.
Figure 47:
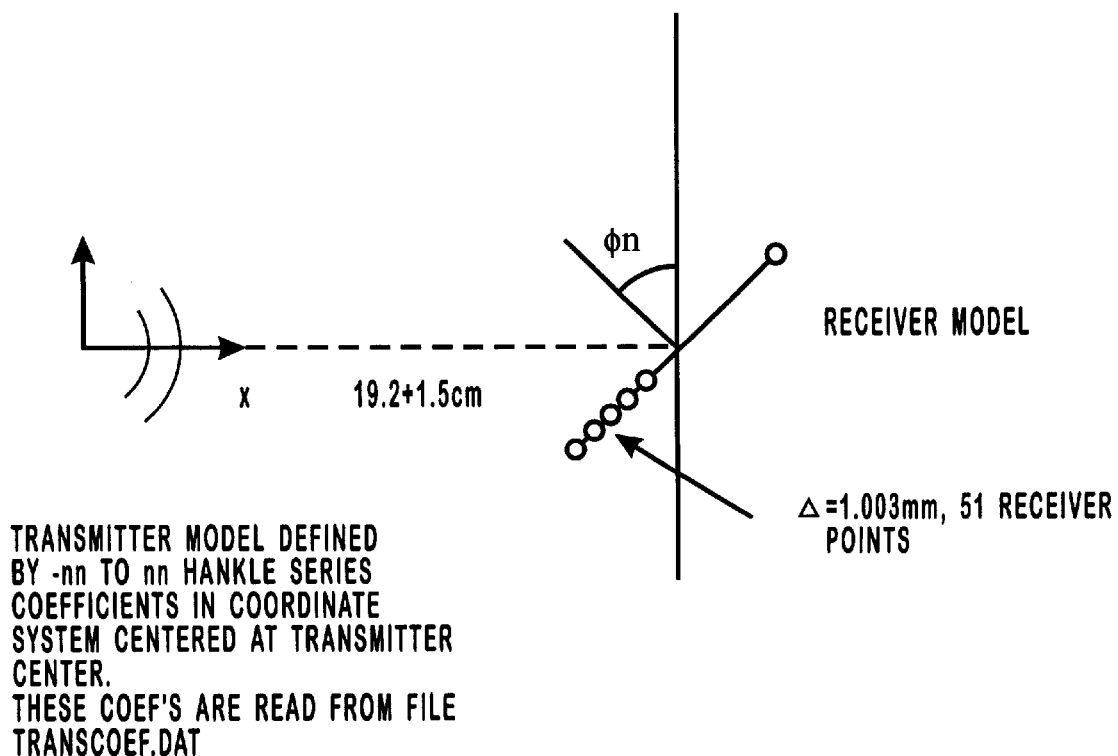
FIG. 47 shows the detailed model used for the receiver in the acoustic 2D case, in a typical calibration setup.
Figure 48:
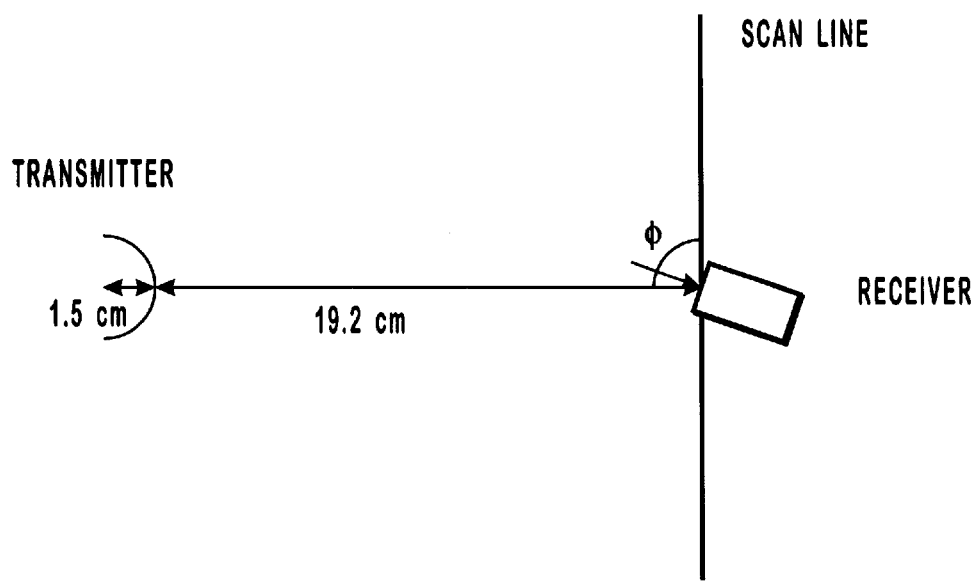
FIG. 48 shows the geometric setup used for the calibration of the receiver and transmitter.
Figure 49:
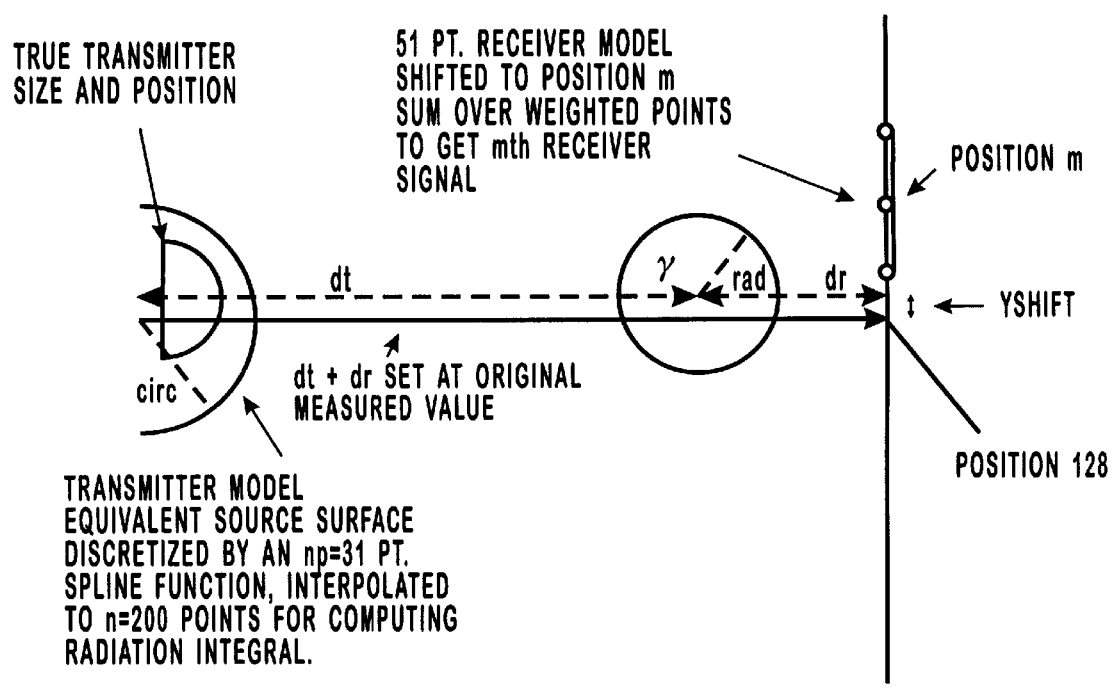
FIG. 49 shows the scattering parameters used in the 2D acoustic calibration procedure typical of the calibration procedure used in inverse scattering, both for acoustic and EM modalities.
Figure 50:
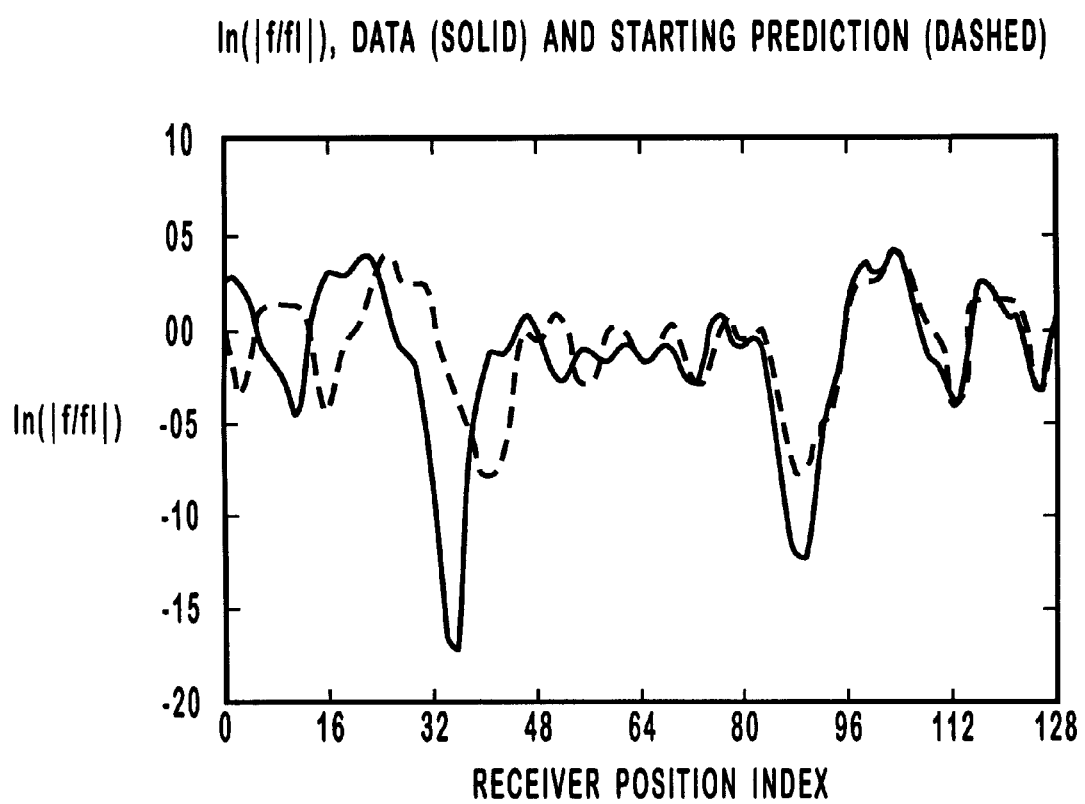
FIG. 50 shows a comparison of the normalized total fields' (predicted and measured) magnitude versus receiver position.
Figure 51:
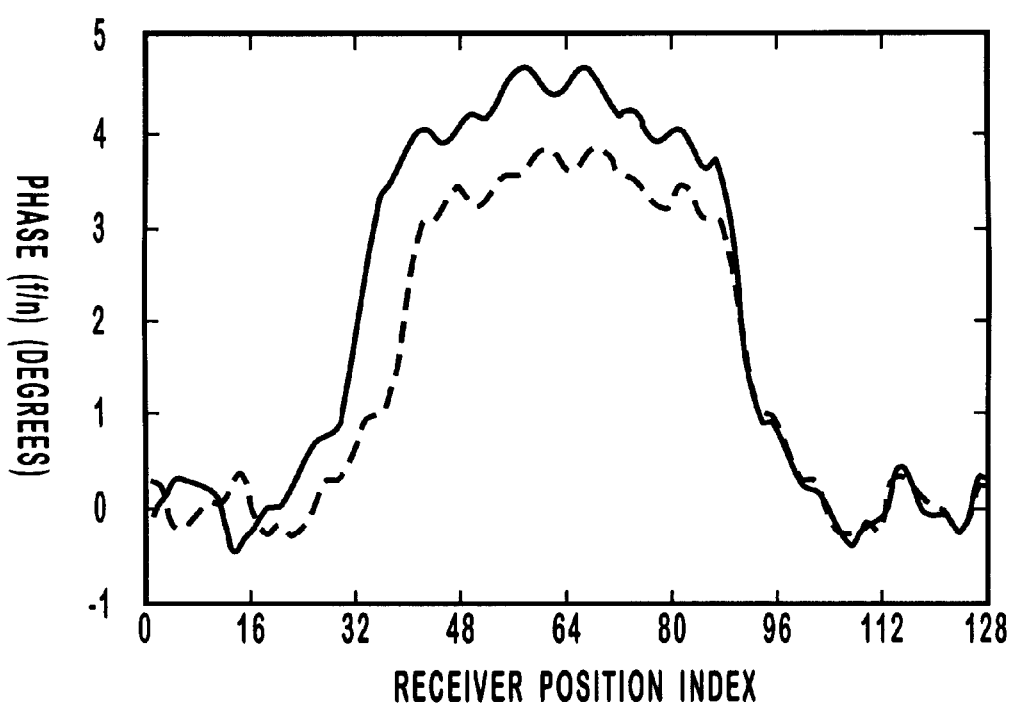
FIG. 51 shows the comparison of the normalized total fields' phase. Again the two fields are the predicted using the starting values for the scattering parameters, and the measured field.

FIG. 45 shows the geometry of an acoustic transducer array illuminating an anatomical region through an aberrating layer of fat. A region of interest (ROI), selected by the user, is also shown. The transducer elements that contribute to the image in the ROI are denoted $e_{m1}$ to $e_{m2}$.

Prologue to "A finite difference method for the inverse scattering problem at fixed frequency" (paper following), This imaging algorithm is a novel approach based on discretization of the complete Helmholtz equation with a five point difference equation. The solution to the equation is then obtained using the measured data on the boundary and completing the field solution via a recursion in a direction parallel to the discretization grid diagonal. It is widely known that this recursion is extremely unstable, however, it is shown in [F. Natterer and F. Wuibbeling, "A Finite Difference Method for the Inverse Scattering Problem at Fixed Frequency," Lecture Notes in Physics, 1993, vol. 422: 157–166, herein included as reference] that this instability is entirely a high spatial frequency phenomenon and can thus be eliminated by band-pass filtering and by recuring in the direction of field propagation. We enclose this paper below as part of our invention disclosure. The main advantage over the parabolic method is that all orders of scattering, including reflected energy, are modeled by this approach.

A finite difference method for the inverse scattering problem at fixed frequency F. Natterer, F. Wübbeling
Fachbereich Mathematik
Universität Münster

Abstract: *We consider the problem of computing numerically the potential $f$ in the Helmholtz equation $\Delta u + k^2(1-f)u = 0$ from plane wave irradiation at a fixed frequency $k$. We discretize the differential equation in the plane by a five point difference star on a grid with stepsize $h$. It turns out that the resulting bilinear system can be solved recursively for $f$ and $u$. We study the stability of this recursion. We find that the method enjoyes some stability properties provided $hk$ is chosen properly. The complexity of the method is $O(h^{-4})$.*

1 Introduction

Consider the scattering problem: Find a function $u$ in $I\!\!R^n$ such that $$\Delta u + k^2(1-f)u = 0 \quad \text{in } I\!\!R^n,$$
$$u(x) = e^{ikx\cdot\theta} + w(x) \quad , \quad \theta \in S^{n-1}, \quad (1.1)$$

where $w$ satisfies the Sommerfeld radiation condition, and $f$ is a function of compact support. The inverse problem calls for the computation of $f$ from knowing $u$ outside the support of $f$ for all directions $\theta$ and a single value of $k$. See [1], [8] for the general background. The uniqueness of the inverse problem has recently been settled for $n=3$ by Sylvester and Uhlmann [10], Nachmann [7] and Ramm [9]. As for numerical methods, [5] seems to be the state of the art.

In this note we study the numerical solution of the inverse problem for $n=2$ by a finite difference method. The method is based on a 5 point discretization of (1.1) which takes into account the high frequency behaviour of $u$. Following a suggestion of Curtis and Morrow [2] and Singer, Grünbaum, Kohn and Zubelli [3] the resulting bilinear system for $u$ and $f$ is solved recursively for $f$ and $u$. Our aim is to analyse the stability of this process. This has been completely ignored in [2], while numerical results in [3] indicate that the recursion is awfully unstable. Ideally we would like to have stability if the stepsize $h$ is tied to the irradiating frequency $k$ by the Nyquist condition $hk = \pi$, in which case it would be possible to resolve details of size $2h = \frac{2\pi}{k}$, the optimal value in the sense of the sampling theorem, see e.g. [4].

As in [3], the recursion proceeds diagonal by diagonal in the finite difference mesh. On each diagonal we do a solution step, in which we solve a linear system for $f$ on the current diagonal, followed by a propagation step, in which we extend the field to the next diagonal. We investigate the stability of these two steps separately.

In the propagation step we solve the initial value problem for the elliptic equation (1.1) by a finite difference method. It belongs to the folklore of numerical analysis that such a method is necessarily unstable. However, a closer look reveals that this instability is exclusively a high frequency phenomenon. If the frequency is restricted to a certain interval $[k_{min}, k_{max}]$ - either by choosing an apropriate step size $h$ or by band-pass filtering - then the propagation step turns out to be stable. We call $[k_{min}, k_{max}]$ the stability interval.

If the physical and numerical directions of propagation coincide, the stability interval is $[-k, k]$. This is completely satisfactory, since we do not expect to be able to resolve frequencies beyond the irradiating frequency $k$. If the said two directions are different, then the stability interval is shifted and does not contain a neighbourhood of zero when they make a right angle. By a suitable organization of the computational process and by sacrifying a certain amount of resolution (i.e. by chosing $hk$ larger than its optimal value $\pi$) we can avoid this extreme case.

In the solution step we have to solve a linear system whose matrix is of the Van der Monde type. Such system are notoriously unstable. However, by exploiting the analyticity of the field $u$ in the direction variable $\theta$ we find that the system is not as unstable as one might expect. Its solution can be reduced to stable cases of analytic continuation, provided that $hk$ is sufficiently large. Thus, again by sacrifying a certain amount of resolution, we can make the solution process stable. Of course this does not imply the stability of the combined process.

The outline of the paper is as follows. In section 2 we describe the finite difference approximation and the recursive solution process. In section 3 we prove the stability of the initial value problem for the Helmholtz equation for frequencies in the stability interval, establishing in this way the stability of the propagation step. In section 4 we study - in a rather heuristic way - the stability of the solution step.

2 The finite difference method

In the following we assume $f$ to be zero outside the unit square $D = \{x \in \mathbb{R}^2 : 0 \leq x_1, x_2 \leq 1\}$, and we assume $u$ to be known outside $D$ for a finite number of direction $\theta_j$, $j = 1, \ldots, p$. We put $$u = e^{ikx \cdot \theta}(1 + v)$$

where $v$ satisfies the differential equation $$\Delta v + 2ik\theta \cdot \nabla v - k^2(1+v)f = 0 \,. \tag{2.1}$$

For $v$ small and $k$ large we have approximately $$2ik\theta \cdot \nabla v - k^2 f = 0$$

or $$v(x, \theta) = \frac{k}{2i} \int_0^\infty f(x - t\theta) dt \,.$$

In particular, for $x \in D + \mathbb{R}_+ \theta$, we have $$v(x, \theta) = \frac{k}{2i} Rf(\theta^\perp, x \cdot \theta^\perp) \tag{2.2}$$

where $R$ is the Radon transform $$(Rf)(\theta, s) = \int_{x \cdot \theta = s} f(x) dx$$

and $\theta^\perp \cdot \theta = 0$.

Doing the discretization on $\Delta u$ would force us to use a stepsize $\bar{h}$ much smaller than $\frac{1}{2}$ of the wavelength $2\pi/k$ of the irradiating waves $e^{ikx \cdot \theta}$. This term is no longer present in $v$, as can be seen from (2.2). Thus for the discretization of $v$ the stepsize $h = \pi/k$ corresponding to the aimed - at resolution suffices.

A natural discretization of (2.1) is $$-4v^j_{\ell,m} + (1 + i\varepsilon\theta_1)v^j_{\ell+1,m} + (1 - i\varepsilon\theta_1)v^j_{\ell-1,m} + (1 + i\varepsilon\theta_2)v^j_{\ell,m+1}$$
$$+ (1 - i\varepsilon\theta_2)v^j_{\ell,m-1} - (1 + v^j_{\ell,m})\varepsilon^2 f_{\ell,m} = 0 \tag{2.3}$$

where $\epsilon = hk$. $v^j_{\ell,m}$ stands for the discrete values of $v(x,\theta_j)$ at $x = h(\ell,m) = x_{\ell,m}$. With the values of $v^j_{\ell,m}$ for $x_{\ell,m} \neq D$ known we can solve (2.3) simultaneously for $v^j_{\ell,m}$, $f_{\ell,m}$ ($x_{\ell,m} \in D$) in the following way.

Assume $v^j_{\ell,m}$ to be already known for $\ell + m \leq n$ and $f_{\ell,m}$ for $\ell + m < n$. Renumber the gridpoints $x_{\ell,m}$ along the diagonal $\ell + m = n$ from left to right by $x_\ell$, $\ell = 0,\ldots,n$, see fig. 1 and the gridpoints on the diagonal $\ell + m = n + 1$, $\ell = 1,\ldots,n$ by $x_{n+1},\ldots,x_{2n}$. Write down the difference equations (2.3) at the gridpoints $0,\ldots,n$. Denoting terms involving only quantities which are already known (i.e. $v^j_{\ell,m}$ for $\ell + m \leq n$ and $f_{\ell,n}$ for $\ell + m < n$) by $b$, these equations read $$\begin{aligned}
(1+v^j_0)\epsilon^2 f_0 &- w_j v^j_{n+1} &&&= b^j_0 \\
(1+v^j_1)\epsilon^2 f_1 &- s_j v^j_{n+1} &- w^j v^j_{n+2} &&= b^j_1 \\
&\ldots \\
(1+v^j_{n-1})\epsilon^2 f_{n-1} &&- s^j v^j_{2n-1} &- w^j v^j_{2n} &= b^j_{n-1} \\
(1+v^j_n)\epsilon f_n &&&- s^j v^j_{2n} &= b^j_n
\end{aligned} \quad (2.4)$$

where $$s_j = 1 + i\epsilon\theta^j_2, \quad w_j = 1 + i\epsilon\theta^j_1.$$

The unknown quantities $v^j_{n+1},\ldots,v^j_{2n}$ in (2.4) are readily eliminated by forming suitable linear combination of successive equations, yielding for each direction $\theta_j$ a single equation for $f_0,\ldots,f_n$:

$$\epsilon^2 \sum_{\ell=0}^n (1+v^j_\ell)\lambda^\ell_j f_\ell = \sum_{\ell=0}^n b^j_\ell \lambda^\ell_j, \quad (2.5)$$

$$\lambda_j = -\frac{w_j}{s_j}.$$

For $p > n$, (2.5) is an overdetermined linear system for $f_0,\ldots,f_n$. Once (2.5) is solved for $f_0,\ldots,f_n$ ("solution step"), the values of $v^j_{n+1},\ldots,v^j_{2n}$ on the diagonal $\ell + n = n + 1$ are readily computed by successive substitution from (2.4) ("propagation step"). In the light of our stability analysis in §3, the order in which $v^j_{n+1},\ldots,v^j_{2n}$ are computed does matter: For directions $\theta_j$ making an angle $\leq 45°$ with the $x_1$-axes we have to start with $v^j_{n+1}$, for the other directions with $v^j_{2n}$.

The number $p$ of directions one needs to make (2.4) overdetermined is $O(h^{-1})$. This agrees with a well known result from tomography which states that for a resolution $h$ the number of directions has to be $O(h^{-1})$. In each propagation step we need $O(pn) = O(h^{-1})$ operations, while $O(n^3) = O(h^{-3})$ operations are needed in each solution step. Thus the complexity of the whole process is $O(h^{-4})$. At a first glance this may look prohibitive. But one has to bear in mind that the standard algorithm in tomography requires $O(h^{-3})$ operations and is executed on special hardware within seconds.

3 Stability of the propagation step

We investigate the stability of the initial value problem for (2.1). We restrict ourselves to the case $f = 0$, i.e. we consider $$\Delta v + 2ik\theta \cdot \nabla v = 0,$$
$$v(0, x_2) = v_0(x_2), \quad \frac{\partial v}{\partial x_1}(0, x_2) = v_1(x_2). \quad (3.1)$$

Let $\hat{v}(x_1, \xi)$ be the partial Fourier transform of $v$ with respect to $x_2$, i.e.

$$v(x_1, x_2) = (2\pi)^{-1/2} \int_{R^1} e^{ix_2\xi} \hat{v}(x_1, \xi) d\xi.$$

The initial value problem (3.1) is readily solved in terms of $\hat{v}$ by $$\hat{v}(x_1, \xi) = e^{-ik\theta_1 x_1} \{\hat{v}_0(\xi) \cos x_1\kappa + \frac{\hat{v}_1(\xi)}{\kappa} \sin x_1\kappa\},$$
$$\kappa = \sqrt{k^2\theta_1^2 - 2k\theta_2\xi - \xi^2}.$$

Thus $\hat{v}$ depends on these initial values in a stable way for real $\kappa > 0$, i.e. for $$k^2\theta_1^2 - 2k\theta_2\xi - \xi^2 > 0,$$

or, equivalently, $$-k(1 + \theta_2) < \xi < k(1 - \theta_2). \quad (3.2)$$

Hence the initial value problem (3.1) which describes wave propagation in the direction $x_1$ is stable in the frequency range (3.2). If $\theta$ points in the direction of $x_1$, i.e. $\theta = \begin{pmatrix} 1 \\ 0 \end{pmatrix}$, then the stability interval is $[-k, k]$. On the other hand, if $\theta$ is perpendicular to the $x_1$ direction, i.e. $\theta = \begin{pmatrix} 0 \\ 1 \end{pmatrix}$, then the stability interval is $[-2k, 0]$ and does not contain all small frequencies. If $\theta$ makes an angle of 45° with the $x_1$-axes, then the stability interval is $[-k(1 + \sqrt{\frac{1}{2}}); k(1 - \sqrt{\frac{1}{2}})]$.

A lengthy analysis reveals that the same holds for the finite difference approximation (2.3), with a stability interval practically identical to (3.2). In order to have a reasonable stability interval for each direction $\theta_j$ we do the propagation in $x_1$-direction for all direction $\theta_j$ which make an angle $\leq 45°$ with the $x_1$-axes and in the $x_2$-direction for the other direction $\theta_j$. In the algorithm of §2 this can be achieved by computing $v_{n+1}^j, \ldots, v_{2n}^j$ from (2.4) starting with $v_{n+1}^j$ in the former case and with $v_{2n}^j$ in the latter case.

4 Stability of the solution step

In this section we show - in a rather heuristic manner - that the system (2.5) can be solved in a stable way, provided that $\epsilon$ is sufficiently large and that enough directions $\theta_j$ are available. In fact we shall assume that the data are available for $\theta = \begin{pmatrix} \cos\varphi \\ \sin\varphi \end{pmatrix}$, $0 \leq \varphi < 2\pi$. Then, (2.5) reads $$\epsilon^2 \sum_{\ell=0}^{n} (1 + v_\ell(\varphi))\lambda^\ell(\varphi) f_\ell = \sum_{\ell=0}^{n} b_\ell(\varphi)\lambda^\ell(\varphi) \qquad (4.1)$$

where $$\lambda(\varphi) = -\frac{1 + i\epsilon\cos\varphi}{1 + i\epsilon\sin\varphi}, \quad 0 \leq \varphi < 2\pi.$$

$v_\ell(\varphi)$ is a discrete approximation to $v(x_\ell, \theta)$ which is an entire function of $\varphi$. Hence $v_\ell(\varphi)$ may be viewed, at least approximately, as an entire function of $\varphi$. The same applies to $b_\ell(\varphi)$ which is a linear combination of expressions such as $v_\ell(\varphi)$ with linear functions of $\sin\varphi$, $\cos\varphi$ as coefficients.

Putting $w = \cos\varphi$, $\sqrt{1 - w^2} = \sin\varphi$ for $0 \leq \varphi \leq \pi$, $-\sqrt{1 - w^2} = \sin\varphi$ for $\pi \leq \varphi \leq 2\pi$ we may view $v_\ell(\varphi)$, $b_\ell(\varphi)$, $\lambda(\varphi)$ as analytic functions $v_\ell(w)$, $b_\ell(w)$, $\lambda(w)$ on the Riemannian surface of $\sqrt{1 - w^2}$ with the cut along $-1 \leq w \leq 1$, and $v_\ell(w)$, $b_\ell(w)$ are known along both shores of this cut. By the monodromy theorem we have on this Riemannian surface $$\epsilon^2 \sum_{\ell=0}^{n}(1 + v_\ell(w))\lambda^\ell(w) f_\ell = \sum_{\ell=0}^{n} b_\ell(w)\lambda^\ell(w), \qquad (4.2)$$

$$\lambda(w) = -\frac{1 + i\epsilon w}{1 + i\epsilon\sqrt{1 - w^2}}. \qquad (4.3)$$

We want to replace the variable $w$ by $\lambda$. Solving (4.3) for $w$ we obtain after some algebra $$w = w(\lambda) = \frac{1}{\epsilon(1 + \lambda^2)} \{i(1 + \lambda) - \lambda\sqrt{(1 + \lambda)^2 + \epsilon^2(1 + \lambda^2)}\}. \qquad (4.4)$$

$w(\lambda)$ is an algebraic function of $\lambda$ with branch points $\lambda_0$ and $\overline{\lambda}_0$ where $$\lambda_0 = -\frac{1}{1 + \epsilon^2} \left(1 - i\epsilon\sqrt{\epsilon^2 + 2}\right).$$

$\lambda_0$, $\bar\lambda_0$ lie on the unit circle. We construct the two-sheeted Riemannian surface $\Lambda$ of $w(\lambda)$ by cutting the $\lambda$-plane along the vertical lines joining $\lambda_0$, $\bar\lambda_0$ with $\infty$. In the upper sheet we define the $\sqrt{\ }$ in (4.4) by its principle value near $\lambda = -1$, i.e. we put $w(-1) = \sqrt{\frac{1}{2}}$ in the upper sheet and $w(-1) = -\sqrt{\frac{1}{2}}$ in the lower sheet.

Besides the branch points $\lambda_0$ $\bar\lambda_0$, the function $w(\lambda)$ has singularities at $\lambda = \pm i$. We study these singularities.

For the principle value we have $\sqrt{z^2} = z$ if $Re z > 0$. Hence we have in the upper sheet of $\Lambda$ for $\lambda$ close to $\pm i$ $$\sqrt{(1+\lambda)^2 + \epsilon^2(1+\lambda^2)} = \sqrt{(1+\lambda)^2(1 + \frac{\epsilon^2(1+\lambda^2)}{(1+\lambda)^2})}$$

$$= (1+\lambda)\sqrt{1 + \frac{\epsilon^2(1+\lambda^2)}{(1+\lambda)^2}}$$

$$= (1+\lambda)(1 + \frac{\epsilon^2(1+\lambda^2)}{2(1+\lambda)^2} + \ldots)$$

where the dots stand for powers of $1 + \lambda^2$ higher than 1. Thus, $$w(\lambda) = \frac{1}{\epsilon(1+\lambda^2)}\{i(1+\lambda) - \lambda(1+\lambda)(1 + \frac{\epsilon^2(1+\lambda^2)}{2(1+\lambda)^2} + \ldots)\}$$

$$= \frac{1+\lambda}{\epsilon(1+\lambda^2)}\{i - \lambda - \frac{\epsilon^2\lambda(1+\lambda^2)}{2(1+\lambda)^2} + \ldots\}$$

$$= -\frac{1+\lambda}{\epsilon(\lambda+i)} - \frac{\epsilon}{2}\frac{\lambda}{1+\lambda} + \mathcal{O}(1+\lambda^2).$$

It follows that $w(\lambda)$ has a pole of order 1 at $\lambda = -i$ in the upper sheet but is regular in the lower sheet. In the same way one can show that $w(\lambda)$ has a pole of order 1 at $\lambda = i$ in the lower sheet but is regular in the upper sheet.

Since $v_\ell$, $b_\ell$ are analytic functions of $w$ it follows that $v_\ell(\lambda) := v_\ell(w(\lambda))$, $b_\ell(\lambda) := b_\ell(w(\lambda))$ are analytic functions on $\Lambda$ whose only finite singularities are at $-i$ in the upper sheet and at $i$ in the lower sheet.

From (4.2) we have $$\epsilon^2 \sum_{\ell=0}^{n}(1 + v_\ell(\lambda))\lambda^\ell f_\ell = \sum_{\ell=0}^{n} b_\ell(\lambda)\lambda^\ell. \qquad (4.5)$$

$v_\ell$, $b_\ell$ are known on the curve $C_\epsilon$ on $\lambda$ whose image under $w = w(\lambda)$ is $[-1,+1]$. $C_\epsilon$ is a closed nonintersecting curve on $\Lambda$, see fig. 3.

Our problem is now reduced to computing $f_\ell$ from (4.5) with $\lambda \in C_\epsilon$. We believe that the stability does not depend on the $v_\ell$. Thus we simplify (4.5) into $$\epsilon^2 \sum_{\ell=0}^{n} \lambda^2 f_\ell = \sum_{\ell=0}^{n} b_\ell(\lambda)\lambda^\ell . \tag{4.6}$$

Let $C$ be the curve on $\Lambda$ depicted in fig. 3. In each of the sheets of $\Lambda$ $C$ is part of the unit circle. Multiplying (4.6) by $\lambda^{-m-1}$ and integrating over $C$ we obtain $$f_m = \frac{1}{2\pi i \epsilon^2} \int_C \sum_{\ell=0}^{n} b_\ell(\lambda)\lambda^{\ell-m-1} d\lambda . \tag{4.7}$$

Note that $b_\ell$ is not known on $C$. For the stable evaluation of the right hand side we use Cauchy's theorem to deform $C$ into parts of $C_\epsilon$ on which $|\lambda| \geq 1$ for $\ell - m < 0$ and $|\lambda| \leq 1$ otherwise. We refer to fig. 3 where $a, b \ldots$ denote points on the upper sheet of $\Lambda$ and $a'$, $b' \ldots$ their counterparts on the lower sheet. For $\ell - m < 0$ we move the arc $a'\lambda_0 c$ of $C$ upwards until it merges with the arc $ac$ of $C_\epsilon$. This is possible because there is no singularity between these two arcs - remember that $i$ is a pole only in the lower sheet. In the same way we move the arc $a\bar\lambda_0 \bar c'$ of $C$ downwards to become the arc $a\bar c'$ of $C_\epsilon$. For $\ell - m \geq 0$ the situation is less obvious. We deform the arc $a'\lambda_0 c$ into $a'\bar b'\lambda_0 bc$ and the arc $a\bar\lambda_0 \bar c'$ into $ab\bar\lambda_0 \bar b'\bar c'$. This is not quite what we want since $\bar b'\lambda_0 b$ and $b\bar\lambda_0 \bar b'$ do not belong to $C_\epsilon$. This means that we do not know the values of $b_\ell$ on $\bar b'\lambda_0 b$ and $b\bar\lambda_0 \bar b'$, and the same applies to the arc $c\bar c$ of $C$ which we have not yet considered. In all these cases, $b_\ell$ can be computed from its values on $C_\epsilon$ by analytic continuation. From [6], Theorem III.2.2 we know that analytic continuation can be done in a stable way except in a neighbourhood of the singularities $\lambda_0$, $\bar\lambda_0$, $\pm i$. Thus the arc $c\bar c$ is no problem at all, while the singularities at the endpoints of $\bar b'\lambda_0 b$ and $b\bar\lambda_0 \bar b'$ are doing little harm since the integrands are zero there.

The conclusion is that the solution step is stable to some degree. Of course this does not guarantee that the whole process is stable. Since we do not know how to carry the theoretical analysis farther the next step is to do numerical experiments.

References

[1] Colton, D. - Kress, R.: Inverse Acoustic and Electromagnetic Scattering Theory. Springer 1992.

[2] Curtis, E.B. - Morrow, J.A.: Determining the resistors in a network, SIAM J. Appl. Math. 50, 918-930 (1990).

[3] Grünbaum, F.A.: Diffuse tomography: the isotopic case, Inverse Problems 8, 409-420 (1992).

[4] Jerry, A.J.: The Shannon sampling theorem - its various extenious and applications: a tutorial review. Proc. IEEE 65, 1565-1596 (1977).

[5] Kleinmann, R.E. - van den Berg, P.M.: A hybrid method for two-dimensional problems in tomography. J. Comp. Appl. Math. 42, 17-35 (1992).

[6] Lavrent'ev, M.M. - Romanov, V.G. - Shishatskii, S.P.: Ill-posed Problems of Mathematical Physics and Analysis. AMS Translations of Mathematical Monographs, Vol. 64 (1986).

[7] Nachmann, A.I.: Reconstruction from boundary measurement, Ann. Math. 128, 531-676 (1988).

[8] Ramm, A.C.: Multidimensional inverse scattering problems. Wiley-1992.

[9] Ramm, A.C.: Recovery of the potential from fixed-energy scattering data, Inverse Problems 4, 877-886 (1988).

[10] Sylvester, J. - Uhlmann, G.: A global uniqueness theorem for an inverse boundary value problem, Ann. Math. 125, 153-169 (1987).

Scientific Background for the Advanced Projection-Backprojection Method--

Prologue to "A finite difference method for the inverse scattering problem at fixed frequency" (paper following).

This imaging algorithm is a novel approach based on discretization of the complete Helmholtz equation with a five point difference equation. The solution to the equation is then obtained using the measured data on the boundary and completing the field solution via a recursion in a direction parallel to the discretization grid diagonal. It is widely known that this recursion is extremely unstable, however, it is shown in [F. Natterer and F. Wübbeling, "A Finite Difference Method for the Inverse Scattering Problem at Fixed Frequency,"Lecture Notes in Physics, 1993, vol. 422:157-166, herein included as reference] that this instability is entirely a high spatial frequency phenomenon and can thus be eliminated by band-pass filtering and by recuring in the direction of field propagation. We enclose this paper below as part of our invention disclosure. The main advantage over the parabolic method is that all orders of scattering, including reflected enrgy, are modeled by this approach.

A Propagation-Backpropagation Method for Ultrasound Tomography

Frank Natterer

University of Münster

Abstract: *Ultrasound tomography is modeled by the inverse problem of a 2D Helmholtz equation at fixed frequency with plane wave irradiation. It is assumed that the field is measured outside the support of the unknown potential $f$ for finitely many incident waves. Starting out from an initial guess $f^0$ for $f$ field through the object $f^0$ to yield a computed field whose difference to the measured field is in turn backpropagated. The backpropagated field is used to update $f^0$. The whole process is done in a single step fashion, i.e. the updating is done immediately after backpropagating a single wave. It is very similar to the well know ART method of X-ray tomography, with the projection and backprojection step replaced by propagation and backpropagation. One complete sweep of the algorithm needs $O(pq^2 \log q)$ operations where $p$ is the number of waves and the reconstruction is done on a $q \times q$ grid.*

1 Description of the method

We consider the following inverse problem for the Helmholtz equation: Find the potential $f$ from $$\Delta u_\theta + k^2(1 - f)u_\theta = 0$$
$$u_\theta(x) = e^{ikx\cdot\theta}(1 + v_\theta) \quad (1.1)$$

where $e^{ikx\cdot\theta}v_\theta$ satisfies the Sommerfeld radiation condition. The positive number $k$ is fixed, and $\theta$ runs through all unit vectors in $I\!R^2$. It is assumed that $f = 0$ and $v_\theta = g_\theta$ outside $\Omega = \{x = |x| < \rho\}$ with $g_\theta$ a given function. In fact it suffices to know $g$ and its normal derivative on a circle containing $\Omega$.

The uniqueness has recently been settled by Nachman [7]. In this paper we give a numerical algorithm which computes an approximation to $f$ from finitely many direction $\theta_0, \ldots, \theta_{p-1}$. Most of the existing algorithms use the Born or Rytov approximation (defraction tomography). The algorithms of defraction tomography are of the filtered backpropagation type (Devaney [2]) or simply inverse Fourier transforms, see Kak-Slaney [5]. Methods which avoid the Born and Rytov approximation have been given by Kleinman and van den Berg [6], Colton and Monk [1] and Gutman and Klibanov [4]. These algorithms are iterative in nature. They suffer from excessive computing times and from their apparent inability to handle problems with large values of $k$. A novel approach which yet has to be tested numerically has been suggested by Stenger and O'Reilly [11].

The method of the present paper is iterative, too. It differs from existing ones in two respects. First we avoid the computation of large Jacobians by considering only one wave at a time, solving a vastly underdetermined problem with the help of an approximate generalized inverse. This generalized inverse can be computed very efficiently by backpropagation. Second we make use of a novel and highly efficient finite difference method for doing the propagation step. It has been introduced in Natterer and Wübbeling [10] and is examined in Wübbeling [12] with respect to its use for the inverse problem. It is essentially a method for solving the Cauchy problem for the Helmholtz equation. Contrary to the general believe, this problem is perfectly stable as long as only spatial frequencies below $k$ are sought for. Since we do not expect to be able to determine frequencies larger than $k$, this restriction is quite natural.

On a more formal level, our algorithm is as follows. Consider a square $Q_j$ circumscribed to $\Omega$ with two edges $\Gamma_j$ parallel to $\theta_j$ and with edges $\Gamma_j^+$, $\Gamma_j^-$ orthogonal to $\theta_j$, with $\Gamma_j^+$ lying in the direction of $\theta_j$, see Fig. 1. Let $R_j : L_2(Q_j) \to L_2(\Gamma_j^+)$ be the (nonlinear) operator which associates with each potential $f \in L_2(\Omega)$ the solution $v_j = v_{\theta_j}$ of (1.1) on $\Gamma_j^+$, the values of $v_j$ on $\Gamma_j \cup \Gamma_j^-$ and the values of $\frac{\partial}{\partial \nu} v_j$ ($\nu$ the interior normal on $\partial Q_j$) on $\Gamma_j^-$ being given by the data function $g_{\theta_j}$. Thus, if $v_j$ is the solution to $$\Delta v_j + 2ik\theta_j \cdot \nabla v_j - k^2(1+v_j)f = 0 \quad \text{in } Q_j$$

$$v_j = g_{\theta_j} \text{ on } \Gamma_j \cup \Gamma_j^-, \quad \frac{\partial}{\partial \nu} v_j = \frac{\partial}{\partial \nu} g_{\theta_j} \text{ on } \Gamma_j^-,$$
(1.2)

then $R_j f = v_j$ on $\Gamma_j^+$. With $g_j$ the function $g_{\theta_j}$ restricted to $\Gamma_j^+$, we have $$R_j(f) = g_j, \quad j = 0, \ldots, p-1.$$
(1.3)

This nonlinear system is solved for $f$ in the following way. Let $f^0$ be an initial approximation. Once $f^r$ is determined, put $f^{r+1} = f^r + \omega d^r$ where $d^r$ is an approximation to the minimal norm solution of $$R_j(d^r + f^r) = g_j, \quad j = r \bmod p.$$
(1.4)

$\omega$ is a relaxation factor. Thus our algorithm is simply a non-linear version of the Kaczmarz method which has become to be known as ART (algebraic reconstruction technique) in $X$-ray tomography, see Herman [3], Natterer [8]. As in ART, we call the successive computation of $p$ iterates a complete sweep.

For the approximate solution of (1.4) we linearize (1.3), writing $$R_j(d+f) = R_j(f) + A_j(f)d + \ldots .$$

Here, $A_j(f) : L_2(\Omega) \to L_2(\Gamma_j^+)$ is the linear operator defined by solving $$\Delta w + 2ik\theta_j \cdot \nabla w - k^2 w f - k^2(1+v_j)d = 0 \quad \text{in } Q_j,$$

$$w = 0 \text{ on } \Gamma_j \cup \Gamma_j^-, \quad \frac{\partial w}{\partial \nu} = 0 \text{ on } \Gamma_j^-,$$
(1.5)

$v_j$ the solution of (1.2), and putting $A_j(f)d$ equal to the restriction of $w$ to $\Gamma_j^+$.

In [9] we used a simpler version of $A_j(f)$, omitting the term $k^2 wf$ in (1.5). Meanwhile numerical experiments showed that the gain in simplicity thus obtained does not make up for the loss in accuracy.

In order to compute an approximate minimal norm solution $d^r$ in (1.4) we make use of the adjoint operator $A_j^*(f) : L_2(\Gamma_j^+) \to L_2(Q_j)$. For $g \in L_2(\Gamma_j^+)$ this operator can be evaluated by solving $$\Delta z + 2ik\theta_j \cdot \nabla z - k^2 \overline{f} z = 0 \quad \text{in} \quad Q_j,$$

$$z = 0 \text{ on } \Gamma_j \cup \Gamma_j^+ \quad, \quad \frac{\partial z}{\partial \nu} = g \quad \text{on } \Gamma_j^+ \tag{1.6}$$

for $z$ and putting $$A_j^*(f)g = k^2(1 + \overline{v}_j)z \tag{1.7}$$

with $v_j$ from (1.2). In fact, for sufficiently smooth functions $w$, $z$ Green's formula and an integration by parts show that $$\int_{Q_j} \left\{ (\Delta w + 2ik\theta_j \cdot \nabla w - k^2 fw)\overline{z} - w\overline{(\Delta z + 2ik\theta_j \cdot \nabla z - k^2 \overline{f} z)} \right\} dx$$

$$= \int_{\partial Q_j} (w \frac{\partial \overline{z}}{\partial \nu} - \frac{\partial w}{\partial \nu} \overline{z}) ds + 2ik \left( \int_{\Gamma_j^+} w \overline{z} ds - \int_{\Gamma_j^-} w \overline{z} ds \right)$$

where $\nu$ is the interior normal and $s$ the arc length on $\partial Q_j$. Applying this to $w$ from (1.5) and $z$ from (1.6) yields $$k^2 \int_{Q_j} d(1 + v_j)\overline{z} dx = \int_{\Gamma_j^+} w \overline{g} ds$$

or $$k^2 (d, (1 + \overline{v}_j)z)_{L_2(Q_j)} = (A_j(f)d, g)_{L_2(\Gamma_j^+)},$$

hence (1.7).

We now define $d^r$ to be $$d^r = A_j(f^r)^* C_j(R_j(f^r) - g_j) \tag{1.8}$$

with some operator $C_j$. If $C_j = (A_j(f^r)A_j(f^r)^*)^{-1}$, then $d^r$ is the minimum norm solution of the linearized system. Since the computation of this operator is very time consuming we simply replace it by the identity. From numerical experience we know that this does not seriously slow down the convergence.

This describes our algorithm apart from discretization and filtering which are discussed later. The algorithm consists of the propagation step, in which the measured field is propagated from $\Gamma_j^-$ to $\Gamma_j^+$, assuming $f^r$ to be the potential, to yield the function $R_j(f^r)$ on $\Gamma_j^+$. Then the function $g = R_j(f^r) - g_j$ is backpropagated from $\Gamma_j^+$ to $Q_j$ by solving the initial value problem (1.6). Finally, the backpropagated field is used to update $f^r$. We call $A_j(f^r)^*$ the backpropagation operator and the whole method the propagation-backpropagation algorithm (PBP).

The similarity of PBP to the ART algorithm of computerized tomography is obvious. The propagation and backpropagation step of PBP corresponds to the projection and backprojection step, resp., of ART. It seems that much of the well understood theory of ART (see e.g. Natterer [8]) applies also to PBP. For instance, fairly small relaxation parameters $\omega$ are used in both algorithms, and reordering of the equations (1.3) has a decisive influence on the behaviour of the iterates.

2 Discretization and filtering

The implementation of PBP is very easy. All we need are subroutines for the initial value problems (1.2), (1.6). We have shown in [10] that (1.6), (1.6) can be solved in a stable way for spatial frequencies $\leq k$, and numerical experience shows that the same applies to (1.2) if the frequencies are restricted by $k\sqrt{1-f}$. It has also be shown that the finite difference method is an expedient and reliable method for the numerical solution of (1.2), (1.6). We give the details only for (1.2).

In $Q_j$ we introduce the grid $Q_j^h = \{x_{\ell,m} = h\ell\theta_j + hm\theta_j^\perp : \ell, m = -q,\ldots,q\}$, $h = 1/q$. On $Q_j^h$ we define the approximation $v_{\ell,m}$ to $v_j(x_{\ell,m})$ by $$v_{\ell+1,m} + v_{\ell-1,m} + v_{\ell,m-1} + v_{\ell,m+1} - 4v_{\ell,m}$$
$$+ i\,\varepsilon(v_{\ell+1,m} - v_{\ell-1,m}) - \varepsilon^2(1 + v_{\ell,m})f(x_{\ell,m})v_{\ell,m} = 0 \qquad (2.1)$$
$$|\ell| < q,\ |m| < q,\quad \varepsilon = hk.$$

These equations are complemented by the boundary conditions $$v_{\ell,m} = g_{\theta_j}(x_{\ell,m}) \qquad \text{for } |m| = q,\ |\ell| \leq q$$

and by the initial conditions $$v_{-q,m} = g_{\theta_j}(x_{\ell,m}),\qquad |m| \leq q,$$
$$v_{1-q,m} = h(1 - i\varepsilon)\frac{\partial}{\partial\nu}g_{\theta_j}(x_{-q,m})$$
$$\quad - \frac{1}{2}g_{\theta_j}(x_{-q,m+1}) - \frac{1}{2}g_{\theta_j}(x_{-q,m-1})$$
$$\quad + 2g_{\theta_j}(x_{-q,m}),\qquad |m| < q.$$

The latter expression has been derived by using central differences in the discretization of $\partial/\partial\nu$ and (2.1) for $\ell = -q$.

(2.1) can be solved recursively for $v_{\ell+1,m}$, $\ell = -q+1,\ldots,q-1$, yielding the approximation $v_{q,m}$ to $R_j f(x_{q,m})$, $|m| \leq q$. The recursion is stable if $h \geq \pi/k\sqrt{1-f}$. If a smaller stepsize is chosen, stability can be restored by filtering the vector $v_{\ell,m}$ as a function of $m$ after each step $\ell \to \ell + 1$. This can be done by the discrete Fourier transform. Putting $$\hat{v}_{\ell,n} = \frac{1}{2q} \sum_{m=-q}^{q-1} e^{-imn\pi/q} v_{\ell,m}$$

the filtered version of $v_{\ell,m}$ is $$v'_{\ell,m} = \sum_{|n| \leq N} e^{+imn\pi/q} \hat{v}_{\ell,n}$$

where $N \leq \frac{\rho}{\pi} k \sqrt{1-f}$. The filtering can be done by the fast Fourier transform (FFT). For details see [10], [12]. After each complete sweep of the algorithm we perform a 2D filtering of the current approximation which annihilates frequency components $> k$ which come in during the iteration.

The number of operations one needs for each initial value problem is $q^2$ or $q^2 \log q$ if filtering is used. For a whole sweep of PBP $2p$ initial value problems have to be solved. Thus a complete sweep needs $pq^2$ or $pq^2 \log q$ operations. Apart from the logarithm this is the complexity of one complete sweep of the ART algorithm in $X$-ray tomography. Thus PBP does ultrasound tomography with almost the same speed as ART does $X$-ray tomography.

3 Numerical experiments

In a first experiment we reconstructed the rotationally symmetric function $$f(r) = \begin{cases} 0.1 & , \ |x| \leq 0.8 \\ 0 & , \ \text{otherwise} \end{cases} \quad (3.1)$$

for $k = 50$ from $p = 100$ directions. The scattered waves can be computed exactly for this potential. Thus we have exact data. The reconstruction region is the square of sidelength 2 with midpoint at the origin. The reconstruction is done on a $129 \times 129$ grid.

This example has been chosen in such a way that the Born approximation, which is the basis of defraction tomography, is not valid. The condition for the Born approximation to hold is - for real potentials $$|Rf| \ll \frac{2\pi}{k} \quad (3.2)$$

where $R$ is the Radon transform (i.e. $Rf$ stands for the set of all line integrals of $f$). This is a slight extension of the condition given in [5], p. 214. In our case we have $$|Rf| \leq 0.16 \quad , \quad \frac{2\pi}{k} = 0.126 \ ,$$

hence (3.2) is not satisfied.

We did the reconstruction with $f^0 = \frac{1}{2}f$ and $\omega = 0.004$. This surprisingly small value of $\omega$ which has been found by trial and error is familiar from X-ray tomography. The choice of $f^0$ is such that $$|R(f - f^0)| \leq \frac{2\pi}{k} \ , \quad (3.3)$$

i.e. the Born approximation is valid for $f - f^0$. This condition for the initial approximation seems to be necessary for convergence, see [12] for a discussion.

The results are displayed in fig. 2. The reconstructed potential (blue line) differs from the exact potential (green line) in the interior only by 3%, but at the boundary a loss in resolution is noticeable. However one has to bear in mind that the wavelength $\lambda = \frac{2\pi}{k}$ of the irradiating wave is 0.126, which sets a limit to the achievable spatial resolution.

In a second numerical test we created a elliptical phantom, see fig. 3. On an elliptical base of density 0.15 sits - slightly misalligned - a smaller ellipse with semi axes 0.8, 0.6 and density 0.2, which contains two circles with density 0.21, 0.19, respectively, and a square with sidelength 0.12 and density 0.25. So far the real part of the potential. The imaginary part is 0.02 in the base and zero elsewhere. The size of the square corresponds to the wavelength $\lambda = \frac{2\pi}{k}$, $k = 50$, of the irradiating wave. Thus the square serves as a test for the spatial resolution, while the two circles serve as a test for the density resolution.

The PBP reconstruction after 3 sweeps with $\omega = 0.004$ is shown in fig. 3. The elliptical base has been used as $f^0$. We see that the spatial resolution is exactly as expected, and the density resolution is better than 5%. The cross section of the reconstruction may look disapointing for some one who is used to look at CT pictures with the same amount of data. But in fact the blue line in fig. 3 is virtually indistinguishable from the corresponding cross-section of the low-pass filtered elliptical phantom, the cut-off being put at $k = 50$.

We computed the data by our forward solver. This is usually considered as "inverse crime". But our forward solver is very reliable. Also, we repeated the caculation after having added 5% white noise to the data - without much change in the reconstruction.

For a third numerical test we chose the "finger" from [12]. In our notation, $$f(x) = \begin{cases} -2, & |x - x_0| \leq 0.1 \\ -1, & |x| < 2/3 \text{ and } |x - x_0| > 1/3 \\ 0, & \text{otherwise}, \end{cases}$$

where $x_0 = (1/3, 0)^T$, see fig. 4. As in [12] we chose $k = 7$ and we used $p = 53$ waves, and we work on a $65 \times 65$ grid. The results of PBP after 3 complete sweeps, again with $\omega = 0.004$, is displayed in fig. 4. As in [12] we used $f^0 = -0.5$ as initial approximation. This example shows that PBP can well recover details below the resolution limit of $\frac{2\pi}{k} = 0.90$. Of course, in order to achieve this, one has to drop the filtering after each sweep which has been mentioned in §2.

All these examples have been done with a random ordering of the directions. This has been suggested by our experience with ART, see [8], p. 165.

References

[1] Colton, D. - Monk, P.: A modified dual space method for solving the electromagnetic inverse scattering problem for an infinite cylinder, *Inverse Problems* 10, 87-108 (1994).

[2] Devaney, A.J.: A filtered backpropagation algorithm for diffraction tomography, *Ultrasonic Imaging* 4, 336-350 (1982).

[3] Herman, G.T.: *Image Reconstruction from Projections: The Fundamentals of Computerized Tomography.* Academic Press 1980.

[4] Gutman, S. - Klibanov, M.: Regularized Quasi -Newton Method for Inverse Scattering Problems, Mathl. Comput. Modelling 18, No. 1, pp. 5-31, Pergamon Press Ltd. (1993).

[5] Kak, A.C. - Slaney, M.: *Principle of Computerized Tomographic Imaging.* IEEE Press 1987.

[6] Kleinman, R.E. - van den Berg, P.M.: A modified gradient method for two-dimensional problems in tomography, *J. Comp. Appl. Math.* 42, 17-35 (1992).

[7] Nachman, A.I.: Global uniqueness for a two-dimensional inverse boundary value problem. *Department of Mathematics, Preprint Series*, Number 19, University of Rochester (1993).

[8] Natterer, F.: *The Mathematics of Computerized Tomography.* Wiley - Teubner 1986.

[9] Natterer, F.: Finite difference methods for inverse problems and Applications to Geophysics, Industry, Medicine and Technology, Proceedings of the International Workshop on Inverse Problems, January 17-19, 1995, HoChiMinh City. *Publications of The HoChiMinh City Mathematical Society* 2, 1995.

[10] Natterer, F. - Wübbeling, F.: A finite difference method for the inverse scattering problem at fixed frequency, Lecture Notes in Physics, Vol. 422, p. 157-166, Springer 1993.

The present invention may be embodied in other specific forms without departing from its spirit or essential characteristics, and the presently preferred embodiments, as described above, are to be considered in all respects only as illustrative and not restrictive. The scope of the invention is, therefore, indicated by the appended claims rather than by the foregoing description, and all changes which come within the meaning and range of equivalency of the claims are to be included within their scope.

APPENDIX A

PROGRAMMING CODE

Copyright © 1992 University of Utah/Techniscan Inc. All Rights Reserved

Directory to Appendices B:

A. "Main" program: two dimensional imaging (rpt2d)
B. Two dimensional layered forward problem solution (lay4)
C. Two dimensional layered Green's function generation (grnlay2d)
D. Two dimensional Cylindrical Recursion Imaging (iter.f)
E. "main" program: 3D Elastic parameter inversion
F. Three dimensional layered forward problem solution (lay43d)
G. Three dimensional layered Green's function generation (grnlay3d)
H. Transmission mode imaging without correlation and including remote detectors (rotate2.f)
I. Full three dimensional vector electromagnetic inversion code (electi.f)
J. Three dimensional elastic parameter inversion code (elasti.f)
K. Ribiere-Polak iteration source code (newrp.f)
L Inverse Parabolic Code
L1 Second Inverse Parabolic Code
M Generalized Born code
M1 projection—backprojection—code (Natterer)
M2 subroutines required for proper execution of Appendix M1
M3 header files required for proper execution of code in Appendix M2

What is claimed and desired to be secured by U.S. Letters Patent is as follows:

1. A method of producing an image of an object in a region from wavefield energy that has been transmitted into and scattered by the object, said image comprising a map of selected physical characteristics at selected points within the region, said image being stored in a computer memory, and said method comprising the steps of:

(a) transducing an electric signal at each of one or more frequencies into wavefield energy propagated from one or more of transmitter transducer positions, each said transmitter transducer position propagating wavefield energy at at least one orientation defined by Euler angles with respect to a selected fixed coordinate system;

(b) for one or more receiver positions each having at least one orientation defined by Euler angles with respect to said selected fixed coordinate system, detecting at each of said one or more receiver positions and respective orientations thereof said wavefield energy;

(c) electronically processing said detected wavefield energy so as to transform said detected wavefield energy into one or more reception stored signals stored in said computer memory and corresponding to a scattered wavefield energy detected;

(d) setting a region characteristics estimate of selected physical characteristics at selected points within the region and storing each said region characteristics estimate in said computer memory;

(e) performing a convergence step comprising the following steps:

(1) preparing, for each said one or more frequencies at each said transmitter transducer positions and respective orientations thereof, an estimate of a total wavefield energy at said selected points derived from a selected incident wavefield energy for said selected points stored in the computer memory and said region characteristics estimate for said selected points by the steps of:

(i) designating a primary set of surfaces of a plurality of selected surfaces and a different secondary set of surfaces of said selected surfaces, each said selected surface intersecting said region;

(ii) setting the estimate of the total wavefield energy equal to an initial total incident wavefield energy estimate for the primary set of surfaces;

(iii) computing the estimate of the total wavefield energy on the secondary set of surfaces using the region characteristics estimate on the union of the primary and secondary sets of surfaces and the total wavefield energy on the primary set of surfaces;

(iv) re-designating the primary set of surfaces to include a sub- set of the secondary set of surfaces and re-designating the secondary set of surfaces to include another set of the selected surfaces; and (v) repeating steps ((iii) through ((iv)) until the estimate of the total wavefield energy is computed for each of the selected surfaces;

(2) deriving, for each of said one or more frequencies at each said transmitter transducer position and orientations thereof, a calculated scattered wavefield energy for one or more of said receiver positions and respective orientations thereof from at least one of said region characteristics estimate at said selected points and said estimate of said total wavefield energy for a corresponding transmitter transducer position and orientations thereof at said selected points by one or more of the following:

(i) designating an external surface situated outside said object, and then approximating an integral on the external surface by the sum of:

(a) a first quantity times the estimate of the total wavefield energy on said external surface times a derivative of a Green's function constructed to map to one or more of said receiver positions and respective orientations thereof; and (b) a second quantity times a derivative of the estimate of the total wavefield energy on said external surface times a Green's function constructed to map to one or more of said receiver positions and respective orientations thereof;

(ii) approximating an integral on at least a portion of the region of the product of:

(a) the estimate of the total wavefield energy at said selected points;

(b) the region characteristics estimate at said selected points; and (c) a Green's function constructed to map to one or more of said receiver positions and respective orientations thereof;

(iii) performing the steps of:

(a) for each selected point of a portion of the selected points, said potion of the selected points corresponding to one of said one or more receiver positions and respective orientations thereof, setting said calculated scattered wavefield energy equal to the estimate of the total wavefield energy less said selected incident wavefield energy; and (b) computing a sum over said portion of said selected points equal to the sum of the calculated scattered wavefield energy for said portion of said selected points times a function constructed to correspond to one or more of said one or more receiver positions and respective orientations thereof, (3) for each said transmitter transducer position and orientations thereof and for each said receiver position and orientation thereof, comparing said scattered wavefield energy detected to said calculated scattered wavefield energy to derive therefrom a comparator; and (4) when said comparator is greater than a selected tolerance, determining and storing in said computer memory said region characteristics estimate by computing one or more derivatives of the comparator or approximations thereof with respect to one or more of said selected physical characteristics at one or more of said selected points, and then using said one or more derivatives of the comparator or approximations thereof to compute a region characteristics correction, and then adding said region characteristics correction to each of said region characteristics estimate for each of said one or more of said selected points, wherein said one or more derivatives of the comparator or approximations thereof is computed from one or more of:

(i) at each said one or more frequencies, said estimate of said total wavefield energy for said selected points for each of said one or more of said transmitter transducer positions and respective orientations thereof;

(ii) at each of said one or more frequencies, said calculated scattered wavefield energy for said one or more receiver positions and respective orientations thereof, and for each of said one or more of said transmitter transducer positions and respective orientations thereof;

(iii) at each of said one or more frequencies, said scattered wavefield energy detected for said one or more receiver positions and respective orientations thereof, and for each of said one or more of said transmitter transducer positions and respective orientations thereof, and (iv) said region characteristics estimate for said selected points;

(f) repeating said convergence step until said comparator is less than or equal to said selected tolerance, and thereafter storing said region characteristics estimate as said image in the computer memory.

2. A methods as defined in claim 1, wherein said convergence step is a Gauss-Newton step computed using conjugate gradients.

3. A method as defined in claim 1, wherein:

A. model calibration parameters and an imaging system simulation model of said imaging device are used to compute at least one of:

(i) said selected incident wavefield energy and said Green's function constructed to map to one or more of said receiver positions and respective orientations thereof;

(ii) said selected incident wavefield energy and said Green's function constructed to map to one or more of said receiver positions and respective orientations thereof; and (iii) said selected incident wavefield energy and said function constructed to correspond to one or more of said receiver positions and respective orientations thereof;

B. said model calibration parameters comprising at least one of:

(i) one or more transmitter equivalent source vectors, said one or more transmitter equivalent source vectors being input to one or more transmitter simulators, said one or more transmitter simulators outputting one or more simulated transmitter wavefields of said interrogating wavefield energy;

(ii) one or more receiver equivalent source vectors, said one or more receiver equivalent source vectors being input to one or more receiver simulators, said one or more receiver simulators outputting one or more simulated receiver sensitivity functions, said one or more receiver sensitivity functions being electrical responses of said one or more receiver simulators to a point source of interrogating wavefield energy placed at substantially any location in said region;

(iii) one or more transmitter simulation positions, each said one of more transmitter simulation positions having one or more transmitter simulation orientations, each said one or more transmitter simulation orientations being defined by Euler angles;

(iv) one or more receiver simulation positions, each said one of more receiver simulation positions having one or more receiver simulation orientations, each said one or more receiver simulation orientations being defined by Euler angles; and (v) one or more electronic system parameters of said imaging device, said electronic system parameters substantially characterizing the analog and digital electronic functions of said imaging device, C. said calibration parameters are derived by the steps of:

(i) collecting a received wavefield energy by a process comprising the steps of:

I. choosing a substantially known matter distribution in said region from a selected set of one or more substantially known matter distributions;

II. choosing one of said one of more transmitter transducers at one of said one or more transmitter positions and at one of said one or more transmitter orientations;

III. choosing one of said one of more receiver transducers at one of said one or more receiver positions and at one of said one or more receiver orientations;

IV. transmitting interrogating wavefield energy from said one of said one of more transmitter transducers at one of said one or more transmitter positions and at one of said one or more transmitter orientations into said region;

V. receiving interrogating wavefield energy at said one of said one or more transducer receivers at one of said one or more receiver positions and at one of said one or more receiver orientations;

VI. repeating C(III) through C(IV) until a selected portion of said one or more receiver transducers at said one or more receiver positions and orientations thereof have been chosen;

VII. repeating steps C(II) through C(VI) until a selected portion of said one or more transmitter transducers at said one or more transmitter positions and orientations thereof have been chosen;

VIII. repeating steps C(I) through C(VII) until all of said selected set of one or more substantially known matter distributions have been chosen;

(ii) constructing said imaging system simulation model of said imaging device and said imaging process used therewith with an input equal to said model calibration parameters and an output equal to a predicted received wavefield energy, said predicted received wavefield energy being an approximation of said received wavefield energy, said imaging system simulation model being derived from at least one of:

I. a mathematical theory of said interrogating wavefield energy;

II. a simulation model of the analog and digital electronic functions of said imaging device;

III. said one or more transmitter simulators; and

IV. said one or more receiver simulators;

(iii) setting a portion of said model calibration parameters equal to selected values;

(iv) solving for substantially all other portions of said model calibration parameters using the steps of:

I. defining a comparator, said comparator being a positive scaler value that is a measure of the difference between said received wavefield energy and said predicted received wavefield energy; and II. using an optimization algorithm to substantially minimize said comparator with respect to said substantially all other portions of said model calibration parameters until said comparator is less than a selected tolerance;

(v) storing said model calibration parameters in a computer memory.

4. A method as defined in claim 1, wherein said convergence step is a Ribiere-Polak step.

5. A method as defined in claim 1, wherein said estimate of said total wavefield energy at said selected points derived from said selected incident wavefield energy for said selected points is prepared, at least in part, by a fast Fourier transform.

6. A method as defined in claim 1, wherein said scattered wavefield energy detected includes a digital representation of said wavefield energy propagating both into and through said region.

7. A method as defined in claim 1, wherein said step of transducing said electric signal at each of one or more frequencies into wavefield energy propagated from one or more of transmitter transducer positions, each said transmitter transducer position propagating wavefield energy, comprises the steps of:

positioning a transducer array adjacent to said object, said transducer array comprising said one or more of transmitter transducer positions and said one or more receiver positions;

sending said electric signal at a first frequency to each said transmitter transducer positions so that each said transmitter transducer positions will in turn propagate wavefield energy at said first frequency; and thereafter changing the frequency of said signal and sending said electrical signal at said changed frequency to each said transmitter transducer position so as to sequentially propagate wavefield energy from each said transmitter transducer position at said changed frequency.

8. A method as defined in claim 7, wherein said transducer array is configured to enclose at least a portion of said object.

9. A method as defined in claim 1, wherein said step of transducing said electric signal at each of one or more frequencies into wavefield energy propagated from one or more of transmitter transducer positions, each said transmitter transducer position propagating wavefield energy, comprises the steps of:

positioning a transducer array adjacent to at least a portion of said region, said transducer array comprising said one or more of transmitter transducer positions and said one or more receiver positions;

generating said electric signal in the form of a waveform which is characterized by one or more different frequencies; and sending said generated waveform in turn to each said transmitter transducer position so as to propagate wavefield energy at said one or more frequencies from each said transmitter transducer position.

10. A method as defined in claim 9, wherein said transducer array is configured to enclose at least a portion of said region.

11. A method as defined in claim 1, wherein said step of detecting at each of said one or more receiver positions and respective orientations thereof said wavefield energy comprises the steps of:

positioning a transducer array adjacent to said object, said transducer array comprising said one or more of transmitter transducer positions and said one or more receiver positions; and after wavefield energy is transmitted from one of said transmitter transducer positions, sequencing each of said one or more receiver positions so as to detect said scattered wavefield energy at each of said one or more receiver positions in turn.

12. A method as defined in claim 11, wherein said step of electronically processing said detected wavefield energy comprises the steps of:

transducing the wavefield energy detected by each of said one or more receiver positions into a corresponding electric signal;

amplifying said corresponding electric signal to produce an amplified signal; and thereafter processing each said amplified signal so as to generate two signals which correspond to mathematical real and imaginary parts of a representation of each said amplified signal.

13. A method as defined in claim 12, wherein the step of processing each said amplified signal comprises the steps of:

inputting each said amplified signal detected at each of said one or more receiver positions to first and second multiplier circuits and multiplying each said amplified signal input to said first multiplier circuit by each said electric signal sent to each of said one or more transmitter transducer positions;

shifting by 90° the phase of an electric signal that is the duplicate of each said electric signal input to said first multiplier circuit, and thereafter multiplying each said amplified signal input to said second multiplier circuit by each said electric signal that is shifted by 90°; and filtering the output of each said multiplier circuit with a low-pass filter and thereafter integrating and digitizing the output of each said low-pass filter.

14. A method as defined in claim 12, wherein said step of processing each said amplified signal comprises the steps of:
inputting each said amplified signal to a high speed analog-to-digital converter so as to digitize each said amplified signal; and
inputting each said digitized signal from said high speed analog-to-digital converter into a parallel processor programmed to take the complex fast Fourier transform of each said digitized signal.

15. A method as defined in claim 11, wherein said transducer array is configured to substantially enclose said region.

16. A method as defined in claim 1, wherein said primary set of surfaces has only one element, and said secondary set of surfaces has only one element.

17. A method as defined in claim 1, wherein said region characteristics estimate of said selected physical characteristics at said selected points within the region is initialized to an average value determined by an estimated average of said region characteristics estimate.

18. A method as defined in claim 1, wherein said estimate of the total wavefield energy at said selected points for said one or more transmitter transducer positions and respective orientations thereof are obtained separately at each said frequency sequentially.

19. A method as defined in claim 1, wherein said region characteristics estimate of said selected physical characteristics at said selected points within the region is formulated using a plurality of frequency-independent components represented as a vector $\Gamma$ multiplied by a frequency-dependent matrix M, and wherein said vector $\Gamma$ is updated so as to determine said region characteristics estimate of said selected physical characteristics at said selected points within the region.

20. A method as defined in claim 19, wherein said vector $\Gamma$ is updated using a conjugate gradient method.

21. A method as defined in claim 1, wherein said region characteristics correction is determined by a conjugate gradient method.

22. A method as defined in claim 1, wherein the each of said plurality of selected surfaces is a plane and where the step of computing the estimate of the total wavefield energy on the secondary set of surfaces using the region characteristics estimate on the union of the primary and secondary sets of surfaces and the total wavefield energy on the primary set of surfaces is computed using a Fast-Fourier-Transform implemented propagator, where said propagator does not involve any approximation to the square root function.

23. The method as defined in claim 1, wherein computing said region characteristics estimate from one or more derivatives of the comparator or approximations thereof with respect to one or more of said selected physical characteristics at one or more of said selected points constructs a steepest descent direction; and then setting said region characteristics estimate equal to a sum of:

(a) a selected quantity times said steepest descent direction; and
(b) a selected function on said one or more of said selected points, wherein said selected quantity and said selected function are selected to reduce the comparator.

24. A method for producing an image of an object in a region from wavefield energy that has been transmitted into and scattered by the object, said image comprising a map of selected physical characteristics at selected points within the region, said image being stored in a computer memory, and said method comprising the steps of:

(a) transducing an electric signal at each of one or more frequencies into wavefield energy propagated from one or more of transmitter transducer positions, each said transmitter transducer position propagating wavefield energy at at least one orientation defined by Euler angles with respect to a selected fixed coordinate system;

(b) for one or more receiver positions each having at least one orientation defined by Euler angles with respect to said selected fixed coordinate system, detecting at each of said one or more receiver positions and respective orientations thereof said wavefield energy;

(c) electronically processing said detected wavefield energy so as to transform said detected wavefield energy into one or more reception stored signals stored in said computer memory and corresponding to a scattered wavefield energy detected;

(d) setting a region characteristics estimate of selected physical characteristics at selected points within the region and storing each said region characteristics estimate in said computer memory;

(e) performing a convergence step comprising the following steps:

(1) preparing, for each said one or more frequencies at each said transmitter transducer positions and respective orientations thereof, an estimate of a total wavefield energy at said selected points derived from a selected incident wavefield energy for said selected points stored in the computer memory and said region characteristics estimate for said selected points by the steps of:

(i) designating a primary set of surfaces of a plurality of selected surfaces and a different secondary set of surfaces of said selected surfaces, each said selected surface intersecting said region;

(ii) setting the estimate of the total wavefield energy equal to an initial total incident wavefield energy estimate for the primary set of surfaces;

(iii) computing the estimate of the total wavefield energy on the secondary set of surfaces using the region characteristics estimate on the union of the primary and secondary sets of surfaces and the total wavefield energy on the primary set of surfaces;

(iv) re-designating the primary set of surfaces to include a sub- set of the secondary set of surfaces and re-designating the secondary set of surfaces to include another set of the selected surfaces; and (v) repeating steps ((iii) through ((iv)) until the estimate of the total wavefield energy is computed for each of the selected surfaces;

(2) deriving, for each of said one or more frequencies at each said transmitter transducer position and orientations thereof, a calculated scattered wavefield energy for one or more of said receiver positions and respective orientations thereof from at least one of said region characteristics estimate at said selected points and said estimate of said total wavefield energy for a corresponding transmitter transducer position and orientations thereof at said selected points by designating an external surface situated outside said object, and then approximating an integral on the external surface by the sum of:

(i) a first quantity times the estimate of the total wavefield energy on said external surface times a derivative of a Green's function constructed to map to one or more of said receiver positions and respective orientations thereof; and (ii) a second quantity times a derivative of the estimate of the total wavefield energy on said external surface times a Green's function constructed to map to one or more of said receiver positions and respective orientations thereof;

(3) for each said transmitter transducer position and orientations thereof and for each said receiver position and orientation thereof, comparing said scattered wavefield energy detected to said calculated scattered wavefield energy to derive therefrom a comparator; and (4) when said comparator is greater than a selected tolerance, determining and storing in said computer memory said region characteristics estimate by computing one or more derivatives of the comparator or approximations thereof with respect to one or more of said selected physical characteristics at one or more of said selected points, and then using said one or more derivatives of the comparator or approximations thereof to compute a region characteristics correction, and then adding said region characteristics correction to each of said region characteristics estimate for each of said one or more of said selected points, wherein said one or more derivatives of the comparator or approximations thereof is computed from one or more of:

(i) at each said one or more frequencies, said estimate of said total wavefield energy for said selected points for each of said one or more of said transmitter transducer positions and respective orientations thereof;

(ii) at each of said one or more frequencies, said calculated scattered wavefield energy for said one or more receiver positions and respective orientations thereof, and for each of said one or more of said transmitter transducer positions and respective orientations thereof;

(iii) at each of said one or more frequencies, said scattered wavefield energy detected for said one or more receiver positions and respective orientations thereof, and for each of said one or more of said transmitter transducer positions and respective orientations thereof; and (iv) said region characteristics estimate for said selected points;

(f) repeating said convergence step until said comparator is less than or equal to said selected tolerance, and thereafter storing said region characteristics estimate as said image in the computer memory.

25. A methods as defined in claim 24, wherein said convergence step is a Gauss-Newton step computed using conjugate gradients.

26. A method as defined in claim 24, wherein:

A. model calibration parameters and an imaging system simulation model of said imaging device are used to compute:

(i) said selected incident wavefield energy;

(ii) said Green's function constructed to map to one or more of said receiver positions and respective orientations thereof; and (iii) said derivative of a Green's function constructed to map to one or more of said receiver positions and respective orientations thereof;

B. said model calibration parameters comprising at least one of:

(i) one or more transmitter equivalent source vectors, said one or more transmitter equivalent source vectors being input to one or more transmitter simulators, said one or more transmitter simulators outputting one or more simulated transmitter wavefields of said interrogating wavefield energy;

(ii) one or more receiver equivalent source vectors, said one or more receiver equivalent source vectors being input to one or more receiver simulators, said one or more receiver simulators outputting one or more simulated receiver sensitivity functions, said one or more receiver sensitivity functions being electrical responses of said one or more receiver simulators to a point source of interrogating wavefield energy placed at substantially any location in said region;

(iii) one or more transmitter simulation positions, each said one of more transmitter simulation positions having one or more transmitter simulation orientations, each said one or more transmitter simulation orientations being defined by Euler angles;

(iv) one or more receiver simulation positions, each said one of more receiver simulation positions having one or more receiver simulation orientations, each said one or more receiver simulation orientations being defined by Euler angles; and (v) one or more electronic system parameters of said imaging device, said electronic system parameters substantially characterizing the analog and digital electronic functions of said imaging device, C. said calibration parameters are derived by the steps of:

(i) collecting a received wavefield energy by a process comprising the steps of:

I. choosing a substantially known matter distribution in said region from a selected set of one or more substantially known matter distributions;

II. choosing one of said one of more transmitter transducers at one of said one or more transmitter positions and at one of said one or more transmitter orientations;

III. choosing one of said one of more receiver transducers at one of said one or more receiver positions and at one of said one or more receiver orientations;

IV. transmitting interrogating wavefield energy from said one of said one of more transmitter transducers at one of said one or more transmitter positions and at one of said one or more transmitter orientations into said region;

V. receiving interrogating wavefield energy at said one of said one or more transducer receivers at one of said one or more receiver positions and at one of said one or more receiver orientations;

VI. repeating C(III) through C(IV) until a selected portion of said one or more receiver transducers at said one or more receiver positions and orientations thereof have been chosen;

VII. repeating steps C(II) through C(VI) until a selected portion of said one or more transmitter transducers at said one or more transmitter positions and orientations thereof have been chosen;

VIII. repeating steps C(I) through C(VII) until all of said selected set of one or more substantially known matter distributions have been chosen;

(ii) constructing said imaging system simulation model of said imaging device and said imaging process used therewith with an input equal to said model calibration parameters and an output equal to a predicted received wavefield energy, said predicted received wavefield energy being an approximation of said received wavefield energy, said imaging system simulation model being derived from at least one of:

I. a mathematical theory of said interrogating wavefield energy;

II. a simulation model of the analog and digital electronic functions of said imaging device;

III. said one or more transmitter simulators; and

IV. said one or more receiver simulators;

(iii) setting a portion of said model calibration parameters equal to selected values;

(iv) solving for substantially all other portions of said model calibration parameters using the steps of:

I. defining a comparator, said comparator being a positive scaler value that is a measure of the difference between said received wavefield energy and said predicted received wavefield energy; and II. using an optimization algorithm to substantially minimize said comparator with respect to said substantially all other portions of said model calibration parameters until said comparator is less than a selected tolerance;

(v) storing said model calibration parameters in a computer memory.

27. A method as defined in claim 24, wherein said convergence step is a Ribiere-Polak step.

28. A method as defined in claim 24, wherein said estimate of said total wavefield energy at said selected points derived from said selected incident wavefield energy for said selected points is prepared, at least in part, by a fast Fourier transform.

29. A method as defined in claim 24, wherein said scattered wavefield energy detected includes a digital representation of said wavefield energy propagating both into and through said region.

30. A method as defined in claim 24, wherein said step of transducing said electric signal at each of one or more frequencies into wavefield energy propagated from one or more of transmitter transducer positions, each said transmitter transducer position propagating wavefield energy comprises the steps of:

positioning a transducer array adjacent to said object, said transducer array comprising said one or more of transmitter transducer positions and said one or more receiver positions;

sending said electric signal at a first frequency to each said transmitter transducer positions so that each said transmitter transducer positions will in turn propagate wavefield energy at said first frequency; and thereafter changing the frequency of said signal and sending said electrical signal at said changed frequency to each said transmitter transducer position so as to sequentially propagate wavefield energy from each said transmitter transducer position at said changed frequency.

31. A method as defined in claim 30, wherein said transducer array is configured to enclose at least a portion of said object.

32. A method as defined in claim 24, wherein said step of transducing said electric signal at each of one or more frequencies into wavefield energy propagated from one or more of transmitter transducer positions, each said transmitter transducer position propagating wavefield energy, comprises the steps of:

positioning a transducer array adjacent to at least a portion of said region, said transducer array comprising said one or more of transmitter transducer positions and said one or more receiver positions;

generating said electric signal in the form of a waveform which is characterized by one or more different frequencies; and sending said generated waveform in turn to each said transmitter transducer position so as to propagate wavefield energy at said one or more frequencies from each said transmitter transducer position.

33. A method as defined in claim 32, wherein said transducer array is configured to enclose at least a portion of said region.

34. A method as defined in claim 24, wherein said step of detecting at each of said one or more receiver positions and respective orientations thereof said wavefield energy comprises the steps of:

positioning a transducer array adjacent to said object, said transducer array comprising said one or more of transmitter transducer positions and said one or more receiver positions; and after wavefield energy is transmitted from one of said transmitter transducer positions, sequencing each of said one or more receiver positions so as to detect said scattered wavefield energy at each of said one or more receiver positions in turn.

35. A method as defined in claim 34, wherein said step of electronically processing said detected wavefield energy comprises the steps of:

transducing the wavefield energy detected by each of said one or more receiver positions into a corresponding electric signal;

amplifying said corresponding electric signal to produce an amplified signal; and thereafter processing each said amplified signal so as to generate two signals which correspond to mathematical real and imaginary parts of a representation of each said amplified signal.

36. A method as defined in claim 35, wherein the step of processing each said amplified signal comprises the steps of:

inputting each said amplified signal detected at each of said one or more receiver positions to first and second multiplier circuits and multiplying each said amplified signal input to said first multiplier circuit by each said electric signal sent to each of said one or more transmitter transducer positions;

shifting by 90° the phase of an electric signal that is the duplicate of each said electric signal input to said first multiplier circuit, and thereafter multiplying each said amplified signal input to said second multiplier circuit by each said electric signal that is shifted by 90°; and filtering the output of each said multiplier circuit with a low-pass filter and thereafter integrating and digitizing the output of each said low-pass filter.

37. A method as defined in claim 35, wherein said step of processing each said amplified signal comprises the steps of:

inputting each said amplified signal to a high speed analog-to-digital converter so as to digitize each said amplified signal; and inputting each said digitized signal from said high speed analog-to-digital converter into a parallel processor programmed to take the complex fast Fourier transform of each said digitized signal.

38. A method as defined in claim 34, wherein said transducer array is configured to substantially enclose said region.

39. A method as defined in claim 24, wherein said primary set of surfaces has only one element, and said secondary set of surfaces has only one element.

40. A method as defined in claim 24, wherein said region characteristics estimate of said selected physical characteristics at said selected points within the region is initialized to an average value determined by an estimated average of said region characteristics estimate.

41. A method as defined in claim 24, wherein said estimate of the total wavefield energy at said selected points for said one or more transmitter transducer positions and respective orientations thereof are obtained separately at each said frequency sequentially.

42. A method as defined in claim 24, wherein said region characteristics estimate of said selected physical characteristics at said selected points within the region is formulated using a plurality of frequency-independent components represented as a vector $\Gamma$ multiplied by a frequency-dependent matrix M, and wherein said vector $\Gamma$ is updated so as to determine said region characteristics estimate of said selected physical characteristics at said selected points within the region.

43. A method as defined in claim 42, wherein said vector $\Gamma$ is updated using a conjugate gradient method.

44. A method as defined in claim 24, wherein said region characteristics correction is determined by a conjugate gradient method.

45. A method as defined in claim 24, wherein the each of said plurality of selected surfaces is a plane and where the step of computing the estimate of the total wavefield energy on the secondary set of surfaces using the region characteristics estimate on the union of the primary and secondary sets of surfaces and the total wavefield energy on the primary set of surfaces is computed using a Fast-Fourier-Transform implemented propagator, where said propagator does not involve any approximation to the square root function.

46. The method as defined in claim 24, wherein computing said region characteristics estimate from one or more derivatives of the comparator or approximations thereof with respect to one or more of said selected physical characteristics at one or more of said selected points constructs a steepest descent direction; and then setting said region characteristics estimate equal to a sum of:
   (a) a selected quantity times said steepest descent direction; and
   (b) a selected function on said one or more of said selected points, wherein said selected quantity and said selected function are selected to reduce the comparator.

47. A method for producing an image of an object in a region from wavefield energy that has been transmitted into and scattered by the object, said image comprising a map of selected physical characteristics at selected points within the region, said image being stored in a computer memory, and said method comprising the steps of:
   (a) transducing an electric signal at each of one or more frequencies into wavefield energy propagated from one or more of transmitter transducer positions, each said transmitter transducer position propagating wavefield energy at at least one orientation defined by Euler angles with respect to a selected fixed coordinate system;
   (b) for one or more receiver positions each having at least one orientation defined by Euler angles with respect to said selected fixed coordinate system, detecting at each of said one or more receiver positions and respective orientations thereof said wavefield energy;
   (c) electronically processing said detected wavefield energy so as to transform said detected wavefield energy into one or more reception stored signals stored in said computer memory and corresponding to a scattered wavefield energy detected;
   (d) setting a region characteristics estimate of selected physical characteristics at selected points within the region and storing each said region characteristics estimate in said computer memory;
   (e) performing a convergence step comprising the following steps:
      (1) preparing, for each said one or more frequencies at each said transmitter transducer positions and respective orientations thereof, an estimate of a total wavefield energy at said selected points derived from a selected incident wavefield energy for said selected points stored in the computer memory and said region characteristics estimate for said selected points by the steps of:
         (i) designating a primary set of surfaces of a plurality of selected surfaces and a different secondary set of surfaces of said selected surfaces, each said selected surface intersecting said region;
         (ii) setting the estimate of the total wavefield energy equal to an initial total incident wavefield energy estimate for the primary set of surfaces;
         (iii) computing the estimate of the total wavefield energy on the secondary set of surfaces using the region characteristics estimate on the union of the primary and secondary sets of surfaces and the total wavefield energy on the primary set of surfaces;
         (iv) re-designating the primary set of surfaces to include a sub- set of the secondary set of surfaces and re-designating the secondary set of surfaces to include another set of the selected surfaces; and
         (v) repeating steps ((iii) through ((iv)) until the estimate of the total wavefield energy is computed for each of the selected surfaces;
      (2) deriving, for each of said one or more frequencies at each said transmitter transducer position and orientations thereof, a calculated scattered wavefield energy for one or more of said receiver positions and respective orientations thereof from at least one of said region characteristics estimate at said selected points and said estimate of said total wavefield energy for a corresponding transmitter transducer position and orientations thereof at said selected points by approximating an integral on at least a portion of the region of the product of:
         (i) the estimate of the total wavefield energy at said selected points;
         (ii) the region characteristics estimate at said selected points; and
         (iii) a Green's function constructed to map to one or more of said receiver positions and respective orientations thereof;
      (3) for each said transmitter transducer position and orientations thereof and for each said receiver position and orientation thereof, comparing said scattered wavefield energy detected to said calculated scattered wavefield energy to derive therefrom a comparator; and
      (4) when said comparator is greater than a selected tolerance, determining and storing in said computer memory said region characteristics estimate by computing one or more derivatives of the comparator or approximations thereof with respect to one or more of said selected physical characteristics at one or more of said selected points, and then using said one or more derivatives of the comparator or approximations thereof to compute a region characteristics correction, and then adding said region characteristics correction to each of said region characteristics estimate for each of said one or more of said selected points, wherein said one or more derivatives of the comparator or approximations thereof is computed from one or more of:

(i) at each said one or more frequencies, said estimate of said total wavefield energy for said selected points for each of said one or more of said transmitter transducer positions and respective orientations thereof;

(ii) at each of said one or more frequencies, said calculated scattered wavefield energy for said one or more receiver positions and respective orientations thereof, and for each of said one or more of said transmitter transducer positions and respective orientations thereof;

(iii) at each of said one or more frequencies, said scattered wavefield energy detected for said one or more receiver positions and respective orientations thereof, and for each of said one or more of said transmitter transducer positions and respective orientations thereof; and (iv) said region characteristics estimate for said selected points;

(f) repeating said convergence step until said comparator is less than or equal to said selected tolerance, and thereafter storing said region characteristics estimate as said image in the computer memory.

48. A methods as defined in claim 47, wherein said convergence step is a Gauss-Newton step using conjugate gradients.

49. A method as defined in claim 47, wherein:

A. model calibration parameters and an imaging system simulation model of said imaging device are used to compute:
  (i) said selected incident wavefield energy; and
  (ii) said Green's function constructed to map to one or more of said receiver positions and respective orientations thereof;

B. said model calibration parameters comprising at least one of:
  (i) one or more transmitter equivalent source vectors, said one or more transmitter equivalent source vectors being input to one or more transmitter simulators, said one or more transmitter simulators outputting one or more simulated transmitter wavefields of said interrogating wavefield energy;
  (ii) one or more receiver equivalent source vectors, said one or more receiver equivalent source vectors being input to one or more receiver simulators, said one or more receiver simulators outputting one or more simulated receiver sensitivity functions, said one or more receiver sensitivity functions being electrical responses of said one or more receiver simulators to a point source of interrogating wavefield energy placed at substantially any location in said region;
  (iii) one or more transmitter simulation positions, each said one of more transmitter simulation positions having one or more transmitter simulation orientations, each said one or more transmitter simulation orientations being defined by Euler angles;
  (iv) one or more receiver simulation positions, each said one of more receiver simulation positions having one or more receiver simulation orientations, each said one or more receiver simulation orientations being defined by Euler angles; and
  (v) one or more electronic system parameters of said imaging device, said electronic system parameters substantially characterizing the analog and digital electronic functions of said imaging device, C. said calibration parameters are derived by the steps of:
  (i) collecting a received wavefield energy by a process comprising the steps of:
    I. choosing a substantially known matter distribution in said region from a selected set of one or more substantially known matter distributions;
    II. choosing one of said one of more transmitter transducers at one of said one or more transmitter positions and at one of said one or more transmitter orientations;
    III. choosing one of said one of more receiver transducers at one of said one or more receiver positions and at one of said one or more receiver orientations;
    IV. transmitting interrogating wavefield energy from said one of said one of more transmitter transducers at one of said one or more transmitter positions and at one of said one or more transmitter orientations into said region;
    V. receiving interrogating wavefield energy at said one of said one or more transducer receivers at one of said one or more receiver positions and at one of said one or more receiver orientations;
    VI. repeating C(III) through C(IV) until a selected portion of said one or more receiver transducers at said one or more receiver positions and orientations thereof have been chosen;
    VII. repeating steps C(II) through C(VI) until a selected portion of said one or more transmitter transducers at said one or more transmitter positions and orientations thereof have been chosen;
    VIII. repeating steps C(I) through C(VII) until all of said selected set of one or more substantially known matter distributions have been chosen;
  (ii) constructing said imaging system simulation model of said imaging device and said imaging process used therewith with an input equal to said model calibration parameters and an output equal to a predicted received wavefield energy, said predicted received wavefield energy being an approximation of said received wavefield energy, said imaging system simulation model being derived from at least one of:
    I. a mathematical theory of said interrogating wavefield energy;
    II. a simulation model of the analog and digital electronic functions of said imaging device;
    III. said one or more transmitter simulators; and
    IV. said one or more receiver simulators;
  (iii) setting a portion of said model calibration parameters equal to selected values;
  (iv) solving for substantially all other portions of said model calibration parameters using the steps of:
    I. defining a comparator, said comparator being a positive scaler value that is a measure of the difference between said received wavefield energy and said predicted received wavefield energy; and II. using an optimization algorithm to substantially minimize said comparator with respect to said substantially all other portions of said model calibration parameters until said comparator is less than a selected tolerance;

(v) storing said model calibration parameters in a computer memory.

50. A method as defined in claim 47, wherein said convergence step is a Ribiere-Polak step.

51. A method as defined in claim 47, wherein said estimate of said total wavefield energy at said selected points derived from said selected incident wavefield energy for said selected points is prepared, at least in part, by a fast Fourier transform.

52. A method as defined in claim 47, wherein said scattered wavefield energy detected includes a digital representation of said wavefield energy propagating both into and through said region.

53. A method as defined in claim 47, wherein said step of transducing said electric signal at each of one or more frequencies into wavefield energy propagated from one or more of transmitter transducer positions, each said transmitter transducer position propagating wavefield energy comprises the steps of:

positioning a transducer array adjacent to said object, said transducer array comprising said one or more of transmitter transducer positions and said one or more receiver positions;

sending said electric signal at a first frequency to each said transmitter transducer positions so that each said transmitter transducer positions will in turn propagate wavefield energy at said first frequency; and thereafter changing the frequency of said signal and sending said electrical signal at said changed frequency to each said transmitter transducer position so as to sequentially propagate wavefield energy from each said transmitter transducer position at said changed frequency.

54. A method as defined in claim 53, wherein said transducer array is configured to enclose at least a portion of said object.

55. A method as defined in claim 47, wherein said step of transducing said electric signal at each of one or more frequencies into wavefield energy propagated from one or more of transmitter transducer positions, each said transmitter transducer position propagating wavefield energy, comprises the steps of:

positioning a transducer array adjacent to at least a portion of said region, said transducer array comprising said one or more of transmitter transducer positions and said one or more receiver positions;

generating said electric signal in the form of a waveform which is characterized by one or more different frequencies; and sending said generated waveform in turn to each said transmitter transducer position so as to propagate wavefield energy at said one or more frequencies from each said transmitter transducer position.

56. A method as defined in claim 55, wherein said transducer array is configured to enclose at least a portion of said region.

57. A method as defined in claim 47, wherein said step of detecting at each of said one or more receiver positions and respective orientations thereof said wavefield energy comprises the steps of:

positioning a transducer array adjacent to said object, said transducer array comprising one or more of transmitter transducer positions and said one or more receiver positions; and after wavefield energy is transmitted from one of said transmitter transducer positions, sequencing each of said one or more receiver positions so as to detect said scattered wavefield energy at each of said one or more receiver positions in turn.

58. A method as defined in claim 57, wherein said step of electronically processing said detected wavefield energy comprises the steps of:

transducing the wavefield energy detected by each of said one or more receiver positions into a corresponding electric signal;

amplifying said corresponding electric signal to produce an amplified signal; and thereafter processing each said amplified signal so as to generate two signals which correspond to mathematical real and imaginary parts of a representation of each said amplified signal.

59. A method as defined in claim 58, wherein the step of processing each said amplified signal comprises the steps of:

inputting each said amplified signal detected at each of said one or more receiver positions to first and second multiplier circuits and multiplying each said amplified signal input to said first multiplier circuit by each said electric signal sent to each of said one or more transmitter transducer positions;

shifting by 90° the phase of an electric signal that is the duplicate of each said electric signal input to said first multiplier circuit, and thereafter multiplying each said amplified signal input to said second multiplier circuit by each said electric signal that is shifted by 90°; and filtering the output of each said multiplier circuit with a low-pass filter and thereafter integrating and digitizing the output of each said low-pass filter.

60. A method as defined in claim 58, wherein said step of processing each said amplified signal comprises the steps of:

inputting each said amplified signal to a high speed analog-to-digital converter so as to digitize each said amplified signal; and inputting each said digitized signal from said high speed analog-to-digital converter into a parallel processor programmed to take the complex fast Fourier transform of each said digitized signal.

61. A method as defined in claim 57, wherein said transducer array is configured to substantially enclose said region.

62. A method as defined in claim 47, wherein said primary set of surfaces has only one element, and said secondary set of surfaces has only one element.

63. A method as defined in claim 47, wherein said region characteristics estimate of said selected physical characteristics at said selected points within the region is initialized to an average value determined by an estimated average of said region characteristics estimate.

64. A method as defined in claim 47, wherein said estimate of the total wavefield energy at said selected points for said one or more transmitter transducer positions and respective orientations thereof are obtained separately at each said frequency sequentially.

65. A method as defined in claim 47, wherein said region characteristics estimate of said selected physical characteristics at said selected points within the region is formulated using a plurality of frequency-independent components represented as a vector $\Gamma$ multiplied by a frequency-dependent matrix M, and wherein said vector $\Gamma$ is updated so as to determine said region characteristics estimate of said selected physical characteristics at said selected points within the region.

66. A method as defined in claim 65, wherein said vector Γ is updated using a conjugate gradient method.

67. A method as defined in claim 47, wherein said region characteristics correction is determined by a conjugate gradient method.

68. A method as defined in claim 47, wherein the each of said plurality of selected surfaces is a plane and where the step of computing the estimate of the total wavefield energy on the secondary set of surfaces using the region characteristics estimate on the union of the primary and secondary sets of surfaces and the total wavefield energy on the primary set of surfaces is computed using a Fast-Fourier-Transform implemented propagator, where said propagator does not involve any approximation to the square root function.

69. The method as defined in claim 47, wherein computing said region characteristics estimate from one or more derivatives of the comparator or approximations thereof with respect to one or more of said selected physical characteristics at one or more of said selected points constructs a steepest descent direction; and then setting said region characteristics estimate equal to a sum of:
   (a) a selected quantity times said steepest descent direction; and
   (b) a selected function on said one or more of said selected points, wherein said selected quantity and said selected function are selected to reduce the comparator.

70. A method for producing an image of an object in a region from wavefield energy that has been transmitted into and scattered by the object, said image comprising a map of selected physical characteristics at selected points within the region, said image being stored in a computer memory, and said method comprising the steps of:
   (a) transducing an electric signal at each of one or more frequencies into wavefield energy propagated from one or more of transmitter transducer positions, each said transmitter transducer position propagating wavefield energy at at least one orientation defined by Euler angles with respect to a selected fixed coordinate system;
   (b) for one or more receiver positions each having at least one orientation defined by Euler angles with respect to said selected fixed coordinate system, detecting at each of said one or more receiver positions and respective orientations thereof said wavefield energy;
   (c) electronically processing said detected wavefield energy so as to transform said detected wavefield energy into one or more reception stored signals stored in said computer memory and corresponding to a scattered wavefield energy detected;
   (d) setting a region characteristics estimate of selected physical characteristics at selected points within the region and storing each said region characteristics estimate in said computer memory;
   (e) performing a convergence step comprising the following steps:
      (1) preparing, for each said one or more frequencies at each said transmitter transducer positions and respective orientations thereof, an estimate of a total wavefield energy at said selected points derived from a selected incident wavefield energy for said selected points stored in the computer memory and said region characteristics estimate for said selected points by the steps of:
         (i) designating a primary set of surfaces of a plurality of selected surfaces and a different secondary set of surfaces of said selected surfaces, each said selected surface intersecting said region;
         (ii) setting the estimate of the total wavefield energy equal to an initial total incident wavefield energy estimate for the primary set of surfaces;
         (iii) computing the estimate of the total wavefield energy on the secondary set of surfaces using the region characteristics estimate on the union of the primary and secondary sets of surfaces and the total wavefield energy on the primary set of surfaces;
         (iv) re-designating the primary set of surfaces to include a sub- set of the secondary set of surfaces and re-designating the secondary set of surfaces to include another set of the selected surfaces; and
         (v) repeating steps ((iii) through ((iv)) until the estimate of the total wavefield energy is computed for each of the selected surfaces;
      (2) deriving, for each of said one or more frequencies at each said transmitter transducer position and orientations thereof, a calculated scattered wavefield energy for one or more of said receiver positions and respective orientations thereof from at least one of said region characteristics estimate at said selected points and said estimate of said total wavefield energy for a corresponding transmitter transducer position and orientations thereof at said selected points by performing the steps of:
         (i) for each selected point of a portion of the selected points, said potion of the selected points corresponding to one of said one or more receiver positions and respective orientations thereof, setting said calculated scattered wavefield energy equal to the estimate of the total wavefield energy less said selected incident wavefield energy; and
         (ii) computing a sum over said portion of said selected points equal to the sum of the calculated scattered wavefield energy for said portion of said selected points times a function constructed to correspond to one or more of said one or more receiver positions and respective orientations thereof;
      (3) for each said transmitter transducer position and orientations thereof and for each said receiver position and orientation thereof, comparing said scattered wavefield energy detected to said calculated scattered wavefield energy to derive therefrom a comparator; and
      (4) when said comparator is greater than a selected tolerance, determining and storing in said computer memory said region characteristics estimate by computing one or more derivatives of the comparator or approximations thereof with respect to one or more of said selected physical characteristics at one or more of said selected points, and then using said one or more derivatives of the comparator or approximations thereof to compute a region characteristics correction, and then adding said region characteristics correction to each of said region characteristics estimate for each of said one or more of said selected points, wherein said one or more derivatives of the comparator or approximations thereof is computed from one or more of:
         (i) at each said one or more frequencies, said estimate of said total wavefield energy for said selected points for each of said one or more of said transmitter transducer positions and respective orientations thereof;

(ii) at each of said one or more frequencies, said calculated scattered wavefield energy for said one or more receiver positions and respective orientations thereof, and for each of said one or more of said transmitter transducer positions and respective orientations thereof;

(iii) at each of said one or more frequencies, said scattered wavefield energy detected for said one or more receiver positions and respective orientations thereof, and for each of said one or more of said transmitter transducer positions and respective orientations thereof; and (iv) said region characteristics estimate for said selected points;

(f) repeating said convergence step until said comparator is less than or equal to said selected tolerance, and thereafter storing said region characteristics estimate as said image in the computer memory.

71. A methods as defined in claim 70, wherein said convergence step is a Gauss-Newton step using conjugate gradients.

72. A method as defined in claim 70, wherein:

A. model calibration parameters and an imaging system simulation model of said imaging device are used to compute:
  (i) said selected incident wavefield energy; and
  (ii) said function constructed to correspond to one or more of said receiver positions and respective orientations thereof;

B. said model calibration parameters comprising at least one of:
  (i) one or more transmitter equivalent source vectors, said one or more transmitter equivalent source vectors being input to one or more transmitter simulators, said one or more transmitter simulators outputting one or more simulated transmitter wavefields of said interrogating wavefield energy;
  (ii) one or more receiver equivalent source vectors, said one or more receiver equivalent source vectors being input to one or more receiver simulators, said one or more receiver simulators outputting one or more simulated receiver sensitivity functions, said one or more receiver sensitivity functions being electrical responses of said one or more receiver simulators to a point source of interrogating wavefield energy placed at substantially any location in said region;
  (iii) one or more transmitter simulation positions, each said one of more transmitter simulation positions having one or more transmitter simulation orientations, each said one or more transmitter simulation orientations being defined by Euler angles;
  (iv) one or more receiver simulation positions, each said one of more receiver simulation positions having one or more receiver simulation orientations, each said one or more receiver simulation orientations being defined by Euler angles; and
  (v) one or more electronic system parameters of said imaging device, said electronic system parameters substantially characterizing the analog and digital electronic functions of said imaging device, C. said calibration parameters are derived by the steps of:
  (i) collecting a received wavefield energy by a process comprising the steps of:
    I. choosing a substantially known matter distribution in said region from a selected set of one or more substantially known matter distributions;
    II. choosing one of said one of more transmitter transducers at one of said one or more transmitter positions and at one of said one or more transmitter orientations;
    III. choosing one of said one of more receiver transducers at one of said one or more receiver positions and at one of said one or more receiver orientations;
    IV. transmitting interrogating wavefield energy from said one of said one of more transmitter transducers at one of said one or more transmitter positions and at one of said one or more transmitter orientations into said region;
    V. receiving interrogating wavefield energy at said one of said one or more transducer receivers at one of said one or more receiver positions and at one of said one or more receiver orientations;
    VI. repeating C(III) through C(IV) until a selected portion of said one or more receiver transducers at said one or more receiver positions and orientations thereof have been chosen;
    VII. repeating steps C(II) through C(VI) until a selected portion of said one or more transmitter transducers at said one or more transmitter positions and orientations thereof have been chosen;
    VIII. repeating steps C(I) through C(VII) until all of said selected set of one or more substantially known matter distributions have been chosen;
  (ii) constructing said imaging system simulation model of said imaging device and said imaging process used therewith with an input equal to said model calibration parameters and an output equal to a predicted received wavefield energy, said predicted received wavefield energy being an approximation of said received wavefield energy, said imaging system simulation model being derived from at least one of:
    I. a mathematical theory of said interrogating wavefield energy;
    II. a simulation model of the analog and digital electronic functions of said imaging device;
    III. said one or more transmitter simulators; and
    IV. said one or more receiver simulators;
  (iii) setting a portion of said model calibration parameters equal to selected values;
  (iv) solving for substantially all other portions of said model calibration parameters using the steps of:
    I. defining a comparator, said comparator being a positive scaler value that is a measure of the difference between said received wavefield energy and said predicted received wavefield energy; and
    II. using an optimization algorithm to substantially minimize said comparator with respect to said substantially all other portions of said model calibration parameters until said comparator is less than a selected tolerance;
  (v) storing said model calibration parameters in a computer memory.

73. A method as defined in claim 70, wherein said convergence step is a Ribiere-Polak step.

74. A method as defined in claim 70, wherein said estimate of said total wavefield energy at said selected points derived from said selected incident wavefield energy for said selected points is prepared, at least in part, by a fast Fourier transform.

75. A method as defined in claim 70, wherein said scattered wavefield energy detected includes a digital representation of said wavefield energy propagating both into and through said region.

76. A method as defined in claim 70, wherein said step of transducing said electric signal at each of one or more frequencies into wavefield energy propagated from one or more of transmitter transducer positions, each said transmitter transducer position propagating wavefield energy comprises the steps of:

positioning a transducer array adjacent to said object, said transducer array comprising said one or more of transmitter transducer positions and said one or more receiver positions;

sending said electric signal at a first frequency to each said transmitter transducer positions so that each said transmitter transducer positions will in turn propagate wavefield energy at said first frequency; and thereafter changing the frequency of said signal and sending said electrical signal at said changed frequency to each said transmitter transducer position so as to sequentially propagate wavefield energy from each said transmitter transducer position at said changed frequency.

77. A method as defined in claim 76, wherein said transducer array is configured to enclose at least a portion of said object.

78. A method as defined in claim 70, wherein said step of transducing said electric signal at each of one or more frequencies into wavefield energy propagated from one or more of transmitter transducer positions, each said transmitter transducer position propagating wavefield energy, comprises the steps of:

positioning a transducer array adjacent to at least a portion of said region, said transducer array comprising said one or more of transmitter transducer positions and said one or more receiver positions;

generating said electric signal in the form of a waveform which is characterized by one or more different frequencies; and sending said generated waveform in turn to each said transmitter transducer position so as to propagate wavefield energy at said one or more frequencies from each said transmitter transducer position.

79. A method as defined in claim 78, wherein said transducer array is configured to enclose at least a portion of said region.

80. A method as defined in claim 70, wherein said step of detecting at each of said one or more receiver positions and respective orientations thereof said wavefield energy comprises the steps of:

positioning a transducer array adjacent to said object, said transducer array comprising said one or more of transmitter transducer positions and said one or more receiver positions; and after wavefield energy is transmitted from one of said transmitter transducer positions, sequencing each of said one or more receiver positions so as to detect said scattered wavefield energy at each of said one or more receiver positions in turn.

81. A method as defined in claim 80, wherein said step of electronically processing said detected wavefield energy comprises the steps of:

transducing the wavefield energy detected by each of said one or more receiver positions into a corresponding electric signal;

amplifying said corresponding electric signal to produce an amplified signal; and thereafter processing each said amplified signal so as to generate two signals which correspond to mathematical real and imaginary parts of a representation of each said amplified signal.

82. A method as defined in claim 81, wherein the step of processing each said amplified signal comprises the steps of:

inputting each said amplified signal detected at each of said one or more receiver positions to first and second multiplier circuits and multiplying each said amplified signal input to said first multiplier circuit by each said electric signal sent to each of said one or more transmitter transducer positions;

shifting by 90° the phase of an electric signal that is the duplicate of each said electric signal input to said first multiplier circuit, and thereafter multiplying each said amplified signal input to said second multiplier circuit by each said electric signal that is shifted by 90°; and filtering the output of each said multiplier circuit with a low-pass filter and thereafter integrating and digitizing the output of each said low-pass filter.

83. A method as defined in claim 81, wherein said step of processing each said amplified signal comprises the steps of:

inputting each said amplified signal to a high speed analog-to-digital converter so as to digitize each said amplified signal; and inputting each said digitized signal from said high speed analog-to-digital converter into a parallel processor programmed to take the complex fast Fourier transform of each said digitized signal.

84. A method as defined in claim 80, wherein said transducer array is configured to substantially enclose said region.

85. A method as defined in claim 70, wherein said primary set of surfaces has only one element, and said secondary set of surfaces has only one element.

86. A method as defined in claim 70, wherein said region characteristics estimate of said selected physical characteristics at said selected points within the region is initialized to an average value determined by an estimated average of said region characteristics estimate.

87. A method as defined in claim 70, wherein said estimate of the total wavefield energy at said selected points for said one or more transmitter transducer positions and respective orientations thereof are obtained separately at each said frequency sequentially.

88. A method as defined in claim 70, wherein said region characteristics estimate of said selected physical characteristics at said selected points within the region is formulated using a plurality of frequency-independent components represented as a vector $\Gamma$ multiplied by a frequency-dependent matrix M, and wherein said vector $\Gamma$ is updated so as to determine said region characteristics estimate of said selected physical characteristics at said selected points within the region.

89. A method as defined in claim 88, wherein said vector $\Gamma$ is updated using a conjugate gradient method.

90. A method as defined in claim 70, wherein said region characteristics correction is determined by a conjugate gradient method.

91. A method as defined in claim 70, wherein the each of said plurality of selected surfaces is a plane and where the step of computing the estimate of the total wavefield energy on the secondary set of surfaces using the region characteristics estimate on the union of the primary and secondary sets of surfaces and the total wavefield energy on the primary set of surfaces is computed using a Fast-Fourier- Transform implemented propagator, where said propagator does not involve any approximation to the square root function.

92. The method as defined in claim 70, wherein computing said region characteristics estimate from one or more derivatives of the comparator or approximations thereof with respect to one or more of said selected physical characteristics at one or more of said selected points constructs a steepest descent direction; and then setting said region characteristics estimate equal to a sum of:
   (a) a selected quantity times said steepest descent direction; and
   (b) a selected function on said one or more of said selected points, wherein said selected quantity and said selected function are selected to reduce the comparator.

93. A method for calibrating an imaging device and an imaging process used therewith, said imaging device and imaging process using model calibration parameters, said imaging device producing with said imaging process an image of matter in a region, said imaging device using interrogating wavefield energy and employing:
   (i) one or more transmitter transducers at one or more transmitter positions; each said one of more transmitter positions having one or more transmitter orientations, each said one or more transmitter orientations being defined by Euler angles; and
   (ii) one or more receiver transducers at one or more receiver positions, each said one of more receiver positions having one or more receiver orientations, each said one or more receiver orientations being defined by Euler angles, said model calibration parameters comprising at least one of:
      (a) one or more transmitter equivalent source vectors, said one or more transmitter equivalent source vectors being input to one or more transmitter simulators, said one or more transmitter simulators outputting one or more simulated transmitter wavefields of said interrogating wavefield energy;
      (b) one or more receiver equivalent source vectors, said one or more receiver equivalent source vectors being input to one or more receiver simulators, said one or more receiver simulators outputting one or more simulated receiver sensitivity functions, said one or more receiver sensitivity functions being electrical responses of said one or more receiver simulators to a point source of interrogating wavefield energy placed at substantially any location in said region;
      (c) one or more transmitter simulation positions, each said one of more transmitter simulation positions having one or more transmitter simulation orientations, each said one or more transmitter simulation orientations being defined by Euler angles;
      (d) one or more receiver simulation positions, each said one of more receiver simulation positions having one or more receiver simulation orientations, each said one or more receiver simulation orientations being defined by Euler angles; and
      (e) one or more electronic system parameters of said imaging device, said electronic system parameters substantially characterizing the analog and digital electronic functions of said imaging device;
   said method comprising the steps of:
      (I) collecting a received wavefield energy by a process comprising the steps of:
         (A) choosing a substantially known matter distribution in said region from a selected set of one or more substantially known matter distributions;
         (B) choosing one of said one of more transmitter transducers at one of said one or more transmitter positions and at one of said one or more transmitter orientations;
         (C) choosing one of said one of more receiver transducers at one of said one or more receiver positions and at one of said one or more receiver orientations;
         (D) transmitting interrogating wavefield energy from said one of said one of more transmitter transducers at one of said one or more transmitter positions and at one of said one or more transmitter orientations into said region;
         (E) receiving interrogating wavefield energy at said one of said one or more transducer receivers at one of said one or more receiver positions and at one of said one or more receiver orientations;
         (F) repeating steps I(C) through I(E) until a selected portion of said one or more receiver transducers at said one or more receiver positions and orientations thereof have been chosen;
         (G) repeating steps I(B) through I(F) until a selected portion of said one or more transmitter transducers at said one or more transmitter positions and orientations thereof have been chosen;
         (H) repeating steps I(A) through I(G) until all of said selected set of one or more substantially known matter distributions have been chosen;
      (II) constructing an imaging system simulation model of said imaging device and said imaging process used therewith with an input equal to said model calibration parameters and an output equal to a predicted received wavefield energy, said predicted received wavefield energy being an approximation of said received wavefield energy, said imaging system simulation model being derived from at least one of the following quadra-parameters:
         (A) a mathematical theory of said interrogating wavefield energy;
         (B) a simulation model of the analog and digital electronic functions of said imaging device;
         (C) said one or more transmitter simulators; and
         (D) said one or more receiver simulators;
      (III) setting a portion of said model calibration parameters equal to selected values;
      (IV) solving for substantially all other portions of said model calibration parameters using the steps of:
         (A) defining a comparator, said comparator being a positive scaler value that is a measure of the difference between said received wavefield energy and said predicted received wavefield energy; and
         (B) using an optimization algorithm to substantially minimize said comparator with respect to said substantially all other portions of said model calibration parameters until said comparator is less than a selected tolerance;
      (V) storing said model calibration parameters in a computer memory.

94. A method as defined in claim 93, wherein said imaging system simulation model is derived from at least two of the quadra-parameters.

95. A method as defined in claim 93, wherein said imaging system simulation model is derived from at least three of the quadra-parameters.

96. A method as defined in claim 93, wherein said portion of said model calibration parameters excludes at least one of:

(I) said one or more transmitter equivalent source vectors; and (II) said one or more receiver equivalent source vectors.

97. A method as defined in claim 94, wherein said portion of said model calibration parameters excludes at least one of:

(I) said one or more transmitter equivalent source vectors; and (I) said one or more receiver equivalent source vectors.

98. A method as defined in claim 95, wherein said portion of said model calibration parameters excludes at least one of:

(I) said one or more transmitter equivalent source vectors; and (II) said one or more receiver equivalent source vectors.

99. A method as defined in claim 93, wherein said selected set of one or more substantially known matter distributions includes at least one object with a substantially known scattering solution.

100. A method as defined in claim 94, wherein said selected set of one or more substantially known matter distributions includes at least one object with a substantially known scattering solution.

101. A method as defined in claim 95, wherein said selected set of one or more substantially known matter distributions includes at least one object with a substantially known scattering solution.

102. A method as defined in claim 96, wherein said selected set of one or more substantially known matter distributions includes at least one object with a substantially known scattering solution.

103. A method as defined in claim 99, wherein said object with a substantially known scattering solution is a concentrically layered sphere of homogeneous matter.

104. A method as defined in claim 99, wherein said object with a substantially known scattering solution is a concentrically layered cylinder of homogeneous matter.

105. A method as defined in claim 99, wherein said substantially known scattering solution involves at least one of a Fourier-Bessel and a Fourier-Legendre series.

106. A method as defined in claim 93, wherein said selected set of one or more substantially known matter distributions includes a homogeneous matter distribution throughout said region.

107. A method as defined in claim 94, wherein said selected set of one or more substantially known matter distributions includes a homogeneous matter distribution throughout said region.

108. A method as defined in claim 95, wherein said selected set of one or more substantially known matter distributions includes a homogeneous matter distribution throughout said region.

109. A method as defined in claim 96, wherein said selected set of one or more substantially known matter distributions includes a homogeneous matter distribution throughout said region.

110. A method as defined in claim 99, wherein said selected set of one or more substantially known matter distributions includes a homogeneous matter distribution throughout said region.

111. A method as defined in claim 103, wherein said selected set of one or more substantially known matter distributions includes a homogeneous matter distribution throughout said region.

112. A method as defined in claim 104, wherein said selected set of one or more substantially known matter distributions includes a homogeneous matter distribution throughout said region.

113. A method as defined in claim 105, wherein said selected set of one or more substantially known matter distributions includes a homogeneous matter distribution throughout said region.

114. A method as defined in claim 93, herein said optimization algorithm is the Gauss-Newton method.

115. A method as defined in claim 94, herein said optimization algorithm is the Gauss-Newton method.

116. A method as defined in claim 95, herein said optimization algorithm is the Gauss-Newton method.

117. A method as defined in claim 96, herein said optimization algorithm is the Gauss-Newton method.

118. A method as defined in claim 99, wherein said optimization algorithm is the Gauss-Newton method.

119. A method as defined in claim 103, wherein said optimization algorithm is the Gauss-Newton method.

120. A method as defined in claim 104, wherein said optimization algorithm is the Gauss-Newton method.

121. A method as defined in claim 105, wherein said optimization algorithm is the Gauss-Newton method.

122. A method as defined in claim 106, wherein said optimization algorithm is the Gauss-Newton method.

123. A method as defined in claim 114, wherein the linear system in said Gauss-Newton method is substantially solved by the conjugate gradient method.

124. A method as defined in claim 93, wherein said optimization algorithm is the method of steepest descents.

125. A method as defined in claim 94, wherein said optimization algorithm is the method of steepest descents.

126. A method as defined in claim 95, wherein said optimization algorithm is the method of steepest descents.

127. A method as defined in claim 96, wherein said optimization algorithm is the method of steepest descents.

128. A method as defined in claim 99, wherein said optimization algorithm is the method of steepest descents.

129. A method as defined in claim 103, wherein said optimization algorithm is the method of steepest descents.

130. A method as defined in claim 104, wherein said optimization algorithm is the method of steepest descents.

131. A method as defined in claim 105, wherein said optimization algorithm is the method of steepest descents.

132. A method as defined in claim 106, wherein said optimization algorithm is the method of steepest descents.

133. A method as defined in claim 93, wherein said optimization algorithm is a nonlinear conjugate gradient method.

134. A method as defined in claim 94, wherein said optimization algorithm is a nonlinear conjugate gradient method.

135. A method as defined in claim 95, wherein said optimization algorithm is a nonlinear conjugate gradient method.

136. A method as defined in claim 96, wherein said optimization algorithm is a nonlinear conjugate gradient method.

137. A method as defined in claim 99, wherein said optimization algorithm is a nonlinear conjugate gradient method.

138. A method as defined in claim 103, wherein said optimization algorithm is a nonlinear conjugate gradient method.

139. A method as defined in claim 104, wherein said optimization algorithm is a nonlinear conjugate gradient method.

140. A method as defined in claim 105, wherein said optimization algorithm is a nonlinear conjugate gradient method.

141. A method as defined in claim 106, wherein said optimization algorithm is a nonlinear conjugate gradient method.

142. A method as defined in claim 93, wherein said optimization algorithm is the Ribiere-Polak method.

143. A method as defined in claim 94, wherein said optimization algorithm is the Ribiere-Polak method.

144. A method as defined in claim 95, wherein said optimization algorithm is the Ribiere-Polak method.

145. A method as defined in claim 96, wherein said optimization algorithm is the Ribiere-Polak method.

146. A method as defined in claim 99, wherein said optimization algorithm is the Ribiere-Polak method.

147. A method as defined in claim 103, wherein said optimization algorithm is the Ribiere-Polak method.

148. A method as defined in claim 104, wherein said optimization algorithm is the Ribiere-Polak method.

149. A method as defined in claim 105, wherein said optimization algorithm is the Ribiere-Polak method.

150. A method as defined in claim 106, wherein said optimization algorithm is the Ribiere-Polak method.

151. A method as defined in claim 93, wherein said comparator is the sum of the squares of the magnitudes of the differences of the values of a transformed received wavefield energy minus the values of a transformed predicted received wavefield energy, said transformed received wavefield energy being equal to a selected linear transformation acting on said received wavefield energy and said transformed predicted received wavefield energy being equal to said selected linear transformation acting on said predicted received wavefield energy.

152. A method as defined in claim 94, wherein said comparator is the sum of the squares of the magnitudes of the differences of the values of a transformed received wavefield energy minus the values of a transformed predicted received wavefield energy, said transformed received wavefield energy being equal to a selected linear transformation acting on said received wavefield energy and said transformed predicted received wavefield energy being equal to said selected linear transformation acting on said predicted received wavefield energy.

153. A method as defined in claim 95, wherein said comparator is the sum of the squares of the magnitudes of the differences of the values of a transformed received wavefield energy minus the values of a transformed predicted received wavefield energy, said transformed received wavefield energy being equal to a selected linear transformation acting on said received wavefield energy and said transformed predicted received wavefield energy being equal to said selected linear transformation acting on said predicted received wavefield energy.

154. A method as defined in claim 96, wherein said comparator is the sum of the squares of the magnitudes of the differences of the values of a transformed received wavefield energy minus the values of a transformed predicted received wavefield energy, said transformed received wavefield energy being equal to a selected linear transformation acting on said received wavefield energy and said transformed predicted received wavefield energy being equal to said selected linear transformation acting on said predicted received wavefield energy.

155. A method as defined in claim 99, wherein said comparator is the sum of the squares of the magnitudes of the differences of the values of a transformed received wavefield energy minus the values of a transformed predicted received wavefield energy, said transformed received wavefield energy being equal to a selected linear transformation acting on said received wavefield energy and said transformed predicted received wavefield energy being equal to said selected linear transformation acting on said predicted received wavefield energy.

156. A method as defined in claim 103, wherein said comparator is the sum of the squares of the magnitudes of the differences of the values of a transformed received wavefield energy minus the values of a transformed predicted received wavefield energy, said transformed received wavefield energy being equal to a selected linear transformation acting on said received wavefield energy and said transformed predicted received wavefield energy being equal to said selected linear transformation acting on said predicted received wavefield energy.

157. A method as defined in claim 104, wherein said comparator is the sum of the squares of the magnitudes of the differences of the values of a transformed received wavefield energy minus the values of a transformed predicted received wavefield energy, said transformed received wavefield energy being equal to a selected linear transformation acting on said received wavefield energy and said transformed predicted received wavefield energy being equal to said selected linear transformation acting on said predicted received wavefield energy.

158. A method as defined in claim 105, wherein said comparator is the sum of the squares of the magnitudes of the differences of the values of a transformed received wavefield energy minus the values of a transformed predicted received wavefield energy, said transformed received wavefield energy being equal to a selected linear transformation acting on said received wavefield energy and said transformed predicted received wavefield energy being equal to said selected linear transformation acting on said predicted received wavefield energy.

159. A method as defined in claim 106, wherein said comparator is the sum of the squares of the magnitudes of the differences of the values of a transformed received wavefield energy minus the values of a transformed predicted received wavefield energy, said transformed received wavefield energy being equal to a selected linear transformation acting on said received wavefield energy and said transformed predicted received wavefield energy being equal to said selected linear transformation acting on said predicted received wavefield energy.

160. A method for increasing the spatial resolution and the contrast resolution of an image of matter in a region, said image produced by an imaging device, said spatial resolution being quantitatively defined as the reciprocal of the width at half maximum of the point spread function of said imaging device and said matter in said region, said contrast resolution being quantitatively defined as the reciprocal of the smallest contrast of an object imbedded in a background for which said object can be distinguished in said image, said contrast of an object being defined as the ratio of the difference of the intensity of the object and the intensity of the background over the sum of the intensity of the object and intensity of the background, said image consisting of a set of image values, said set of image values corresponding to selected points in said region, said imaging device generating electrical signals that are passed through transmitter beam formers, said transmitter beam formers producing focused electrical signals by applying a set of transmitter time delays and a set of transmitter amplitude scale factors to said generated electrical signals, said focused electrical signals then being transduced into transmitted wavefield energy by one or more transducer arrays, said transducer arrays including one or more transducer elements, said transmitted wavefield energy being transmitted into said region and being scattered from matter in said region, said transducer arrays transducing into receiver electrical signals reflected wavefield energy that was scattered by said matter, said receiver electrical signals being passed through receiver beam formers, said receiver beam formers producing focused receiver electrical signals by applying a set of receiver time delays and a set of receiver amplitude scale factors to said receiver electrical signals, said focused receiver electrical signals then being used to construct said set of image values, said method comprising the steps of:

(a) defining an image resolution measure function as a scaler value computed from one or more portions of said set of image values, said image resolution measure function defined such that said spatial and contrast resolutions are increased for an increase in said image resolution measure function up to a maximum;

(b) defining a set of control parameters and defining a control function such that a primary machine focusing set is equal to the sum of the output of said control function having as an input said set of control parameters plus a selected initial machine focusing set, wherein said primary machine focusing set is the union of said set of transmitter time delays, said set of transmitter amplitude scale factors, said set of receiver time delays, and said set of receiver amplitude scale factors, and wherein said selected initial machine focusing set is the union of said selected initial set of transmitter time delays, said selected initial set of transmitter amplitude scale factors, said selected initial set of receiver time delays, and said selected initial set of receiver amplitude scale factors;

(c) setting said set of control parameters equal to a selected set of starting values, computing said primary machine focusing set by inputting said control parameters into said control function and adding said initial machine focusing set to the output of said control function, and re-computing said image resolution measure function from said one or more portions of said set of image values, setting an initial resolution measure function equal to said image resolution measure function;

(d) setting a set of auxiliary vectors equal to a set of initial vector values;

(e) performing an optimization step comprising the following steps of:
  (i) computing a gradient vector of said image resolution measure function with respect to said set of control parameters;
  (ii) computing a search direction vector equal to the sum of:
    (A) said gradient vector; plus
    (B) an auxiliary direction vector derived from said set of auxiliary vectors and said gradient vector, when said optimization step is the first step, setting a initial gradient vector equal to said gradient vector and computing a magnitude of said initial gradient vector;
  (iii) update said set of auxiliary vectors using said gradient vector;
  (iv) computing a search length and then adding said search direction vector multiplied by said search length to said set of control parameters, said search length computed such that said image resolution measure function is increased;
  (v) computing said primary machine focusing set by inputting said set of control parameters into said control function and adding said initial machine focusing set to the output of said control function, and re-computing said image resolution measure function from said one or more portions of said set of image values, computing one of:
    (A) an absolute value of the percent change in said image resolution measure function using said image resolution measure function and said initial image resolution function; and
    (B) a magnitude of said gradient vector and a percent change in said magnitude of said gradient vector using said magnitude of said gradient vector and said magnitude of said initial gradient vector;
  (vi) repeating steps e(i)1 through e(v)5 when one of:
    (A) said absolute value of the percent change in said image resolution measure function is greater than a selected tolerance; and
    (B) said percent change in said magnitude of said gradient vector is greater than a selected tolerance;

(f) storing said set of image values in a computer memory when one of:
  (A) said absolute value of the percent change in said image resolution measure function is less than or equal to a selected tolerance; and
  (B) said percent change in said magnitude of said gradient vector is less than or equal to a selected tolerance.

161. A method as defined in claim 160, wherein said image resolution measure function is set equal to the sum of the elements of a set of weighted values, said set of weighted values being equal to the elementwise product:
  (a) a set of the square of the elements of said one or more portions of said set of image values; and
  (b) a selected weight set with a number of elements equal to the number of elements in said one or more portions of said set of image values.

162. A method as defined in claim 160, wherein said image resolution measure function is set equal to the sum of the elements of a set of weighted values, said set of weighted values being equal to the elementwise product of:
  (a) a set of the cube of the elements of said one or more portions of said set of image values; and
  (b) a selected weight set with a number of elements equal to the number of elements in said one or more portions of said set of image values.

163. A method as defined in claim 160,
  (a) wherein said set of control parameters correspond to one or more sets of basis expansion coefficients used in one or more basis expansions of at least one of:
    (i) said set of transmitter time delays;
    (ii) said set of transmitter amplitude scale factors;
    (iii) said set of receiver time delays; and
    (iv) said set of receiver amplitude scale factors;
  (b) wherein the basis functions used in said one or more basis expansions have as independent variables at least one of:
    (i) one or more element number indices enumerating the elements of one or more transducer arrays; and
    (ii) one or more focused beam indices enumerating a set of focused beams, said set of focused beams being produced by one or more transducer arrays, said focused beams substantially covering at least a portion of said region;

(c) and wherein said control function is substantially defined by said one or more basis expansions.

164. A method as defined in claim 160, wherein said optimization step is a steepest descent step.

165. A method as defined in claim 161, wherein said optimization step is a steepest descent step.

166. A method as defined in claim 162, wherein said optimization step is a steepest descent step.

167. A method as defined in claim 163, wherein said optimization step is a steepest descent step.

168. A method as defined in claim 160, wherein said optimization step is a nonlinear conjugate gradient step.

169. A method as defined in claim 161, wherein said optimization step is a nonlinear conjugate gradient step.

170. A method as defined in claim 162, wherein said optimization step is a nonlinear conjugate gradient step.

171. A method as defined in claim 163, wherein said optimization step is a nonlinear conjugate gradient step.

172. A method as defined in claim 160, wherein said optimization step is a Ribiere-Polak step.

173. A method as defined in claim 161, wherein said optimization step is a Ribiere-Polak step.

174. A method as defined in claim 162, wherein said optimization step is a Ribiere-Polak step.

175. A method as defined in claim 163, wherein said optimization step is a Ribiere- Polak step.

176. A method as defined in claim 160, wherein each of said focused receiver electrical signals is substantially enveloped prior to constructing said set of image values.

177. A method as defined in claim 160, wherein each of said focused receiver electrical signals is substantially rectified prior to constructing said set of image values.

178. A method as defined in claim 160, wherein said image resolution measure function is set equal to the sum of the elements of a set of weighted values, said set of weighted values being equal to the elementwise product:

(a) a set of the elements of said one or more portions of said set of image values, wherein each said element of said set of elements is raised to a power; and (b) a selected weight set with a number of elements equal to the number of elements in said set of element of said one or more portions of said set of image values.

179. A method for producing an image of a region from wavefield energy that has been transmitted into and scattered by matter in the region, said region being defined by boundaries, said image comprising a map of selected physical characteristics at selected points within the region, said image being stored in a computer memory, said method comprising the steps of:

(a) transducing an electric signal at each of one or more frequencies into wavefield energy propagated from one or more of transmitter transducer positions, each said transmitter transducer position propagating wavefield energy at at least one orientation defined by Euler angles with respect to a selected fixed coordinate system;

(b) for one or more receiver positions each having at least one orientation defined by Euler angles with respect to said selected fixed coordinate system, detecting at each of said one or more receiver positions and respective orientations thereof said wavefield energy;

(c) electronically processing said detected wavefield energy so as to transform said detected wavefield energy into one or more reception stored signals stored in said computer memory and corresponding to a scattered wavefield energy detected;

(d) setting a region characteristics estimate of selected physical characteristics at selected points within the region and storing each said region characteristics estimate in said computer memory;

(e) performing a convergence step comprising the following steps:

(1) preparing, for each said one or more frequencies at each said transmitter transducer position and respective orientations thereof, each said orientation of each said transmitter transducer position being determined by a fixed orientation vector, an estimate of a total wavefield energy at said selected points, by performing the steps:

(i) designating a backscattering surface on a portion of the boundaries of said region, said backscattering surface being substantially perpendicular to said fixed orientation vector, and composed of a portion of said selected points, said backscattering surface having a measured total wavefield energy derived from said scattered wavefield energy detected;

(ii) designating two substantially parallel surfaces that are substantially parallel to said fixed orientation vector, each said substantially parallel surfaces having a measured total wavefield energy derived from said scattered wavefield energy detected;

(iii) designating a forwardscattering surface on a portion of said boundaries that is substantially parallel to and substantially different from said backscattering surface;

(iv) setting the normal derivative of the estimate of the total wavefield energy on said backscattering surface equal to a measured total wavefield energy normal derivative;

(v) setting the estimate of the total wavefield energy on said backscattering surface equal to said measured total wavefield energy for said backscattering surface;

(vi) setting the estimate of the total wavefield energy on each said two substantially parallel surfaces equal to said measured total wavefield energy on said two substantially parallel surfaces;

(vii) designating a first primary set of surfaces of a plurality of selected surfaces and a different first secondary set of surfaces of said plurality of selected surfaces, said plurality of selected surfaces being substantially composed of said selected points;

(viii) determining an estimate of the total wavefield energy on said first secondary set of surfaces using the region characteristics estimate on the union of the first primary and first secondary sets of surfaces and the estimate of the total wavefield energy on the first primary set of surfaces;

(ix) re-designating the first primary set of surfaces to include a subset of the first secondary set of surfaces and re-designating the first secondary set of surfaces to include another set of the plurality of the selected surfaces;

(x) performing a low-pass filter on the estimate of the total wavefield energy on the first secondary set of surfaces to obtain a low- pass filtered estimate;

(xi) setting the estimate of total wavefield energy on the first secondary set of surfaces equal to the low-pass filtered estimate;

(xii) repeating steps (vii) through (xi) until the estimate of the total wavefield energy is computed for each selected surface of said plurality of selected surfaces;

(2) subtracting the measured total wavefield energy on said forwardscattering surface from the estimate of the total wavefield energy on said forwardscattering surface to form a difference wavefield energy;

(3) backpropagating said difference wavefield energy on said forwardscattering surface to the selected points, to obtain an estimate of a backpropagated wavefield energy, by solving an under-determined system of equations derived from derivative information, said derivative information being derivatives of the estimate total energy with respect to said region characteristic estimates; and (4) backpropagating said difference wavefield energy on said forwardscattering surface to the selected points, to obtain an estimate of a backpropagated wavefield energy by adding said estimate of the backpropagated wavefield energy to said region characteristics estimate on said selected points to obtain an updated region characteristics estimate on said selected points;

(f) calculating a comparator from said region characteristics estimate and said updated region characteristics estimate on selected points;

(g) performing said convergence step when comparator is greater than a selected tolerance; and (h) storing said region characteristics estimate in computer memory.

180. A method as defined in claim 179, wherein said measured total wavefield energy and said measured total wavefield energy normal derivative are computed on said backscattering surface, said substantially parallel surfaces, and said forwardscattering surface by performing an inversion of a Green's function matrix, said Green's function matrix constructed to map said measured total wavefield energy and said measured total wavefield energy normal derivative evaluated on said backscattering surface, said substantially parallel surfaces, and said forwardscattering surface, into said scattered wavefield energy detected.

181. A method of reconstructing an image of matter in a region using a processing unit programmed to process data derived from an incident wavefield energy that has been transmitted at one or more frequencies, and one or more transmitter positions, each said transmitter position propagating wavefield energy at at least one orientation defined by Euler angles with respect to a selected fixed coordinate system, scattered by matter within said region, and detected by one or more receivers at one or more positions and orientations thereof, said orientations defined by Euler angles with respect to a selected fixed coordinate system, said method comprising the steps of:

(a) choosing a forward scattering model, which generates a total wavefield energy given one or more physical characteristics of said matter defined at selected points within said region, and said incident wavefield energy;

(b) propagating said incident wavefield energy, each said incident wavefield energy having one or more frequencies, toward said region from one or more transmitter positions and orientations thereof;

(c) for one or more receiver positions each having at least one orientation defined by Euler angles with respect to said selected fixed coordinate system, detecting at each of said one or more receiver positions and respective orientations thereof, a detected wavefield energy;

(d) electronically processing said detected wavefield energy so as to transform said detected wavefield energy into one or more reception stored signals stored in said computer memory and corresponding to said detected wavefield energy (e) setting a region characteristics estimate of selected physical characteristics at said selected points within the region and storing said region characteristics estimate in said computer memory;

(f) said processing unit calculating a fixed target characteristics estimate from the detected wavefield energy, said fixed target characteristics estimate being defined such that when operated on by a selected fixed approximation of the forward scattering model, the detected wavefield energy results;

(g) said processing unit performing a convergence step comprising the following steps:

(1) preparing, for each said one or more frequencies at each said transmitter positions and respective orientations thereof, an estimate of said total wavefield energy at said selected points derived from said incident wavefield energy for said selected points stored in the computer memory and said region characteristics estimate for said selected points;

(2) deriving, for each of said one or more frequencies at each said transmitter position and orientations thereof, a calculated scattered wavefield energy for one or more of said receiver positions and respective orientations thereof from at least one of (i) said region characteristics estimate at said selected points, and (ii) said estimate of said total wavefield energy at said selected points (3) deriving from said calculated scattered field a variable region characteristic by solving a system whose right hand side is said calculated scattered wavefield energy, and whose left hand side is the result of applying said fixed approximation of the scattering model to said variable region characteristics;

(4) comparing said variable regions characteristic to said fixed target characteristics estimate to derive a comparator;

(5) when said comparator is greater than a selected tolerance, said processing unit computing and storing in said memory an updated region characteristics estimate from:

(i) said estimate of said internal field, (ii) said fixed target characteristics estimate;

(iii) said variable region characteristics; and (iv) the square Jacobian of the variable region characteristics with respect to the region characteristics estimate, said Jacobian utilization being implemented via a method of the family of gradient methods specifically designed for square systems; and then setting said region characteristics estimate equal to said updated region characteristics estimate;

(h) repeating said processing unit convergence step until said comparator is less than or equal to said selected tolerance, said processing unit thereafter storing said updated region characteristics estimate in said memory.

182. A method as defined in claim 181, wherein said measured total wavefield energy and said measured total wavefield energy normal derivative are computed on said backscattering surface, said substantially parallel surfaces, and said forwardscattering surface by performing an inversion of a Green's function matrix, said Green's function matrix constructed from Green's theorem to map said measured total wavefield energy and said measured total wavefield energy normal derivative evaluated on said backscattering surface, said substantially parallel surfaces, and said forwardscattering surface, into said scattered wavefield energy detected.

183. A method for producing an image of matter in a region using a processing unit programmed to process data derived from incident wavefield energy that have been transmitted at one or more frequencies from one or more transmitter positions, each said transmitter position propagating wavefield energy at at least one transmitter orientation defined by Euler angles with respect to a selected fixed coordinate system, wherein said propagated wavefield energy is scattered by matter within said region and is detected by one or more receivers at one or more receiver positions and receiver orientations thereof, said receiver orientations defined by Euler angles with respect to said selected fixed coordinate system, said method comprising the steps of:

(a) choosing a forward scattering model which generates a total wavefield energy given said incident wavefield energy and one or more physical characteristics of said matter defined at selected points within said region;

(b) propagating said incident wavefield energy toward said region from said one or more transmitter positions and transmitter orientations thereof, said incident wavefield energy having one or more frequencies;

(c) detecting detected wavefield energy at each of said one or more receiver positions and respective receiver orientations thereof;

(d) electronically processing said detected wavefield energy so as to transform said detected wavefield energy into detected scattered wavefield energy that is stored in said computer memory and that corresponds to said detected wavefield energy;

(e) selecting a region characteristics estimate of selected physical characteristics at said selected points within the region and storing said region characteristics estimate in said computer memory;

(f) said processing unit calculating a fixed target characteristics estimate from the detected wavefield energy, said fixed target characteristics estimate being defined such that when operated on by a selected fixed approximation of the forward scattering model, the detected wavefield energy results;

(g) said processing unit performing a convergence step comprising the following steps:

(1) preparing, for each of said one or more frequencies at each said transmitter position and respective transmitter orientations thereof, an estimate of said total wavefield energy at said selected points derived from said incident wavefield energy for said selected points stored in the computer memory and said region characteristics estimate for said selected points;

(2) deriving, for each of said one or more frequencies at each said transmitter position and respective transmitter orientations thereof, a calculated scattered wavefield energy for one or more of said receiver positions and respective receiver orientations thereof from at least one of:

(i) said region characteristics estimate at said selected points, and (ii) said estimate of said total wavefield energy at said selected points;

(3) deriving from said calculated scattered field one or more variable region characteristics by solving a system whose right hand side is said calculated scattered wavefield energy, and whose left hand side is the result of applying said fixed approximation of the scattering model to said one or more variable region characteristics;

(4) comparing said one or more variable region characteristics to said fixed target characteristics estimate to derive a comparator;

(5) when said comparator is greater than a selected tolerance, said processing unit computing and storing in said computer memory an updated region characteristics estimate from:

(i) said estimate of said internal field;

(ii) said fixed target characteristics estimate;

(iii) said one or more variable region characteristics; and (iv) the square Jacobian of the one or more variable region characteristics with respect to the region characteristics estimate, said square Jacobian utilization being implemented via a method of the family of gradient methods specifically designed for square systems, and then setting said region characteristics estimate equal to said updated region characteristics estimate;

(h) repeating said processing unit convergence step until said comparator is less than or equal to said selected tolerance, said processing unit thereafter storing said updated region characteristics estimate in said computer memory.

184. A method as defined in claim 183, wherein said method from the family of the gradient methods specifically designed for square systems is the biconjugate gradient method.

185. A method as defined in claim 183, wherein said method from the family of the gradient methods specifically designed for square systems is the biconjugate gradient stabilized method.

186. A method as defined in claim 183, wherein said fixed approximation of the scattering model is the Born approximation.

187. A method as defined in claim 183, wherein said fixed approximation of the forward scattering model is the Rytov approximation.

188. A method for producing an image of matter in a region using a processing unit programmed to process data derived from incident wavefield energy that have been transmitted at one or more frequencies from one or more transmitter positions, each said transmitter position propagating wavefield energy at at least one transmitter orientation defined by Euler angles with respect to a selected fixed coordinate system, wherein said propagated wavefield energy is scattered by matter within said region and is detected by one or more receivers at one or more receiver positions and receiver orientations thereof, said receiver orientations defined by Euler angles with respect to said selected fixed coordinate system, said method comprising the steps of:

(a) choosing a forward scattering model which generates a total wavefield energy given said incident wavefield energy and one or more physical characteristics of said matter defined at selected points within said region;

(b) propagating said incident wavefield energy toward said region from said one or more transmitter positions and transmitter orientations thereof, said incident wavefield energy having one or more frequencies;

(c) for said one or more receiver positions, detecting at each said one or more receiver positions and respective receiver orientations thereof, a detected wavefield energy;

(d) electronically processing said detected wavefield energy so as to transform said detected wavefield energy into detected scattered wavefield energy stored in said computer memory and corresponding to said detected wavefield energy;

(e) selecting a variable scattered wavefield;

(f) said processing unit performing a convergence step comprising the following steps:

(1) deriving from said variable scattered wavefield a set of variable region characteristics by solving a system whose right hand side is said variable scattered wavefield, and whose left hand side is the result of applying a fixed approximation of the forward scattering model to said set of variable region characteristics, (2) preparing, for each of said one or more frequencies at each said transmitter position and respective orientations thereof, an estimate of said total wavefield energy at said selected points derived from said incident wavefield energy for said selected points stored in the computer memory and said set of variable region characteristics for said selected points;

(3) deriving, for each of said one or more frequencies at each said transmitter position and orientations thereof, a calculated scattered wavefield energy for said one or more of said receiver positions and respective receiver orientations thereof from at least one of:

(i) said set of variable region characteristics at said selected points, and (ii) said estimate of said total wavefield energy at said selected points;

(4) comparing said calculated scattered wavefield energy determined by said processing unit to said detected scattered wavefield energy to derive a comparator;

(5) when said comparator is greater than a selected tolerance, said processing unit computing an updated variable scattered wavefieldom:

(i) said estimate of said total wave field;
(ii) said detected scattered wavefield energy;
(iii) said variable region characteristics; and
(iv) the square Jacobian of the calculated scattered wavefield with respect to the varible scattered wavefield, said square Jacobian utilization being implemented via a method of the family of gradient methods specifically designed for square systems, and then setting said region characteristics estimate equal to said updated region characteristics estimate;

(h) repeating said processing unit convergence step until said comparator is less than or equal to said selected tolerance; and (i) deriving from said calculated scattered wavefield a region characteristics estimate by solving a system whose right hand side is said calculated scattered wavefield, and whose left hand side is the result of applying said fixed approximation of the forward scattering model to said region characteristics estimate, and storing said region characteristics estimate in said computer memory.

189. A method as defined in claim 188, wherein said fixed approximation of the forward scattering model is the Born approximation.

190. A method as defined in claim 188, wherein said fixed approximation of the forward scattering model is the Rytov approximation.

191. A method as defined in claim 188, wherein said method from the family of the gradient methods specifically designed for square systems is the biconjugate gradient method.

192. A method as defined in claim 188, wherein said method of the family of gradient methods specifically designed for square systems is the biconjugate gradient stabilized method.

193. A method of producing an image of an object from wavefield energy that has been transmitted into and scattered by the object, said image comprising a matrix of scattering parameters at points within the object, said image being stored in a memory of a central processing unit (CPU), and said method comprising the steps of:

(a) electronically transmitting an electric signal at one or more frequencies and transducing said electric signal at each said frequency into wavefield energy propagated toward said object from one or more of transducer transmitter positions;

(b) electronically processing said-electric signal to determine from said one or more transmitter positions an incident field corresponding to said propagated wavefield energy, said incident field being stored in the memory of the CPU in the form of digitized electric signals;

(c) detecting at one or more of transducer receiver positions said wavefield energy transmitted into and scattered by said object;

(d) electronically processing said detected wavefield energy so as to transform said detected wavefield energy into one or more digitized electric signals stored in said memory of said CPU and corresponding to a scattered field detected at said one or more transducer receiver positions;

(e) said CPU setting a present estimate of one or more scattering parameters for said object at each said frequency and storing each said present estimate of one or more scattering parameters in said memory;

(f) said CPU performing a convergence step at each of said one ore more frequencies comprising the following steps:

(1) said CPU preparing, using a first Fourier marching method, a composite field representing the incident field and the scattered field derived from:

((a)) said incident field, and
((b)) said present estimate of said one or more scattering parameters, where said composite field at each of said one or more frequencies comprises multiple orders of scattering; and (2) comparing said scattered field detected at said one or more transducer receiver positions to said composite field determined by said CPU to derive a comparator;

(3) when said comparator is greater than a selected tolerance, said CPU determining, using a second Fourier marching method, and storing in said memory, a matrix of updated scattering parameters calculated from:

((a)) said composite field,
((b)) said present estimate of one or more scattering parameters,
((c)) said scattered field detected at said one or more transducer receiver positions; and ((d)) said CPU utilizing the Jacobian of the composite field with respect to the present estimate of one or more scattering parameters and the Hermitian conjugate thereof, and then setting the present estimate of one or more scattering parameters equal to the matrix of the updated scattering parameters;

(g) repeating said CPU convergence step until said comparator is less than or equal to said selected tolerance, said CPU thereafter using the matrix of the updated scattering parameters to store in said CPU memory and to produce said image.

* * * * *

UNITED STATES PATENT AND TRADEMARK OFFICE
CERTIFICATE OF CORRECTION

PATENT NO. : 6,005,916

DATED : December 21, 1999

INVENTOR(S) : Steven A. Johnson, et al.

It is certified that error appears in the above-identified patent and that said Letters Patent is hereby corrected as shown below:

Col. 1, line 6, after "Aug. 29," change "1996" to --1997--

Col. 1, line 36, after "consist" change "or" to --of--

Col. 2, line 41, after "size" add --,-- (a comma)

Col. 3, line 8, before "longitudinal" change "pureiy" to --purely--

Col. 9, line 7, after "coordinate" change "recursionL" to --recursion--

Col. 10, line 63, after "determine" change "of" to --if--

Col. 11, line 40, after "the" change "previously" to --previous--

Col. 11, line 43, after "for" add --.-- (a period)

Col. 11, line 43, after "for." change "these" to --These--

Col. 13, line 2, after "design" add --of--

Col. 13, line 14, before "development" delete [new]

Col. 13, line 60, after "finding" delete [the]

Col. 14, line 30, after "$R^3$" add --is--

Col. 15, line 39, after "extent" add --.-- (a period)

UNITED STATES PATENT AND TRADEMARK OFFICE
CERTIFICATE OF CORRECTION

PATENT NO. : 6,005,916
DATED : December 21, 1999
INVENTOR(S) : Steven A. Johnson, et al.

It is certified that error appears in the above-identified patent and that said Letters Patent is hereby corrected as shown below:

Col. 16, line 67, after "function" change "has" to --as--

Col. 17, line 54, after "stated," change "in" to --it--

Col. 26, line 59, after "solve" change "th e" to --the--

Col. 29, line 24, after "example 1" change "read" to --reads--

Col. 29, line 62, after "(LS)$f$-F $^1$[(" change "G" to -- --

Col. 33, line 60, after "they" add --are--

Col. 37, line 3, before, "interference" change "and" to --an--

Col. 38, line 66, after "then" delete [then] (ours)

Col. 39, line 19, after "interferometer." change "There" to --Their--

Col. 41, line 33, after "are" change "parameter's" to --parameters--

Col. 55, line 54, after "{S} =" change "$f$ " to --$f^2$ --

Col. 56, line 33, after "leads" add --to--

Col. 59, line 59, after "algorithm" change "the used" to --that uses--

Col. 62, line 40, after "transfer" change "function" to --functions--

UNITED STATES PATENT AND TRADEMARK OFFICE
CERTIFICATE OF CORRECTION

PATENT NO. : 6,005,916

DATED : December 21, 1999

INVENTOR(S) : Steven A. Johnson, et al.

It is certified that error appears in the above-identified patent and that said Letters Patent is hereby corrected as shown below:

Col. 63, line 8, before "Johnson" add --|-- ( a bracket)

Col. 64, line 46, after "problem" add --.-- (a period)

Col. 72, line 8, after "upon" change "The" to --the--

Col. 72, line 40, after " $f = t$ " change "x" to -- --

Col. 72, line 42, after "where" change "x" to -- --

Col. 81, line 29, after "explicit" change "repreintation" to --representation--

Col. 84, line 15, after "for" change "for" to --each--

Col. 85, line 42, after "f =t +n " change " " to -- --

Col. 87, line 60, after "number" add -- --

Col. 92, line 34, after "rescaling" change "(emphasising" to --(emphasizing--

Col. 92, line 35, after "values and" change "deemphasising" to --deemphasizing--

Col. 97, line 33, after "FIG. 22" change "the illustrates" to --illustrates the--

Col. 97, line 63, after "'FIG, 1'" delete |0|

Col. 100, line 5, after "arrays" change "70is" to --70 is--

UNITED STATES PATENT AND TRADEMARK OFFICE
CERTIFICATE OF CORRECTION

PATENT NO. : 6,005,916
DATED : December 21, 1999
INVENTOR(S) : Steven A. Johnson, et al.

It is certified that error appears in the above-identified patent and that said Letters Patent is hereby corrected as shown below:

Col. 102, line 14, after "motor" change "46and" to --46 and--

Col. 102, line 46, after "data" change "are" to --is--

Col. 106, line 25, after "must be" change "change" to --changed--

Col. 118, line 43, after "other" change "scenario" to --scenarios--

Col. 118, line 57, after "requires" add --a--

Col. 126, line 29, after "where" change " " to -- --

Col. 127, line 20, after "used" change "a" to --as--

Col. 130, line 13, after "slice" change "y= jis" to --y= j is--

Col. 130, line 66, after "box" change "9292, to --2222,--

Col. 131, line 63, after "the" delete [the]

Col. 132, line 17, after "transferred" delete [to]

Col. 133, line 8, after "on" change " ³¹" to -- --

Col. 133, line 63, before "is then" change "contol" to --control--

Col. 135, line 44, before "is true" delete [it]

UNITED STATES PATENT AND TRADEMARK OFFICE
CERTIFICATE OF CORRECTION

PATENT NO.  : 6,005,916

DATED  : December 21, 1999

INVENTOR(S) : Steven A. Johnson, et al.

It is certified that error appears in the above-identified patent and that said Letters Patent is hereby corrected as shown below:

Col. 185, line 57, after "energy" delete [at]

Col. 188, line 34, after "one" change "of" to --or--

Col. 188, line 35, after "having" add --each said--

Col. 188, line 39, after "one" change "of" to --or--

Col. 188, line 53, after "one of said one" change "of" to --or--

Col. 188, line 57, after "one of said one" change "of" to --or--

Col. 188, line 62, after "one of said one" change "of" to --or--

Col. 192, line 8, after "energy" delete [at]

Col. 193, line 54, after "25. A" change "methods" to --method--

Col. 194, line 38, after "one of said one" change "of" to --or--

Col. 194, line 43, after "one of said one" change "of" to --or--

Col. 194, line 47, after "said one of said one" change "of" to --or--

Col. 197, line 63, after "energy" delete [at]

Col. 199, line 37, after "48. A" change "methods" to --method--

UNITED STATES PATENT AND TRADEMARK OFFICE
CERTIFICATE OF CORRECTION

PATENT NO. : 6,005,916

DATED : December 21, 1999

INVENTOR(S) : Steven A. Johnson, et al.

It is certified that error appears in the above-identified patent and that said Letters Patent is hereby corrected as shown below:

Col. 199, line 66, after "said one" change "of" to --or--

Col. 200, line 4, after "said one" change "of" to --or--

Col. 200, line 17, after "one of said one" change "of to --or--

Col. 200, line 22, after "one of said one" change "of" to --or--

Col. 200, line 26, after "one of said one" change "of" to --or--

Col. 203, line 41, after "energy" delete [at]

Col. 205, line 21, after "71. A" change "methods" to --method--

Col. 205, line 49, after "said one" change "of" to --or--

Col. 205, line 54, after "said one" change "of" to --or--

Col. 206, line 5, after "one of said one" change "of" to --or--

UNITED STATES PATENT AND TRADEMARK OFFICE
CERTIFICATE OF CORRECTION

PATENT NO. : 6,005,916

DATED : December 21, 1999

INVENTOR(S) : Steven A. Johnson, et al.

It is certified that error appears in the above-identified patent and that said Letters Patent is hereby corrected as shown below:

Col. 206, line 10, after "one of said one" change "of to --or--

Col. 208, line 61, after "wherein" delete [the]

Col. 209, line 22, after "each said one" change "of" to --or--

Col. 209, line 27, after "each said one" change "of" to --or--

Signed and Sealed this

Third Day of April, 2001

Attest:

NICHOLAS P. GODICI

Attesting Officer     Acting Director of the United States Patent and Trademark Office